US012692275B2

(12) United States Patent
Zhou et al.

(10) Patent No.: US 12,692,275 B2
(45) Date of Patent: Jul. 28, 2026

(54) AROYL SUBSTITUTED TRICYCLIC COMPOUND, PREPARATION METHOD THEREFOR AND USE THEREOF

(71) Applicants: GENFLEET THERAPEUTICS (SHANGHAI) INC., Shanghai (CN); ZHEJIANG GENFLEET THERAPEUTICS CO., LTD., Zhejiang (CN)

(72) Inventors: Fusheng Zhou, Shanghai (CN); Tao Jiang, Shanghai (CN); Yingtao Liu, Shanghai (CN); Chonglan Lin, Shanghai (CN); Leitao Zhang, Shanghai (CN); Zhubo Liu, Shanghai (CN); Kai Ma, Shanghai (CN); Wan He, Shanghai (CN); Xiaoming Xu, Shanghai (CN); Lijian Feng, Shanghai (CN); Xiaoling Lan, Shanghai (CN); Qian Ding, Shanghai (CN); Qiang Lv, Shanghai (CN); Jiong Lan, Shanghai (CN)

(73) Assignees: GENFLEET THERAPEUTICS (SHANGHAI) INC., Shanghai (CN); ZHEJIANG GENFLEET THERAPEUTICS CO., LTD., Zhejiang (CN)

( * ) Notice: Subject to any disclaimer, the term of this patent is extended or adjusted under 35 U.S.C. 154(b) by 567 days.

(21) Appl. No.: 18/245,167

(22) PCT Filed: Sep. 21, 2021

(86) PCT No.: PCT/CN2021/119507

§ 371 (c)(1),
(2) Date: Mar. 14, 2023

(87) PCT Pub. No.: WO2022/063101

PCT Pub. Date: Mar. 31, 2022

(65) Prior Publication Data

US 2024/0360154 A1 Oct. 31, 2024

(30) Foreign Application Priority Data

Sep. 23, 2020 (CN) ......................... 202011009451.3
Feb. 3, 2021 (CN) ......................... 202110150660.8
Sep. 6, 2021 (CN) ......................... 202111038855.X

(51) Int. Cl.

| | |
|---|---|
| ***C07D 498/22*** | (2006.01) |
| ***A61K 31/4985*** | (2006.01) |
| ***A61K 31/5386*** | (2006.01) |
| ***A61P 35/00*** | (2006.01) |
| ***C07D 471/14*** | (2006.01) |
| ***C07D 471/22*** | (2006.01) |
| ***C07D 491/22*** | (2006.01) |

(52) U.S. Cl.

CPC ........ *C07D 498/22* (2013.01); *A61K 31/4985* (2013.01); *A61K 31/5386* (2013.01); *A61P 35/00* (2018.01); *C07D 471/14* (2013.01); *C07D 471/22* (2013.01); *C07D 491/22* (2013.01)

(58) Field of Classification Search

CPC .. C07D 498/22; C07D 471/14; C07D 471/22; C07D 491/22

See application file for complete search history.

(56) References Cited

U.S. PATENT DOCUMENTS

| | | | |
|---|---|---|---|
| 10,253,023 | B2 | 4/2019 | Gaillard et al. |
| 2016/0096834 | A1 | 4/2016 | Gaillard et al. |
| 2022/0177462 | A1 | 6/2022 | Zhou et al. |

FOREIGN PATENT DOCUMENTS

| | | | |
|---|---|---|---|
| AU | 2012250576 | A1 | 11/2013 |
| CN | 107001362 | A | 8/2017 |
| CN | 107344940 | A | 11/2017 |
| CN | 113508109 | B | 2/2023 |
| WO | 2006124731 | A2 | 11/2006 |
| WO | 2007002433 | A1 | 1/2007 |
| WO | 2012085176 | A1 | 6/2012 |
| WO | 2014007951 | A2 | 1/2014 |
| WO | 2016057500 | A1 | 4/2016 |

OTHER PUBLICATIONS

Nov. 25, 2021 International Search Report issued in International Patent Application No. PCT/CN2021/119507.

(Continued)

*Primary Examiner* — Susanna Moore

(74) *Attorney, Agent, or Firm* — Houston Beshining Law Office PLLC; Liangang Ye

(57) ABSTRACT

Disclosed are an aroyl substituted tricyclic compound, a preparation method therefor and use thereof. Specifically, the aroyl substituted tricyclic compound of the present invention has a structure of formula (C), and has, as a BTK inhibitor, the advantages of high activity, good selectivity and low toxic and side effects.

(C)

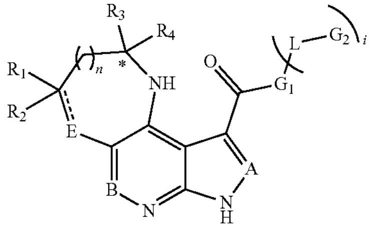

17 Claims, No Drawings

(56) References Cited

OTHER PUBLICATIONS

Nov. 25, 2021 Written Opinion of the International Searching Authority issued in International Patent Application No. PCT/CN2021/119507.
Jul. 26, 2022 Taiwan First Office Action issued in Patent Application No. 110135177.
Feb. 13, 2023 Taiwan Refusal Decision issued in Patent Application No. 110135177.
Sep. 20, 2023 Taiwan First Office Action after re-examination issued in Patent Application No. 110135177.
Mar. 22, 2024 First Search Report issued in Chinese Patent Application No. 2021800630019.
Mar. 22, 2024 First Office Action issued in Chinese Patent Application No. 2021800630019.
Eric R. Goedken et al., "Tricyclic Covalent Inhibitors Selectively Target Jak3 through an Active Site Thiol", Journal of Biological Chemistry, vol. 290, No. 8, pp. 4573-4589, Feb. 20, 2015.
Sakamoto et al., "Hetera-p-carbophanes. III. Conformation of Amide Groups in and Internal Rotation of Diaza[n] paracyclophanes with Two Alkoxy Groups at the Benzene Ring," Bulletin of the Chemical Society of Japan, vol. 48(2), pp. 497-504, 1975.

AROYL SUBSTITUTED TRICYCLIC COMPOUND, PREPARATION METHOD THEREFOR AND USE THEREOF

The present application is a National Stage of International Application No. PCT/CN2021/119507, filed on Sep. 22, 2021, which claims the priorities of the Chinese Patent Application NO. CN202011009451.3 filed on Sep. 23, 2020, the Chinese Patent Application NO. CN202110150660.8 filed on Feb. 3, 2021, and the Chinese Patent Application NO. CN202111038855.X filed on Sep. 6, 2021. The contents of the above Chinese patent applications are incorporated herein by reference in their entireties.

TECHNICAL FIELD

The present disclosure belongs to the field of medicine, and specifically relates to an aroyl-substituted tricyclic compound, a preparation method therefor and a use thereof.

BACKGROUND

Bruton's tyrosine kinase (BTK), a member of the Tec family of non-receptor tyrosine kinases, is a key kinase in B-cell antigen receptor (BCR) signaling pathway. The signals sent by BCR control a series of effector reactions, including activation, proliferation and differentiation of cells that produce mature antibodies. Aberrant BCR-mediated signal transduction can lead to misregulated B cell activation and/or formation of pathogenic autoantibodies, resulting in a variety of human diseases, including cancer, autoimmune and heteroimmune diseases. Ibrutinib (trade name: Imbmvica) achieved great success as the first BTK inhibitor to enter the market. However, like many other anticancer drugs, some patients show resistance to the drugs. Studies have found that a C481S mutation in BTK kinase is a major cause of drug resistance. Ibrutinib exerts a pharmacodynamic effect through irreversible covalent binding to a C481 tryptophan residue of BTK kinase. The C481S mutation converts the tryptophan into a serine, thereby losing the ability to bind covalently to ibrutinib. Under the above background, there is still a need to develop more efficient inhibitors against BTK in this field.

CONTENT OF THE PRESENT INVENTION

The present disclosure provides an aroyl-substituted tricyclic compound, which acts as a BTK inhibitor and has the advantages of high activity, good selectivity and low toxic and side effects and the like.

In one aspect, the present disclosure provides a compound of formula (C), a pharmaceutically acceptable salt thereof, a stereoisomer thereof, a solvate thereof or a prodrug thereof:

(C)

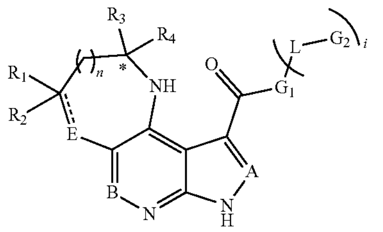

in the formula, $R_1$ and $R_2$ are each independently selected from: H, $C_{1-6}$ alkyl, $C_{2-6}$ alkenyl, $C_{2-6}$ alkynyl, $C_{3-20}$ cycloalkyl, 3- to 20-membered heterocyclyl, $C_{1-6}$ alkoxy and $C_{1-6}$ thioalkyl; or $R_1$ and $R_2$ combining with the carbon atoms to which they are attached form: $C_{3-20}$ cycloalkyl, 3- to 20-membered heterocyclyl, carbonyl (C═O) or C═S; the $C_{1-6}$ alkyl, the $C_{2-6}$ alkenyl, the $C_{2-6}$ alkynyl, the $C_{3-20}$ cycloalkyl, the 3- to 20-membered heterocyclyl, the $C_{1-6}$ alkoxy and the $C_{1-6}$ thioalkyl are each independently unsubstituted or substituted by 1, 2, 3 or 4 substituents independently selected from group S1;

$R_3$ and $R_4$ are each independently selected from: H, $C_{1-6}$ alkyl, $C_{2-6}$ alkenyl, $C_{2-6}$ alkynyl, $C_{3-20}$ cycloalkyl and 3- to 20-membered heterocyclyl; or $R_3$ and $R_4$ combining with the carbon atoms to which they are attached form: $C_{3-20}$ cycloalkyl, 3- to 20-membered heterocyclyl or carbonyl (C═O); the $C_{1-6}$ alkyl, the $C_{2-6}$ alkenyl, the $C_{2-6}$ alkynyl, the $C_{3-20}$ cycloalkyl and the 3- to 20-membered heterocyclyl are each independently unsubstituted or substituted by 1, 2, 3 or 4 substituents independently selected from group S1;

n is 0, 1, 2 or 3;

E is $NR_5$, O or N; wherein, $R_5$ is H, $C_{1-6}$ alkyl, halo $C_{1-6}$ alkyl, deuterated $C_{1-6}$ alkyl, $C_{2-6}$ alkenyl, $C_{2-6}$ alkynyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-deuterated $C_{1-6}$ alkyl, —$C_{1-4}$ alkylene-halo $C_{1-6}$ alkoxy, —$C_{1-4}$ alkylene-deuterated $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, the —$C_{1-4}$ alkylene- is unsubstituted, or 1 or 2 hydrogen atoms on the —$C_{1-4}$ alkylene- are each independently substituted by a group selected from halogen, cyano, hydroxyl, $C_{1-6}$ alkyl, halo $C_{1-6}$ alkyl and deuterated $C_{1-6}$ alkyl, or two hydrogen atoms on the same carbon on the —$C_{1-4}$ alkylene- are simultaneously substituted by —$(CH_2)_j$— to further form cycloalkyl, wherein j is 2, 3, 4, 5 or 6; the $C_{3-6}$ monocyclic cycloalkyl and the 3- to 6-membered monocyclic heterocyclyl are optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy;

when E is $NR_5$ or O, "$\equiv$" connected with E represents a single bond;

when E is N, "$\equiv$" connected with E represents a double bond and $R_2$ is absent;

A is $CR_6$ or N; wherein, $R_6$ is H, halogen, $C_{1-6}$ alkyl, halo $C_{1-6}$ alkyl, deuterated $C_{1-6}$ alkyl or —$C_{3-6}$ cycloalkyl;

B is $CR_7$ or N; wherein, $R_7$ is H, halogen, $C_{1-6}$ alkyl, halo $C_{1-6}$ alkyl, deuterated $C_{1-6}$ alkyl or —$C_{3-6}$ cycloalkyl;

$G_1$ is $C_{6-14}$ aryl, 5- to 6-membered monocyclic heteroaryl or 8- to 10-membered bicyclic heteroaryl; and the $C_{6-14}$ aryl, the 5- to 6-membered monocyclic heteroaryl and the 8- to 10-membered bicyclic heteroaryl are unsubstituted or substituted by 1, 2, 3 or 4 substituents independently selected from group S2;

$G_2$ is $C_{6-14}$ aryl, 5- to 6-membered monocyclic heteroaryl or 8- to 10-membered bicyclic heteroaryl; and the $C_{6-14}$ aryl, the 5- to 6-membered monocyclic heteroaryl and the 8- to 10-membered bicyclic heteroaryl are unsubstituted or substituted by 1, 2, 3 or 4 substituents independently selected from group S2;

L is a bond, $CR^8R^9$, O, NH, NHC(O), $C_{1-2}$ alkylene-NHC (O) or NHC(O)—$C_{1-2}$ alkylene-; wherein, $R^8$ and $R^9$ are each independently H, halogen, hydroxyl, cyano, $C_{1-6}$ alkyl, halo $C_{1-6}$ alkyl, deuterated $C_{1-6}$ alkyl, $C_{1-6}$ alkoxy, halo $C_{1-6}$ alkoxy, deuterated $C_{1-6}$ alkoxy, —$C_{3-6}$ monocyclic cycloalkyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-$NR^aR^b$, —$C_{1-4}$ alkylene-C(O)$NR^aR^b$, —$C_{1-4}$ alkylene-$SO_2C_{1-3}$ alkyl or —$C_{1-4}$ alkylene-carboxyl;

i is 0 or 1;

substituents in the groups S1 and S2 are each independently selected from: deuterium, halogen, cyano, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy, deuterated $C_{1-6}$ alkoxy, $C_{3-20}$ cycloalkyl (for example, —$C_{3-6}$ monocyclic cycloalkyl), halo $C_{3-20}$ cycloalkyl (for example, -halo $C_{3-6}$ monocyclic cycloalkyl), —O—$C_{3-20}$ cycloalkyl (for example, —O—$C_{3-6}$ monocyclic cycloalkyl), 3- to 20-membered heterocyclyl (for example, 3- to 6-membered monocyclic heterocyclyl), —O-3- to 20-membered heterocyclyl (for example, —O-3- to 6-membered monocyclic heterocyclyl), $C_{6-14}$ aryl (for example, phenyl), —O—$C_{6-14}$ aryl (for example, —O-phenyl), 5- to 6-membered monocyclic heteroaryl, —O-5- to 6-membered monocyclic heteroaryl, 8- to 10-membered bicyclic heteroaryl, —O-8- to 10-membered bicyclic heteroaryl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-deuterated $C_{1-6}$ alkyl, —$C_{1-4}$ alkylene-halo $C_{1-6}$ alkoxy, —$C_{1-4}$ alkylene-deuterated $C_{1-6}$ alkoxy, —$C_{1-4}$ alkylene-$C_{3-20}$ cycloalkyl (for example, —$C_{1-4}$ alkylene-$C_{3-6}$ monocyclic cycloalkyl), —$C_{1-4}$ alkylene-O—$C_{3-20}$ cycloalkyl (for example, —$C_{1-4}$ alkylene-O—$C_{3-6}$ monocyclic cycloalkyl), —$C_{1-4}$ alkylene-3- to 20-membered heterocyclyl (for example, —$C_{1-4}$ alkylene-3- to 6-membered monocyclic heterocyclyl), —$C_{1-4}$ alkylene-O-3- to 20-membered heterocyclyl (for example, —$C_{1-4}$ alkylene-O-3- to 6-membered monocyclic heterocyclyl), —$C_{1-4}$ alkylene-$C_{6-14}$ aryl (for example, —$C_{1-4}$ alkylene-phenyl), —$C_{1-4}$ alkylene-O—$C_{6-14}$ aryl (for example, —$C_{1-4}$ alkylene-O-phenyl), —$C_{1-4}$ alkylene-5- to 6-membered monocyclic heteroaryl, —$C_{1-4}$ alkylene-O-5- to 6-membered monocyclic heteroaryl, —$C_{1-4}$ alkylene-8- to 10-membered bicyclic heteroaryl, —$C_{1-4}$ alkylene-O-8- to 10-membered bicyclic heteroaryl, —$C_{1-4}$ alkylene-$NR^aR^b$, —$C_{1-4}$ alkylene-C(O)$NR^aR^b$, —$C_{1-4}$ alkylene-$NR^dC(O)R^c$, —$C_{1-4}$ alkylene-$NR^dC(O)NR^aR^b$, —$C_{1-4}$ alkylene-$SO_2R^c$, —$C_{1-4}$ alkylene-$NR^dSO_2R^c$, —$C_{1-4}$ alkylene-$SO_2NR^aR^b$, —$C_{1-4}$ alkylene-$NR^dSO_2NR^aR^b$, —$C_{1-4}$ alkylene-carboxyl, —C(O)$C_{1-6}$ alkyl, —C(O) halo $C_{1-6}$ alkyl, —C(O)deuterated $C_{1-6}$ alkyl, —C(O) $C_{3-20}$ cycloalkyl (for example, —C(O)$C_{3-6}$ monocyclic cycloalkyl), —C(O)3- to 20-membered heterocyclyl (for example, —C(O)3- to 6-membered monocyclic heterocyclyl), —C(O)$C_{6-14}$ aryl (for example, —C(O) phenyl), —C(O)5- to 6-membered monocyclic heteroaryl, —C(O)8- to 10-membered bicyclic heteroaryl, —C(O)$NR^aR^b$, —$NR^dC(O)R^c$, —$NR^dC(O)NR^aR^b$, —$SO_2R^c$, —$NR^dSO_2R^c$, —$SO_2NR^aR^b$, —$NR^dSO_2NR^aR^b$, —$NR^aR^b$ and —$OR^c$; the —$C_{1-4}$ alkylene- is unsubstituted, or hydrogen atoms on the —$C_{1-4}$ alkylene- are each independently substituted by a group selected from halogen, cyano, hydroxyl, $C_{1-6}$ alkyl, halo $C_{1-6}$ alkyl and deuterated $C_{1-6}$ alkyl, or two hydrogen atoms on the same carbon on the —$C_{1-4}$ alkylene- are simultaneously substituted by —$(CH_2)_j$— to further form cycloalkyl, wherein j is 2, 3, 4, 5 or 6; the $C_{3-20}$ cycloalkyl, the 3- to 20-membered heterocyclyl, the $C_{6-14}$ aryl, the 5- to 6-membered monocyclic heteroaryl and the 8- to 10-membered bicyclic heteroaryl are each independently optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy;

in the above groups, $R^a$ and $R^b$ are each independently H, $C_{1-6}$ alkyl, halo $C_{1-6}$ alkyl, deuterated $C_{1-6}$ alkyl, $C_{3-6}$ monocyclic cycloalkyl, —$C_{1-4}$ alkylene-$C_{3-6}$ monocyclic cycloalkyl, —$C_{1-4}$ alkylene-$C_{1-6}$ alkoxy, —$C_{1-4}$ alkylene-halo $C_{1-6}$ alkoxy, —$C_{1-4}$ alkylene-deuterated $C_{1-6}$ alkoxy, 3- to 6-membered monocyclic heterocyclyl, —$C_{1-4}$ alkylene-3- to 6-membered monocyclic heterocyclyl, $C_{6-14}$ aryl, 5- to 6-membered monocyclic heteroaryl, 8- to 10-membered bicyclic heteroaryl, —$C_{1-4}$ alkylene-$C_{6-14}$ aryl, —$C_{1-4}$ alkylene-5- to 6-membered monocyclic heteroaryl, —$C_{1-4}$ alkylene-8- to 10-membered bicyclic heteroaryl or C(O)$C_{1-6}$ alkyl; the $C_{3-6}$ monocyclic cycloalkyl, the 3- to 6-membered monocyclic heterocyclyl, the $C_{6-14}$ aryl, the 5- to 6-membered monocyclic heteroaryl and the 8- to 10-membered bicyclic heteroaryl are optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy; or in the above groups, $R^a$, $R^b$ combining with the nitrogen atoms to which they are attached form 3- to 6-membered nitrogen-containing heterocyclyl; and the 3- to 6-membered nitrogen-containing heterocyclyl is optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy;

in the above groups, $R^c$ is each independently H, $C_{1-6}$ alkyl, halo $C_{1-6}$ alkyl, deuterated $C_{1-6}$ alkyl, $C_{1-6}$ alkoxy, halo $C_{1-6}$ alkoxy, deuterated $C_{1-6}$ alkoxy, —$C_{1-4}$ alkylene-halo $C_{1-6}$ alkyl, —$C_{1-4}$ alkylene-deuterated $C_{1-6}$ alkyl, —$C_{1-4}$ alkylene-$C_{1-6}$ alkoxy, —$C_{1-4}$ alkylene-halo $C_{1-6}$ alkoxy, —$C_{1-4}$ alkylene-deuterated $C_{1-6}$ alkoxy, $C_{3-6}$ monocyclic cycloalkyl, —$C_{1-4}$ alkylene-$C_{3-6}$ monocyclic cycloalkyl, 3- to 6-membered monocyclic heterocyclyl, —$C_{1-4}$ alkylene-3- to 6-membered monocyclic heterocyclyl, $C_{6-14}$ aryl, 5- to 6-membered monocyclic heteroaryl, 8- to 10-membered bicyclic heteroaryl, —$C_{1-4}$ alkylene-$C_{6-14}$ aryl, —$C_{1-4}$ alkylene-5- to 6-membered monocyclic heteroaryl or —$C_{1-4}$ alkylene-8- to 10-membered bicyclic heteroaryl; the $C_{3-6}$ monocyclic cycloalkyl, the 3- to 6-membered monocyclic heterocyclyl, the $C_{6-14}$ aryl, the 5- to 6-membered monocyclic heteroaryl and the 8- to 10-membered bicyclic heteroaryl are optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy;

in the above groups, $R^d$ is each independently H, $C_{1-6}$ alkyl or deuterated $C_{1-6}$ alkyl;

a carbon atom marked at "*" is a chiral carbon atom (for example, R configuration, S configuration or a mixture thereof) or an achiral carbon atom.

In an embodiment, in the compound of formula (C), the pharmaceutically acceptable salt thereof, the stereoisomer thereof, the solvate thereof or the prodrug thereof, some groups have the following definitions, and those not mentioned are defined as described in any embodiment of the present disclosure (hereinafter referred to as "in an embodiment" or "in a preferred embodiment").

In an embodiment, the compound of formula (C) has a structure shown in formula (D):

(D)

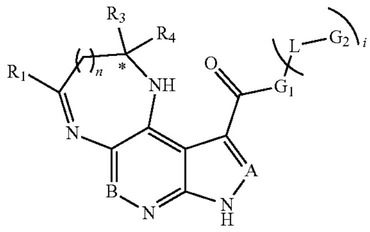

in the formula, A, B, $R_1$, $R_3$, $R_4$, L, $G_1$, $G_2$, n, i and "*" are as defined in the present disclosure.

In an embodiment, the compound of formula (C) has a structure shown in formula (E) or formula (F):

(E)

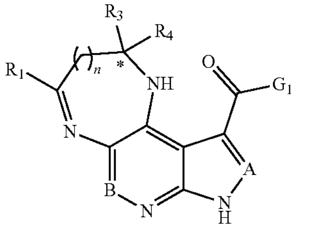

(F)

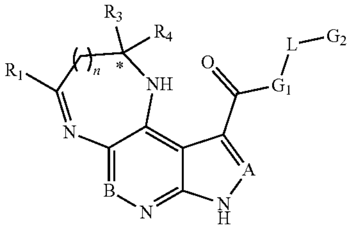

in the formula, A, B, $R_1$, $R_3$, $R_4$, L, $G_1$, $G_2$, n and "*" are as defined in the present disclosure.

In an embodiment, the compound of formula (C) has a structure shown in formula (II'), formula (B1'), formula (B2'), formula (C1), formula (C2) or formula (C3):

II'

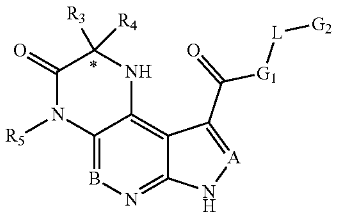

-continued

B1'

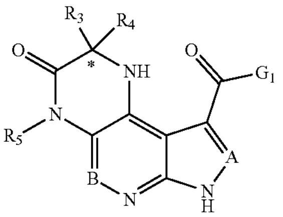

B2'

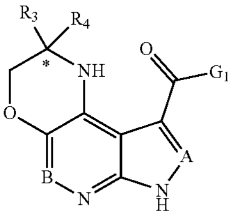

C1

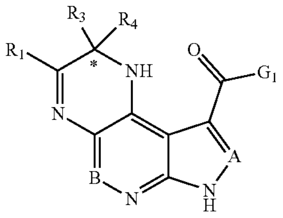

C2

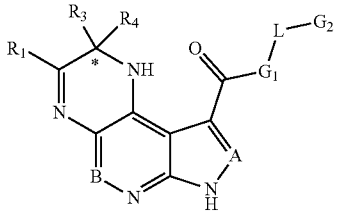

C3

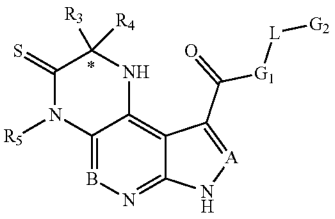

in the formula, A, B, $R_1$, $R_3$, $R_4$, $R_5$, L, $G_1$, $G_2$ and "*" are as defined in the present disclosure.

In an embodiment, the compound of formula (C) has a structure shown in formula (IIb'), formula (B1a'), formula (B2a'), formula (C1a), formula (C2a) or formula (C3a):

IIb'

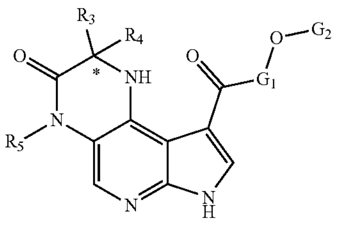

-continued

B1a'

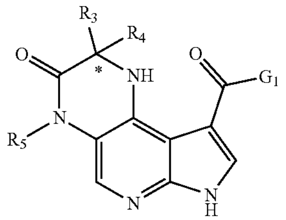

B2a'

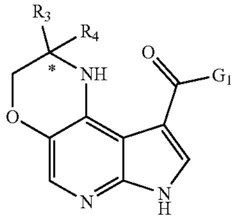

C1a

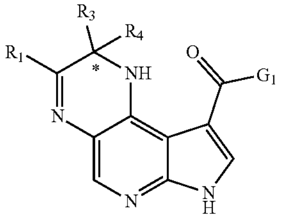

C2a

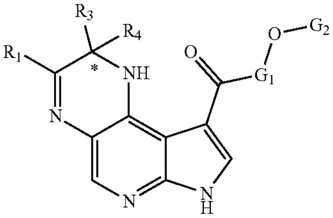

C3a

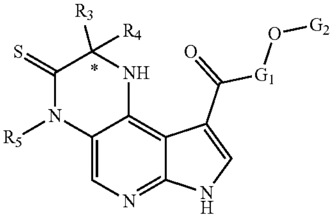

in the formula, $R_1$, $R_3$, $R_4$, $R_5$, $G_1$, $G_2$ and "*" are as defined in the present disclosure.

In an embodiment, the compound of formula (C) has a structure shown in formula (C1a-1), formula (C1a-2), formula (C2a-1), formula (C2a-2), formula (C3a-1) or formula (C3a-2):

C1a-1

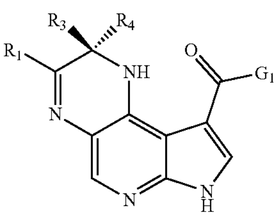

-continued

C2a-1

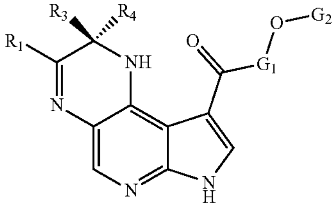

C3a-1

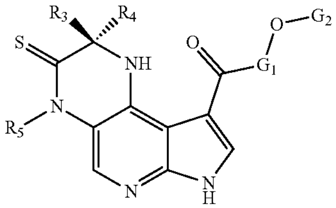

C1a-2

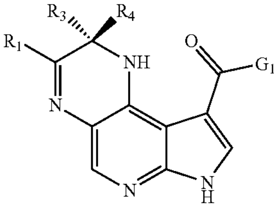

C2a-2

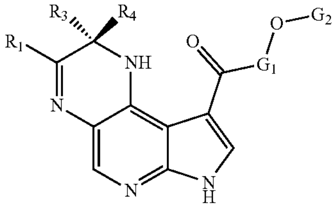

C3a-2

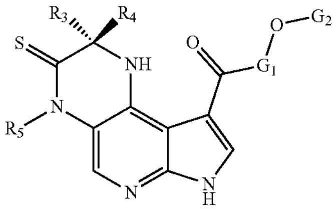

in the formula, $R_1$, $R_3$, $R_4$, $R_5$, $G_1$, $G_2$ are as defined in the present disclosure.

In an embodiment, in formula C, formula D, formula E, formula F, formula C1, formula C2, formula C1a, formula C2a, formula C1a-1, formula C1a-2, formula C2a-1 or formula C2a-2, $R_1$ is $C_{1-6}$ alkoxy (for example, methoxy) or $C_{1-6}$ thioalkyl (for example, methylthio or ethylthio).

In another aspect, the present disclosure provides a compound of formula (A), a pharmaceutically acceptable salt thereof, a stereoisomer thereof, a solvate thereof or a prodrug thereof:

(A)

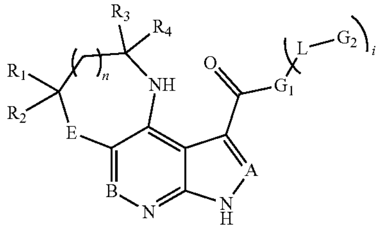

in the formula, $R_1$ and $R_2$ are each independently selected from: H, $C_{1-6}$ alkyl, $C_{2-6}$ alkenyl, $C_{2-6}$ alkynyl, $C_{3-20}$ cycloalkyl and 3- to 20-membered heterocyclyl; or $R_1$ and $R_2$ combining with the carbon atoms to which they are attached form: $C_{3-20}$ cycloalkyl, 3- to 20-membered heterocyclyl or carbonyl (C═O); the $C_{1-6}$ alkyl, the $C_{2-6}$ alkenyl, the $C_{2-6}$ alkynyl, the $C_{3-20}$ cycloalkyl and the 3- to 20-membered heterocyclyl are each independently unsubstituted or substituted by 1, 2, 3 or 4 substituents independently selected from group S1;

$R_3$ and $R_4$ are each independently selected from: H, $C_{1-6}$ alkyl, $C_{2-6}$ alkenyl, $C_{2-6}$ alkynyl, $C_{3-20}$ cycloalkyl and 3- to 20-membered heterocyclyl; or $R_3$ and $R_4$ combining with the carbon atoms to which they are attached form: $C_{3-20}$ cycloalkyl, 3- to 20-membered heterocyclyl or carbonyl (C═O); the $C_{1-6}$ alkyl, the $C_{2-6}$ alkenyl, the $C_{2-6}$ alkynyl, the $C_{3-20}$ cycloalkyl and the 3- to 20-membered heterocyclyl are each independently unsubstituted or substituted by 1, 2, 3 or 4 substituents independently selected from group S1;

n is 0, 1, 2 or 3;

E is $NR_5$ or O; wherein, $R_5$ is H, $C_{1-6}$ alkyl, halo $C_{1-6}$ alkyl, deuterated $C_{1-6}$ alkyl, $C_{2-6}$ alkenyl, $C_{2-6}$ alkynyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-deuterated $C_{1-6}$ alkyl, —$C_{1-4}$ alkylene-halo $C_{1-6}$ alkoxy, —$C_{1-4}$ alkylene-deuterated $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, the —$C_{1-4}$ alkylene- is unsubstituted, or 1 or 2 hydrogen atoms on the —$C_{1-4}$ alkylene- are each independently substituted by a group selected from halogen, cyano, hydroxyl, $C_{1-6}$ alkyl, halo $C_{1-6}$ alkyl and deuterated $C_{1-6}$ alkyl, or two hydrogen atoms on the same carbon on the —$C_{1-4}$ alkylene- are simultaneously substituted by —$(CH_2)_j$— to further form cycloalkyl, wherein j is 2, 3, 4, 5 or 6; the $C_{3-6}$ monocyclic cycloalkyl and the 3- to 6-membered monocyclic heterocyclyl are optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy;

A is $CR_6$ or N; wherein, $R_6$ is H, halogen, $C_{1-6}$ alkyl, halo $C_{1-6}$ alkyl, deuterated $C_{1-6}$ alkyl or —$C_{3-6}$ cycloalkyl;

B is $CR_7$ or N; wherein, $R_7$ is H, halogen, $C_{1-6}$ alkyl, halo $C_{1-6}$ alkyl, deuterated $C_{1-6}$ alkyl or —$C_{3-6}$ cycloalkyl;

$G_1$ is $C_{6-14}$ aryl, 5- to 6-membered monocyclic heteroaryl or 8- to 10-membered bicyclic heteroaryl; and the $C_{6-14}$ aryl, the 5- to 6-membered monocyclic heteroaryl and the 8- to 10-membered bicyclic heteroaryl are unsubstituted or substituted by 1, 2, 3 or 4 substituents independently selected from group S2;

$G_2$ is $C_{6-14}$ aryl, 5- to 6-membered monocyclic heteroaryl or 8- to 10-membered bicyclic heteroaryl; and the $C_{6-14}$ aryl, the 5- to 6-membered monocyclic heteroaryl and the 8- to 10-membered bicyclic heteroaryl are unsubstituted or substituted by 1, 2, 3 or 4 substituents independently selected from group S2;

L is a bond, $CR^8R^9$, O, NH, NHC(O), $C_{1-2}$ alkylene-NHC(O) or NHC(O)—$C_{1-2}$ alkyl; wherein, $R^8$, $R^9$ are each independently H, halogen, hydroxyl, cyano, $C_{1-6}$ alkyl, halo $C_{1-6}$ alkyl, deuterated $C_{1-6}$ alkyl, $C_{1-6}$ alkoxy, halo $C_{1-6}$ alkoxy, deuterated $C_{1-6}$ alkoxy, —$C_{3-6}$ monocyclic cycloalkyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-$NR^aR^b$, —$C_{1-4}$ alkylene-C(O)$NR^aR^b$, —$C_{1-4}$ alkylene-$SO_2C_{1-3}$ alkyl or —$C_{1-4}$ alkylene-carboxyl;

i is 0 or 1;

substituents in the group S1 or S2 are each independently selected from: deuterium, halogen, cyano, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy, deuterated $C_{1-6}$ alkoxy, $C_{3-20}$ cycloalkyl (for example, —$C_{3-6}$ monocyclic cycloalkyl), halo $C_{3-20}$ cycloalkyl (for example, -halo $C_{3-6}$ monocyclic cycloalkyl), —O—$C_{3-20}$ cycloalkyl (for example, —O—$C_{3-6}$ monocyclic cycloalkyl), 3- to 20-membered heterocyclyl (for example, 3- to 6-membered monocyclic heterocyclyl), —O-3- to 20-membered heterocyclyl (for example, —O-3- to 6-membered monocyclic heterocyclyl), $C_{6-14}$ aryl (for example, phenyl), —O—$C_{6-14}$ aryl (for example, —O-phenyl), 5- to 6-membered monocyclic heteroaryl, —O-5- to 6-membered monocyclic heteroaryl, 8- to 10-membered bicyclic heteroaryl, —O-8- to 10-membered bicyclic heteroaryl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-deuterated $C_{1-6}$ alkyl, —$C_{1-4}$ alkylene-halo $C_{1-6}$ alkoxy, —$C_{1-4}$ alkylene-deuterated $C_{1-6}$ alkoxy, —$C_{1-4}$ alkylene-$C_{3-20}$ cycloalkyl (for example, —$C_{1-4}$ alkylene-$C_{3-6}$ monocyclic cycloalkyl), —$C_{1-4}$ alkylene-O—$C_{3-20}$ cycloalkyl (for example, —$C_{1-4}$ alkylene-O—$C_{3-6}$ monocyclic cycloalkyl), —$C_{1-4}$ alkylene-3- to 20-membered heterocyclyl (for example, —$C_{1-4}$ alkylene-3- to 6-membered monocyclic heterocyclyl), —$C_{1-4}$ alkylene-O-3- to 20-membered heterocyclyl (for example, —$C_{1-4}$ alkylene-O-3- to 6-membered monocyclic heterocyclyl), —$C_{1-4}$ alkylene-$C_{6-14}$ aryl (for example, —$C_{1-4}$ alkylene-phenyl), —$C_{1-4}$ alkylene-O—$C_{6-14}$ aryl (for example, —$C_{1-4}$ alkylene-O-phenyl), —$C_{1-4}$ alkylene-5- to 6-membered monocyclic heteroaryl, —$C_{1-4}$ alkylene-O-5- to 6-membered monocyclic heteroaryl, —$C_{1-4}$ alkylene-8- to 10-membered bicyclic heteroaryl, —$C_{1-4}$ alkylene-O-8- to 10-membered bicyclic heteroaryl, —$C_{1-4}$ alkylene-$NR^aR^b$, —$C_{1-4}$ alkylene-C(O)$NR^aR^b$, —$C_{1-4}$ alkylene-$NR^dC(O)R^c$, —$C_{1-4}$ alkylene-$NR^dC(O)NR^aR^b$, —$C_{1-4}$ alkylene-$SO_2R^c$, —$C_{1-4}$ alkylene-$NR^dSO_2R^c$, —$C_{1-4}$ alkylene-$SO_2NR^aR^b$, —$C_{1-4}$ alkylene-$NR^dSO_2NR^aR^b$, —$C_{1-4}$ alkylene-carboxyl, —C(O)$C_{1-6}$ alkyl, —C(O) halo $C_{1-6}$ alkyl, —C(O)deuterated $C_{1-6}$ alkyl, —C(O) $C_{3-20}$ cycloalkyl (for example, —C(O)$C_{3-6}$ monocyclic cycloalkyl), —C(O)3- to 20-membered heterocyclyl (for example, —C(O)3- to 6-membered monocyclic heterocyclyl), —C(O)$C_{6-14}$ aryl (for example, —C(O)

phenyl), —C(O)5- to 6-membered monocyclic heteroaryl, —C(O)8- to 10-membered bicyclic heteroaryl, —C(O)$NR^aR^b$, —$NR^dC(O)R^c$, —$NR^dC(O)NR^aR^b$, —$SO_2R^c$, —$NR^dSO_2R^c$, —$SO_2NR^aR^b$, —$NR^dSO_2NR^aR^b$, —$NR^aR^b$ and —$OR^c$; the —$C_{1-4}$ alkylene- is unsubstituted, or hydrogen atoms on the —$C_{1-4}$ alkylene- are each independently substituted by a group selected from halogen, cyano, hydroxyl, $C_{1-6}$ alkyl, halo $C_{1-6}$ alkyl and deuterated $C_{1-6}$ alkyl, or two hydrogen atoms on the same carbon on the —$C_{1-4}$ alkylene- are simultaneously substituted by —$(CH_2)_j$— to further form cycloalkyl, wherein j is 2, 3, 4, 5 or 6; the $C_{3-20}$ cycloalkyl, the 3- to 20-membered heterocyclyl, the $C_{6-14}$ aryl, the 5- to 6-membered monocyclic heteroaryl and the 8- to 10-membered bicyclic heteroaryl are each independently optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy;

in the above groups, $R^a$ and $R^b$ are each independently H, $C_{1-6}$ alkyl, halo $C_{1-6}$ alkyl, deuterated $C_{1-6}$ alkyl, $C_{3-6}$ monocyclic cycloalkyl, —$C_{1-4}$ alkylene-$C_{3-6}$ monocyclic cycloalkyl, —$C_{1-4}$ alkylene-$C_{1-6}$ alkoxy, —$C_{1-4}$ alkylene-halo $C_{1-6}$ alkoxy, —$C_{1-4}$ alkylene-deuterated $C_{1-6}$ alkoxy, 3- to 6-membered monocyclic heterocyclyl, —$C_{1-4}$ alkylene-3- to 6-membered monocyclic heterocyclyl, $C_{6-14}$ aryl, 5- to 6-membered monocyclic heteroaryl, 8- to 10-membered bicyclic heteroaryl, —$C_{1-4}$ alkylene-$C_{6-14}$ aryl, —$C_{1-4}$ alkylene-5- to 6-membered monocyclic heteroaryl, —$C_{1-4}$ alkylene-8- to 10-membered bicyclic heteroaryl or C(O)$C_{1-6}$ alkyl; the $C_{3-6}$ monocyclic cycloalkyl, the 3- to 6-membered monocyclic heterocyclyl, the $C_{6-14}$ aryl, the 5- to 6-membered monocyclic heteroaryl and the 8- to 10-membered bicyclic heteroaryl are optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy; or in the above groups, $R^a$, $R^b$ combining with the nitrogen atoms to which they are attached form 3- to 6-membered nitrogen-containing heterocyclyl; and the 3- to 6-membered nitrogen-containing heterocyclyl is optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy;

in the above groups, $R^c$ is each independently H, $C_{1-6}$ alkyl, halo $C_{1-6}$ alkyl, deuterated $C_{1-6}$ alkyl, $C_{1-6}$ alkoxy, halo $C_{1-6}$ alkoxy, deuterated $C_{1-6}$ alkoxy, —$C_{1-4}$ alkylene-halo $C_{1-6}$ alkyl, —$C_{1-4}$ alkylene-deuterated $C_{1-6}$ alkyl, —$C_{1-4}$ alkylene-$C_{1-6}$ alkoxy, —$C_{1-4}$ alkylene-halo $C_{1-6}$ alkoxy, —$C_{1-4}$ alkylene-deuterated $C_{1-6}$ alkoxy, $C_{3-6}$ monocyclic cycloalkyl, —$C_{1-4}$ alkylene-$C_{3-6}$ monocyclic cycloalkyl, 3- to 6-membered monocyclic heterocyclyl, —$C_{1-4}$ alkylene-3- to 6-membered monocyclic heterocyclyl, $C_{6-14}$ aryl, 5- to 6-membered monocyclic heteroaryl, 8- to 10-membered bicyclic heteroaryl, —$C_{1-4}$ alkylene-$C_{6-14}$ aryl, —$C_{1-4}$ alkylene-5- to 6-membered monocyclic heteroaryl or —$C_{1-4}$ alkylene-8- to 10-membered bicyclic heteroaryl; the $C_{3-6}$ monocyclic cycloalkyl, the 3- to 6-membered monocyclic heterocyclyl, the $C_{6-14}$ aryl, the 5- to 6-membered monocyclic heteroaryl and the 8- to 10-membered bicyclic heteroaryl are optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy;

in the above groups, $R^d$ is each independently H, $C_{1-6}$ alkyl or deuterated $C_{1-6}$ alkyl.

Herein, the 3- to 20-membered heterocyclyl has 1, 2, 3 or 4 heteroatoms selected from N, O and S as ring atoms.

Herein, the 3- to 6-membered monocyclic heterocyclyl has 1, 2 or 3 heteroatoms selected from N, O and S as ring atoms.

Herein, the 5- to 6-membered monocyclic heteroaryl has 1, 2 or 3 heteroatoms selected from N, O and S as ring atoms.

Herein, the 8- to 10-membered bicyclic heteroaryl has 1, 2, 3, 4 or 5 heteroatoms selected from N, O and S as ring atoms.

Herein, the 3- to 6-membered nitrogen-containing heterocyclyl has 1 nitrogen atom and optionally 1 or 2 heteroatoms selected from N, O and S as ring atoms.

In another aspect, the present disclosure provides a compound of formula (B), a pharmaceutically acceptable salt thereof, a stereoisomer thereof, a solvate thereof or a prodrug thereof:

(B)

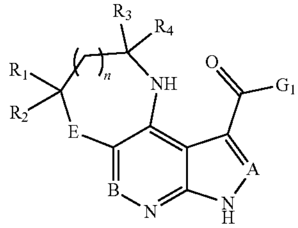

in the formula, $R_1$ and $R_2$ are each independently selected from: H, $C_{1-6}$ alkyl, $C_{2-6}$ alkenyl, $C_{2-6}$ alkynyl, $C_{3-20}$ cycloalkyl and 3- to 20-membered heterocyclyl; or $R_1$ and $R_2$ combining with the carbon atoms to which they are attached form: $C_{3-20}$ cycloalkyl, 3- to 20-membered heterocyclyl or carbonyl (C═O); the 3- to 20-membered heterocyclyl has 1, 2, 3 or 4 heteroatoms selected from N, O and S as ring atoms; the $C_{1-6}$ alkyl, the $C_{2-6}$ alkenyl, the $C_{2-6}$ alkynyl, the $C_{3-20}$ cycloalkyl and the 3- to 20-membered heterocyclyl are each independently unsubstituted or substituted by 1, 2, 3 or 4 substituents independently selected from group S1;

$R_3$ and $R_4$ are each independently selected from: H, $C_{1-6}$ alkyl, $C_{2-6}$ alkenyl, $C_{2-6}$ alkynyl, $C_{3-20}$ cycloalkyl and 3- to 20-membered heterocyclyl; or $R_3$ and $R_4$ combining with the carbon atoms to which they are attached form: $C_{3-20}$ cycloalkyl, 3- to 20-membered heterocyclyl or carbonyl (C═O); the 3- to 20-membered heterocyclyl has 1, 2, 3 or 4 heteroatoms selected from N, O and S as ring atoms; the $C_{1-6}$ alkyl, the $C_{2-6}$ alkenyl, the $C_{2-6}$ alkynyl, the $C_{3-20}$ cycloalkyl and the 3- to 20-membered heterocyclyl are each independently unsubstituted or substituted by 1, 2, 3 or 4 substituents independently selected from group S1;

n is 0, 1, 2 or 3;

E is $NR_5$ or O; wherein, $R_5$ is H, $C_{1-6}$ alkyl, halo $C_{1-6}$ alkyl, deuterated $C_{1-6}$ alkyl, $C_{2-6}$ alkenyl, $C_{2-6}$ alkynyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-deuterated $C_{1-6}$ alkyl, —$C_{1-4}$ alkylene-halo $C_{1-6}$ alkoxy, —$C_{1-4}$ alkylene-deuterated $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-$C(O)NR^aR^b$, —$C_{1-4}$ alkylene-$C(O)OC_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, the —$C_{1-4}$ alkylene- is unsubstituted, or 1 or 2 hydrogen atoms on the —$C_{1-4}$ alkylene- are each independently substituted by a group selected from halogen, cyano, hydroxyl, $C_{1-6}$ alkyl, halo $C_{1-6}$ alkyl and deuterated $C_{1-6}$ alkyl, or two hydrogen atoms on the same carbon on the —$C_{1-4}$ alkylene- are simultaneously substituted by —$(CH_2)_j$— to further form cycloalkyl, wherein j is 2, 3, 4, 5 or 6; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy;

A is $CR_6$ or N; wherein, $R_6$ is H, halogen, $C_{1-6}$ alkyl, halo $C_{1-6}$ alkyl, deuterated $C_{1-6}$ alkyl or —$C_{3-6}$ cycloalkyl;

B is $CR_7$ or N; wherein, $R_7$ is H, halogen, $C_{1-6}$ alkyl, halo $C_{1-6}$ alkyl, deuterated $C_{1-6}$ alkyl or —$C_{3-6}$ cycloalkyl;

$G_1$ is $C_{6-14}$ aryl, 5- to 6-membered monocyclic heteroaryl or 8- to 10-membered bicyclic heteroaryl; wherein, the 5- to 6-membered monocyclic heteroaryl has 1, 2 or 3 heteroatoms selected from N, O and S as ring atoms; the 8- to 10-membered bicyclic heteroaryl has 1, 2, 3, 4 or 5 heteroatoms selected from N, O and S as ring atoms; and the $C_{6-14}$ aryl, the 5- to 6-membered monocyclic heteroaryl and the 8- to 10-membered bicyclic heteroaryl are unsubstituted or substituted by 1, 2, 3 or 4 substituents independently selected from group S2;

substituents in the group S1 or S2 are each independently selected from: deuterium, halogen, cyano, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy, deuterated $C_{1-6}$ alkoxy, $C_{3-20}$ cycloalkyl (for example, —$C_{3-6}$ monocyclic cycloalkyl), halo $C_{3-20}$ cycloalkyl (for example, -halo $C_{3-6}$ monocyclic cycloalkyl), —O—$C_{3-20}$ cycloalkyl (for example, —O—$C_{3-6}$ monocyclic cycloalkyl), 3- to 20-membered heterocyclyl (for example, 3- to 6-membered monocyclic heterocyclyl), —O-3- to 20-membered heterocyclyl (for example, —O-3- to 6-membered monocyclic heterocyclyl), $C_{6-14}$ aryl (for example, phenyl), —O—$C_{6-14}$ aryl (for example, —O-phenyl), 5- to 6-membered monocyclic heteroaryl, —O-5- to 6-membered monocyclic heteroaryl, 8- to 10-membered bicyclic heteroaryl, —O-8- to 10-membered bicyclic heteroaryl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-deuterated $C_{1-6}$ alkyl, —$C_{1-4}$ alkylene-halo $C_{1-6}$ alkoxy, —$C_{1-4}$ alkylene-deuterated $C_{1-6}$ alkoxy, —$C_{1-4}$ alkylene-$C_{3-20}$ cycloalkyl (for example, —$C_{1-4}$ alkylene-$C_{3-6}$ monocyclic cycloalkyl), —$C_{1-4}$ alkylene-O—$C_{3-20}$ cycloalkyl (for example, —$C_{1-4}$ alkylene-O—$C_{3-6}$ monocyclic cycloalkyl), —$C_{1-4}$ alkylene-3- to 20-membered heterocyclyl (for example, —$C_{1-4}$ alkylene-3- to 6-membered monocyclic heterocyclyl), —$C_{1-4}$ alkylene-O-3- to 20-membered heterocyclyl (for example, —$C_{1-4}$ alkylene-O-3- to 6-membered monocyclic heterocyclyl), —$C_{1-4}$ alkylene-$C_{6-14}$ aryl (for example, —$C_{1-4}$ alkylene-phenyl), —$C_{1-4}$ alkylene-O—$C_{6-14}$ aryl (for example, —$C_{1-4}$ alkylene-O-phenyl), —$C_{1-4}$ alkylene-5- to 6-membered monocyclic heteroaryl, —$C_{1-4}$ alkylene-O-5- to 6-membered monocyclic heteroaryl, —$C_{1-4}$ alkylene-8- to 10-membered bicyclic heteroaryl, —$C_{1-4}$ alkylene-O-8- to 10-membered bicyclic heteroaryl, —$C_{1-4}$ alkylene-$NR^aR^b$, —$C_{1-4}$ alkylene-$C(O)NR^aR^b$, —$C_{1-4}$ alkylene-$NHC(O)R^c$, —$C_{1-4}$ alkylene-$SO_2C_{1-3}$ alkyl, —$C_{1-4}$ alkylene-$SO_2$-halo $C_{1-3}$ alkyl, —$C_{1-4}$ alkylene-$SO_2$-deuterated $C_{1-3}$ alkyl, —$C_{1-4}$ alkylene-$SO_2C_{6-14}$ aryl, —$C_{1-4}$ alkylene-$SO_2$-5- to 6-membered monocyclic heteroaryl, —$C_{1-4}$ alkylene-$SO_2$-8- to 10-membered bicyclic heteroaryl, —$C_{1-4}$ alkylene-carboxyl, —C(O)$C_{1-6}$ alkyl, —C(O)halo $C_{1-6}$ alkyl, —C(O)deuterated $C_{1-6}$ alkyl, —C(O)$C_{3-20}$ cycloalkyl (for example, —C(O)$C_{3-6}$ monocyclic cycloalkyl), —C(O)3- to 20-membered heterocyclyl (for example, —C(O)3- to 6-membered monocyclic heterocyclyl), —C(O)$C_{6-14}$ aryl (for example, —C(O)phenyl), —C(O)5- to 6-membered monocyclic heteroaryl, —C(O)8- to 10-membered bicyclic heteroaryl, —$C(O)NR^aR^b$, —$NHC(O)R^c$, —$NR^aR^b$ and —$OR^c$; the 3- to 20-membered heterocyclyl has 1, 2, 3 or 4 heteroatoms selected from N, O and S as ring atoms (for example, the 3- to 6-membered monocyclic heterocyclyl has 1, 2 or 3 heteroatoms selected from N, O and S as ring atoms); the —$C_{1-4}$ alkylene- is unsubstituted, or hydrogen atoms on the —$C_{1-4}$ alkylene- are each independently substituted by a group selected from halogen, cyano, hydroxyl, $C_{1-6}$ alkyl, halo $C_{1-6}$ alkyl and deuterated $C_{1-6}$ alkyl, or two hydrogen atoms on the same carbon on the —$C_{1-4}$ alkylene- are simultaneously substituted by —$(CH_2)_j$— to further form cycloalkyl, wherein j is 2, 3, 4, 5 or 6; the $C_{3-20}$ cycloalkyl, the 3- to 20-membered heterocyclyl, the $C_{6-14}$ aryl, the 5- to 6-membered monocyclic heteroaryl and the 8- to 10-membered bicyclic heteroaryl are each independently optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy;

in the above groups, $R^a$ and $R^b$ are each independently H, $C_{1-6}$ alkyl, halo $C_{1-6}$ alkyl, deuterated $C_{1-6}$ alkyl, $C_{3-6}$ monocyclic cycloalkyl, —$C_{1-4}$ alkylene-$C_{3-6}$ monocyclic cycloalkyl, —$C_{1-4}$ alkylene-$C_{1-6}$ alkoxy, —$C_{1-4}$ alkylene-halo $C_{1-6}$ alkoxy, —$C_{1-4}$ alkylene-deuterated $C_{1-6}$ alkoxy, 3- to 6-membered monocyclic heterocyclyl, —$C_{1-4}$ alkylene-3- to 6-membered monocyclic heterocyclyl, $C_{6-14}$ aryl, 5- to 6-membered monocyclic heteroaryl, 8- to 10-membered bicyclic heteroaryl, —$C_{1-4}$ alkylene-$C_{6-14}$ aryl, —$C_{1-4}$ alkylene-5- to 6-membered monocyclic heteroaryl, —$C_{1-4}$ alkylene-8- to 10-membered bicyclic heteroaryl or C(O)$C_{1-6}$ alkyl; wherein, the 3- to 6-membered monocyclic heterocyclyl has 1, 2 or 3 heteroatoms selected from N, O and S as ring atoms; the $C_{3-6}$ monocyclic cycloalkyl, the 3- to 6-membered monocyclic heterocyclyl, the $C_{6-14}$ aryl, the 5- to 6-membered monocyclic heteroaryl and the 8- to 10-membered bicyclic heteroaryl are optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy; or in the above groups, $R^a$, $R^b$ combining with the nitrogen atoms to which they are attached form 3- to 6-membered nitrogen-containing heterocyclyl; wherein, the 3- to 6-membered nitrogen-containing heterocyclyl has 1 nitrogen atom and optionally 1 or 2 heteroatoms selected from N, O and S as ring atoms; and the 3- to 6-membered nitrogen-containing heterocyclyl is optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy;

in the above groups, $R^c$ is H, $C_{1-6}$ alkyl, halo $C_{1-6}$ alkyl, deuterated $C_{1-6}$ alkyl, $C_{1-6}$ alkoxy, halo $C_{1-6}$ alkoxy, deuterated $C_{1-6}$ alkoxy, —$C_{1-4}$ alkylene-halo $C_{1-6}$ alkyl, —$C_{1-4}$ alkylene-deuterated $C_{1-6}$ alkyl, —$C_{1-4}$ alkylene-$C_{1-6}$ alkoxy, —$C_{1-4}$ alkylene-halo $C_{1-6}$ alkoxy, —$C_{1-4}$ alkylene-deuterated $C_{1-6}$ alkoxy, $C_{3-6}$ monocyclic cycloalkyl, —$C_{1-4}$ alkylene-$C_{3-6}$ monocyclic cycloalkyl, 3- to 6-membered monocyclic heterocyclyl, —$C_{1-4}$ alkylene-3- to 6-membered monocyclic heterocyclyl, $C_{6-14}$ aryl, 5- to 6-membered monocyclic heteroaryl, 8- to 10-membered bicyclic heteroaryl, —$C_{1-4}$ alkylene-$C_{6-14}$ aryl, —$C_{1-4}$ alkylene-5- to 6-membered monocyclic heteroaryl or —$C_{1-4}$ alkylene-8- to 10-membered bicyclic heteroaryl; the $C_{3-6}$ monocyclic cycloalkyl, the 3- to 6-membered monocyclic heterocyclyl, the $C_{6-14}$ aryl, the 5- to 6-membered monocyclic heteroaryl and the 8- to 10-membered bicyclic heteroaryl are optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy.

In an embodiment, the compound of formula (B) has a structure shown in formula B1:

B1

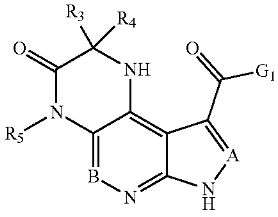

in each formula, A, B, $R_3$, $R_4$, $R_5$, $G_1$ are each defined as in formula B.

In an embodiment, the compound of formula (B) has a structure shown in formula B1a:

B1a

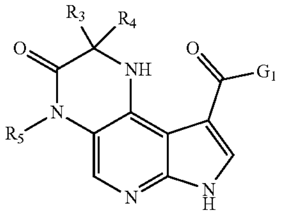

in each formula, $R_3$, $R_4$, $R_5$, $G_1$ are each defined as in formula B.

In an embodiment, the compound of formula (B) has a structure shown in formula B1a-1 or formula B1a-2:

B1a-1

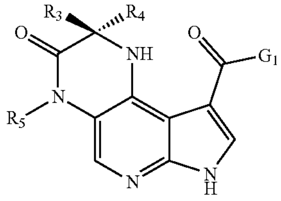

B1a-2

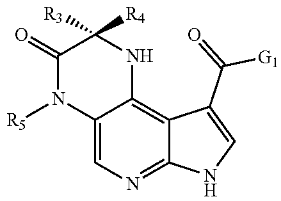

in each formula, $R_3$, $R_4$, $R_5$, $G_1$ are each defined as in formula B.

In an embodiment, in formula B1, formula B1a, formula B1a-1 or formula B1a-2, $R_5$ is H, $C_{1-6}$ alkyl, $C_{2-6}$ alkenyl, $C_{2-6}$ alkynyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-deuterated $C_{1-6}$ alkyl, —$C_{1-4}$ alkylene-halo $C_{1-6}$ alkoxy, —$C_{1-4}$ alkylene-deuterated $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-$C(O)NR^aR^b$, —$C_{1-4}$ alkylene-$C(O)OC_{1-6}$ alkyl, —$C_{1-4}$ alkylene-$SO_2C_{1-3}$ alkyl, —$C_{1-4}$ alkylene-carboxyl, 3- to 6-membered monocyclic heterocyclyl or $C_{3-6}$ monocyclic cycloalkyl; wherein, 1 or 2 hydrogen atoms on the "—$C_{1-4}$ alkylene-" are optionally substituted by $C_{1-6}$ alkyl, or two hydrogen atoms on the same carbon on the "—$C_{1-4}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-6}$ alkyl, halo $C_{1-6}$ alkyl, deuterated $C_{1-6}$ alkyl; $R^a$ and $R^b$ are each defined as in formula (B).

In an embodiment, in formula B1, formula B1a, formula B1a-1 or formula B1a-2, $R_5$ is H, $C_{1-4}$ alkyl, $C_{2-4}$ alkenyl, $C_{2-4}$ alkynyl, —$C_{1-2}$ alkylene-hydroxy, —$C_{1-2}$ alkylene-cyano, —$C_{1-2}$ alkylene-$C_{1-4}$ alkoxy, —$C_{1-2}$ alkylene-halo $C_{1-4}$ alkyl, —$C_{1-2}$ alkylene-deuterated $C_{1-4}$ alkyl, —$C_{1-2}$ alkylene-halo $C_{1-4}$ alkoxy, —$C_{1-2}$ alkylene-deuterated $C_{1-4}$ alkoxy, —$C_{1-2}$ alkylene-$C_{3-6}$ monocyclic cycloalkyl, —$C_{1-2}$ alkylene-3- to 6-membered monocyclic heterocyclyl, —$C_{1-2}$ alkylene-$NR^aR^b$, —$C_{1-2}$ alkylene-$C(O)NR^aR^b$, —$C_{1-2}$ alkylene-$C(O)OC_{1-4}$ alkyl, —$C_{1-2}$ alkylene-$SO_2C_{1-3}$ alkyl, —$C_{1-2}$ alkylene-carboxyl, 3- to 6-membered monocyclic heterocyclyl or $C_{3-6}$ monocyclic cycloalkyl; wherein, 1 or 2 hydrogen atoms on the "—$C_{1-2}$ alkylene-" are optionally substituted by $C_{1-4}$ alkyl, or two hydrogen atoms on the same carbon on the "—$C_{1-2}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-4}$ alkyl, halo $C_{1-4}$ alkyl and deuterated $C_{1-4}$ alkyl; $R^a$ and $R^b$ are each defined as in formula (B).

In an embodiment, in formula B1, formula B1a, formula B1a-1 or formula B1a-2, $R_3$ and $R_4$ are each independently selected from: H, $C_{1-6}$ alkyl, $C_{2-6}$ alkenyl, $C_{2-6}$ alkynyl, $C_{3-6}$ monocyclic cycloalkyl and 3- to 6-membered monocyclic heterocyclyl; the 3- to 6-membered monocyclic heterocyclyl has 1, 2 or 3 heteroatoms selected from N, O and S as ring atoms; the $C_{1-6}$ alkyl, the $C_{2-6}$ alkenyl, the $C_{2-6}$ alkynyl, the $C_{3-6}$ monocyclic cycloalkyl and the 3- to 6-membered monocyclic heterocyclyl are each independently unsubstituted or substituted by 1, 2, 3 or 4 substituents independently selected from group S1.

In an embodiment, in formula B1, formula B1a, formula B1a-1 or formula B1a-2, $R_3$ and $R_4$ are each independently selected from: $C_{1-6}$ alkyl, $C_{3-6}$ monocyclic cycloalkyl and 3- to 6-membered monocyclic heterocyclyl; the 3- to 6-membered monocyclic heterocyclyl has 1, 2 or 3 heteroatoms selected from N, O and S as ring atoms; the $C_{1-6}$ alkyl, the $C_{3-6}$ monocyclic cycloalkyl and the 3- to 6-membered monocyclic heterocyclyl are each independently unsubstituted or substituted by 1, 2, 3 or 4 substituents independently selected from group S1.

In an embodiment, in formula B1, formula B1a, formula B1a-1 or formula B1a-2, $R_3$ and $R_4$ are each independently selected from: $C_{1-6}$ alkyl; the $C_{1-6}$ alkyl is unsubstituted or substituted by 1, 2, 3 or 4 substituents independently selected from group S1; wherein, substituents in the group S1 are selected from: halogen, hydroxyl, —$C_{1-3}$ alkoxy, -deuterated $C_{1-3}$ alkoxy, -halo $C_{1-3}$ alkoxy, —$C_{3-6}$ monocyclic cycloalkyl, —O—$C_{3-6}$ monocyclic cycloalkyl and —$NR^aR^b$; wherein, $R^a$ and $R^b$ are each independently H, $C_{1-3}$ alkyl, deuterated $C_{1-3}$ alkyl or cyclopropyl; or $R^a$, $R^b$ combining with the nitrogen atoms to which they are attached form 3- to 6-membered nitrogen-containing heterocyclyl; wherein, the 3- to 6-membered nitrogen-containing heterocyclyl has 1 nitrogen atom and optionally 1 or 2 heteroatoms selected from N, O and S as ring atoms.

In an embodiment, in formula B1, formula B1a, formula B1a-1 or formula B1a-2, $R_3$ is selected from: $C_{1-6}$ alkyl and $C_{3-6}$ monocyclic cycloalkyl; the $C_{1-6}$ alkyl is unsubstituted or substituted by deuterium, or halogen; $R_4$ is selected from: $C_{1-6}$ alkyl; the $C_{1-6}$ alkyl is unsubstituted or substituted by 1, 2, 3 or 4 substituents independently selected from group S1; substituents in the group S1 are selected from: hydroxyl, $C_{1-6}$ alkoxy, halo $C_{1-6}$ alkoxy, deuterated $C_{1-6}$ alkoxy, —$C_{3-6}$ monocyclic cycloalkyl, —O—$C_{3-6}$ monocyclic cycloalkyl and —$NR^aR^b$; wherein, $R^a$ and $R^b$ are each independently H, $C_{1-6}$ alkyl, deuterated $C_{1-6}$ alkyl, $C_{3-6}$ monocyclic cycloalkyl, —$C_{1-4}$ alkylene-$C_{1-6}$ alkoxy, 3- to 6-membered monocyclic heterocyclyl, —$C_{1-4}$ alkylene-3- to 6-membered monocyclic heterocyclyl or C(O)$C_{1-6}$ alkyl; wherein, the 3- to 6-membered monocyclic heterocyclyl has 1, 2 or 3 heteroatoms selected from N, O and S as ring atoms; and the 3- to 6-membered monocyclic heterocyclyl is optionally substituted by 1 or 2 substituents selected from the following group: $C_{1-6}$ alkyl; or $R^a$, $R^b$ combining with the nitrogen atoms to which they are attached form 3- to 6-membered nitrogen-containing heterocyclyl; wherein, the 3- to 6-membered nitrogen-containing heterocyclyl has 1 nitrogen atom and optionally 1 or 2 heteroatoms selected from N, O and S as ring atoms; and the 3- to 6-membered nitrogen-containing heterocyclyl is optionally substituted by 1 or 2 substituents selected from the following group: $C_{1-6}$ alkyl.

In an embodiment, in formula B1, formula B1a, formula B1a-1 or formula B1a-2, $R_3$ is methyl, trifluoromethyl, ethyl, n-propyl or cyclopropyl; $R_4$ is methyl or ethyl; the methyl and the ethyl are unsubstituted or substituted by 1 substituent selected from group S1; the substituent in the group S1 is selected from: hydroxyl, methoxy, deuterated methoxy, trifluoromethoxy, ethoxy, n-propoxy, isopropoxy, n-butoxy, —O-cyclopropyl, —O-cyclobutyl, —$N(CH_3)_2$, —$N(CH_2CH_3)_2$, —$N(CH_2CH_3)(CH_3)$, —$N(CH_2CH_2CH_3)(CH_3)$ and —$N(CH_2CH_2CH_3)(CH_2CH_3)$.

In an embodiment, in formula B1, formula B1a, formula B1a-1 or formula B1a-2, $R_3$ is methyl or ethyl; $R_4$ is methyl or ethyl; the methyl and the ethyl are unsubstituted or substituted by 1 substituent selected from group S1; the substituent in the group S1 is selected from: hydroxyl, methoxy, deuterated methoxy, trifluoromethoxy, ethoxy, n-propoxy, isopropoxy, n-butoxy, —O-cyclopropyl, —O-cyclobutyl, —$N(CH_3)_2$, —$N(CH_2CH_3)_2$, —$N(CH_2CH_3)(CH_3)$, —$N(CH_2CH_2CH_3)(CH_3)$ and —$N(CH_2CH_2CH_3)(CH_2CH_3)$; $R_5$ is H.

In an embodiment, in formula B1, formula B1a, formula B1a-1 or formula B1a-2, $R_3$ is methyl, and the methyl is unsubstituted or substituted by deuterium or halogen; $R_4$ is methyl, and the methyl is unsubstituted or substituted by methoxy, deuterated methoxy, halomethoxy, ethoxy, deuterated ethoxy or haloethoxy; $R_5$ is H, $C_{1-6}$ alkyl, halo $C_{1-6}$ alkyl, deuterated $C_{1-6}$ alkyl, —$C_{3-6}$ monocyclic cycloalkyl, -halo $C_{3-6}$ monocyclic cycloalkyl, -deuterated $C_{3-6}$ monocyclic cycloalkyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl, 3- to 6-membered monocyclic heterocyclyl or $C_{3-6}$ monocyclic cycloalkyl; wherein, 1 or 2 hydrogen atoms on the "—$C_{1-4}$ alkylene-" are optionally substituted by $C_{1-6}$ alkyl, or two hydrogen atoms on the same carbon on the "—$C_{1-4}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-6}$ alkyl; $R^a$ and $R^b$ are each defined as in formula (B).

In an embodiment, in formula B1, formula B1a, formula B1a-1 or formula B1a-2, $R_3$ and $R_4$ are each independently methyl; the methyl is each independently unsubstituted or substituted by deuterium, halogen, hydroxyl, methoxy, deuterated methoxy, halomethoxy, ethoxy, deuterated ethoxy or haloethoxy.

In an embodiment, in formula B1, formula B1a, formula B1a-1 or formula B1a-2, $R_3$ and $R_4$ combining with the carbon atoms to which they are attached form: $C_{3-6}$ monocyclic cycloalkyl, 3- to 6-membered monocyclic heterocyclyl or carbonyl (C═O); the 3- to 6-membered monocyclic heterocyclyl has 1, 2 or 3 heteroatoms selected from N, O and S as ring atoms; the $C_{3-6}$ monocyclic cycloalkyl and the 3- to 6-membered monocyclic heterocyclyl are each independently unsubstituted or substituted by 1, 2, 3 or 4 substituents independently selected from group S1.

In an embodiment, in formula B1, formula B1a, formula B1a-1 or formula B1a-2, $R_3$ and $R_4$ combining with the carbon atoms to which they are attached form: cyclopropyl, cyclobutyl, cyclopentyl, cyclohexyl, oxetanyl, azetidinyl, tetrahydropyrrole, tetrahydrofuran, tetrahydropyran, piperidine or carbonyl (C═O); the cyclopropyl, the cyclobutyl, the cyclopentyl, the cyclohexyl, the oxetanyl, the azetidinyl, the tetrahydropyrrole, the tetrahydrofuran, the tetrahydropyran and the piperidine are each independently unsubstituted or substituted by 1, 2, 3 or 4 substituents independently selected from group S1.

In an embodiment, in formula B1, formula B1a, formula B1a-1 or formula B1a-2, $R_3$ and $R_4$ combining with the carbon atoms to which they are attached form: cyclopropyl, cyclobutyl, cyclopentyl, cyclohexyl, oxetanyl, azetidinyl, tetrahydropyrrole, tetrahydrofuran, tetrahydropyran, piperidine or carbonyl (C═O); the cyclopropyl, the cyclobutyl, the cyclopentyl, the cyclohexyl, the oxetanyl, the azetidinyl, the tetrahydropyrrole, the tetrahydrofuran, the tetrahydropyran and the piperidine are each independently unsubstituted or substituted by 1, 2, 3 or 4 substituents independently selected from group S1; wherein, substituents in the group S1 are selected from: cyano, hydroxyl, methyl, ethyl, propyl, halomethyl, methoxy, ethoxy, —$C(O)CH_3$, —C(O)cyclopropyl, —$C(O)NH_2$, —$C(O)N(CH_3)_2$, —$CH_2OH$, —$CH_2CH_2OH$, —$CH_2OCH_3$, —$CH_2CH_2OCH_3$—$CH_2N(CH_3)_2$, —$CH_2CH_2N(CH_3)_2$, —$NHC(O)CH_3$ and —$N(CH_3)_2$.

In an embodiment, the compound of formula (B) has a structure shown in formula B2:

B2

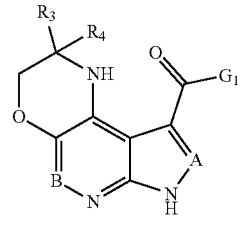

in each formula, A, B, $R_3$, $R_4$, $R_5$, $G_1$ are each defined as in formula B.

In an embodiment, the compound of formula (B) has a structure shown in formula B2a:

B2a

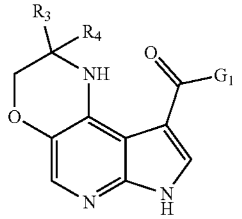

in each formula, $R_3$, $R_4$, $R_5$, $G_1$ are each defined as in formula B.

In an embodiment, the compound of formula (B) has a structure shown in formula B2a-1 or formula B2a-2:

B2a-1

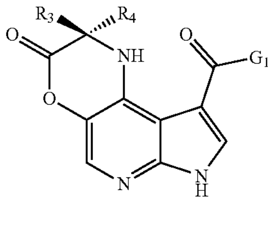

-continued

B2a-2

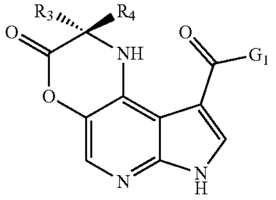

in each formula, $R_3$, $R_4$, $R_5$, $G_1$ are each defined as in formula B.

In an embodiment, in formula B2, formula B2a, formula B2a-1 or formula B2a-2, $R_3$ and $R_4$ are each independently selected from: H, $C_{1-6}$ alkyl, $C_{2-6}$ alkenyl, $C_{2-6}$ alkynyl, $C_{3-6}$ monocyclic cycloalkyl and 3- to 6-membered monocyclic heterocyclyl; the 3- to 6-membered monocyclic heterocyclyl has 1, 2 or 3 heteroatoms selected from N, O and S as ring atoms; the $C_{1-6}$ alkyl, the $C_{2-6}$ alkenyl, the $C_{2-6}$ alkynyl, the $C_{3-6}$ monocyclic cycloalkyl and the 3- to 6-membered monocyclic heterocyclyl are each independently unsubstituted or substituted by 1, 2, 3 or 4 substituents independently selected from group S1.

In an embodiment, in formula B2, formula B2a, formula B2a-1 or formula B2a-2, $R_3$ and $R_4$ are each independently selected from: $C_{1-6}$ alkyl, $C_{3-6}$ monocyclic cycloalkyl and 3- to 6-membered monocyclic heterocyclyl; the 3- to 6-membered monocyclic heterocyclyl has 1, 2 or 3 heteroatoms selected from N, O and S as ring atoms; the $C_{1-6}$ alkyl, the $C_{3-6}$ monocyclic cycloalkyl and the 3- to 6-membered monocyclic heterocyclyl are each independently unsubstituted or substituted by 1, 2, 3 or 4 substituents independently selected from group S1.

In an embodiment, in formula B2, formula B2a, formula B2a-1 or formula B2a-2, $R_3$ and $R_4$ are each independently selected from: $C_{1-6}$ alkyl; the $C_{1-6}$ alkyl is unsubstituted or substituted by 1, 2, 3 or 4 substituents independently selected from group S1; wherein, substituents in the group S1 are selected from: halogen, hydroxyl, —$C_{1-3}$ alkoxy, -deuterated $C_{1-3}$ alkoxy, -halo $C_{1-3}$ alkoxy, —$C_{3-6}$ monocyclic cycloalkyl, —O—$C_{3-6}$ monocyclic cycloalkyl and —$NR^aR^b$; wherein, $R^a$ and $R^b$ are each independently H, $C_{1-3}$ alkyl, deuterated $C_{1-3}$ alkyl or cyclopropyl; or $R^a$, $R^b$ combining with the nitrogen atoms to which they are attached form 3- to 6-membered nitrogen-containing heterocyclyl; wherein, the 3- to 6-membered nitrogen-containing heterocyclyl has 1 nitrogen atom and optionally 1 or 2 heteroatoms selected from N, O and S as ring atoms.

In an embodiment, in formula B2, formula B2a, formula B2a-1 or formula B2a-2, $R_3$ and $R_4$ are each independently methyl; the methyl is each independently unsubstituted or substituted by deuterium, halogen, hydroxyl, methoxy, deuterated methoxy, halomethoxy, ethoxy, deuterated ethoxy or haloethoxy.

In an embodiment, in formula B2, formula B2a, formula B2a-1 or formula B2a-2, $R_3$ and $R_4$ combining with the carbon atoms to which they are attached form: $C_{3-6}$ monocyclic cycloalkyl, 3- to 6-membered monocyclic heterocyclyl or carbonyl (C═O); the 3- to 6-membered monocyclic heterocyclyl has 1, 2 or 3 heteroatoms selected from N, O and S as ring atoms; the $C_{3-6}$ monocyclic cycloalkyl and the 3- to 6-membered monocyclic heterocyclyl are each independently unsubstituted or substituted by 1, 2, 3 or 4 substituents independently selected from group S1.

In an embodiment, in formula B2, formula B2a, formula B2a-1 or formula B2a-2, $R_3$ and $R_4$ combining with the carbon atoms to which they are attached form: cyclopropyl, cyclobutyl, cyclopentyl, cyclohexyl, oxetanyl, azetidinyl, tetrahydropyrrole, tetrahydrofuran, tetrahydropyran, piperidine or carbonyl (C═O); the cyclopropyl, the cyclobutyl, the cyclopentyl, the cyclohexyl, the oxetanyl, the azetidinyl, the tetrahydropyrrole, the tetrahydrofuran, the tetrahydropyran and the piperidine are each independently unsubstituted or substituted by 1, 2, 3 or 4 substituents independently selected from group S1.

In an embodiment, in formula B2, formula B2a, formula B2a-1 or formula B2a-2, $R_3$ and $R_4$ combining with the carbon atoms to which they are attached form: cyclopropyl, cyclobutyl, cyclopentyl, cyclohexyl, oxetanyl, azetidinyl, tetrahydropyrrole, tetrahydrofuran, tetrahydropyran, piperidine or carbonyl (C═O); the cyclopropyl, the cyclobutyl, the cyclopentyl, the cyclohexyl, the oxetanyl, the azetidinyl, the tetrahydropyrrole, the tetrahydrofuran, the tetrahydropyran and the piperidine are each independently unsubstituted or substituted by 1, 2, 3 or 4 substituents independently selected from group S1; wherein, substituents in the group S1 are selected from: cyano, hydroxyl, methyl, ethyl, propyl, halomethyl, methoxy, ethoxy, —C(O)$CH_3$, —C(O)cyclopropyl, —C(O)$NH_2$, —C(O)N$(CH_3)_2$, —$CH_2OH$, —$CH_2CH_2OH$, —$CH_2OCH_3$, —$CH_2CH_2OCH_3$—$CH_2N(CH_3)_2$, —$CH_2CH_2N(CH_3)_2$, —NHC(O)$CH_3$ and —N$(CH_3)_2$.

In another aspect, the present disclosure provides a compound of formula (I), a pharmaceutically acceptable salt thereof, a stereoisomer thereof, a solvate thereof or a prodrug thereof:

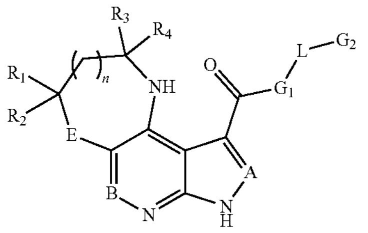

I in the formula, $R_1$ and $R_2$ are each independently selected from: H, $C_{1-6}$ alkyl, $C_{2-6}$ alkenyl, $C_{2-6}$ alkynyl, $C_{3-20}$ cycloalkyl and 3- to 20-membered heterocyclyl; or $R_1$ and $R_2$ combining with the carbon atoms to which they are attached form: $C_{3-20}$ cycloalkyl, 3- to 20-membered heterocyclyl or carbonyl (C═O); the 3- to 20-membered heterocyclyl has 1, 2 or 3 heteroatoms selected from N, O and S as ring atoms; the $C_{1-6}$ alkyl, the $C_{2-6}$ alkenyl, the $C_{2-6}$ alkynyl, the $C_{3-20}$ cycloalkyl and the 3- to 20-membered heterocyclyl are each independently unsubstituted or substituted by 1, 2, 3 or 4 substituents independently selected from group S1;

$R_3$ and $R_4$ are each independently selected from: H, $C_{1-6}$ alkyl, $C_{2-6}$ alkenyl, $C_{2-6}$ alkynyl, $C_{3-20}$ cycloalkyl and 3- to 20-membered heterocyclyl; or $R_3$ and $R_4$ combining with the carbon atoms to which they are attached form: $C_{3-20}$ cycloalkyl, 3- to 20-membered heterocyclyl or carbonyl (C═O); the 3- to 20-membered heterocyclyl has 1, 2 or 3 heteroatoms selected from N, O and S as ring atoms; the $C_{1-6}$ alkyl, the $C_{2-6}$ alkenyl, the $C_{2-6}$ alkynyl, the $C_{3-20}$ cycloalkyl and the 3- to 20-membered heterocyclyl are each independently unsubstituted or substituted by 1, 2, 3 or 4 substituents independently selected from group S1;

n is 0, 1, 2 or 3;

E is $NR_5$ or O; wherein, $R_5$ is H, $C_{1-6}$ alkyl, halo $C_{1-6}$ alkyl, deuterated $C_{1-6}$ alkyl, $C_{2-6}$ alkenyl, $C_{2-6}$ alkynyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-deuterated $C_{1-6}$ alkyl, —$C_{1-4}$ alkylene-halo $C_{1-6}$ alkoxy, —$C_{1-4}$ alkylene-deuterated $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, 1 or 2 hydrogen atoms on the "—$C_{1-4}$ alkylene-" are optionally substituted by $C_{1-6}$ alkyl, or two hydrogen atoms on the same carbon on the "—$C_{1-4}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-6}$ alkyl;

A is $CR_6$ or N; wherein, $R_6$ is H, halogen, $C_{1-6}$ alkyl, halo $C_{1-6}$ alkyl, deuterated $C_{1-6}$ alkyl or —$C_{3-6}$ cycloalkyl;

B is $CR_7$ or N; wherein, $R_7$ is H, halogen, $C_{1-6}$ alkyl, halo $C_{1-6}$ alkyl, deuterated $C_{1-6}$ alkyl or —$C_{3-6}$ cycloalkyl;

$G_1$ is $C_{6-14}$ aryl, 5- to 6-membered monocyclic heteroaryl or 8- to 10-membered bicyclic heteroaryl; wherein, the 5- to 6-membered monocyclic heteroaryl has 1, 2 or 3 heteroatoms selected from N, O and S as ring atoms; the 8- to 10-membered bicyclic heteroaryl has 1, 2, 3, 4 or 5 heteroatoms selected from N, O and S as ring atoms; and the $C_{6-14}$ aryl, the 5- to 6-membered monocyclic heteroaryl and the 8- to 10-membered bicyclic heteroaryl are unsubstituted or substituted by 1, 2, 3 or 4 substituents independently selected from group S2;

$G_2$ is $C_{6-14}$ aryl, 5- to 6-membered monocyclic heteroaryl or 8- to 10-membered bicyclic heteroaryl; wherein, the 5- to 6-membered monocyclic heteroaryl has 1, 2 or 3 heteroatoms selected from N, O and S as ring atoms; the 8- to 10-membered bicyclic heteroaryl has 1, 2, 3, 4 or 5 heteroatoms selected from N, O and S as ring atoms; and the $C_{6-14}$ aryl, the 5- to 6-membered monocyclic heteroaryl and the 8- to 10-membered bicyclic heteroaryl are unsubstituted or substituted by 1, 2, 3 or 4 substituents independently selected from group S2;

L is a bond, $CR^8R^9$, O, NH, NHC(O), $C_{1-2}$ alkylene-NHC(O) or NHC(O)—$C_{1-2}$ alkylene; wherein, $R^8$, $R^9$ are each independently H, halogen, hydroxyl, cyano, $C_{1-6}$ alkyl, halo $C_{1-6}$ alkyl, deuterated $C_{1-6}$ alkyl, $C_{1-6}$ alkoxy, halo $C_{1-6}$ alkoxy, deuterated $C_{1-6}$ alkoxy, —$C_{3-6}$ monocyclic cycloalkyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-$NR^aR^b$, —$C_{1-4}$ alkylene-C(O)$NR^aR^b$, —$C_{1-4}$ alkylene-$SO_2C_{1-3}$ alkyl or —$C_{1-4}$ alkylene-carboxyl;

substituents in the group S1 or S2 are each independently selected from: deuterium, halogen, cyano, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy, deuterated $C_{1-6}$ alkoxy, —$C_{3-6}$ monocyclic cycloalkyl, -halo $C_{3-6}$ monocyclic cycloalkyl, —O—$C_{3-6}$ monocyclic cycloalkyl, 3- to 6-membered monocyclic heterocyclyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-$C(O)NR^aR^b$, —$C_{1-4}$ alkylene-$SO_2C_{1-3}$ alkyl, —$C_{1-4}$ alkylene-carboxyl, —$C(O)C_{1-6}$ alkyl, —$C(O)C_{3-6}$ monocyclic cycloalkyl, —$C(O)NR^aR^b$, —$NHC(O)R^c$ and —$NR^aR^b$; the 3- to 6-membered monocyclic heterocyclyl has 1, 2 or 3 heteroatoms selected from N, O and S as ring atoms;

in the above groups, $R^a$ and $R^b$ are each independently H, $C_{1-6}$ alkyl, deuterated $C_{1-6}$ alkyl, $C_{3-6}$ monocyclic cycloalkyl, —$C_{1-4}$ alkylene-$C_{1-6}$ alkoxy, 3- to 6-membered monocyclic heterocyclyl, —$C_{1-4}$ alkylene-3- to 6-membered monocyclic heterocyclyl or $C(O)C_{1-6}$ alkyl; wherein, the 3- to 6-membered monocyclic heterocyclyl has 1, 2 or 3 heteroatoms selected from N, O and S as ring atoms; and the 3- to 6-membered monocyclic heterocyclyl is optionally substituted by 1 or 2 substituents selected from the following group: $C_{1-6}$ alkyl; or in the above groups, $R^a$, $R^b$ combining with the nitrogen atoms to which they are attached form 3- to 6-membered nitrogen-containing heterocyclyl; wherein, the 3- to 6-membered nitrogen-containing heterocyclyl has 1 nitrogen atom and optionally 1 or 2 heteroatoms selected from N, O and S as ring atoms; and the 3- to 6-membered nitrogen-containing heterocyclyl is optionally substituted by 1 or 2 substituents selected from the following group: $C_{1-6}$ alkyl;

in the above groups, $R^c$ is hydrogen, $C_{1-6}$ alkyl or halo $C_{1-6}$ alkyl.

In an embodiment, the compound of formula (I) has a structure shown in formula II:

II

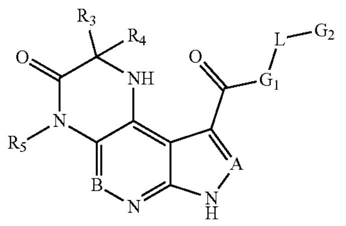

in the formula, A, B, $R_3$, $R_4$, $R_5$, L, $G_1$, $G_2$ are each defined as in formula (I).

In an embodiment, the compound of formula (I) has a structure shown in formula IIa:

IIa

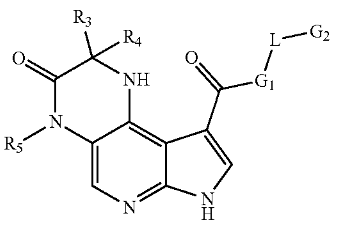

in the formula, $R_3$, $R_4$, $R_5$, L, $G_1$, $G_2$ are each defined as in formula (I).

In an embodiment, the compound of formula (I) has a structure shown in formula IIb, formula IIc, formula IId, formula IIe, formula IIf, formula IIg, formula IIh, formula IIi, formula IIj or formula IIk:

IIb

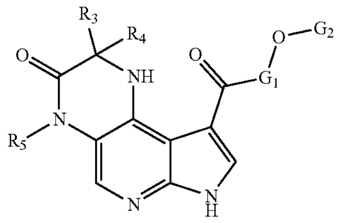

IIc

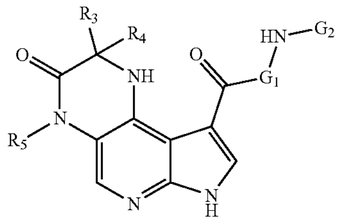

IId

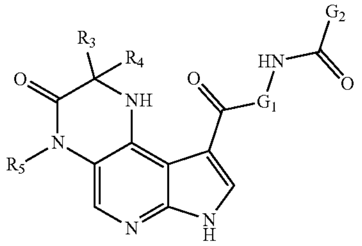

IIe

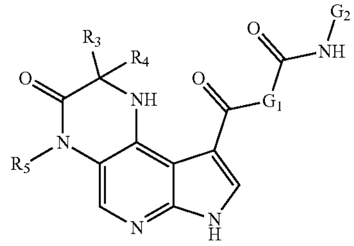

IIf

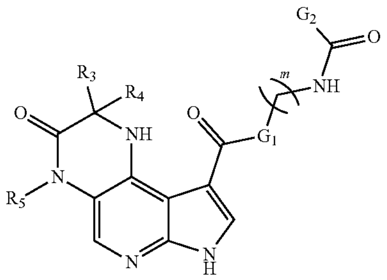

IIg

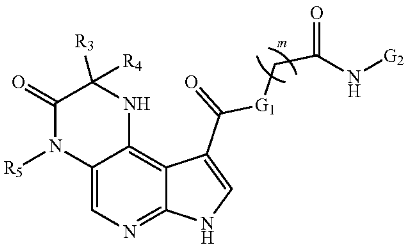

-continued

IIh

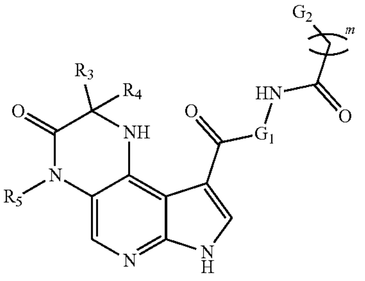

IIi

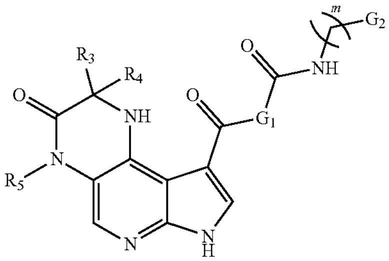

IIj

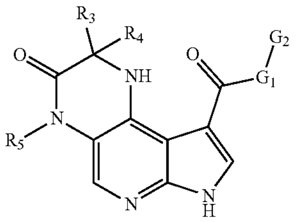

IIk

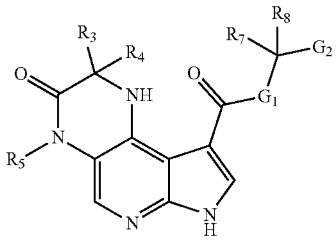

in each formula, $R_3$, $R_4$, $R_5$, $R_7$, $R_8$, $G_1$, $G_2$ are each defined as in formula (I); m is each independently 1 or 2.

In an embodiment, the compound of formula (I) has a structure shown in formula IIb-1, formula IIc-1, formula IId-1, formula IIe-1, formula IIf-1, formula IIg-1, formula IIh-1, formula IIi-1, formula IIj-1, formula IIk-1, formula IIb-2, formula IIc-2, formula IId-2, formula IIe-2, formula IIf-2, formula IIg-2, formula IIh-2, formula IIi-2, formula IIj-2 or formula IIk-2:

IIb-1

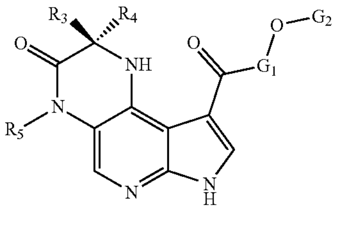

-continued

IIb-2

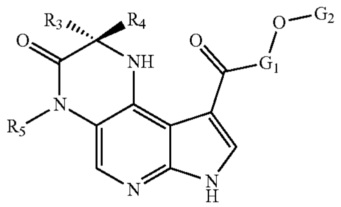

IIc-1

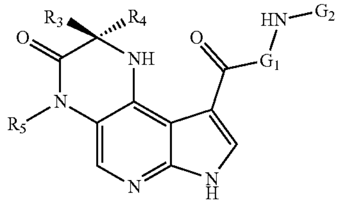

IIc-2

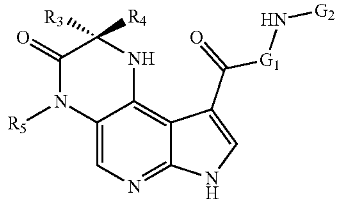

IId-1

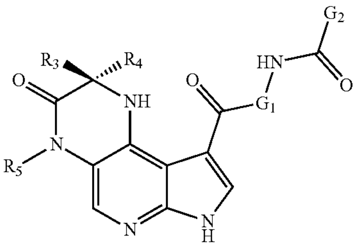

IId-2

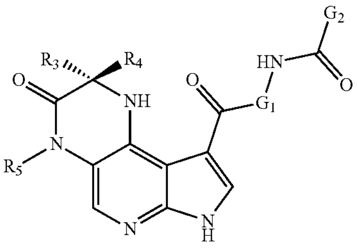

IIe-1

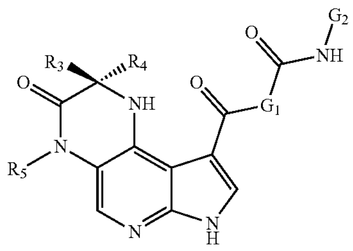

-continued
IIe-2
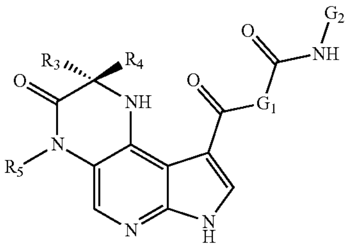
IIf-1
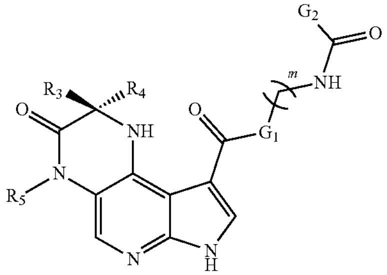
IIf-2
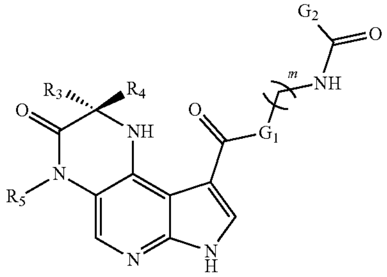
IIj-1
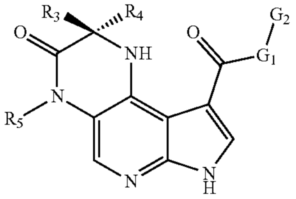
IIj-2
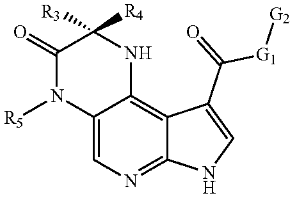
IIg-1
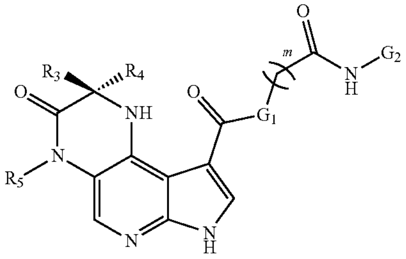
-continued
IIg-2
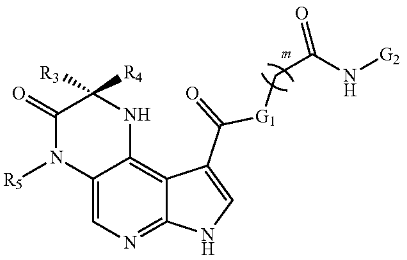
IIk-1
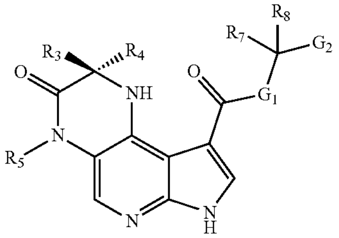
IIk-2
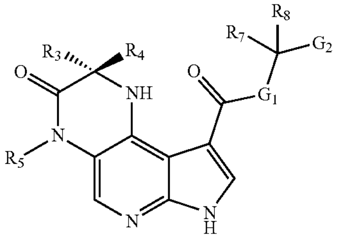
IIh-1
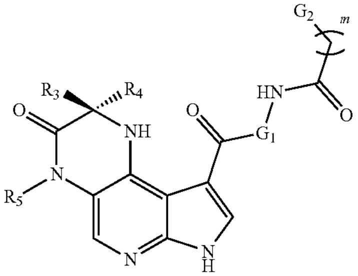
IIh-2
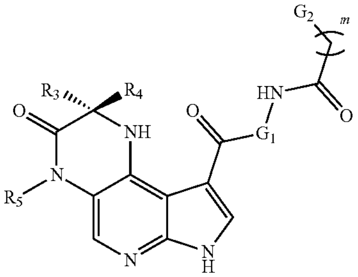
IIi-1
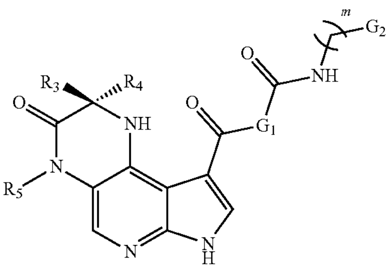

-continued

IIi-2

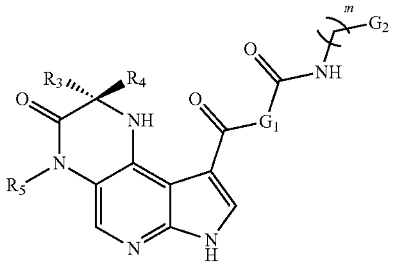

in each formula, $R_3$, $R_4$, $R_5$, $R_7$, $R_8$, $G_1$, $G_2$ are each defined as in formula (I); m is each independently 1 or 2.

In an embodiment, in formula IIk, $R_7$, $R_8$ are each independently selected from: H.

In an embodiment, in formula II, formula IIa, formula IIb, formula IIc, formula IId, formula IIe, formula IIf, formula IIg, formula IIh, formula IIi, formula IIj, formula IIk, formula IIb-1, formula IIc-1, formula IId-1, formula IIe-1, formula IIf-1, formula IIg-1, formula IIh-1, formula IIi-1, formula IIj-1, formula IIk-1, formula IIb-2, formula IIc-2, formula IId-2, formula IIe-2, formula IIf-2, formula IIg-2, formula IIh-2, formula IIi-2, formula IIj-2 or formula IIk-2, $R_3$ and $R_4$ are each independently selected from: methyl, ethyl, n-propyl, n-butyl, n-pentyl; the methyl, the ethyl, the n-propyl, the n-butyl, the n-pentyl are each independently unsubstituted or substituted by 1, 2, 3 or 4 substituents independently selected from group S1.

In an embodiment, in formula II, formula IIa, formula IIb, formula IIc, formula IId, formula IIe, formula IIf, formula IIg, formula IIh, formula IIi, formula IIj, formula IIk, formula IIb-1, formula IIc-1, formula IId-1, formula IIe-1, formula IIf-1, formula IIg-1, formula IIh-1, formula IIi-1, formula IIj-1, formula IIk-1, formula IIb-2, formula IIc-2, formula IId-2, formula IIe-2, formula IIf-2, formula IIg-2, formula IIh-2, formula IIi-2, formula IIj-2 or formula IIk-2, $R_5$ is H, $C_{1-4}$ alkyl, halo $C_{1-4}$ alkyl, deuterated $C_{1-6}$ alkyl, $C_{2-4}$ alkenyl, $C_{2-4}$ alkynyl, —$C_{1-2}$ alkylene-hydroxy, —$C_{1-2}$ alkylene-cyano, —$C_{1-2}$ alkylene-$C_{1-2}$ alkoxy, —$C_{1-2}$ alkylene-halo $C_{1-2}$ alkyl, —$C_{1-2}$ alkylene-deuterated $C_{1-2}$ alkyl, —$C_{1-2}$ alkylene-halo $C_{1-2}$ alkoxy, —$C_{1-2}$ alkylene-deuterated $C_{1-2}$ alkoxy, —$C_{1-2}$ alkylene-$C_{3-6}$ monocyclic cycloalkyl, —$C_{1-2}$ alkylene-3- to 6-membered monocyclic heterocyclyl, —$C_{1-2}$ alkylene-$NR^aR^b$, —$C_{1-2}$ alkylene-C(O)$NR^aR^b$, —$C_{1-2}$ alkylene-C(O)O$C_{1-4}$ alkyl, —$C_{1-2}$ alkylene-$SO_2C_{1-3}$ alkyl, —$C_{1-2}$ alkylene-carboxyl, 3- to 6-membered monocyclic heterocyclyl or $C_{3-6}$ monocyclic cycloalkyl; wherein, the —$C_{1-2}$ alkylene- is unsubstituted, or 1 or 2 hydrogen atoms on —$C_{1-2}$ alkylene- are each independently substituted by a group selected from halogen, cyano, hydroxyl, —$C_{1-2}$ alkyl, -halo $C_{1-2}$ alkyl and -deuterated $C_{1-2}$ alkyl, or two hydrogen atoms on the same carbon on the —$C_{1-2}$ alkylene- are simultaneously substituted by —$(CH_2)_j$— to further form cycloalkyl, wherein j is 2 or 3; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: halogen, hydroxyl, carboxyl, nitro, $C_{1-4}$ alkyl, -halo $C_{1-4}$ alkyl, -deuterated $C_{1-4}$ alkyl, —$C_{1-4}$ alkoxy, -halo $C_{1-4}$ alkoxy and -deuterated $C_{1-4}$ alkoxy.

In an embodiment, in formula II, formula IIa, formula IIb, formula IIc, formula IId, formula IIe, formula IIf, formula IIg, formula IIh, formula IIi, formula IIj, formula IIk, formula IIb-1, formula IIc-1, formula IId-1, formula IIe-1, formula IIf-1, formula IIg-1, formula IIh-1, formula IIi-1, formula IIj-1, formula IIk-1, formula IIb-2, formula IIc-2, formula IId-2, formula IIe-2, formula IIf-2, formula IIg-2, formula IIh-2, formula IIi-2, formula IIj-2 or formula IIk-2, $R_3$ and $R_4$ are each independently selected from: H, $C_{1-6}$ alkyl, $C_{2-6}$ alkenyl, $C_{2-6}$ alkynyl, $C_{3-6}$ monocyclic cycloalkyl and 3- to 6-membered monocyclic heterocyclyl; the 3- to 6-membered monocyclic heterocyclyl has 1, 2 or 3 heteroatoms selected from N, O and S as ring atoms; the $C_{1-6}$ alkyl, the $C_{2-6}$ alkenyl, the $C_{2-6}$ alkynyl, the $C_{3-6}$ monocyclic cycloalkyl and the 3- to 6-membered monocyclic heterocyclyl are each independently unsubstituted or substituted by 1, 2, 3 or 4 substituents independently selected from group S1;

$R_5$ is H, $C_{1-6}$ alkyl, $C_{2-6}$ alkenyl, $C_{2-6}$ alkynyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, 1 or 2 hydrogen atoms on the "—$C_{1-4}$ alkylene-" are optionally substituted by $C_{1-6}$ alkyl, or two hydrogen atoms on the same carbon on the "—$C_{1-4}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-6}$ alkyl; $R^a$ and $R^b$ are each defined as in formula (I).

In an embodiment, in formula II, formula IIa, formula IIb, formula IIc, formula IId, formula IIe, formula IIf, formula IIg, formula IIh, formula IIi, formula IIj, formula IIk, formula IIb-1, formula IIc-1, formula IId-1, formula IIe-1, formula IIf-1, formula IIg-1, formula IIh-1, formula IIi-1, formula IIj-1, formula IIk-1, formula IIb-2, formula IIc-2, formula IId-2, formula IIe-2, formula IIf-2, formula IIg-2, formula IIh-2, formula IIi-2, formula IIj-2 or formula IIk-2, $R_3$ and $R_4$ are each independently selected from: $C_{1-6}$ alkyl, $C_{3-6}$ monocyclic cycloalkyl and 3- to 6-membered monocyclic heterocyclyl; the 3- to 6-membered monocyclic heterocyclyl has 1, 2 or 3 heteroatoms selected from N, O and S as ring atoms; the $C_{1-6}$ alkyl, the $C_{3-6}$ monocyclic cycloalkyl and the 3- to 6-membered monocyclic heterocyclyl are each independently unsubstituted or substituted by 1, 2, 3 or 4 substituents independently selected from group S1;

$R_5$ is H, $C_{1-6}$ alkyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, 1 or 2 hydrogen atoms on the "—$C_{1-4}$ alkylene-" are optionally substituted by $C_{1-6}$ alkyl, or two hydrogen atoms on the same carbon on the "—$C_{1-4}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms;

the 3- to 6-membered monocyclic heterocyclyl is optionally substituted by 1 or 2 substituents selected from the following group: $C_{1-6}$ alkyl; $R^a$ and $R^b$ are each defined as in formula (I).

In an embodiment, in formula II, formula IIa, formula IIb, formula IIc, formula IId, formula IIe, formula IIf, formula IIg, formula IIh, formula IIi, formula IIj, formula IIk, formula IIb-1, formula IIc-1, formula IId-1, formula IIe-1, formula IIf-1, formula IIg-1, formula IIh-1, formula IIi-1, formula IIj-1, formula IIk-1, formula IIb-2, formula IIc-2, formula IId-2, formula IIe-2, formula IIf-2, formula IIg-2, formula IIh-2, formula IIi-2, formula IIj-2 or formula IIk-2, $R_3$ and $R_4$ are each independently selected from: $C_{1-6}$ alkyl; the $C_{1-6}$ alkyl is unsubstituted or substituted by 1, 2, 3 or 4 substituents independently selected from group S1; wherein, substituents in the group S1 are selected from: hydroxyl, —$C_{1-3}$ alkoxy, —O—$C_{3-6}$ monocyclic cycloalkyl and —$NR^aR^b$; wherein, $R^a$ and $R^b$ are each independently H, $C_{1-3}$ alkyl, deuterated $C_{1-3}$ alkyl or cyclopropyl; or $R^a$, $R^b$ combining with the nitrogen atoms to which they are attached form 3- to 6-membered nitrogen-containing heterocyclyl; wherein, the 3- to 6-membered nitrogen-containing heterocyclyl has 1 nitrogen atom and optionally 1 or 2 heteroatoms selected from N, O and S as ring atoms;

$R_5$ is H, $C_{1-6}$ alkyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, 1 or 2 hydrogen atoms on the "—$C_{1-4}$ alkylene-" are optionally substituted by $C_{1-6}$ alkyl, or two hydrogen atoms on the same carbon on the "—$C_{1-4}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-6}$ alkyl; $R^a$ and $R^b$ are each defined as in formula (I).

In an embodiment, in formula II, formula IIa, formula IIb, formula IIc, formula IId, formula IIe, formula IIf, formula IIg, formula IIh, formula IIi, formula IIj, formula IIk, formula IIb-1, formula IIc-1, formula IId-1, formula IIe-1, formula IIf-1, formula IIg-1, formula IIh-1, formula IIi-1, formula IIj-1, formula IIk-1, formula IIb-2, formula IIc-2, formula IId-2, formula IIe-2, formula IIf-2, formula IIg-2, formula IIh-2, formula IIi-2, formula IIj-2 or formula IIk-2, $R_3$ is selected from: $C_{1-6}$ alkyl and $C_{3-6}$ monocyclic cycloalkyl; the $C_{1-6}$ alkyl is unsubstituted or substituted by halogen; $R_4$ is selected from: $C_{1-6}$ alkyl; the $C_{1-6}$ alkyl is unsubstituted or substituted by 1, 2, 3 or 4 substituents independently selected from group S1; substituents in the group S1 are selected from: hydroxyl, $C_{1-6}$ alkoxy, halo $C_{1-6}$ alkoxy, deuterated $C_{1-6}$ alkoxy, —O—$C_{3-6}$ monocyclic cycloalkyl and —$NR^aR^b$; wherein, $R^a$ and $R^b$ are each independently H, $C_{1-6}$ alkyl, deuterated $C_{1-6}$ alkyl, $C_{3-6}$ monocyclic cycloalkyl, —$C_{1-4}$ alkylene-$C_{1-6}$ alkoxy, 3- to 6-membered monocyclic heterocyclyl, —$C_{1-4}$ alkylene-3- to 6-membered monocyclic heterocyclyl and C(O)$C_{1-6}$ alkyl; wherein, the 3- to 6-membered monocyclic heterocyclyl has 1, 2 or 3 heteroatoms selected from N, O and S as ring atoms; and the 3- to 6-membered monocyclic heterocyclyl is optionally substituted by 1 or 2 substituents selected from the following group: $C_{1-6}$ alkyl; or $R^a$, $R^b$ combining with the nitrogen atoms to which they are attached form 3- to 6-membered nitrogen-containing heterocyclyl; wherein, the 3- to 6-membered nitrogen-containing heterocyclyl has 1 nitrogen atom and optionally 1 or 2 heteroatoms selected from N, O and S as ring atoms; and the 3- to 6-membered nitrogen-containing heterocyclyl is optionally substituted by 1 or 2 substituents selected from the following group: $C_{1-6}$ alkyl;

$R_5$ is H, $C_{1-6}$ alkyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, 1 or 2 hydrogen atoms on the "—$C_{1-4}$ alkylene-" are optionally substituted by $C_{1-6}$ alkyl, or two hydrogen atoms on the same carbon on the "—$C_{1-4}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-6}$ alkyl; $R^a$ and $R^b$ are each defined as in formula (I).

In an embodiment, in formula II, formula IIa, formula IIb, formula IIc, formula IId, formula IIe, formula IIf, formula IIg, formula IIh, formula IIi, formula IIj, formula IIk, formula IIb-1, formula IIc-1, formula IId-1, formula IIe-1, formula IIf-1, formula IIg-1, formula IIh-1, formula IIi-1, formula IIj-1, formula IIk-1, formula IIb-2, formula IIc-2, formula IId-2, formula IIe-2, formula IIf-2, formula IIg-2, formula IIh-2, formula IIi-2, formula IIj-2 or formula IIk-2, $R_3$ is methyl, trifluoromethyl, ethyl, n-propyl or cyclopropyl; $R_4$ is methyl or ethyl; the methyl and the ethyl are unsubstituted or substituted by 1 substituent selected from group S1; the substituent in the group S1 is selected from: hydroxyl, methoxy, deuterated methoxy, trifluoromethoxy, deuterated methoxy, ethoxy, n-propoxy, isopropoxy, n-butoxy, —O— cyclopropyl, —O-cyclobutyl, —$N(CH_3)_2$, —$N(CH_2CH_3)_2$, —$N(CH_2CH_3)(CH_3)$, —$N(CH_2CH_2CH_3)(CH_3)$ and —$N(CH_2CH_2CH_3)(CH_2CH_3)$;

$R_5$ is H, $C_{1-6}$ alkyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, 1 or 2 hydrogen atoms on the "—$C_{1-4}$ alkylene-" are optionally substituted by $C_{1-6}$ alkyl, or two hydrogen atoms on the same carbon on the "—$C_{1-4}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-6}$ alkyl; $R^a$ and $R^b$ are each defined as in formula (I).

In an embodiment, in formula II, formula IIa, formula IIb, formula IIc, formula IId, formula IIe, formula IIf, formula IIg, formula IIh, formula IIi, formula IIj, formula IIk, formula IIb-1, formula IIc-1, formula IId-1, formula IIe-1, formula IIf-1, formula IIg-1, formula IIh-1, formula IIi-1, formula IIj-1, formula IIk-1, formula IIb-2, formula IIc-2, formula IId-2, formula IIe-2, formula IIf-2, formula IIg-2, formula IIh-2, formula IIi-2, formula IIj-2 or formula IIk-2, $R_3$ and $R_4$ combining with the carbon atoms to which they are attached form: $C_{3-6}$ monocyclic cycloalkyl, 3- to 6-membered monocyclic heterocyclyl or carbonyl (C═O); the 3- to 6-membered monocyclic heterocyclyl has 1, 2 or 3 heteroatoms selected from N, O and S as ring atoms; the $C_{3-6}$ monocyclic cycloalkyl and the 3- to 6-membered monocyclic heterocyclyl are each independently unsubstituted or substituted by 1, 2, 3 or 4 substituents independently selected from group S1;

$R_5$ is H, $C_{1-6}$ alkyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, 1 or 2 hydrogen atoms on the "—$C_{1-4}$ alkylene-" are optionally substituted by $C_{1-6}$ alkyl, or two hydrogen atoms on the same carbon on the "—$C_{1-4}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-6}$ alkyl; $R^a$ and $R^b$ are each defined as in formula (I).

In an embodiment, in formula II, formula IIa, formula IIb, formula IIc, formula IId, formula IIe, formula IIf, formula IIg, formula IIh, formula IIi, formula IIj, formula IIk, formula IIb-1, formula IIc-1, formula IId-1, formula IIe-1, formula IIf-1, formula IIg-1, formula IIh-1, formula IIi-1, formula IIj-1, formula IIk-1, formula IIb-2, formula IIc-2, formula IId-2, formula IIe-2, formula IIf-2, formula IIg-2, formula IIh-2, formula IIi-2, formula IIj-2 or formula IIk-2, $R_3$ and $R_4$ combining with the carbon atoms to which they are attached form: cyclopropyl, cyclobutyl, cyclopentyl, cyclohexyl, oxetanyl, azetidinyl, tetrahydropyrrole, tetrahydrofuran, tetrahydropyran, piperidine or carbonyl (C═O); the cyclopropyl, the cyclobutyl, the cyclopentyl, the cyclohexyl, the oxetanyl, the azetidinyl, the tetrahydropyrrole, the tetrahydrofuran, the tetrahydropyran and the piperidine are each independently unsubstituted or substituted by 1, 2, 3 or 4 substituents independently selected from group S1;

$R_5$ is H, $C_{1-6}$ alkyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, 1 or 2 hydrogen atoms on the "—$C_{1-4}$ alkylene-" are optionally substituted by $C_{1-6}$ alkyl, or two hydrogen atoms on the same carbon on the "—$C_{1-4}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-6}$ alkyl; $R^a$ and $R^b$ are each defined as in formula (I).

In an embodiment, in formula II, formula IIa, formula IIb, formula IIc, formula IId, formula IIe, formula IIf, formula IIg, formula IIh, formula IIi, formula IIj, formula IIk, formula IIb-1, formula IIc-1, formula IId-1, formula IIe-1, formula IIf-1, formula IIg-1, formula IIh-1, formula IIi-1, formula IIj-1, formula IIk-1, formula IIb-2, formula IIc-2, formula IId-2, formula IIe-2, formula IIf-2, formula IIg-2, formula IIh-2, formula IIi-2, formula IIj-2 or formula IIk-2, $R_3$ and $R_4$ combining with the carbon atoms to which they are attached form: cyclopropyl, cyclobutyl, cyclopentyl, cyclohexyl, oxetanyl, azetidinyl, tetrahydropyrrole, tetrahydrofuran, tetrahydropyran, piperidine or carbonyl (C═O); the cyclopropyl, the cyclobutyl, the cyclopentyl, the cyclohexyl, the oxetanyl, the azetidinyl, the tetrahydropyrrole, the tetrahydrofuran, the tetrahydropyran and the piperidine are each independently unsubstituted or substituted by 1, 2, 3 or 4 substituents independently selected from group S1; wherein, substituents in the group S1 are selected from: cyano, hydroxyl, methyl, ethyl, propyl, halomethyl, methoxy, ethoxy, —C(O)$CH_3$, —C(O)cyclopropyl, —C(O)$NH_2$, —C(O)N$(CH_3)_2$, —$CH_2OH$, —$CH_2CH_2OH$, —$CH_2OCH_3$, —$CH_2CH_2OCH_3$—$CH_2N(CH_3)_2$, —$CH_2CH_2N(CH_3)_2$, —NHC(O)$CH_3$ and —N$(CH_3)_2$;

$R_5$ is H, $C_{1-6}$ alkyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, 1 or 2 hydrogen atoms on the "—$C_{1-4}$ alkylene-" are optionally substituted by $C_{1-6}$ alkyl, or two hydrogen atoms on the same carbon on the "—$C_{1-4}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-6}$ alkyl; $R^a$ and $R^b$ are each defined as in formula (I).

In an embodiment, in formula II, formula IIa, formula IIb, formula IIc, formula IId, formula IIe, formula IIf, formula IIg, formula IIh, formula IIi, formula IIj, formula IIk, formula IIb-1, formula IIc-1, formula IId-1, formula IIe-1, formula IIf-1, formula IIg-1, formula IIh-1, formula IIi-1, formula IIj-1, formula IIk-1, formula IIb-2, formula IIc-2, formula IId-2, formula IIe-2, formula IIf-2, formula IIg-2, formula IIh-2, formula IIi-2, formula IIj-2 or formula IIk-2, $R_3$ and $R_4$ are each independently methyl; the methyl is each independently unsubstituted or substituted by deuterium, halogen, hydroxyl, methoxy, deuterated methoxy, halomethoxy, ethoxy, deuterated ethoxy or haloethoxy; $R_5$ is H, $C_{1-6}$ alkyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, 1 or 2 hydrogen atoms on the "—$C_{1-4}$ alkylene-" are optionally substituted by $C_{1-6}$ alkyl, or two hydrogen atoms on the same carbon on the "—$C_{1-4}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-6}$ alkyl; $R^a$ and $R^b$ are each defined as in formula (I).

In an embodiment, the compound of formula (I) has a structure shown in formula IIb', formula IIc', formula IId', formula IIe', formula IIf', formula IIg', formula IIh', formula IIi', formula IIj' or formula IIk':

IIb'

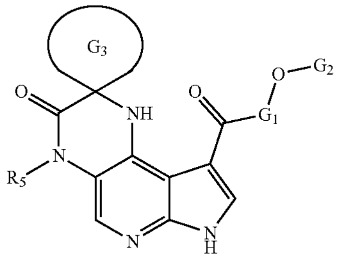

IIc'

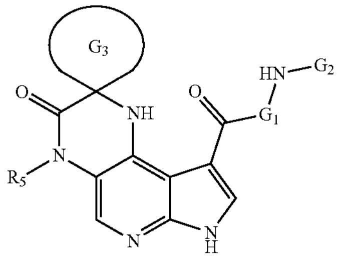

IId'

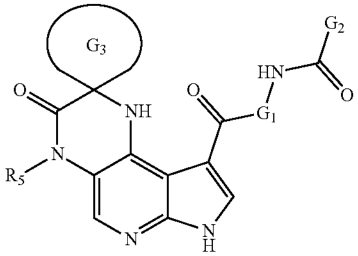

IIe'

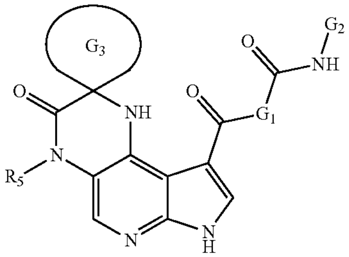

IIf'

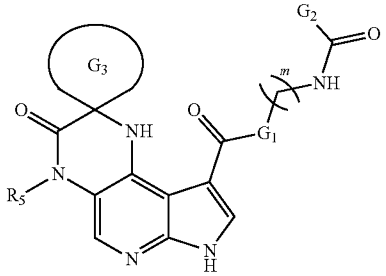

-continued

IIg'

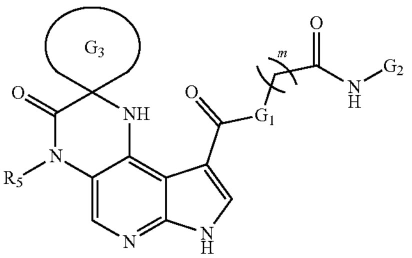

IIh'

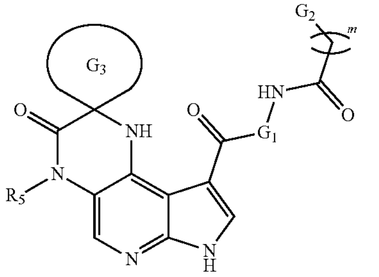

IIi'

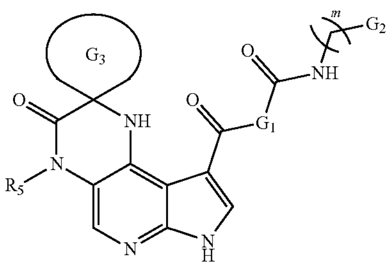

IIj'

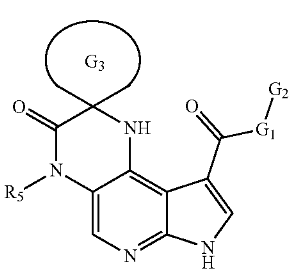

IIk'

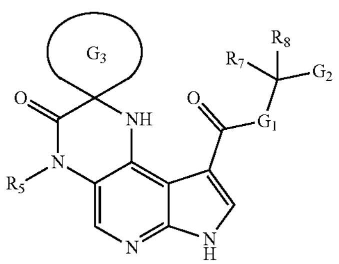

in each formula, $R_5$, $R_7$, $R_8$, $G_1$, $G_2$ are each defined as in formula (I); m is each independently 1 or 2; 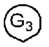 is $C_{3-20}$ cycloalkyl or 3- to 20-membered heterocyclyl; the 3- to 20-membered heterocyclyl has 1, 2 or 3 heteroatoms selected from N, O and S as ring atoms; the $C_{3-20}$ cycloalkyl and the 3- to 20-membered heterocyclyl are each independently unsubstituted or substituted by 1, 2, 3 or 4 substituents independently selected from group S1.

In an embodiment, in formula IIk', $R_7$ and $R_8$ are each independently selected from: H.

In an embodiment, in formula IIb', formula IIc', formula IId', formula IIe', formula IIf', formula IIg', formula IIh', formula IIi', formula IIj' or formula IIk', 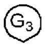 is $C_{3-6}$ monocyclic cycloalkyl or 3- to 6-membered monocyclic heterocyclyl; the 3- to 6-membered monocyclic heterocyclyl has 1, 2 or 3 heteroatoms selected from N, O and S as ring atoms; the $C_{3-6}$ monocyclic cycloalkyl and the 3- to 6-membered monocyclic heterocyclyl are each independently unsubstituted or substituted by 1, 2, 3 or 4 substituents independently selected from group S1; $R_5$ is H, $C_{1-6}$ alkyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, 1 or 2 hydrogen atoms on the "—$C_{1-4}$ alkylene-" are optionally substituted by $C_{1-6}$ alkyl, or two hydrogen atoms on the same carbon on the "—$C_{1-4}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-6}$ alkyl; $R^a$ and $R^b$ are each defined as in formula (I).

In an embodiment, in formula IIb', formula IIc', formula IId', formula IIe', formula IIf', formula IIg', formula IIh', formula IIi', formula IIj' or formula IIk', 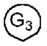 is cyclopropyl, cyclobutyl, cyclopentyl, cyclohexyl, oxetanyl, azetidinyl, tetrahydropyrrole, tetrahydrofuran, tetrahydropyran or piperidine; the cyclopropyl, the cyclobutyl, the cyclopentyl, the cyclohexyl, the oxetanyl, the azetidinyl, the tetrahydropyrrole, the tetrahydrofuran, the tetrahydropyran and the piperidine are each independently unsubstituted or substituted by 1, 2, 3 or 4 substituents independently selected from group S1; $R_5$ is H, $C_{1-6}$ alkyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, 1 or 2 hydrogen atoms on the "—$C_{1-4}$ alkylene-" are optionally substituted by $C_{1-6}$ alkyl, or two hydrogen atoms on the same carbon on the "—$C_{1-4}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-6}$ alkyl; $R^a$ and $R^b$ are each defined as in formula (I).

In an embodiment, in formula IIb', formula IIc', formula IId', formula IIe', formula IIf', formula IIg', formula IIh', formula IIi', formula IIj' or formula IIk', 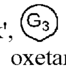 is cyclopropyl, cyclobutyl, cyclopentyl, cyclohexyl, oxetanyl, azetidinyl, tetrahydropyrrole, tetrahydrofuran, tetrahydropyran or piperidine; the cyclopropyl, the cyclobutyl, the cyclopentyl, the cyclohexyl, the oxetanyl, the azetidinyl, the tetrahydropyrrole, the tetrahydrofuran, the tetrahydropyran and the piperidine are each independently unsubstituted or substituted by 1, 2, 3 or 4 substituents independently selected from group S1; wherein, substituents in the group S1 are selected from: cyano, hydroxyl, methyl, ethyl, propyl, halomethyl, methoxy, ethoxy, —C(O)$CH_3$, —C(O)cyclopropyl, —C(O)$NH_2$, —C(O)$N(CH_3)_2$, —$CH_2OH$, —$CH_2CH_2OH$, —$CH_2OCH_3$, —$CH_2CH_2OCH_3$—$CH_2N(CH_3)_2$, —$CH_2CH_2N(CH_3)_2$, —NHC(O)$CH_3$ and —$N(CH_3)_2$; $R_5$ is H, $C_{1-6}$ alkyl, —$C_{1-4}$ alkylene-hydroxy, —$C_{1-4}$ alkylene-cyano, —$C_{1-4}$ alkylene-$C_{1-6}$ alkoxy, —$C_{1-4}$ alkylene-halo $C_{1-6}$ alkyl, —$C_{1-4}$ alkylene-halo $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl, —$C_{1-4}$ alkylene-$NR^aR^b$, —$C_{1-4}$ alkylene-C(O)$NR^aR^b$, —$C_{1-4}$ alkylene-C(O)O$C_{1-6}$ alkyl, —$C_{1-4}$ alkylene-$SO_2C_{1-3}$ alkyl, —$C_{1-4}$ alkylene-carboxyl or $C_{3-6}$ monocyclic cycloalkyl; wherein, 1 or 2 hydrogen atoms on the "—$C_{1-4}$ alkylene-" are optionally substituted by $C_{1-6}$ alkyl, or two hydrogen atoms on the same carbon on the "—$C_{1-4}$ alkylene-" are simultaneously substituted by —$CH_2CH_2$— to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-6}$ alkyl; $R^a$ and $R^b$ are each defined as in formula (I).

In an embodiment, the compound of formula (I) has a structure shown in formula III:

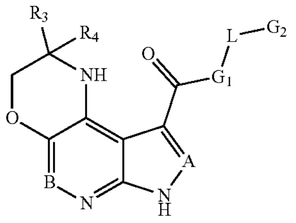

III in the formula, A, B, $R_3$, $R_4$, L, $G_1$, $G_2$ are each defined as in formula (I).

In an embodiment, the compound of formula (I) has a structure shown in formula IIIa:

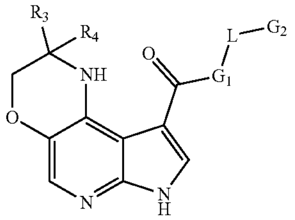

IIIa in the formula, $R_3$, $R_4$, L, $G_1$, $G_2$ are each defined as in formula (I).

In an embodiment, the compound of formula (I) has a structure shown in formula IIIb, formula IIIc, formula IIId, formula IIIe, formula IIIf, formula IIIg, formula IIIh, formula IIIi, formula IIIj or formula IIIk:

-continued

IIIb

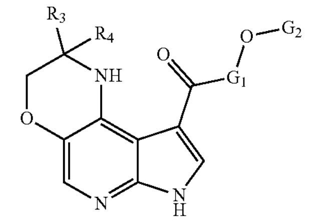

IIIc

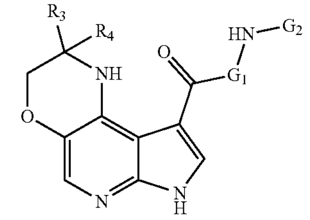

IIId

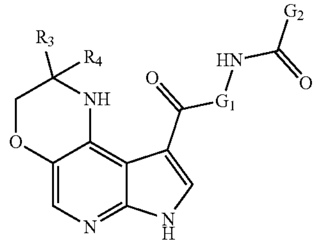

IIIe

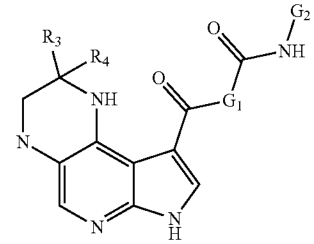

IIIf

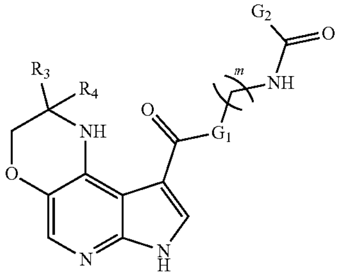

IIIg

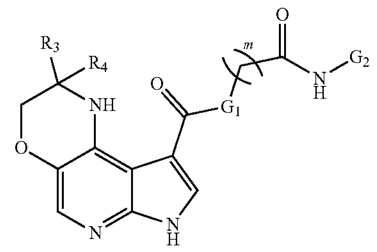

IIIh

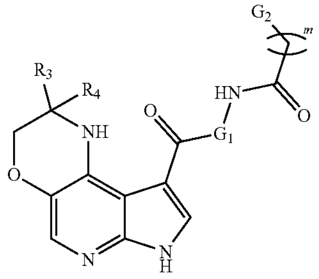

IIIi

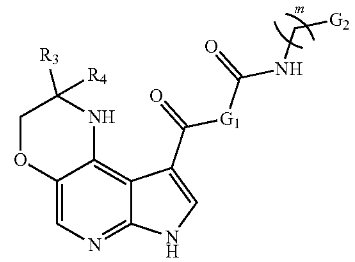

IIIj

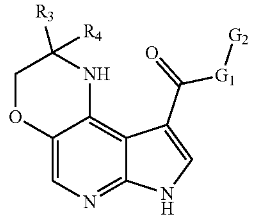

IIIk

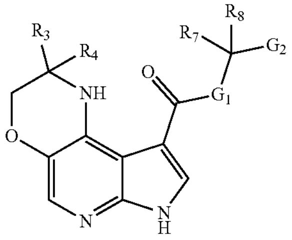

in each formula, $R_3$, $R_4$, $R_7$, $R_8$, $G_1$, $G_2$ are each defined as in formula (I); m is each independently 1 or 2.

In an embodiment, the compound of formula (I) has a structure shown in formula IIIb-1, formula IIIc-1, formula IIId-1, formula IIIe-1, formula IIIf-1, formula IIIg-1, formula IIIh-1, formula IIIi-1, formula IIIj-1, formula IIIk-1, formula IIIb-2, formula IIIc-2, formula IIId-2, formula IIIe-2, formula IIIf-2, formula IIIg-2, formula IIIh-2, formula IIIi-2, formula IIIj-2 or formula IIIk-2:

IIIb-1

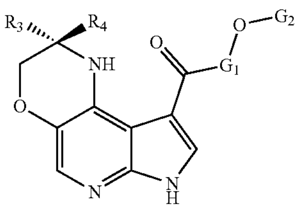

-continued
IIIb-2
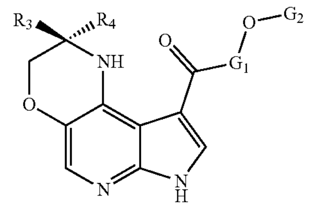
IIIc-1
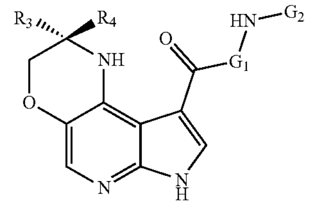
IIIc-2
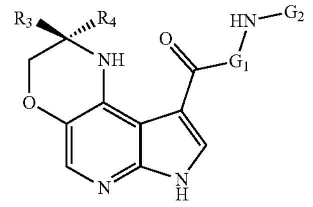
IIId-1
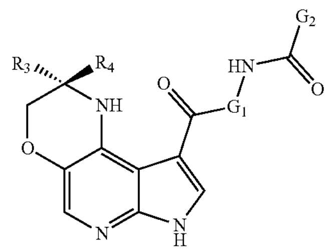
IIId-2
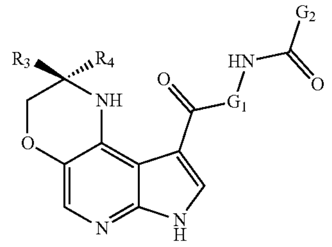
IIIe-1
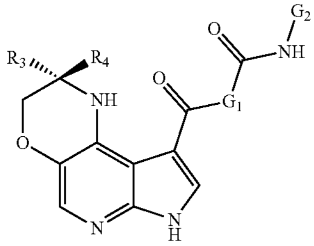
-continued
IIIe-2
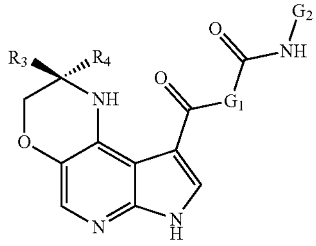
IIIf-1
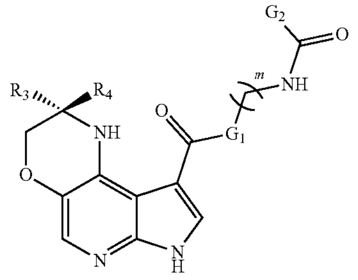
IIIf-2
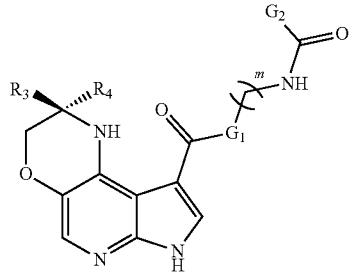
IIIg-1
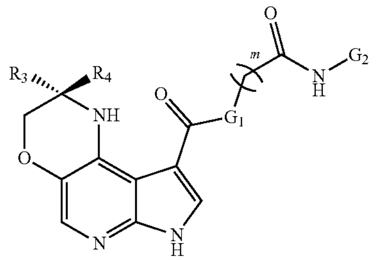
IIIg-2
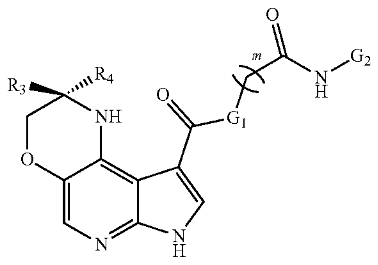
IIIh-1
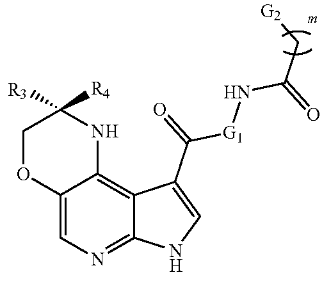

-continued

IIIh-2

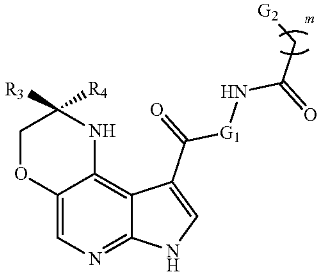

IIIi-1

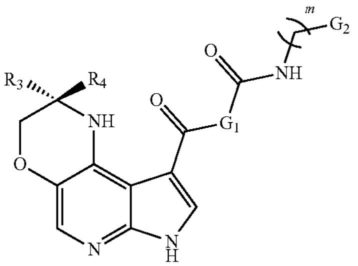

IIIi-2

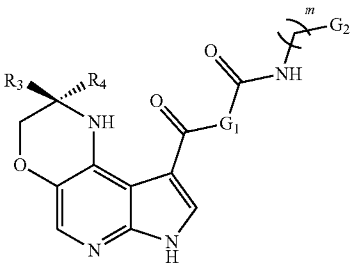

IIIj-1

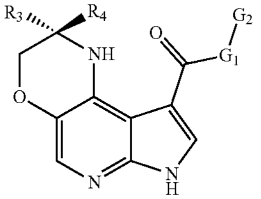

IIIj-2

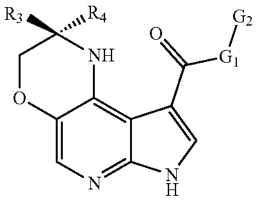

IIIk-1

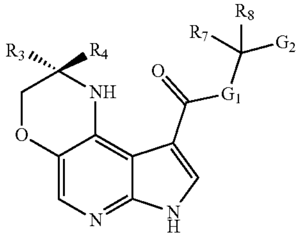

-continued

IIIk-2

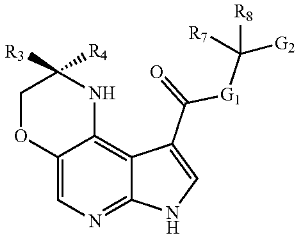

in each formula, $R_3$, $R_4$, $R_7$, $R_8$, $G_1$, $G_2$ are each defined as in formula (I); m is each independently 1 or 2.

In an embodiment, in formula III, formula IIIa, formula IIIb, formula IIIc, formula IIId, formula IIIe, formula IIIf, formula IIIg, formula IIIh, formula IIIi, formula IIIj, formula IIIk, formula IIIb-1, formula IIIc-1, formula IIId-1, formula IIIe-1, formula IIIf-1, formula IIIg-1, formula IIIh-1, formula IIIi-1, formula IIIj-1, formula IIIk-1, formula IIIb-2, formula IIIc-2, formula IIId-2, formula IIIe-2, formula IIIf-2, formula IIIg-2, formula IIIh-2, formula IIIi-2, formula IIIj-2 or formula IIIk-2, $R_3$ and $R_4$ are each independently selected from: H, $C_{1-6}$ alkyl, $C_{3-6}$ monocyclic cycloalkyl and 3- to 6-membered monocyclic heterocyclyl; the 3- to 6-membered monocyclic heterocyclyl has 1, 2 or 3 heteroatoms selected from N, O and S as ring atoms; the $C_{1-6}$ alkyl, the $C_{3-6}$ monocyclic cycloalkyl and the 3- to 6-membered monocyclic heterocyclyl are each independently unsubstituted or substituted by 1, 2, 3 or 4 substituents independently selected from group S1.

In an embodiment, in formula III, formula IIIa, formula IIIb, formula IIIc, formula IIId, formula IIIe, formula IIIf, formula IIIg, formula IIIh, formula IIIi, formula IIIj, formula IIIk, formula IIIb-1, formula IIIc-1, formula IIId-1, formula IIIe-1, formula IIIf-1, formula IIIg-1, formula IIIh-1, formula IIIi-1, formula IIIj-1, formula IIIk-1, formula IIIb-2, formula IIIc-2, formula IIId-2, formula IIIe-2, formula IIIf-2, formula IIIg-2, formula IIIh-2, formula IIIi-2, formula IIIj-2 or formula IIIk-2, $R_3$ and $R_4$ are each independently selected from: $C_{1-6}$ alkyl, $C_{3-6}$ monocyclic cycloalkyl and 3- to 6-membered monocyclic heterocyclyl; the 3- to 6-membered monocyclic heterocyclyl has 1, 2 or 3 heteroatoms selected from N, O and S as ring atoms; the $C_{1-6}$ alkyl, the $C_{3-6}$ monocyclic cycloalkyl and the 3- to 6-membered monocyclic heterocyclyl are each independently unsubstituted or substituted by 1, 2, 3 or 4 substituents independently selected from group S1.

In an embodiment, in formula III, formula IIIa, formula IIIb, formula IIIc, formula IIId, formula IIIe, formula IIIf, formula IIIg, formula IIIh, formula IIIi, formula IIIj, formula IIIk, formula IIIb-1, formula IIIc-1, formula IIId-1, formula IIIe-1, formula IIIf-1, formula IIIg-1, formula IIIh-1, formula IIIi-1, formula IIIj-1, formula IIIk-1, formula IIIb-2, formula IIIc-2, formula IIId-2, formula IIIe-2, formula IIIf-2, formula IIIg-2, formula IIIh-2, formula IIIi-2, formula IIIj-2 or formula IIIk-2, $R_3$ and $R_4$ are each independently selected from: $C_{1-6}$ alkyl; the $C_{1-6}$ alkyl is unsubstituted or substituted by 1, 2, 3 or 4 substituents independently selected from group S1; wherein, substituents in the group S1 are selected from: hydroxyl, —$C_{1-3}$ alkoxy, —O—$C_{3-6}$ monocyclic cycloalkyl and —$NR^aR^b$; wherein, $R^a$ and $R^b$ are each independently H, $C_{1-3}$ alkyl, deuterated $C_{1-3}$ alkyl or cyclopropyl; or $R^a$, $R^b$ combining with the nitrogen atoms to which they are attached form 3- to 6-membered nitrogen-containing heterocyclyl; wherein, the 3- to 6-membered nitrogen-containing heterocyclyl has 1 nitrogen atom and optionally 1 or 2 heteroatoms selected from N, O and S as ring atoms.

In an embodiment, in formula III, formula IIIa, formula IIIb, formula IIIc, formula IIId, formula IIIe, formula IIIf, formula IIIg, formula IIIh, formula IIIi, formula IIIj, formula IIIk, formula IIIb-1, formula IIIc-1, formula IIId-1, formula IIIe-1, formula IIIf-1, formula IIIg-1, formula IIIh-1, formula IIIi-1, formula IIIj-1, formula IIIk-1, formula IIIb-2, formula IIIc-2, formula IIId-2, formula IIIe-2, formula IIIf-2, formula IIIg-2, formula IIIh-2, formula IIIi-2, formula IIIj-2 or formula IIIk-2, $R_3$ and $R_4$ combining with the carbon atoms to which they are attached form: $C_{3-6}$ monocyclic cycloalkyl, 3- to 6-membered monocyclic heterocyclyl or carbonyl (C═O); the 3- to 6-membered monocyclic heterocyclyl has 1, 2 or 3 heteroatoms selected from N, O and S as ring atoms; the $C_{3-6}$ monocyclic cycloalkyl and the 3- to 6-membered monocyclic heterocyclyl are each independently unsubstituted or substituted by 1, 2, 3 or 4 substituents independently selected from group S1.

In an embodiment, in formula III, formula IIIa, formula IIIb, formula IIIc, formula IIId, formula IIIe, formula IIIf, formula IIIg, formula IIIh, formula IIIi, formula IIIj, formula IIIk, formula IIIb-1, formula IIIc-1, formula IIId-1, formula IIIe-1, formula IIIf-1, formula IIIg-1, formula IIIh-1, formula IIIi-1, formula IIIj-1, formula IIIk-1, formula IIIb-2, formula IIIc-2, formula IIId-2, formula IIIe-2, formula IIIf-2, formula IIIg-2, formula IIIh-2, formula IIIi-2, formula IIIj-2 or formula IIIk-2, $R_3$ and $R_4$ combining with the carbon atoms to which they are attached form: cyclopropyl, cyclobutyl, cyclopentyl, cyclohexyl, oxetanyl, azetidinyl, tetrahydropyrrole, tetrahydrofuran, tetrahydropyran, piperidine or carbonyl (C═O); the cyclopropyl, the cyclobutyl, the cyclopentyl, the cyclohexyl, the oxetanyl, the azetidinyl, the tetrahydropyrrole, the tetrahydrofuran, the tetrahydropyran and the piperidine are each independently unsubstituted or substituted by 1, 2, 3 or 4 substituents independently selected from group S1.

In an embodiment, in formula III, formula IIIa, formula IIIb, formula IIIc, formula IIId, formula IIIe, formula IIIf, formula IIIg, formula IIIh, formula IIIi, formula IIIj, formula IIIk, formula IIIb-1, formula IIIc-1, formula IIId-1, formula IIIe-1, formula IIIf-1, formula IIIg-1, formula IIIh-1, formula IIIi-1, formula IIIj-1, formula IIIk-1, formula IIIb-2, formula IIIc-2, formula IIId-2, formula IIIe-2, formula IIIf-2, formula IIIg-2, formula IIIh-2, formula IIIi-2, formula IIIj-2 or formula IIIk-2, $R_3$ and $R_4$ combining with the carbon atoms to which they are attached form: cyclopropyl, cyclobutyl, cyclopentyl, cyclohexyl, oxetanyl, azetidinyl, tetrahydropyrrole, tetrahydrofuran, tetrahydropyran, piperidine or carbonyl (C═O); the cyclopropyl, the cyclobutyl, the cyclopentyl, the cyclohexyl, the oxetanyl, the azetidinyl, the tetrahydropyrrole, the tetrahydrofuran, the tetrahydropyran and the piperidine are each independently unsubstituted or substituted by 1, 2, 3 or 4 substituents independently selected from group S1; wherein, substituents in the group S1 are selected from: cyano, hydroxyl, methyl, ethyl, propyl, halomethyl, methoxy, ethoxy, —C(O)$CH_3$, —C(O)cyclopropyl, —C(O)$NH_2$, —C(O)$N(CH_3)_2$, —$CH_2OH$, —$CH_2CH_2OH$, —$CH_2OCH_3$, —$CH_2CH_2OCH_3$—$CH_2N(CH_3)_2$, —$CH_2CH_2N(CH_3)_2$, —NHC(O)$CH_3$ and —$N(CH_3)_2$.

In an embodiment, in formula III, formula IIIa, formula IIIb, formula IIIc, formula IIId, formula IIIe, formula IIIf, formula IIIg, formula IIIh, formula IIIi, formula IIIj, formula IIIk, formula IIIb-1, formula IIIc-1, formula IIId-1, formula IIIe-1, formula IIIf-1, formula IIIg-1, formula IIIh-1, formula IIIi-1, formula IIIj-1, formula IIIk-1, formula IIIb-2, formula IIIc-2, formula IIId-2, formula IIIe-2, formula IIIf-2, formula IIIg-2, formula IIIh-2, formula IIIi-2, formula IIIj-2 or formula IIIk-2, $R_3$ and $R_4$ are each independently methyl; the methyl is each independently unsubstituted or substituted by deuterium, halogen, hydroxyl, methoxy, deuterated methoxy, halomethoxy, ethoxy, deuterated ethoxy or haloethoxy.

In an embodiment, $G_1$ and $G_2$ are unsubstituted.

In an embodiment, $G_1$ is unsubstituted, and $G_2$ is substituted; the substituents are defined as above.

In an embodiment, $G_1$ is substituted; the substituents are defined as above; $G_2$ is unsubstituted.

In an embodiment, $G_1$ and $G_2$ are substituted; the substituents are defined as above.

In a preferred embodiment, $R^a$ and $R^b$ are each independently $C_{1-6}$ alkyl, for example, $C_{1-4}$ alkyl, for another example, methyl.

In a preferred embodiment, $R^c$ is —$C_{1-4}$ alkylene-$C_{1-6}$ alkoxy (for example, —$C_{1-2}$ alkylene-$C_{1-3}$ alkoxy, for another example, —$CH_2CH_2OCH_3$ or —$CH_2CH_2OCH_2CH_3$) or 3- to 6-membered monocyclic heterocyclyl substituted by 1 or 2 halogens (for example, halogen in the 3- to 6-membered monocyclic heterocyclyl substituted by 1 or 2 halogens is fluorine, chlorine or bromine; for example, 3- to 6-membered monocyclic heterocyclyl in the 3- to 6-membered monocyclic heterocyclyl substituted by 1 or 2 halogens is cyclopropyl).

In an embodiment, substituents in the group S1 are selected from: deuterium, halogen, cyano, hydroxyl, $C_{1-6}$ alkyl, halo $C_{1-6}$ alkyl, deuterated $C_{1-6}$ alkyl, $C_{1-6}$ alkoxy, halo $C_{1-6}$ alkoxy, deuterated $C_{1-6}$ alkoxy, —$C_{3-6}$ monocyclic cycloalkyl, -halo $C_{3-6}$ monocyclic cycloalkyl, —O—$C_{3-6}$ monocyclic cycloalkyl, —$C_{1-4}$ alkylene-hydroxy, —$C_{1-4}$ alkylene-cyano, —$C_{1-4}$ alkylene-$C_{1-6}$ alkoxy, —C(O)$C_{1-6}$ alkyl, —C(O)$C_{3-6}$ monocyclic cycloalkyl, —C(O)$NR^aR^b$, —NHC(O)$R^c$ and —$NR^aR^b$; wherein, $R^a$ and $R^b$ are each independently H, $C_{1-6}$ alkyl, deuterated $C_{1-6}$ alkyl, $C_{3-6}$ monocyclic cycloalkyl, —$C_{1-4}$ alkylene-$C_{1-6}$ alkoxy, 3- to 6-membered monocyclic heterocyclyl, —$C_{1-4}$ alkylene-3- to 6-membered monocyclic heterocyclyl or C(O)$C_{1-6}$ alkyl; wherein, the 3- to 6-membered monocyclic heterocyclyl has 1, 2 or 3 heteroatoms selected from N, O and S as ring atoms; and the 3- to 6-membered monocyclic heterocyclyl is optionally substituted by 1 or 2 substituents selected from the following group: $C_{1-6}$ alkyl; or $R^a$, $R^b$ combining with the nitrogen atoms to which they are attached form 3- to 6-membered nitrogen-containing heterocyclyl; wherein, the 3- to 6-membered nitrogen-containing heterocyclyl has 1 nitrogen atom and optionally 1 or 2 heteroatoms selected from N, O and S as ring atoms; and the 3- to 6-membered nitrogen-containing heterocyclyl is optionally substituted by 1 or 2 substituents selected from the following group: $C_{1-6}$ alkyl; $R^c$ is hydrogen, $C_{1-6}$ alkyl or halo $C_{1-6}$ alkyl.

In an embodiment, substituents in the group S1 are selected from: deuterium, halogen, cyano, hydroxyl, —$C_{1-3}$ alkyl, -halo $C_{1-3}$ alkyl, -deuterated $C_{1-3}$ alkyl, —$C_{1-3}$ alkoxy, -halo $C_{1-3}$ alkoxy, -deuterated $C_{1-3}$ alkoxy, -cyclopropyl, -halocyclopropyl, —O-cyclopropyl, —$C_{1-2}$ alkylene-hydroxy, —$C_{1-2}$ alkylene-cyano, —$C_{1-2}$ alkylene-$C_{1-3}$ alkoxy, —C(O)$C_{1-3}$ alkyl, —C(O)cyclopropyl, —C(O)$NR^aR^b$, —NHC(O)$R^c$ and —$NR^aR^b$; wherein, $R^a$ and $R^b$ are each independently H, $C_{1-3}$ alkyl, deuterated $C_{1-3}$ alkyl or cyclopropyl; or $R^a$, $R^b$ combining with the nitrogen atoms to which they are attached form 3- to 6-membered nitrogen-containing heterocyclyl; wherein, the 3- to 6-membered nitrogen-containing heterocyclyl has 1 nitrogen atom and optionally 1 or 2 heteroatoms selected from N, O and S as ring atoms; $R^c$ is hydrogen, $C_{1-3}$ alkyl or halo $C_{1-3}$ alkyl.

In an embodiment, substituents in the group S1 are selected from: deuterium, halogen, cyano, hydroxyl, methyl, ethyl, propyl, halomethyl, deuterated methyl, methoxy, ethoxy, halomethoxy, deuterated methoxy, —C(O)$CH_3$, —C(O)cyclopropyl, —C(O)$NH_2$, —C(O)N$(CH_3)_2$, —$CH_2OH$, —$CH_2CH_2OH$, —$CH_2OCH_3$, —$CH_2CH_2OCH_3$, —$CH_2N(CH_3)_2$, —$CH_2CH_2N(CH_3)_2$, —NHC(O)$CH_3$ and —N$(CH_3)_2$.

In an embodiment, substituents in the group S1 are selected from: deuterium, halogen, cyano, hydroxyl, $C_{1-6}$ alkyl (for example, $C_{1-3}$ alkyl), $C_{1-6}$ alkoxy (for example, $C_{1-3}$ alkyl), halo $C_{1-6}$ alkoxy (for example, halo $C_{1-3}$ alkoxy, for another example, difluoromethoxy or trifluoromethoxy), deuterated $C_{1-6}$ alkoxy (for example, deuterated $C_{1-3}$ alkoxy), —$C_{1-4}$ alkylene-hydroxy (for example, —$C_{1-2}$ alkylene-hydroxy), —C(O)$C_{1-6}$ alkyl (for example, —C(O) $C_{1-3}$ alkyl), —C(O)$C_{3-20}$ cycloalkyl (for example, —C(O) $C_{3-6}$ monocyclic cycloalkyl), 3- to 20-membered heterocyclyl (for example, 3- to 6-membered monocyclic heterocyclyl, wherein the 3- to 6-membered monocyclic heterocyclyl has 1 or 2 heteroatoms selected from N and O as ring atoms), —O—$C_{3-6}$ monocyclic cycloalkyl, —$NR^aR^b$ and —$OR_c$ (for example, —O—$C_{1-4}$ alkylene-$C_{1-6}$ alkoxy), wherein, the 3- to 20-membered heterocyclyl has 1, 2 or 3 heteroatoms selected from N, O and S as ring atoms.

In an embodiment, substituents in the group S1 are selected from: deuterium, fluorine, cyano, hydroxyl, methyl, methoxy, ethoxy, difluoromethoxy, trifluoromethoxy, deuterated methoxy (—$OCD_3$), —$CH_2OH$, —C(O)$CH_3$, —C(O)-cyclopropyl, morpholinyl ( 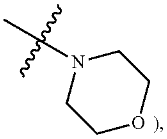 ), —O-cyclopropyl, —N$(CH_3)_2$, —$OCH_2CH_2OCH_3$ and —$CH_2CH_2OCH_2CH_3$.

In an embodiment, substituents in the group S2 are selected from: fluorine, chlorine, —$C_{1-3}$ alkyl, -halo $C_{1-3}$ alkyl and —$C_{3-6}$ monocyclic cycloalkyl.

In an embodiment, substituents in the group S2 are selected from: fluorine, chlorine, methyl, trifluoromethyl and cyclopropyl.

In an embodiment, substituents in the group S2 are selected from: halogen, cyano, —$C_{1-6}$ alkyl (for example, —$C_{1-3}$ alkyl), halo $C_{1-6}$ alkyl (for example, halo $C_{1-3}$ alkyl), deuterated $C_{1-6}$ alkyl (for example, deuterated $C_{1-3}$ alkyl, for another example, deuterated methyl), $C_{1-6}$ alkoxy (for example, $C_{1-3}$ alkoxy), halo $C_{1-6}$ alkoxy (for example, halo $C_{1-3}$ alkoxy), deuterated $C_{1-6}$ alkoxy (for example, deuterated $C_{1-3}$ alkoxy), $C_{3-20}$ cycloalkyl (for example, $C_{3-6}$ monocyclic cycloalkyl), halo $C_{3-20}$ cycloalkyl (for example, halo $C_{3-6}$ monocyclic cycloalkyl, for another example, halocyclopropyl), —O—$C_{3-20}$ cycloalkyl (for example, —$OC_{3-6}$ monocyclic cycloalkyl), —$NR^aR^b$ and —$OR_c$.

In an embodiment, substituents in the group S2 are selected from: fluorine, chlorine, bromine, iodine, cyano, methyl, isopropyl, trifluoromethyl, methoxy, trifluoromethoxy, deuterated methoxy, cyclopropyl, —O-cyclopropyl, —O-cyclopentyl, —N$(CH_3)_2$ and —$OCH_2CH_2OCH_3$.

In an embodiment, $R_1$ and $R_2$ are each independently selected from: H, $C_{1-6}$ alkyl, $C_{3-6}$ monocyclic cycloalkyl and 3- to 6-membered monocyclic heterocyclyl; or $R_1$ and $R_2$ combining with the carbon atoms to which they are attached form: $C_{3-6}$ monocyclic cycloalkyl, 3- to 6-membered monocyclic heterocyclyl or carbonyl (C═O); the 3- to 6-membered monocyclic heterocyclyl has 1, 2 or 3 heteroatoms selected from N, O and S as ring atoms; the $C_{1-6}$ alkyl, the $C_{3-6}$ monocyclic cycloalkyl and the 3- to 6-membered monocyclic heterocyclyl are each independently unsubstituted or substituted by 1, 2, 3 or 4 substituents independently selected from group S1.

In an embodiment, $R_1$ and $R_2$ are each independently selected from: H, methyl, ethyl, n-propyl, isopropyl, cyclopropyl and cyclobutyl; or $R_1$ and $R_2$ combining with the carbon atoms to which they are attached form: cyclopropyl, cyclobutyl, cyclopentyl, cyclohexyl, oxetanyl, azetidinyl, tetrahydropyrrole, tetrahydrofuran, tetrahydropyran, piperidine or carbonyl (C═O); the methyl, the ethyl, the n-propyl, the isopropyl, the cyclopropyl, the cyclobutyl, the cyclopentyl, the cyclohexyl, the oxetanyl, the azetidinyl, the tetrahydropyrrole, the tetrahydrofuran, the tetrahydropyran and the piperidine are each independently unsubstituted or substituted by 1, 2, 3 or 4 substituents independently selected from group S1.

In an embodiment, $R_1$ and $R_2$ are each independently H.

In an embodiment, $R_1$ and $R_2$ combining with the carbon atoms to which they are attached form carbonyl (C═O).

In an embodiment, $R_1$ and $R_2$ are each independently selected from: H, $C_{1-6}$ alkyl (for example, methyl, ethyl, n-propyl, isopropyl, cyclopropyl, cyclobutyl), $C_{3-6}$ monocyclic cycloalkyl (for example, cyclopropyl, cyclobutyl), 3- to 6-membered monocyclic heterocyclyl, $C_{1-6}$ alkoxy (for example, methoxy) and $C_{1-6}$ thioalkyl (for example, methylthio, ethylthio); or $R_1$ and $R_2$ combining with the carbon atoms to which they are attached form: $C_{3-6}$ monocyclic cycloalkyl (for example, cyclopropyl, cyclobutyl, cyclopentyl, cyclohexyl), 3- to 6-membered monocyclic heterocyclyl (for example, oxetanyl, azetidinyl, tetrahydropyrrole, tetrahydrofuran, tetrahydropyran, piperidine), carbonyl (C═O) or C═S; the 3- to 6-membered monocyclic heterocyclyl has 1, 2 or 3 heteroatoms selected from N, O and S as ring atoms; the $C_{1-6}$ alkyl, the $C_{3-6}$ monocyclic cycloalkyl, the 3- to 6-membered monocyclic heterocyclyl, $C_{1-6}$ alkoxy, $C_{1-6}$ thioalkyl are each independently unsubstituted or substituted by 1, 2, 3 or 4 substituents independently selected from group S1.

In an embodiment, $R_1$ and $R_2$ are each independently selected from: H, $C_{1-6}$ alkoxy (for example, $C_{1-3}$ alkoxy, for another example, methoxy) and $C_{1-6}$ thioalkyl (for example, $C_{1-3}$ thioalkyl, for another example, methylthio, ethylthio); or $R_1$ and $R_2$ combining with the carbon atoms to which they are attached form: carbonyl (C═O) or C═S, the $C_{1-6}$ alkoxy and the $C_{1-6}$ thioalkyl are each independently unsubstituted or substituted by 1, 2, 3 or 4 substituents independently selected from group S1.

In an embodiment, $R_1$ and $R_2$ are each independently selected from: methoxy, methylthio and ethylthio.

In an embodiment, $R_1$ and $R_2$ combining with the carbon atoms to which they are attached form carbonyl (C═O) or C═S.

In an embodiment, $R_1$ and $R_2$ combining with the carbon atoms to which they are attached form C═S.

In an embodiment, $R_3$ and $R_4$ are each independently selected from: H, $C_{1-6}$ alkyl, $C_{3-6}$ monocyclic cycloalkyl and 3- to 6-membered monocyclic heterocyclyl; or $R_3$ and $R_4$ combining with the carbon atoms to which they are attached form: $C_{3-6}$ monocyclic cycloalkyl, 3- to 6-membered monocyclic heterocyclyl or carbonyl (C═O); the 3- to 6-membered monocyclic heterocyclyl has 1, 2 or 3 heteroatoms selected from N, O and S as ring atoms; the $C_{1-6}$ alkyl, the $C_{3-6}$ monocyclic cycloalkyl and the 3- to 6-membered monocyclic heterocyclyl are each independently unsubstituted or substituted by 1, 2, 3 or 4 substituents independently selected from group S1.

In an embodiment, $R_3$ and $R_4$ are each independently selected from: H, methyl, ethyl, n-propyl, isopropyl, cyclopropyl and cyclobutyl; or $R_3$ and $R_4$ combining with the carbon atoms to which they are attached form: cyclopropyl, cyclobutyl, cyclopentyl, cyclohexyl, oxetanyl, azetidinyl, tetrahydropyrrole, tetrahydrofuran, tetrahydropyran, piperidine or carbonyl (C═O); the methyl, the ethyl, the n-propyl, the isopropyl, the cyclopropyl, the cyclobutyl, the cyclopentyl, the cyclohexyl, the oxetanyl, the azetidinyl, the tetrahydropyrrole, the tetrahydrofuran, the tetrahydropyran and the piperidine are each independently unsubstituted or substituted by 1, 2, 3 or 4 substituents independently selected from group S1.

In an embodiment, $R_3$ and $R_4$ are each independently selected from: methyl, ethyl, n-propyl, isopropyl, cyclopropyl and cyclobutyl; the methyl, the ethyl, the n-propyl, the isopropyl, the cyclopropyl and the cyclobutyl are each independently unsubstituted or substituted by 1, 2, 3 or 4 substituents independently selected from group S1.

In an embodiment, $R_3$ and $R_4$ are each independently selected from: $C_{1-6}$ alkyl (for example, $C_{1-3}$ alkyl, for another example, methyl or ethyl) and $C_{3-20}$ cycloalkyl (for example, $C_{3-6}$ monocyclic cycloalkyl, for another example, cyclopropyl); or $R_3$ and $R_4$ combining with the carbon atoms to which they are attached form: $C_{3-20}$ cycloalkyl (for example, $C_{3-6}$ monocyclic cycloalkyl, for another example, cyclopropyl, cyclopentyl, cyclohexyl) or 3- to 20-membered heterocyclyl, the 3- to 20-membered heterocyclyl has 1, 2 or 3 heteroatoms selected from N, O and S as ring atoms (for example, 3- to 6-membered monocyclic heterocyclyl, wherein the 3- to 6-membered monocyclic heterocyclyl has 1 or 2 heteroatoms selected from N and O as ring atoms, for another example, oxetanyl, azetidinyl, tetrahydropyrrole, tetrahydrofuran, tetrahydropyran or piperidine); the $C_{1-6}$ alkyl, the $C_{3-6}$ monocyclic cycloalkyl and the 3- to 6-membered monocyclic heterocyclyl are each independently unsubstituted or substituted by 1, 2, 3 or 4 substituents independently selected from group S1. In a preferred embodiment, substituents in the group S1 are selected from: deuterium, halogen (for example, F), cyano, hydroxyl, $C_{1-6}$ alkyl (for example, methyl), $C_{1-6}$ alkoxy (for example, methoxy, ethoxy), deuterated $C_{1-6}$ alkoxy (for example, deuterated methoxy), —$C_{1-4}$ alkylene-hydroxy (for example, —$CH_2OH$), —C(O)$C_{1-6}$ alkyl (for example, —C(O)$CH_3$), —C(O)$C_{3-20}$ cycloalkyl (for example, —C(O)-cyclopropyl), 3- to 20-membered heterocyclyl (for example, morpholinyl ( 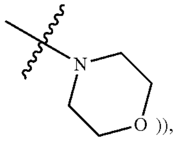 )), —O—$C_{3-6}$ monocyclic cycloalkyl (for example, —O-cyclopropyl), —$NR^aR^b$ (for example, —$N(CH_3)_2$) and —$OR^c$ (for example, —$OC_{1-4}$ alkylene-$C_{1-6}$ alkoxy, for another example, —$CH_2OCH_2CH_2OCH_3$).

In an embodiment, $R_3$ and $R_4$ are each independently selected from: —$CH_3$, —$CH_2CH_3$, cyclopropyl, trifluoromethyl, deuterated methyl, —$CH_2OH$, —$CH_2OCH_3$, —$CH_2OCF_3$, —$CH_2OCHF_2$, —$CH_2OCD_3$, —$CH_2OCH_2CH_3$, —$CH_2OCH_2CH_2OCH_3$, —$CH_2CH_2OCH_2CH_3$, —$CH_2$O-cyclopropyl, —$CH_2N(CH_3)_2$, —CH(OH)$CH_3$ and —$CH_2CH_3OCH_3$.

In an embodiment, $R_3$ is selected from: $C_{1-6}$ alkyl and $C_{3-6}$ monocyclic cycloalkyl; the $C_{1-6}$ alkyl and the $C_{3-6}$ monocyclic cycloalkyl are each independently unsubstituted or substituted by 1, 2, 3 or 4 substituents independently selected from group S1.

In an embodiment, $R_3$ is selected from: $C_{1-6}$ alkyl and $C_{3-6}$ monocyclic cycloalkyl; the $C_{1-6}$ alkyl and the $C_{3-6}$ monocyclic cycloalkyl are unsubstituted or substituted by halogen.

In an embodiment, $R_3$ is selected from: methyl, trifluoromethyl, ethyl, n-propyl and cyclopropyl.

In an embodiment, $R_3$ is selected from: $C_{1-6}$ alkyl (for example, methyl or ethyl) and $C_{3-6}$ monocyclic cycloalkyl (for example, cyclopropyl); the $C_{1-6}$ alkyl and the $C_{3-6}$ monocyclic cycloalkyl are each independently unsubstituted or substituted by 1, 2, 3 or 4 substituents independently selected from group S1. In a preferred embodiment, substituents in the group S1 are selected from: deuterium and halogen (for example, F). In an embodiment, $R_3$ is selected from: —$CH_3$, —$CH_2CH_3$, trifluoromethyl, deuterated methyl and cyclopropyl.

In an embodiment, $R_4$ is selected from: $C_{1-6}$ alkyl; the $C_{1-6}$ alkyl is unsubstituted or substituted by 1, 2, 3 or 4 substituents independently selected from group S1; substituents in the group S1 are selected from: hydroxyl, $C_{1-6}$ alkoxy, halo $C_{1-6}$ alkoxy, deuterated $C_{1-6}$ alkoxy, —O—$C_{3-6}$ monocyclic cycloalkyl and —$NR^aR^b$; wherein, $R^a$ and $R^b$ are each independently H, $C_{1-6}$ alkyl, deuterated $C_{1-6}$ alkyl, $C_{3-6}$ monocyclic cycloalkyl, —$C_{1-4}$ alkylene-$C_{1-6}$ alkoxy, 3- to 6-membered monocyclic heterocyclyl, —$C_{1-4}$ alkylene-3- to 6-membered monocyclic heterocyclyl or C(O)$C_{1-6}$ alkyl; wherein, the 3- to 6-membered monocyclic heterocyclyl has 1, 2 or 3 heteroatoms selected from N, O and S as ring atoms; and the 3- to 6-membered monocyclic heterocyclyl is optionally substituted by 1 or 2 substituents selected from the following group: $C_{1-6}$ alkyl; or $R^a$, $R^b$ combining with the nitrogen atoms to which they are attached form 3- to 6-membered nitrogen-containing heterocyclyl; wherein, the 3- to 6-membered nitrogen-containing heterocyclyl has 1 nitrogen atom and optionally 1 or 2 heteroatoms selected from N, O and S as ring atoms; and the 3- to 6-membered nitrogen-containing heterocyclyl is optionally substituted by 1 or 2 substituents selected from the following group: $C_{1-6}$ alkyl.

In an embodiment, $R_4$ is selected from: methyl and ethyl; the methyl and the ethyl are each independently unsubstituted or substituted by 1 substituent selected from group S1; substituent in the group S1 is selected from: hydroxyl, methoxy, deuterated methoxy, trifluoromethoxy, ethoxy, deuterated ethoxy, haloethoxy, n-propoxy, isopropoxy, n-butoxy, —O— cyclopropyl, —O-cyclobutyl, —$N(CH_3)_2$, —$N(CH_2CH_3)_2$, —$N(CH_2CH_3)(CH_3)$, —$N(CH_2CH_2CH_3)(CH_3)$ and —$N(CH_2CH_2CH_3)(CH_2CH_3)$.

In an embodiment, $R_4$ is selected from: $C_{1-6}$ alkyl (for example, methyl, ethyl); the $C_{1-6}$ alkyl is unsubstituted or substituted by 1, 2, 3 or 4 substituents independently selected from group S1; substituents in the group S1 are selected from: hydroxyl, $C_{1-6}$ alkoxy, halo $C_{1-6}$ alkoxy, deuterated $C_{1-6}$ alkoxy, —O—$C_{3-6}$ monocyclic cycloalkyl, —$NR^aR^b$ and —$OR^c$ (for example, —$OC_{1-4}$ alkylene-$C_{1-6}$ alkoxy); wherein, $R^a$ and $R^b$ are each independently H, $C_{1-6}$ alkyl, deuterated $C_{1-6}$ alkyl, $C_{3-6}$ monocyclic cycloalkyl, —$C_{1-4}$ alkylene-$C_{1-6}$ alkoxy, 3- to 6-membered monocyclic heterocyclyl, —$C_{1-4}$ alkylene-3- to 6-membered monocyclic heterocyclyl or $C(O)C_{1-6}$ alkyl; wherein, the 3- to 6-membered monocyclic heterocyclyl has 1, 2 or 3 heteroatoms selected from N, O and S as ring atoms; and the 3- to 6-membered monocyclic heterocyclyl is optionally substituted by 1 or 2 substituents selected from the following group: $C_{1-6}$ alkyl; or $R^a$, $R^b$ combining with the nitrogen atoms to which they are attached form 3- to 6-membered nitrogen-containing heterocyclyl; wherein, the 3- to 6-membered nitrogen-containing heterocyclyl has 1 nitrogen atom and optionally 1 or 2 heteroatoms selected from N, O and S as ring atoms; and the 3- to 6-membered nitrogen-containing heterocyclyl is optionally substituted by 1 or 2 substituents selected from the following group: $C_{1-6}$ alkyl.

In an embodiment, $R_4$ is selected from: methyl and ethyl; the methyl and the ethyl are unsubstituted or substituted by 1 substituent selected from group S1; substituent in the group S1 is selected from: hydroxyl, methoxy, deuterated methoxy, difluoromethoxy, trifluoromethoxy, ethoxy, deuterated ethoxy, haloethoxy, n-propoxy, isopropoxy, n-butoxy, —$OCH_2CH_2OCH_3$, —$OCH_2CH_2OCH_2CH_3$, —O-cyclopropyl, —O-cyclobutyl, —$N(CH_3)_2$, —$N(CH_2CH_3)_2$, —$N(CH_2CH_3)(CH_3)$, —$N(CH_2CH_2CH_3)(CH_3)$ and —$N(CH_2CH_2CH_3)(CH_2CH_3)$. In a preferred embodiment, substituent in the group S1 is selected from: hydroxyl, methoxy, deuterated methoxy, ethoxy, —$OCH_2CH_2OCH_3$, —O-cyclopropyl and —$N(CH_3)_2$. In an embodiment, $R_4$ is selected from: —$CH_3$, —$CH_2OH$, —$CH_2OCH_3$, —$CH_2OCF_3$, —$CH_2OCHF_2$, —$CH_2OCF_3$, —$CH_2OCHF_2$, —$CH_2OCD_3$, —$CH_2OCH_2CH_3$, —$CH_2OCH_2CH_2OCH_3$, —$CH_2CH_2OCH_2CH_3$, —$CH_2$O-cyclopropyl, —$CH_2N(CH_3)_2$, —$CH(OH)CH_3$ and —$CH_2CH_3OCH_3$.

In an embodiment, $R_3$ and $R_4$ combining with the carbon atoms to which they are attached form: cyclopropyl, cyclobutyl, cyclopentyl, cyclohexyl, oxetanyl, azetidinyl, tetrahydropyrrole, tetrahydrofuran, tetrahydropyran, piperidine or carbonyl (C═O); the cyclopropyl, the cyclobutyl, the cyclopentyl, the cyclohexyl, the oxetanyl, the azetidinyl, the tetrahydropyrrole, the tetrahydrofuran, the tetrahydropyran and the piperidine are each independently unsubstituted or substituted by 1, 2, 3 or 4 substituents independently selected from group S1. In a preferred embodiment, substituents in the group S1 are selected from: cyano, hydroxyl, $C_{1-6}$ alkyl (for example, methyl), $C_{1-6}$ alkoxy (for example, methoxy), —$C_{1-4}$ alkylene-hydroxy (for example, —$CH_2OH$), —$C(O)C_{1-6}$ alkyl (for example, —$C(O)CH_3$), —$C(O)C_{3-20}$ cycloalkyl (for example, —C(O)-cyclopropyl) and 3- to 20-membered heterocyclyl (for example, morpholinyl ( 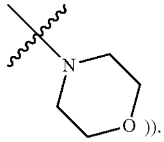 )).

In an embodiment, $R_3$ and $R_4$ combining with the carbon atoms to which they are attached form:

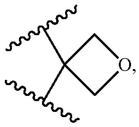 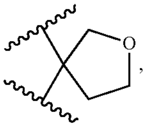, 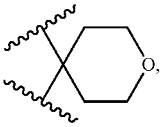

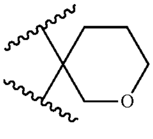, 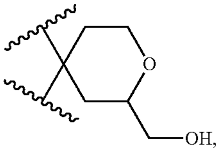

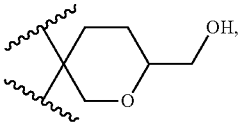 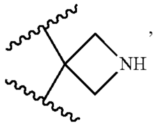,

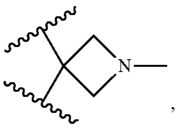, 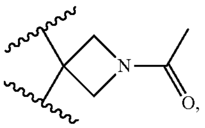

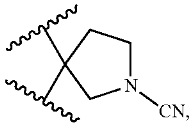 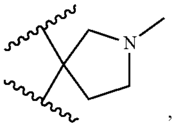,

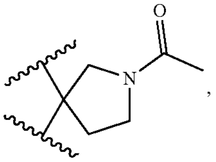, 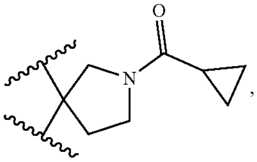,

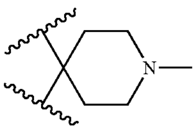, 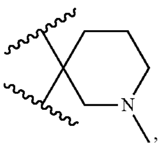 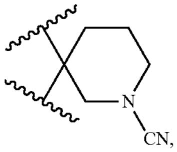

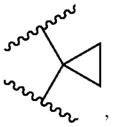, 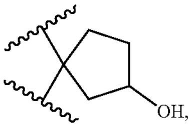 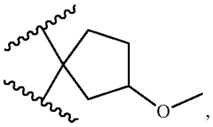,

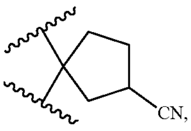 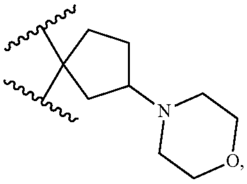

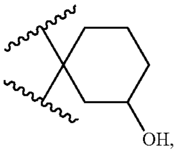 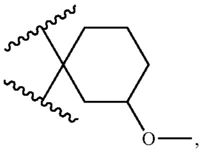

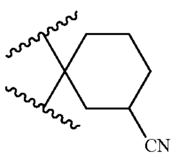 or 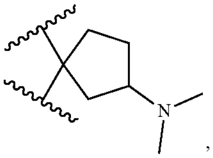, for example

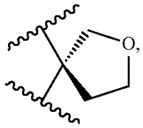,
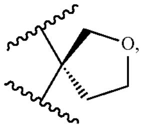,
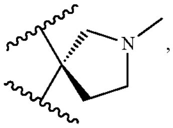,
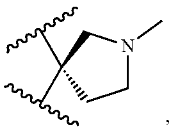,
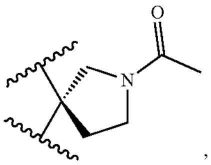,
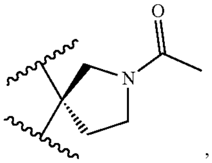,
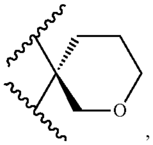,
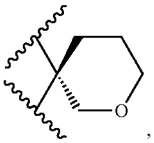,
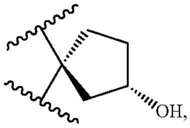,
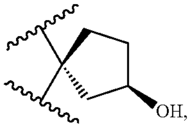,
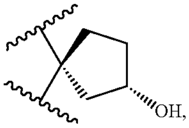,
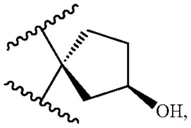,
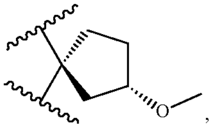,
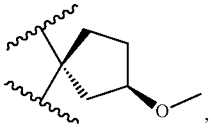,
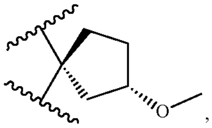,
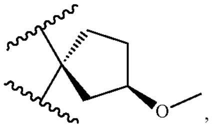,
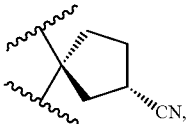,
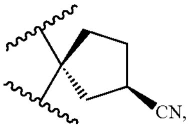,
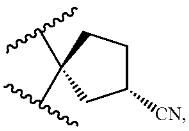,
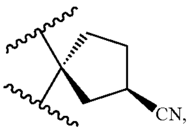,
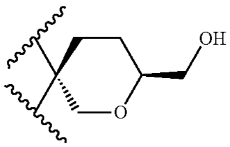 or 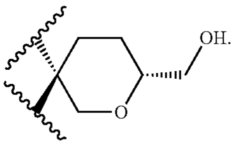.

The cyclopropyl, the cyclobutyl, the cyclopentyl, the cyclohexyl, the oxetanyl (for example,

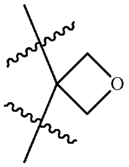 or 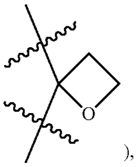), the azetidinyl (for example,

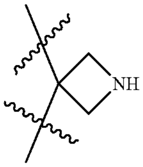 or 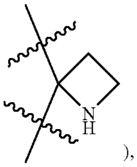), the tetrahydropyrrole (for example,

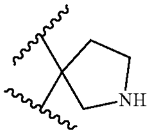 or 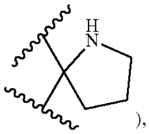), the tetrahydrofuran (for example,

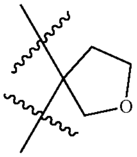 or 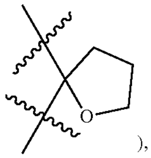), the tetrahydropyran (for example,

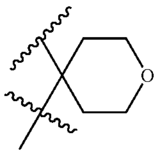, 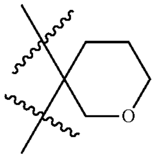 or 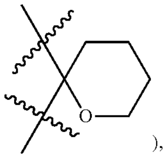), the piperidine (for example,

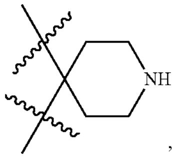, 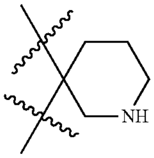 or 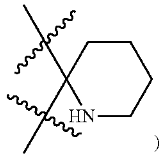)

combining with the rest of a molecule by any one ring atom form a spiro ring.

In an embodiment, $R_5$ is H, $C_{1-3}$ alkyl, —$C_{1-2}$ alkylene-hydroxy, —$C_{1-2}$ alkylene-cyano, —$C_{1-2}$ alkylene-$C_{1-3}$ alkoxy, —$C_{1-2}$ alkylene-halo $C_{1-3}$ alkyl, —$C_{1-2}$ alkylene-halo $C_{1-3}$ alkoxy, —$C_{1-2}$ alkylene-$C_{3-6}$ monocyclic cycloalkyl, —$C_{1-2}$ alkylene-3- to 6-membered monocyclic heterocyclyl, $—C_{1-2}$ alkylene-$NR^aR^b$, $—C_{1-2}$ alkylene-C(O)$NR^aR^b$, $—C_{1-2}$ alkylene-C(O)O$C_{1-3}$ alkyl, $—C_{1-2}$ alkylene-$SO_2C_{1-3}$ alkyl, $—C_{1-2}$ alkylene-carboxyl or $C_{3-6}$ monocyclic cycloalkyl; wherein, 1 or 2 hydrogen atoms on the "$—C_{1-2}$ alkylene-" are optionally substituted by $C_{1-3}$ alkyl, or two hydrogen atoms on the same carbon on the "$—C_{1-2}$ alkylene-" are simultaneously substituted by $—CH_2CH_2—$ to form cycloalkyl; the 3- to 6-membered monocyclic heterocyclyl has 1, 2 or 3 heteroatoms selected from N, O and S as ring atoms; the 3- to 6-membered monocyclic heterocyclyl is optionally substituted by 1 or 2 substituents selected from the following group: $C_{1-6}$ alkyl; $R^a$ and $R^b$ are each defined as in formula (I).

In an embodiment, $R_5$ is H, $C_{1-6}$ alkyl, $—C_{1-4}$ alkylene-$NR^aR^b$ or $C_{3-6}$ monocyclic cycloalkyl; $R^a$ and $R^b$ are each defined as in formula (I).

In an embodiment, $R_5$ is H, methyl, ethyl, n-propyl, isopropyl, n-butyl, isobutyl or $—CH_2CH_2N(CH_3)_2$.

In an embodiment, $R_5$ is H, $C_{1-6}$ alkyl (for example, methyl, ethyl, n-propyl, isopropyl, n-butyl, isobutyl, for another example, methyl, ethyl), deuterated $C_{1-6}$ alkyl (for example, deuterated $C_{1-3}$ alkyl, for another example, deuterated methyl), $—C_{1-4}$ alkylene-hydroxy (for example, $—C_{1-2}$ alkylene-hydroxy, for another example, $—CH_2CH_2OH$), $—C_{1-4}$ alkylene-$C_{1-6}$ alkoxy (for example, $—C_{1-2}$ alkylene-$C_{1-3}$ alkoxy, for another example, $—CH_2CH_2OCH_3$) or $—C_{1-4}$ alkylene-$NR^aR^b$ (for example, $—C_{1-2}$ alkylene-$NR^aR^b$, for another example, $—CH_2CH_2N(CH_3)_2$).

In an embodiment, L is a bond.

In an embodiment, L is $CR^8R^9$; wherein, $R^8$, $R^9$ are each independently H, $C_{1-6}$ alkyl, halo $C_{1-6}$ alkyl, deuterated $C_{1-6}$ alkyl, $C_{1-6}$ alkoxy, halo $C_{1-6}$ alkoxy, deuterated $C_{1-6}$ alkoxy, $—C_{1-4}$ alkylene-hydroxy, $—C_{1-4}$ alkylene-cyano, $—C_{1-4}$ alkylene-$C_{1-6}$ alkoxy, $—C_{1-4}$ alkylene-halo $C_{1-6}$ alkyl, $—C_{1-4}$ alkylene-halo $C_{1-6}$ alkoxy.

In an embodiment, L is $CH_2$.

In an embodiment, L is O.

In an embodiment, L is NH.

In an embodiment, L is NHC(O).

In an embodiment, L is $CH_2NHC(O)$.

In an embodiment, L is $NHC(O)CH_2$.

In an embodiment, n is 0 or 1.

In an embodiment, E is $NR_5$.

In an embodiment, E is O.

In an embodiment, E is N.

In an embodiment, A is $CR_6$; wherein, $R_6$ is H.

In an embodiment, A is N.

In an embodiment, B is N.

In an embodiment, B is $CR_7$; wherein, $R_7$ is H.

In an embodiment, $G_1$ is phenyl, pyridinyl, pyrimidinyl, furyl, pyrrolyl, thiazolyl or pyrazolyl; the phenyl, the pyridinyl, the pyrimidinyl, the furyl, the pyrrolyl, the thiazolyl or the pyrazolyl is each independently unsubstituted or substituted by 1, 2, 3 or 4 substituents independently selected from group S2.

In an embodiment, $G_1$ is phenyl or pyridyl; the phenyl or the pyridinyl is each independently unsubstituted or substituted by 1, 2, 3 or 4 substituents independently selected from group S2.

In an embodiment, $G_1$ is phenyl or pyridyl; the phenyl or the pyridinyl is each independently unsubstituted or substituted by 1, 2, 3 or 4 substituents independently selected from group S2; wherein, substituents in the group S2 are selected from: fluorine, chlorine, $—C_{1-3}$ alkyl, -halo $C_{1-3}$ alkyl, $—C_{3-6}$ monocyclic cycloalkyl.

In an embodiment, $G_1$ is $C_{6-14}$ aryl or 5- to 6-membered monocyclic heteroaryl; the 5- to 6-membered monocyclic heteroaryl has 1, 2 or 3 heteroatoms selected from N, O and S as ring atoms, and the $C_{6-14}$ aryl and the 5- to 6-membered monocyclic heteroaryl are each independently unsubstituted or substituted by 1, 2, 3 or 4 substituents independently selected from group S2.

In an embodiment, $G_1$ is phenyl or pyridyl; the phenyl and the pyridinyl are each independently unsubstituted or substituted by 1, 2, 3 or 4 substituents independently selected from group S2; wherein, substituents in the group S2 are selected from the following group: fluorine, chlorine, bromine, cyano, $—C_{1-3}$ alkyl, -halo $C_{1-3}$ alkyl, -deuterated $C_{1-3}$ alkyl, $—C_{3-6}$ monocyclic cycloalkyl, -halo $C_{3-6}$ monocyclic cycloalkyl, $—O—C_{3-6}$ monocyclic cycloalkyl, —O-halo $C_{3-6}$ monocyclic cycloalkyl.

In an embodiment, $G_1$ is phenyl, pyridinyl, pyrimidinyl, furyl, pyrrolyl, thiazolyl, pyrazolyl or thienyl; the phenyl, the pyridinyl, the pyrimidinyl, the furyl, the pyrrolyl, the thiazolyl, the pyrazolyl and the thienyl are each independently unsubstituted or substituted by 1, 2, 3 or 4 substituents independently selected from group S2.

In an embodiment, $G_1$ is phenyl, pyridinyl, furyl or thienyl; the phenyl, the pyridinyl, the furyl and the thienyl are each independently unsubstituted or substituted by 1, 2, 3 or 4 substituents independently selected from group S2.

In an embodiment, in $G_1$, substituents in the group S2 are selected from: halogen, cyano, $—C_{1-6}$ alkyl, halo $C_{1-6}$ alkyl, $C_{1-6}$ alkoxy, halo $C_{1-6}$ alkoxy, $C_{3-20}$ cycloalkyl, $—O—C_{3-20}$ cycloalkyl, $—NR^aR^b$ and $—OR^c$; for example, fluorine, chlorine, bromine, iodine, cyano, methyl, isopropyl, trifluoromethyl, methoxy, trifluoromethoxy, cyclopropyl, —O-cyclopropyl, —O-cyclopentyl, $—N(CH_3)_2$ and $—OCH_2CH_2OCH_3$.

In an embodiment, $G_1$ is phenyl, 2-chlorophenyl, 2-fluorophenyl, 2-trifluoromethylphenyl, 2-chloro-6-fluorophenyl, 2-chloro-3,4-difluorophenyl, 2-chloro-3-fluoro-4-methoxyphenyl, 2-chloro-4-cyclopentyloxyphenyl, 2-chloro-4-(2-methoxyethyl)phenyl, 2-chloro-4-dimethylaminophenyl, 2-chloro-4-cyclopropyloxyphenyl, 2-chloro-4-methoxyphenyl, 2-chloro-4-isopropylphenyl, 2-chloro-4-cyclopropylphenyl, 2-chloro-4-methylphenyl, 2-chlorofuryl, furyl, thienyl, 2-bromothienyl, 2-chlorothienyl, pyridinyl, 3-chloropyridinyl, 2-methylphenyl, 2-chloro-4-cyanophenyl, 2-chloro-4-fluorophenyl, 2-iodophenyl, 2-chloro-5-fluorophenyl, 2-chloro-3-fluorophenyl, 2-chloro-trifluoromethoxyphenyl, 2-chloro-4-bromophenyl or 2,4-dichlorophenyl.

In an embodiment, $G_2$ is $C_{6-14}$ aryl or 5- to 6-membered monocyclic heteroaryl; the 5- to 6-membered monocyclic heteroaryl has 1, 2 or 3 heteroatoms selected from N, O and S as ring atoms, and the $C_{6-14}$ aryl and the 5- to 6-membered monocyclic heteroaryl are each independently unsubstituted or substituted by 1, 2, 3 or 4 substituents independently selected from group S2.

In an embodiment, $G_2$ is phenyl, pyridinyl, pyrimidinyl, furyl, pyrrolyl, thiazolyl or pyrazolyl; the phenyl, the pyridinyl, the pyrimidinyl, the furyl, the pyrrolyl, the thiazolyl or the pyrazolyl is each independently unsubstituted or substituted by 1, 2, 3 or 4 substituents independently selected from group S2.

In an embodiment, $G_2$ is phenyl, pyridyl or pyrazolyl; the phenyl, the pyridinyl and the pyrazolyl are each independently unsubstituted or substituted by 1, 2, 3 or 4 substituents independently selected from group S2.

In an embodiment, $G_2$ is phenyl or pyridyl; the phenyl or the pyridinyl is each independently unsubstituted or substituted by 1, 2, 3 or 4 substituents independently selected from group S2.

In an embodiment, $G_2$ is phenyl or pyridyl; the phenyl or the pyridinyl is each independently unsubstituted or substituted by 1, 2, 3 or 4 substituents independently selected from group S2; wherein, substituents in the group S2 are selected from: fluorine, chlorine, —$C_{1-3}$ alkyl, -halo $C_{1-3}$ alkyl, —$C_{3-6}$ monocyclic cycloalkyl.

In an embodiment, $G_2$ is phenyl or pyridyl; the phenyl or the pyridinyl is each independently unsubstituted or substituted by 1, 2, 3 or 4 substituents independently selected from group S2; wherein, substituents in the group S2 are selected from the following group: fluorine, chlorine, bromine, cyano, —$C_{1-3}$ alkyl, —$C_{1-3}$ alkoxy, -halo $C_{1-3}$ alkyl, -deuterated $C_{1-3}$ alkyl, -halo $C_{1-3}$ alkoxy, -deuterated $C_{1-3}$ alkoxy, —$C_{3-6}$ monocyclic cycloalkyl, —O—$C_{3-6}$ monocyclic cycloalkyl, -halo $C_{3-6}$ monocyclic cycloalkyl and —O-halo $C_{3-6}$ monocyclic cycloalkyl.

In an embodiment, in $G_2$, substituents in the group S2 are selected from: halogen, cyano, —$C_{1-6}$ alkyl, halo $C_{1-6}$ alkyl, $C_{1-6}$ alkoxy, deuterated $C_{1-6}$ alkoxy and $C_{3-20}$ cycloalkyl, for example, fluorine, chlorine, cyano, methyl, trifluoromethyl, methoxy, deuterated methoxy and cyclopropyl.

In an embodiment, $G_2$ is phenyl, 2-fluorophenyl, 3-fluorophenyl, 4-trifluoromethylpyridinyl, 3-methylpyridinyl, 3-trifluoromethylpyridinyl, 4-methylpyridinyl, 4-cyclopropylpyridinyl, 4,6-dimethylpyridinyl, 4-chloro-6-methylpyridinyl, 2-methyl-6-chloropyridinyl, 3-cyanophenyl, 3-fluoro-4-methylpyridinyl, pyridinyl, 3-fluoropyridinyl, 2-methoxyphenyl, 2-chlorophenyl, 3-methoxyphenyl, 2-fluoro-6-methoxyphenyl, pyrazolyl, 3-methylpyrazolyl, 2-methoxy-3-fluorophenyl, 2-fluoro-3-deuterated methoxyphenyl, 2,4-dimethylpyridinyl, 2-chloropyridyl, 2-methoxy-3-fluorophenyl, 2-deuterated methoxy-3-fluorophenyl.

In an embodiment, $G_1$ is phenyl, and the phenyl is substituted by fluorine or chlorine; $G_2$ is phenyl or pyridyl, and the phenyl or the pyridyl is each independently unsubstituted or substituted by fluorine, chlorine, methyl, trifluoromethyl or cyclopropyl.

In an embodiment, $G_1$ is phenyl, and the phenyl is substituted by fluorine or chlorine; $G_2$ is phenyl or pyridyl, and the phenyl or the pyridyl is each independently unsubstituted or substituted by one, two or three substituents selected from fluorine, chlorine, bromine, cyano, methyl, deuterated methyl, methoxy, deuterated methoxy, trifluoromethyl, trifluoromethoxy, cyclopropyl, halocyclopropyl, —O-cyclopropyl, —O-halocyclopropyl.

In an embodiment, $G_1$ is phenyl, and the phenyl is substituted by fluorine or chlorine; $G_2$ is phenyl, and the phenyl is unsubstituted or substituted by fluorine, chlorine, methyl, trifluoromethyl or cyclopropyl.

In an embodiment, $G_1$ is phenyl, and the phenyl is substituted by fluorine or chlorine; $G_2$ is pyridinyl, and the pyridinyl is unsubstituted or substituted by fluorine, chlorine, methyl, trifluoromethyl or cyclopropyl.

In an embodiment, in formula B, formula B1, formula B1a, formula B1a-1, formula B1a-2, formula B2, formula B2a, formula B2a-1 or formula B2a-2, $G_1$ is selected from the following group:

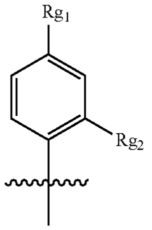
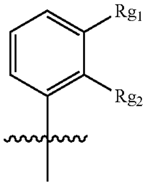
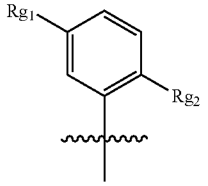
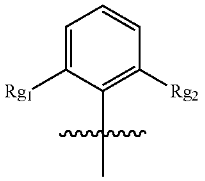
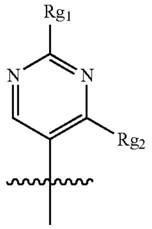
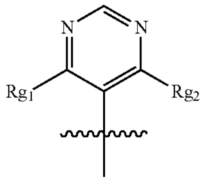
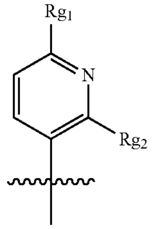
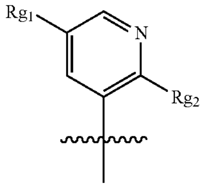
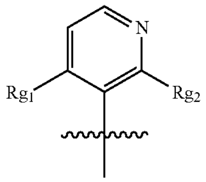
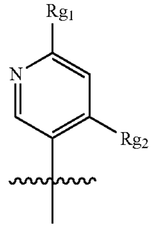
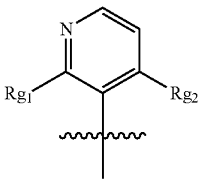
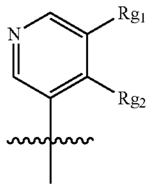
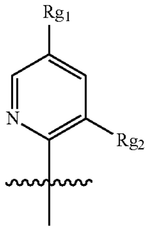
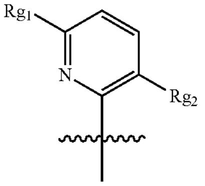
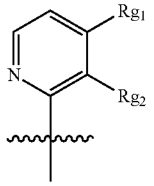
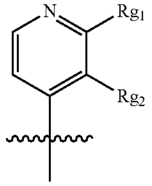
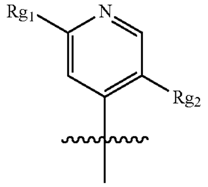
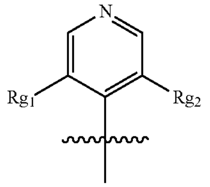
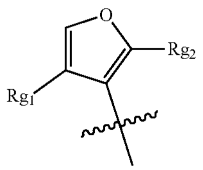
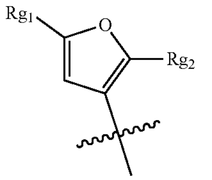

-continued

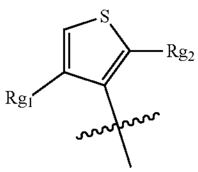 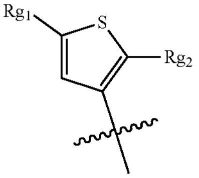

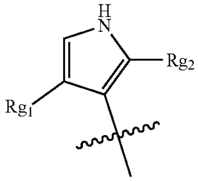 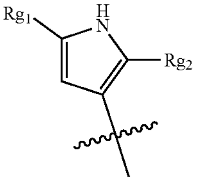

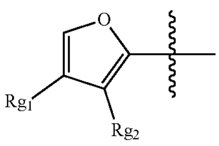 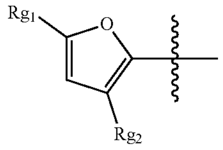

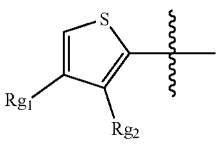 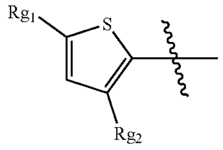

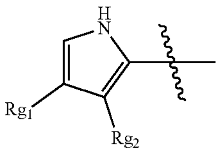 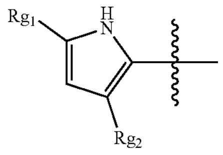

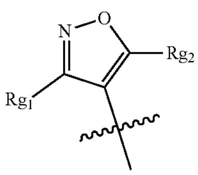 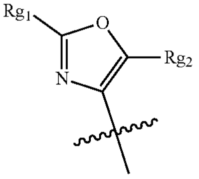

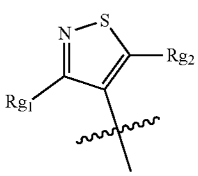 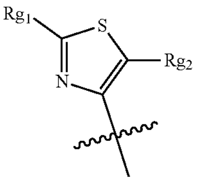

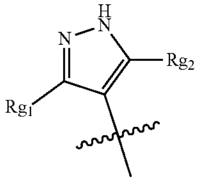 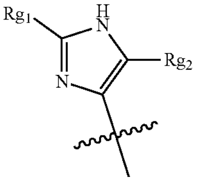

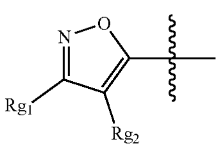 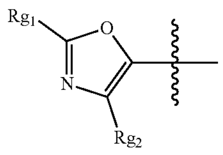

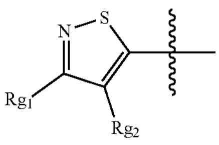 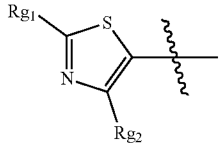

-continued

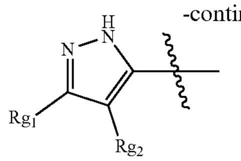 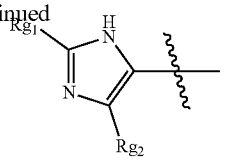

in each formula, $Rg_1$, $Rg_2$ are each independently hydrogen or a substituent selected from group S2.

In an embodiment, i, $G_1$, L, $G_2$ have any one of the following definitions:

(1) i is 0, $G_1$ is phenyl, pyridinyl, furyl or thienyl; the phenyl, the pyridinyl, the furyl and the thienyl are each independently unsubstituted or substituted by 1, 2, 3 or 4 substituents independently selected from group S2;

(2) i is 1, L is $CR^8R^9$ or O, $G_1$ is phenyl or pyridyl, $G_2$ is phenyl, pyridyl or pyrazolyl; the phenyl, the pyridinyl and the pyrazolyl are each independently unsubstituted or substituted by 1, 2, 3 or 4 substituents independently selected from group S2;

(3) i is 1, L is $CR^8R^9$, $G_1$ is phenyl, $G_2$ is pyrazolyl; the phenyl and the pyrazolyl are each independently unsubstituted or substituted by 1, 2, 3 or 4 substituents independently selected from group S2;

(4) i is 1, L is O, $G_1$ is phenyl or pyridyl, $G_2$ is phenyl or pyridyl; the phenyl and the pyridinyl are each independently unsubstituted or substituted by 1, 2, 3 or 4 substituents independently selected from group S2.

In a preferred embodiment, i is 0, $G_1$ is selected from:

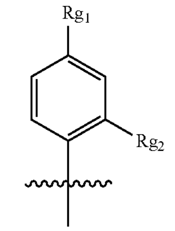 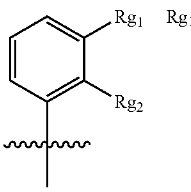 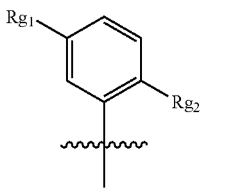

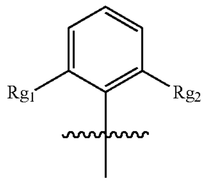 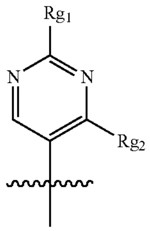 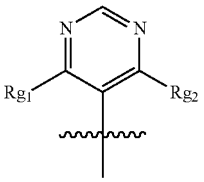

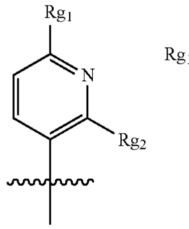 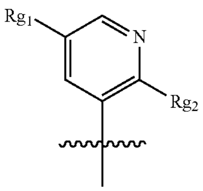 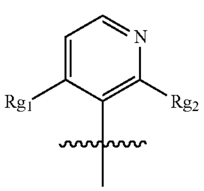

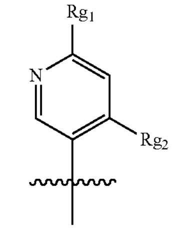 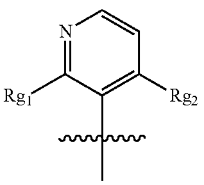 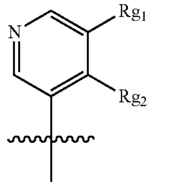

-continued

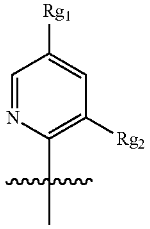 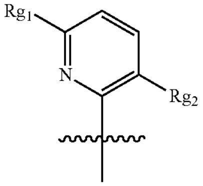 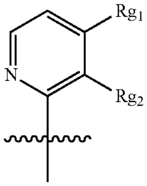

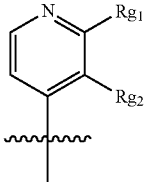 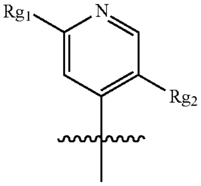 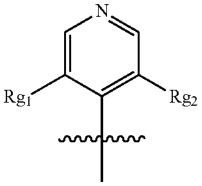

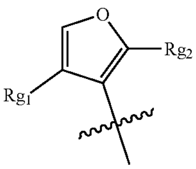 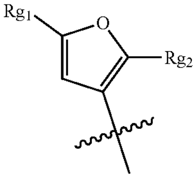

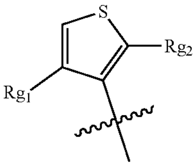 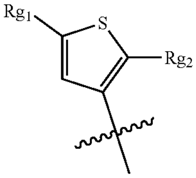

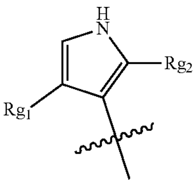 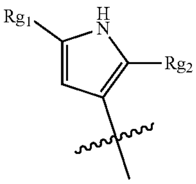

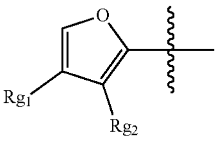 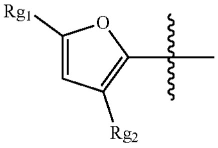

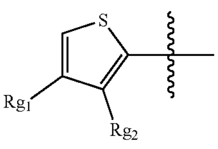 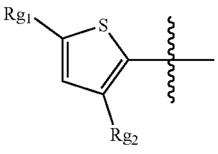

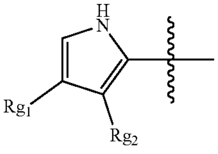 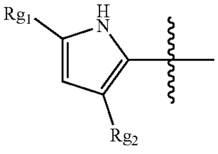

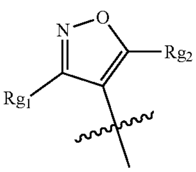 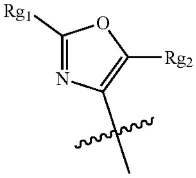

-continued

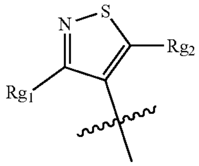 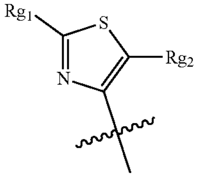

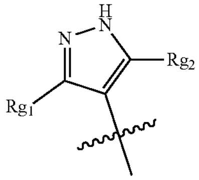 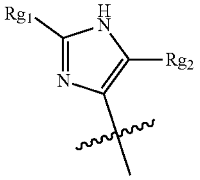

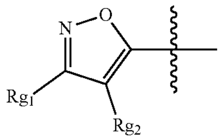 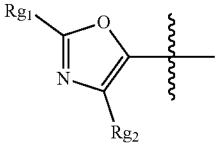

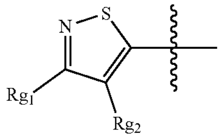 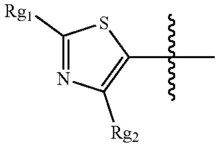

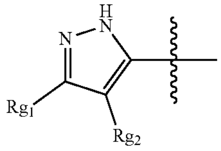 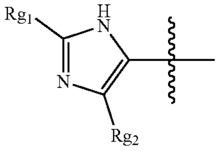

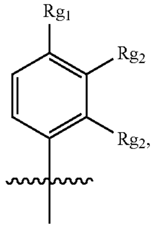

$Rg_1$ and $Rg_2$ are each independently hydrogen or a substituent selected from group S2.

In an embodiment, $Rg_2$ is hydrogen or selected from the following group: deuterium, halogen, cyano, $C_{1-6}$ alkyl, halo $C_{1-6}$ alkyl, deuterated $C_{1-6}$ alkyl, —$C_{3-6}$ monocyclic cycloalkyl, -halo $C_{3-6}$ monocyclic cycloalkyl.

In an embodiment, $Rg_1$ is hydrogen or selected from the following group: deuterium, halogen, cyano, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy, deuterated $C_{1-6}$ alkoxy, —$C_{3-6}$ monocyclic cycloalkyl, -halo $C_{3-6}$ monocyclic cycloalkyl, —O—$C_{3-6}$ monocyclic cycloalkyl, 3- to 6-membered monocyclic heterocyclyl, —O-3- to 6-membered monocyclic heterocyclyl, —$NR^aR^b$ and —$OR^c$; the 3- to 6-membered monocyclic heterocyclyl has 1, 2 or 3 heteroatoms selected from N, O and S as ring atoms; the $C_{3-6}$ monocyclic cycloalkyl and the 3- to 6-membered monocyclic heterocyclyl are each independently optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy;

in the above groups, $R^a$ and $R^b$ are each independently H, $C_{1-6}$ alkyl, halo $C_{1-6}$ alkyl, deuterated $C_{1-6}$ alkyl, $C_{3-6}$ monocyclic cycloalkyl, —$C_{1-4}$ alkylene-$C_{3-6}$ monocyclic cycloalkyl, —$C_{1-4}$ alkylene-$C_{1-6}$ alkoxy, —$C_{1-4}$ alkylene-halo $C_{1-6}$ alkoxy, —$C_{1-4}$ alkylene-deuterated $C_{1-6}$ alkoxy, 3- to 6-membered monocyclic heterocyclyl, —$C_{1-4}$ alkylene-3- to 6-membered monocyclic heterocyclyl or $C(O)C_{1-6}$ alkyl; wherein, the 3- to 6-membered monocyclic heterocyclyl has 1, 2 or 3 heteroatoms selected from N, O and S as ring atoms; the $C_{3-6}$ monocyclic cycloalkyl, the 3- to 6-membered monocyclic heterocyclyl are optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy; or in the above groups, $R^a$, $R^b$ combining with the nitrogen atoms to which they are attached form 3- to 6-membered nitrogen-containing heterocyclyl; wherein, the 3- to 6-membered nitrogen-containing heterocyclyl has 1 nitrogen atom and optionally 1 or 2 heteroatoms selected from N, O and S as ring atoms; and the 3- to 6-membered nitrogen-containing heterocyclyl is optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy;

in the above groups, $R^c$ is H, —$C_{1-4}$ alkylene-halo $C_{1-6}$ alkyl, —$C_{1-4}$ alkylene-deuterated $C_{1-6}$ alkyl, —$C_{1-4}$ alkylene-$C_{1-6}$ alkoxy, —$C_{1-4}$ alkylene-halo $C_{1-6}$ alkoxy, —$C_{1-4}$ alkylene-deuterated $C_{1-6}$ alkoxy, —$C_{1-4}$ alkylene-$C_{3-6}$ monocyclic cycloalkyl, —$C_{1-4}$ alkylene-3- to 6-membered monocyclic heterocyclyl; the $C_{3-6}$ monocyclic cycloalkyl, the 3- to 6-membered monocyclic heterocyclyl are optionally substituted by 1 or 2 substituents selected from the following group: halogen, hydroxyl, carboxyl, nitro, $C_{1-6}$ alkyl, halo $C_{1-6}$ alkyl, deuterated $C_{1-6}$ alkyl, $C_{1-6}$ alkoxy, halo $C_{1-6}$ alkoxy and deuterated $C_{1-6}$ alkoxy.

In a preferred embodiment, $Rg_1$ is hydrogen or selected from the following group: halogen (for example, fluorine, chlorine, bromine, iodine), cyano, $C_{1-6}$ alkyl (for example, methyl), halo $C_{1-6}$ alkyl (for example, trifluoromethyl), deuterated $C_{1-6}$ alkyl (for example, deuterated methyl), $C_{1-6}$ alkoxy (for example, methoxy), halo $C_{1-6}$ alkoxy (for example, trifluoromethoxy), deuterated $C_{1-6}$ alkoxy (for example, deuterated methoxy), —O—$C_{3-6}$ monocyclic cycloalkyl (for example, —O-cyclopropyl, —O-cyclopentyl), —$NR^aR^b$ (for example, —$N(CH_3)_2$) or —$OR^c$ (for example, —O—$CH_2CH_2OCH_3$).

In a preferred embodiment, $Rg_2$ is halogen (for example, fluorine, chlorine, bromine, iodine), cyano, $C_{1-6}$ alkyl (for example, methyl), halo $C_{1-6}$ alkyl (for example, trifluoromethyl), deuterated $C_{1-6}$ alkyl (for example, deuterated methyl), $C_{1-6}$ alkoxy (for example, methoxy), halo $C_{1-6}$ alkoxy (for example, trifluoromethoxy), deuterated $C_{1-6}$ alkoxy (for example, deuterated methoxy), —O—$C_{3-6}$ monocyclic cycloalkyl (for example, —O-cyclopropyl, —O-cyclopentyl), —$NR^aR^b$ (for example, —$N(CH_3)_2$) or —$OR^c$ (for example, —O—$CH_2CH_2OCH_3$).

In an embodiment, the structural moiety

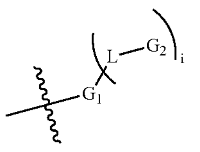

is selected from:

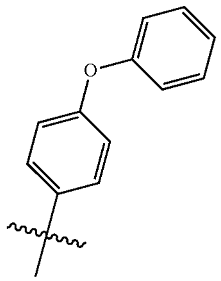
,
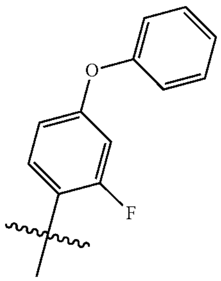
,
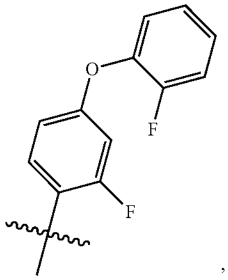
,
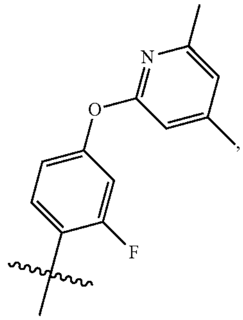
,
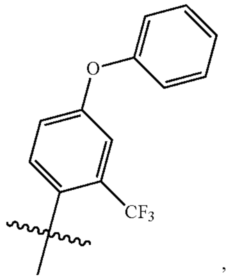
,
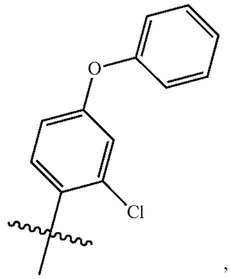
,
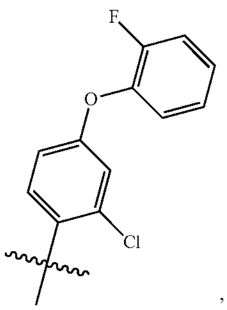
,
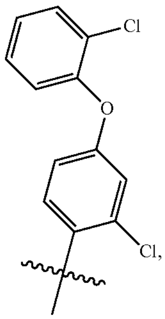
, -continued
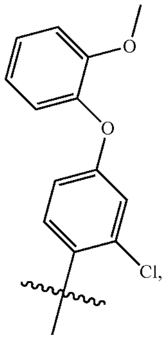
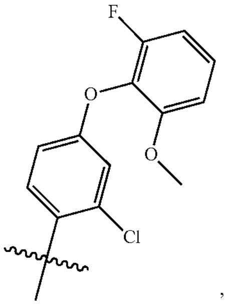
,
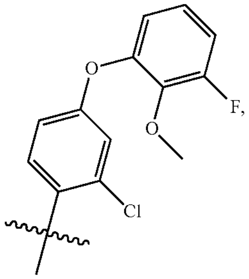
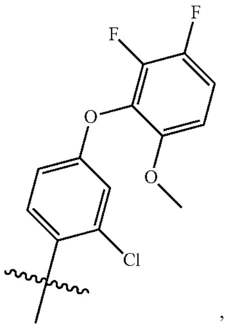
,
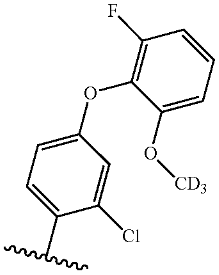
,
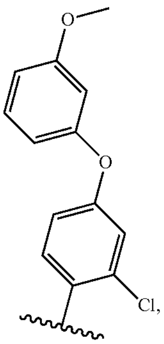
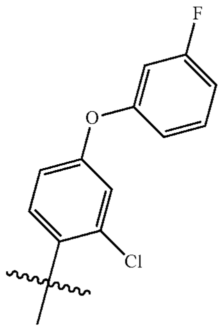
,
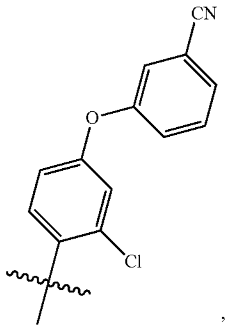
,
-continued
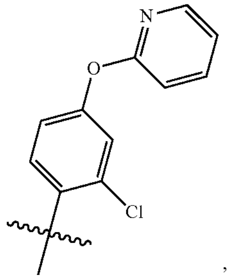
,
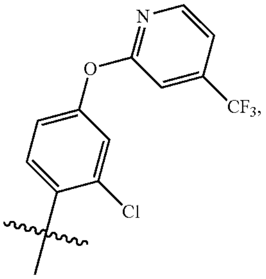
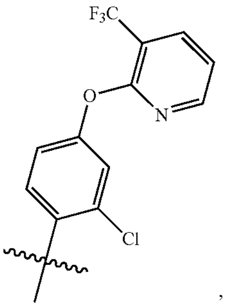
,
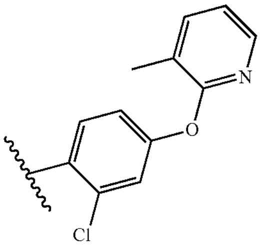
,
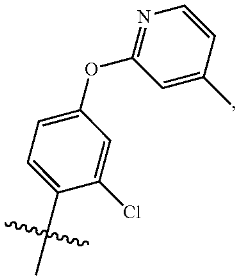
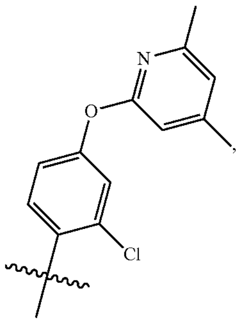
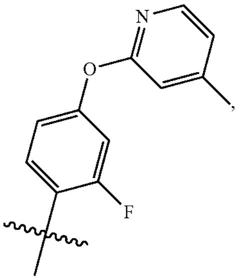
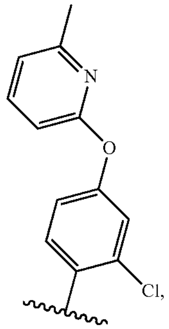

-continued
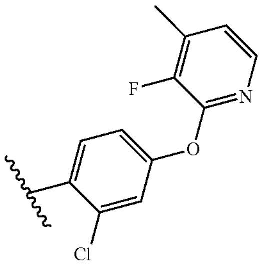
,
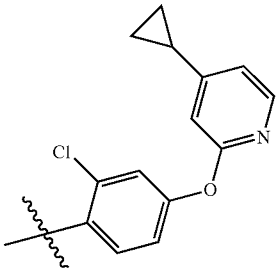
,
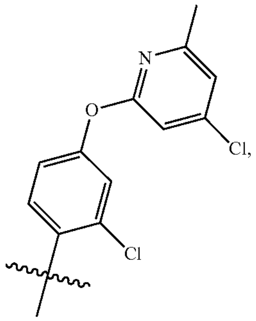
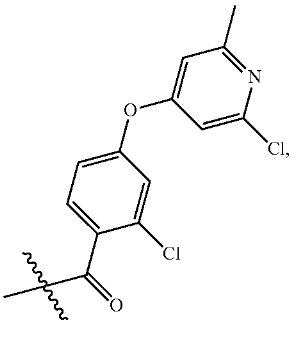
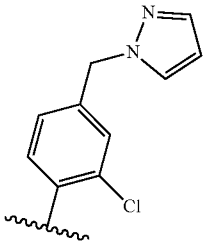
,
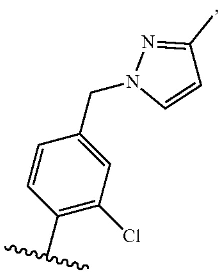
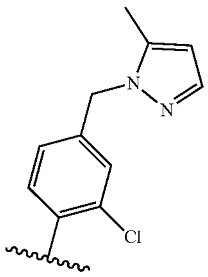
,
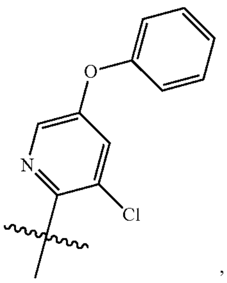
,
-continued
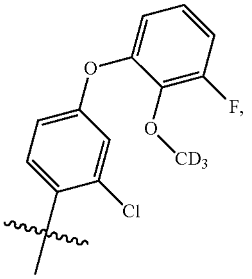
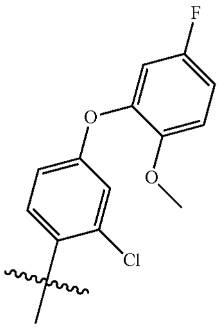
,
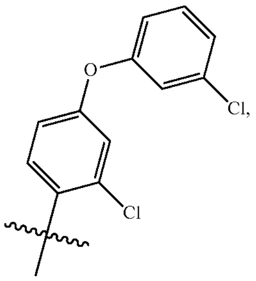
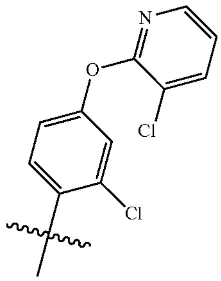
,
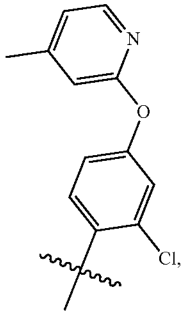
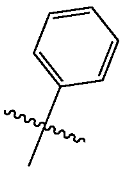
,
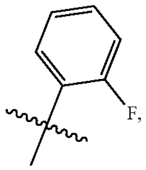
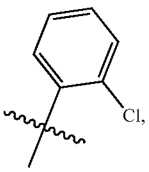
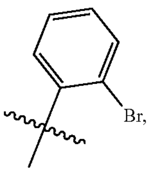
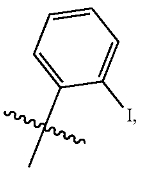

-continued
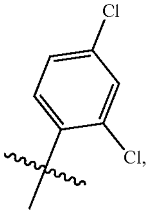
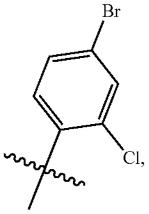
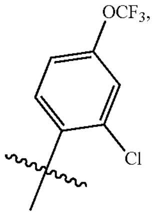
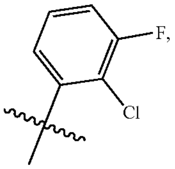
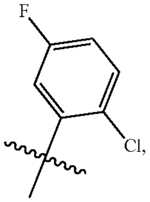
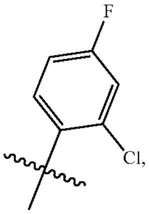
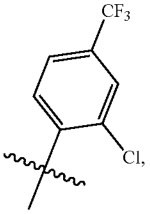
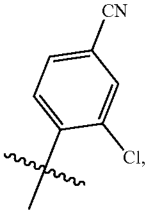
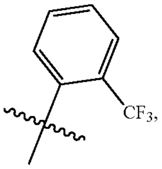
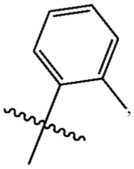
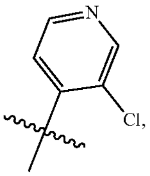
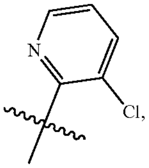
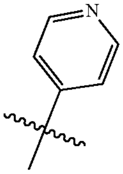
,
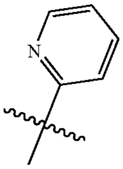
,
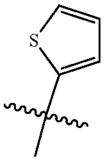
,
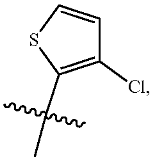
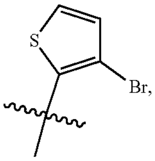
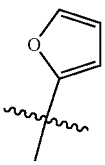
,
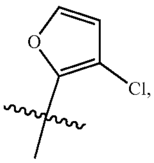
-continued
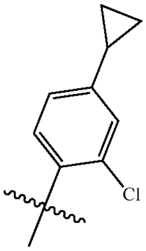
,
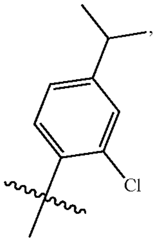
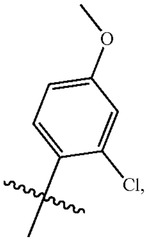
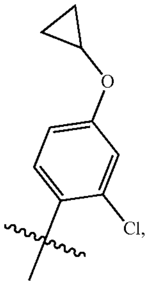
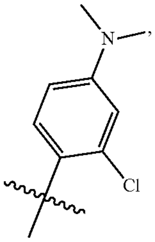
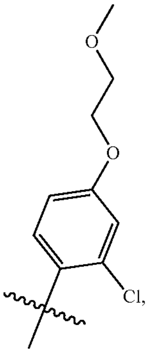
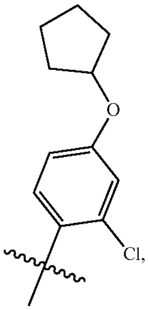
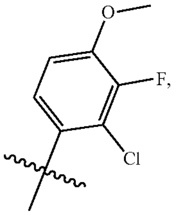
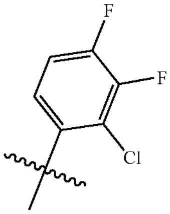
and
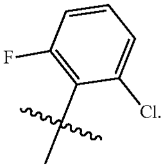
In an embodiment, in each formula, $R_1$, $R_2$, $R_3$, $R_4$, n, E, A, B, $G_1$, L, $G_2$, i are each independently the corresponding group in each specific compound in the embodiment.

In an embodiment, $R_1$, $R_2$, $R_3$, $R_4$, n, E, A, B, $G_1$, L, G, i are defined as follows:

$R_1$ and $R_2$ are each independently selected from: H, $C_{1-6}$ alkoxy, $C_{1-6}$ thioalkyl; or $R_1$ and $R_2$ combining with the carbon atoms to which they are attached form: carbonyl (C═O) or C═S; the $C_{1-6}$ alkoxy and the $C_{1-6}$ thioalkyl are each independently unsubstituted or substituted by 1, 2, 3 or 4 substituents independently selected from group S1;

$R_3$ and $R_4$ are each independently selected from: $C_{1-6}$ alkyl and $C_{3-20}$ cycloalkyl; or $R_3$ and $R_4$ combining with the carbon atoms to which they are attached form: $C_{3-20}$ cycloalkyl and 3- to 20-membered heterocyclyl; the $C_{1-6}$ alkyl, the $C_{3-20}$ cycloalkyl and the 3- to 20-membered heterocyclyl are each independently unsubstituted or substituted by 1, 2, 3 or 4 substituents independently selected from group S1;

n is 0;

E is $NR_5$, O or N; wherein, $R_5$ is H, $C_{1-6}$ alkyl, deuterated $C_{1-6}$ alkyl, —$C_{1-4}$ alkylene-hydroxy, —$C_{1-4}$ alkylene-$C_{1-6}$ alkoxy or —$C_{1-4}$ alkylene-$NR^aR^b$;

when E is $NR_5$ or O, "---" connected with E represents a single bond;

when E is N, "---" connected with E represents a double bond and $R_2$ is absent;

A is $CR_6$;

B is $CR_7$;

$G_1$ is $C_{6-14}$ aryl or 5- to 6-membered monocyclic heteroaryl; and the $C_{6-14}$ aryl and 5- to 6-membered monocyclic heteroaryl are each independently unsubstituted or substituted by 1, 2, 3 or 4 substituents independently selected from group S2;

$G_2$ is $C_{6-14}$ aryl or 5- to 6-membered monocyclic heteroaryl; and the $C_{6-14}$ aryl and the 5- to 6-membered monocyclic heteroaryl are each independently unsubstituted or substituted by 1, 2, 3 or 4 substituents independently selected from group S2;

L is $CR^8R^9$ or O;

i is 0 or 1.

In an embodiment, the compound of the present disclosure is selected from the compounds prepared in the embodiments of the present disclosure. For example,

Z1

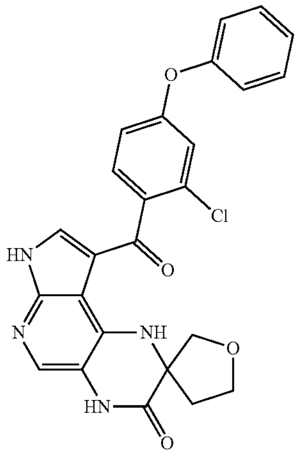

-continued

Z1-1

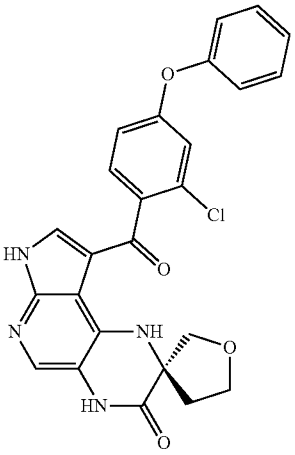

Z1-2

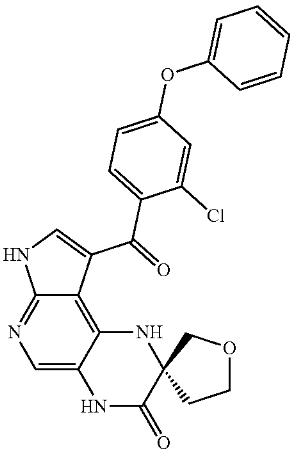

Z2

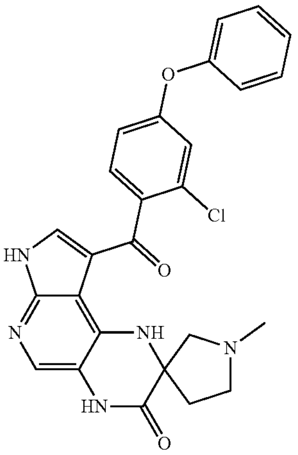

-continued
Z2-1
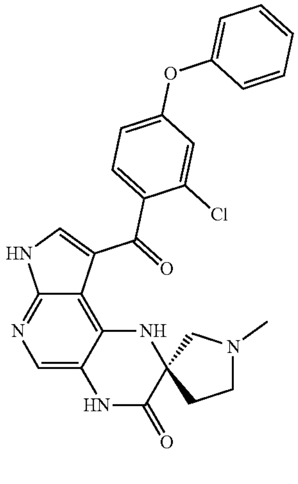
Z2-2
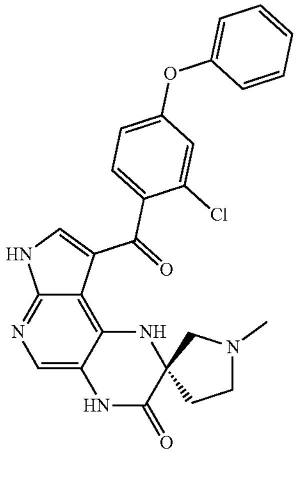
Z3
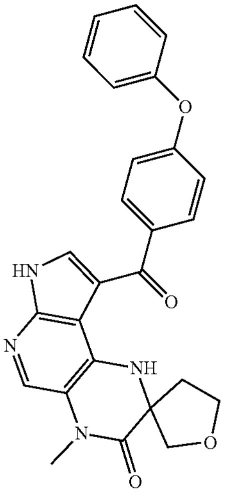
-continued
Z4
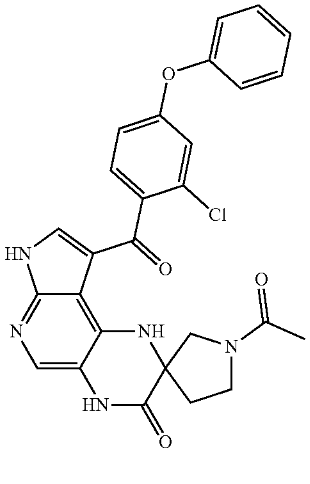
Z4-1
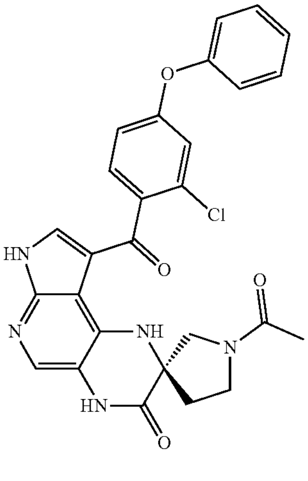
Z4-2
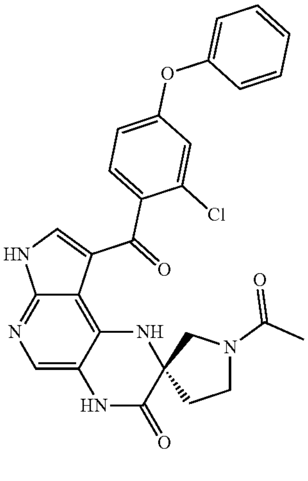

-continued
Z5
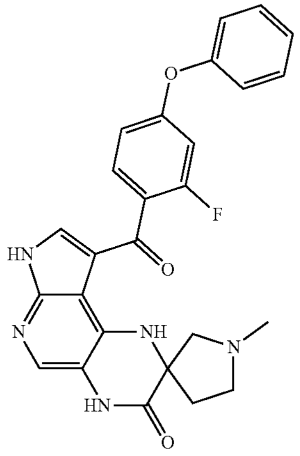
Z6
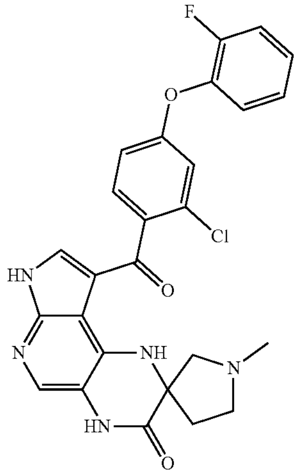
Z7
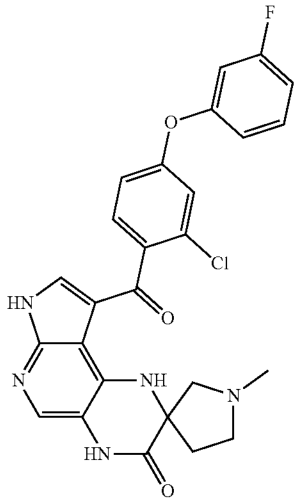
-continued
Z8
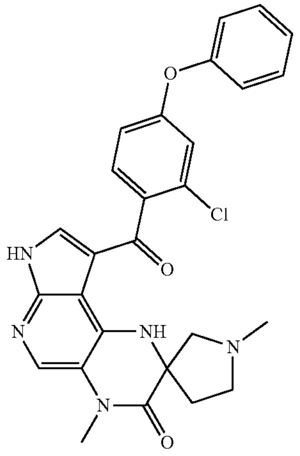
Z9
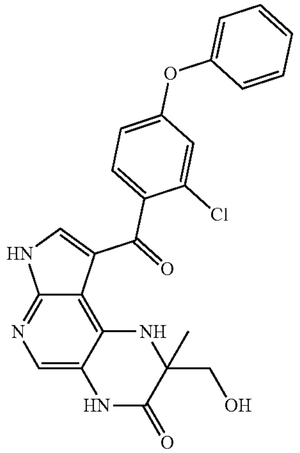
Z9-1
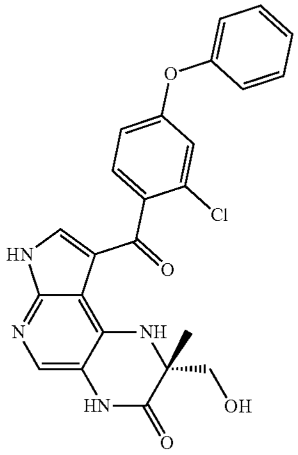

-continued
Z9-2
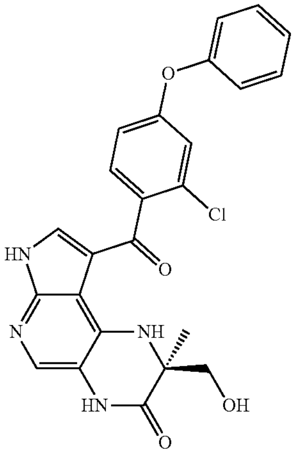
Z10
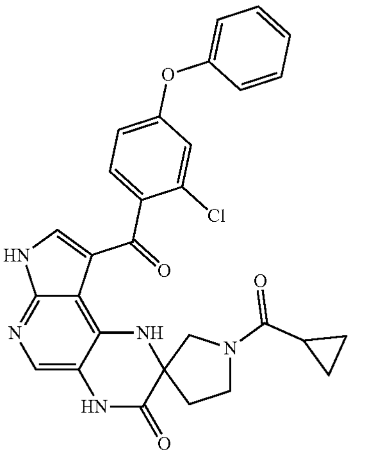
Z11
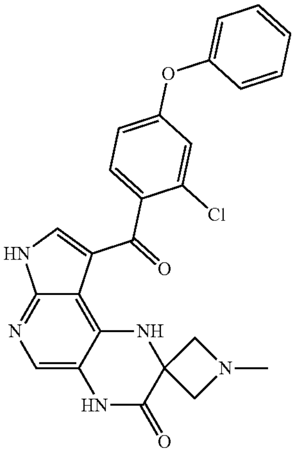
-continued
Z12
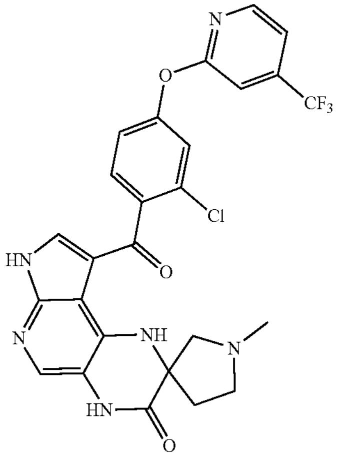
Z13
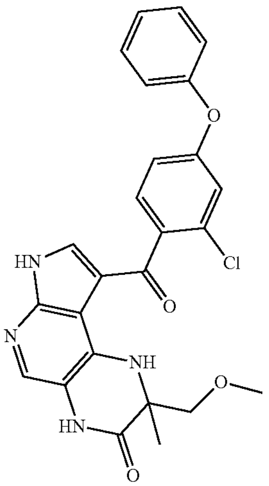
Z13-1
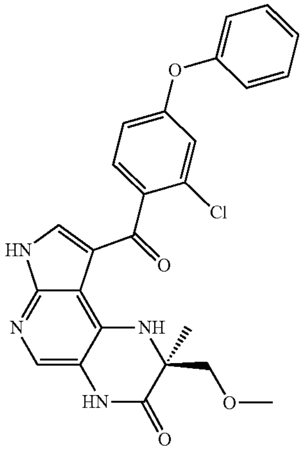

-continued
Z13-2
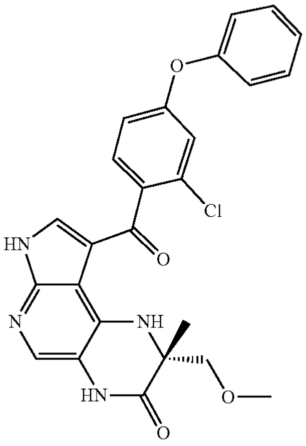
Z14
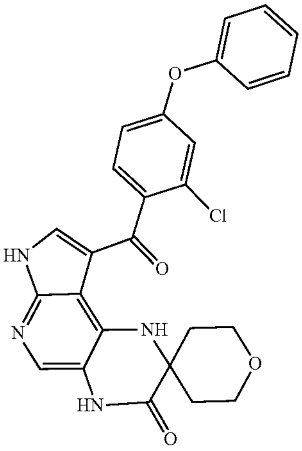
Z15
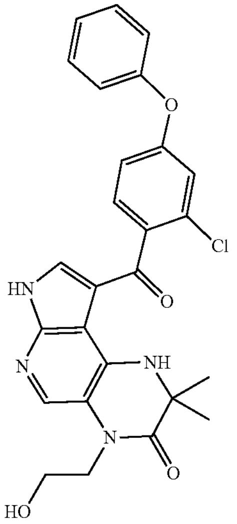
-continued
Z16
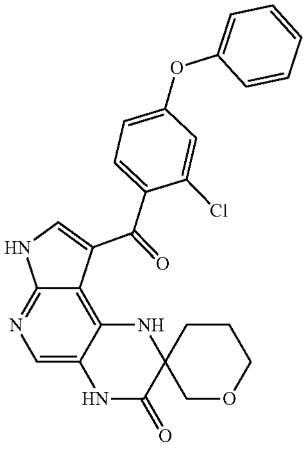
Z16-1
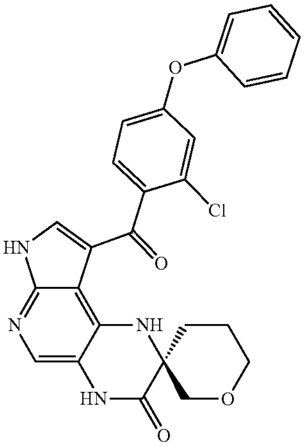
Z16-2
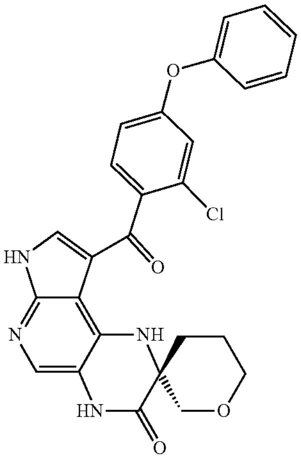

-continued
Z17
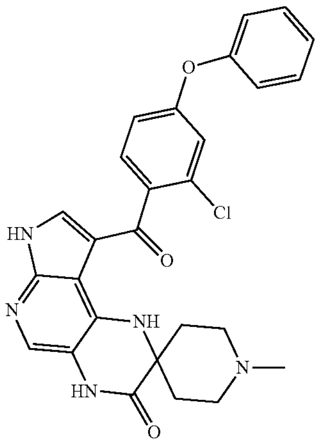
Z18
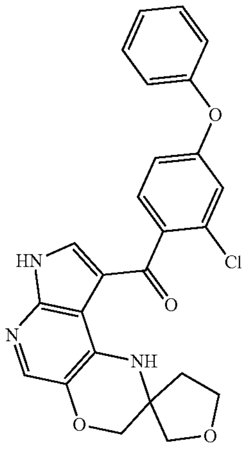
Z19
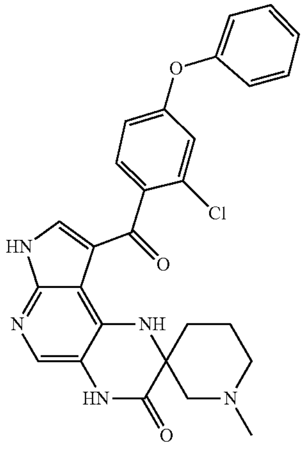
-continued
Z20
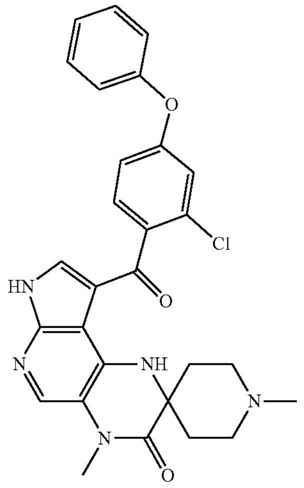
Z21
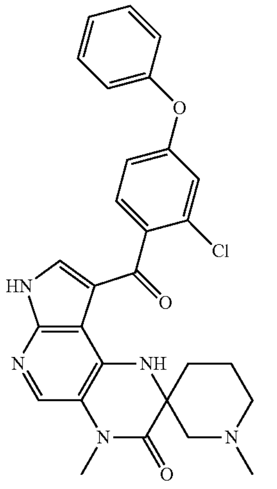
Z22
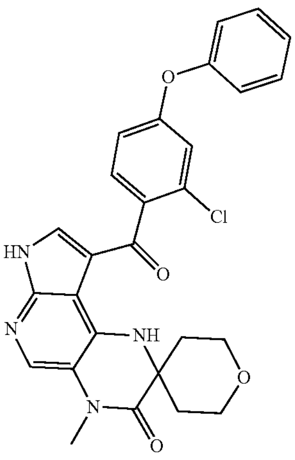

-continued
Z23
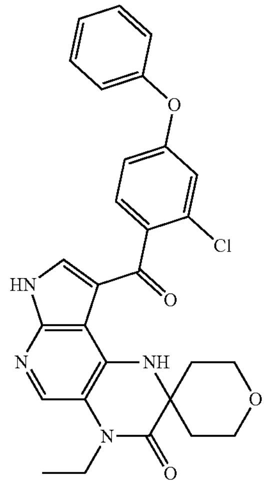
Z24-1
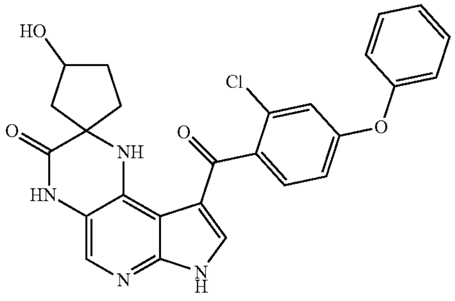
Z24-a
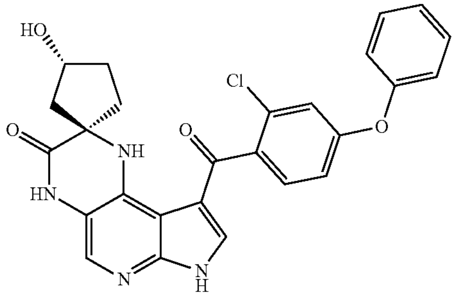
Z24-b
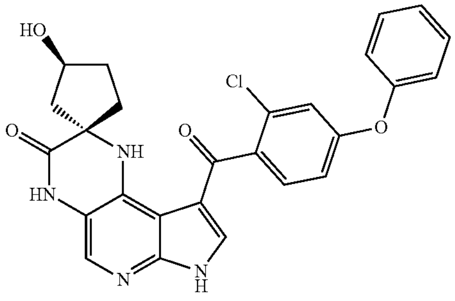
-continued
Z24-2
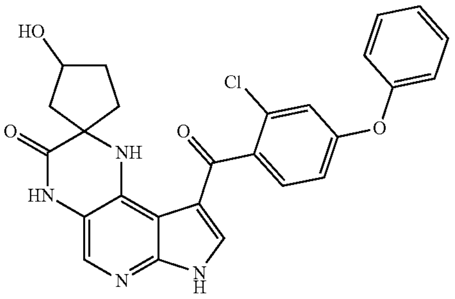
Z24-d
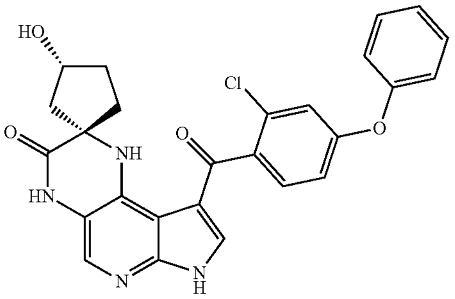
Z24-c
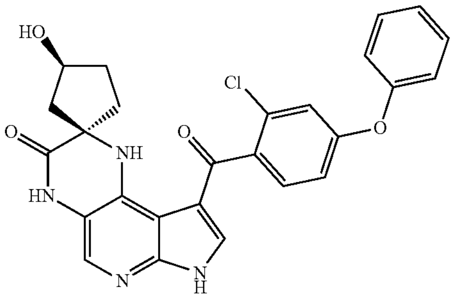
Z25
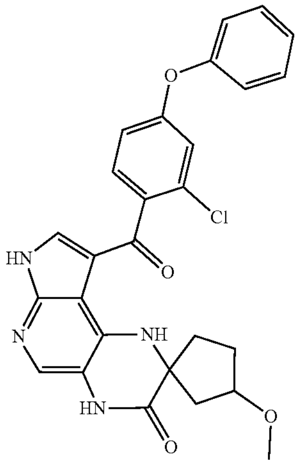

-continued
Z25-1
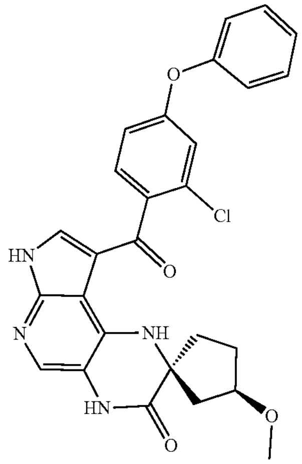
Z25-2
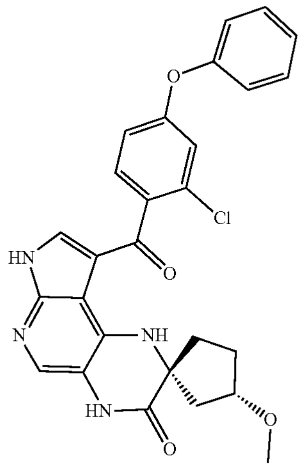
Z25-3a
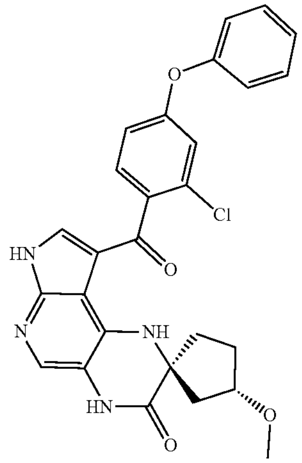
-continued
Z25-3b
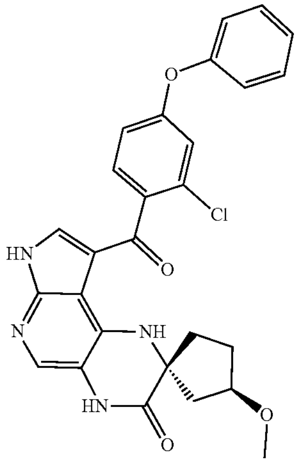
Z26
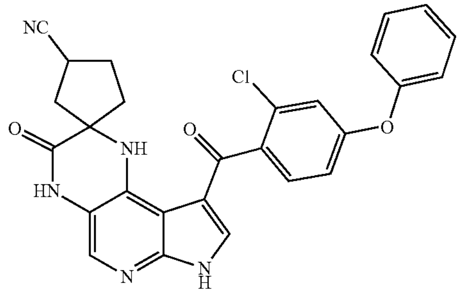
Z26-1
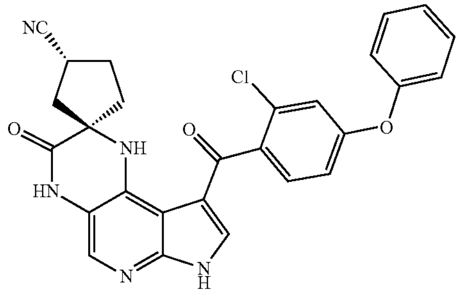
Z26-2
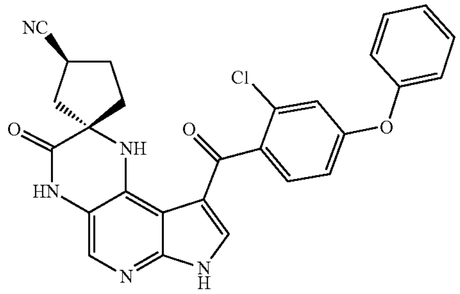

-continued
Z26-3
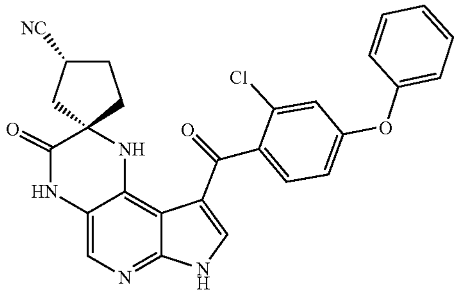
Z26-4
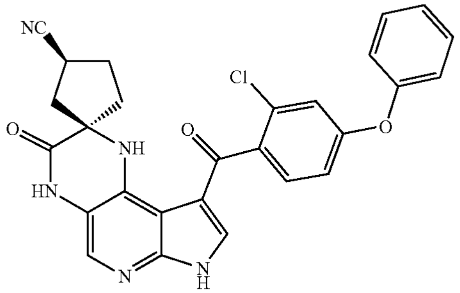
Z27
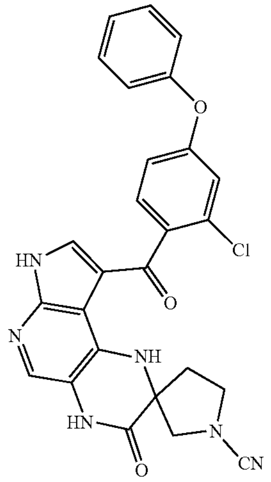
Z28
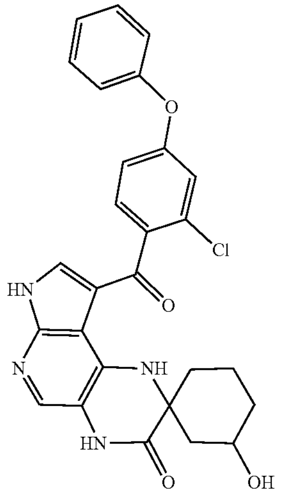
-continued
Z29
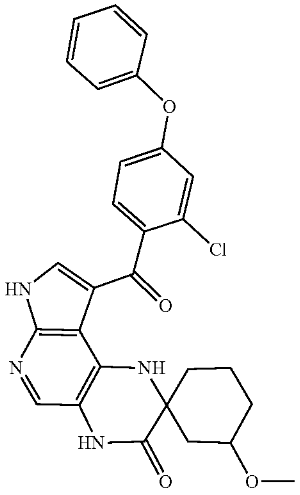
Z30
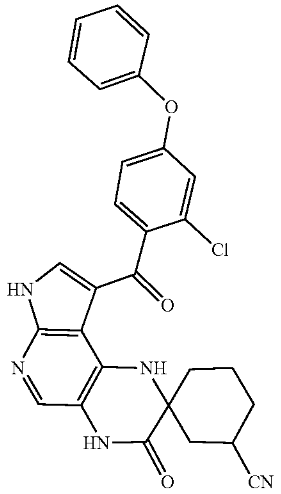
Z31
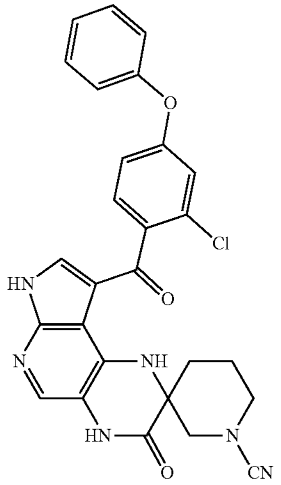

-continued
Z32
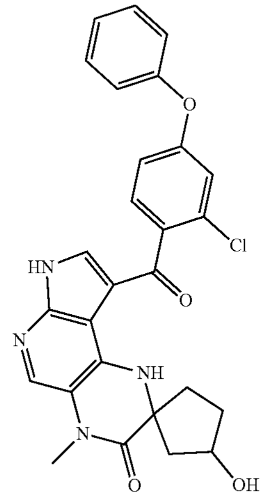
Z33
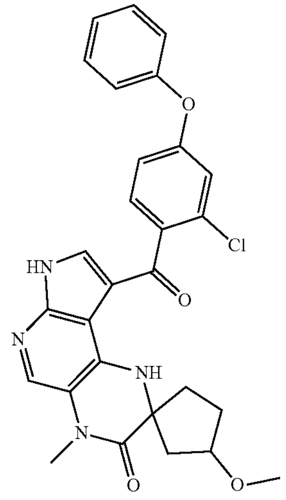
Z34
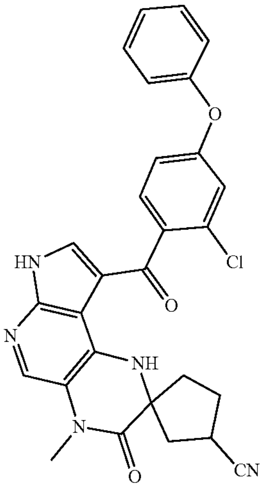
-continued
Z35
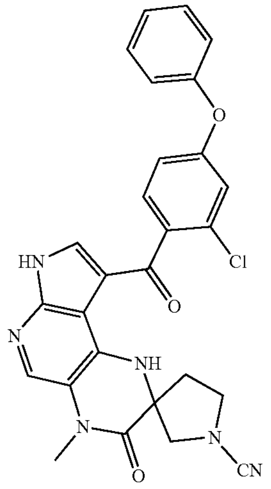
Z36
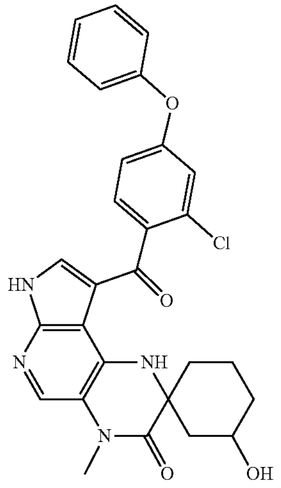
Z37
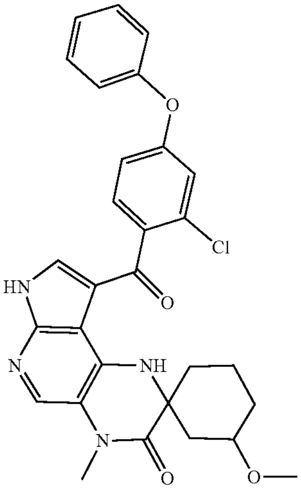

-continued
Z38
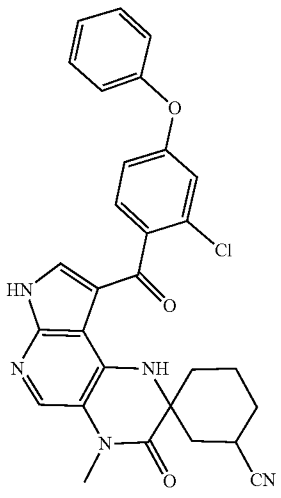
Z39
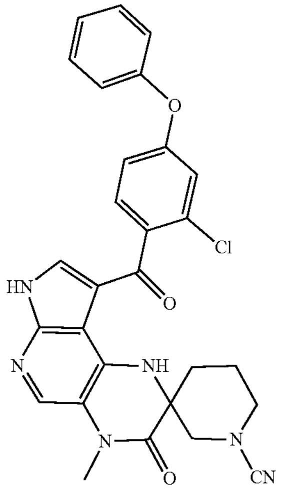
Z40
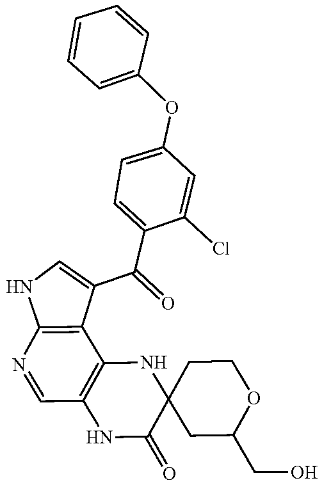
-continued
Z41-2
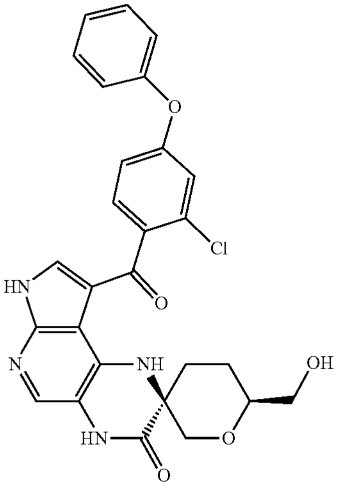
Z41-2a
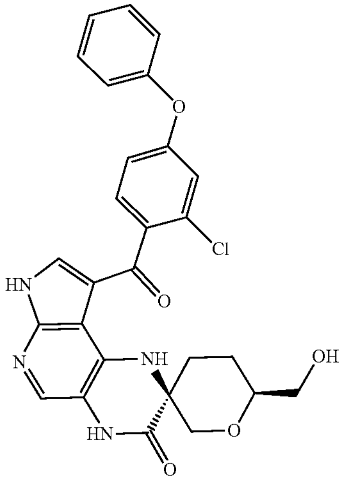
Z41-2b
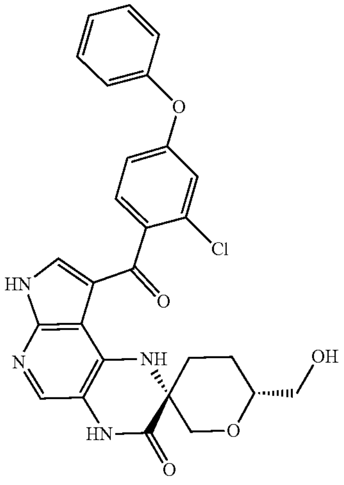

-continued
Z42
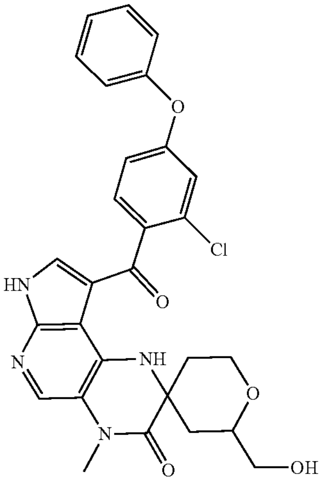
Z43
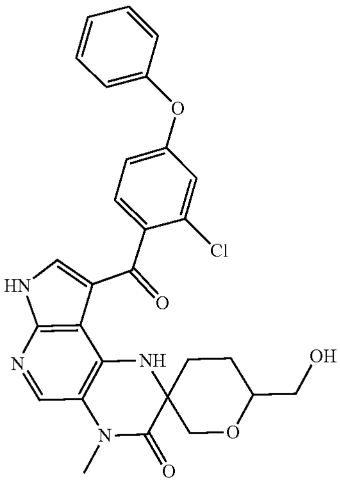
Z44
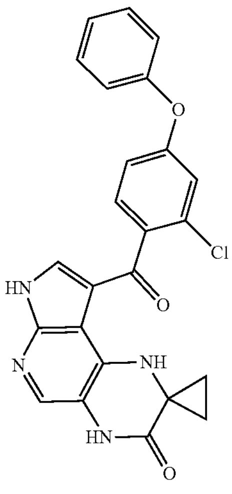
-continued
Z45
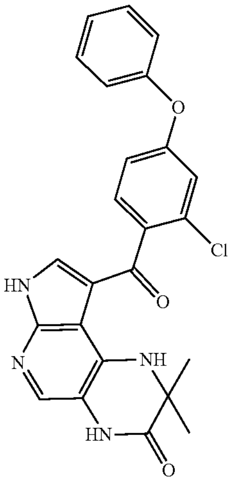
Z46
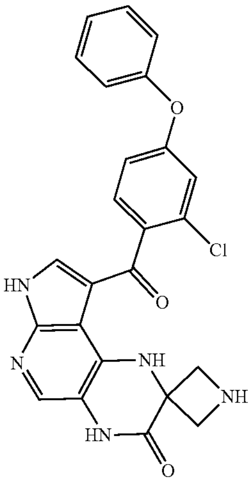
Z47
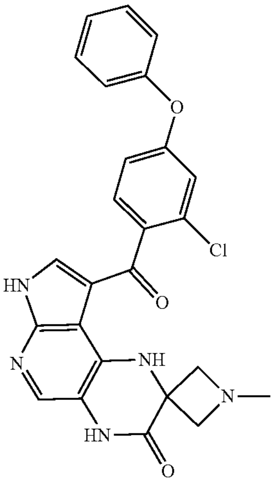

-continued
Z48
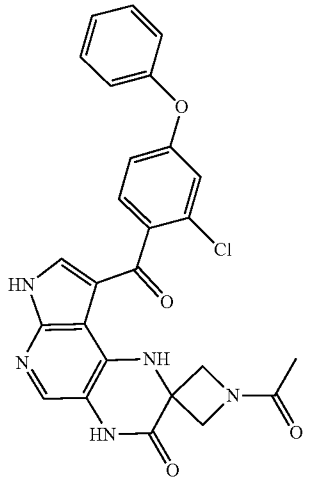
Z49
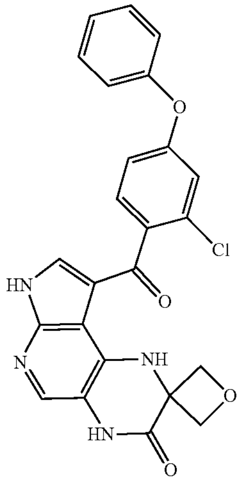
Z50
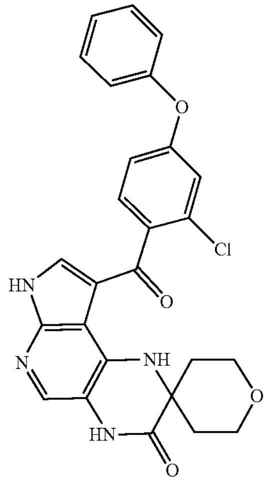
-continued
Z51
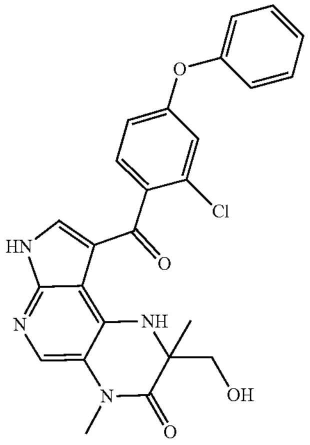
Z52
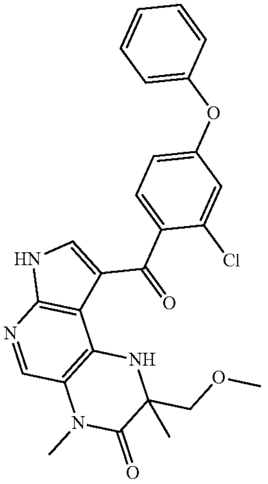
Z52-1
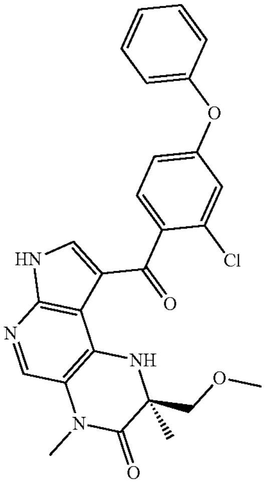

-continued
Z52-2
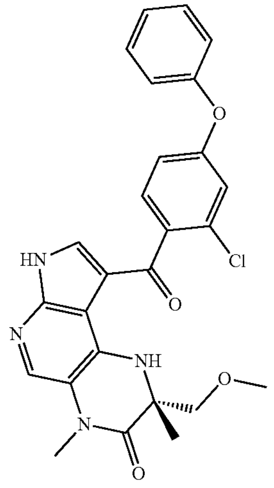
Z53-1
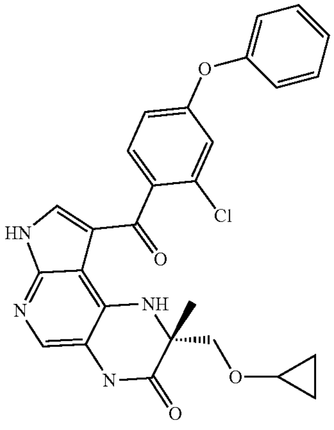
Z54-1
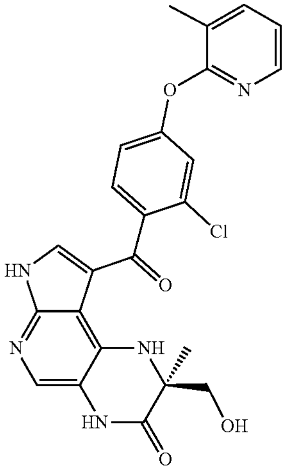
-continued
Z55
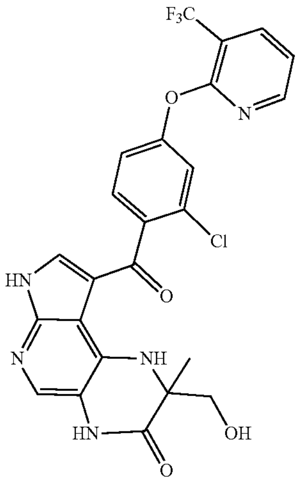
Z56
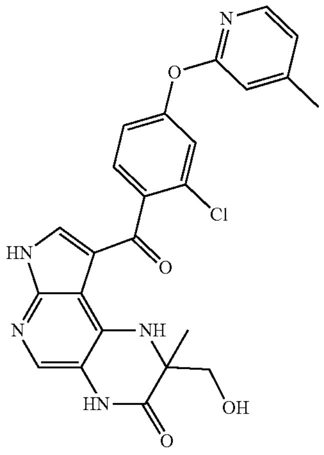
Z57
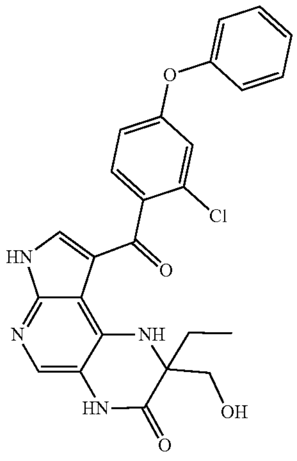

-continued
Z58
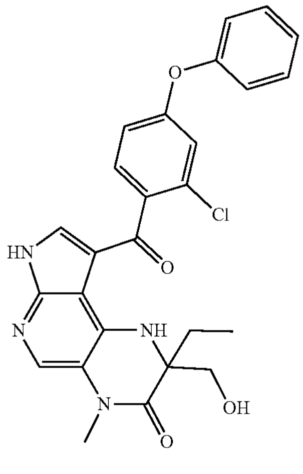
Z59
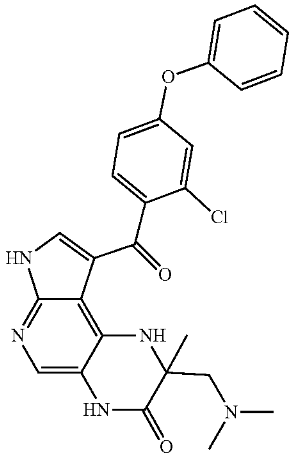
Z60
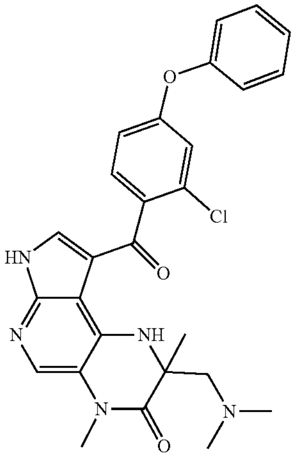
-continued
Z61
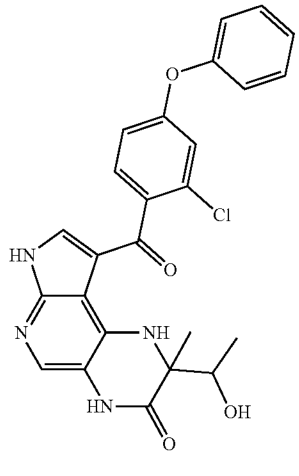
Z62
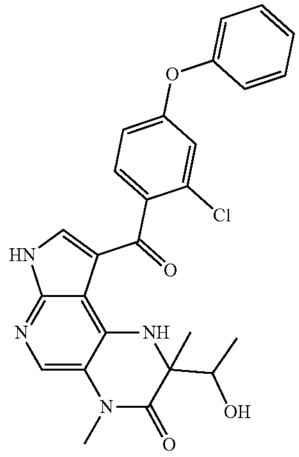
Z63
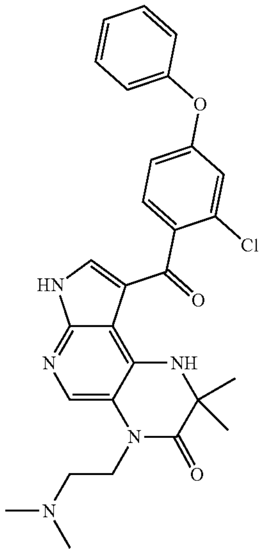

-continued
Z64
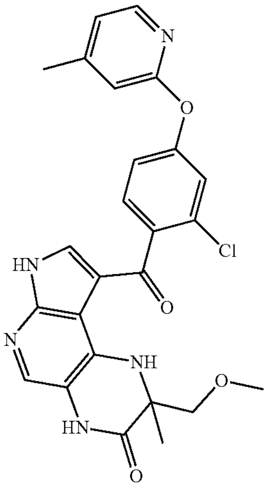
Z64-1
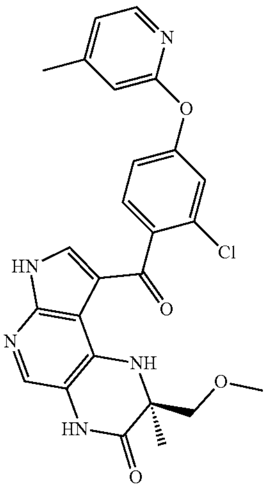
Z64-2
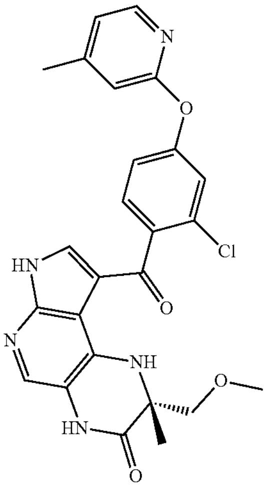
-continued
Z65
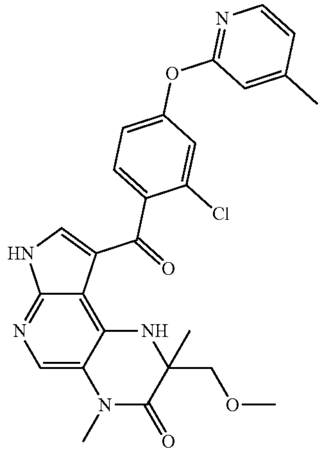
Z66
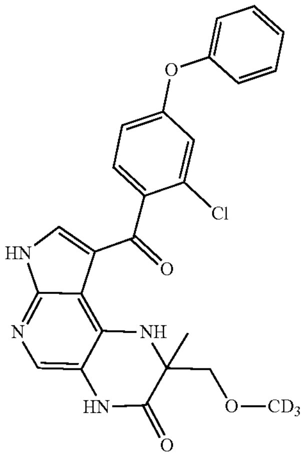
Z66-1
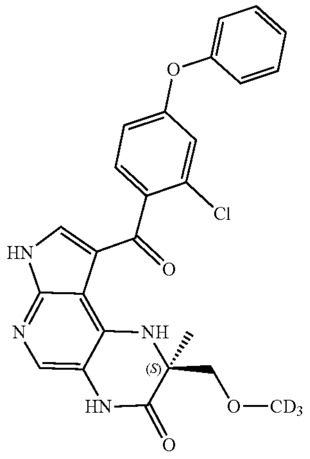

Z66-2
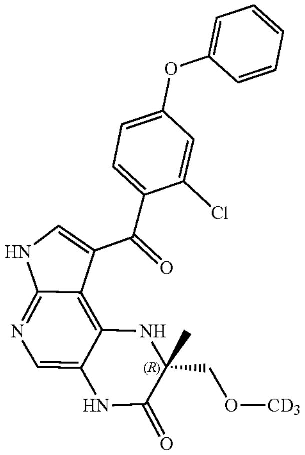
Z67
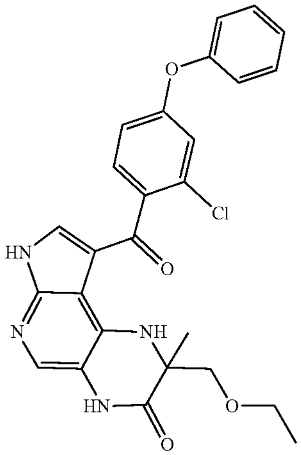
Z67-1
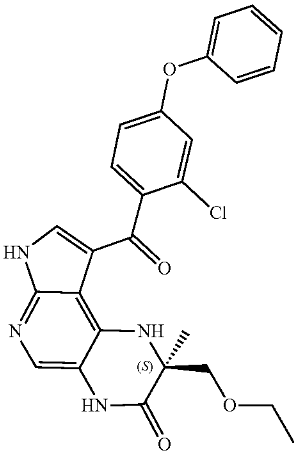
Z67-2
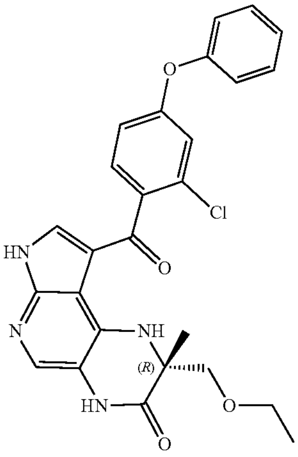
Z68
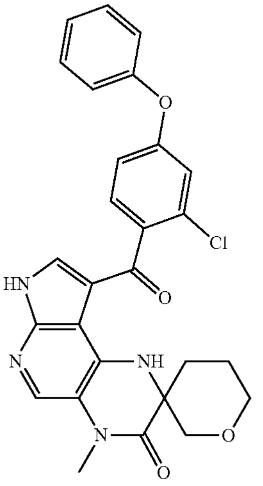
Z69
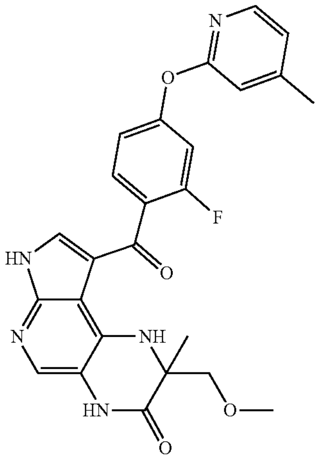

-continued
Z69-1
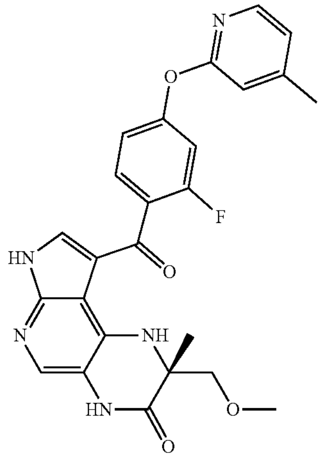
Z69-2
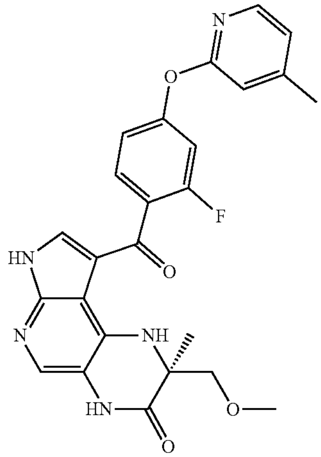
Z70
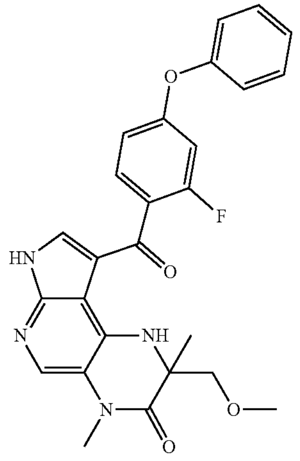
-continued
Z71
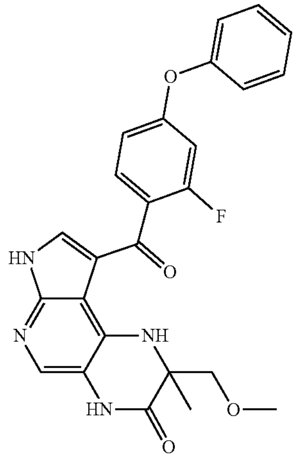
Z71-1
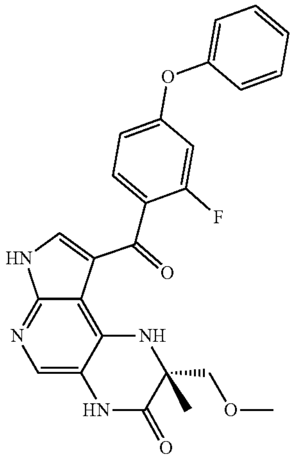
Z71-2
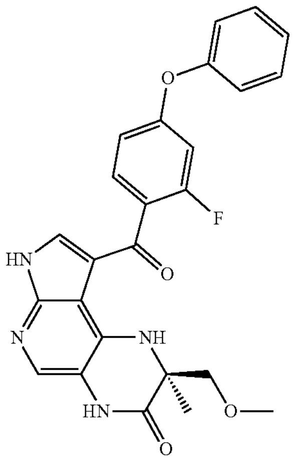

-continued
Z72
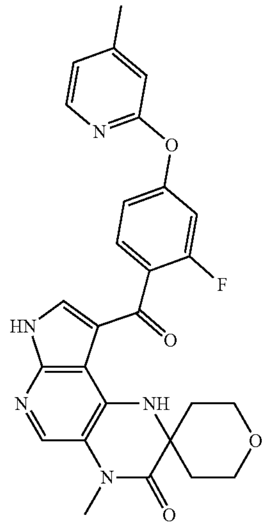
Z73
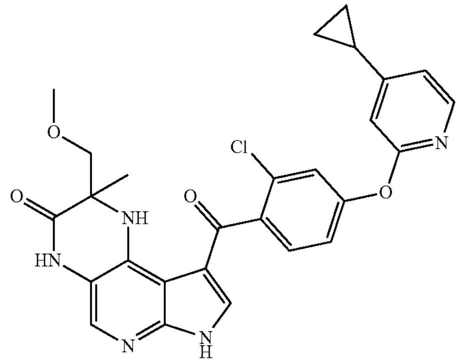
Z73-1
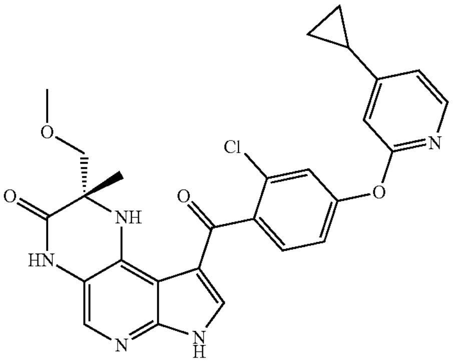
Z73-2
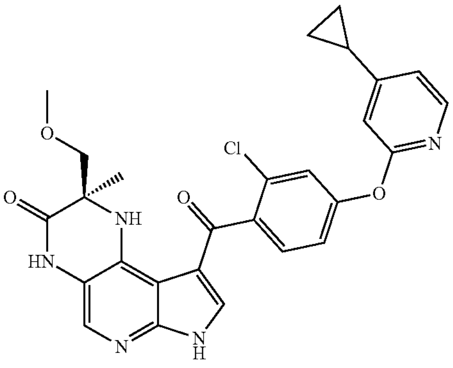
-continued
Z74
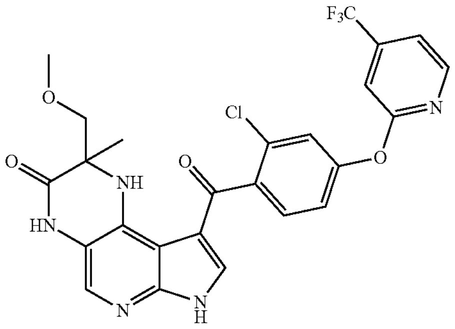
Z75
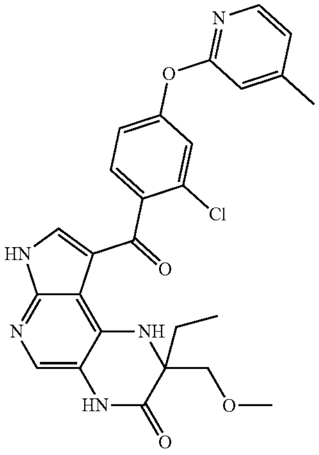
Z76
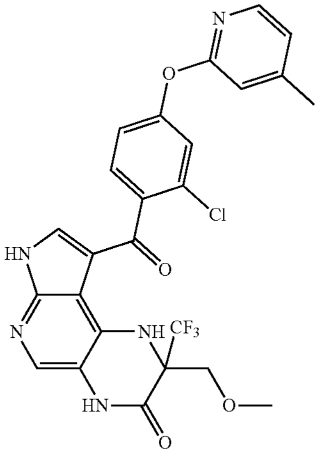

-continued
Z77
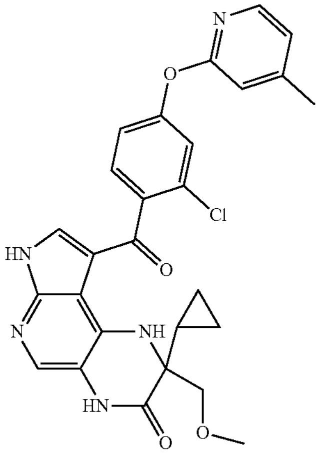
Z78
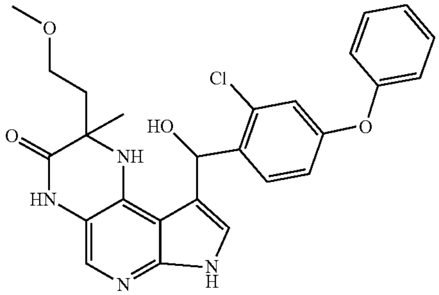
Z78-1
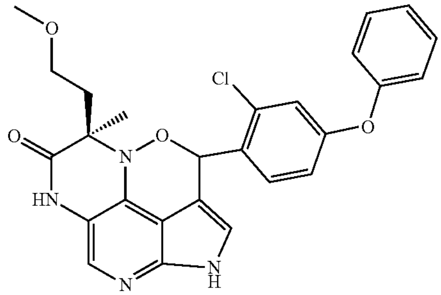
Z78-2
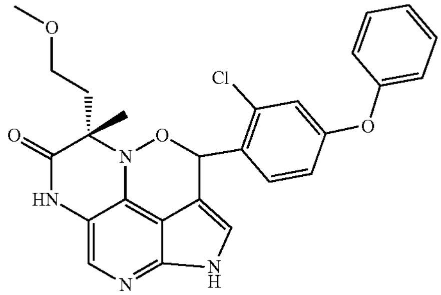
-continued
Z79
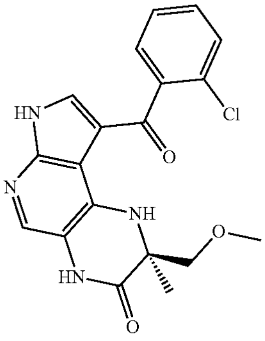
Z80
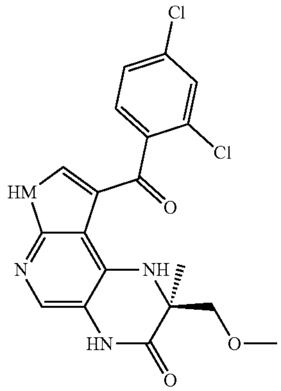
Z81
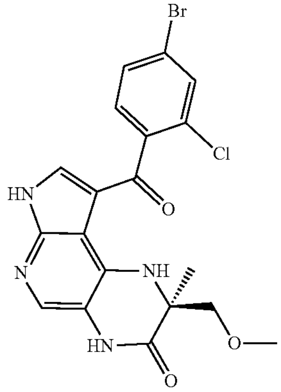
Z82
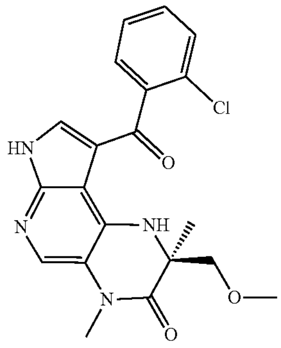

-continued
Z836
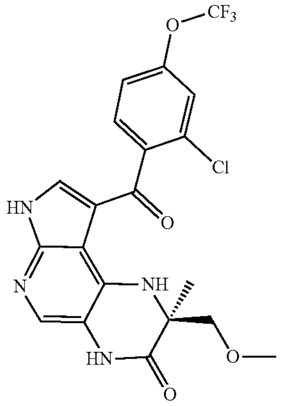
Z84
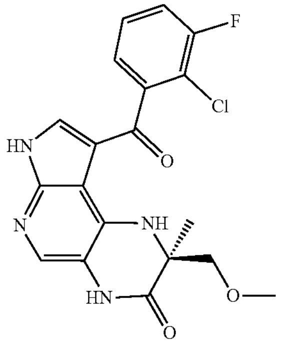
Z85
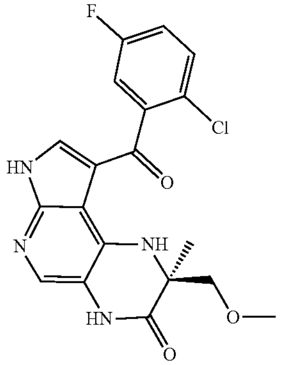
Z86
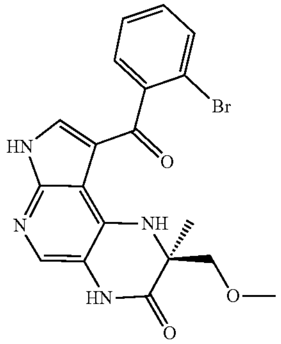
-continued
Z87
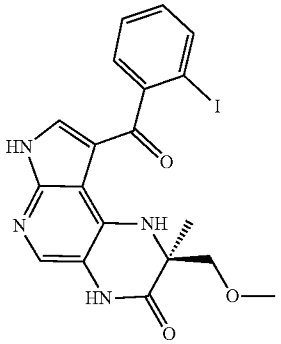
Z88
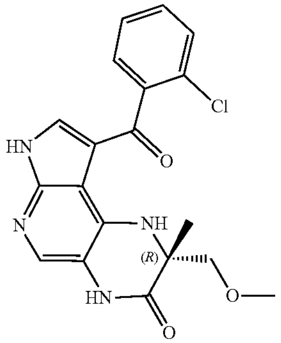
Z89
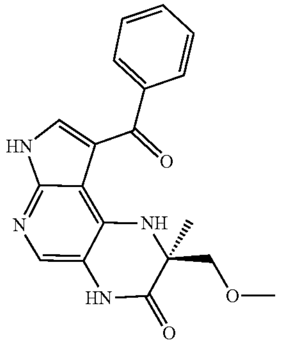
Z90
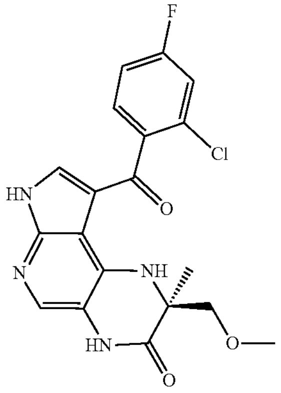

-continued
Z91
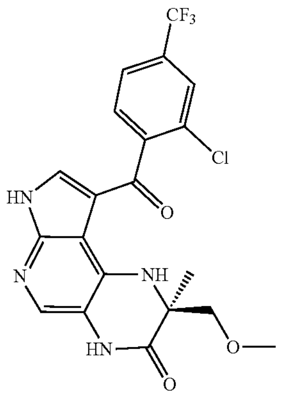
Z92
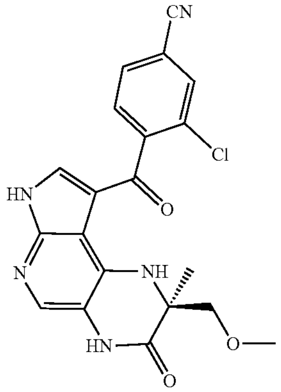
Z93
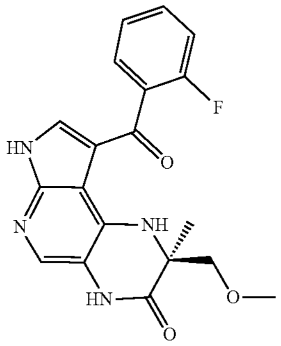
Z94
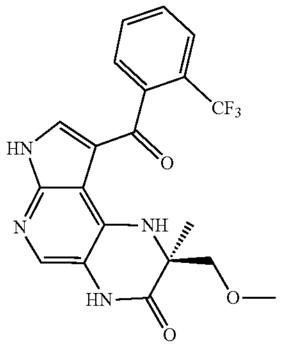
-continued
Z95
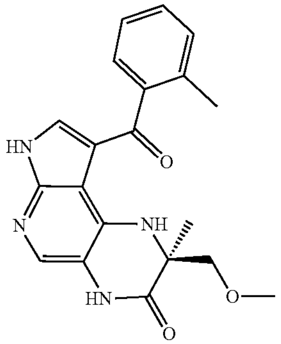
Z96
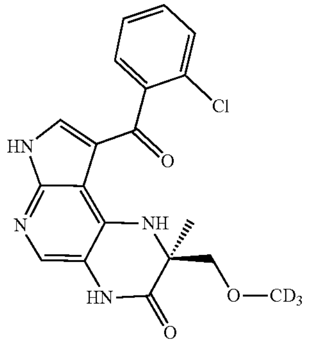
Z97
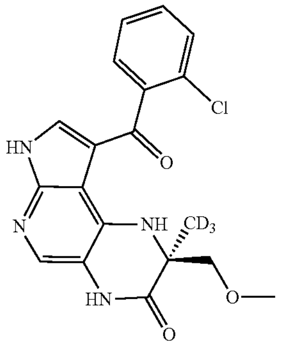
Z98
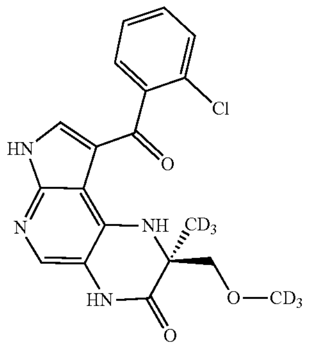

-continued
Z99
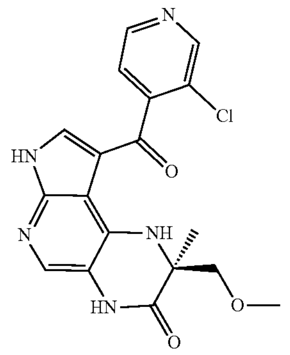
Z100
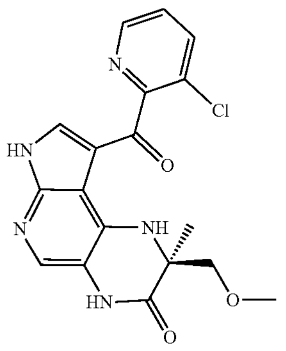
Z101
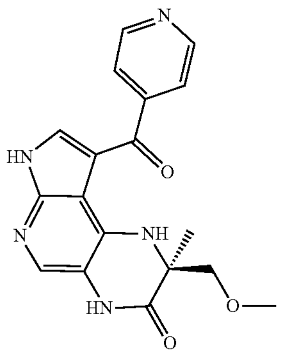
Z102
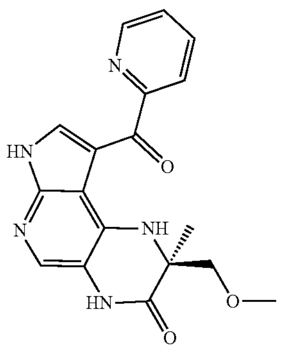
-continued
Z103
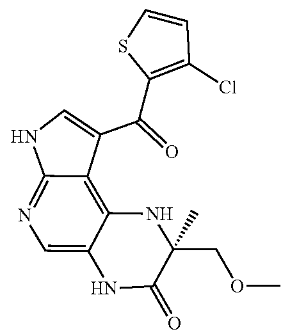
Z104
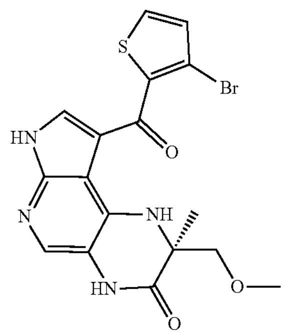
Z105
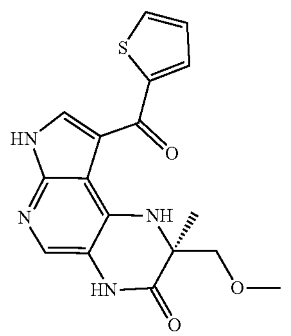
Z106
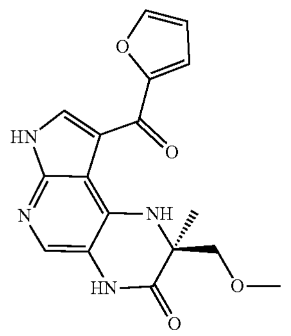

-continued
Z107
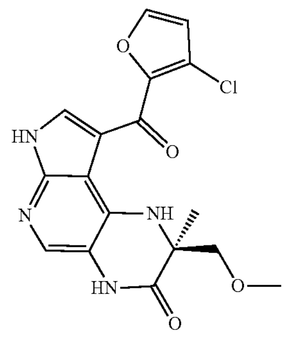
Z108
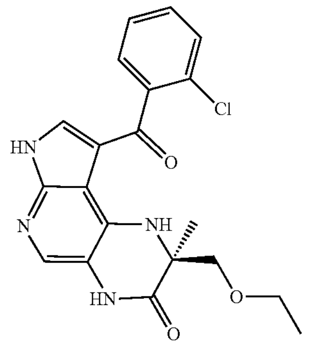
Z109
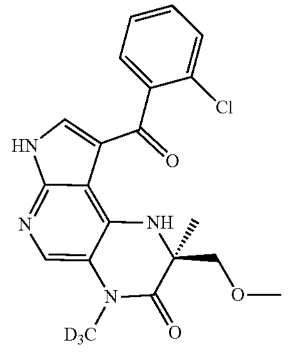
Z110
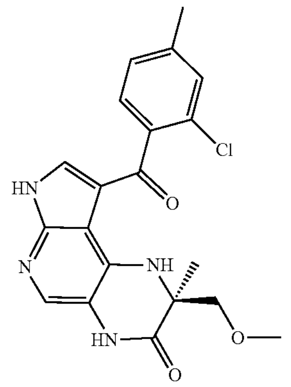
-continued
Z111
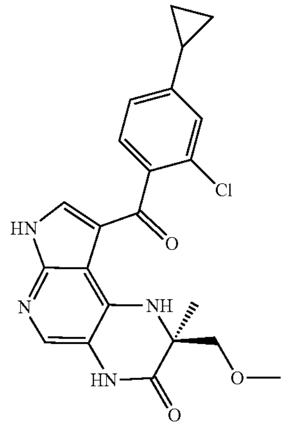
Z112
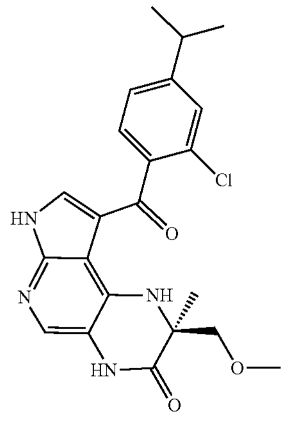
Z113
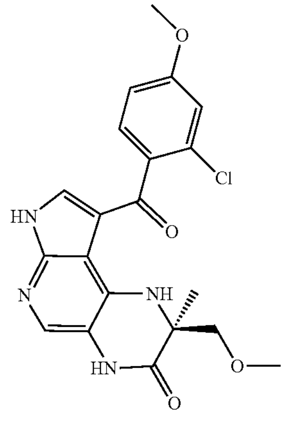

-continued
Z114
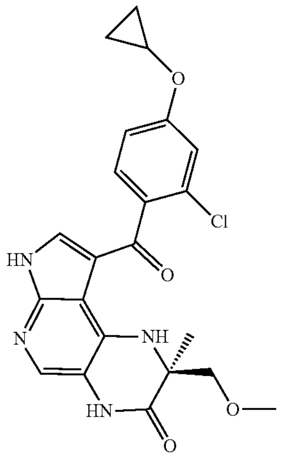
Z115
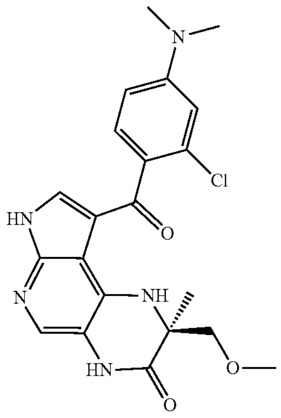
Z116
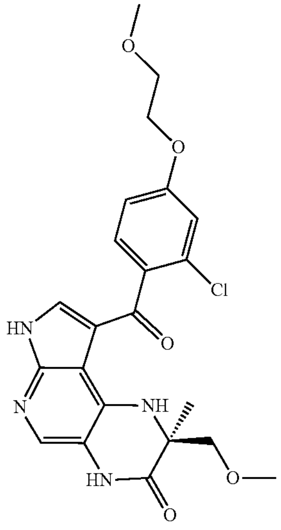
-continued
Z117
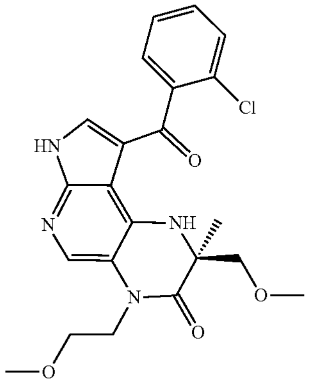
Z118
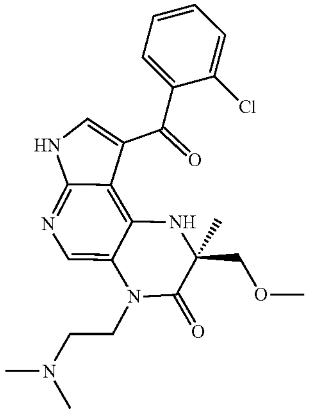
Z119
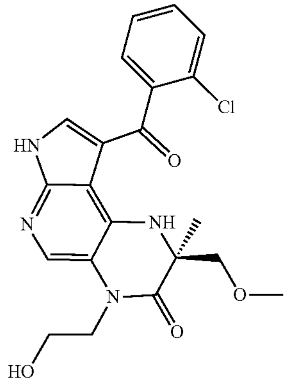
Z120
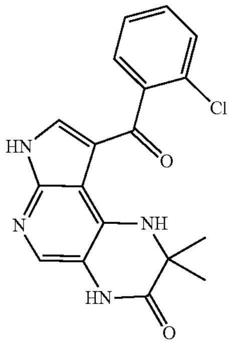

-continued
Z121
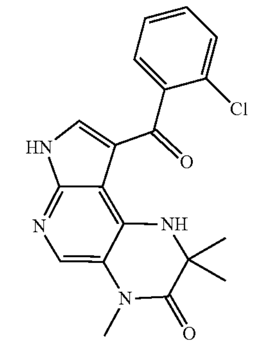
Z122
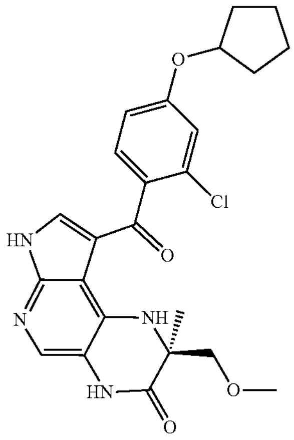
Z124-1
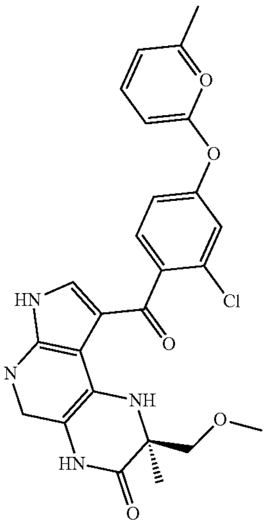
-continued
Z125-1
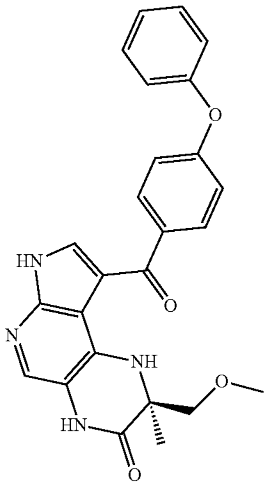
Z126
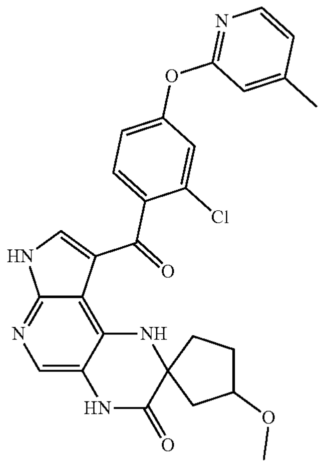
Z127-1
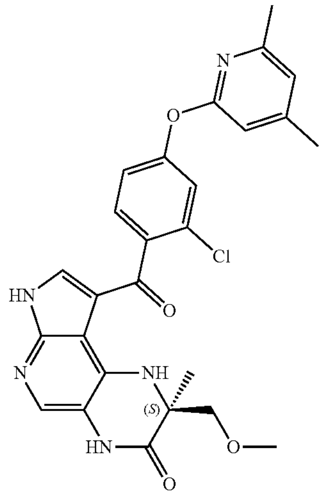

Z131
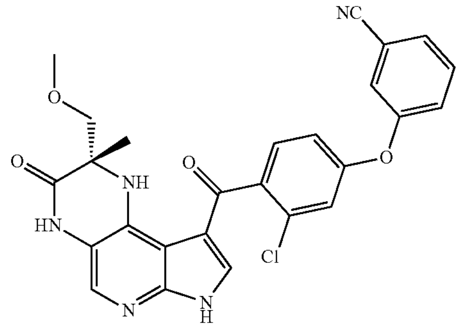
Z132
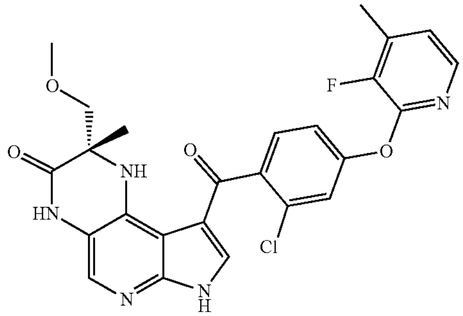
Z133
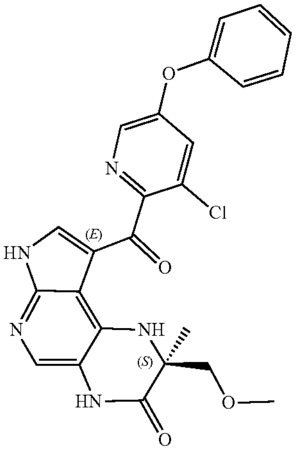
Z134
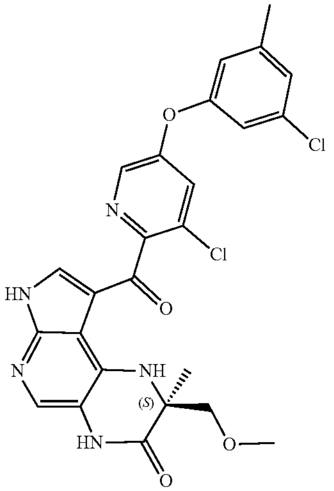
Z135
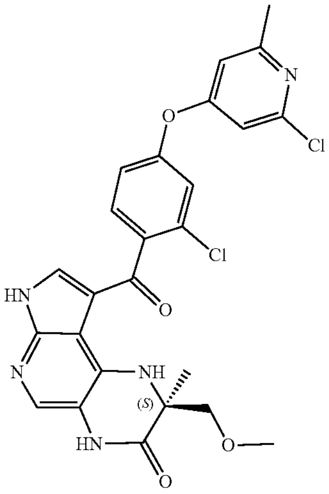
Z136
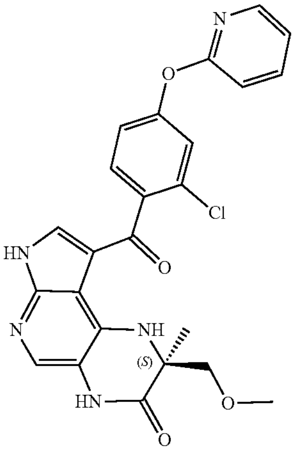
Z138
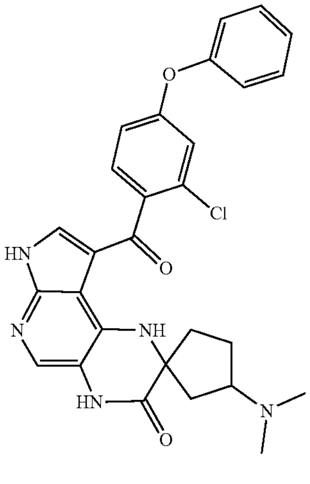

-continued
Z139
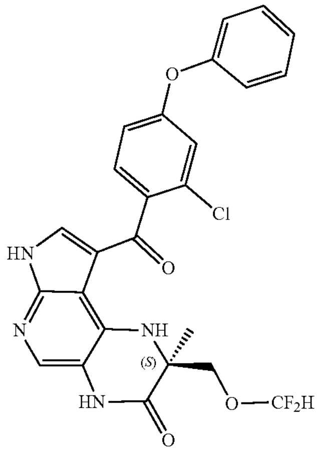
Z140
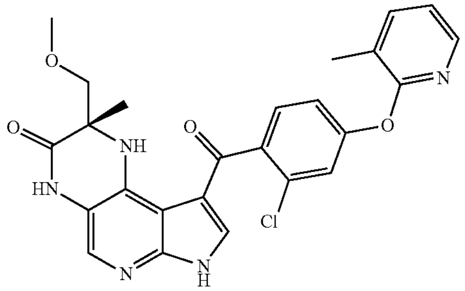
Z141
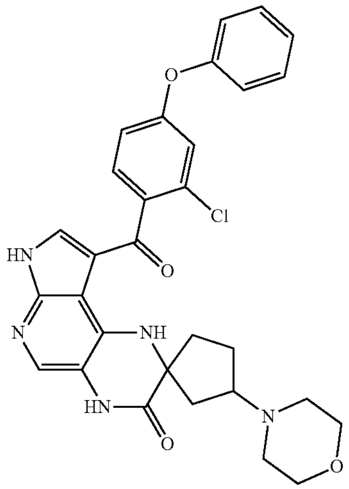
-continued
Z142
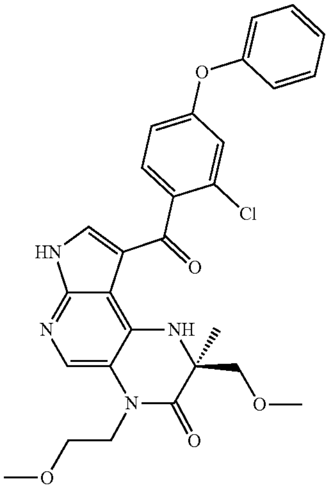
Z143
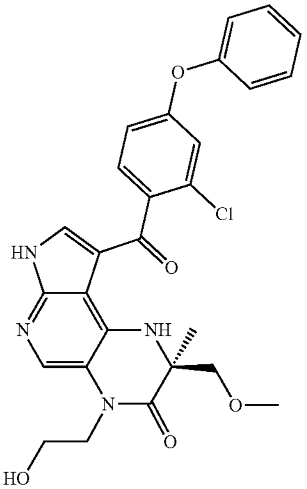
Z144
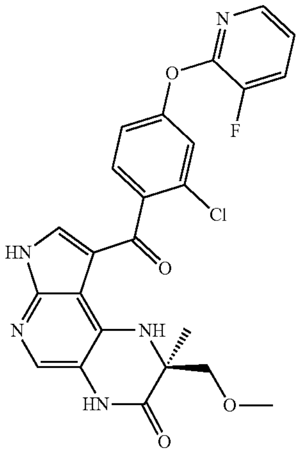

-continued
Z145
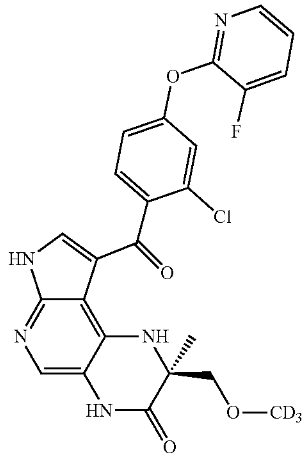
Z146
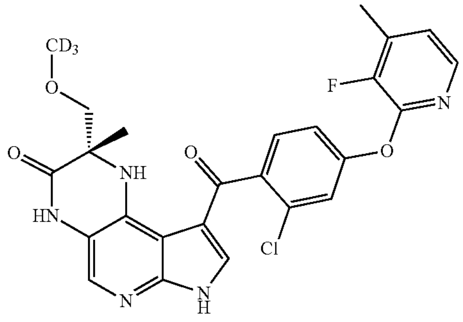
Z149
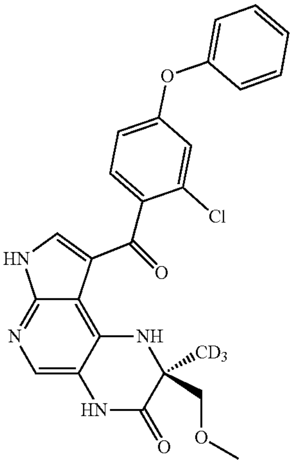
-continued
Z150
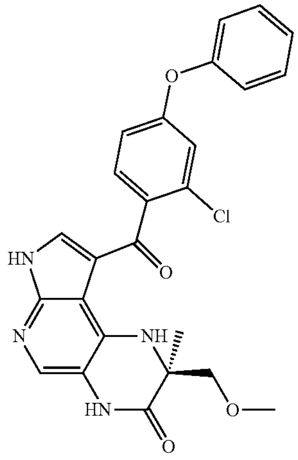
Z153
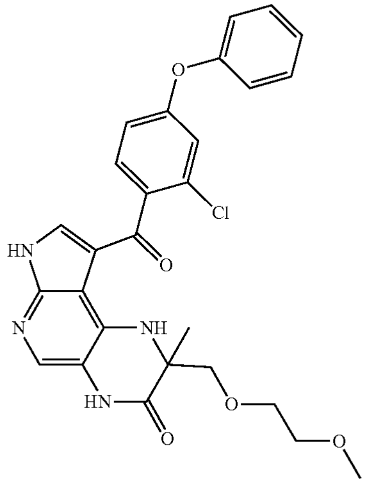
Z153-1
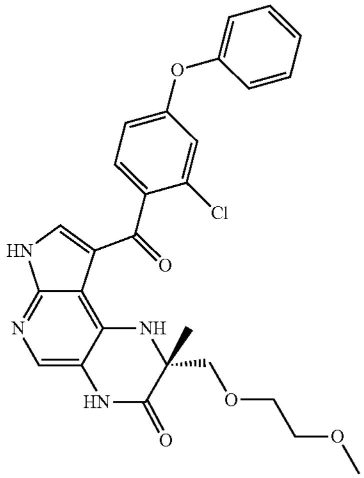

-continued
Z153-2
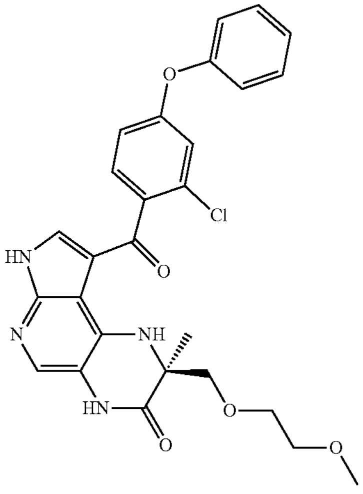
Z155
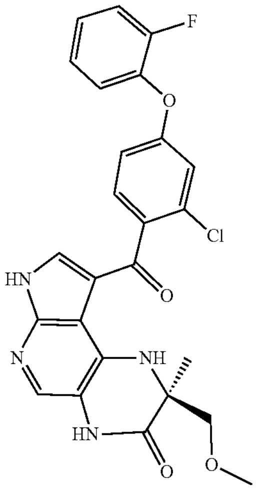
Z156
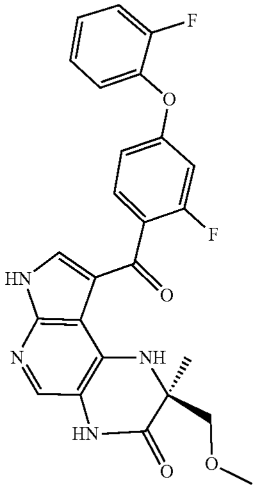
-continued
Z157
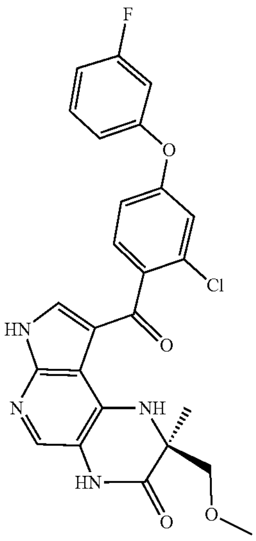
Z160
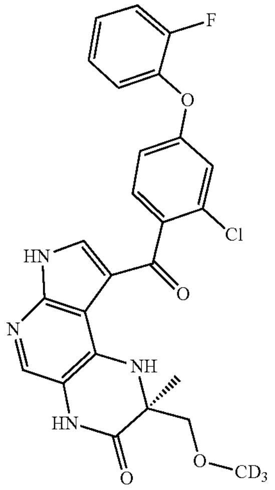
Z161
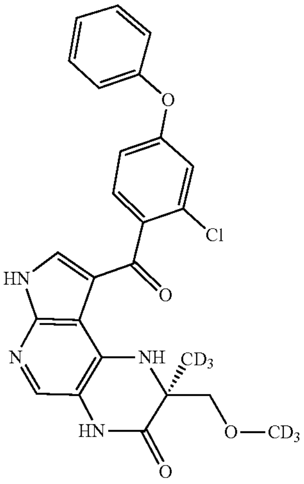

-continued
Z162
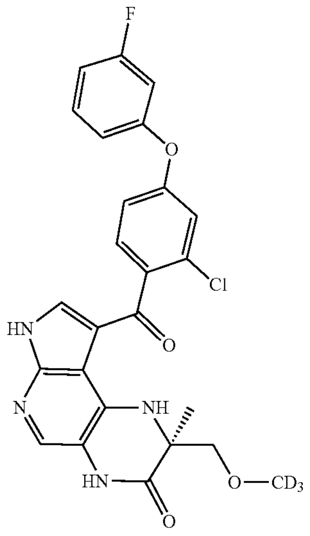
Z163
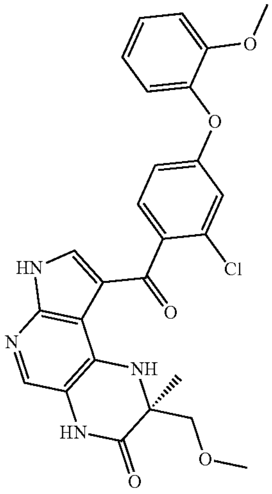
Z164
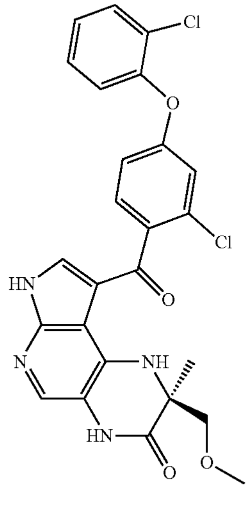
-continued
Z166
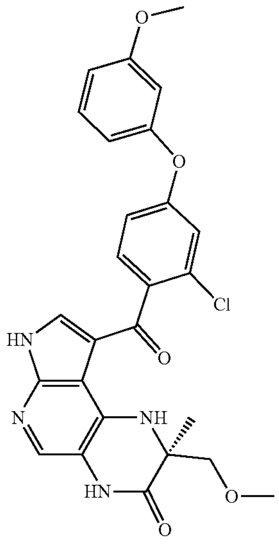
Z167
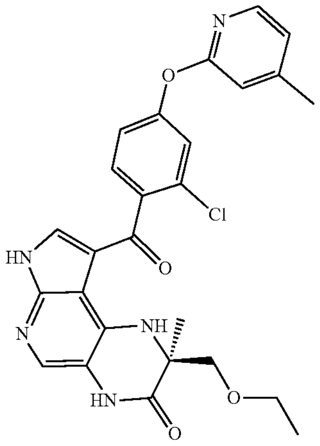
Z168
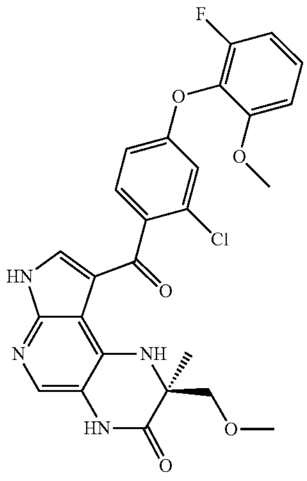

-continued
Z170
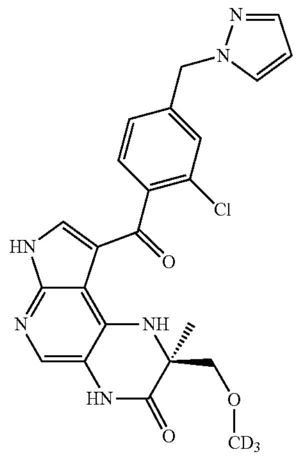
Z174
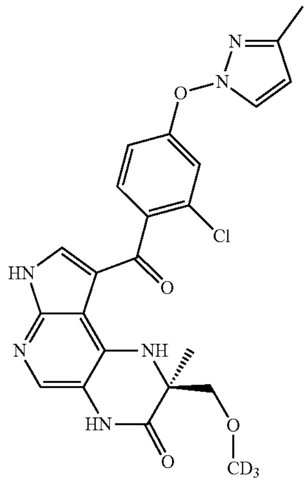
Z175
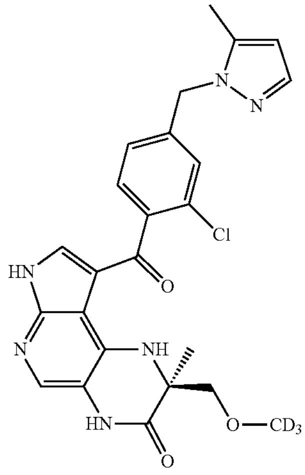
-continued
Z173
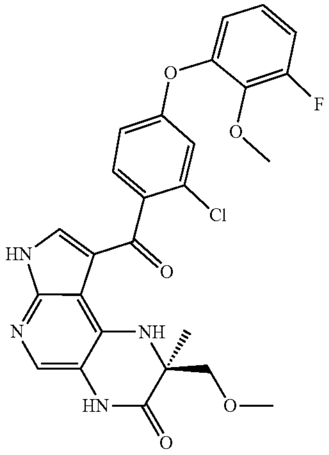
Z177
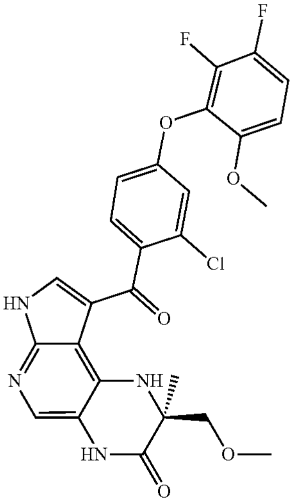
Z187
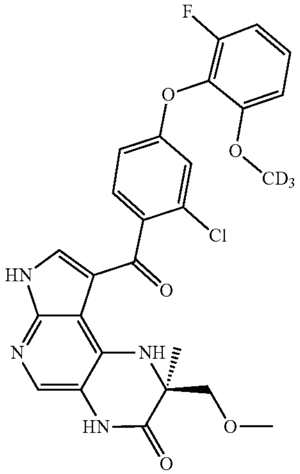

-continued
Z189-1
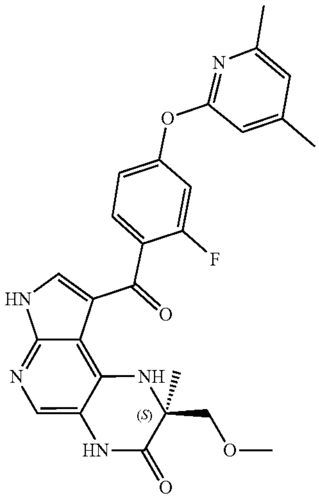
Z190
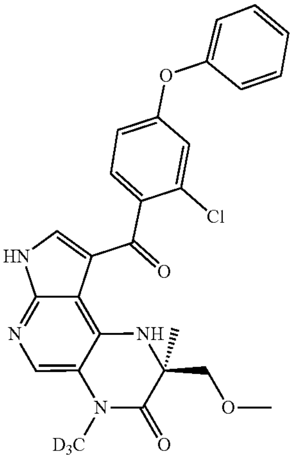
Z191
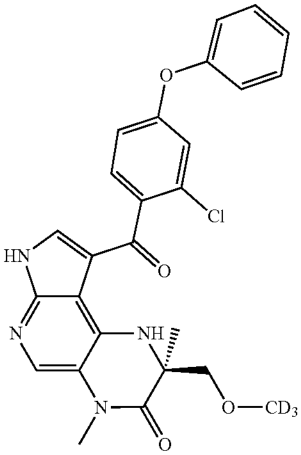
-continued
Z192
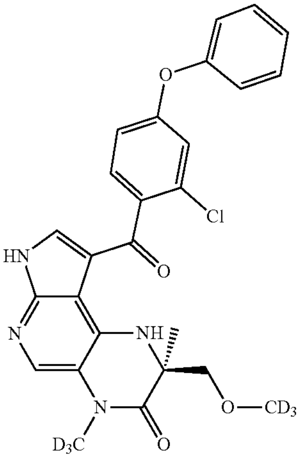
Z193
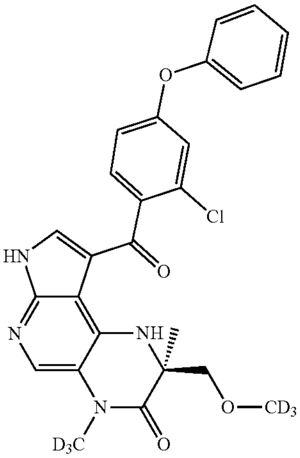
Z194
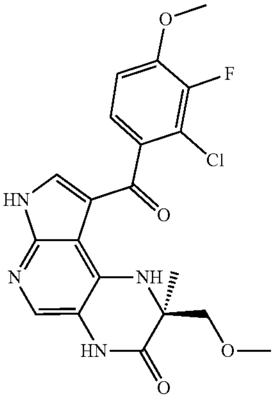

-continued
Z195
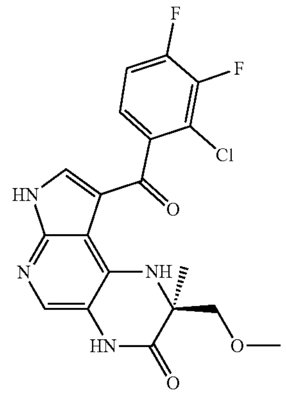
Z196
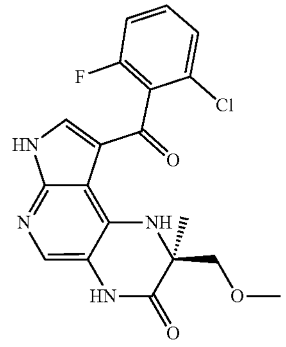
Z197
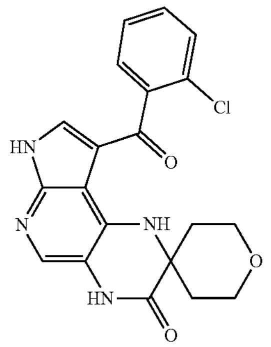
Z198
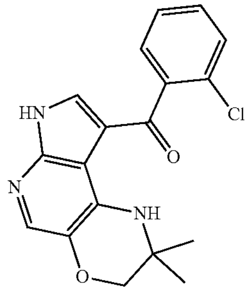
-continued
Z199
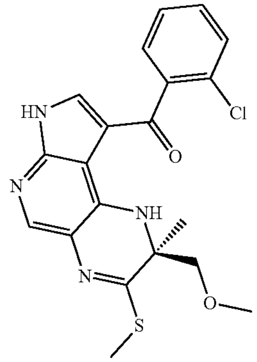
Z200
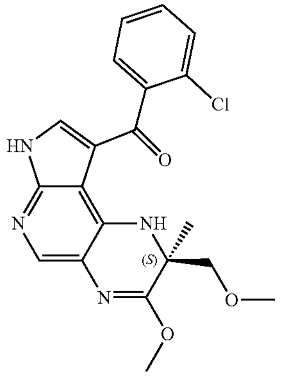
Z201
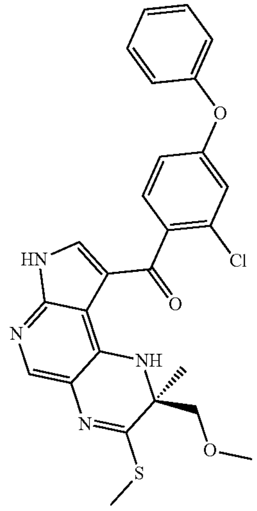

-continued
Z202
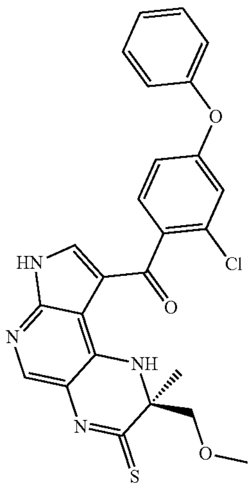
Z203
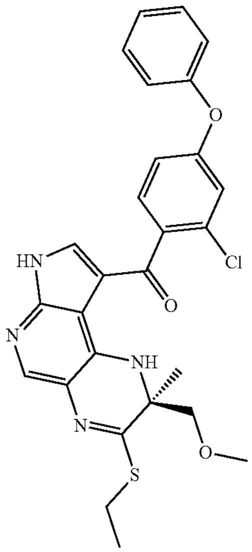
Z204
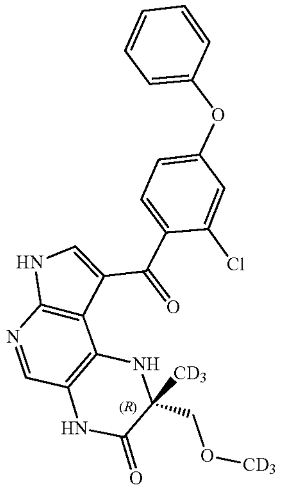
-continued
Z178
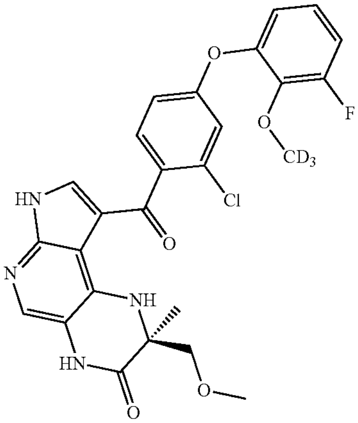
Z169
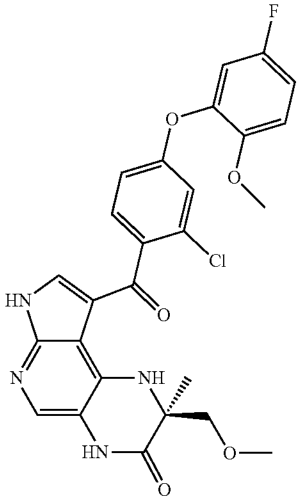
Z165
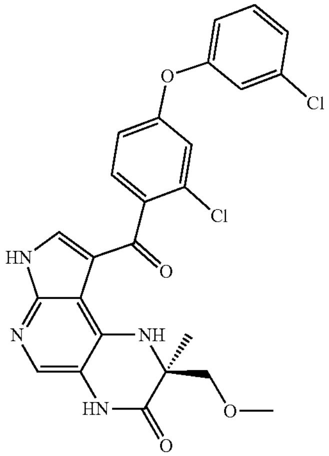

-continued
Z147
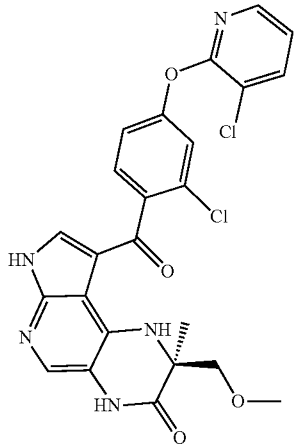
Z41-1a
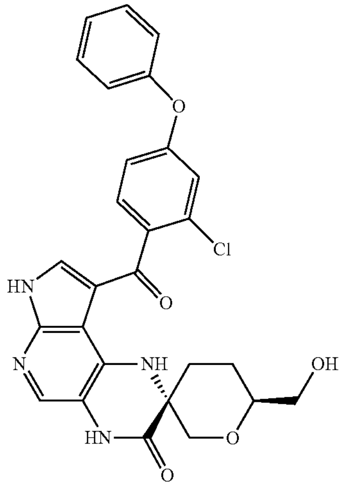
Z41-1b
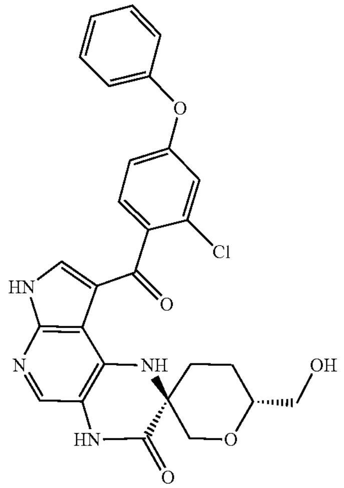
-continued
Z65
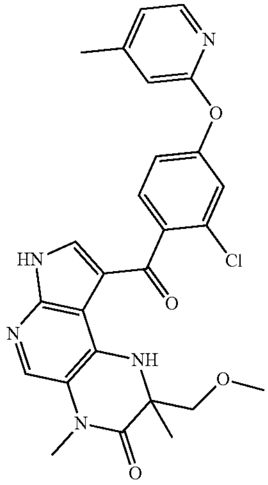
Z72
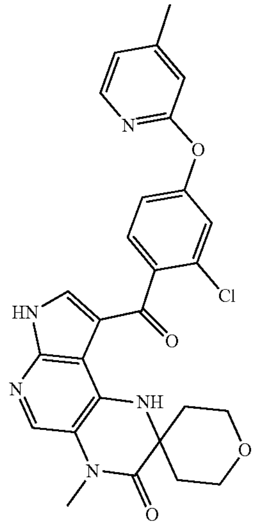
Z51
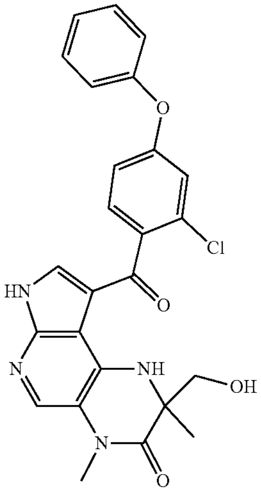

-continued

Z51-1

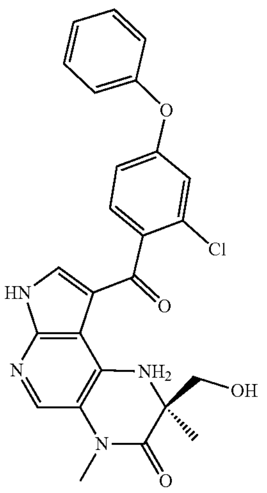

Z51-2

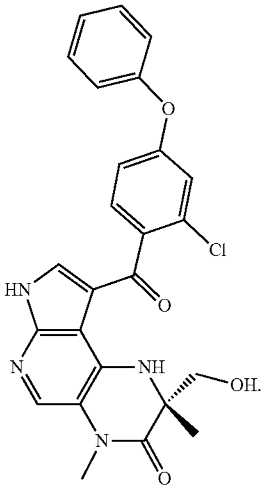

In another aspect, the present disclosure provides a pharmaceutical composition, comprising the compound, the pharmaceutically acceptable salt thereof, the stereoisomer thereof, the solvate thereof or the prodrug thereof described in the above aspect; and a pharmaceutically acceptable carrier.

As used herein, the term "pharmaceutically acceptable carrier" refers to any formulation or a carrier media representative carrier capable of delivering an effective amount of the active substance of the present disclosure without interfering with the biological activity of the active substance and with no toxic side effects to a host or a subject, including water, oils, vegetables and minerals, cream bases, lotion bases, ointment bases, etc. Such bases include suspending agents, tackifiers, transdermal penetration enhancer, etc. Their formulations are well known to those skilled in the field of cosmetics or topical pharmaceuticals.

In embodiments of the present disclosure, the pharmaceutical composition can be administered in any of the following ways: orally, by spray inhalation, rectally, nasally, buccally, topically, parenterally, e.g., injected or inputted subcutaneously, intravenously, intramuscularly, intraperitoneally, intrathecally, intraventricularly, intrasternally and intracranially, or administered by means of an external reservoir. Where, administered orally, intraperitoneally or intravenously is preferred. When administered orally, the compounds of the present disclosure can be prepared into any orally acceptable formulation, including but not limited to tablets, capsules, aqueous solutions, or aqueous suspensions. Carriers for tablets typically include lactose and cornstarch. In addition, lubricants such as magnesium stearate can also be added. Diluents used in capsule formulations typically include lactose and dried cornstarch. Aqueous suspension formulations are usually prepared by mixing active ingredients with suitable emulsifiers and suspending agents. If desired, some sweeteners, flavoring agents, or colorants may also be added to the oral formulations. When administered topically, particularly in the treatment of affected surfaces or organs prone to topical application such as eye, skin or lower intestinal neurological diseases, the compounds of the present disclosure can be prepared into different topical pharmaceutics according to different affected surfaces or organs. When administered topically to eyes, the compounds of the present disclosure can be formulated in the form of micronized suspensions or solutions. The carrier used is sterile saline at an isotonic pH, to which a preservative such as benzyl alkanol chloride may or may not be added. For eye use, the compounds can also be prepared into ointments such as Vaseline ointments. When administered topically to the skin, the compounds of the present disclosure can be prepared into suitable ointment, lotion or cream formulations, with the active ingredients being suspended or dissolved in one or more carriers. Carriers that can be used in ointment formulations include but are not limited to mineral oils, liquid Vaseline, white Vaseline, propylene glycol, polyethylene oxide, polypropylene oxide, emulsified wax, and water. Carriers that can be used in lotions or creams include but are not limited to mineral oils, sorbitan monostearate, Tween 60, cetyl esters wax, hexadecen-aryl alcohol, 2-octyldodecanol, benzyl alcohol, and water. The compounds of the present disclosure can also be administered in the form of sterile injection formulations, including sterile injectable water or oil suspensions or sterile injectable solutions. Carriers and solvents that can be used include water, Ringer's solution, and isotonic sodium chloride solution. In addition, sterile nonvolatile oils can also be used as solvents or suspending media, e.g., monoglycerides or diglycerides.

In another aspect, the present disclosure provides the compound, the pharmaceutically acceptable salt thereof, the stereoisomer thereof, the solvate thereof or the prodrug thereof described in the above aspect for use as a medicament.

In another aspect, the present disclosure provides a use of the compound, the pharmaceutically acceptable salt thereof, the stereoisomer thereof, the solvate thereof or the prodrug thereof described in the above aspect or the pharmaceutical composition described in the above aspect in the manufacture of a medicament for preventing and/or treating a disease or a disorder; the disease or the disorder is associated with BTK and/or associated with abnormal B-cell activation.

In an embodiment, the disease or disorder is selected from the following group: heteroimmune disease, autoimmune disease, inflammatory disease and cancer.

In an embodiment, the heteroimmune disease, autoimmune disease and inflammatory disease may be selected from the following group: rheumatic disease, glomerulonephritis, Goodpasture syndrome, atherosclerosis, autoimmune hematopathy, autoimmune gastritis, autoimmune inflammatory bowel disease, irritable bowel syndrome, allograft rejection, chronic thyroiditis, Graves' disease, Sjögren's disease, scleroderma, diabetes mellitus, hepatitis, pancreatitis, primary cirrhosis, myasthenia gravis, multiple sclerosis, systemic lupus erythematosus, psoriasis, atopic dermatitis, dermatomyositis, contact dermatitis, eczema, vasculitis, chronic renal insufficiency, Stevens-Johnson syndrome, inflammatory pain, idiopathic diarrhea, cachexia, sarcoidosis, Guillain-Barre syndrome, uveitis, conjunctivitis, otitis media, periodontal disease, Parkinson's disease, Alzheimer's disease, septic shock, pulmonary interstitial fibrosis, asthma, bronchitis, rhinitis, sinusitis, pneumoconiosis, pulmonary insufficiency syndrome, emphysema, pulmonary fibrosis, chronic inflammatory lung disease, and other inflammatory or obstructive diseases on an airway.

In an embodiment, the cancer is leukemia or lymphoma.

In an embodiment, the cancer may be selected from the following group: small lymphocytic lymphoma (SLL), acute lymphoblastic leukemia (ALL), chronic lymphocytic leukemia (CLL), acute myelogenous leukemia (AML), chronic myelogenous leukemia (CML), acute promyelocytic leukemia, chronic myeloid leukemia, diffuse large B-cell lymphoma, intravascular large B-cell lymphoma, primary exudative lymphoma, Waldenstrom's macroglobulinemia, follicular lymphoma, multiple myeloma, mantle cell lymphoma (MCL), marginal zone lymphoma (MZL), non-Hodgkin lymphoma.

In another aspect, the present disclosure provides a use of the compound, the pharmaceutically acceptable salt thereof, the stereoisomer thereof, the solvate thereof or the prodrug thereof described in the above aspect or the pharmaceutical composition described in the above aspect in the manufacture of a BTK inhibitor.

In another aspect, the present disclosure provides a method of treating cancer, comprising a step of administering to a subject in need thereof a therapeutically effective amount of the compound, the pharmaceutically acceptable salt thereof, the stereoisomer thereof, the solvate thereof or the prodrug thereof described in the above aspect, or any combination thereof, or administering the pharmaceutical composition described in the above aspect.

As used herein, the term "subject" refers to an animal, especially a mammal, preferably human.

As used herein, the term "effective amount" or "therapeutically effective amount" refers to a sufficient amount of nontoxic drugs or pharmaceutics that can achieve the expected effects. In embodiments of the present disclosure, when treating a patient according to the present disclosure, the amount of a given drug depends on many factors, such as the specific dosage regimen, the disease or condition type and its severity, and the uniqueness (e.g., body weight) of the subject or host in need of treatment. However, depending on the particular circumstances, including, for example, the adopted specific drug, administration route, the treated condition, and the treated subject or host, the administered dosage can be conventionally determined by the known method in the art. Usually, for a dosage used for treating an adult, the administered dosage is typically in a range of 0.02 to 5000 mg/day, for example, about 1 to 1500 mg/day. The desired dosage can be conveniently shown as a single dose, or divided doses administered simultaneously (or in short time) or at appropriate intervals, for example, two, three, four or more divided doses each day. It will be understood by a person skilled in the art that although the dosage range is given, the specific effective amount can be adjusted appropriately according to the patient's condition in combination with the doctor's diagnosis.

As used herein, the term "pharmaceutically acceptable salt" refers to a salt of a compound of the present disclosure that is pharmaceutically acceptable and has the pharmacological activity of the parent compound. Such salts include: acid addition salts formed with inorganic acids and organic acids, and the inorganic acids are for example nitric acid, phosphoric acid, and carbonic acid; or the organic acids are for example propionic acid, hexanoic acid, cyclopentylpropionic acid, glycolic acid, pyruvic acid, gluconic acid, stearic acid, and muconic acid; or salts formed by replacing acidic protons present on the parent compounds with metal ions, such as alkali metal ions or alkaline earth metal ions; or coordination compounds formed with organic bases such as ethanolamine. The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred. In addition to salt forms, the compounds provided in the present disclosure also exist in prodrug forms. The prodrugs of the compounds described herein easily undergo chemical changes under physiological conditions to be converted into the compounds of the present disclosure. Furthermore, the prodrugs may be converted to the compounds of the present disclosure by chemical or biochemical methods in an in vivo environment.

As used herein, the terms "solvent compound" and "solvate" refer to a substrate formed by a compound of the present disclosure combined with a pharmaceutically acceptable solvent. The pharmaceutically acceptable solvent includes acetic acid, etc. The solvent compound includes a stoichiometric amount of a solvent compound and a non-stoichiometric amount of a solvent compound. Some compounds of the present disclosure may exist in a non-solvated or solvated form. Generally speaking, the solvated form is equivalent to the non-solvated form, and both are included in the scope of the present disclosure.

As used herein, the term "stereoisomer" includes a conformational isomer and a configurational isomer, wherein the configurational isomer mainly includes a cis-trans isomer and an optical isomer. The compounds of the present disclosure can be present in the form of stereoisomers and thus encompass all possible stereoisomer forms, including but not limited to cis-trans isomers, tautomers, enantiomers, diastereoisomers, atropisomers, etc. The compounds of the present disclosure can also be present in the form of any combination or any mixture of the stereoisomers, for example, a mixture of equal amounts of a mesomer, a raceme, and an atropisomer. For example, each compound can be present as a single enantiomer, a single diastereoisomer or a mixture thereof, or a single atropisomer or a mixture thereof. When containing an olefinic double bond, the compounds of the present disclosure include cis isomers and trans isomer and any combination thereof unless specified otherwise. The atropisomers of the present disclosure are stereoisomers based on axial or planar chirality resulting from restricted intramolecular rotation. As drugs, stereoisomers having excellent activity are preferred. The compound of the present disclosure has optical isomers derived from asymmetric carbon, etc., and a single isomer can, if desired, be obtained by resolution by methods known in the art, e.g., crystallization or chiral chromatography.

As used herein, the term "alkyl" refers to a linear or branched saturated aliphatic hydrocarbyl group. The term "$C_{1-20}$ alkyl" refers to linear or branched alkyl with 1 to 20 carbon atoms, preferably $C_{1-10}$ alkyl, more preferably $C_{1-6}$ alkyl (i.e., linear or branched alkyl with 1, 2, 3, 4, 5 or 6 carbon atoms), further preferably, $C_{1-4}$ alkyl and still further preferably $C_{1-3}$ alkyl. Specific examples of alkyl include but are not limited to methyl, ethyl, n-propyl, isopropyl, n-butyl, isobutyl, tert-butyl, sec-butyl, n-amyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylamyl, 3-methylamyl, 4-methylamyl, 2,3-dimethylbutyl, and various branched isomers thereof, etc.

As used herein, the term "alkoxy" refers to a group with an —O-alkyl structure, wherein the alkyl is defined as above. The term "$C_{1-10}$ alkoxy" refers to alkoxy with 1 to 10 carbon atoms, preferably $C_{1-6}$ alkoxy, more preferably $C_{1-4}$ alkoxy, and further preferably $C_{1-3}$ alkoxy. Specific examples of alkoxy include but are not limited to methoxy, ethoxy, n-propoxy, isopropoxy, n-butoxy, tert-butoxy, isobutoxy, n-pentyloxy, etc.

As used herein, the term "thioalkyl" refers to a group with a —S-alkyl structure, wherein the alkyl is defined as above. The term "$C_{1-10}$ thioalkyl" refers to thioalkyl with 1 to 10 carbon atoms, preferably $C_{1-6}$ thioalkyl, more preferably $C_{1-6}$ thioalkyl, and further preferably $C_{1-3}$ thioalkyl. Specific examples of thioalkyl include but are not limited to thiomethyl, thioethyl, n-thiopropyl, thioisopropyl, n-thiobutyl, thio-tert-butyl, thioisobutyl, n-thioamyl, etc.

As used herein, the term "alkenyl" refers to alkyl defined as above with one or more C—C double bonds at any site of the chain, and the term "$C_{2-8}$ alkenyl" refers to alkenyl with 2 to 8 carbon atoms and at least one C—C double bond (e.g., 1 to 2), preferably $C_{2-6}$ alkenyl (i.e., alkenyl with 2 to 6 carbon atoms and 1 to 2 C—C double bonds), more preferably $C_{2-4}$ alkenyl (i.e., alkenyl with 2 to 4 carbon atoms and 1 to 2 C—C double bonds). Specific examples of alkenyl include but are not limited to ethenyl, 1-propenyl, 2-propenyl, 1-, 2- or 3-butenyl, pentenyl, hexenyl, butadienyl, etc.

As used herein, the term "alkynyl" refers to alkyl defined as above with one or more C—C triple bonds at any site of the chain, and the term "$C_{2-8}$ alkynyl" refers to alkynyl with 2 to 8 carbon atoms and at least one C—C triple bond (e.g., 1 to 2), preferably $C_{2-6}$ alkynyl (i.e., alkynyl with 2 to 6 carbon atoms and 1 to 2 C—C triple bonds), more preferably $C_{2-4}$ alkynyl (i.e., alkynyl with 2 to 4 carbon atoms and 1 to 2 C—C triple bonds). Specific examples of alkynyl include but are not limited to ethynyl, 1-propynyl, 2-propynyl, 1-, 2- or 3-butynyl, etc.

As used herein, the term "halogen" refers to fluorine, chlorine, bromine or iodine.

As used herein, the term "halo" refers to fluoro, chloro, bromo or iodo.

As used herein, the term "haloalkyl" refers to alkyl in which one or more (e.g., 1, 2, 3, 4 or 5) hydrogen atoms are substituted by halogen, wherein the alkyl is defined as above. The term "halo $C_{1-10}$ alkyl" refers to haloalkyl with 1 to 10 carbon atoms, preferably halo $C_{1-6}$ alkyl, more preferably halo $C_{1-4}$ alkyl, and further preferably halo $C_{1-3}$ alkyl. Specific examples of haloalkyl include but are not limited to monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, etc.

As used herein, the term "haloalkoxy" refers to alkoxy in which one or more (e.g., 1, 2, 3, 4 or 5) hydrogen atoms are substituted by halogen, wherein the alkoxy is defined as above. The term "halo $C_{1-10}$ alkoxy" refers to haloalkoxy with 1 to 10 carbon atoms, preferably halo $C_{1-6}$ alkoxy, more preferably halo $C_{1-4}$ alkoxy, and further preferably halo $C_{1-3}$ alkoxy. Specific examples of haloalkoxy include but are not limited to trifluoromethoxy, trifluoroethoxy, monofluoromethoxy, monofluoroethoxy, difluoromethoxy, difluoroethoxy, etc.

As used herein, the term "deuterated" refers to one or more hydrogen atoms in a group are substituted by deuterium atoms.

As used herein, the term "deuterated alkyl" refers to alkyl in which one or more (e.g., 1, 2, 3, 4, or 5) hydrogen atoms are substituted by deuterium atoms, wherein the alkyl is defined as above. The term "deuterated $C_{1-10}$ alkyl" refers to deuterated alkyl with 1 to 10 carbon atoms, preferably deuterated $C_{1-6}$ alkyl, more preferably deuterated $C_{1-4}$ alkyl, and further preferably deuterated $C_{1-3}$ alkyl. Specific examples of deuterated $C_{1-10}$ alkyl include but are not limited to monodeuterium methyl, dideuterium methyl, trideuterium methyl, monodeuterium ethyl, 1,2-dideuterium ethyl, trideuterium ethyl, etc.

As used herein, the term "deuterated alkoxy" refers to alkoxy in which one or more (e.g., 1, 2, 3, 4 or 5) hydrogen atoms are substituted by deuterium atoms, wherein the alkoxy is defined as above. The term "deuterated $C_{1-10}$ alkoxy" refers to deuterated alkoxy with 1 to 10 carbon atoms, preferably deuterated $C_{1-6}$ alkoxy, more preferably deuterated $C_{1-4}$ alkoxy, and further preferably deuterated $C_{1-3}$ alkoxy. Specific examples of deuterated haloalkoxy include but are not limited to trideuterium methoxy, trideuterium ethoxy, monodeuterium methoxy, monodeuterium ethoxy, dideuterium methoxy, dideuterium ethoxy, etc.

As used herein, the terms "cycloalkyl" and "cycloalkyl ring" can be used interchangeably, which refer to saturated monocyclic or polycyclic cyclohydrocarbyl, including, for example, monocyclic cycloalkyl, spirocycloalkyl, fused cycloalkyl, and bridged cycloalkyl. The ring carbon atoms of the cycloalkyl in the present disclosure can optionally be substituted by 1, 2 or 3 oxo to form a cycloketone structure. The term "3- to 20-membered cycloalkyl" or "$C_{3-20}$ cycloalkyl" refers to cycloalkyl with 3 to 20 ring carbon atoms, including monocyclic cycloalkyl, spirocycloalkyl, fused cycloalkyl and bridged cycloalkyl, preferably $C_{3-12}$ cycloalkyl, $C_{5-20}$ spirocycloalkyl, $C_{5-20}$ fused cycloalkyl or $C_{5-20}$ bridged cycloalkyl, more preferably $C_{3-8}$ monocyclic cycloalkyl.

The terms "$C_{3-8}$ monocyclic cycloalkyl" and "3- to 8-membered monocyclic cycloalkyl" refer to saturated monocyclic cyclohydrocarbyl with 3 to 8 ring carbon atoms, preferably $C_{3-6}$ monocyclic cycloalkyl (i.e., 3- to 6-membered monocyclic cycloalkyl) or $C_{4-6}$ monocyclic cycloalkyl (i.e., 4- to 6-membered monocyclic cycloalkyl), more preferably $C_3$, $C_4$, $C_5$ or $C_6$ monocyclic cycloalkyl. Specific examples of monocyclic cycloalkyl include but are not limited to cyclopropyl, cyclobutyl, cyclopentyl, cyclohexyl, cycloheptyl, cyclooctyl, etc.

As used herein, the terms "spirocycloalkyl" and "spirocycloalkyl ring" refer to polycyclic cyclohydrocarbyl formed with two or more monocycles sharing one carbon atom (called a spiro-atom). Spirocycloalkyl is classified as monospirocycloalkyl, bispirocycloalkyl or polyspirocycloalkyl depending on the number of spiro-atoms shared between rings. The term "5- to 20-membered spirocycloalkyl" or "$C_{5-20}$ spirocycloalkyl" refers to polycyclic cyclohydrocarbyl with 5 to 20 ring carbon atoms, wherein the monocycles sharing a spiro-atom are 3- to 8-membered monocyclic cycloalkyl rings, preferably 6- to 14-membered (i.e., $C_{6-14}$) spirocycloalkyl, more preferably 6- to 14-membered monospirocycloalkyl, further preferably 7- to 11-membered (i.e., $C_{7-11}$) spirocycloalkyl, still further preferably 7- to 11-membered monospirocycloalkyl, and most preferably 7-membered (4-membered monocyclic cycloalkyl ring/4-membered monocyclic cycloalkyl ring), 8-membered (4-membered monocyclic cycloalkyl ring/5-membered monocyclic cycloalkyl ring), 9-membered (4-membered monocyclic cycloalkyl ring/6-membered monocyclic cycloalkyl ring, 5-membered monocyclic cycloalkyl ring/5-membered monocyclic cycloalkyl ring), 10-membered (5-membered monocyclic cycloalkyl ring/6-membered monocyclic cycloalkyl ring) or 11-membered (6-membered monocyclic cycloalkyl ring/6-membered monocyclic cycloalkyl ring) monospirocycloalkyl. Specific examples of spirocycloalkyl include but are not limited to:

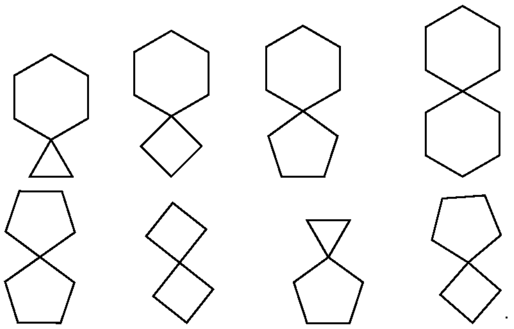

These spirocycloalkyl can be attached to the rest of the molecule through any one of the ring atoms.

As used herein, the terms “fused cycloalkyl” and “fused cycloalkyl ring” refer to polycyclic cyclohydrocarbyl formed by two or more monocycles sharing an adjacent pair of carbon atoms. According to the number of formed rings, fused cycloalkyl can be divided into bicyclic, tricyclic, tetracyclic or polycyclic fused cycloalkyl. The term “5- to 20-membered fused cycloalkyl” or “$C_{5-20}$ fused cycloalkyl” refers to a polycyclic cyclohydrocarbyl with 5 to 20 ring carbon atoms, wherein the monocycle sharing adjacent carbon atom pairs is a 3- to 8-membered monocyclic cycloalkyl ring. Preferably 6- to 14-membered (i.e., $C_{6-14}$) fused cycloalkyl, more preferably 6- to 14-membered bicyclic fused cycloalkyl, further preferably 7- to 10-membered (i.e., $C_{7-10}$) fused cycloalkyl, still further preferably 7- to 10-membered bicyclic cycloalkyl. Most preferably 8-membered (formed by 5-membered monocyclic cycloalkyl ring fused with 5-membered monocyclic cycloalkyl ring), 9-membered (formed by 5-membered monocyclic cycloalkyl ring fused with 6-membered monocyclic cycloalkyl ring) or 10-membered (formed by 6-membered monocyclic cycloalkyl ring fused with 6-membered monocyclic cycloalkyl ring) bicyclic fused cycloalkyl. Specific examples of fused cycloalkyl include, but are not limited to:

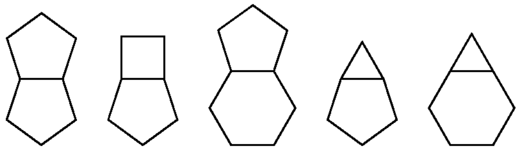

-continued

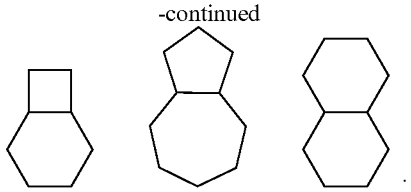

These fused cycloalkyl can be attached to the rest of the molecule through any one of the ring atoms.

As used herein, the terms “bridged cycloalkyl” and “bridged cycloalkyl ring” refer to polycyclic cyclohydrocarbyl formed between two or more monocycles by sharing two carbon atoms that are not directly connected. According to the number of formed rings, they can be divided into bicyclic, tricyclic, tetracyclic or polycyclic bridged cycloalkyl. The terms “5- to 20-membered bridged cycloalkyl” and “$C_{5-20}$ bridged cycloalkyl” refer to polycyclic cyclohydrocarbyl with 5 to 20 ring carbon atoms, wherein any two rings share two carbon atoms that are not directly connected. Preferably 6- to 14-membered (i.e., $C_{6-14}$) bridged cycloalkyl, more preferably 7- to 10-membered (i.e., $C_{7-10}$) bridged cycloalkyl. Specific examples of bridged cycloalkyl include, but are not limited to:

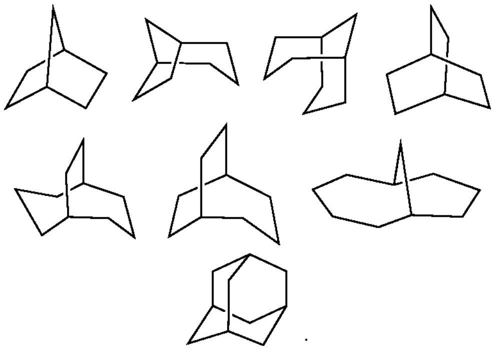

These bridged cycloalkyl can be attached to the rest of the molecule through any one of the ring atoms.

As used herein, the term “halocycloalkyl” refers to cycloalkyl in which one or more (e.g., 1, 2, 3, 4 or 5) hydrogen atoms are substituted by halogen, wherein cycloalkyl is defined as above.

As used herein, the term “halo $C_{3-8}$ monocyclic cycloalkyl” refers to halo monocyclic cycloalkyl with 3 to 8 ring carbon atoms, preferably halo $C_{3-6}$ monocyclic cycloalkyl, more preferably halo $C_3$, halo $C_4$, halo $C_5$ or halo $C_6$ monocyclic cycloalkyl. Specific examples include but are not limited to trifluorocyclopropyl, monofluocyclopropyl, monofluocyclohexyl, difluorocyclopropyl, difluorocyclohexyl, etc.

As used herein, the terms “heterocyclyl” and “heterocyclyl ring” can be used interchangeably and refer to saturated or partially unsaturated monocyclic or polycyclic cyclohydrocarbyl, including, for example, monocyclic heterocyclyl, spiroheterocyclyl, fused heterocyclyl and bridged heterocyclyl. The ring carbon atoms of the heterocyclyl in the present disclosure can be optionally substituted by 1, 2 or 3 oxo to form a cycloketone, cyclolactone or cyclolactam structure. The term “3- to 20-membered heterocyclyl” refers to saturated or partially unsaturated monocyclic or polycyclic cyclohydrocarbyl with 3 to 20 ring atoms, wherein one or more (preferably 1, 2, 3 or 4) ring atoms are heteroatoms selected from nitrogen, oxygen or S(═O)$_{m}$' (wherein m' is an integer from 0 to 2), but excluding ring moieties of —O—O—, —O—S— or —S—S—, and the rest ring atoms are carbon. Where when the ring atom is a nitrogen atom, it may be substituted or unsubstituted (i.e., N or NR, R is hydrogen or other substituents already defined herein). The 3- to 20-membered heterocyclyl of the present disclosure includes monocyclic heterocyclyl (e.g., 3- to 8-membered monocyclic heterocyclyl), spiroheterocyclyl, fused heterocyclyl and bridged heterocyclyl.

As used herein, the terms "3- to 8-membered monocyclic heterocyclyl" and "3- to 8-membered monocyclic heterocyclyl ring" refer to saturated or partially unsaturated monocyclic cyclohydrocarbyl with 3 to 8 ring atoms, wherein 1, 2, or 3 ring atoms are heteroatoms selected from nitrogen, oxygen, or S(═O)$_{m}$' (wherein m' is an integer from 0 to 2). Preferably 3- to 6-membered monocyclic heterocyclyl with 3 to 6 ring atoms, wherein 1 or 2 ring atoms are heteroatoms. More preferably 4- to 6-membered monocyclic heterocyclyl with 4 to 6 ring atoms, wherein 1 or 2 ring atoms are heteroatoms. Further preferably 5- or 6-membered monocyclic heterocyclyl with 5 or 6 ring atoms, wherein 1 or 2 ring atoms are heteroatoms. When the heteroatom is a nitrogen atom, the nitrogen atom can be substituted or unsubstituted (i.e., N or NR, R is hydrogen or other substituents already defined herein). When the heteroatom is a sulfur atom, the sulfur atom can be optionally oxidated (i.e., S(═O)$_{m}$', m' is an integer from 0 to 2). The ring carbon atoms of the monocyclic heterocyclyl can be each optionally substituted by 1, 2, or 3 oxo to form cycloketone, cyclolactone or cyclolactam structures. Specific examples of monocyclic heterocyclyl include but are not limited to aziridine, oxirane, azetidine, azetidin-2-one, oxetane, oxetan-2-one, oxazolidine, pyrrolidin-2-one, pyrrolidin-2,5-dione, 1,3-dioxolane, dihydrofuran-2(3H)-one, dihydrofuran-2,5-dione, piperidin-2-one, piperidin-2,6-dione, tetrahydro-2H-pyran-2-one, imidazolidine, tetrahydrofuran, tetrahydrothiophene, tetrahydropyrrole, 1,3-dioxolan-2-one, oxazolidin-2-one, imidazolidin-2-one, piperidine, piperazine, piperazin-2-one, morpholine, morpholin-3-one, morpholin-2-one, thiomorpholin-3-one 1,1-dioxide, thiomorpholine, thiomorpholine-1,1-dioxide, tetrahydropyran, 1,2-dihydroazacyclobutadiene, 1,2-dihydrooxacyclobutadiene, 2,5-dihydro-1H-pyrrole, 2,5-dihydrofuran, 2,3-dihydrofuran, 2,3-dihydro-1H-pyrrole, 3,4-dihydro-2H-pyran, 1,2,3,4-tetrahydropyridine, 3,6-dihydro-2H-pyran, 1,2,3,6-tetrahydropyridine, 1,3-oxazinane, hexahydropyrimidine, 1,4-dioxane, tetrahydropyrimidin-2(1H)-one, 1,4-dioxan-2-one, 5,6-dihydro-2H-pyran-2-one, 5,6-dihydropyrimidin-4(3H)-one, 3,4-dihydropyridin-2(1H)-one, 5,6-dihydropyridin-2(1H)-one, 5,6-dihydropyrimidin-4(1H)-one, pyrimidin-4(3H)-one, pyrimidin-4(1H)-one, 4,5-dihydro-1H-imidazole, 2,3-dihydro-1H-imidazole, 2,3-dihydrooxazole, 1,3-dioxacyclopentene, 2,3-dihydrothiophene, 2,5-dihydrothiophene, 3,4-dihydro-2H-1,4-oxazine, 3,4-dihydro-2H-1,4-thiazine 1,1-dioxide, 1,2,3,4-tetrahydropyrazine, 1,3-dihydro-2H-pyrrol-2-one, 1,5-dihydro-2H-pyrrol-2-one, 1H-pyrrol-2,5-dione, furan-2(3H)-one, furan-2(5H)-one, 1,3-dioxacyclopenten-2-one, oxazol-2(3H)-one, 1,3-dihydro-2H-imidazol-2-one, furan-2,5-dione, 3,6-dihydropyridin-2(1H)-one, pyridin-2,6-(1H, 3H)-dione, 5,6-dihydro-2H-pyran-2-one, 3,6-dihydro-2H-pyran-2-one, 3,4-dihydro-2H-1,3-oxazine, 3,6-dihydro-2H-1,3-oxazine, 1,2,3,4-tetrahydropyrimidine, etc.

As used herein, the term "3- to 6-membered nitrogen-containing heterocyclyl" refers to saturated or partially unsaturated monocyclic cyclohydrocarbyl with 3 to 6 ring atoms, wherein one ring atom is a nitrogen atom and the other one or two ring atoms are heteroatoms selected from nitrogen, oxygen or S(═O)$_{m}$' (wherein m' is an integer of 0 to 2). Specific examples include, but are not limited to, aziridinyl, azetidinyl, azacyclopentyl (i.e., tetrahydropyrrole), azacyclohexyl (i.e., hexahydropyridine), morpholinyl, piperazinyl, oxazolidine.

As used herein, the term "3- to 8-membered monocyclic heterocycloalkyl" refers to saturated monocyclic cyclohydrocarbyl with 3 to 8 ring atoms, wherein 1 or 2 ring atoms are heteroatoms. Preferably 3- to 6-membered monocyclic heterocycloalkyl, i.e., saturated monocyclic cyclohydrocarbyl with 3 to 6 ring atoms, wherein 1 or 2 ring atoms are heteroatoms. Specific examples of heterocycloalkyl include, but are not limited to, aziridinyl, oxiranyl, azetidinyl, oxetanyl, oxazolidinyl, 1,3-dioxolanyl, dioxanyl, imidazolidinyl, tetrahydrofuryl, tetrahydrothienyl, tetrahydropyrrolyl, piperidinyl, piperazinyl, morpholinyl, thiomorpholinyl, thiomorpholin-1,1-dioxide, tetrahydropyranyl, 1,4-oxazacycloheptyl, 1,3-oxazacycloheptyl, 1,3-oxazinanyl, hexahydropyrimidinyl, 1,4-dioxanyl.

The two ring atoms attached to the monocyclic heterocyclyl ring, including C—C, N—C, can both optionally fuse with cycloalkyl such as monocyclic cycloalkyl ring, monocyclic heterocyclyl ring, monocyclic aryl ring, 5- or 6-membered monocyclic heteroaryl ring, heterocyclyl, aryl or heteroaryl defined in the present disclosure to form a fused polycyclic ring. The two ring atoms attached to the monocyclic heterocyclyl forming a fused ring with other rings are preferably C—C.

As used herein, the terms "spiroheterocyclyl" and "spiroheterocyclyl ring" refer to polycyclic heterocyclyl formed by two or more saturated or partially unsaturated monocycles sharing a carbon atom (called a spiro atom), wherein one or more (e.g., 1, 2 or 3) ring atoms are heteroatoms selected from nitrogen, oxygen or S(═O)$_{m}$' (wherein m' is an integer from 0 to 2) and the rest ring atoms are carbon. When the heteroatom is a nitrogen atom, the nitrogen atom can be substituted or unsubstituted (i.e., N or NR, R is hydrogen or other substituents already defined herein). Each monocycle can contain one or more double bonds, but no ring has a fully conjugated π-electron system. According to the number of shared spiro atoms between rings, the spiroheterocyclyl can be divided into monospiroheterocyclyl, bispiroheterocyclyl or polyspiroheterocyclyl. The term "5- to 20-membered spiroheterocyclyl" refers to spiroheterocyclyl with 5 to 20 ring atoms, wherein one of the monocycles sharing the spiro atoms is a 3- to 8-membered monocyclic heterocyclyl ring, and the other monocycle is a 3 to 8-membered monocyclic heterocyclyl ring or a 3 to 8-membered monocyclic cycloalkyl ring. Preferably 6- to 14-membered spiroheterocyclyl with 6 to 14 ring atoms, wherein 1 or 2 ring atoms are heteroatoms. More preferably 7- or 11-membered spiroheterocyclyl with 7 or 11 ring atoms, wherein 1 or 2 ring atoms are heteroatoms. Most preferably 7-membered (4-membered monocyclic heterocyclyl ring/4-membered monocyclic heterocyclyl ring or 4-membered monocyclic heterocyclyl ring/4-membered monocyclic cycloalkyl or 4-membered monocyclic cyclocycloalkyl ring/4-membered monocyclic heterocyclyl ring), 8-membered (4-membered monocyclic heterocyclyl ring/5-membered monocyclic heterocyclyl ring), 9-membered (4-membered monocyclic heterocyclyl ring/6-membered monocyclic heterocyclyl ring, 5-membered monocyclic heterocyclyl ring/5-membered monocyclic heterocyclyl ring), 10-membered (5-membered monocyclic heterocyclyl ring/6-membered monocyclic heterocyclyl ring) or 11-membered (6-membered monocyclic heterocyclyl ring/6-membered monocyclic heterocyclyl ring) monospiroheterocyclyl. Specific examples of spiroheterocyclyl include, but are not limited to:

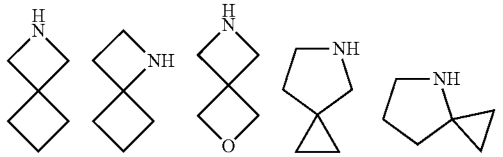

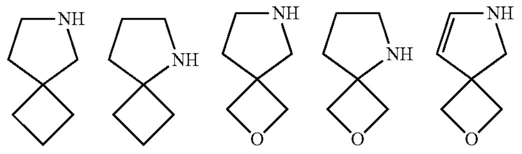

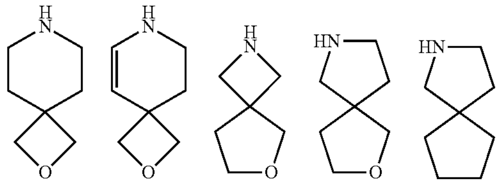

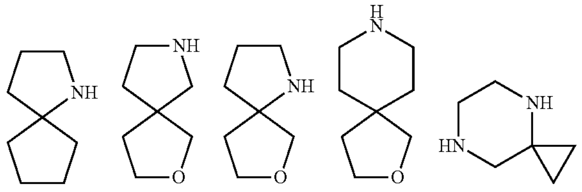

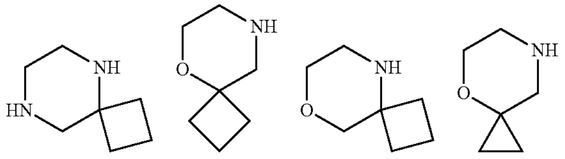

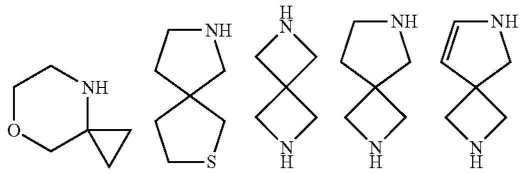

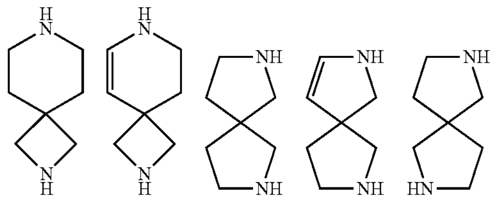

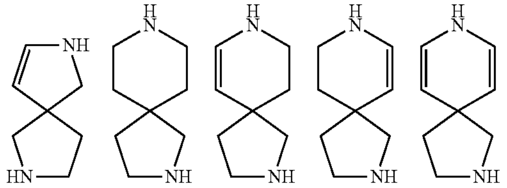

-continued

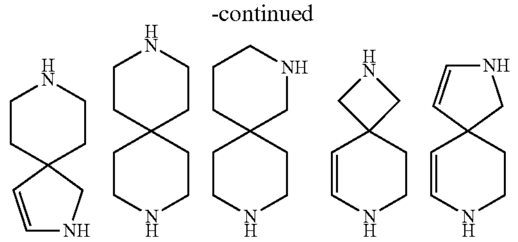

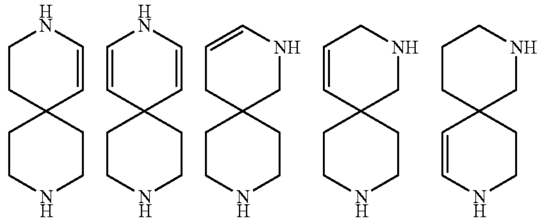

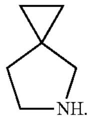

These spiroheterocyclyl can be attached to the rest of the molecule by any one of the suitable ring atoms.

As used herein, the terms "fused heterocyclyl" and "fused heterocyclyl ring" refer to polycyclic heterocyclyl formed by two or more saturated or partially unsaturated monocycles sharing an adjacent pair of ring atoms, wherein one or more (e.g., 1, 2 or 3) ring atoms are heteroatoms selected from nitrogen, oxygen or $S(=O)_{m'}$ (where m' is an integer from 0 to 2) and the rest ring atoms are carbon. When the heteroatom is a nitrogen atom, the nitrogen atom can be substituted or unsubstituted (i.e., N or NR, R is hydrogen or other substituents already defined herein). Each monocycle can contain one or more double bonds, but no ring has a fully conjugated π-electron system. The shared adjacent ring atom pair can be C—C or N—C. According to the number of formed rings, they can be divided into bicyclic, tricyclic, tetracyclic or polycyclic fused heterocyclyl. The term "5- to 20-membered fused heterocyclyl" refers to fused heterocyclyl with 5 to 20 ring atoms, wherein the monocycles sharing adjacent ring atom pair are 3- to 8-membered monocyclic heterocyclyl rings. Preferably 6- to 14-membered fused heterocyclyl with 6 to 14 ring atoms, wherein 1 or 2 ring atoms are heteroatoms. More preferably 6- or 10-membered fused heterocyclyl with 6 or 10 ring atoms, wherein 1 or 2 ring atoms are heteroatoms. More preferably 8- or 10-membered fused heterocyclyl with 8 or 10 ring atoms, wherein 1 or 2 ring atoms are heteroatoms. Most preferably 8-membered (formed by 5-membered monocyclic heterocyclyl ring fused with 5-membered monocyclic heterocyclyl ring), 9-membered (formed by 5-membered monocyclic heterocyclyl ring fused with 6-membered monocyclic heterocyclyl ring) or 10-membered (formed by 6-membered monocyclic heterocyclyl ring fused with 6-membered monocyclic heterocyclyl ring) bicyclic fused heterocyclyl. Specific examples of fused heterocyclyl include, but are not limited to:

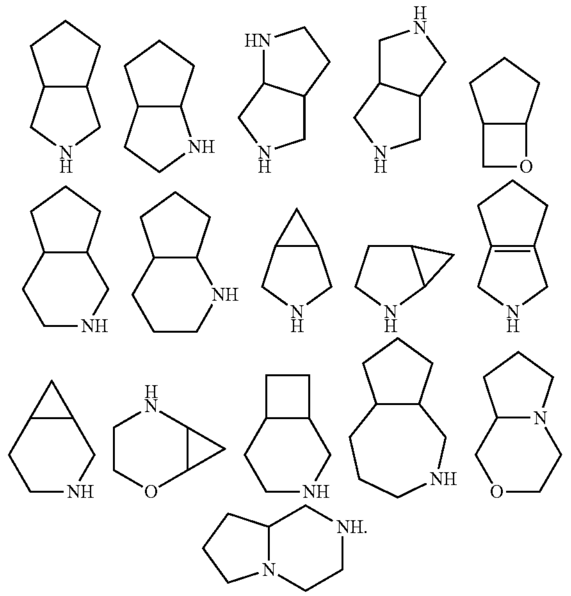

These fused heterocyclyl can be attached to the rest of the molecule by any one of the suitable ring atoms.

As used herein, the terms “bridged heterocyclyl” and “bridged heterocyclyl ring” refer to polycyclic heterocyclyl formed by two or more saturated or partially unsaturated monocycles by sharing two ring atoms that are not directly connected, wherein one or more (e.g., 1, 2 or 3) ring atoms are heteroatoms selected from nitrogen, oxygen or $S(=O)_{m}'$ (wherein m' is an integer from 0 to 2), and the rest ring atoms are carbon. According to the number of formed rings, they can be divided into bicyclic, tricyclic, tetracyclic or polycyclic bridged cycloalkyl. The term “5- to 20-membered bridged heterocyclyl” refers to saturated or partially unsaturated polycyclic heterocyclyl with 5 to 20 ring atoms, wherein any two rings share two ring atoms that are not directly connected, and each monocycle can contain one or more double bonds, but none of the rings has a fully conjugated π-electron system. Preferably 6- to 14-membered bridged heterocyclyl. More preferably 7- to 10-membered bridged heterocyclyl. Specific examples of bridged heterocyclyl include, but are not limited to:

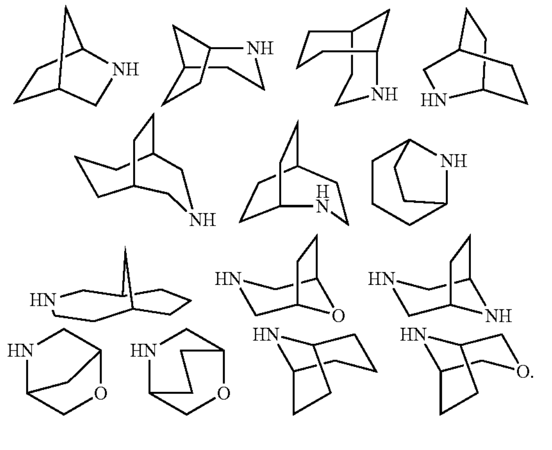

These bridged heterocyclyl can be attached to the rest of the molecule through any one of the suitable ring atoms.

In the present disclosure, the various heterocyclyl can be optionally substituted, and when substituted, the substituent is preferably one or more substituents described in the present disclosure.

As used herein, the terms “aryl”, “aryl ring” and “aromatic ring” can be used interchangeably, and refer to all-carbon monocyclic, all-carbon non-fused polycyclic (rings and rings are connected by covalent bonds, non-fused) or all-carbon fused polycyclic (i.e., rings sharing adjacent carbon atom pairs) groups. At least one ring in the group is aromatic, that is, has a conjugated π-electron system. The term “$C_{6-14}$ aryl” refers to aryl with 6 to 14 ring atoms. Preferably $C_{6-10}$ aryl. $C_{6-14}$ aryl in the present disclosure includes monocyclic aryl, non-fused polycyclic aryl and aromatic fused polycyclic ring, wherein examples of monocyclic aryl include phenyl, and examples of non-fused polycyclic aryl include biphenyl, etc.

In the present disclosure, when $C_{6-14}$ aryl is an aromatic fused polycyclic ring, the aromatic fused polycyclic ring can be a polycyclic group formed by a monocyclic aryl ring fused with one or more monocyclic aryl rings, and non-limiting examples thereof include naphthyl, anthracyl, etc.

In some embodiments of the present disclosure, when $C_{6-14}$ aryl is an aromatic fused polycyclic ring, the aromatic fused polycyclic ring can also be a polycyclic group formed by a monocyclic aryl ring (such as phenyl) fused with one or more non-aromatic rings, wherein the ring attached to the parent structure is aromatic or non-aromatic ring. The non-aromatic rings include, but are not limited to, 3- to 6-membered monocyclic heterocyclyl ring (preferably 5- or 6-membered monocyclic heterocyclyl ring, wherein the ring carbon atom of the monocyclic heterocyclyl ring can be substituted by 1 to 2 oxo to form a cyclolactam or cyclolactone structure), 3- to 6-membered monocyclic cycloalkyl ring (preferably 5- or 6-membered monocyclic cycloalkyl ring, wherein the ring carbon atom of the monocyclic cycloalkyl ring can be substituted by 1 or 2 oxo to form a cycloketone structure). The polycyclic group formed by the monocyclic aryl rings fused with one or more non-aromatic rings can be connected to other groups or to the parent structure through a nitrogen atom or a carbon atom, and the ring attached to the parent structure is a monocyclic aryl ring or non-aromatic ring.

In the present disclosure, the above types of aryl can be substituted or unsubstituted, and when substituted, the substituents are preferably one or more of the substituents described in the present disclosure.

As used herein, the terms “heteroaryl”, “heteroaryl ring” and “heteroaromatic ring” can be used interchangeably, which refer to a monocyclic or fused polycyclic (i.e., sharing a pair of adjacent ring atoms which can be C—C or N—C) group with a ring atom being substituted by at least one heteroatom independently selected from nitrogen, oxygen, or sulfur, wherein nitrogen and sulfur atoms can be each optionally oxidated, and the nitrogen atom can be optionally quaternized. The heteroaryl has shared 6, 10 or 14 π electrons, and at least one ring in the group is aromatic. The term “5- to 14-membered heteroaryl” refers to heteroaryl with 5 to 14 ring atoms, wherein 1, 2, 3, or 4 ring atoms are heteroatoms selected from nitrogen, oxygen or $S(=O)_{m}'$ (wherein m' is an integer from 0 to 2). Preferably 5- to 10-membered heteroaryl with 5 to 10 ring atoms, wherein 1, 2, 3, or 4 ring atoms are heteroatoms. In the present disclosure, 5- to 14-membered heteroaryl can be monocyclic heteroaryl, fused bicyclic heteroaryl or fused tricyclic heteroaryl.

As used herein, the term “5- or 6-membered monocyclic heteroaryl” refers to monocyclic heteroaryl with 5 or 6 ring atoms, wherein 1, 2 or 3 ring atoms are heteroatoms selected from nitrogen, oxygen or S(═O)$_{m'}$ (wherein m' is an integer from 0 to 2). Specific examples of monocyclic heteroaryl include, but are not limited to, thiophene, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine, pyrazine, etc.

As used herein, the terms “8- to 10-membered bicyclic heteroaryl” refers to fused bicyclic heteroaryl with 8 to 10 ring atoms, wherein 1, 2, 3, 4 or 5 ring atoms are heteroatoms selected from nitrogen, oxygen or S(═O)$_{m'}$ (wherein m' is an integer from 0 to 2). The fused bicyclic heteroaryl can be a bicyclic group (preferably a 9- or 10-membered bicyclic heteroaryl ring) formed by a monocyclic aryl ring (e.g., phenyl) fused with a monocyclic heteroaryl ring (preferably a 5- or 6-membered monocyclic heteroaryl ring), or a bicyclic group formed by a monocyclic heteroaryl ring (preferably a 5- or 6-membered monocyclic heteroaryl ring) fused with a monocyclic heteroaryl ring (preferably a 5- or 6-membered monocyclic heteroaryl ring).

Any two linked ring atoms, including C—C, N—C and N—N, on the monocyclic heteroaryl ring can be fused with cycloalkyl such as a monocyclic cycloalkyl ring, a monocyclic heterocyclyl ring, a monocyclic aryl ring and a 5- or 6-membered monocyclic heteroaryl ring, heterocyclyl, aryl or heteroaryl, as defined in the present disclosure, to form fused polycycles. The two linked ring atoms on the monocyclic heteroaryl ring that forms a fused ring with other ring are preferably C—C, non-restrictively including the following forms:

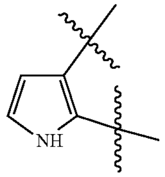
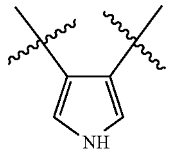
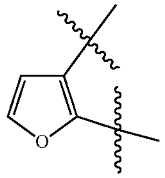
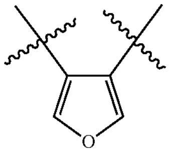
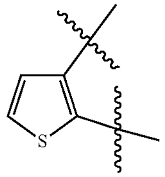
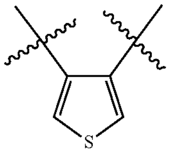
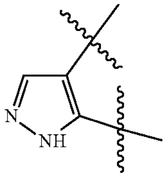
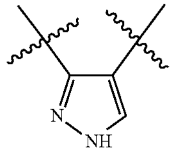

-continued

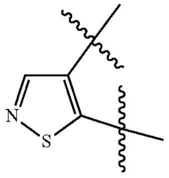
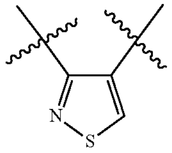
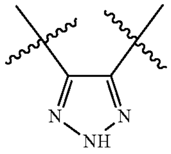
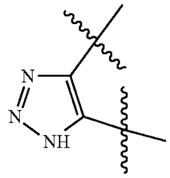
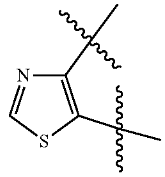
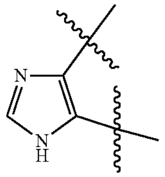
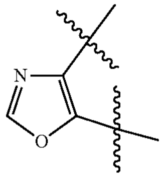
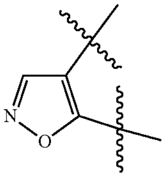
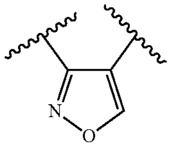
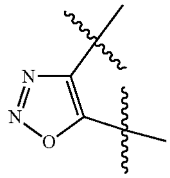
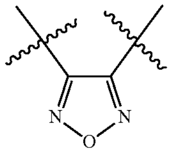
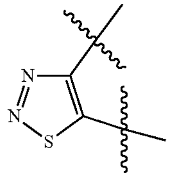
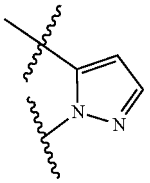
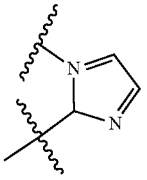
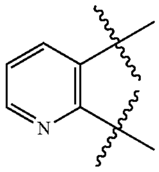
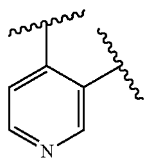
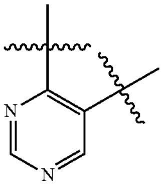
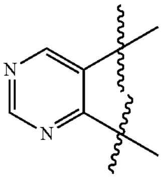

-continued

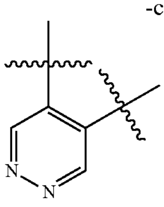
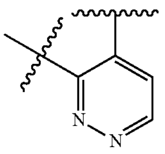
and
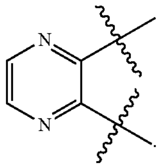

The ring atoms marked by "  " in the groups are attached to the rest of the molecule.

Non-limiting examples of 8- to 10-membered bicyclic heteroaryl include: benzo[d]isoxazole, 1H-indole, isoindole, 1H-benzo[d]imidazole, benzo[d]isothiazole, 1H-benzo[d][1,2,3]triazole, benzo[d]oxazole, benzo[d]thiazole, indazole, benzofuran, benzo[b]thiophene, quinoline, isoquinoline, quinazoline, quinoxaline, cinnoline, pyrido[3,2-d]pyrimidine, pyrido[2,3-d]pyrimidine, pyrido[3,4-d]pyrimidine, pyrido[4,3-d]pyrimidine, 1,8-naphthyridine, 1,7-naphthyridine, 1,6-naphthyridine, 1,5-naphthyridine, pyrazolo[1,5-a]pyrimidine, imidazo[1,2-b]pyridazine, etc.

Specific examples of bicyclic heteroaryl include, but are not limited to:

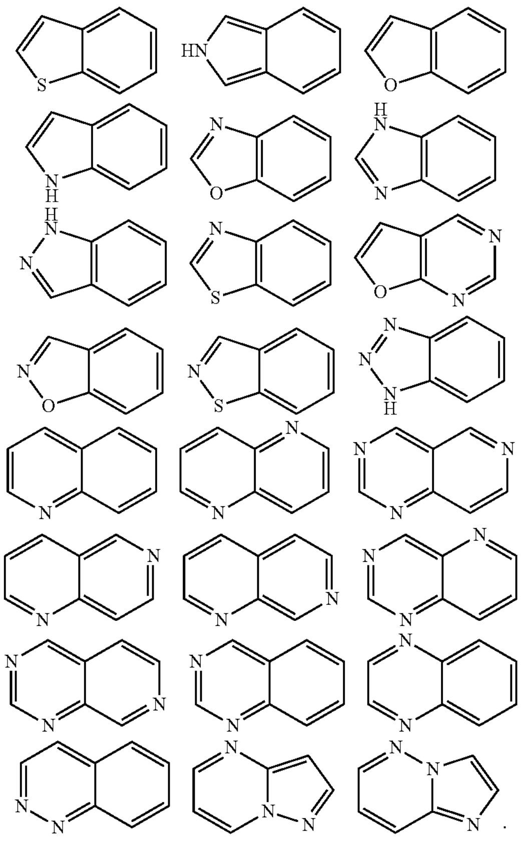

These groups can be attached to the rest of the molecule by any one of the suitable ring atoms. The ring attached to the parent structure can be a monocyclic heteroaryl ring or a benzene ring.

In some embodiments of the present disclosure, the fused bicyclic heteroaryl or the fused tricyclic heteroaryl can also be a polycyclic group formed by a monocyclic heteroaryl ring (preferably a 5- or 6-membered monocyclic heteroaryl ring) fused with one or more non-aromatic rings, wherein the ring attached to the parent structure is a monocyclic heteroaryl ring or a non-aromatic ring. The non-aromatic rings include, but are not limited to, 3- to 6-membered monocyclic heterocyclyl ring (preferably 5- or 6-membered monocyclic heterocyclyl ring, wherein the ring carbon atom of the monocyclic heterocyclyl ring can be substituted by 1 to 2 oxo to form a cyclolactam or cyclolactone structure), 3- to 6-membered monocyclic cycloalkyl ring (preferably 5- or 6-membered monocyclic cycloalkyl ring, wherein the ring carbon atom of the monocyclic cycloalkyl ring can be substituted by 1 or 2 oxo to form a cycloketone structure). The polycyclic group formed by the monocyclic heteroaryl rings fused with one or more non-aromatic rings can be connected to other groups or to the parent structure through a nitrogen atom or a carbon atom, and the ring attached to the parent structure is a monocyclic heteroaryl ring or non-aromatic ring.

In the present disclosure, the various heteroaryl can be substituted or unsubstituted, and when substituted, the substituent is preferably one or more substituents described in the present disclosure.

As used herein, the term "hydroxyl" refers to —OH.

As used herein, the term "hydroxymethyl" refers to $—CH_2OH$, and "hydroxyethyl" refers to $—CH_2CH_2OH$ or $—CH(OH)CH_3$.

As used herein, the term "cyanomethyl" refers to $—CH_2CN$, and "cyanoethyl" refers to $—CH_2CH_2CN$ or $—CHCNCH_3$.

As used herein, the term "amino" refers to $—NH_2$.

As used herein, the term "cyano" refers to —CN.

As used herein, the term "nitro" refers to $—NO_2$.

As used herein, the term "benzyl" refers to $—CH_2—$benzene.

As used herein, the term "oxo" refers to =O.

As used herein, the term "carboxyl" refers to —C(O)OH.

As used herein, the term "carboxylate group" refers to —C(O)O(alkyl) or —C(O)O(cycloalkyl).

As used herein, the term "acetyl" refers to $—COCH_3$.

As used herein, the term "substituted" refers to any one or more hydrogen atoms at a particular atom being substituted by a substituent, which can include heavy hydrogen and variants of hydrogen as long as the valence state of the particular atom is normal and the substituted compound is stable. When the substituent is an oxo (i.e., =O), it means that two hydrogen atoms are substituted. The substitution of oxo will not occur on aryl. The term "optionally substituted" or "optionally be substituted" means that a group may be substituted and may also not be substituted. Unless stated otherwise, the types and the number of substituents can be chosen arbitrarily provided that they can be achieved chemically.

When any variable (e.g., R) occurs in the composition or structure of a compound once or more than once, it is independently defined at each occurrence. Thus, for example, if a group is substituted by 0 to 2 R, the group can be optionally substituted by up to two R, wherein the definition of R at each occurrence is independent. Moreover, a combination of the substituent and/or the variant thereof is allowed only when the combination results in a stable compound.

In any embodiment, any or all of the hydrogens present in the compound, or in particular groups or moieties within the compound, may be replaced by deuterium or tritium. From one to the maximum number of hydrogens present in the compound may be replaced by deuterium. From one to the maximum number of hydrogens present in any group in a compound of general formula or in a specific compound may be deuterated. For example, when a group is described as ethyl, the ethyl may be $C_2H_5$ or $C_2H_5$ in which x (1 to 5) hydrogens are replaced by deuterium, such as $C_2D_xH_{5-x}$. When a group is described as deuterated ethyl, the deuterated ethyl may be $C_2H_5$ in which x (1 to 5) hydrogens are replaced by deuterium, such as $C_2D_xH_{5-x}$.

DETAILED DESCRIPTION OF THE PREFERRED EMBODIMENT

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art. Preferred implementations include, but are not limited to, embodiments of the present disclosure.

The present disclosure will be specifically described below by way of embodiments, but the scope of the present disclosure is not limited thereto. The present disclosure has been described in detail herein, and its specific implementations have also been disclosed; for one skilled in the art, it is obvious to make various modifications and improvements to the specific implementations of the present disclosure without departing from the spirit and scope of the present disclosure. Embodiments without indicating specific conditions are carried out according to the conventional conditions or conditions suggested by the manufacturer. The reagents or instruments used without indicating the manufacturer are conventional products that are commercially available.

The reagents used in the following embodiments are abbreviated as follows: DMSO: dimethyl sulfoxide; DDQ: 2,3-dichloro-5,6-dicyano-p-benzoquinone; $NH_4HCO_3$: ammonium bicarbonate; CAN: acetonitrile.

Unless otherwise specified, the preparative HPLC used in the following embodiments can adopt the following conditions: column type: Waters XBridge C18, 190*250 mm, 5 μm; mobile phase system: A: 0.1% aqueous ammonium bicarbonate solution; B: preparative grade acetonitrile; flow rate: 15 mL/min; B %=20%-100%; column temperature: room temperature.

Preparation Embodiment 1: Synthesis of 4-chloro-5-nitro-1-(phenylsulfonyl)-1H-pyrrolo[2,3-b]pyridine

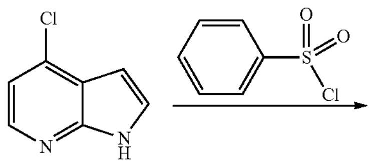

-continued

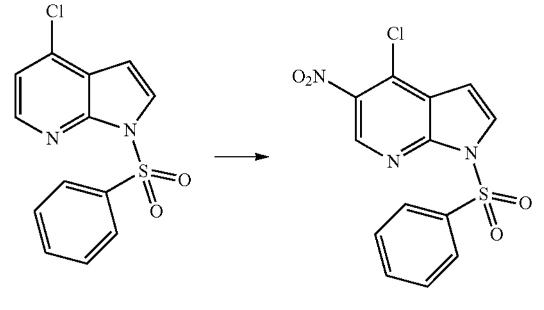

Step 1: 4-Chloro-1H-pyrrolo[2,3-b]pyridine (5.0 g, 32.89 mmol) was suspended in dichloromethane (100 mL), then triethylamine (6.9 mL, 49.34 mmol), 4-dimethylaminopyridine (400 mg, 3.29 mmol) and benzenesulfonyl chloride (4.6 mL, 36.18 mmol) were added thereto in turn, and the reaction was stirred at room temperature for 18 hours. The reaction solution was added with 200 mL of dichloromethane, washed twice with 1.0 M 60 mL of dilute hydrochloric acid, washed with 80 mL of saturated sodium bicarbonate, 50 mL of water, 60 mL of saturated brine in turn, dried and concentrated to obtain 4-chloro-1-(phenylsulfonyl)-1H-pyrrolo[2,3-b]pyridine (9.5 g, yield of 99%) as a brown solid. ES-API: $[M+H]^+$=293.0.

Step 2: 4-Chloro-1-(phenylsulfonyl)-1H-pyrrolo[2,3-b]pyridine (5.0 g, 17.12 mmol) was dissolved in dichloromethane (75 mL), cooled to −10° C. under nitrogen atmosphere, and tetramethylammonium nitrate (3.49 g, 25.68 mmol) was added thereto. Trifluoroacetic anhydride (3.74 mL, 26.54 mmol) was slowly added dropwise thereto, and the reaction was stirred at −5° C. to 0° C. for 30 minutes after the dropwise addition, and then slowly heated to room temperature and reacted for 18 hours. The reaction solution was added with 200 mL of dichloromethane, washed twice with 100 mL of water, washed with 100 mL of saturated sodium carbonate, 100 mL of saturated sodium bicarbonate, 100 mL of water, 100 mL of saturated brine in turn, dried over anhydrous sodium sulfate, filtered through silica gel, and the filtrate was concentrated to obtain 4-chloro-5-nitro-1-(phenylsulfonyl)-1H-pyrrolo[2,3-b]pyridine (4.05 g, yield of 70%) as a white solid. ES-API: $[M+H]^+$=338.0.

Preparation Embodiment 2: Synthesis of (S)-2-(methoxymethyl)-2-methyl-7-(phenylsulfonyl)-1,2,4,7-tetrahydro-3H-pyrrolo[3',2':5,6]pyrido[3,4-b]pyrazin-3-one

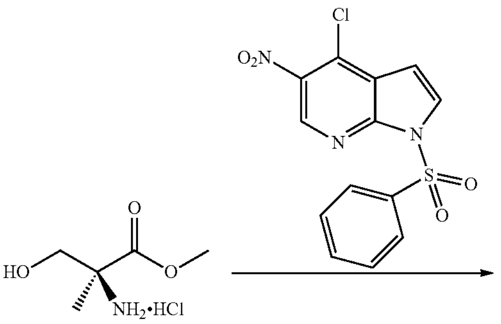

-continued

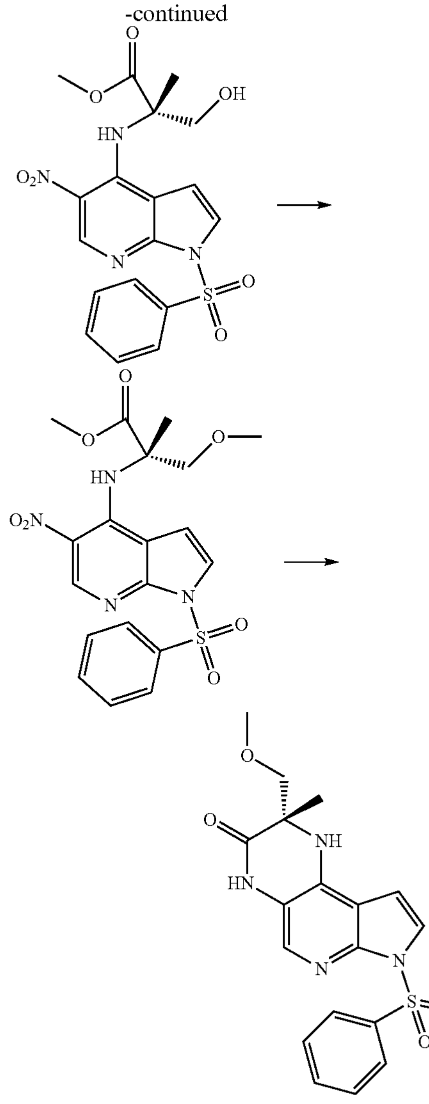

A

Step 1: Methyl (S)-2-amino-3-hydroxy-2-methylpropanoate hydrochloride (10.0 g, 58.96 mmol) and 4-chloro-5-nitro-1-(phenylsulfonyl)-1H-pyrrolo[2,3-b]pyridine (19.0 g, 56.26 mmol) were dissolved in N,N-dimethylacetamide (250 mL), and anhydrous N,N-diisopropylethylamine (36.36 g, 281.29 mmol) was added thereto, and the reaction was stirred at 110° C. for 17 hours. The reaction solution was added with 1000 mL of ethyl acetate, washed twice with 500 mL of water and 3 times with 500 mL of saturated brine, dried and concentrated, and the crude product was purified by a flash silica gel column (ethyl acetate/petroleum ether: 0-50%) to obtain methyl (S)-3-hydroxy-2-methyl-2-((5-nitro-1-(phenylsulfonyl)-1H-pyrrolo[2,3-b]pyridin-4-yl)amino)propanoate (16.0 g, yield of 65.5%) as a yellow solid. ES-API: $[M+H]^+=435.1$.

Step 2: Methyl (S)-3-hydroxy-2-methyl-2-((5-nitro-1-(phenylsulfonyl)-1H-pyrrolo[2,3-b]pyridin-4-yl)amino)propanoate (5.0 g, 11.51 mmol) was dissolved in acetonitrile (150 mL), and silver (II) oxide (26.67 g, 115.10 mmol) and iodomethane (16.34 g, 115.10 mmol) were added thereto, and the reaction was stirred at 35° C. for 48 hours. The reaction solution was cooled to room temperature and then filtered through diatomite, and the filter cake was washed with ethyl acetate (200 mL). The resulting filtrate was concentrated under vacuum to obtain methyl (S)-3-methoxy-2-methyl-2-((5-nitro-1-(phenylsulfonyl)-1H-pyrrolo[2,3-b]pyridin-4-yl)amino)propanoate (5 g, yield of 97%) as a yellow solid. ES-API: $[M+H]^+=449.1$.

Step 3: Methyl (S)-3-methoxy-2-methyl-2-((5-nitro-1-(phenylsulfonyl)-1H-pyrrolo[2,3-b]pyridin-4-yl)amino)propanoate (5 g, 11.15 mmol) was dissolved in acetic acid (100 mL), andiron powder (6.23 g, 111.5 mmol) was added thereto, and the reaction was stirred at 90° C. for 2 hours. The reaction solution was cooled to room temperature and then filtered through diatomite, and the filter cake was washed with ethyl acetate (200 mL). The filtrate was concentrated under vacuum and the resulting crude product was purified by a flash silica gel column (ethyl acetate/petroleum ether: 0-100%) to obtain (S)-2-(methoxymethyl)-2-methyl-7-(phenylsulfonyl)-1,2,4,7-tetrahydro-3H-pyrrolo[3',2':5,6]pyrido[3,4-b]pyrazin-3-one (4 g, yield of 93%) as a pale yellow solid. ES-API: $[M+H]^+=387.2$.

Preparation Embodiment 3: Synthesis of (S)-2-((methoxy-$d_3$)methyl)-2-methyl-7-(phenylsulfonyl)-1,2,4,7-tetrahydro-3H-pyrrolo[3',2':5,6]pyrido[3,4-b]pyrazin-3-one

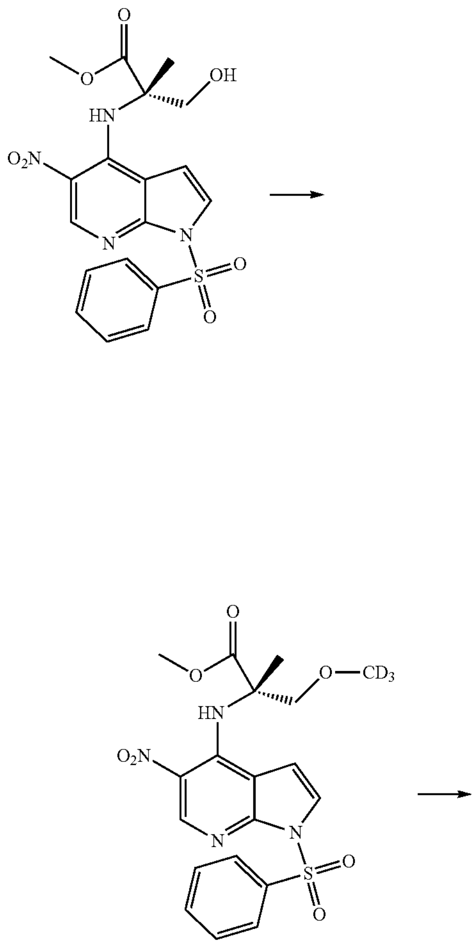

-continued

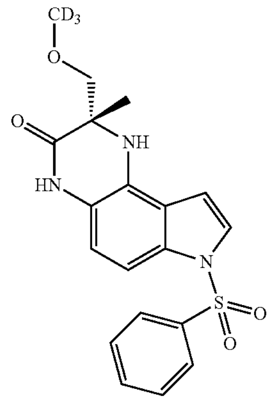

B

-continued

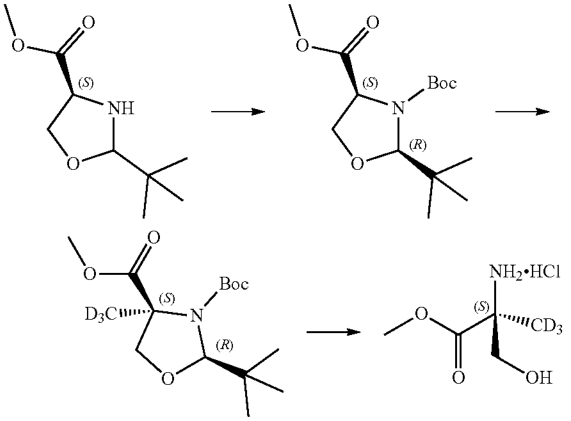

Step 1: Methyl (S)-3-hydroxy-2-methyl-2-((5-nitro-1-(phenylsulfonyl)-1H-pyrrolo[2,3-b]pyridin-4-yl)amino)propanoate (5.0 g, 11.51 mmol) was dissolved in acetonitrile (150 mL), and silver (II) oxide (26.67 g, 115.10 mmol) and deuterated iodomethane (16.34 g, 115.10 mmol) were added thereto, and the reaction was heated to 35° C. and stirred for 48 hours under dark conditions. The reaction solution was cooled to room temperature and then filtered through diatomite, and the filter cake was washed with ethyl acetate (200 mL). The resulting filtrate was concentrated under vacuum to obtain methyl (S)-3-(methoxy-$d_3$)-2-methyl-2-((5-nitro-1-(phenylsulfonyl)-1H-pyrrolo[2,3-b]pyridin-4-yl)amino) propanoate (5 g, yield of 96%) as a yellow solid. ES-API: $[M+H]^+=452.1$.

Step 2: Methyl (S)-3-(methoxy-$d_3$)-2-methyl-2-((5-nitro-1-(phenylsulfonyl)-1H-pyrrolo[2,3-b]pyridin-4-yl)amino) propanoate (5 g, 11.07 mmol) was dissolved in acetic acid (100 mL), andiron powder (6.23 g, 111.5 mmol) was added thereto, and the reaction was stirred at 90° C. for 2 hours. The reaction solution was cooled to room temperature and then filtered through diatomite, and the filter cake was washed with ethyl acetate (200 mL). The filtrate was concentrated under vacuum and the resulting crude product was purified by a flash silica gel column (ethyl acetate/petroleum ether: 0-100%) to obtain (S)-2-((methoxy-$d_3$)methyl)-2-methyl-7-(phenylsulfonyl)-1,2,4,7-tetrahydro-3H-pyrrolo [3',2':5,6]pyrido[3,4-b]pyrazin-3-one (4 g, yield of 93%) as a pale yellow solid. ES-API: $[M+H]^+=390.2$.

Preparation Embodiment 4: Synthesis of methyl (S)-2-amino-2-(hydroxymethyl)propanoate-3,3,3-$d_3$ Hydrochloride

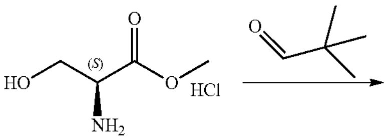

Step 1: Methyl (S)-2-amino-3-hydroxypropionate (10 g, 64.3 mmol) was dissolved in tetrahydrofuran (100 mL), then pivalaldehyde (6.63 g, 77.1 mmol) and triethylamine (7.14 g, 70.7 mmol) were added thereto, and the mixture was reacted at 70° C. for 4 hours, cooled to room temperature, and the reaction solution was directly used for next step of reaction without treatment.

Step 2: To the reaction solution of the previous step was added potassium carbonate solution (13.3 g, 96.5 mmol) and di-tert-butyl dicarbonate (15.4 g, 70.7 mmol), and the mixture was reacted at room temperature for 16 hours, and water and ethyl acetate were added thereto to separate the phases. The organic phase was washed with brine, dried, concentrated, and purified by column chromatography (petroleum ether/ethyl acetate=5/1) to obtain 3-(tert-butyl) 4-methyl (2R,4S)-2-(tert-butyl)oxazolidine-3,4-dicarboxylate (7.5 g, yield: 40.7%). ES-API: $[M-55]^+=232.2$.

Step 3: 3-(tert-Butyl) 4-methyl (2R,4S)-2-(tert-butyl)oxazolidine-3,4-dicarboxylate (5.1 g, 17.7 mmol) was dissolved in tetrahydrofuran (50 mL), cooled to −78° C., and 1M lithium bis(trimethylsilyl)amide tetrahydrofuran solution (53 mL) was added thereto, reacted for 0.5 hours, and deuterated iodomethane (12.83 g, 88.5 mmol) was added thereto, and reacted at −78° C. for 1 hour. The reaction was quenched with ammonium chloride (50 mL), extracted with ethyl acetate (50 mL×1), and the organic phase was washed with brine (50 mL×1), dried over anhydrous sodium sulfate, concentrated, and the crude product was purified by column chromatography (petroleum ether/ethyl acetate=5/1) to obtain 3-(tert-butyl) 4-methyl (2R,4S)-2-(tert-butyl)-4-(methyl-$d_3$)oxazolidine-3,4-dicarboxylate (4.5 g, yield: 80.6%). ES-API: $[M-55]^+=260.2$.

Step 4: 3-(tert-Butyl) 4-methyl (2R,4S)-2-(tert-butyl)-4-(methyl-$d_3$)oxazolidine-3,4-dicarboxylate (4.5 g, 14.8 mmol) was dissolved in dioxane (25 mL), then 6N hydrochloric acid (25 mL) was added thereto, and the mixture was reacted at 50° C. for 2 hours, and the solvent was concentrated to dryness. The crude product was dissolved in 1M hydrochloric acid (25 mL), and back-extraction was performed with ethyl acetate (25 mL×3), and the aqueous phase was concentrated to dryness to obtain methyl (S)-2-amino-2-(hydroxymethyl)propanoate-3,3,3-$d_3$ hydrochloride (2.55 g, yield: 100%). ES-API: $[M+H]^+=137.1$. $^1H$ NMR (400 MHz, $CDCl_3$) δ 8.68 (s, 2H), 7.53-7.27 (m, 1H), 3.7 (s, 3H), 3.63-3.60 (m, 1H).

Embodiment 1: Synthesis of Z1, Z1-1 and Z1-2

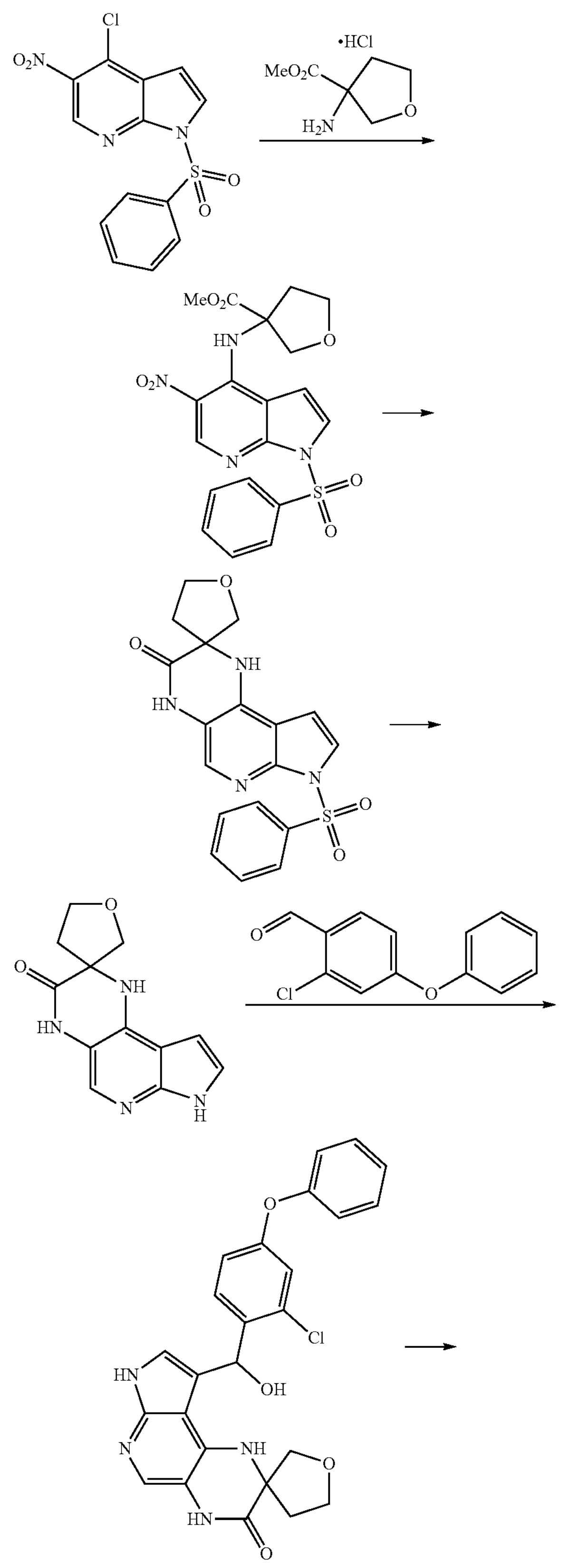

-continued

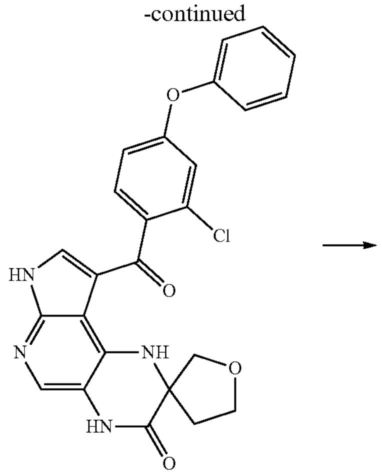

Z1

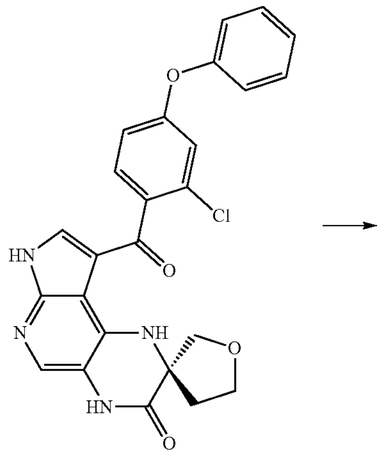

Z1-1

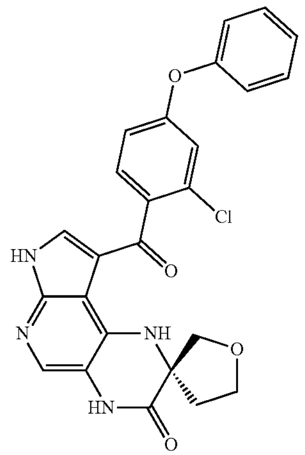

Z1-2

Step 1: 4-Chloro-5-nitro-1-(phenylsulfonyl)-1H-pyrrolo [2,3-b]pyridine (1.0 g, 2.97 mmol) and methyl 3-aminotetrahydrofuran-3-carboxylate hydrochloride (806 mg, 4.45 mmol) were dissolved in N,N-dimethylformamide (15 mL), and N,N-diisopropylethylamine (1.34 g, 10.40 mmol) was added thereto, and the reaction was stirred at 95° C. for 16 hours. The reaction solution was added with 100 mL of ethyl acetate, washed twice with 60 mL of water and 3 times with 30 mL of saturated brine, dried and concentrated, and the crude product was purified by a flash silica gel column (ethyl acetate/petroleum ether: 0-50%) to obtain methyl 3-((5-nitro-1-(phenylsulfonyl)-1H-pyrrolo[2,3-b]pyridin-4-yl)amino)tetrahydrofuran-3-carboxylate (660 mg, yield: 50%) as a yellow solid. ES-API: $[M+H]^+$=447.1.

Step 2: Methyl 3-((5-nitro-1-(phenylsulfonyl)-1H-pyrrolo[2,3-b]pyridin-4-yl)amino)tetrahydrofuran-3-carboxylate (635 mg, 1.42 mmol) was dissolved in acetic acid (15 mL), and iron powder (558 mg, 9.97 mmol) was added thereto, and the reaction was stirred at 85° C. for 3 hours. The reaction solution was added with 100 mL of ethyl acetate, washed twice with 60 mL of water, twice with 40 mL of saturated sodium carbonate, twice with 40 mL of saturated sodium bicarbonate, and with 40 mL of saturated brine in turn, dried and concentrated, and the crude product was slurried with ethyl acetate to obtain 7'-(phenylsulfonyl)-4,4',5,7'-tetrahydro-2H-spiro[furan-3,2'-pyrrolo[3',2':5,6]pyrido[3,4-b]pyrazin]-3'(1'H)-one (530 mg, yield of 97%) as a yellow solid. ES-API: $[M+H]^+$=385.1

Step 3: 7'-(Phenylsulfonyl)-4,4',5,7'-tetrahydro-2H-spiro[furan-3,2'-pyrrolo[3',2':5,6]pyrido[3,4-b]pyrazin]-3'(1'H)-one (200 mg, 0.52 mmol) was dissolved in 10 mL of methanol, 5 mL of tetrahydrofuran and 2 mL of water, and sodium hydroxide (146 mg, 3.64 mmol) was added thereto, and the reaction was stirred at 65° C. for 7 hours. To the reaction solution was added 15 mL of water and 4 mL of saturated ammonium chloride solution, and the mixture was extracted with 100 mL of ethyl acetate. The organic phase was washed with 20 mL of saturated sodium bicarbonate solution and 20 mL of saturated brine in turn, dried and then concentrated to obtain 4,4',5,7'-tetrahydro-2H-spiro[furan-3,2'-pyrrolo[3',2':5,6]pyrido[3,4-b]pyrazin]-3'(1'H)-one (105 mg, yield of 82%) as an off-white solid. ES-API: $[M+H]^+$=245.1.

Step 4: 4,4',5,7'-Tetrahydro-2H-spiro[furan-3,2'-pyrrolo[3',2':5,6]pyrido[3,4-b]pyrazin]-3'(1'H)-one (105 mg, 0.43 mmol) and 2-chloro-4-phenoxybenzaldehyde (100 mg, 0.43 mmol) were dissolved in methanol (8 mL), and the reaction was cooled to 0° C., and potassium hydroxide (168 mg, 3.01 mmol) was added thereto. The reaction was stirred at room temperature for 48 hours. The reaction solution was poured into 60 mL of water, and the pH of the reaction solution was adjusted to 8 with 1.0 M dilute hydrochloric acid, and the reaction solution was extracted with 80 mL of ethyl acetate. The organic phase was washed with 25 mL of saturated brine, dried and then concentrated, and the crude product was purified by a thin-layer preparative plate (dichloromethane/7M ammonia methanol=100:7.5) to obtain 9'-((2-chloro-4-phenoxyphenyl)(hydroxy)methyl)-4,4',5,7'-tetrahydro-2H-spiro[furan-3,2'-pyrrolo[3',2':5,6]pyrido[3,4-b]pyrazin]-3'(1'H)-one (70 mg, yield of 34%) as a pale yellow solid. ES-API: $[M+H]^+$=477.1.

Step 5: 9'-((2-Chloro-4-phenoxyphenyl)(hydroxy)methyl)-4,4',5,7'-tetrahydro-2H-spiro[furan-3,2'-pyrrolo[3',2':5,6]pyrido[3,4-b]pyrazin]-3'(1'H)-one (70 mg, 0.15 mmol) was dissolved in 6 mL of tetrahydrofuran. Dess-Martin periodinane (94 mg, 0.22 mmol) was added thereto, and the reaction was stirred at room temperature for 4 hours, then Dess-Martin periodinane (94 mg, 0.22 mmol) was added thereto again, and the reaction was stirred at room temperature for 18 hours. To the reaction solution was added 5 mL of saturated sodium thiosulfate solution and 20 mL of saturated sodium bicarbonate solution, and the mixture was extracted with 60 mL of ethyl acetate. The organic phase was washed with 15 mL of saturated brine, dried and then concentrated, and the crude product was purified by preparative HPLC to obtain 9'-(2-chloro-4-phenoxybenzoyl)-4,4',5,7'-tetrahydro-2H-spiro[furan-3,2'-pyrrolo[3',2':5,6]pyrido[3,4-b]pyrazin]-3'(1'H)-one (Z1, 27 mg, yield of 39%) as a pale yellow solid. $^1$H NMR (500 MHz, DMSO-$d_6$) δ 12.56 (s, 1H), 10.70 (s, 1H), 8.51 (s, 1H), 7.78 (s, 1H), 7.67 (s, 1H), 7.57 (d, J=8.5 Hz, 1H), 7.51-7.43 (m, 2H), 7.26 (t, J=7.5 Hz, 1H), 7.21-7.15 (m, 3H), 7.02 (dd, J=8.5, 2.0 Hz, 1H), 4.06-3.96 (m, 2H), 3.94-3.89 (m 1H), 3.80 (d, J=9.0 Hz, 1H), 2.55-2.50 (m, 2H), 2.11-1.98 (m, 1H). ES-API: $[M+H]^+$=475.0.

Step 6: The compound Z1 (14 mg, 0.03 mmol) obtained in the above steps was resolved by chiral preparation (column: AB, 250 mm*4.6 mm*5 μM; mobile phase: hexane: EtOH=50:50; flow rate: 1 mL/min; column temperature: 30° C.) to obtain two single isomer compounds. One isomer with a structure arbitrarily designated as Z1-1 (4 mg, peak 1, retention time: 7.186 min, yield of 28%), ES-API: $[M+H]^+$=475.1, was a white solid. The other isomer with a structure arbitrarily designated as Z1-2 (4 mg, peak 2, retention time: 8.731 min, yield of 28%), ES-API: $[M+H]^+$=475.1, was an off-white solid.

Embodiment 2: Synthesis of Z2

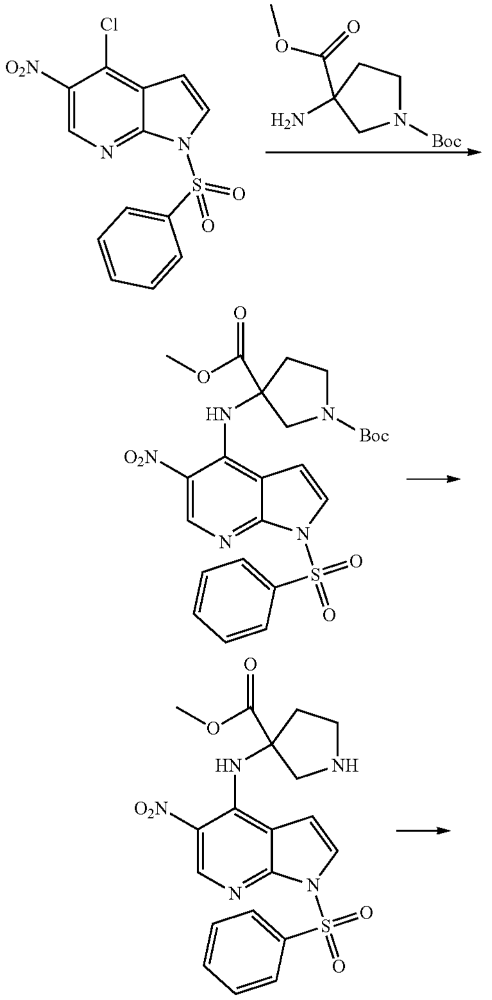

-continued

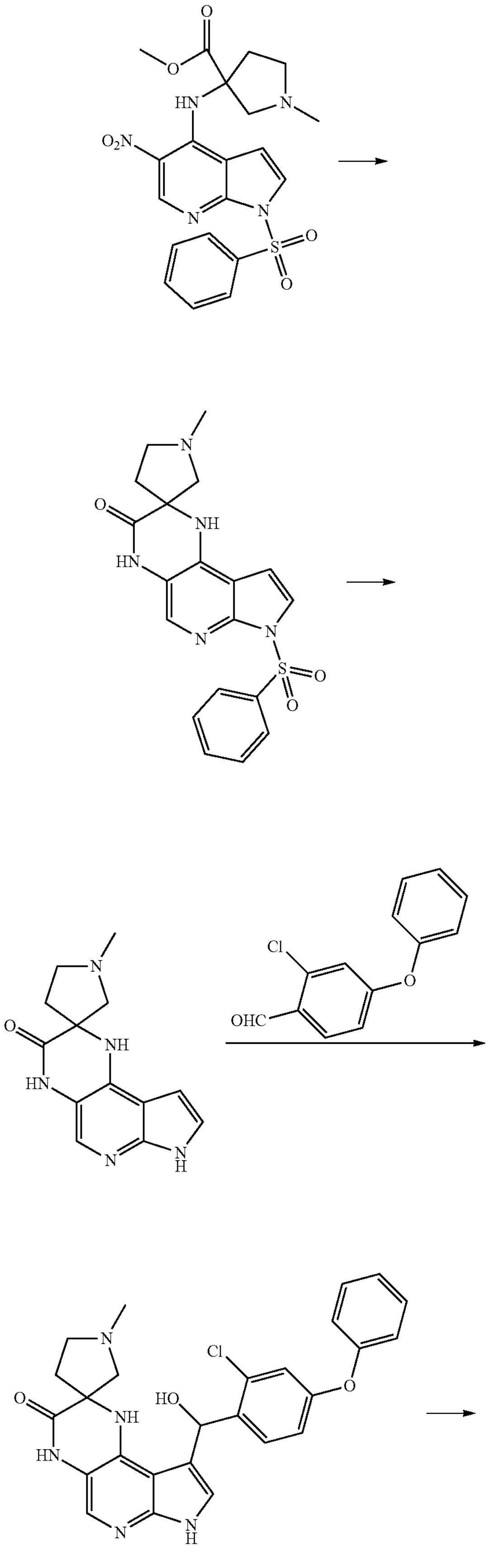

-continued

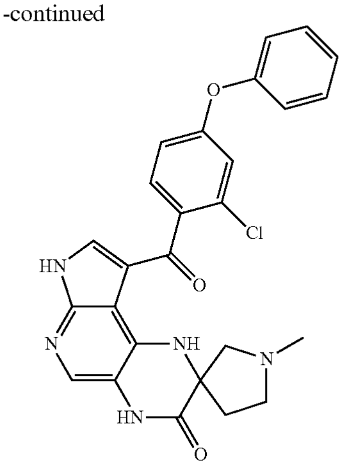

Z2

Step 1: 4-Chloro-5-nitro-1-(phenylsulfonyl)-1H-pyrrolo[2,3-b]pyridine (1.0 g, 2.97 mmol) and 1-(tert-butyl) 3-methyl-3-aminopyrrolidine-1,3-dicarboxylate (1.01 g, 4.16 mmol) were dissolved in 15 mL of N,N-dimethylacetamide, and N,N-diisopropylethylamine (958 mg, 7.42 mmol) was added thereto, and the reaction was stirred at 95° C. for 16 hours. The reaction solution was added with 100 mL of ethyl acetate, washed 3 times with 30 mL of dilute brine and washed with 30 mL of saturated brine in turn, dried and concentrated, and the crude product was purified by a flash silica gel column (ethyl acetate/petroleum ether: 0-50%) to obtain 1-(tert-butyl) 3-methyl 3-((5-nitro-1-(phenylsulfonyl)-1H-pyrrolo[2,3-b]pyridin-4-yl)amino)pyrrolidine-1,3-dicarboxylate (660 mg, yield of 40%) as a yellow solid. ES-API: $[M+H]^+$=546.1.

Step 2: 1-(tert-Butyl) 3-methyl 3-((5-nitro-1-(phenylsulfonyl)-1H-pyrrolo[2,3-b]pyridin-4-yl)amino)pyrrolidine-1,3-dicarboxylate (270 mg, 0.50 mmol) was dissolved in 3 mL of dichloromethane, then 1.5 mL of trifluoroacetic acid was added thereto, and the reaction was stirred at room temperature for 1 hour. The reaction solution was concentrated, and 15 mL of saturated sodium bicarbonate solution was added thereto, and the mixture was extracted with 60 mL of ethyl acetate. The organic phase was washed with 15 mL of saturated brine, dried and then concentrated to obtain methyl 3-((5-nitro-1-(phenylsulfonyl)-1H-pyrrolo[2,3-b]pyridin-4-yl)amino)pyrrolidine-3-carboxylate (220 mg, yield of 100%) as a yellow solid. ES-API: $[M+H]^+$=446.2.

Step 3: Methyl 3-((5-nitro-1-(phenylsulfonyl)-1H-pyrrolo[2,3-b]pyridin-4-yl)amino)pyrrolidine-3-carboxylate (220 mg, 0.49 mmol) was dissolved in 10 mL of acetonitrile, then sodium triacetoxyborohydride (416 mg, 1.96 mmol) and 37% aqueous formaldehyde solution (159 mg, 1.96 mmol) were added thereto in turn under an ice bath, and the reaction was stirred at room temperature for 2 hours. To the reaction solution was added 20 mL of saturated sodium bicarbonate solution, and the mixture was extracted with 90 mL of ethyl acetate. The organic phase was washed with 30 mL of saturated brine, dried and then concentrated to obtain methyl 1-methyl-3-((5-nitro-1-(phenylsulfonyl)-1H-pyrrolo[2,3-b]pyridin-4-yl)amino)pyrrolidine-3-carboxylate (225 mg, yield of 99%) as a yellow solid. ES-API: $[M+H]^+$=460.1.

Step 4: Methyl 1-methyl-3-((5-nitro-1-(phenylsulfonyl)-1H-pyrrolo[2,3-b]pyridin-4-yl)amino)pyrrolidine-3-carboxylate (225 mg, 0.49 mmol) was dissolved in acetic acid (7 mL), and iron powder (192 mg, 3.43 mmol) was added thereto, and the reaction was stirred at 85° C. for 2 hours. The reaction solution was concentrated, and added with 20 mL of saturated sodium bicarbonate solution and 100 mL of dichloromethane/methanol=10:1. The suspension was filtered through diatomite, and the filter cake was washed with dichloromethane/methanol=10:1, and the organic phase was separated, washed with 25 mL of saturated brine, dried and concentrated to obtain 1-methyl-7'-(phenylsulfonyl)-4',7'-dihydrospiro[pyrrolidine-3,2'-pyrrolo[3',2':5,6]pyrido[3,4-b]pyrazin]-3'(1'H)-one (195 mg, yield of 100%) as an off-white solid. ES-API: $[M+H]^+$=398.1

Step 5: 1-Methyl-7'-(phenylsulfonyl)-4',7'-dihydrospiro[pyrrolidine-3,2'-pyrrolo[3',2':5,6]pyrido[3,4-b]pyrazin]-3'(1'H)-one (195 mg, 0.49 mmol) was dissolved in 10 mL of methanol, 5 mL of tetrahydrofuran and 2 mL of water, and sodium hydroxide (98 mg, 2.45 mmol) was added thereto, and the reaction was stirred at 65° C. for 16 hours. The pH of the reaction solution was adjusted to 8 with 1.0 M dilute hydrochloric acid. To the reaction solution was added 10 mL of saturated sodium bicarbonate solution, and the mixture was extracted with 100 mL of ethyl acetate. The organic phase was washed with 20 mL of saturated brine in turn, dried and then concentrated to obtain 1-methyl-4',7'-dihydrospiro[pyrrolidine-3,2'-pyrrolo[3',2':5,6]pyrido[3,4-b]pyrazin]-3'(1'H)-one (80 mg, yield of 63%) as alight brown solid. ES-API: $[M+H]^+$=258.1.

Step 6: 1-Methyl-4',7'-dihydrospiro[pyrrolidine-3,2'-pyrrolo[3',2':5,6]pyrido[3,4-b]pyrazin]-3'(1'H)-one (80 mg, 0.31 mmol) and 2-chloro-4-phenoxybenzaldehyde (108 mg, 0.46 mmol) were dissolved in methanol (8 mL), and the reaction was cooled to 0° C., and potassium hydroxide (122 mg, 2.17 mmol) was added thereto. The reaction was stirred at room temperature for 18 hours. The reaction solution was poured into 30 mL of water, and the pH of the reaction solution was adjusted to 8 with 1.0 M dilute hydrochloric acid, and the reaction solution was extracted with 80 mL of ethyl acetate. The organic phase was washed with 25 mL of saturated brine, dried and then concentrated, and the crude product was purified by a thin-layer preparative plate (dichloromethane/7M ammonia methanol=10:1) to obtain 9'-((2-chloro-4-phenoxyphenyl)(hydroxy)methyl)-1-methyl-4',7'-dihydrospiro[pyrrolidine-3,2'-pyrrolo[3',2':5,6]pyrido[3,4-b]pyrazin]-3'(1'H)-one (53 mg, yield of 35%) as a yellow solid. ES-API: $[M+H]^+$=490.1.

Step 7: 9'-((2-Chloro-4-phenoxyphenyl)(hydroxy)methyl)-1-methyl-4',7'-dihydrospiro[pyrrolidine-3,2'-pyrrolo[3',2':5,6]pyrido[3,4-b]pyrazin]-3'(1'H)-one (53 mg, 0.11 mmol) was dissolved in 6 mL of tetrahydrofuran, cooled to 0° C., and Dess-Martin periodinane (94 mg, 0.22 mmol) was added thereto, and the reaction was stirred at room temperature for 18 hours. To the reaction solution was added 3 mL of saturated sodium thiosulfate solution and 10 mL of saturated sodium bicarbonate solution, and the mixture was extracted with 40 mL of ethyl acetate. The organic phase was washed with 10 mL of saturated brine, dried and then concentrated, and the crude product was purified by preparative HPLC to obtain a target product (Z2, 11 mg, yield of 20%) as a pale yellow solid. ES-API: $[M+H]^+$=488.1.

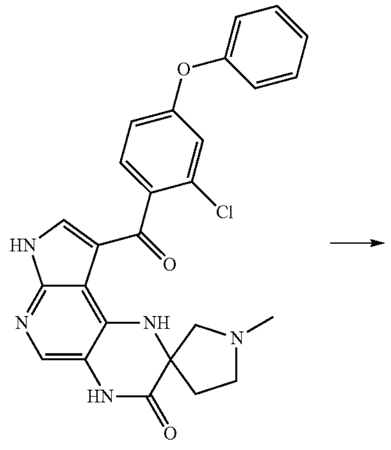

Z2

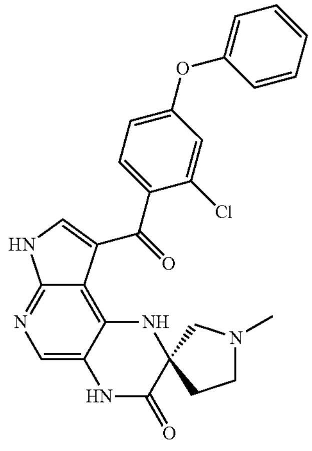

Z2-1

+

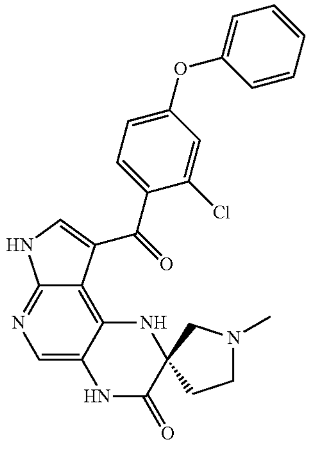

Z2-2

Step 8: The compound Z2 (17 mg, 0.035 mmol) obtained in the above steps was resolved by chiral preparation (column: IF, 250 mm*4.6 mm*5 μM, mobile phase: n-hexane: ethanol:diethylamine=70:30:2, flow rate: 1 mL/min, column temperature: 30° C.) to obtain two single isomer compounds. One single isomer with a structure arbitrarily designated as Z2-1 (7.0 mg, peak 1, retention time: 10.161 min, yield of 41%) was a white solid. ES-API: $[M+H]^+$=488.0. The other single isomer with a structure arbitrarily designated as Z2-2 (6.8 mg, peak 2, retention time: 13.023 min, yield of 40%) was an off-white solid. $^{1}H$ NMR (500 MHz, DMSO-$d_6$) δ 12.65 (s, 1H), 10.74 (s, 1H), 8.67 (s, 1H), 7.77 (s, 1H), 7.68 (s, 1H), 7.57 (d, J=8.5 Hz, 1H), 7.48 (t, J=7.5 Hz, 2H), 7.25 (t, J=7.5 Hz, 1H), 7.21-7.15 (m, 3H), 7.02 (dd, J=8.5, 2.5 Hz, 1H), 4.05-3.97 (m, 2H), 3.95-3.88 (m, 1H), 3.82 (d, J=9.0 Hz, 1H), 2.58-2.52 (m, 1H), 2.11-2.01 (m, 1H). ES-API: $[M+H]^+$=488.0.

Embodiment 3: Synthesis of Z3

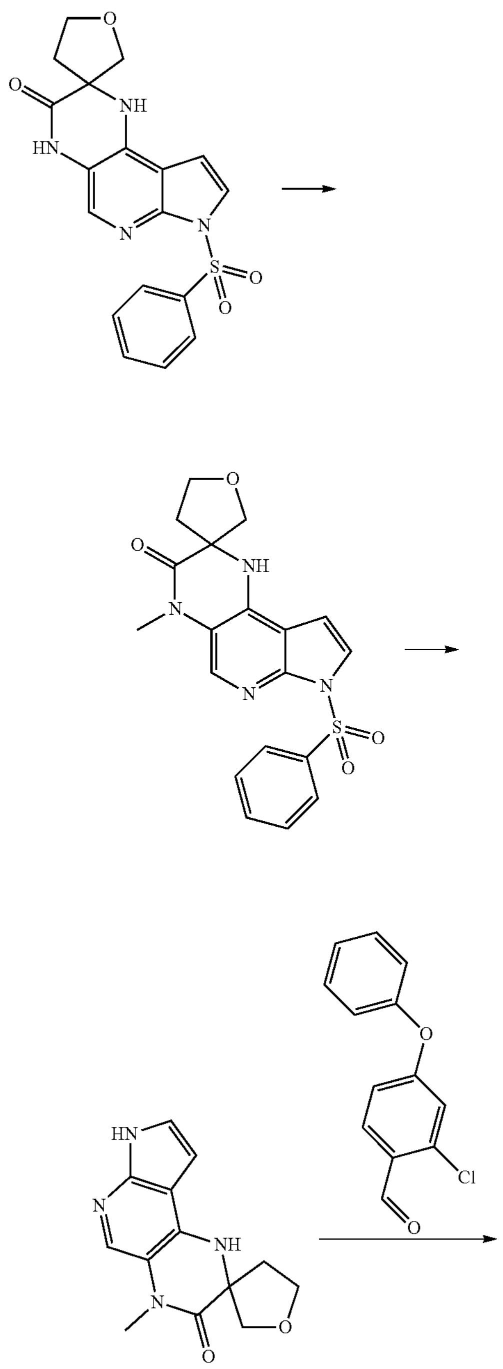

-continued

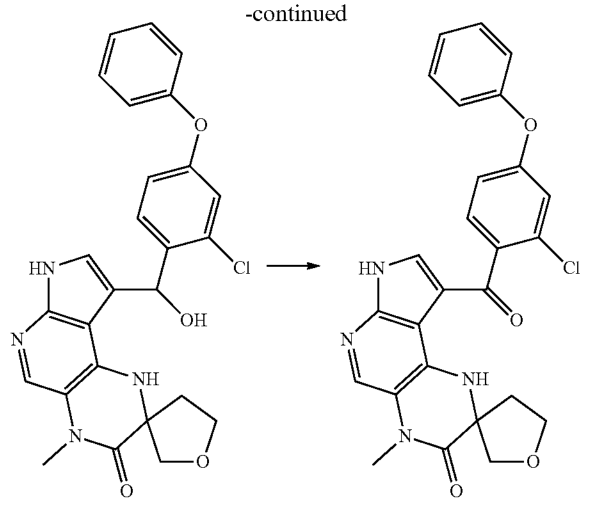

Z3

Step 1: 7'-(Phenylsulfonyl)-4,4',5,7'-tetrahydro-2H-spiro[furan-3,2'-pyrrolo[3',2':5,6]pyrido[3,4-b]pyrazin]-3'(1'H)-one (see step 1 and step 2 of Embodiment 1 for the preparation method) (150 mg, 0.39 mmol) was dissolved in 6 mL of acetone, and anhydrous potassium carbonate (118 mg, 0.86 mmol) and iodomethane (72 mg, 0.51 mmol) were added thereto in turn, and the reaction was stirred at room temperature for 18 hours. Anhydrous potassium carbonate (118 mg, 0.86 mmol) and iodomethane (72 mg, 0.51 mmol) were additionally added thereto, and the reaction was stirred at room temperature for 96 hours. The reaction solution was poured into 15 mL of water and extracted with 60 mL of ethyl acetate. The organic phase was washed with 15 mL of saturated brine, dried and concentrated to obtain 4'-methyl-7'-(phenylsulfonyl)-4,4',5,7'-tetrahydro-2H-spiro[furan-3,2'-pyrrolo[3',2':5,6]pyrido[3,4-b]pyrazin]-3'(1'H)-one (155 mg, yield of 100%) as a yellow solid. ES-API: $[M+H]^+$=399.1.

Step 2: 4'-Methyl-7'-(phenylsulfonyl)-4,4',5,7'-tetrahydro-2H-spiro[furan-3,2'-pyrrolo[3',2':5,6]pyrido[3,4-b]pyrazin]-3'(1'H)-one (155 mg, 0.39 mmol) was dissolved in 10 mL of methanol, 5 mL of tetrahydrofuran and 2 mL of water, and sodium hydroxide (78 mg, 1.95 mmol) was added thereto, and the reaction was stirred at 65° C. for 16 hours. The pH of the reaction solution was adjusted to 8 with 1.0 M dilute hydrochloric acid. To the reaction solution was added 10 mL of saturated sodium bicarbonate solution, and the mixture was extracted with 100 mL of ethyl acetate. The organic phase was washed with 20 mL of saturated brine, dried and then concentrated to obtain 4'-methyl-4,4',5,7'-tetrahydro-2H-spiro[furan-3,2'-pyrrolo[3',2':5,6]pyrido[3,4-b]pyrazin]-3'(1'H)-one (95 mg, yield of 94%) as a light brown solid. ES-API: $[M+H]^+$=259.1.

Step 3: 4'-Methyl-4,4',5,7'-tetrahydro-2H-spiro[furan-3,2'-pyrrolo[3',2':5,6]pyrido[3,4-b]pyrazin]-3'(1'H)-one (80 mg, 0.31 mmol) and 2-chloro-4-phenoxybenzaldehyde (108 mg, 0.47 mmol) were dissolved in methanol (8 mL), and the reaction was cooled to 0° C., and potassium hydroxide (122 mg, 2.17 mmol) was added thereto. The reaction was stirred at room temperature for 24 hours. The reaction solution was poured into 30 mL of water, and the pH of the reaction solution was adjusted to 8 with 1.0 M dilute hydrochloric acid, and the reaction solution was extracted with 80 mL of ethyl acetate. The organic phase was washed with 25 mL of saturated brine, dried and then concentrated, and the crude product was purified by a thin-layer preparative plate (dichloromethane/methanol=10:1) to obtain 9'-((2-chloro-4-phenoxyphenyl)(hydroxy)methyl)-4'-methyl-4,4',5,7'-tetrahydro-2H-spiro[furan-3,2'-pyrrolo[3',2':5,6]pyrido[3,4-b]pyrazin]-3'(1'H)-one (80 mg, yield of 52%) as an off-white solid. ES-API: $[M+H]^+$=491.1.

Step 4: 9'-((2-Chloro-4-phenoxyphenyl)(hydroxy)methyl)-4'-methyl-4,4',5,7'-tetrahydro-2H-spiro[furan-3,2'-pyrrolo[3',2':5,6]pyrido[3,4-b]pyrazin]-3'(1'H)-one (75 mg, 0.15 mmol) was dissolved in 6 mL of tetrahydrofuran, cooled to 0° C., and Dess-Martin periodinane (130 mg, 0.30 mmol) was added thereto, and the reaction was stirred at room temperature for 2 hours. To the reaction solution was added 4 mL of saturated sodium thiosulfate solution and 15 mL of saturated sodium bicarbonate solution, and the mixture was extracted with 40 mL of ethyl acetate. The organic phase was washed with 15 mL of saturated brine, dried and then concentrated, and the crude product was purified by preparative HPLC to obtain a target product (Z3, 48 mg, yield of 64%) as a pale yellow solid. $^1H$ NMR (500 MHz, DMSO-$d_6$) δ 8.74 (s, 1H), 8.03 (s, 1H), 7.70 (s, 1H), 7.56 (d, J=8.5 Hz, 1H), 7.48 (t, J=8.0 Hz, 2H), 7.25 (t, J=7.5 Hz, 1H), 7.22-7.14 (m, 3H), 7.02 (dd, J=8.5, 2.5 Hz, 1H), 4.04-4.00 (m, 2H), 3.94-3.89 (m, 1H), 3.78 (d, J=9.0 Hz, 1H), 3.42 (s, 3H), 2.54-2.48 (m, 1H), 2.07-1.98 (m, 1H). ES-API: $[M+H]^+$=489.1.

Embodiment 4: Synthesis of Z4, Z4-1 and Z4-2

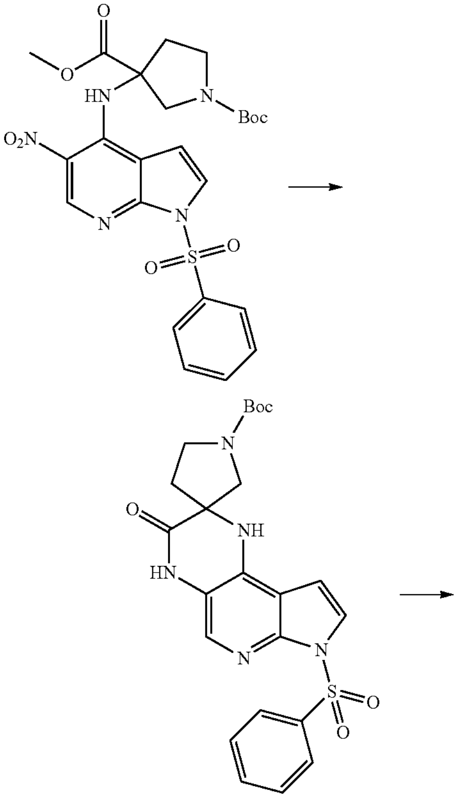

-continued

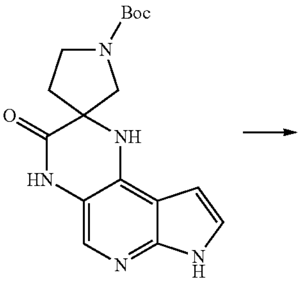

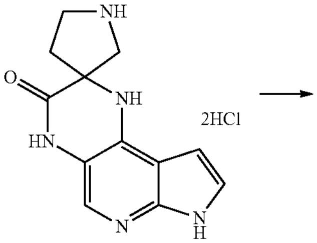

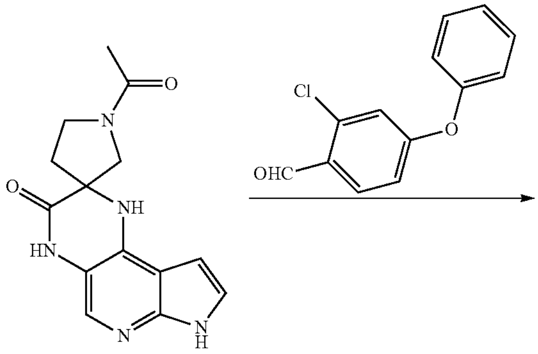

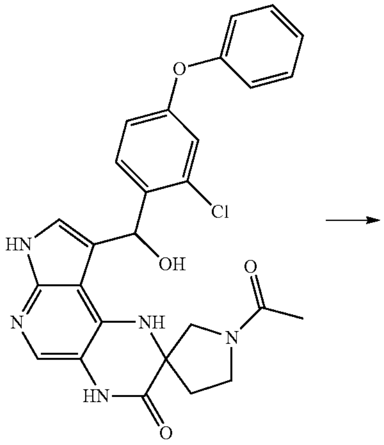

-continued

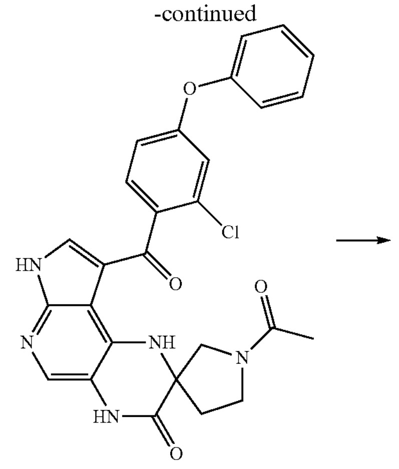

Z4

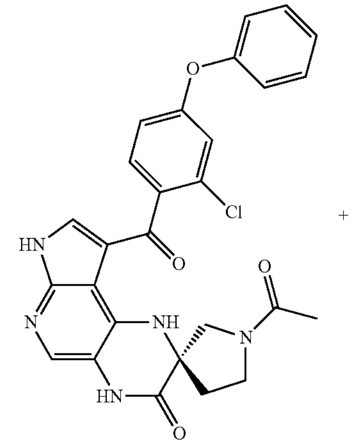

Z4-1

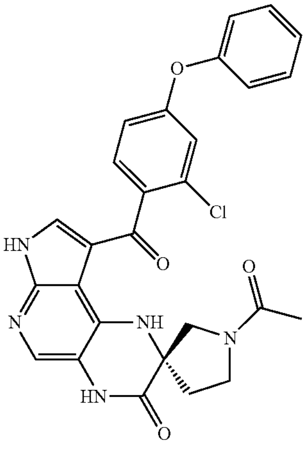

Z4-2

Step 1: 1-(tert-Butyl) 3-methyl 3-((5-nitro-1-(phenylsulfonyl)-1H-pyrrolo[2,3-b]pyridin-4-yl)amino)pyrrolidine-1,3-dicarboxylate (220 mg, 0.40 mmol) was dissolved in acetic acid (8 mL), and iron powder (224 mg, 4.0 mmol) was added thereto, and the reaction was stirred at 85° C. for 1 hour. The reaction solution was cooled to room temperature, poured into 30 mL of water, and extracted twice with 30 mL of ethyl acetate. The combined organic phases were washed with 25 mL of water, washed 3 times with 30 mL of saturated sodium bicarbonate solution, and washed with 30 mL of saturated brine in turn, dried and concentrated to obtain tert-butyl 3'-oxo-7'-(phenylsulfonyl)-1',3',4',7'-tetrahydrospiro[pyrrolidine-3,2'-pyrrolo[3',2':5,6]pyrido[3,4-b]pyrazine]-1-carboxylate (195 mg, yield of 100%) as a light brown solid. ES-API: $[M+H]^+$=484.1

Step 2: tert-Butyl 3'-oxo-7'-(phenylsulfonyl)-1',3',4',7'-tetrahydrospiro[pyrrolidine-3,2'-pyrrolo[3',2':5,6]pyrido[3,4-b]pyrazine]-1-carboxylate (195 mg, 0.40 mmol) was dissolved in 10 mL of methanol, 5 mL of tetrahydrofuran and 2 mL of water, and then sodium hydroxide (80 mg, 2.00 mmol) and triethylamine (202 mg, 2.0 mmol) were added thereto, and the reaction was stirred at 65° C. for 16 hours. The pH of the reaction solution was adjusted to 8 with 1.0 M dilute hydrochloric acid. To the reaction solution was added 10 mL of saturated sodium bicarbonate solution, and the mixture was extracted with 100 mL of ethyl acetate. The organic phase was washed with 20 mL of saturated brine, dried and then concentrated to obtain tert-butyl 3'-oxo-1',3',4',7'-tetrahydrospiro[pyrrolidine-3,2'-pyrrolo[3',2':5,6]pyrido[3,4-b]pyrazine]-1-carboxylate (130 mg, yield of 94%) as a light brown solid. ES-API: $[M+H]^+$=344.2.

Step 3: tert-Butyl 3'-oxo-1',3',4',7'-tetrahydrospiro[pyrrolidine-3,2'-pyrrolo[3',2':5,6]pyrido[3,4-b]pyrazine]-1-carboxylate (130 mg, 0.38 mmol) was dissolved in 2 mL of methanol, and 4.0 M hydrogen chloride methanol solution (5 mL, 20.0 mmol) was added thereto, and the reaction was stirred at room temperature for 4 hours. The reaction solution was concentrated to obtain 4',7'-dihydrospiro[pyrrolidine-3,2'-pyrrolo[3',2':5,6]pyrido[3,4-b]pyrazin]-3'(1'H)-one hydrochloride (110 mg, yield of 92%) as a light green solid. ES-API: $[M+H]^+$=244.1 (free base).

Step 4: 4',7'-Dihydrospiro[pyrrolidine-3,2'-pyrrolo[3',2':5,6]pyrido[3,4-b]pyrazin]-3'(1'H)-one hydrochloride (110 mg, 0.35 mmol) was suspended in dichloromethane (15 mL), cooled to 0° C., and triethylamine (177 mg, 1.75 mmol) and 0.5 mL of a solution of acetyl chloride (68 mg, 0.87 mmol) in dichloromethane were added thereto in turn, and the reaction was stirred for 2 hours under an ice bath. The reaction solution was added with 2 mL of methanol, concentrated, and then the crude product was purified by a thin-layer preparation plate (dichloromethane/methanol=8:1) to obtain 1-acetyl-4',7'-dihydrospiro[pyrrolidine-3,2'-pyrrolo[3',2':5,6]pyrido[3,4-b]pyrazin]-3'(1'H)-one (50 mg, yield of 50%) as a light brown solid. ES-API: $[M+H]^+$=286.1

Step 5: 1-Acetyl-4',7'-dihydrospiro[pyrrolidine-3,2'-pyrrolo[3',2':5,6]pyrido[3,4-b]pyrazin]-3'(1'H)-one (45 mg, 0.16 mmol) and 2-chloro-4-phenoxybenzaldehyde (74 mg, 0.32 mmol) were dissolved in methanol (6 mL), and the reaction was cooled to 0° C., and potassium hydroxide (63 mg, 1.12 mmol) was added thereto. The reaction was stirred at room temperature for 18 hours. The pH of the reaction solution was adjusted to 8 with 1.0 M dilute hydrochloric acid, and the reaction solution was concentrated, then the crude product was purified by a thin-layer preparative plate (dichloromethane/methanol=10:1) to obtain 1-acetyl-9'-((2-chloro-4-phenoxyphenyl)(hydroxy)methyl)-4',7'-dihydrospiro[pyrrolidine-3,2'-pyrrolo[3',2':5,6]pyrido[3,4-b]pyrazin]-3'(1'H)-one (48 mg, yield of 58%) as an off-white solid. ES-API: $[M+H]^+$=518.2.

Step 6: 1-Acetyl-9'-((2-chloro-4-phenoxyphenyl)(hydroxy)methyl)-4',7'-dihydrospiro[pyrrolidine-3,2'-pyrrolo[3',2':5,6]pyrido[3,4-b]pyrazin]-3'(1'H)-one (43 mg, 0.083 mmol) was dissolved in 6 mL of tetrahydrofuran, cooled to 0° C., and Dess-Martin periodinane (70 mg, 0.166 mmol) was added thereto, and the reaction was stirred at room temperature for 16 hours. To the reaction solution was added 3 mL of saturated sodium thiosulfate solution and 10 mL of saturated sodium bicarbonate solution, and the mixture was extracted with 60 mL of ethyl acetate. The organic phase was washed with 20 mL of saturated brine, dried and then concentrated, and the crude product was purified by preparative HPLC to obtain a target product (Z4, 20 mg, yield of 51%) as a white solid. ES-API: $[M+H]^+=516.0$.

Step 7: The compound Z4 (19 mg, 0.037 mmol) obtained in the above steps was resolved by chiral preparation (column: IC, 250 mm*4.6 mm*5 μM, mobile phase: methanol: ethanol=50:50, flow rate: 1 mL/min, column temperature: 30° C.) to obtain two single isomer compounds. One single isomer with a structure arbitrarily designated as Z4-1 (5 mg, peak 1, retention time: 5.370 min, yield of 26%) was a white solid. ES-API: $[M+H]^+=516.0$. The other single isomer with a structure arbitrarily designated as Z4-2 (7 mg, peak 2, retention time: 8.524 min, yield of 37%) was a white solid. ES-API: $[M+H]^+=516.0$.

-continued

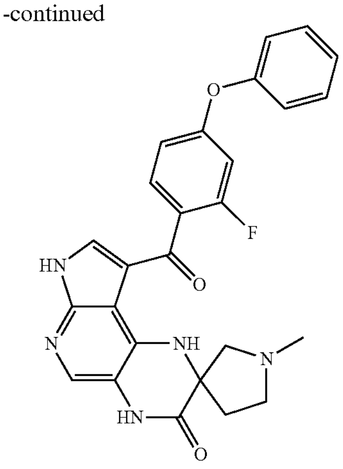

Z5

Embodiment 5: Synthesis of Z5

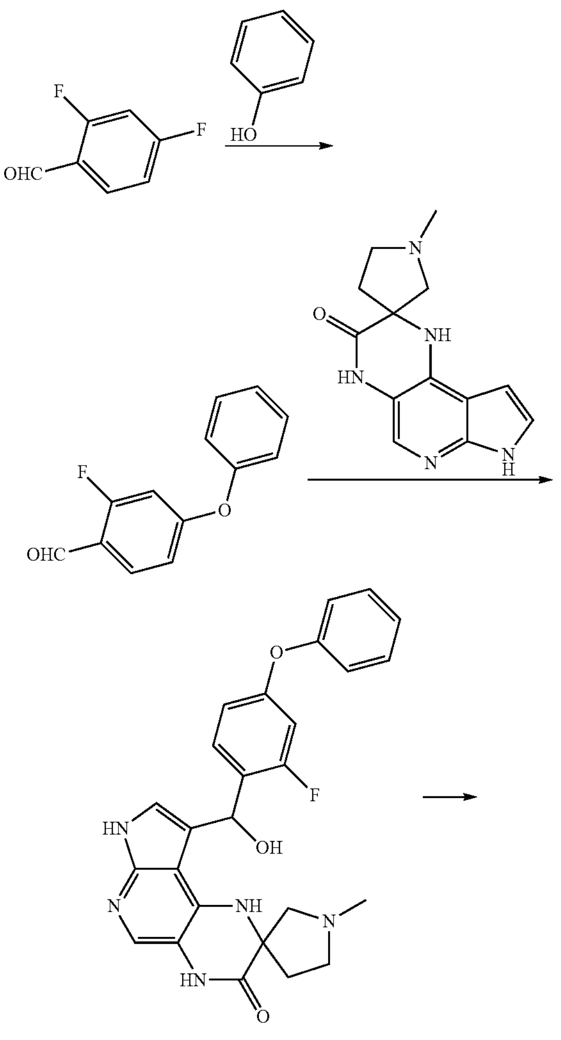

Step 1: 2,4-Difluorobenzaldehyde (2.84 g, 20.0 mmol) and phenol (1.69 g, 18.0 mmol) were dissolved in 50 mL of N,N-dimethylformamide, and cesium carbonate (8.80 g, 30.0 mmol) was added thereto, and the reaction was stirred at 75° C. for 16 hours. The reaction solution was poured into 100 mL of water and extracted with 80 mL of ethyl acetate. The organic phase was washed 4 times with 40 mL of saturated brine, dried and concentrated, and the crude product was purified by a flash silica gel column (ethyl acetate/petroleum ether: 0-3%) to obtain 2-fluoro-4-phenoxybenzaldehyde (1.4 g, yield of 36%) as a colorless liquid. $^1H$ NMR (500 MHz, DMSO-$d_6$) δ 10.11 (s, 1H), 7.85 (t, J=8.5 Hz, 1H), 7.54-7.44 (m, 2H), 7.34-7.29 (m, 1H), 7.22-7.16 (m, 2H), 6.95 (dd, J=12.5, 2.5 Hz, 1H), 6.89 (dd, J=8.5, 2.5 Hz, 1H). ES-API: $[M+H]^+=217.1$.

Step 2: 1-Methyl-4',7'-dihydrospiro[pyrrolidine-3,2'-pyrrolo[3',2':5,6]pyrido[3,4-b]pyrazin]-3'(1'H)-one (50 mg, 0.19 mmol) and 2-fluoro-4-phenoxybenzaldehyde (123 mg, 0.57 mmol) were dissolved in methanol (6 mL), and the reaction was cooled to 0° C., and potassium hydroxide (74 mg, 1.33 mmol) was added thereto. The reaction was stirred at room temperature for 18 hours. The pH of the reaction solution was adjusted to 8 with 1.0 M dilute hydrochloric acid, and the reaction solution was concentrated, then the crude product was purified by a thin-layer preparative plate (dichloromethane/7M ammonia methanol=10:1) to obtain 9'-((2-fluoro-4-phenoxyphenyl)(hydroxy)methyl)-1-methyl-4',7'-dihydrospiro[pyrrolidine-3,2'-pyrrolo[3',2':5,6]pyrido[3,4-b]pyrazin]-3'(1'H)-one (37 mg, yield of 40%) as a pale yellow solid. ES-API: $[M+H]^+=474.1$.

Step 3: 9'-((2-Fluoro-4-phenoxyphenyl)(hydroxy)methyl)-1-methyl-4',7'-dihydrospiro[pyrrolidine-3,2'-pyrrolo[3',2':5,6]pyrido[3,4-b]pyrazin]-3'(1'H)-one (37 mg, 0.078 mmol) was dissolved in 8 mL of tetrahydrofuran, cooled to 0° C., and Dess-Martin periodinane (99 mg, 0.23 mmol) was added thereto, and the reaction was stirred at room temperature for 18 hours. To the reaction solution was added 2 mL of saturated sodium thiosulfate solution and 8 mL of saturated sodium bicarbonate solution, and the mixture was extracted with 40 mL of ethyl acetate. The organic phase was washed with 15 mL of saturated brine, dried and then concentrated, and the crude product was purified by preparative HPLC to obtain a target product (Z5, 6 mg, yield of 16%) as a white solid. $^1H$ NMR (500 MHz, $CDCl_3$) δ 13.13 (s, 1H), 12.13 (s, 1H), 7.89 (s, 1H), 7.52-7.46 (m, 2H), 7.43 (t, J=8.0 Hz, 2H), 7.23 (t, J=7.5 Hz, 1H), 7.12 (d, J=7.5

Hz, 2H), 6.86 (dd, J=8.5, 2.5 Hz, 1H), 6.79 (dd, J=11.0, 2.0 Hz, 1H), 3.37 (s, 1H), 2.96-2.63 (m, 4H), 2.46 (s, 3H), 2.20-2.11 (m, 1H). ES-API: $[M+H]^+$=472.1.

Embodiment 6: Synthesis of Z6

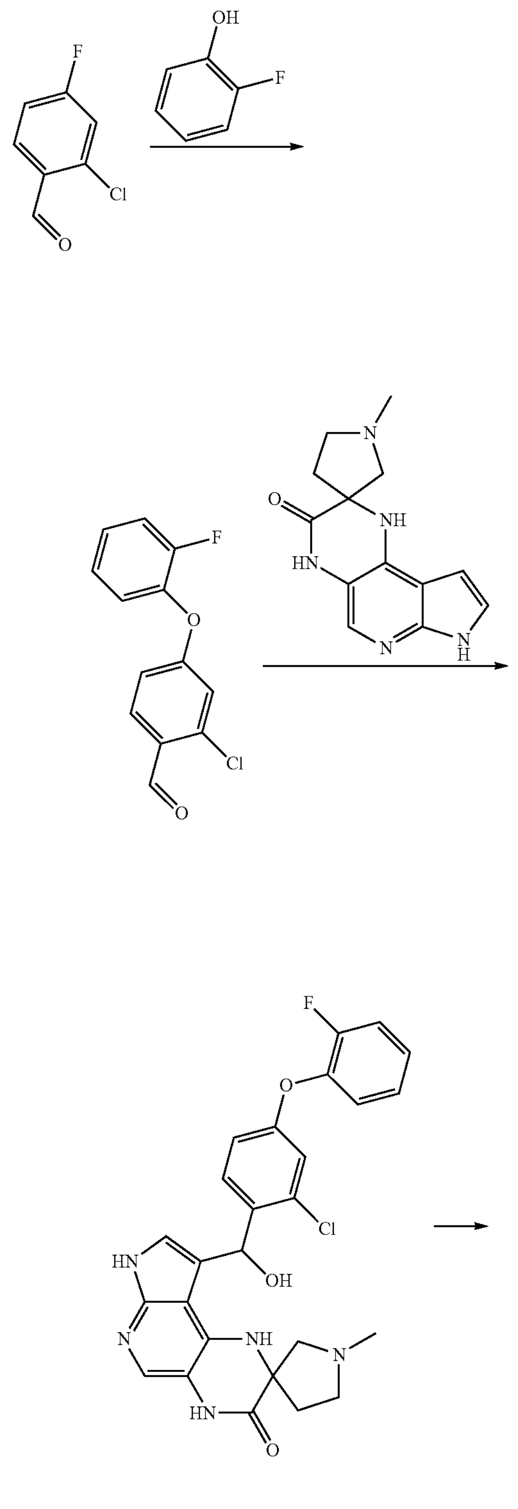

-continued

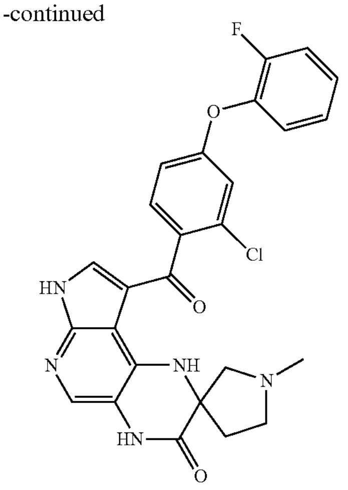

Z6

Step 1: 2-Chloro-4-fluorobenzaldehyde (1.0 g, 6.33 mmol) and 2-fluorophenol (744 mg, 6.65 mmol) were dissolved in 15 mL of N,N-dimethylformamide, and cesium carbonate (2.47 g, 7.60 mmol) was added thereto, and the reaction was stirred at 75° C. for 16 hours. The reaction solution was poured into 30 mL of water and extracted with 100 mL of ethyl acetate. The organic phase was washed 3 times with 30 mL of saturated brine, dried and concentrated, and the crude product was purified by a flash silica gel column (ethyl acetate/petroleum ether: 0-4%) to obtain 2-chloro-4-(2-fluorophenoxy)benzaldehyde (1.15 g, yield of 72%) as a white solid. ES-API: $[M+H]^+$=251.1.

Step 2: 1-Methyl-4',7'-dihydrospiro[pyrrolidine-3,2'-pyrrolo[3',2':5,6]pyrido[3,4-b]pyrazin]-3'(1'H)-one (50 mg, 0.19 mmol) and 2-chloro-4-(2-fluorophenoxy)benzaldehyde (143 mg, 0.57 mmol) were dissolved in methanol (6 mL), and the reaction was cooled to 0° C., and potassium hydroxide (75 mg, 1.33 mmol) was added thereto. The reaction was stirred at room temperature for 18 hours. The pH of the reaction solution was adjusted to 8 with 1.0 M dilute hydrochloric acid, and the reaction solution was concentrated, then the crude product was purified by a thin-layer preparative plate (dichloromethane/7M ammonia methanol=10:1) to obtain 9'-((2-chloro-4-(2-fluorophenoxy)phenyl)(hydroxy)methyl)-1-methyl-4',7'-dihydrospiro[pyrrolidine-3,2'-pyrrolo[3',2':5,6]pyrido[3,4-b]pyrazin]-3'(1'H)-one (41 mg, yield of 41%) as a yellow solid. ES-API: $[M+H]^+$=508.1.

Step 3: 9'-((2-Chloro-4-(2-fluorophenoxy)phenyl)(hydroxy)methyl)-1-methyl-4',7'-dihydrospiro[pyrrolidine-3,2'-pyrrolo[3',2':5,6]pyrido[3,4-b]pyrazin]-3'(1'H)-one (41 mg, 0.08 mmol) was dissolved in 6 mL of tetrahydrofuran, cooled to 0° C., and Dess-Martin periodinane (51 mg, 0.12 mmol) was added thereto, and the reaction was stirred at room temperature for 3 hours, then additional Dess-Martin periodinane (51 mg, 0.12 mmol) was added thereto, and the reaction was stirred at room temperature for 16 hours. To the reaction solution was added 2 mL of saturated sodium thiosulfate solution and 10 mL of saturated sodium bicarbonate solution, and the mixture was extracted with 40 mL of ethyl acetate. The organic phase was washed with 15 mL of saturated brine, dried and then concentrated, and the crude product was purified by preparative HPLC to obtain a target product (Z6, 2.5 mg, yield of 6%) as a pale yellow solid. ES-API: $[M+H]^+$=506.0.

Embodiment 7: Synthesis of Z7

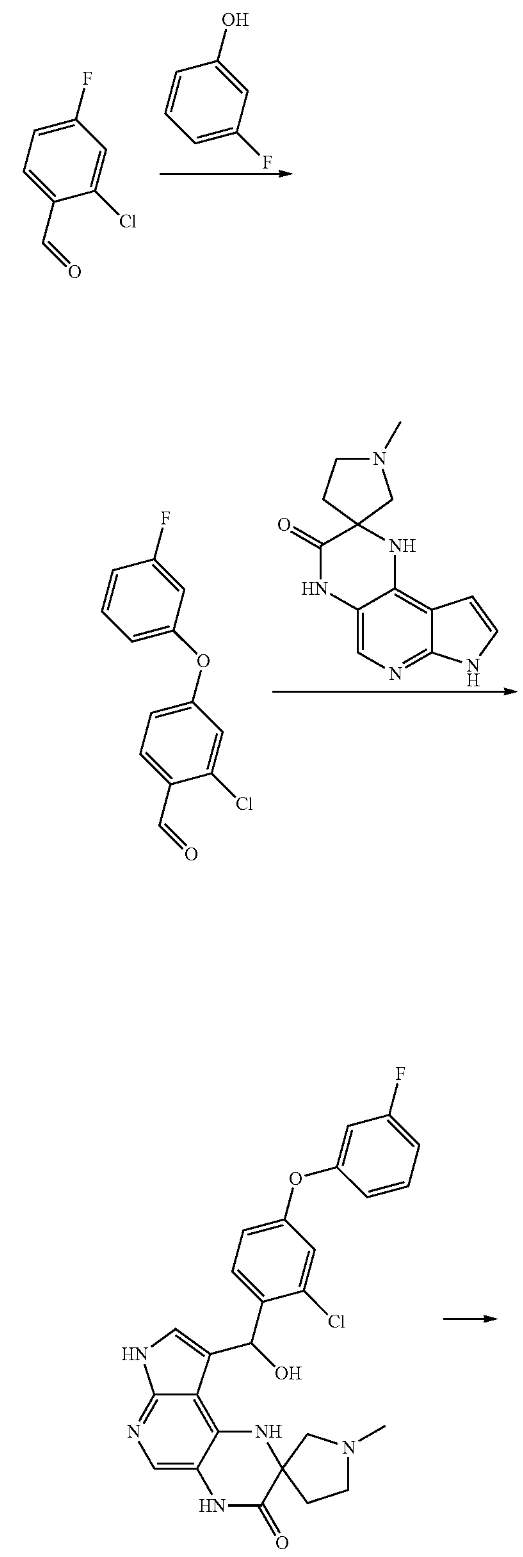

-continued

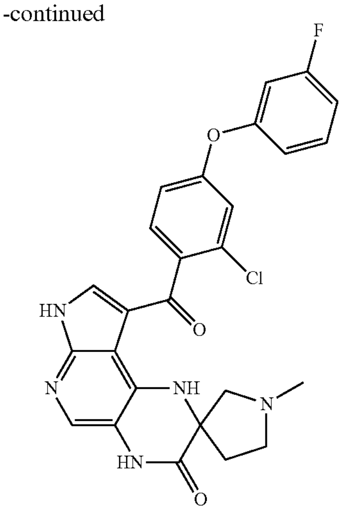

Z7

Step 1: 2-Chloro-4-fluorobenzaldehyde (1.0 g, 6.33 mmol) and 3-fluorophenol (744 mg, 6.65 mmol) were dissolved in 15 mL of N,N-dimethylformamide, and cesium carbonate (2.47 g, 7.60 mmol) was added thereto, and the reaction was stirred at 75° C. for 16 hours. The reaction solution was poured into 30 mL of water and extracted with 100 mL of ethyl acetate. The organic phase was washed 3 times with 30 mL of saturated brine, dried and concentrated, and the crude product was purified by a flash silica gel column (ethyl acetate/petroleum ether: 0-4%) to obtain 2-chloro-4-(3-fluorophenoxy)benzaldehyde (930 mg, yield of 59%) as a white solid. ES-API: $[M+H]^+$=251.1.

Step 2: 1-Methyl-4',7'-dihydrospiro[pyrrolidine-3,2'-pyrrolo[3',2':5,6]pyrido[3,4-b]pyrazin]-3'(1'H)-one (50 mg, 0.19 mmol) and 2-chloro-4-(3-fluorophenoxy)benzaldehyde (143 mg, 0.57 mmol) were dissolved in methanol (6 mL), and the reaction was cooled to 0° C., and potassium hydroxide (75 mg, 1.33 mmol) was added thereto. The reaction was stirred at room temperature for 18 hours. The pH of the reaction solution was adjusted to 8 with 1.0 M dilute hydrochloric acid, and the reaction solution was concentrated, then the crude product was purified by a thin-layer preparative plate (dichloromethane/7M ammonia methanol=10:1) to obtain 9'-((2-chloro-4-(3-fluorophenoxy)phenyl)(hydroxy)methyl)-1-methyl-4',7'-dihydrospiro[pyrrolidine-3,2'-pyrrolo[3',2':5,6]pyrido[3,4-b]pyrazin]-3'(1'H)-one (50 mg, yield of 50%) as a yellow solid. ES-API: $[M+H]^+$=508.0.

Step 3: 9'-((2-Chloro-4-(3-fluorophenoxy)phenyl)(hydroxy)methyl)-1-methyl-4',7'-dihydrospiro[pyrrolidine-3,2'-pyrrolo[3',2':5,6]pyrido[3,4-b]pyrazin]-3'(1'H)-one (50 mg, 0.10 mmol) was dissolved in 6 mL of tetrahydrofuran, cooled to 0° C., and Dess-Martin periodinane (64 mg, 0.15 mmol) was added thereto, and the reaction was stirred at room temperature for 3 hours, then additional Dess-Martin periodinane (64 mg, 0.15 mmol) was added thereto, and the reaction was stirred at room temperature for 16 hours. To the reaction solution was added 2 mL of saturated sodium thiosulfate solution and 10 mL of saturated sodium bicarbonate solution, and the mixture was extracted with 40 mL of ethyl acetate. The organic phase was washed with 15 mL of saturated brine, dried and then concentrated, and the crude product was purified by preparative HPLC to obtain a target product (Z7, 5 mg, yield of 10%) as a pale yellow solid. $^1H$ NMR (500 MHz, $CDCl_3$) δ 13.12 (s, 1H), 12.15 (s, 1H), 7.42-7.35 (m, 2H), 7.30 (dd, J=15.0, 8.0 Hz, 1H), 7.06 (d, J=2.5 Hz, 1H), 6.93 (dd, J=8.5, 2.5 Hz, 1H), 6.88-6.71 (m, 3H), 3.37 (s, 1H), 3.05-2.58 (m, 4H), 2.48 (s, 3H), 2.20-2.10 (m, 1H). ES-API: $[M+H]^+$=506.0.

Embodiment 8: Synthesis of Z8

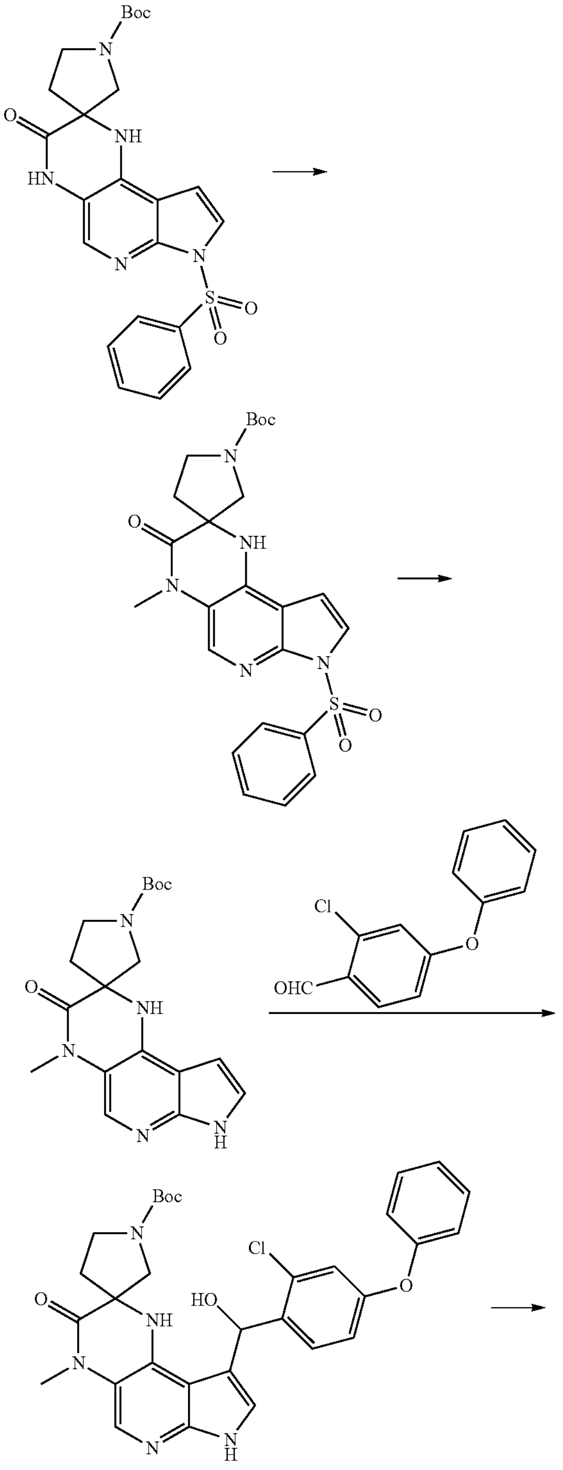 [SMILES: CC(C)(C)OC(=O)N1CCC2(C1)Nc1c(cnc3c1ccn3S(=O)(=O)c1ccccc1)NC2=O ; CN1C(=O)C2(CCN(C(=O)OC(C)(C)C)C2)Nc2c1cnc1c2ccn1S(=O)(=O)c1ccccc1 ; CN1C(=O)C2(CCN(C(=O)OC(C)(C)C)C2)Nc2c1cnc1[nH]ccc21 ; O=Cc1ccc(Oc2ccccc2)cc1Cl ; CN1C(=O)C2(CCN(C(=O)OC(C)(C)C)C2)Nc2c1cnc1[nH]cc(C(O)c3ccc(Oc4ccccc4)cc3Cl)c21]

-continued

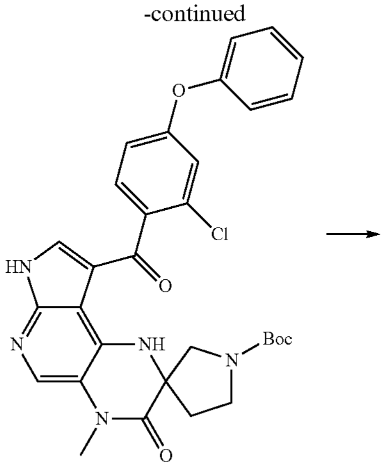

Z7

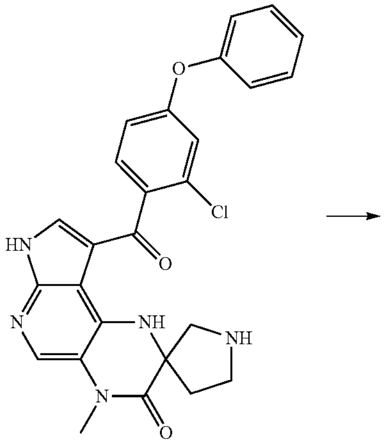

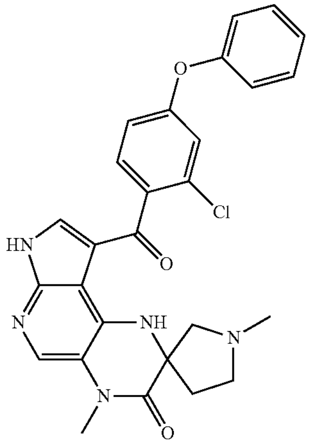

Z8

Step 1: tert-Butyl 3'-oxo-7'-(phenylsulfonyl)-1',3',4',7'-tetrahydrospiro[pyrrolidine-3,2'-pyrrolo[3',2':5,6]pyrido[3,4-b]pyrazine]-1-carboxylate (225 mg, 0.47 mmol) was dissolved in 12 mL of acetone, then anhydrous potassium carbonate (324 mg, 2.35 mmol) and iodomethane (267 mg, 1.88 mmol) were added thereto in turn, and the reaction was stirred at room temperature for 72 hours. The reaction solution was poured into 15 mL of water and extracted with 60 mL of ethyl acetate. The organic phase was washed with 15 mL of saturated brine, dried and concentrated, and the crude product was purified by a flash silica gel column (ethyl acetate/petroleum ether: 0-50%) to obtain tert-butyl 4'-methyl-3'-oxo-7'-(phenylsulfonyl)-1',3',4',7'-tetrahydrospiro[pyrrolidine-3,2'-pyrrolo[3',2':5,6]pyrido[3,4-b] pyrazine]-1-carboxylate (180 mg, yield of 78%) as a pale yellow solid. ES-API: $[M+H]^+$=498.1.

Step 2: tert-Butyl 4'-methyl-3'-oxo-7'-(phenylsulfonyl)-1',3',4',7'-tetrahydrospiro[pyrrolidine-3,2'-pyrrolo[3',2':5,6] pyrido[3,4-b]pyrazine]-1-carboxylate (180 mg, 0.36 mmol) was dissolved in 10 mL of methanol, 5 mL of tetrahydrofuran and 2 mL of water, then sodium hydroxide (72 mg, 1.80 mmol) was added thereto, and the reaction was stirred at 65° C. for 16 hours. The pH of the reaction solution was adjusted to 8 with 1.0 M dilute hydrochloric acid. To the reaction solution was added 10 mL of saturated sodium bicarbonate solution, and the mixture was extracted with 100 mL of ethyl acetate. The organic phase was washed with 25 mL of saturated brine, dried and then concentrated to obtain tert-butyl 4'-methyl-3'-oxo-1',3',4',7'-tetrahydrospiro [pyrrolidine-3,2'-pyrrolo[3',2':5,6]pyrido[3,4-b]pyrazine]-1-carboxylate (125 mg, yield of 97%) as a light brown solid. ES-API: $[M+H]^+$=358.2.

Step 3: tert-Butyl 4'-methyl-3'-oxo-1',3',4',7'-tetrahydrospiro[pyrrolidine-3,2'-pyrrolo[3',2':5,6]pyrido[3,4-b] pyrazine]-1-carboxylate (125 mg, 0.35 mmol) and 2-chloro-4-phenoxybenzaldehyde (244 mg, 1.05 mmol) were dissolved in methanol (12 mL), and the reaction was cooled to 0° C., and potassium hydroxide (137 mg, 2.45 mmol) was added thereto. The reaction was stirred at room temperature for 18 hours. The pH of the reaction solution was adjusted to 8 with 1.0 M dilute hydrochloric acid, and the reaction solution was added with 80 mL of ethyl acetate. The organic phase was washed with 25 mL of saturated brine, dried and then concentrated, and the crude product was purified by a thin-layer preparative plate (dichloromethane/methanol=10:1) to obtain tert-butyl 9'-((2-chloro-4-phenoxyphenyl)(hydroxy)methyl)-4'-methyl-3'-oxo-1',3',4',7'-tetrahydrospiro [pyrrolidine-3,2'-pyrrolo[3',2':5,6]pyrido[3,4-b]pyrazine]-1-carboxylate (168 mg, yield of 81%) as a white solid. ES-API: $[M+H]^+$=590.2.

Step 4: tert-Butyl 9'-((2-chloro-4-phenoxyphenyl)(hydroxy)methyl)-4'-methyl-3'-oxo-1',3',4',7'-tetrahydrospiro [pyrrolidine-3,2'-pyrrolo[3',2':5,6]pyrido[3,4-b]pyrazine]-1-carboxylate (153 mg, 0.26 mmol) was dissolved in 20 mL of tetrahydrofuran, cooled to 0° C., and Dess-Martin periodinane (165 mg, 0.39 mmol) was added thereto, and the reaction was stirred at room temperature for 16 hours. To the reaction solution was added 4 mL of saturated sodium thiosulfate solution and 10 mL of saturated sodium bicarbonate solution, and the mixture was extracted with 60 mL of ethyl acetate. The organic phase was washed with 20 mL of saturated sodium bicarbonate solution and 20 mL of saturated brine in turn, dried and then concentrated to obtain tert-butyl 9'-(2-chloro-4-phenoxybenzoyl)-4'-methyl-3'-oxo-1',3',4',7'-tetrahydrospiro[pyrrolidine-3,2'-pyrrolo[3',2':5,6]pyrido[3,4-b]pyrazine]-1-carboxylate (150 mg, yield of 100%) as a yellow solid. ES-API: $[M+H]^+$=588.1.

Step 5: tert-Butyl 9'-(2-chloro-4-phenoxybenzoyl)-4'-methyl-3'-oxo-1',3',4',7'-tetrahydrospiro[pyrrolidine-3,2'-pyrrolo[3',2':5,6]pyrido[3,4-b]pyrazine]-1-carboxylate (150 mg, 0.25 mmol) was dissolved in 4.5 mL of dichloromethane, cooled to 0° C., and 1.5 mL of trifluoroacetic acid was added thereto, and the reaction was stirred at room temperature for 1 hour. The reaction solution was concentrated, and 10 mL of saturated sodium bicarbonate solution was added thereto, and the mixture was extracted twice with 40 mL of ethyl acetate. The organic phase was washed with 25 mL of saturated brine, dried and then concentrated to obtain 9'-(2-chloro-4-phenoxybenzoyl)-4'-methyl-4',7'-dihydrospiro [pyrrolidine-3,2'-pyrrolo[3',2':5,6]pyrido[3,4-b]pyrazin]-3' (1'H)-one (124 mg, yield of 100%) as a light brown solid. ES-API: $[M+H]^+$=488.0.

Step 6: 9'-(2-Chloro-4-phenoxybenzoyl)-4'-methyl-4',7'-dihydrospiro[pyrrolidine-3,2'-pyrrolo[3',2':5,6]pyrido[3,4-b]pyrazin]-3'(1'H)-one (104 mg, 0.21 mmol) was dissolved in 10 mL of methanol and 2 mL of dichloromethane, then 37% aqueous formaldehyde solution (85 mg, 1.05 mmol) and 1 drop of acetic acid were added thereto in turn at room temperature. The reaction was stirred at room temperature for 30 minutes, then sodium cyanoborohydride (26 mg, 0.42 mmol) was added thereto, and the reaction was stirred at room temperature for 2 hours. The reaction solution was concentrated, and the crude product was purified by a thin-layer preparative plate (dichloromethane/7M ammonia methanol=10:1) to obtain 58 mg of a crude product, then purified by preparative HPLC to obtain a target product (Z8, 8 mg, yield of 7%) as a yellow solid. ES-API: $[M+H]^+$=502.1.

Embodiment 9: Synthesis of Z9, Z9-1 and Z9-2

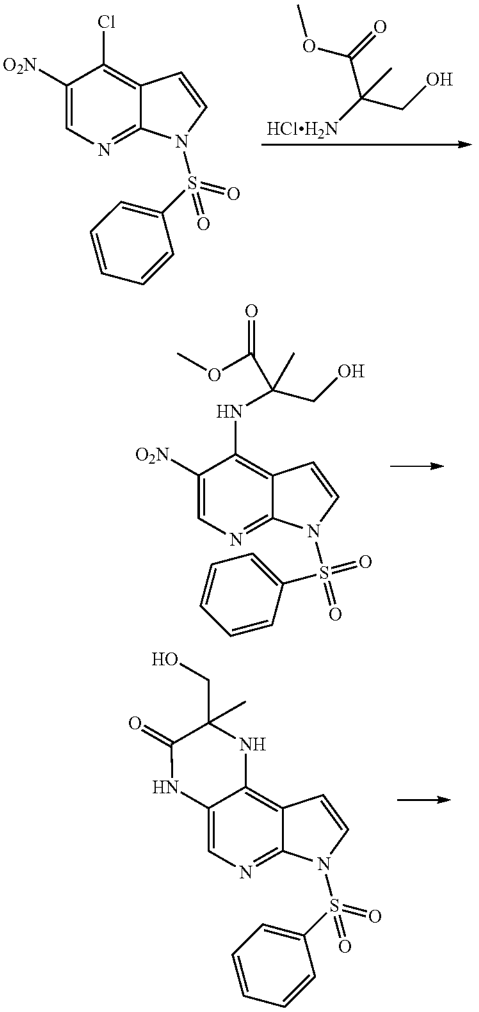

-continued

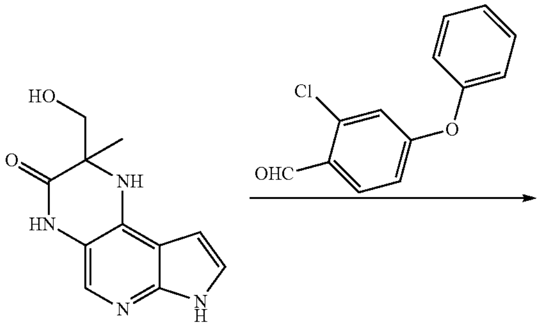

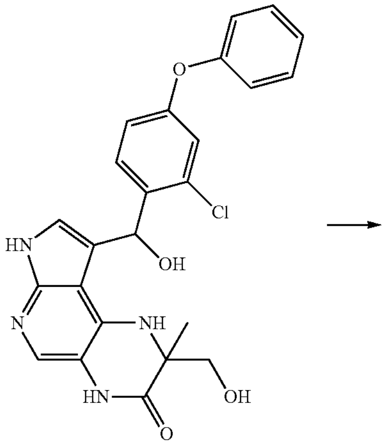

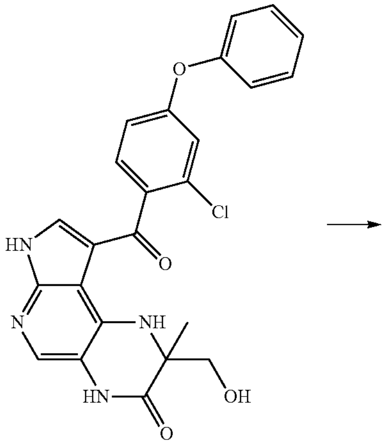

Z9

-continued

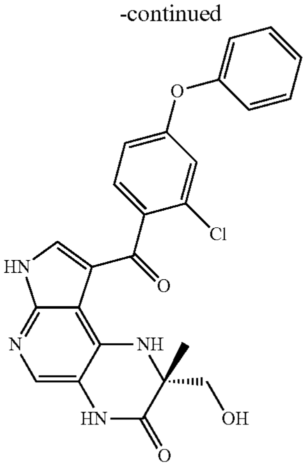

Z9-1

+

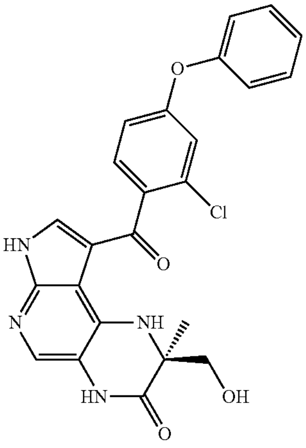

Z9-2

Step 1: 4-Chloro-5-nitro-1-(phenylsulfonyl)-1H-pyrrolo[2,3-b]pyridine (0.9 g, 2.671 mmol) and methyl 2-amino-3-hydroxy-2-methylpropanoate hydrochloride (1.0 g, 5.915 mmol) were dissolved in N,N-dimethylformamide (30 mL), and N,N-diisopropylethylamine (7.64 g, 59.15 mmol) was added thereto, and the reaction was stirred at 95° C. for 16 hours. The reaction solution was added with 100 mL of ethyl acetate, washed twice with 60 mL of water and 3 times with 30 mL of saturated brine, dried and concentrated, and the crude product was purified by a flash silica gel column (ethyl acetate/petroleum ether: 0-50%) to obtain 3-hydroxy-2-methyl-2-methyl-((5-nitro-1-(phenylsulfonyl)-1H-pyrrolo[2,3-b]pyridin-4-yl)amino)propanoate (620 mg, yield of 53%) as a pale yellow solid. ES-API: $[M+H]^+$=435.1.

Step 2: 3-Hydroxy-2-methyl-2-methyl-((5-nitro-1-(phenylsulfonyl)-1H-pyrrolo[2,3-b]pyridin-4-yl)amino)propanoate (550 mg, 1.267 mmol) was dissolved in acetic acid (15 mL), and iron powder (1.40 g, 25.00 mmol) was added thereto, and the reaction was stirred at 80° C. for 1 hour. The solvent was evaporated to dryness by rotary evaporation under reduced pressure, then 200 mL of ethyl acetate was added thereto. The mixture was washed twice with 80 mL of water, twice with 60 mL of saturated sodium carbonate, twice with 80 mL of saturated sodium bicarbonate, and with 80 mL of saturated brine in turn, dried and concentrated, and the crude product was slurried with ethyl acetate to obtain 2-(hydroxymethyl)-2-methyl-7-(phenylsulfonyl)-1,2,4,7-tetrahydro-3H-pyrrolo[3',2':5,6]pyrido[3,4-b]pyrazin-3-one (380 mg, yield of 80.6%) as a yellow solid. ES-API: $[M+H]^+$=373.1

Step 3: 2-(Hydroxymethyl)-2-methyl-7-(phenylsulfonyl)-1,2,4,7-tetrahydro-3H-pyrrolo[3',2':5,6]pyrido[3,4-b]pyrazin-3-one (200 mg, 0.5376 mmol) was dissolved in 12 mL of methanol, 2 mL of tetrahydrofuran and 2 mL of water, then sodium hydroxide (215 mg, 5.376 mmol) was added thereto, and the reaction was stirred at 65° C. for 7 hours. To the reaction solution was added 20 mL of water and 5 mL of saturated ammonium chloride solution, and the mixture was extracted with 150 mL of ethyl acetate. The organic phase was washed with 30 mL of saturated sodium bicarbonate solution and 80 mL of saturated brine in turn, dried over anhydrous sodium sulfate and then concentrated to obtain 2-(hydroxymethyl)-2-methyl-1,2,4,7-tetrahydro-3H-pyrrolo[3',2':5,6]pyrido[3,4-b]pyrazin-3-one (300 mg, crude product) as an off-white solid. ES-API: $[M+H]^+$=233.0.

Step 4: 2-(Hydroxymethyl)-2-methyl-1,2,4,7-tetrahydro-3H-pyrrolo[3',2':5,6]pyrido[3,4-b]pyrazin-3-one (300 mg, 1.293 mmol) and 2-chloro-4-phenoxybenzaldehyde (350 mg, 1.510 mmol) were dissolved in methanol (12.0 mL), and the reaction was cooled to 0° C., and potassium hydroxide (300 mg, 5.375 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and then concentrated to obtain a crude target product 9-((2-chloro-4-phenoxyphenyl)(hydroxy)methyl)-2-(hydroxymethyl)-2-methyl-1,2,4,7-tetrahydro-3H-pyrrolo[3',2':5,6]pyrido[3,4-b]pyrazin-3-one (320 mg, crude product) as a pale yellow solid. ES-API: $[M+H]^+$=465.1.

Step 5: 9-((2-Chloro-4-phenoxyphenyl)(hydroxy)methyl)-2-(hydroxymethyl)-2-methyl-1,2,4,7-tetrahydro-3H-pyrrolo[3',2':5,6]pyrido[3,4-b]pyrazin-3-one (320 mg, 0.6896 mmol) was dissolved in 30 mL of dichloromethane, and 2,3-dichloro-5,6-dicyano-1,4-benzoquinone (320 mg, 1.410 mmol) was added thereto, and the reaction was stirred at room temperature for 2 hours. To the reaction solution was added 60 mL of saturated sodium bicarbonate solution, and the mixture was extracted with 80 mL of ethyl acetate. The organic phase was washed with 60 mL of saturated brine, dried over anhydrous sodium sulfate and then concentrated, and the crude product was purified by preparative HPLC to obtain 9-(2-chloro-4-phenoxybenzoyl)-2-(hydroxymethyl)-2-methyl-1,2,4,7-tetrahydro-3H-pyrrolo[3',2':5,6]pyrido[3,4-b]pyrazin-3-one (Z9, 26 mg, yield of 8%) as a pale yellow solid, ES-API: $[M+H]^+$=463.0. $^1H$ NMR (500 MHz, DMSO-$d_6$) δ 12.39 (s, 1H), 10.39 (s, 1H), 8.23 (s, 1H), 7.67 (s, 1H), 7.57 (s, 1H), 7.54 (d, J=8.4 Hz, 1H), 7.48 (t, J=8.0 Hz, 2H), 7.25 (t, J=7.4 Hz, 1H), 7.22-7.13 (m, 3H), 7.02 (dd, J=8.4, 2.4 Hz, 1H), 5.21 (t, J=5.4 Hz, 1H), 3.69 (dd, J=10.6, 6.0 Hz, 1H), 3.48 (dd, J=10.7, 4.8 Hz, 1H), 1.36 (s, 3H).

Step 6: The compound Z9 (20 mg, 0.0433 mmol) obtained in the above steps was resolved by chiral preparation (column: IC, 150 mm*4.6 mm*5 μM, mobile phase: n-hexane:ethanol:diethylamine=70:30:0.2, flow rate: 1 mL/min, column temperature: 30° C.) to obtain two single isomer compounds. One single isomer with a structure arbitrarily designated as Z9-1 (7 mg, peak 1, retention time: 10.019 min, yield of 35%) was a pale white solid. ES-API: $[M+H]^+$=463.0. The other single isomer with a structure arbitrarily designated as Z9-2 (6.5 mg, peak 2, retention time: 11.323 min, yield of 34%) was a pale white solid. ES-API: $[M+H]^+$=463.0.

Embodiment 10: Synthesis of Z10

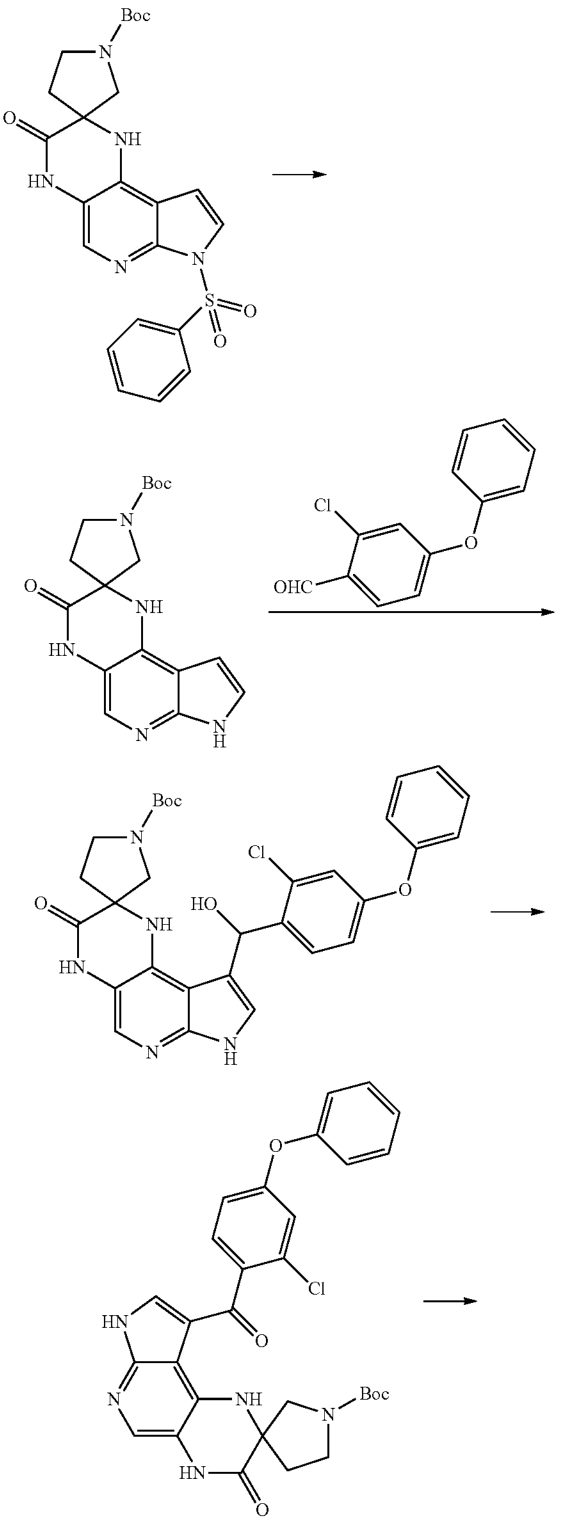 [SMILES: CC(C)(C)OC(=O)N1CCC2(C1)Nc1c(cnc3c1ccn3S(=O)(=O)c1ccccc1)NC2=O ; CC(C)(C)OC(=O)N1CCC2(C1)Nc1c(cnc3[nH]ccc13)NC2=O ; O=Cc1ccc(Oc2ccccc2)cc1Cl ; CC(C)(C)OC(=O)N1CCC2(C1)Nc1c(cnc3[nH]cc(C(O)c4ccc(Oc5ccccc5)cc4Cl)c13)NC2=O ; CC(C)(C)OC(=O)N1CCC2(C1)Nc1c(cnc3[nH]cc(C(=O)c4ccc(Oc5ccccc5)cc4Cl)c13)NC2=O]

-continued

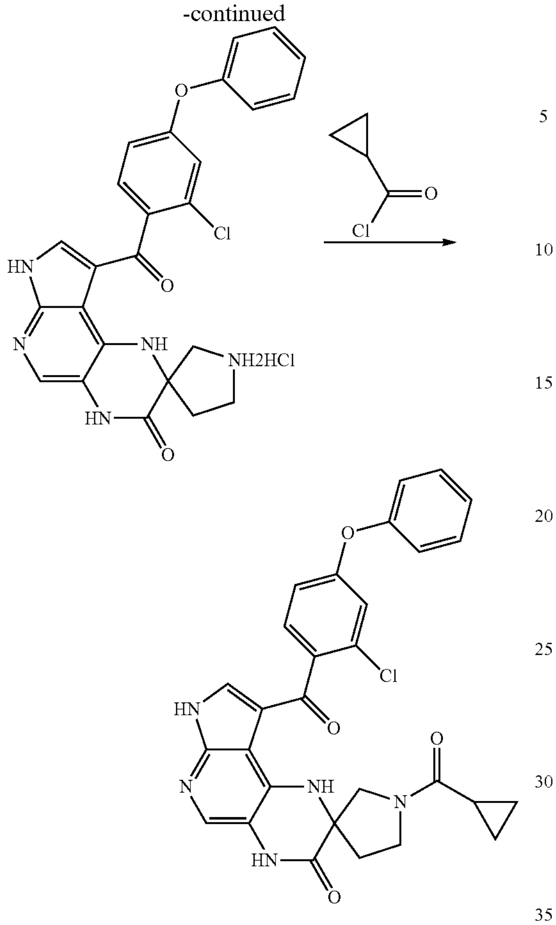

Z10

Step 1: tert-Butyl 3'-oxo-7'-(phenylsulfonyl)-1',3',4',7'-tetrahydrospiro[pyrrolidine-3,2'-pyrrolo[3',2':5,6]pyrido[3,4-b]pyrazine]-1-carboxylate (300 mg, 0.62 mmol) was dissolved in 10 mL of methanol, 5 mL of tetrahydrofuran and 2 mL of water, and sodium hydroxide (124 mg, 3.10 mmol) was added thereto, and the reaction was stirred at 60° C. for 16 hours. The pH of the reaction solution was adjusted to 8 with 1.0 M dilute hydrochloric acid. To the reaction solution was added 10 mL of saturated sodium bicarbonate solution, and the mixture was extracted with 100 mL of ethyl acetate. The organic phase was washed with 25 mL of saturated brine, dried and then concentrated to obtain tert-butyl 3'-oxo-1',3',4',7'-tetrahydrospiro[pyrrolidine-3,2'-pyrrolo[3',2':5,6]pyrido[3,4-b]pyrazine]-1-carboxylate (170 mg, yield of 80%) as a light brown solid. ES-API: [M+H]$^+$=344.2.

Step 2: tert-Butyl 3'-oxo-1',3',4',7'-tetrahydrospiro[pyrrolidine-3,2'-pyrrolo[3',2':5,6]pyrido[3,4-b]pyrazine]-1-carboxylate (170 mg, 0.50 mmol) and 2-chloro-4-phenoxybenzaldehyde (345 mg, 1.50 mmol) were dissolved in methanol (15 mL), and the reaction was cooled to 0° C., and potassium hydroxide (196 mg, 3.50 mmol) was added thereto. The reaction was stirred at room temperature for 18 hours. The pH of the reaction solution was adjusted to 8 with 1.0 M dilute hydrochloric acid, and the reaction solution was concentrated, then the crude product was purified by a thin-layer preparative plate (dichloromethane/methanol=10:1) to obtain tert-butyl 9'-((2-chloro-4-phenoxyphenyl)(hydroxy)methyl)-3'-oxo-1',3',4',7'-tetrahydrospiro[pyrrolidine-3,2'-pyrrolo[3',2':5,6]pyrido[3,4-b]pyrazine]-1-carboxylate (145 mg, yield of 51%) as a yellow solid. ES-API: [M+H]$^+$=576.1.

Step 3: tert-Butyl 9'-((2-chloro-4-phenoxyphenyl)(hydroxy)methyl)-3'-oxo-1',3',4',7'-tetrahydrospiro[pyrrolidine-3,2'-pyrrolo[3',2':5,6]pyrido[3,4-b]pyrazine]-1-carboxylate (130 mg, 0.26 mmol) was dissolved in 10 mL of tetrahydrofuran, cooled to 0° C., and Dess-Martin periodinane (146 mg, 0.34 mmol) was added thereto, and the reaction was stirred at room temperature for 18 hours. To the reaction solution was added 4 mL of saturated sodium thiosulfate solution and 10 mL of saturated sodium bicarbonate solution, and the mixture was extracted with 40 mL of ethyl acetate. The organic phase was washed with 10 mL of saturated sodium bicarbonate solution and 10 mL of saturated brine in turn, dried and then concentrated to obtain tert-butyl 9'-(2-chloro-4-phenoxybenzoyl)-3'-oxo-1',3',4',7'-tetrahydrospiro[pyrrolidine-3,2'-pyrrolo[3',2':5,6]pyrido[3,4-b]pyrazine]-1-carboxylate (129 mg, yield of 100%) as a yellow solid. S-API: [M+H]$^+$=574.2.

Step 4: tert-Butyl 9'-(2-chloro-4-phenoxybenzoyl)-3'-oxo-1',3',4',7'-tetrahydrospiro[pyrrolidine-3,2'-pyrrolo[3',2':5,6]pyrido[3,4-b]pyrazine]-1-carboxylate (30 mg, 0.25 mmol) was dissolved in 2 mL of methanol, and 2 mL of 4.0 M hydrogen chloride dioxane solution was added thereto, and the reaction was stirred at room temperature for 2 hours. The reaction solution was concentrated to obtain 9'-(2-chloro-4-phenoxybenzoyl)-4',7'-dihydrospiro[pyrrolidine-3,2'-pyrrolo[3',2':5,6]pyrido[3,4-b]pyrazin]-3'(1'H)-one hydrochloride (30 mg, yield of 100%) as a yellow solid. ES-API: [M+H]$^+$=474.0 (free base).

Step 5: 9'-(2-Chloro-4-phenoxybenzoyl)-4',7'-dihydrospiro[pyrrolidine-3,2'-pyrrolo[3',2':5,6]pyrido[3,4-b]pyrazin]-3'(1'H)-one hydrochloride (30 mg, 0.05 mmol) was dissolved in 5 mL of dichloromethane, then triethylamine (27 mg, 0.26 mmol) and 0.5 mL of a solution of cyclopropanoyl chloride (7 mg, 0.06 mmol) in dichloromethane were added thereto in turn under an ice bath, and the reaction was stirred for 15 min under an ice bath. The reaction solution was added with 2 mL of methanol, concentrated, and the crude product was purified by preparative HPLC to obtain a target product (Z10, 15 mg, yield of 54%) as a white solid. H NMR (500 MHz, DMSO-$d_6$) δ 12.58 (s, 1H), 10.78-10.74 (m, 1H), 8.58-8.51 (m, 1H), 7.83-7.80 (m, 1H), 7.70-7.66 (m, 1H), 7.58-7.52 (m, 1H), 7.50-7.42 (m, 2H), 7.25 (t, J=6.9 Hz, 1H), 7.21-7.13 (m, 3H), 7.02 (dd, J=8.5, 1.5 Hz, 1H), 4.17-3.80 (m, 2H), 3.75-3.48 (m, 2H), 2.57-2.33 (m, 1H), 2.21-2.00 (m, 1H), 1.85-1.72 (m, 1H), 0.80-0.60 (m, 4H). ES-API: [M+H]$^+$=542.1.

Embodiment 11: Synthesis of Z11

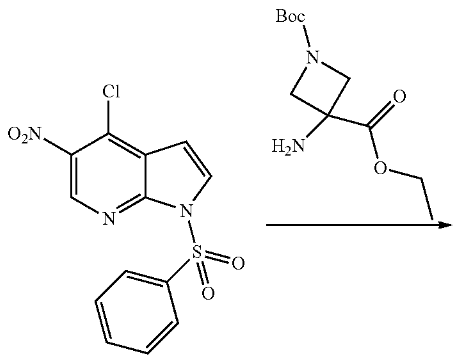

-continued

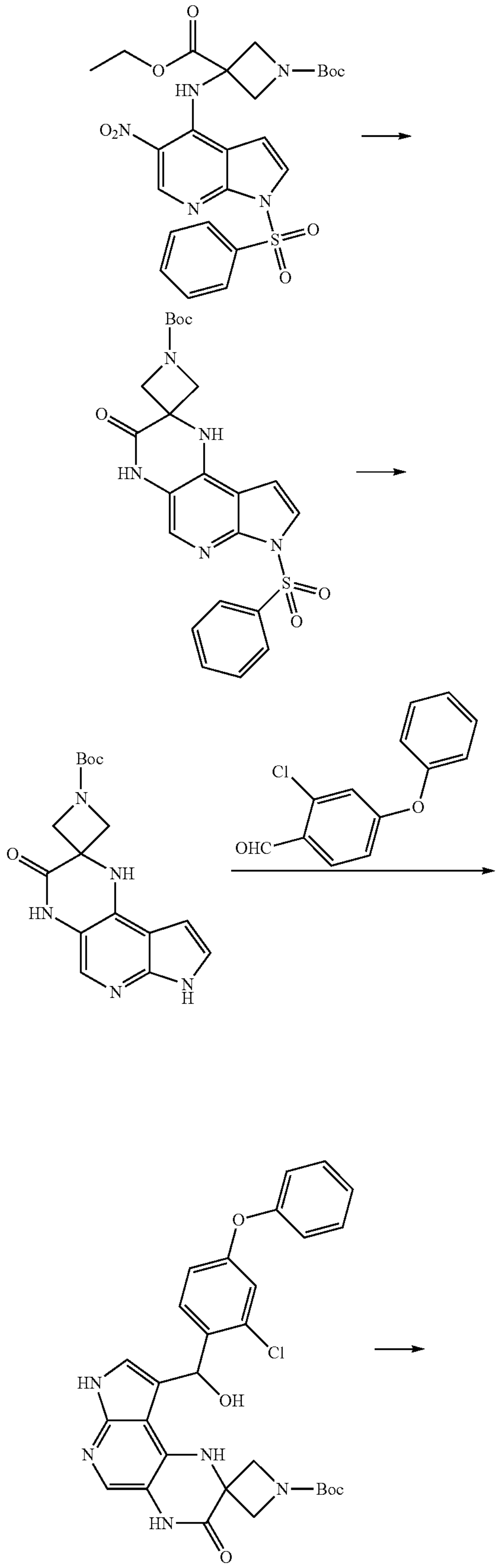

-continued

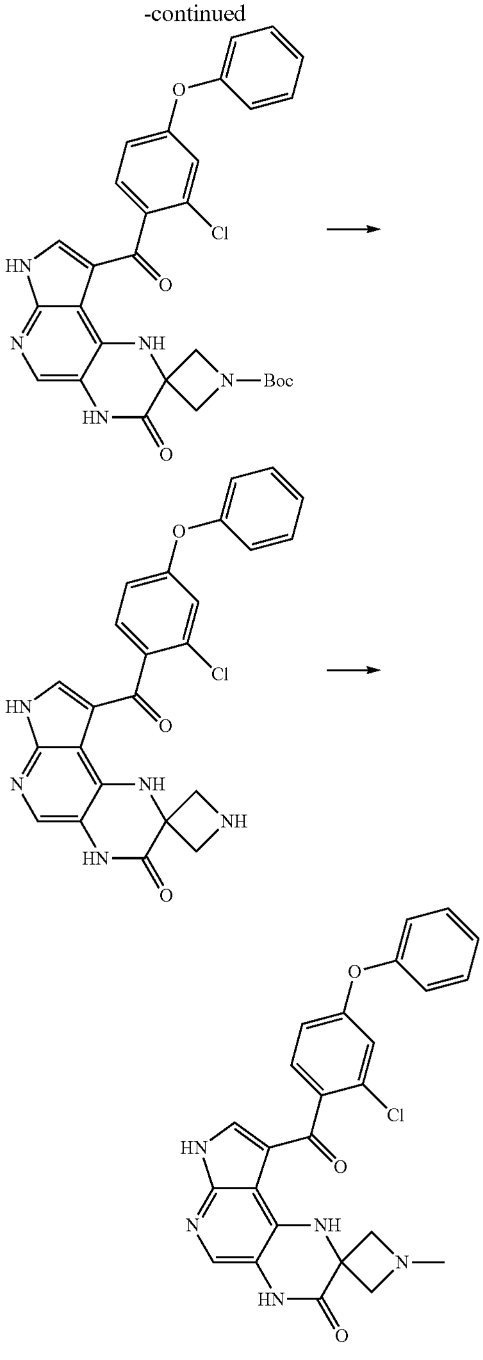

Z11

Step 1: 4-Chloro-5-nitro-1-(phenylsulfonyl)-1H-pyrrolo[2,3-b]pyridine (950 mg, 2.819 mmol) and 1-(tert-butyl) 3-ethyl 3-aminoazetidine-1,3-dicarboxylate (1.0 g, 4.096 mmol) were dissolved in N,N-dimethylformamide (30 mL), and N,N-diisopropylethylamine (3.643 g, 28.19 mmol) was added thereto, and the reaction was stirred at 95° C. for 16 hours. The reaction solution was cooled to room temperature, then added with 100 mL of ethyl acetate, washed twice with 80 mL of water and 3 times with 60 mL of saturated brine, dried and concentrated, and the crude product was purified by a flash silica gel column (ethyl acetate/petroleum ether: 0-50%) to obtain 1-(tert-butyl) 3-ethyl 3-((5-nitro-1-(phenylsulfonyl)-1H-pyrrolo[2,3-b]pyridin-4-yl)amino)azetidine-1,3-dicarboxylate (860 mg, yield of 56%) as a pale yellow solid. ES-API: $[M+H]^+$=546.1.

Step 2: 1-(tert-Butyl) 3-ethyl 3-((5-nitro-1-(phenylsulfonyl)-1H-pyrrolo[2,3-b]pyridin-4-yl)amino)azetidine-1,3-dicarboxylate (700 mg, 1.284 mmol) was dissolved in acetic acid (50 mL), and iron powder (700 mg, 12.50 mmol) was added thereto, and the reaction was stirred at 80° C. for 1 hour. The solvent was evaporated to dryness by rotary evaporation under reduced pressure, then 200 mL of ethyl acetate was added thereto. The mixture was washed twice with 80 mL of water, twice with 60 mL of saturated sodium carbonate, twice with 60 mL of saturated sodium bicarbonate, and with 60 mL of saturated brine in turn, dried and concentrated, and the crude product was slurried with ethyl acetate to obtain tert-butyl 3'-oxo-7'-(phenylsulfonyl)-1',3',4',7'-tetrahydrospiro[azetidine-3,2'-pyrrolo[3',2':5,6]pyrido[3,4-b]pyrazine]-1-carboxylate (530 mg, yield of 88%) as a pale yellow solid. ES-API: $[M+H]^+$=470.1

Step 3: tert-Butyl 3'-oxo-7'-(phenylsulfonyl)-1',3',4',7'-tetrahydrospiro[azetidine-3,2'-pyrrolo[3',2':5,6]pyrido[3,4-b]pyrazine]-1-carboxylate (330 mg, 0.7035 mmol) was dissolved in 12 mL of methanol, 2 mL of tetrahydrofuran and 2 mL of water, and sodium hydroxide (300 mg, 7.50 mmol) was added thereto, and the reaction was stirred at 65° C. for 6 hours. To the reaction solution was added 15 mL of water and 10 mL of saturated ammonium chloride solution, and the mixture was extracted with 100 mL of ethyl acetate. The organic phase was washed with 40 mL of saturated sodium bicarbonate solution and 60 mL of saturated brine in turn, dried over anhydrous sodium sulfate and then concentrated to obtain tert-butyl 3'-oxo-1',3',4',7'-tetrahydrospiro[azetidine-3,2'-pyrrolo[3',2':5,6]pyrido[3,4-b]pyrazine]-1-carboxylate (200 mg, yield of 86%) as an off-white solid. ES-API: $[M+H]^+$=330.1.

Step 4: tert-Butyl 3'-oxo-1',3',4',7'-tetrahydrospiro[azetidine-3,2'-pyrrolo[3',2':5,6]pyrido[3,4-b]pyrazine]-1-carboxylate (200 mg, 0.6079 mmol) and 2-chloro-4-phenoxybenzaldehyde (300 mg, 1.293 mmol) were dissolved in methanol (12 mL), then the reaction was cooled to 0° C., and potassium hydroxide (240 mg, 4.285 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and then concentrated to obtain a crude target product tert-butyl 9'-((2-chloro-4-phenoxyphenyl)(hydroxy)methyl)-3'-oxo-1',3',4',7'-tetrahydrospiro[azetidine-3,2'-pyrrolo[3',2':5,6]pyrido[3,4-b]pyrazine]-1-carboxylate (412 mg, crude product) as a pale yellow solid. ES-API: $[M+H]^+$=562.2.

Step 5: tert-Butyl 9'-((2-chloro-4-phenoxyphenyl)(hydroxy)methyl)-3'-oxo-1',3',4',7'-tetrahydrospiro[azetidine-3,2'-pyrrolo[3',2':5,6]pyrido[3,4-b]pyrazine]-1-carboxylate (412 mg, 0.7341 mmol) was dissolved in 30 mL of dichloromethane, and 2,3-dichloro-5,6-dicyano-1,4-benzoquinone (400 mg, 1.762 mmol) was added thereto, and the reaction was stirred at room temperature for 3 hours. To the reaction solution was added 60 mL of saturated sodium bicarbonate solution, and the mixture was extracted with 150 mL of ethyl acetate. The organic phase was washed with 60 mL of saturated brine, dried and then concentrated, and the crude product was purified by a flash silica gel column (methanol/dichloromethane: 0-20%) to obtain tert-butyl 9'-(2-chloro-4-phenoxybenzoyl)-3'-oxo-1',3',4',7'-tetrahydrospiro[azetidine-3,2'-pyrrolo[3',2':5,6]pyrido[3,4-b]pyrazine]-1-carboxylate (230 mg, yield of 67%) as a pale yellow solid. ES-API: $[M+H]^+$=560.2.

Step 6: tert-Butyl 9'-(2-chloro-4-phenoxybenzoyl)-3'-oxo-1',3',4',7'-tetrahydrospiro[azetidine-3,2'-pyrrolo[3',2':5,6]pyrido[3,4-b]pyrazine]-1-carboxylate (230 mg, 0.4113 mmol) was dissolved in 8 mL of dichloromethane, and trifluoroacetic acid (469.0 mg, 4.113 mmol) was added thereto. The mixture was reacted at room temperature for 2 hours. After the reaction was completed, the solvent was evaporated to dryness by rotary evaporation under reduced pressure to obtain a crude target compound 9'-(2-chloro-4-phenoxybenzoyl)-4',7'-dihydrospiro[azetidine-3,2'-pyrrolo[3',2':5,6]pyrido[3,4-b]pyrazin]-3'(1'H)-one (330 mg, crude product) as a brown oily liquid. ES-API: $[M+H]^+$=460.1.

Step 7: To 30 mL of acetonitrile was added 9'-(2-chloro-4-phenoxybenzoyl)-4',7'-dihydrospiro[azetidine-3,2'-pyrrolo[3',2':5,6]pyrido[3,4-b]pyrazin]-3'(1'H)-one (330 mg, 0.7189 mmol), then formaldehyde (333 mg, 4.11 mmol) was added thereto after the mixture was cooled to 0 to 5° C. under an ice water bath, and finally sodium cyanoborohydride (260 mg, 4.110 mmol) was added thereto. After reacting at room temperature for 2 hours, 50 mL of saturated sodium bicarbonate and 80 mL of ethyl acetate were added thereto. The organic phase was dried over anhydrous sodium sulfate and then evaporated to dryness by rotary evaporation under reduced pressure. The crude product was purified by preparative HPLC to obtain 9'-(2-chloro-4-phenoxybenzoyl)-1-methyl-4',7'-dihydrospiro[azetidine-3,2'-pyrrolo[3',2':5,6]pyrido[3,4-b]pyrazin]-3'(1'H)-one (Z11, 10.0 mg, yield of 5%) as a pale yellow solid. ES-API: $[M+H]^+$=474.1.

Embodiment 12: Synthesis of Z12

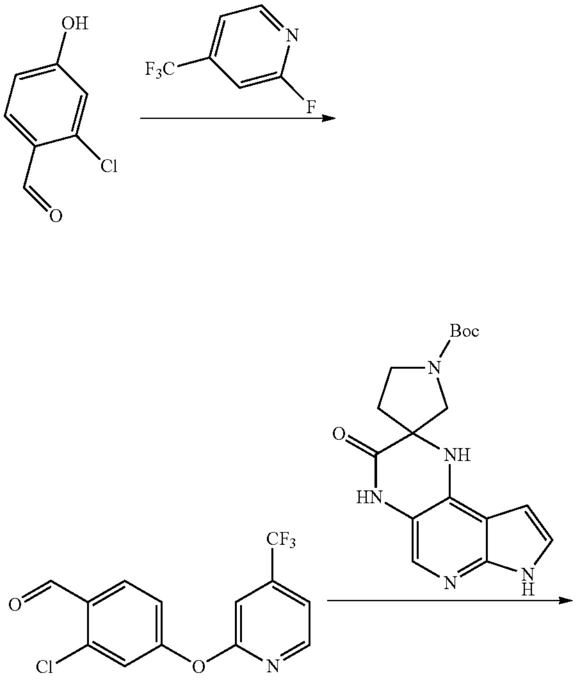

-continued

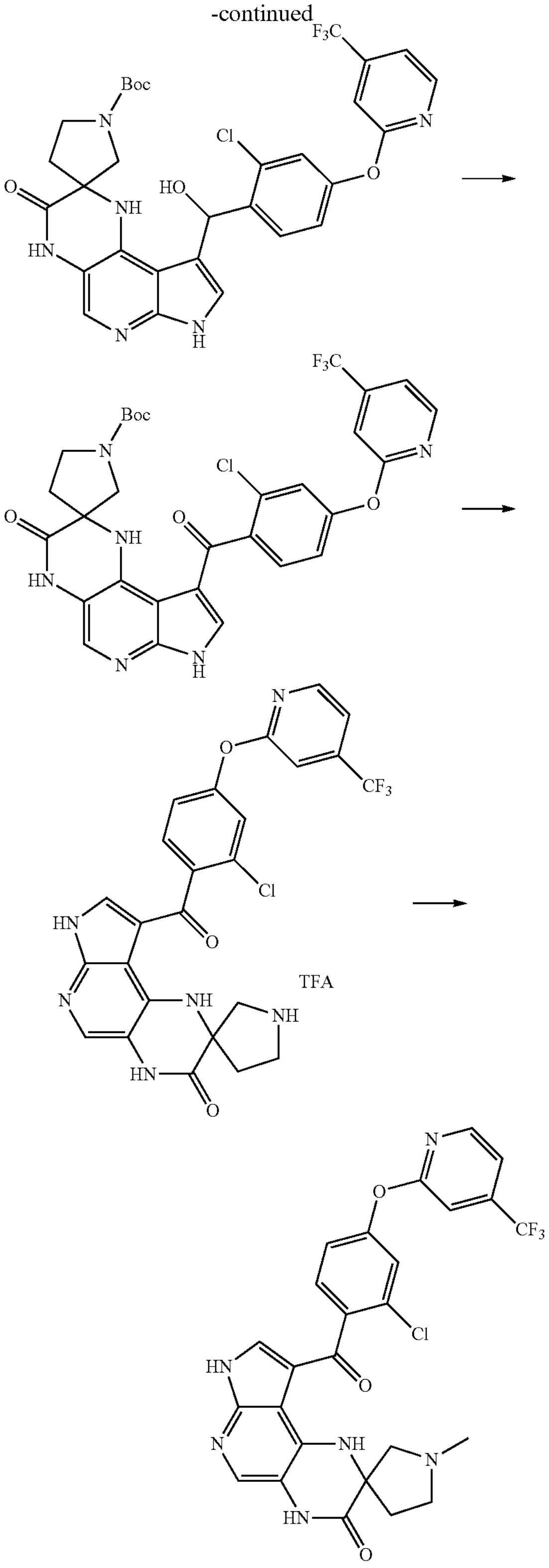

Z12

Step 1: 2-Chloro-4-hydroxybenzaldehyde (500 mg, 3.20 mmol) and 2-fluoro-4-(trifluoromethyl)pyridine (686 mg, 4.16 mmol) were dissolved in 12 mL of N,N-dimethylformamide, and potassium carbonate (883 mg, 6.40 mmol) was added thereto, and the reaction was stirred at 95° C. for 20 hours. The reaction solution was poured into 40 mL of water and extracted with 60 mL of ethyl acetate. The organic phase was washed 3 times with 25 mL of saturated brine, dried and concentrated, and the crude product was purified by a flash silica gel column (ethyl acetate/petroleum ether: 0-5%) to obtain 2-chloro-4-((4-(trifluoromethyl)pyridin-2-yl)oxy)benzaldehyde (720 mg, yield of 75%) as a colorless liquid. ES-API: $[M+H]^+$=302.0.

Step 2: tert-Butyl 3'-oxo-1',3',4',7'-tetrahydrospiro[pyrrolidine-3,2'-pyrrolo[3',2':5,6]pyrido[3,4-b]pyrazine]-1-carboxylate (130 mg, 0.38 mmol) and 2-chloro-4-((4-(trifluoromethyl)pyridin-2-yl)oxy)benzaldehyde (343 mg, 1.14 mmol) were dissolved in methanol (10 mL), and the reaction was cooled to 0° C., and potassium hydroxide (149 mg, 2.66 mmol) was added thereto. The reaction was stirred at room temperature for 18 hours. The pH of the reaction solution was adjusted to 8 with 1.0 M dilute hydrochloric acid, and the reaction solution was concentrated, then the crude product was purified by a thin-layer preparative plate (dichloromethane/methanol=10:1) to obtain tert-butyl 9'-((2-chloro-4-((4-(trifluoromethyl)pyridin-2-yl)oxy)phenyl)(hydroxy)methyl)-3'-oxo-1',3',4',7'-tetrahydrospiro[3,2'-pyrrolo[3',2':5,6]pyrido[3,4-b]pyrazine]-1-carboxylate (135 mg, yield of 55%) as alight brown solid. ES-API: $[M+H]^+$= 645.1.

Step 3: tert-Butyl 9'-((2-chloro-4-((4-(trifluoromethyl)pyridin-2-yl)oxy)phenyl)(hydroxy)methyl)-3'-oxo-1',3',4',7'-tetrahydrospiro[3,2'-pyrrolo[3',2':5,6]pyrido[3,4-b]pyrazine]-1-carboxylate (122 mg, 0.19 mmol) was dissolved in 10 mL of tetrahydrofuran, cooled to 0° C., and Dess-Martin periodinane (104 mg, 0.25 mmol) was added thereto, and the reaction was stirred at room temperature for 18 hours. To the reaction solution was added 4 mL of saturated sodium thiosulfate solution and 10 mL of saturated sodium bicarbonate solution, and the mixture was extracted with 40 mL of ethyl acetate. The organic phase was washed with 10 mL of saturated sodium bicarbonate solution and 10 mL of saturated brine in turn, dried and then concentrated to obtain tert-butyl 9'-(2-chloro-4-((4-(trifluoromethyl)pyridin-2-yl)oxy)benzoyl)-3'-oxo-1',3',4',7'-tetrahydrospiro[pyrrolidine-3,2'-pyrrolo[3',2':5,6]pyrido[3,4-b]pyrazine]-1-carboxylate (121 mg, yield of 100%) as a yellow solid. ES-API: $[M+H]^+$= 643.2.

Step 4: tert-Butyl 9'-(2-chloro-4-((4-(trifluoromethyl)pyridin-2-yl)oxy)benzoyl)-3'-oxo-1',3',4',7'-tetrahydrospiro[pyrrolidine-3,2'-pyrrolo[3',2':5,6]pyrido[3,4-b]pyrazine]-1-carboxylate (60 mg, 0.093 mmol) was dissolved in 2 mL of dichloromethane, cooled to 0° C., and 0.5 mL of trifluoroacetic acid was added thereto, and the reaction was stirred at room temperature for 1 hour. The reaction solution was concentrated to obtain 9'-(2-chloro-4-((4-(trifluoromethyl)pyridin-2-yl)oxy)benzoyl)-4',7'-dihydrospiro[pyrrolidine-3,2'-pyrrolo[3',2':5,6]pyrido[3,4-b]pyrazin]-3'(1'H)-one trifluoroacetate (75 mg, crude product). ES-API: $[M+H]^+$= 543.1 (free base).

Step 5: 9'-(2-Chloro-4-((4-(trifluoromethyl)pyridin-2-yl)oxy)benzoyl)-4',7'-dihydrospiro[pyrrolidine-3,2'-pyrrolo[3',2':5,6]pyrido[3,4-b]pyrazin]-3'(1'H)-one trifluoroacetate (70 mg, crude product) was dissolved in 3 mL of acetonitrile, then 37% aqueous formaldehyde solution (50 mg, 0.61 mmol) was added thereto in turn at room temperature. The reaction was stirred at room temperature for 30 minutes, then sodium cyanoborohydride (19 mg, 0.31 mmol) was added thereto, and the reaction was stirred at room temperature for 30 minutes. The reaction solution was concentrated, and the crude product was purified by preparative HPLC to obtain a target product (Z12, 8 mg, yield of 15%) as a white solid. $^{1}$H NMR (500 MHz, DMSO-$d_6$) δ 12.56 (s, 1H), 10.58 (s, 1H), 8.48 (d, J=5.0 Hz, 1H), 8.45 (s, 1H), 8.33 (s, 1H), 7.76 (s, 1H), 7.64 (d, J=8.5 Hz, 1H), 7.62-7.56 (m, 3H), 7.54 (d, J=2.0 Hz, 1H), 7.31 (dd, J=8.5, 2.0 Hz, 1H), 2.99-2.91 (m, 1H), 2.82 (d, J=9.5 Hz, 1H), 2.70 (d, J=9.5 Hz, 1H), 2.55-2.50 (m, 1H), 2.34-2.22 (m, 4H), 1.90-1.80 (m, 1H). ES-API: $[M+H]^+$=557.0.
Embodiment 13: Synthesis of Z13, Z13-1 and Z13-2
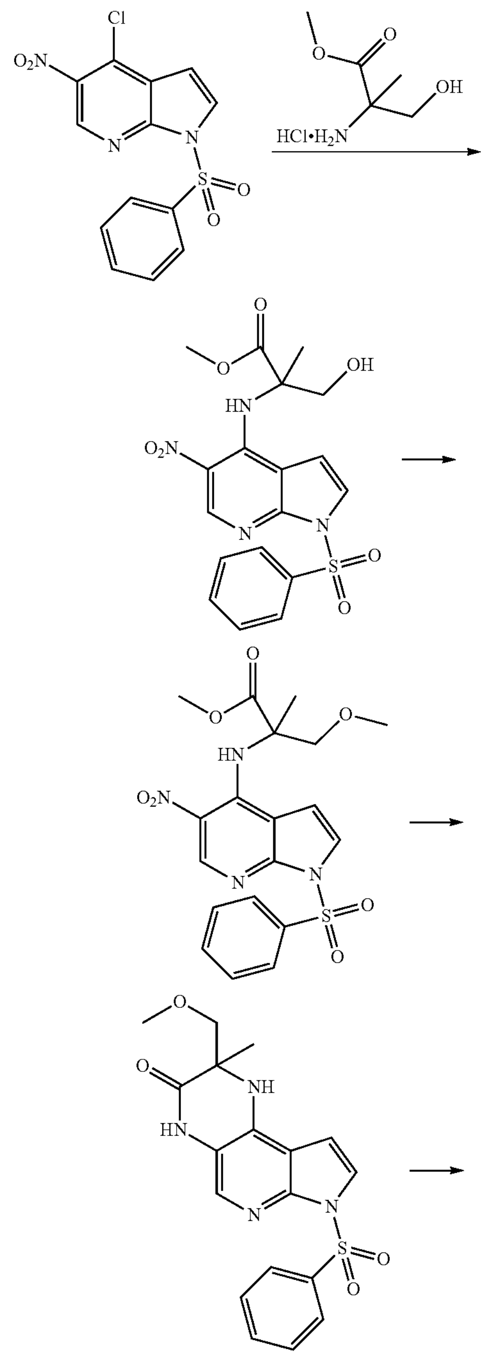
-continued
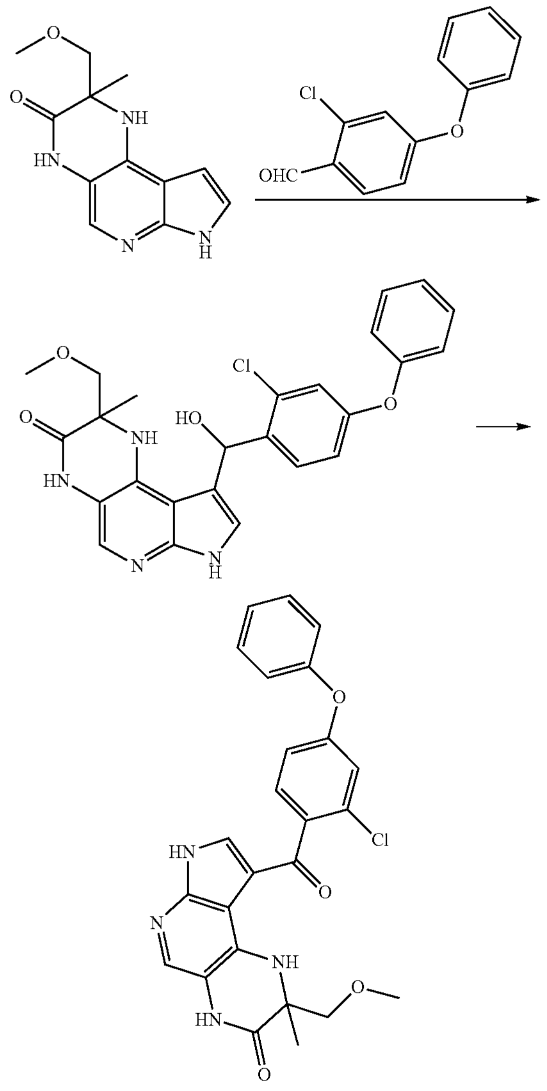
Z13
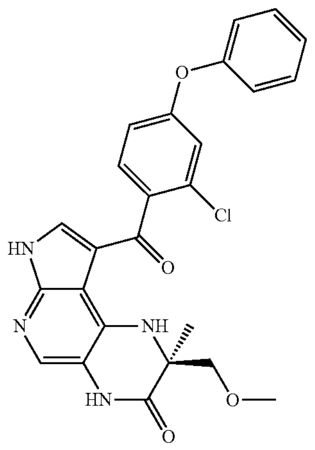
+
Z13-1

-continued

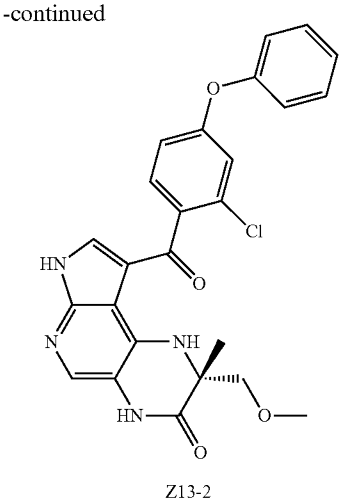

Z13-2

Step 1: 4-Chloro-5-nitro-1-(phenylsulfonyl)-1H-pyrrolo [2,3-b]pyridine (0.9 g, 2.671 mmol) and methyl 2-amino-3-hydroxy-2-methylpropanoate hydrochloride (1.0 g, 5.915 mmol) were dissolved in N,N-dimethylformamide (30 mL), and N,N-diisopropylethylamine (7.64 g, 59.15 mmol) was added thereto, and the reaction was stirred at 95° C. for 16 hours. The reaction solution was added with 100 mL of ethyl acetate, washed twice with 60 mL of water and 3 times with 30 mL of saturated brine, dried and concentrated, and the crude product was purified by a flash silica gel column (ethyl acetate/petroleum ether: 0-50%) to obtain 3-hydroxy-2-methyl-2-methyl-((5-nitro-1-(phenylsulfonyl)-1H-pyrrolo [2,3-b]pyridin-4-yl)amino)propanoate (620 mg, yield of 530%) as a pale yellow solid. ES-API: $[M+H]^+$=435.1.

Step 2: 3-Hydroxy-2-methyl-2-methyl-((5-nitro-1-(phenylsulfonyl)-1H-pyrrolo[2,3-b]pyridin-4-yl)amino)propanoate (700 mg, 1.613 mmol) was dissolved in acetonitrile (30 mL), and silver oxide (1.87 g, 8.065 mmol) and iodomethane (2.29 g, 16.13 mmol) were added thereto in turn, and the reaction was stirred in the dark at room temperature for 48 hours under nitrogen atmosphere. After the reaction was completed, the reaction solution was filtered through diatomite, and the filtrate was evaporated to dryness by rotary evaporation under reduced pressure. The crude product was purified by a flash silica gel column (ethyl acetate/petroleum ether: 0-50%) to obtain methyl 3-methoxy-2-methyl-2-((5-nitro-1-(phenylsulfonyl)-1H-pyrrolo[2,3-b]pyridin-4-yl)amino)propanoate (570 mg, yield of 78%) as a yellow solid. ES-API: $[M+H]^+$=449.0.

Step 3: Methyl 3-methoxy-2-methyl-2-((5-nitro-1-(phenylsulfonyl)-1H-pyrrolo[2,3-b]pyridin-4-yl)amino)propanoate (700 mg, 1.613 mmol) was dissolved in acetic acid (30 mL), and iron powder (1.80 g, 32.26 mmol) was added thereto. The mixture was gradually heated to 80° C. and stirred for 1 hour. After the reaction was completed, the solvent was evaporated to dryness by rotary evaporation under reduced pressure, then 200 mL of ethyl acetate was added thereto. The mixture was washed twice with 80 mL of water, twice with 60 mL of saturated sodium carbonate, twice with 80 mL of saturated sodium bicarbonate, and with 80 mL of saturated brine in turn, dried and concentrated, and the crude product was slurried with ethyl acetate to obtain 2-(methoxymethyl)-2-methyl-7-(phenylsulfonyl)-1,2,4,7-tetrahydro-3H-pyrrolo[3',2':5,6]pyrido[3,4-b]pyrazin-3-one (400 mg, yield of 64%) as a yellow solid. ES-API: $[M+H]^+$=387.1

Step 4: 2-(Methoxymethyl)-2-methyl-7-(phenylsulfonyl)-1,2,4,7-tetrahydro-3H-pyrrolo[3',2':5,6]pyrido[3,4-b]pyrazin-3-one (400 mg, 1.0362 mmol) was dissolved in 12 mL of methanol, 3 mL of tetrahydrofuran and 2 mL of water, and sodium hydroxide (290 mg, 7.264 mmol) was added thereto, and the reaction was stirred at 65° C. for 7 hours. To the reaction solution was added 20 mL of water and 15 mL of saturated ammonium chloride solution, and the mixture was extracted with 150 mL of ethyl acetate. The organic phase was washed with 30 mL of saturated sodium bicarbonate solution and 80 mL of saturated brine in turn, dried over anhydrous sodium sulfate and then concentrated to obtain 2-(methoxymethyl)-2-methyl-1,2,4,7-tetrahydro-3H-pyrrolo[3',2':5,6]pyrido[3,4-b]pyrazin-3-one (480 mg, crude product) as a pale white solid. ES-API: $[M+H]^+$=247.1.

Step 5: 2-(Methoxymethyl)-2-methyl-1,2,4,7-tetrahydro-3H-pyrrolo[3',2':5,6]pyrido[3,4-b]pyrazin-3-one (480 mg, crude product) and 2-chloro-4-phenoxybenzaldehyde (480 mg, 2.0724 mmol) were dissolved in methanol (20.0 mL), and the reaction was cooled to 0° C., and potassium hydroxide (406 mg, 7.253 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and then concentrated to obtain a crude target product 9-((2-chloro-4-phenoxyphenyl)(hydroxy)methyl)-2-(methoxymethyl)-2-methyl-1,2,4,7-tetrahydro-3H-pyrrolo[3',2':5,6]pyrido[3,4-b]pyrazin-3-one (620 mg, crude product) as a pale yellow solid. ES-API: $[M+H]^+$=479.0.

Step 6: 9-((2-Chloro-4-phenoxyphenyl)(hydroxy) methyl)-2-(methoxymethyl)-2-methyl-1,2,4,7-tetrahydro-3H-pyrrolo[3',2':5,6]pyrido[3,4-b]pyrazin-3-one (620 mg, crude product) was dissolved in 30 mL of dichloromethane, and 2,3-dichloro-5,6-dicyano-1,4-benzoquinone (470 mg, 2.0724 mmol) was added thereto, and the reaction was stirred at room temperature for 2 hours. To the reaction solution was added 60 mL of saturated sodium bicarbonate solution, and the mixture was extracted with 80 mL of ethyl acetate. The organic phase was washed with 60 mL of saturated brine, dried over anhydrous sodium sulfate and then concentrated, and the crude product was purified by preparative HPLC to obtain 9-(2-chloro-4-phenoxybenzoyl)-2-(methoxymethyl)-2-methyl-1,2,4,7-tetrahydro-3H-pyrrolo[3',2':5,6]pyrido[3,4-b]pyrazin-3-one (Z13, 126 mg, 3-step yield of 25%) as a pale yellow solid, ES-API: $[M+H]^+$=477.1. $^1$H NMR (500 MHz, DMSO-$d_6$) δ 12.45 (s, 1H), 10.48 (s, 1H), 8.27 (s, 1H), 7.69 (s, 1H), 7.60 (s, 1H), 7.56 (d, J=8.5 Hz, 1H), 7.48 (dd, J=8.5, 7.5 Hz, 2H), 7.25 (t, J=7.5 Hz, 1H), 7.22-7.11 (m, 3H), 7.02 (dd, J=8.5, 2.5 Hz, 1H), 3.64 (d, J=9.5 Hz, 1H), 3.47 (d, J=9.5 Hz, 1H), 3.29 (s, 3H), 1.39 (s, 3H).

Step 7: The compound Z13 (126 mg, 0.2646 mmol) obtained in the above steps was resolved by chiral preparation (column: IC, 150 mm*4.6 mm*5 μM, mobile phase: n-hexane:ethanol:diethylamine=70:30:0.2, flow rate: 1 mL/min, column temperature: 30° C.) to obtain two single isomer compounds. One single isomer (51.45 mg, peak 1, retention time of 8.881 min, yield of 40%) was a pale white solid. ES-API: $[M+H]^+$=477.1. $^1$H NMR (500 MHz, DMSO-$d_6$) δ 12.46 (s, 1H), 10.49 (s, 1H), 8.28 (s, 1H), 7.69 (s, 1H), 7.60 (s, 1H), 7.56 (d, J=8.5 Hz, 1H), 7.48 (t, J=8.0 Hz, 2H), 7.25 (t, J=7.5 Hz, 1H), 7.21-7.16 (m, 3H), 7.02 (dd, J=8.5, 2.5 Hz, 1H), 3.65 (d, J=9.5 Hz, 1H), 3.47 (d, J=9.5 Hz, 1H), 3.29 (s, 3H), 1.39 (s, 3H). The other single isomer (53.0 mg, peak 2, retention time of 11.86 min, yield of 42%) was a pale white solid. ES-API: $[M+H]^+=477.1$. $^1H$ NMR (400 MHz, DMSO-$d_6$) δ 12.46 (s, 1H), 10.49 (s, 1H), 8.28 (s, 1H), 7.69 (s, 1H), 7.60 (s, 1H), 7.56 (d, J=8.4 Hz, 1H), 7.52-7.44 (m, 2H), 7.29-7.23 (m, 1H), 7.22-7.16 (m, 3H), 7.02 (dd, J=8.4, 2.4 Hz, 1H), 3.65 (d, J=9.6 Hz, 1H), 3.47 (d, J=9.6 Hz, 1H), 3.29 (s, 3H), 1.39 (s, 3H).

Embodiment 13A: Synthesis of Z13-1

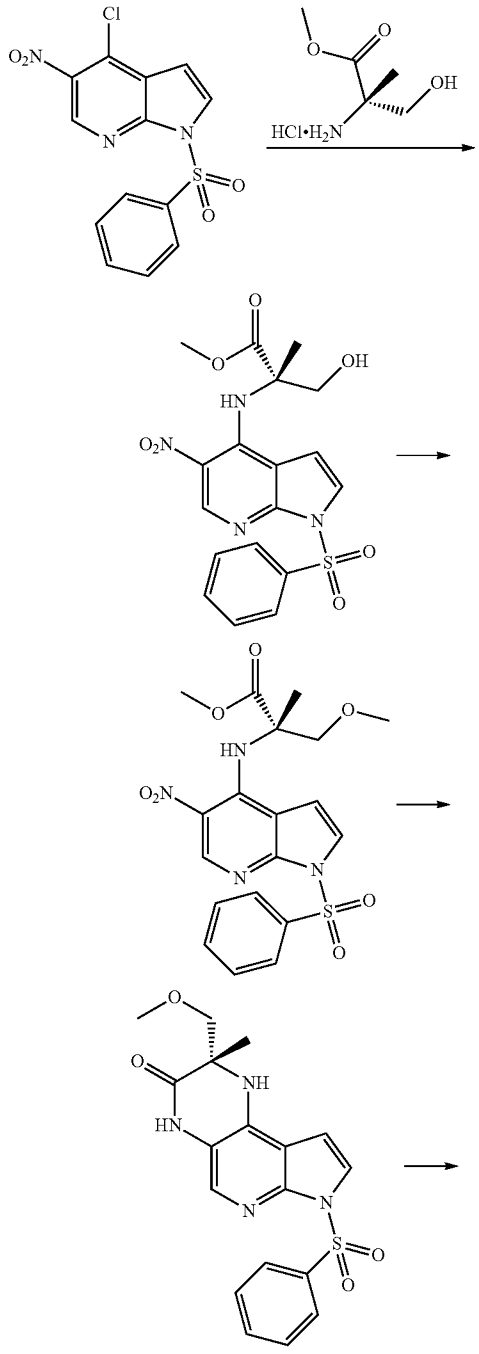

-continued

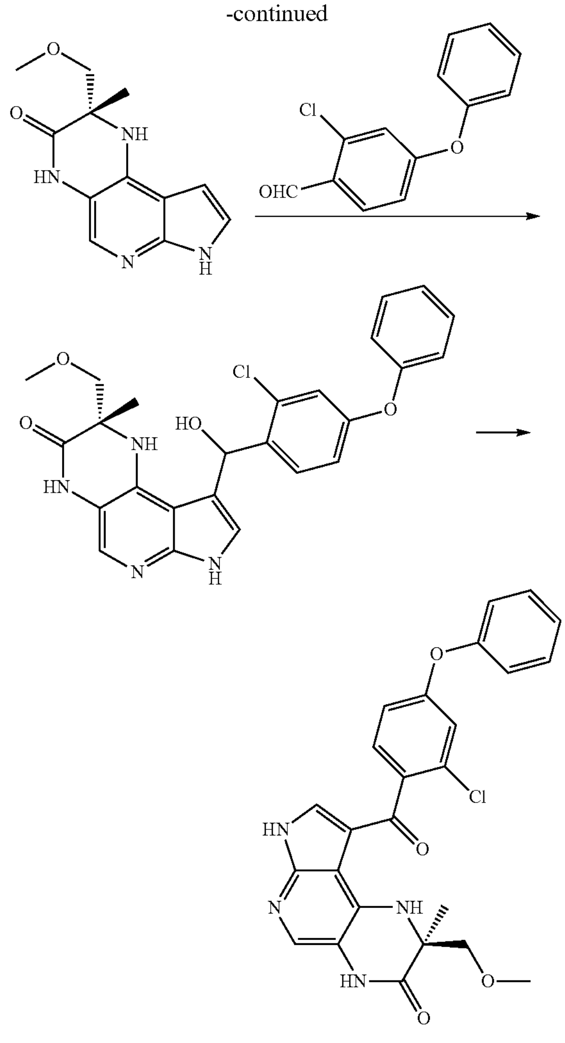

Z13-1

This embodiment referred to the steps of Embodiment 13, with the difference that step 1 of this embodiment used

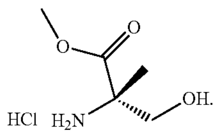

to replace

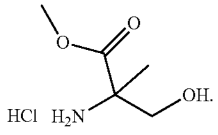

in step 1 of Embodiment 13, and after the resulting final product was subjected to chiral analysis (column: IC 150 mm*4.6 mm*5 μM, mobile phase: n-hexane:ethanol:diethylamine=70:30:0.2, flow rate: 1 mL/min, column temperature: 30° C.), it was determined that no racemization occurred, so the final product was determined to be Z13-1. Comparing the two single isomers obtained in step 7 of Embodiment 13 with the product Z13-1 prepared in Embodiment 13A, it was determined that the structure of the isomer with a retention time of 8.881 min was compound Z13-1; and the structure of the isomer with retention time of 11.86 min was compound Z13-2.

Embodiment 14: Synthesis of Z14

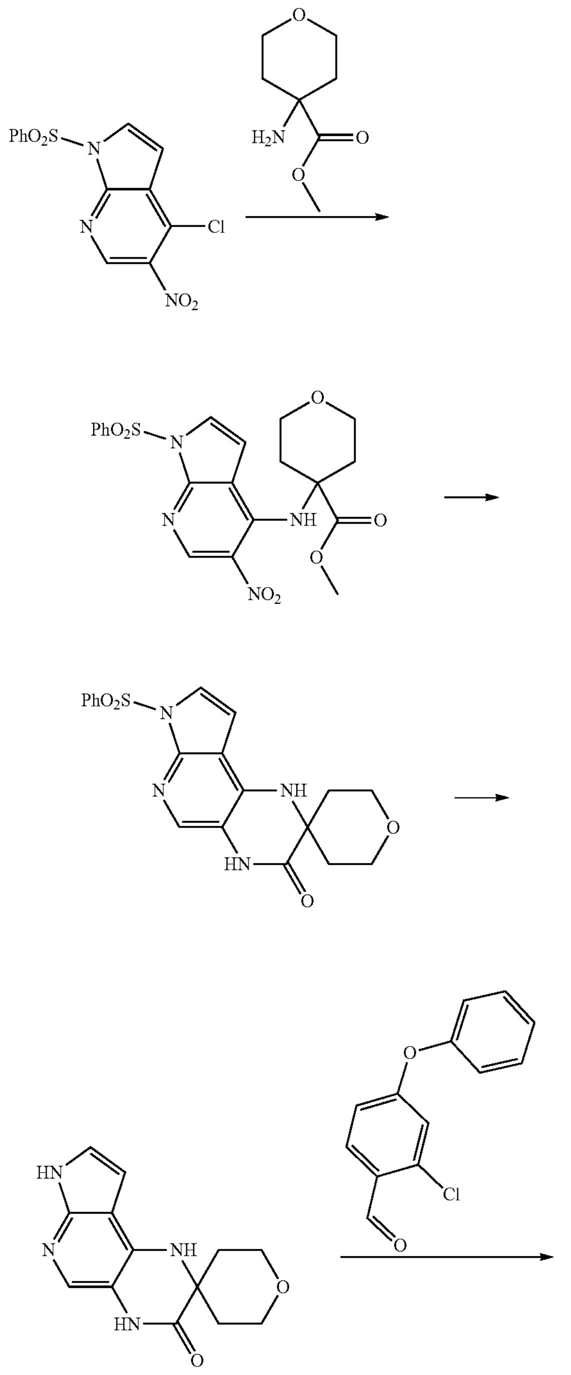

-continued

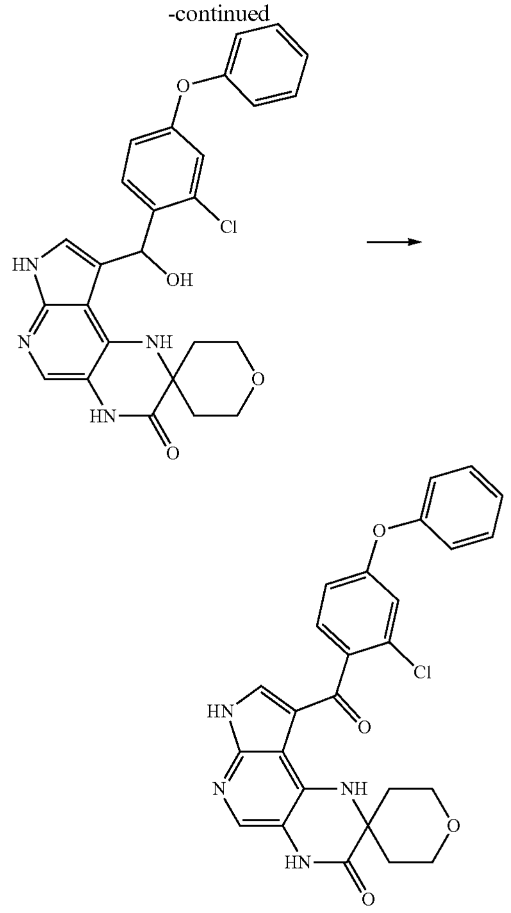

Z14

Step 1: 4-Chloro-5-nitro-1-(phenylsulfonyl)-1H-pyrrolo[2,3-b]pyridine (500 mg, 1.48 mmol) and methyl 4-aminotetrahydro-2H-pyran-4-carboxylate (260 mg, 1.63 mmol) were dissolved in 5 mL of N,N-dimethylacetamide, and N,N-diisopropylethylamine (480 mg, 3.71 mmol) was added thereto, and the reaction was stirred at 120° C. under microwave irradiation for 1 hour. The reaction solution was added with 100 mL of ethyl acetate, washed three times with 30 mL of dilute brine, washed with 30 mL of saturated brine in turn, dried and concentrated, and the crude product was purified by a flash silica gel column (ethyl acetate/petroleum ether: 0-50%) to obtain 4-((5-nitro-1-(phenylsulfonyl)-1H-pyrrolo[2,3-b]pyridin-4-yl)amino)methyl)tetrahydro-2H-pyran-4-carboxylate (300 mg, yield of 44%) as a yellow solid. ES-API: $[M+H]^+$=461.0.

Step 2: 4-((5-Nitro-1-(phenylsulfonyl)-1H-pyrrolo[2,3-b]pyridin-4-yl)amino)methyl)tetrahydro-2H-pyran-4-carboxylate (300 mg, 0.65 mmol) was dissolved in 10 mL of acetic acid, and iron powder (182 mg, 3.26 mmol) was added thereto, stirred at 80° C. for 3 hours. The reaction solution was concentrated, added with 60 mL of ethyl acetate, filtered and concentrated, and the residue was purified by a flash silica gel column (0-100% of ethyl acetate/petroleum ether) to obtain 7'-(phenylsulfonyl)-2,3,4',5,6,7'-hexahydrospiro[pyran-4,2'-pyrrolo[3',2':5,6]pyrido[3,4-b]pyrazin]-3'(1'H)-one (200 mg, yield of 77%) as a yellow solid. ES-API: $[M+H]^+$=399.1.

Step 3: 7'-(Phenylsulfonyl)-2,3,4',5,6,7'-hexahydrospiro[pyran-4,2'-pyrrolo[3',2':5,6]pyrido[3,4-b]pyrazin]-3'(1'H)- one (200 mg, 0.50 mmol) was dissolved in 2 mL of methanol and 0.4 mL of water, sodium hydroxide (100 mg, 2.50 mmol) was added thereto, and the reaction was stirred under microwave irradiation at 120° C. for 1 hour. The reaction solution was dried and then concentrated to obtain the crude product 2,3,4',5,6,7'-hexahydrospiro[pyran-4,2'-pyrrolo[3',2':5,6]pyrido[3,4-b]pyrazin]-3'(1'H)-one (200 mg) as a black solid. ES-API: $[M+H]^+=259.1$.

Step 4: 2,3,4',5,6,7'-Hexahydrospiro[pyran-4,2'-pyrrolo[3',2':5,6]pyrido[3,4-b]pyrazin]-3'(1'H)-one (200 mg, 0.77 mmol) and 2-chloro-4-phenoxybenzaldehyde (360 mg, 1.55 mmol) were dissolved in methanol (10 mL), then the reaction was cooled to 0° C., and potassium hydroxide (304 mg, 5.42 mmol) was added thereto. The reaction was stirred at room temperature for 5 hours. The reaction solution was poured into 30 mL of water, and the pH of the reaction solution was adjusted to 8 with 1.0 M dilute hydrochloric acid, and the reaction solution was extracted with 80 mL of ethyl acetate. The organic phase was washed with 25 mL of saturated brine, dried and then concentrated, and the crude product was purified by a flash silica gel column (0-20% of methanol/dichloromethane) to obtain to obtain 9'-((2-chloro-4-phenoxyphenyl)(hydroxy)methyl)-2,3,4',5,6,7'-hexahydrospiro[pyran-4,2'-pyrrolo[3',2':5,6]pyrido[3,4-b]pyrazin]-3'(1'H)-one (70 mg, yield of 18%) as a yellow solid. ES-API: $[M+H]^+=491.0$.

Step 5: 9'-((2-Chloro-4-phenoxyphenyl)(hydroxy)methyl)-2,3,4',5,6,7'-hexahydrospiro[pyran-4,2'-pyrrolo[3',2':5,6]pyrido[3,4-b]pyrazin]-3'(1'H)-one (70 mg, 0.14 mmol) was dissolved in 2 mL of 1,4-dioxane and 0.2 mL of water, cooled to 0° C., and 2,3-dichloro-5,6-dicyano-1,4-benzoquinone (49 mg, 0.21 mmol) was added thereto, and the reaction was stirred at room temperature for 2 hours. To the reaction solution was added 3 mL of saturated sodium thiosulfate solution and 10 mL of saturated sodium bicarbonate solution, and the mixture was extracted with 40 mL of ethyl acetate. The organic phase was washed with 10 mL of saturated brine, dried and then concentrated, and the crude product was purified by preparative HPLC to obtain a target product (Z14, 24 mg, yield of 34%) as a pale yellow solid. $^1H$ NMR (400 MHz, DMSO-$d_6$) δ 12.58 (s, 1H), 10.54 (s, 1H), 8.86 (s, 1H), 7.78 (s, 1H), 7.70 (s, 1H), 7.60 (d, J=8.4 Hz, 1H), 7.53-7.44 (m, 2H), 7.29-7.23 (m, 1H), 7.21-7.19 (m, 2H), 7.19-7.17 (m, 1H), 7.04 (dd, J=8.4, 2.0 Hz, 1H), 3.89-3.80 (m, 2H), 3.80-3.69 (m, 2H), 2.14-2.02 (m, 2H), 1.61 (d, J=12.8 Hz, 2H). ES-API: $[M+H]^+=489.1$.

-continued

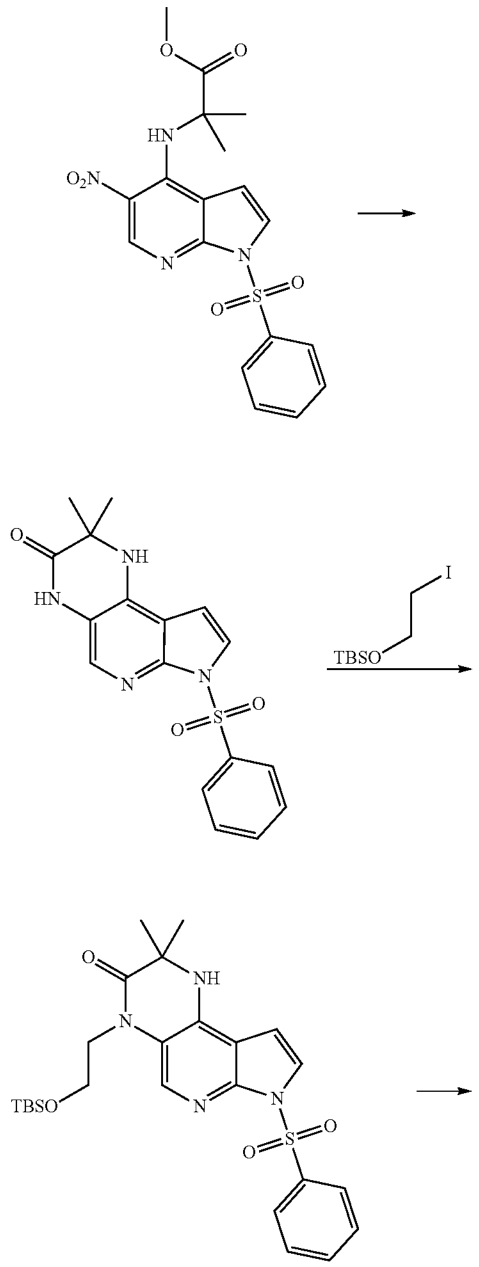

Embodiment 15: Synthesis of Z15

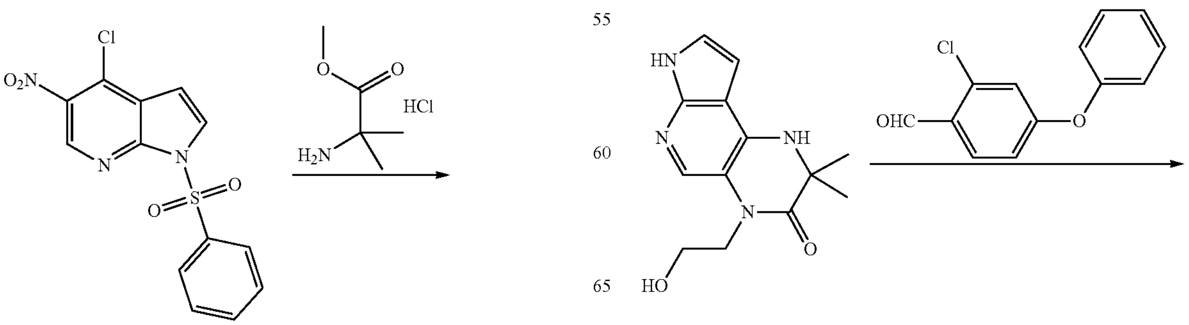

-continued

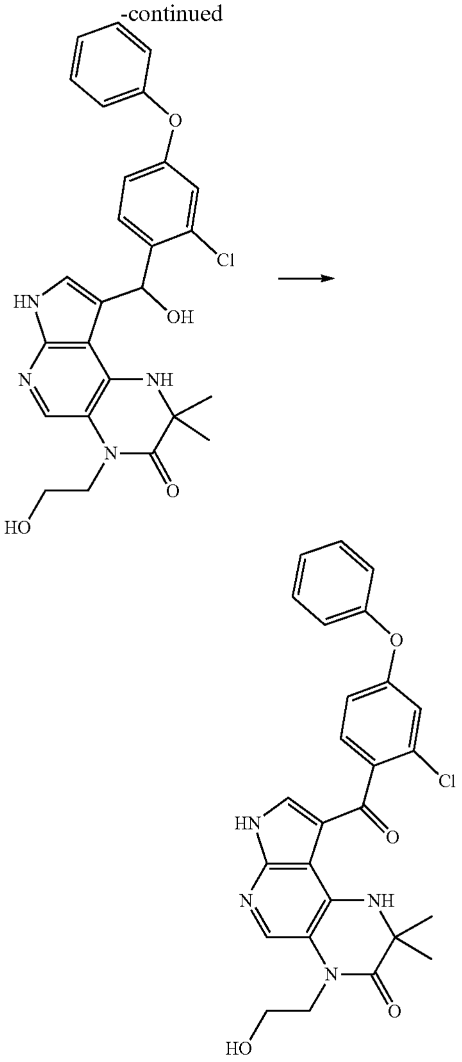

Z15

Step 1: 4-Chloro-5-nitro-1-(phenylsulfonyl)-1H-pyrrolo [2,3-b]pyridine (1.0 g, 2.97 mmol) and methyl 2-amino-2-methylpropanoate hydrochloride (908 mg, 5.94 mmol) were dissolved in N,N-dimethylformamide (10 mL), and N,N-diisopropylethylamine (2.3 mL, 13.36 mmol) was added thereto, and the reaction was stirred at 80° C. for 16 hours. The reaction solution was added with 100 mL of ethyl acetate, washed twice with 40 mL of water and 3 times with 30 mL of saturated brine, dried and concentrated, and the crude product was purified by a flash silica gel column (ethyl acetate/petroleum ether: 0-40%) to obtain methyl 2-methyl-2-((5-nitro-1-(phenylsulfonyl)-1H-pyrrolo[2,3-b]pyridin-4-yl)amino)propanoate (870 mg, yield of 70%) as a yellow solid. ES-API: $[M+H]^+$=419.0.

Step 2: Methyl 2-methyl-2-((5-nitro-1-(phenylsulfonyl)-1H-pyrrolo[2,3-b]pyridin-4-yl)amino)propanoate (870 mg, 2.08 mmol) was dissolved in acetic acid (15 mL), and iron powder (466 mg, 8.32 mmol) was added thereto, and the reaction was stirred at 85° C. for 4 hours. The reaction solution was poured into 45 mL of water, then the insoluble solid was filtered, and the filter cake was washed with a small amount of water, and dried under vacuum to obtain 2,2-dimethyl-7-(phenylsulfonyl)-1,2,4,7-tetrahydro-3H-pyrrolo[3',2':5,6]pyrido[3,4-b]pyrazin-3-one (670 mg, yield of 90%) as an off-white solid. ES-API: $[M+H]^+$=357.1

Step 3: 2,2-Dimethyl-7-(phenylsulfonyl)-1,2,4,7-tetrahydro-3H-pyrrolo[3',2':5,6]pyrido[3,4-b]pyrazin-3-one (300 mg, 0.84 mmol) was dissolved in 12 mL of N,N-dimethylformamide, then anhydrous potassium carbonate (464 mg, 3.36 mmol) and tert-butyl (2-iodomethoxy)dimethylsilane (721 mg, 2.52 mmol) were added thereto, and the reaction was stirred at 60° C. for 24 hours. The reaction solution was poured into 40 mL of water and extracted with 80 mL of ethyl acetate. The organic phase was washed 3 times with 30 mL of saturated brine, dried and concentrated, and the crude product was purified by a flash silica gel column (ethyl acetate/petroleum ether: 0-40%) to obtain 4-(2-((tert-butyldimethylsilyl)oxy)ethyl)-2,2-dimethyl-7-(phenylsulfonyl)-1,2,4,7-tetrahydro-3H-pyrrolo[3',2':5,6]pyrido[3,4-b] pyrazin-3-one (400 mg, yield of 92%) as a white solid. ES-API: $[M+H]^+$=515.2.

Step 4: 4-(2-((tert-Butyldimethylsilyl)oxy)ethyl)-2,2-dimethyl-7-(phenylsulfonyl)-1,2,4,7-tetrahydro-3H-pyrrolo [3',2':5,6]pyrido[3,4-b]pyrazin-3-one (350 mg, 0.68 mmol) was dissolved in 15 mL of methanol, 5 mL of tetrahydrofuran and 3 mL of water, and sodium hydroxide (136 mg, 3.40 mmol) was added thereto, and the reaction was stirred at 60° C. for 16 hours. The pH of the reaction solution was adjusted to 8 with 1.0 M dilute hydrochloric acid. To the reaction solution was added 10 mL of saturated sodium bicarbonate solution, and the mixture was extracted with 100 mL of ethyl acetate. The organic phase was washed with 20 mL of saturated sodium bicarbonate solution and 20 mL of saturated brine in turn, dried and then concentrated to obtain 4-(2-hydroxyethyl)-2,2-dimethyl-1,2,4,7-tetrahydro-3H-pyrrolo[3',2':5,6]pyrido[3,4-b]pyrazin-3-one (177 mg, yield of 100%) as a white solid. ES-API: $[M+H]^+$=261.1.

Step 5: 4-(2-Hydroxyethyl)-2,2-dimethyl-1,2,4,7-tetrahydro-3H-pyrrolo[3',2':5,6]pyrido[3,4-b]pyrazin-3-one (75 mg, 0.29 mmol) and 2-chloro-4-phenoxybenzaldehyde (135 mg, 0.58 mmol) were dissolved in methanol (7 mL), then the reaction was cooled to 0° C., and potassium hydroxide (114 mg, 2.03 mmol) was added thereto. The reaction was stirred at room temperature for 16 hours. The pH of the reaction solution was adjusted to 8 with 1.0 M dilute hydrochloric acid, and the reaction solution was extracted with 60 mL of ethyl acetate. The organic phase was washed with 15 mL of saturated brine, dried and then concentrated, and the crude product was purified by a thin-layer preparative plate (dichloromethane/methanol=10:1) to obtain 9-((2-chloro-4-phenoxyphenyl)(hydroxy)methyl)-4-(2-hydroxyethyl)-2,2-dimethyl-1,2,4,7-tetrahydro-3H-pyrrolo[3',2':5,6]pyrido[3,4-b]pyrazin-3-one (95 mg, yield of 67%) as a pale yellow solid. ES-API: $[M+H]^+$=493.1.

Step 6: 9-((2-Chloro-4-phenoxyphenyl)(hydroxy)methyl)-4-(2-hydroxyethyl)-2,2-dimethyl-1,2,4,7-tetrahydro-3H-pyrrolo[3',2':5,6]pyrido[3,4-b]pyrazin-3-one (90 mg, 0.18 mmol) was dissolved in 6 mL of dichloromethane, and 2,3-dichloro-5,6-dicyano-p-benzoquinone (83 mg, 0.36 mmol) was added thereto at room temperature, and the reaction was stirred at room temperature for 16 hours. To the reaction solution was added 5 mL of saturated sodium thiosulfate solution and 10 mL of saturated sodium bicarbonate solution, and the mixture was extracted with 50 mL of ethyl acetate. The organic phase was washed with 15 mL of saturated sodium bicarbonate solution and 15 mL of saturated brine in turn, dried and then concentrated, and the crude product was purified by preparative HPLC to obtain a target product (Z15, 70 mg, yield of 78%) as a white solid. $^1H$ NMR (400 MHz, DMSO-$d_6$) δ 12.61 (s, 1H), 8.33 (s, 1H), 8.15 (s, 1H), 7.68 (s, 1H), 7.57 (d, J=8.4 Hz, 1H), 7.51-7.44 (m, 2H), 7.28-7.22 (m, 1H), 7.21-7.15 (m, 3H), 7.02 (dd, J=8.4, 2.4 Hz, 1H), 4.89 (s, 1H), 4.04 (t, J=6.0 Hz, 2H), 3.59 (t, J=6.0 Hz, 2H), 1.38 (s, 6H). ES-API: $[M+H]^+$= 491.1.
Embodiment 16: Synthesis of Z16, Z16-1 and Z16-2
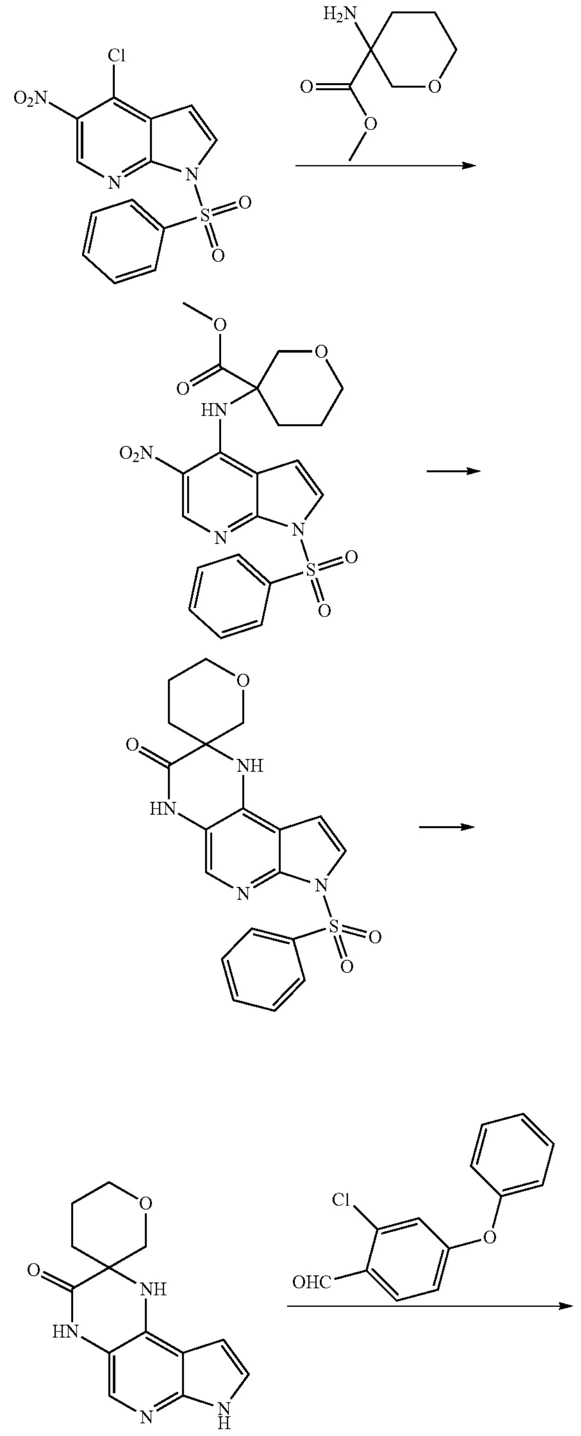
-continued
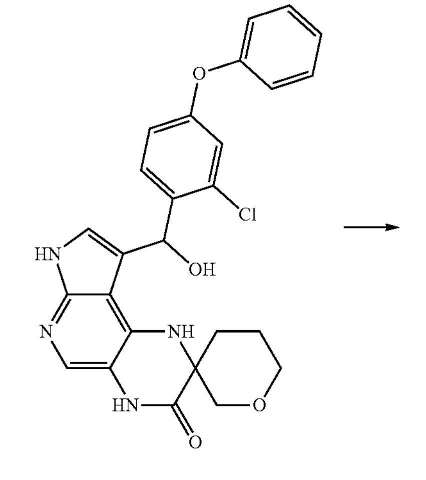
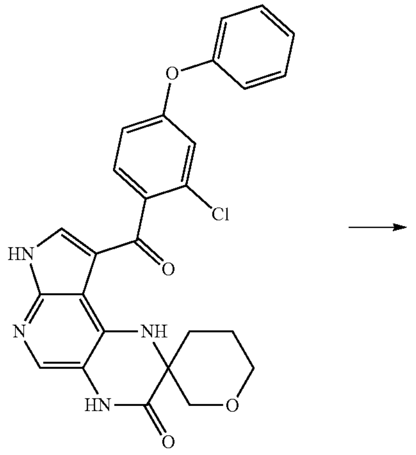
Z16
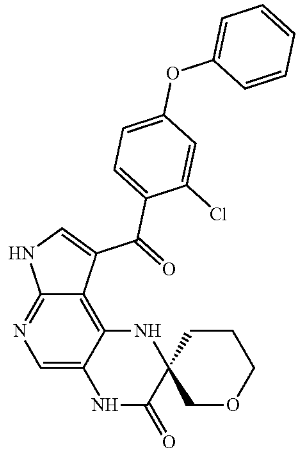
+
Z16-1

-continued

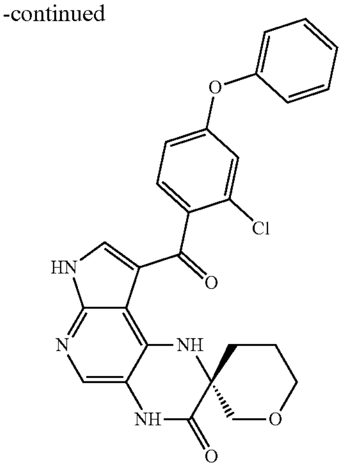

Z16-2

Step 1: 4-Chloro-5-nitro-1-(phenylsulfonyl)-1H-pyrrolo[2,3-b]pyridine (0.60 g, 1.7804 mmol) and methyl 3-aminotetrahydro-2H-pyran-3-carboxylate (351.23 mg, 2.209 mmol) were dissolved in N,N-dimethylformamide (30 mL), and N,N-diisopropylethylamine (7.64 g, 59.15 mmol) was added thereto, and the reaction was stirred at 95° C. for 12 hours. The reaction solution was added with 100 mL of ethyl acetate, washed twice with 60 mL of water and 3 times with 30 mL of saturated brine, dried and concentrated, and the crude product was purified by a flash silica gel column (ethyl acetate/petroleum ether: 0-50%) to obtain methyl 3-((5-nitro-1-(phenylsulfonyl)-1H-pyrrolo[2,3-b]pyridin-4-yl)amino)tetrahydro-2H-pyran-3-carboxylate (320 mg, yield of 39%) as a pale yellow solid. ES-API: $[M+H]^+$=461.0.

Step 2: Methyl 3-((5-nitro-1-(phenylsulfonyl)-1H-pyrrolo[2,3-b]pyridin-4-yl)amino)tetrahydro-2H-pyran-3-carboxylate (320 mg, 0.6956 mmol) was dissolved in acetic acid (20 mL), and iron powder (0.780 g, 13.91 mmol) was added thereto, and the reaction was stirred at 80° C. for 1 hour. The solvent was evaporated to dryness by rotary evaporation under reduced pressure, then 200 mL of ethyl acetate was added thereto. The mixture was washed twice with 80 mL of water, twice with 60 mL of saturated sodium carbonate, twice with 80 mL of saturated sodium bicarbonate, and with 80 mL of saturated brine in turn, dried and concentrated, and the crude product was slurried with ethyl acetate to obtain 7'-(phenylsulfonyl)-4',5,6,7'-tetrahydro-2H,4H-spiro[pyran-3,2'-pyrrolo[3',2':5,6]pyrido[3,4-b]pyrazin]-3'(1'H)-one (240 mg, yield of 85.0%) as a pale yellow solid. ES-API: $[M+H]^+$=399.1.

Step 3: 7'-(Phenylsulfonyl)-4',5,6,7'-tetrahydro-2H,4H-spiro[pyran-3,2'-pyrrolo[3',2':5,6]pyrido[3,4-b]pyrazin]-3'(1'H)-one (240 mg, 0.6030 mmol) was dissolved in 12 mL of methanol, 3 mL of tetrahydrofuran and 2 mL of water, and sodium hydroxide (170 mg, 4.221 mmol) was added thereto, and the reaction was stirred at 65° C. for 7 hours. To the reaction solution was added 20 mL of water and 5 mL of saturated ammonium chloride solution, and the mixture was extracted with 160 mL of ethyl acetate. The organic phase was washed with 40 mL of saturated sodium bicarbonate solution and 60 mL of saturated brine in turn, dried over anhydrous sodium sulfate and then concentrated to obtain 4',5,6,7'-tetrahydro-2H,4H-spiro[pyran-3,2'-pyrrolo[3',2':5,6]pyrido[3,4-b]pyrazin]-3'(1'H)-one (340 mg, crude product) as an off-white solid. ES-API: $[M+H]^+$=259.1.

Step 4: 4',5,6,7'-Tetrahydro-2H,4H-spiro[pyran-3,2'-pyrrolo[3',2':5,6]pyrido[3,4-b]pyrazin]-3'(1'H)-one (340 mg, crude product) and 2-chloro-4-phenoxybenzaldehyde (280 mg, 1.206 mmol) were dissolved in methanol (12.0 mL), then the reaction was cooled to 0° C., and potassium hydroxide (236 mg, 4.221 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 120 mL of ethyl acetate. The organic phase was washed with 63 mL of saturated brine, dried and then concentrated to obtain a crude target product 9'-((2-chloro-4-phenoxyphenyl)(hydroxy)methyl)-4',5,6,7'-tetrahydro-2H,4H-spiro[pyran-3,2'-pyrrolo[3',2':5,6]pyrido[3,4-b]pyrazin]-3'(1'H)-one (400 mg, crude product) as a pale yellow solid. ES-API: $[M+H]^+$=491.2.

Step 5: 9'-((2-Chloro-4-phenoxyphenyl)(hydroxy)methyl)-4',5,6,7'-tetrahydro-2H,4H-spiro[pyran-3,2'-pyrrolo[3',2':5,6]pyrido[3,4-b]pyrazin]-3'(1'H)-one (400 mg, crude product) was dissolved in 20 mL of dichloromethane, and 2,3-dichloro-5,6-dicyano-1,4-benzoquinone (400 mg, 1.762 mmol) was added thereto, and the reaction was stirred at room temperature for 2 hours. To the reaction solution was added 60 mL of saturated sodium bicarbonate solution, and the mixture was extracted with 80 mL of ethyl acetate. The organic phase was washed with 60 mL of saturated brine, dried over anhydrous sodium sulfate and then concentrated, and the crude product was purified by preparative HPLC to obtain 9'-(2-chloro-4-phenoxybenzoyl)-4',5,6,7'-tetrahydro-2H,4H-spiro[pyran-3,2'-pyrrolo[3',2':5,6]pyrido[3,4-b]pyrazin]-3'(1'H)-one (Z16, 65 mg, 3-step yield of 20%) as a pale yellow solid, ES-API: $[M+H]^+$=489.1.

Step 6: The compound Z16 (65 mg, 0.1332 mmol) obtained in the above steps was resolved by chiral preparation (column: IC, 150 mm*4.6 mm*5 μM, mobile phase: n-hexane:ethanol=50:50, flow rate: 1 mL/min, column temperature: 30° C.) to obtain two single isomer compounds. One single isomer with a structure arbitrarily designated as Z16-1 (15.15 mg, peak 1, retention time: 8.132 min, yield of 23%) was a pale white solid. ES-API: $[M+H]^+$=489.1; $^1H$ NMR (400 MHz, DMSO-$d_6$) δ 12.52 (s, 1H), 10.54 (s, 1H), 8.79 (s, 1H), 7.75 (s, 1H), 7.66 (s, 1H), 7.58 (d, J=8.4 Hz, 1H), 7.52-7.43 (m, 2H), 7.22 (dt, J=9.4, 7.4 Hz, 4H), 7.03 (dd, J=8.4, 2.3 Hz, 1H), 3.92 (d, J=9.2 Hz, 1H), 3.80 (q, J=11.6 Hz, 2H), 3.40 (d, J=8.4 Hz, 1H), 1.97-1.80 (m, 3H), 1.51 (d, J=6.7 Hz, 1H). The other single isomer with a structure arbitrarily designated as Z16-2 (15.30 mg, peak 2, retention time: 11.960 min, yield of 23.5%) was a pale white solid. ES-API: $[M+H]^+$=489.1; $^1H$ NMR (400 MHz, DMSO-$d_6$) δ 12.52 (s, 1H), 10.54 (s, 1H), 8.79 (s, 1H), 7.75 (s, 1H), 7.66 (s, 1H), 7.58 (d, J=8.4 Hz, 1H), 7.52-7.43 (m, 2H), 7.21 (ddd, J=11.6, 9.7, 4.1 Hz, 4H), 7.03 (dd, J=8.4, 2.4 Hz, 1H), 3.92 (d, J=8.3 Hz, 1H), 3.80 (q, J=11.4 Hz, 2H), 3.42 (t, J=9.8 Hz, 1H), 1.98-1.81 (m, 3H), 1.51 (d, J=7.1 Hz, 1H).

Embodiment 17: Synthesis of Z17

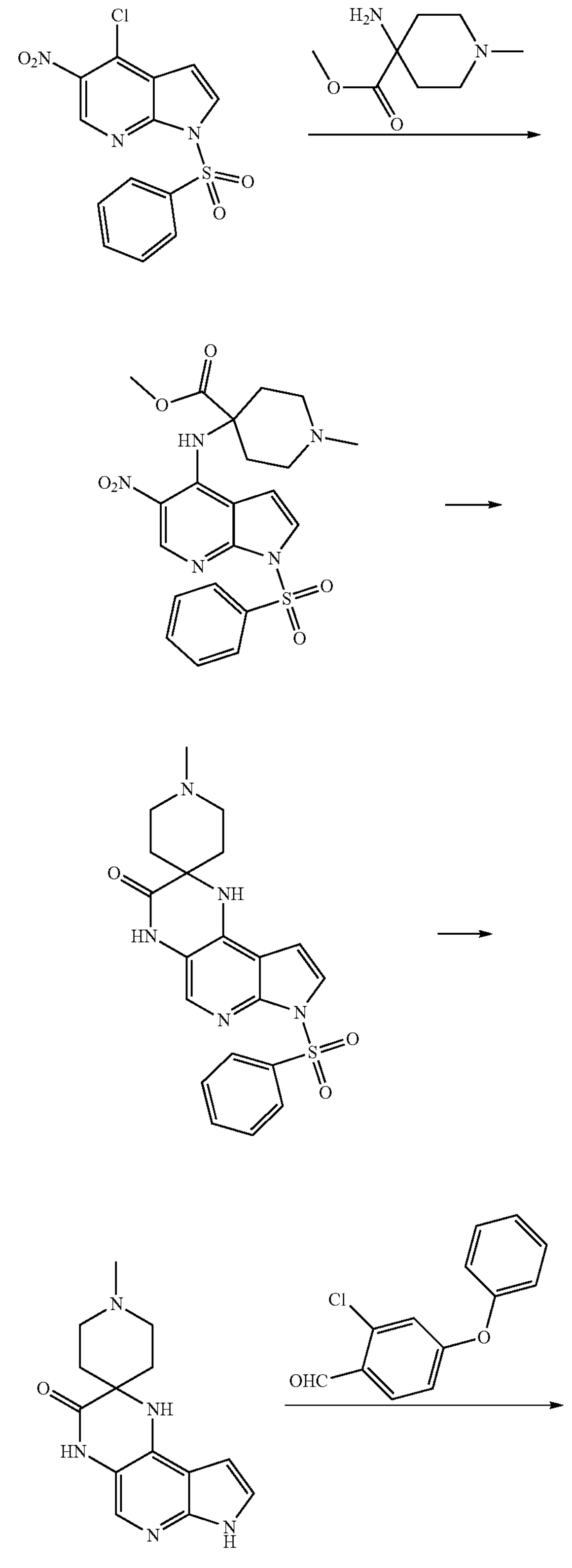

-continued

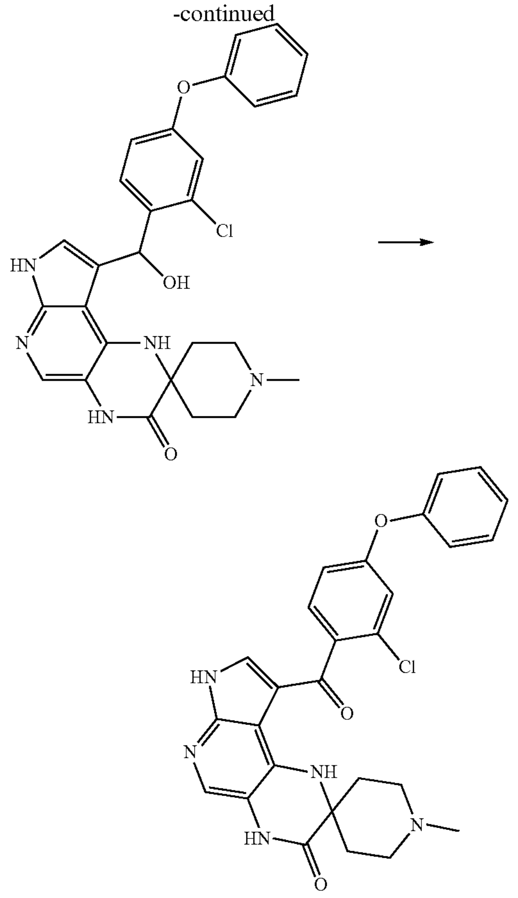

Z17

Step 1: 4-Chloro-5-nitro-1-(phenylsulfonyl)-1H-pyrrolo[2,3-b]pyridine (500 mg, 1.49 mmol) and methyl 4-amino-1-methylpiperidine-4-carboxylate (333 g, 1.94 mmol) were dissolved in 15 mL of N,N-dimethylacetamide, and N,N-diisopropylethylamine (577 mg, 4.47 mmol) was added thereto, and the reaction was stirred at 95° C. for 16 hours. The reaction solution was added with 100 mL of ethyl acetate, washed three times with 30 mL of dilute brine, washed with 30 mL of saturated brine in turn, dried and concentrated, and the crude product was purified by a flash silica gel column (ethyl acetate/petroleum ether: 0-50%) to obtain 1-methyl-4-((5-nitro-1-(phenylsulfonyl)-1H-pyrrolo[2,3-b]pyridin-4-yl)amino)piperidine-4-carboxylate (296 mg, yield of 42%) as a yellow solid. ES-API: [M+H]$^+$=474.1.

Step 2: 1-Methyl-4-((5-nitro-1-(phenylsulfonyl)-1H-pyrrolo[2,3-b]pyridin-4-yl)amino)piperidine-4-carboxylate (296 mg, 0.63 mmol) was dissolved in acetic acid (7 mL), and iron powder (247 mg, 4.41 mmol) was added thereto, and the reaction was stirred at 85° C. for 2 hours. The reaction solution was concentrated, and added with 20 mL of saturated sodium bicarbonate solution and 100 mL of dichloromethane/methanol=10:1. The suspension was filtered through diatomite, and the filter cake was washed with dichloromethane/methanol=10:1, and the organic phase was separated, washed with 25 mL of saturated brine, dried and concentrated to obtain 1-methyl-7'-(phenylsulfonyl)-4',7'-dihydrospiro[piperidine-4,2'-pyrrolo[3',2':5,6]pyrido[3,4-b]pyrazin]-3'(1'H)-one (258 mg, yield of 100%, crude product)

as an off-white solid, which was directly used for the next step of reaction. ES-API: [M+H]$^+$=412.3.

Step 3: 1-Methyl-7'-(phenylsulfonyl)-4',7'-dihydrospiro[piperidine-4,2'-pyrrolo[3',2':5,6]pyrido[3,4-b]pyrazin]-3'(1'H)-one (258 mg, 0.63 mmol) was dissolved in 10 mL of methanol, 5 mL of tetrahydrofuran and 2 mL of water, and sodium hydroxide (176 mg, 4.41 mmol) was added thereto, and the reaction was stirred at 65° C. for 16 hours. The pH of the reaction solution was adjusted to 8 with 1.0 M dilute hydrochloric acid. To the reaction solution was added 10 mL of saturated sodium bicarbonate solution, and the mixture was extracted with 100 mL of ethyl acetate. The organic phase was washed with 20 mL of saturated brine in turn, dried and then concentrated to obtain 1-methyl-4',7'-dihydrospiro[piperidine-4,2'-pyrrolo[3',2':5,6]pyrido[3,4-b]pyrazin]-3'(1'H)-one (76 mg, yield of 45%) as a light brown solid. ES-API: [M+H]$^+$=272.2.

Step 4: 1-Methyl-4',7'-dihydrospiro[piperidine-4,2'-pyrrolo[3',2':5,6]pyrido[3,4-b]pyrazin]-3'(1'H)-one (76 mg, 0.28 mmol) and 2-chloro-4-phenoxybenzaldehyde (79 mg, 0.34 mmol) were dissolved in methanol (8 mL), then the reaction was cooled to 0° C., and potassium hydroxide (110 mg, 1.96 mmol) was added thereto. The reaction was stirred at room temperature for 18 hours. The pH of the reaction solution was adjusted to 8 with 1.0 M dilute hydrochloric acid, and the reaction solution was directly concentrated, then the crude product was purified by a thin-layer preparative plate (dichloromethane/7M ammonia methanol=10:1) to obtain 9'-((2-chloro-4-phenoxyphenyl)(hydroxy)methyl)-1-methyl-4',7'-dihydrospiro[piperidine-4,2'-pyrrolo[3',2':5,6]pyrido[3,4-b]pyrazin]-3'(1'H)-one (56 mg, yield of 33%) as a yellow solid. ES-API: [M+H]$^+$=504.2.

Step 5: 9'-((2-Chloro-4-phenoxyphenyl)(hydroxy)methyl)-1-methyl-4',7'-dihydrospiro[piperidine-4,2'-pyrrolo[3',2':5,6]pyrido[3,4-b]pyrazin]-3'(1'H)-one (56 mg, 0.11 mmol) was dissolved in 6 mL of tetrahydrofuran, cooled to 0° C., and Dess-Martin periodinane (94 mg, 0.22 mmol) was added thereto, and the reaction was stirred at room temperature for 2 hours. To the reaction solution was added 3 mL of saturated sodium thiosulfate solution and 10 mL of saturated sodium bicarbonate solution, and the mixture was extracted with 40 mL of ethyl acetate. The organic phase was washed with 10 mL of saturated brine, dried and then concentrated, and the crude product was purified by preparative HPLC to obtain 9'-(2-chloro-4-phenoxybenzoyl)-1-methyl-4',7'-dihydrospiro[piperidine-4,2'-pyrrolo[3',2':5,6]pyrido[3,4-b]pyrazin]-3'(1'H)-one (Z17, 0.61 mg, yield of 1.1%) as a pale yellow solid. ES-API: [M+H]$^+$=502.2.

Embodiment 18: Synthesis of Z63

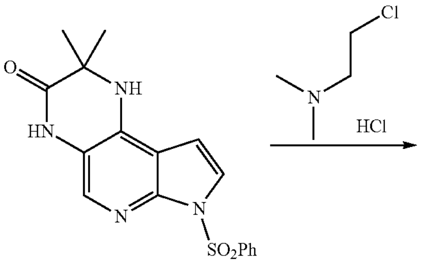

-continued

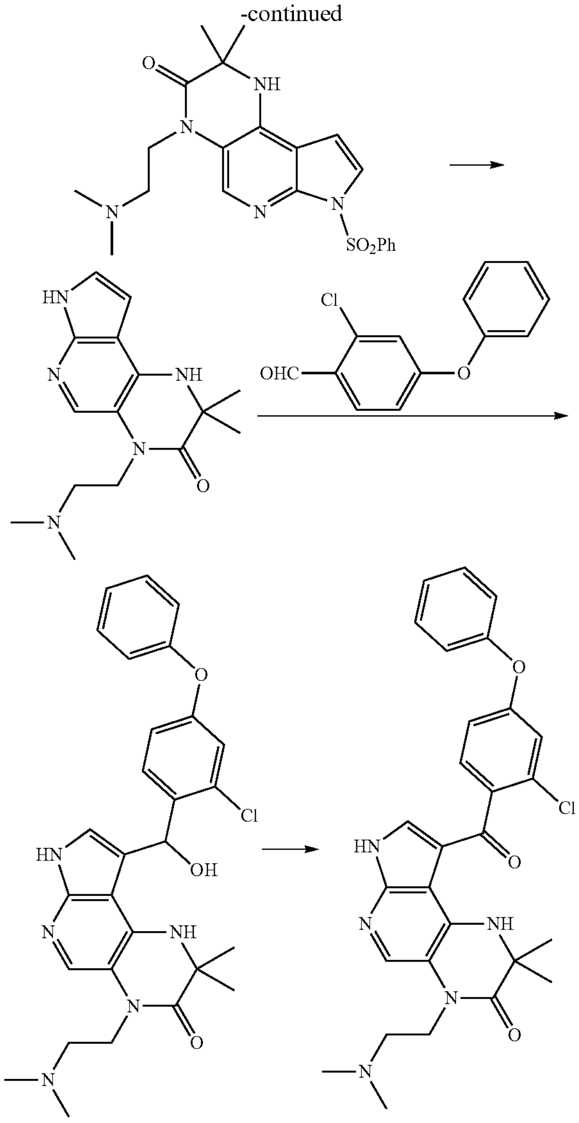

Z63

Step 1: 2,2-Dimethyl-7-(phenylsulfonyl)-1,2,4,7-tetrahydro-3H-pyrrolo[3',2':5,6]pyrido[3,4-b]pyrazin-3-one (400 mg, 1.12 mmol) was dissolved in 12 mL of N,N-dimethylformamide, then anhydrous potassium carbonate (773 mg, 5.60 mmol) and 2-chloro-N,N-dimethylethan-1-amine hydrochloride (323 mg, 2.24 mmol) were added thereto, and the reaction was stirred at 60° C. for 16 hours. The reaction solution was cooled to room temperature, additionally added with anhydrous potassium carbonate (309 mg, 2.24 mmol) and 2-chloro-N,N-dimethylethan-1-amine hydrochloride (161 mg, 1.12 mmol), and the reaction was stirred at 60° C. for 8 hours. The reaction solution was poured into 40 mL of water and extracted twice with 40 mL of ethyl acetate. The combined organic phases were washed 3 times with 25 mL of saturated brine, dried and concentrated, and the crude product was purified by a flash silica gel column (methanol/dichloromethane: 0-7%) to obtain 4-(2-(dimethylamino)ethyl)-2,2-dimethyl-7-(phenylsulfonyl)-1,2,4,7-tetrahydro-3H-pyrrolo[3',2':5,6]pyrido[3,4-b]pyrazin-3-one (300 mg, yield of 62%) as a pale yellow solid. $^1$H NMR (400 MHz, DMSO-$d_6$) δ 8.10-8.05 (m, 2H), 7.94 (s, 1H), 7.74-7.69 (m 1H), 7.65-7.58 (m, 3H), 7.34 (s, 1H), 6.93 (d, J=4.0 Hz, 1H), 4.00 (t, J=7.2 Hz, 2H), 2.41 (t, J=7.2 Hz, 2H), 2.20 (s, 6H), 1.29 (s, 6H). ES-API: $[M+H]^+$=428.1.

Step 2: 4-(2-(Dimethylamino)ethyl)-2,2-dimethyl-7-(phenylsulfonyl)-1,2,4,7-tetrahydro-3H-pyrrolo[3',2':5,6]pyrido[3,4-b]pyrazin-3-one (250 mg, 0.58 mmol) was dissolved in 10 mL of methanol, 3 mL of tetrahydrofuran and 2 mL of water, and sodium hydroxide (94 mg, 2.32 mmol) and triethylamine (1.17 g, 11.60 mmol) were added thereto, and the reaction was stirred at 60° C. for 16 hours. The pH of the reaction solution was adjusted to 8 with 1.0 M dilute hydrochloric acid, and the reaction solution was added with 100 mL of ethyl acetate, washed twice with 30 mL of saturated sodium bicarbonate solution, washed with 30 mL of saturated brine in turn, dried and concentrated to obtain 4-(2-(dimethylamino)ethyl)-2,2-dimethyl-1,2,4,7-tetrahydro-3H-pyrrolo[3',2':5,6]pyrido[3,4-b]pyrazin-3-one (150 mg, yield of 89%) as a white solid. ES-API: $[M+H]^+$=288.3.

Step 3: 4-(2-(Dimethylamino)ethyl)-2,2-dimethyl-1,2,4,7-tetrahydro-3H-pyrrolo[3',2':5,6]pyrido[3,4-b]pyrazin-3-one (75 mg, 0.26 mmol) and 2-chloro-4-phenoxybenzaldehyde (151 mg, 0.65 mmol) were dissolved in methanol (6 mL), then the reaction was cooled to 0° C., and potassium hydroxide (102 mg, 1.82 mmol) was added thereto. The reaction was stirred at room temperature for 16 hours. The pH of the reaction solution was adjusted to 8 with 1.0 M dilute hydrochloric acid, and the reaction solution was concentrated, then the crude product was purified by a thin-layer preparative plate (dichloromethane/7.0M ammonia methanol solution=10:1) to obtain 9-((2-chloro-4-phenoxyphenyl)(hydroxy)methyl)-4-(2-(dimethylamino)ethyl)-2,2-dimethyl-1,2,4,7-tetrahydro-3H-pyrrolo[3',2':5,6]pyrido[3,4-b]pyrazin-3-one (100 mg, yield of 74%) as a pale yellow solid. ES-API: $[M+H]^+$=520.2.

Step 4: 9-((2-Chloro-4-phenoxyphenyl)(hydroxy)methyl)-4-(2-(dimethylamino)ethyl)-2,2-dimethyl-1,2,4,7-tetrahydro-3H-pyrrolo[3',2':5,6]pyrido[3,4-b]pyrazin-3-one (95 mg, 0.18 mmol) was dissolved in 1,4-dioxane (5 mL) and water (0.5 mL), and 2,3-dichloro-5,6-dicyano-p-benzoquinone (82 mg, 0.36 mmol) was added thereto at room temperature, and the reaction was stirred at room temperature for 2 hours. To the reaction solution was added 6 mL of saturated sodium thiosulfate solution and 10 mL of saturated sodium bicarbonate solution, and the mixture was extracted with 80 mL of ethyl acetate. The organic phase was washed with 20 mL of saturated sodium bicarbonate solution and 20 mL of saturated brine in turn, dried and then concentrated, and the crude product was purified by preparative HPLC to obtain a target product (Z63, 70 mg, yield of 74%) as a white solid. $^1H$ NMR (400 MHz, DMSO-$d_6$) δ 12.60 (s, 1H), 8.33 (s, 1H), 8.03 (s, 1H), 7.68 (s, 1H), 7.57 (d, J=8.4 Hz, 1H), 7.52-7.43 (m, 2H), 7.25 (t, J=7.2 Hz, 1H), 7.23-7.14 (m, 3H), 7.02 (dd, J=8.4, 2.4 Hz, 1H), 4.09 (t, J=7.2 Hz, 2H), 2.44 (t, J=7.2 Hz, 2H), 2.21 (s, 6H), 1.38 (s, 6H). ES-API: $[M+H]^+$=518.2.

Embodiment 19: Synthesis of Z18

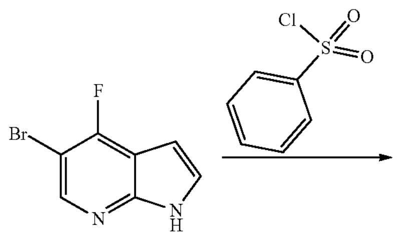

-continued

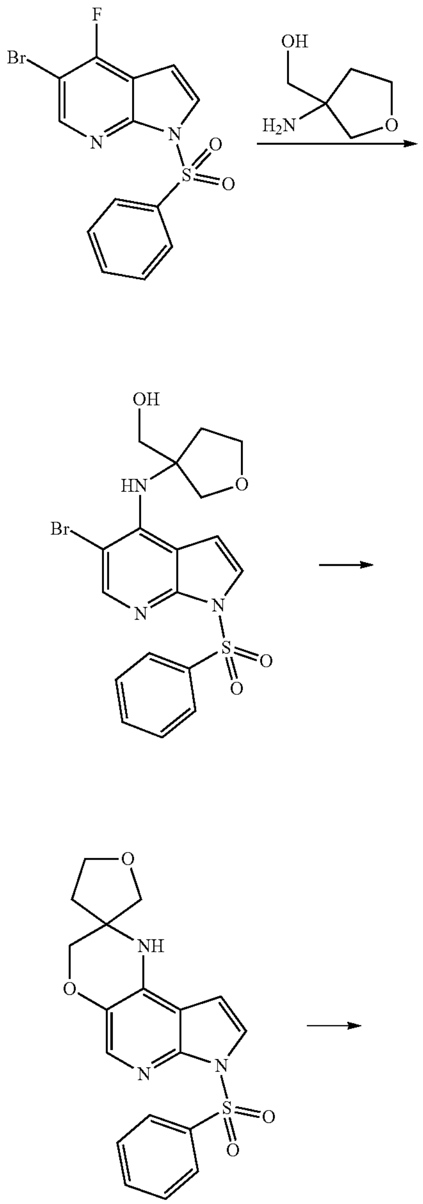

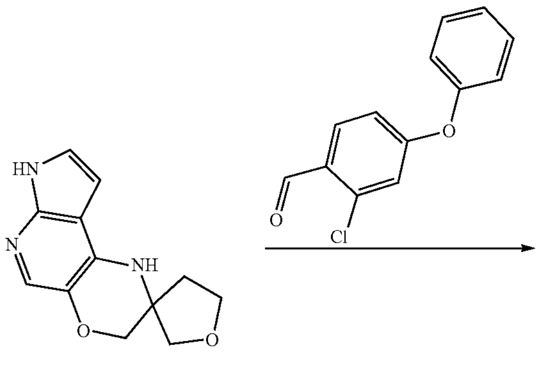

-continued

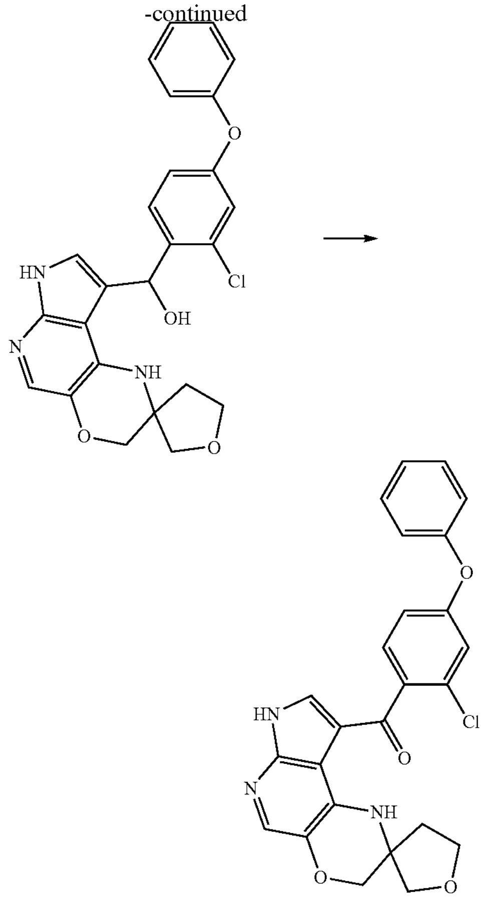

Z18

Step 1: 5-Bromo-4-fluoro-1H-pyrrolo[2,3-b]pyridine (950 mg, 4.42 mmol) was dissolved in 25 mL of tetrahydrofuran, cooled to 0° C. under nitrogen atmosphere, and sodium hydride (1.01 g, 5.75 mmol, 60% dispersed in mineral oil) was added thereto, and the reaction was stirred at room temperature for 30 minutes. After cooling to 0° C. again, a solution of benzenesulfonyl chloride (1.01 g, 5.75 mmol) in tetrahydrofuran (2 mL) was slowly added dropwise thereto, and the reaction was stirred at room temperature for 16 hours. The reaction solution was added with 40 mL of water and extracted with 80 mL of ethyl acetate. The organic phase was washed with 30 mL of saturated brine, dried and concentrated, and the crude product was purified by a flash silica gel column (ethyl acetate/petroleum ether: 0-100%) to obtain 5-bromo-4-fluoro-1-(phenylsulfonyl)-1H-pyrrolo[2,3-b]pyridine (1.5 g, yield of 95%) as a white solid. ES-API: $[M+H]^+$=355.0, 357.0.

Step 2: To a 20 mL microwave tube was added 5-bromo-4-fluoro-1-(phenylsulfonyl)-1H-pyrrolo[2,3-b]pyridine (500 mg, 1.41 mmol), (3-aminotetrahydrofuran-3-yl)methanol (330 mg, 2.82 mmol), N,N-dimethylacetamide (7 mL) and N,N-diisopropylethylamine (546 mg, 13.36 mmol) sequentially, reacted in a microwave reactor at 160° C. for 8 hours. The reaction solution was added with 100 mL of ethyl acetate, washed three times with 30 mL of dilute brine, washed with 30 mL of saturated brine, dried and concentrated, and the crude product was slurried with ethyl acetate/petroleum ether=1:1 to obtain (3-((5-bromo-1-(phenylsulfonyl)-1H-pyrrolo[2,3-b]pyridin-4-yl)amino)tetrahydrofuran-3-yl)methanol (240 mg, yield of 38%) as a white solid. $^1$H NMR (400 MHz, DMSO-$d_6$) δ 8.16 (s, 1H), 8.08 (d, J=7.6 Hz, 2H), 7.77-7.69 (m, 2H), 7.62 (t, J=7.6 Hz, 2H), 6.81 (d, J=4.0 Hz, 1H), 5.67 (s, 1H), 5.44 (t, J=5.2 Hz, 1H), 3.95-3.59 (m, 6H), 2.30-2.10 (m, 2H). ES-API: $[M+H]^+$=452.0, 454.0.

Step 3: To a 5 mL microwave tube was added (3-((5-bromo-1-(phenylsulfonyl)-1H-pyrrolo[2,3-b]pyridin-4-yl)amino)tetrahydrofuran-3-yl)methanol (115 mg, 0.25 mmol), palladium acetate (12 mg, 0.05 mmol), 2-(di-tert-butylphosphino)-1,1'-binaphthyl (30 mg, 0.075 mmol), cesium carbonate (122 mg, 0.375 mmol) and toluene (4 mL), then the mixture was replaced with nitrogen for 2 minutes and reacted at 115° C. for 1 hour in a microwave reactor. The reaction solution was filtered, washed with dichloromethane, and the filtrate was concentrated, and the crude product was purified by a flash silica gel column (methanol/dichloromethane: 0-3%) to obtain 7'-(phenylsulfonyl)-1',4,5,7'-tetrahydro-2H,3'H-spiro[furan-3,2'-pyrrolo[3',2':5,6]pyrido[3,4-b][1,4]oxazine] (105 mg, crude product) as a pale yellow solid. ES-API: $[M+H]^+$=372.1

Step 4: 7'-(Phenylsulfonyl)-1',4,5,7'-tetrahydro-2H,3'H-spiro[furan-3,2'-pyrrolo[3',2':5,6]pyrido[3,4-b][1,4]oxazine] (180 mg, crude product) was dissolved in 8 mL of methanol, 2 mL of tetrahydrofuran and 2 mL of water, and sodium hydroxide (78 mg, 1.94 mmol) was added thereto, and the reaction was stirred at 65° C. for 16 hours. The pH of the reaction solution was adjusted to 8 with 1.0 M dilute hydrochloric acid. To the reaction solution was added 10 mL of saturated sodium bicarbonate solution, and the mixture was extracted with 80 mL of ethyl acetate. The organic phase was washed with 20 mL of saturated sodium bicarbonate solution and 20 mL of saturated brine in turn, dried and concentrated, and the crude product was prepared by a thin-layer preparative plate (dichloromethane/methanol=10:1) to obtain 1',4,5,7'-tetrahydro-2H,3'H-spiro[furan-3,2'-pyrrolo[3',2':5,6]pyrido[3,4-b][1,4]oxazine] (90 mg, 2-step yield of 82%) as a pale yellow solid. ES-API: $[M+H]^+$=232.1.

Step 5: 1',4,5,7'-Tetrahydro-2H,3'H-spiro[furan-3,2'-pyrrolo[3',2':5,6]pyrido[3,4-b][1,4]oxazine] (85 mg, 0.37 mmol) and 2-chloro-4-phenoxybenzaldehyde (256 mg, 1.10 mmol) were dissolved in methanol (8 mL), and the reaction was cooled to 0° C., and potassium hydroxide (145 mg, 2.59 mmol) was added thereto. The reaction was stirred at room temperature for 16 hours. The pH of the reaction solution was adjusted to 8 with 1.0 M dilute hydrochloric acid, and the reaction solution was extracted with 60 mL of ethyl acetate. The organic phase was washed with 20 mL of saturated brine, dried and then concentrated, and the crude product was purified by a thin-layer preparative plate (dichloromethane/methanol=10:1) to obtain (2-chloro-4-phenoxyphenyl)(1',4,5,7'-tetrahydro-2H,3'H-spiro[furan-3,2'-pyrrolo[3',2':5,6]pyrido[3,4-b][1,4]oxazin]-9'-yl)methanol (120 mg, yield of 70%) as a pale yellow solid. ES-API: $[M+H]^+$=464.1.

Step 6: (2-Chloro-4-phenoxyphenyl)(1',4,5,7'-tetrahydro-2H,3'H-spiro[furan-3,2'-pyrrolo[3',2':5,6]pyrido[3,4-b][1,4]oxazin]-9'-yl)methanol (120 mg, 0.26 mmol) was dissolved in 1,4-dioxane (5 mL) and water (0.5 mL), and 2,3-dichloro-5,6-dicyano-p-benzoquinone (83 mg, 0.36 mmol) was added thereto at room temperature, and the reaction was stirred at room temperature for 1 hour. To the reaction solution was added 5 mL of saturated sodium thiosulfate solution and 10 mL of saturated sodium bicarbonate solution, and the mixture was extracted with 50 mL of ethyl acetate. The organic phase was washed with 15 mL of saturated sodium bicarbonate solution and 15 mL of saturated brine in turn, dried and then concentrated, and the crude product was purified by preparative HPLC to obtain a target product (Z18, 40 mg, yield of 33%) as a pale yellow solid. $^1H$ NMR (400 MHz, DMSO-$d_6$) δ 8.39 (s, 1H), 7.75 (s, 1H), 7.57-7.52 (m, 2H), 7.47 (t, J=8.0 Hz, 2H), 7.25 (t, J=7.6 Hz, 1H), 7.21-7.15 (m, 3H), 7.01 (dd, J=8.4, 2.4 Hz, 1H), 6.06 (s, 1H), 4.11 (d, J=10.6 Hz, 1H), 4.04-3.89 (m, 3H), 3.76 (d, J=8.8 Hz, 1H), 3.56 (d, J=8.8 Hz, 1H), 2.18-2.08 (m, 1H), 1.99-1.89 (m, 1H). ES-API: $[M+H]^+$=462.0.
Embodiment 20: Synthesis of Z19
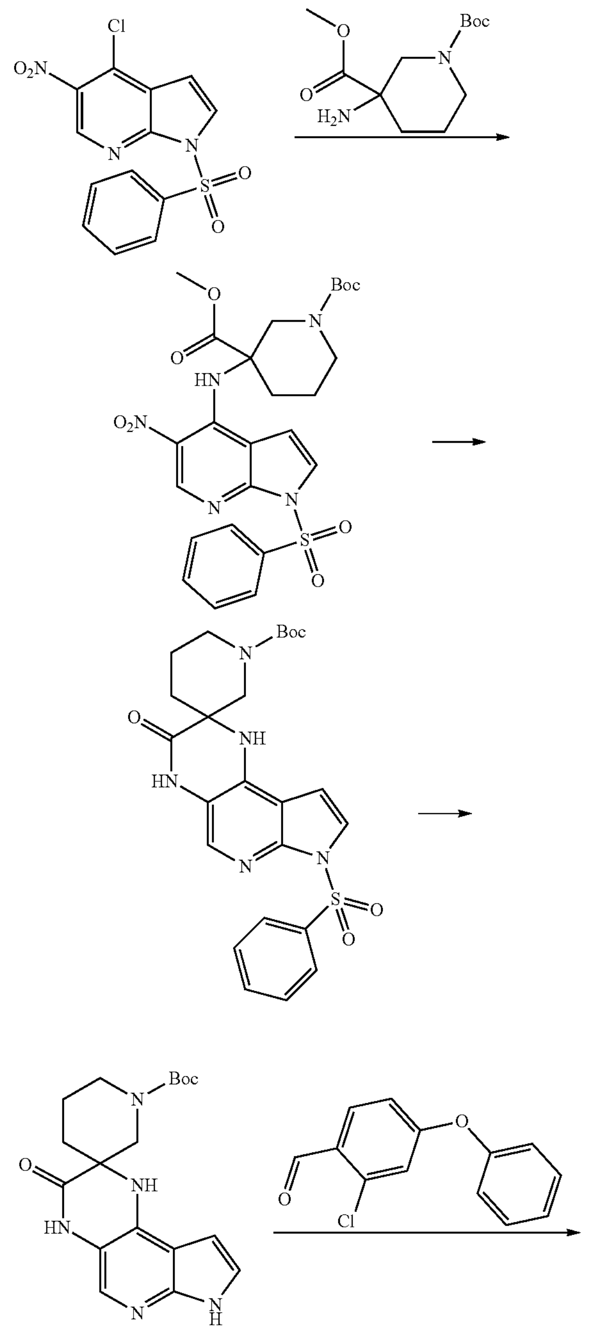
-continued
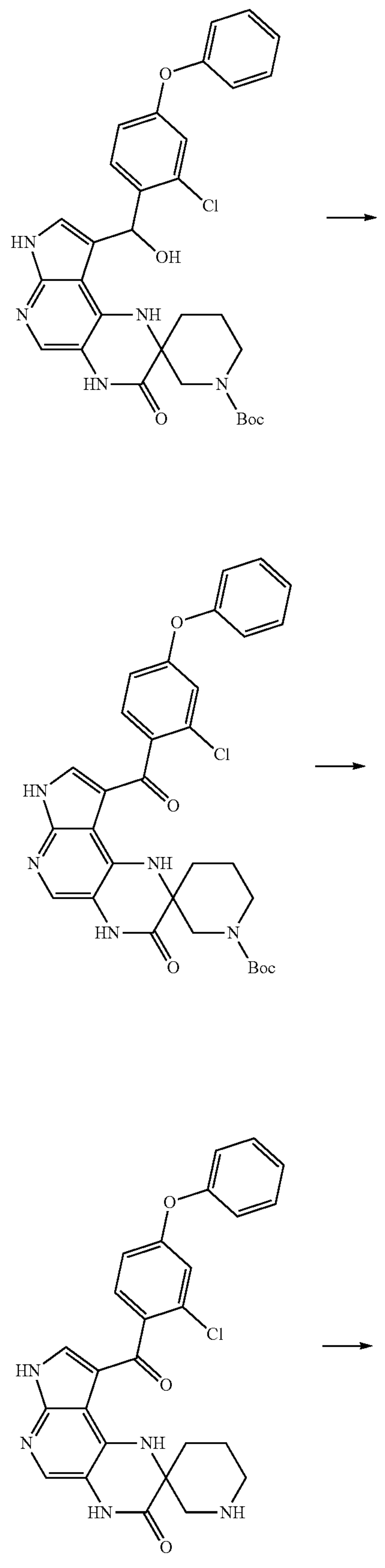

-continued

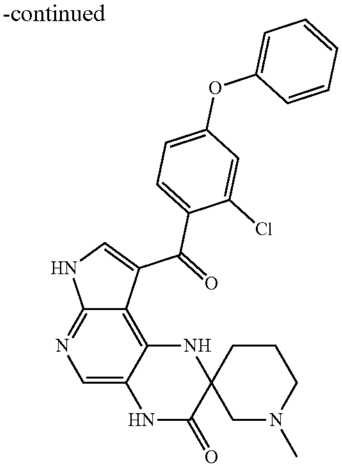

Z19

Step 1: 4-Chloro-5-nitro-1-(phenylsulfonyl)-1H-pyrrolo[2,3-b]pyridine (0.60 g, 1.7804 mmol) and 1-(tert-butyl) 3-methyl 3-aminopiperidine-1,3-dicarboxylate (450 mg, 1.540 mmol) were dissolved in N,N-dimethylformamide (20 mL), and N,N-diisopropylethylamine (7.64 g, 59.15 mmol) was added thereto, and the reaction was stirred at 95° C. for 12 hours. The reaction solution was added with 120 mL of ethyl acetate, washed twice with 80 mL of water and 3 times with 60 mL of saturated brine, dried and concentrated, and the crude product was purified by a flash silica gel column (ethyl acetate/petroleum ether: 0-50%) to obtain 1-(tert-butyl) 3-methyl 3-((5-nitro-1-(phenylsulfonyl)-1H-pyrrolo[2,3-b]pyridin-4-yl)amino)piperidine-1,3-dicarboxylate (367 mg, yield of 36%) as a pale yellow solid. ES-API: $[M+H]^+$=560.2.

Step 2: 1-(tert-Butyl) 3-methyl 3-((5-nitro-1-(phenylsulfonyl)-1H-pyrrolo[2,3-b]pyridin-4-yl)amino)piperidine-1,3-dicarboxylate (320 mg, 0.6563 mmol) was dissolved in acetic acid (20 mL), and iron powder (0.672 g, 12.0 mmol) was added thereto, and the reaction was stirred at 80° C. for 1 hour. The solvent was evaporated to dryness by rotary evaporation under reduced pressure, then 200 mL of ethyl acetate was added thereto. The mixture was washed twice with 80 mL of water, twice with 60 mL of saturated sodium carbonate, twice with 80 mL of saturated sodium bicarbonate, and with 80 mL of saturated brine in turn, dried and concentrated, and the crude product was slurried with ethyl acetate to obtain tert-butyl 3'-oxo-7'-(phenylsulfonyl)-1',3',4',7'-tetrahydrospiro[piperidine-3,2'-pyrrolo[3',2':5,6]pyrido[3,4-b]pyrazine]-1-carboxylate (230 mg, yield of 70%) as a pale yellow solid. ES-API: $[M+H]^+$=498.2.

Step 3: tert-Butyl 3'-oxo-7'-(phenylsulfonyl)-1',3',4',7'-tetrahydrospiro[piperidine-3,2'-pyrrolo[3',2':5,6]pyrido[3,4-b]pyrazine]-1-carboxylate (230 mg, 0.4626 mmol) was dissolved in 12 mL of methanol, 3 mL of tetrahydrofuran and 2 mL of water, and sodium hydroxide (129 mg, 3.2381 mmol) was added thereto, and the reaction was stirred at 65° C. for 7 hours. To the reaction solution was added 20 mL of water and 5 mL of saturated ammonium chloride solution, and the mixture was extracted with 160 mL of ethyl acetate. The organic phase was washed with 40 mL of saturated sodium bicarbonate solution and 60 mL of saturated brine in turn, dried over anhydrous sodium sulfate and then concentrated to obtain tert-butyl 3'-oxo-1',3',4',7'-tetrahydrospiro[piperidine-3,2'-pyrrolo[3',2':5,6]pyrido[3,4-b]pyrazine]-1-carboxylate (382 mg, crude product) as an off-white solid. ES-API: $[M+H]^+$=358.3.

Step 4: tert-Butyl 3'-oxo-1',3',4',7'-tetrahydrospiro[piperidine-3,2'-pyrrolo[3',2':5,6]pyrido[3,4-b]pyrazine]-1-carboxylate (382 mg, crude product) and 2-chloro-4-phenoxybenzaldehyde (215 mg, 0.9252 mmol) were dissolved in methanol (12.0 mL), and the reaction was cooled to 0° C., and potassium hydroxide (181 mg, 3.238 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 120 mL of ethyl acetate. The organic phase was washed with 63 mL of saturated brine, dried and then concentrated to obtain a crude target product tert-butyl 9'-((2-chloro-4-phenoxyphenyl)(hydroxy)methyl)-3'-oxo-1',3',4',7'-tetrahydrospiro[piperidine-3,2'-pyrrolo[3',2':5,6]pyrido[3,4-b]pyrazine]-1-carboxylate (500 mg, crude product) as a pale yellow solid. ES-API: $[M+H]^+$=590.2.

Step 5: tert-Butyl 9'-((2-chloro-4-phenoxyphenyl)(hydroxy)methyl)-3'-oxo-1',3',4',7'-tetrahydrospiro[piperidine-3,2'-pyrrolo[3',2':5,6]pyrido[3,4-b]pyrazine]-1-carboxylate (500 mg, crude product) was dissolved in 20 mL of dichloromethane, and 2,3-dichloro-5,6-dicyano-1,4-benzoquinone (210 mg, 0.9252 mmol) was added thereto, and the reaction was stirred at room temperature for 2 hours. To the reaction solution was added 60 mL of saturated sodium bicarbonate solution, and the mixture was extracted with 80 mL of ethyl acetate. The organic phase was washed with 60 mL of saturated brine, dried over anhydrous sodium sulfate and then concentrated, and the crude product was purified by a flash silica gel column (methanol/dichloromethane: 0-30%) to obtain tert-butyl 9'-(2-chloro-4-phenoxybenzoyl)-3'-oxo-1',3',4',7'-tetrahydrospiro[piperidine-3,2'-pyrrolo[3',2':5,6]pyrido[3,4-b]pyrazine]-1-carboxylate (260 mg, 3-step yield of 95%) as a pale yellow solid. ES-API: $[M+H]^+$=588.2.

Step 6: tert-Butyl 9'-(2-chloro-4-phenoxybenzoyl)-3'-oxo-1',3',4',7'-tetrahydrospiro[piperidine-3,2'-pyrrolo[3',2':5,6]pyrido[3,4-b]pyrazine]-1-carboxylate (260 mg, 0.4429 mmol) was dissolved in dichloromethane (12 mL), and finally trifluoroacetic acid (3.0 mL) was added thereto. The mixture was reacted at room temperature for 3 hours and the solvent was evaporated to dryness by rotary evaporation under reduced pressure to obtain a crude product 9'-(2-chloro-4-phenoxybenzoyl)-4',7'-dihydrospiro[piperidine-3,2'-pyrrolo[3',2':5,6]pyrido[3,4-b]pyrazin]-3'(1'H)-one (300 mg, crude product). ES-API: $[M+H]^+$=488.1. The crude product was directly used in the next step of reaction.

Step 7: Under an ice-water bath, tert-butyl 9'-(2-chloro-4-phenoxybenzoyl)-3'-oxo-1',3',4',7'-tetrahydrospiro[piperidine-3,2'-pyrrolo[3',2':5,6]pyrido[3,4-b]pyrazine]-1-carboxylate (300 mg, crude product) was dissolved in acetonitrile (20 mL), and sodium cyanoborohydride (139 mg, 2.21 mmol) was added thereto, and then aqueous formaldehyde solution (180 mg, 2.21 mmol, 37% a.q.) was added dropwise thereto. The system was slowly heated to room temperature and stirred for 2 hours. After the reaction was completed, saturated sodium bicarbonate (30 mL) and ethyl acetate (60 mL) were added to the system, and the ethyl acetate phase was dried over anhydrous sodium sulfate, filtered, and evaporated to dryness by rotary evaporation under reduced pressure. The crude product was purified by preparative HPLC to obtain 9'-(2-chloro-4-phenoxybenzoyl)-1-methyl-4',7'-dihydrospiro[piperidine-3,2'-pyrrolo[3',2':5,6]pyrido[3,4-b]pyrazin]-3'(1'H)-one (Z19, 13 mg, 2-step yield of 6%). ES-API: $[M+H]^+$=502.2.

Embodiment 21: Synthesis of Z22

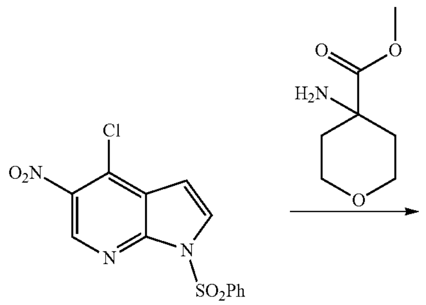

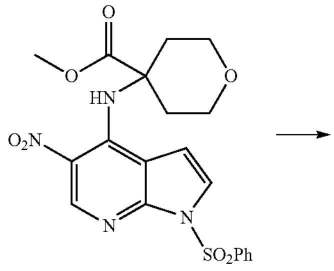

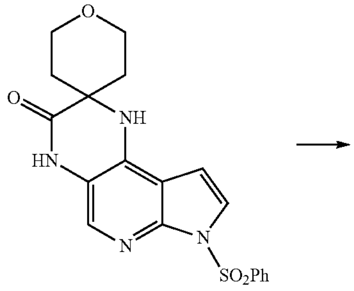

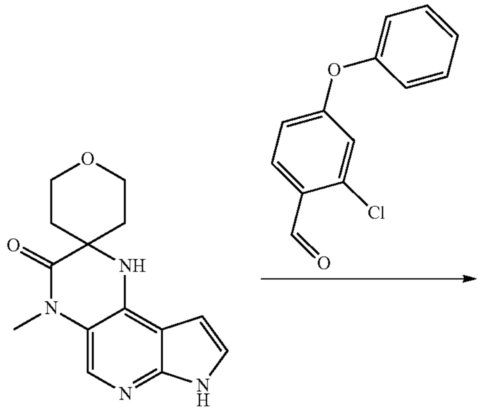

-continued

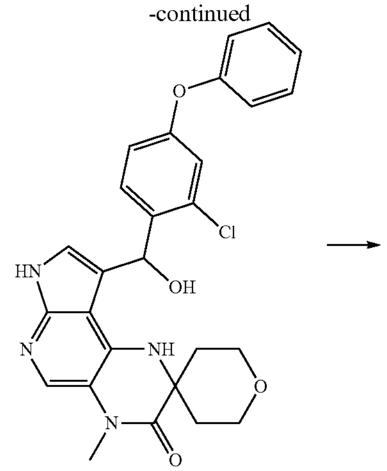

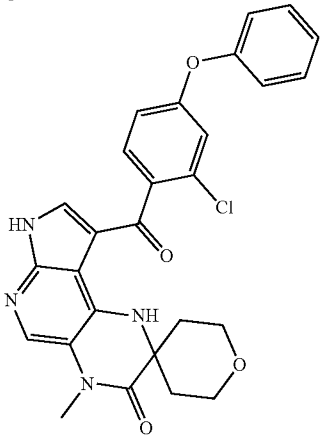

Z22

Step 1: 4-Chloro-5-nitro-1-(phenylsulfonyl)-1H-pyrrolo[2,3-b]pyridine (500 mg, 1.48 mmol) and methyl 4-amino-tetrahydro-2H-pyran-4-carboxylate (283 mg, 1.78 mmol) were dissolved in N,N-dimethylacetamide (5 mL), and N,N-diisopropylethylamine (573 g, 4.44 mmol) was added thereto, reacted under microwave irradiation and stirred at 120° C. for 1.5 hours. The reaction solution was added with 100 mL of ethyl acetate, washed twice with 60 mL of water and 3 times with 30 mL of saturated brine, dried and concentrated, and the crude product was purified by a flash silica gel column (ethyl acetate/petroleum ether: 0-50%) to obtain methyl 4-((5-nitro-1-(phenylsulfonyl)-1H-pyrrolo[2,3-b]pyridin-4-yl)amino)tetrahydro-2H-pyran-4-carboxylate (374 mg, yield of 55%) as a yellow solid. ES-API: $[M+H]^+=461.1$.

Step 2: Methyl 4-((5-nitro-1-(phenylsulfonyl)-1H-pyrrolo[2,3-b]pyridin-4-yl)amino)tetrahydro-2H-pyran-4-carboxylate (374 mg, 0.813 mmol) was dissolved in acetic acid (10 mL), and iron powder (455 mg, 8.13 mmol) was added thereto, and the reaction was stirred at 80° C. for 3 hours. The reaction solution was added with 100 mL of ethyl acetate, washed twice with 60 mL of water, twice with 40 mL of saturated sodium carbonate, twice with 40 mL of saturated sodium bicarbonate, and with 40 mL of saturated brine in turn, dried and concentrated, and the crude product was slurried with ethyl acetate to obtain 7'-(phenylsulfonyl)-2,3,4',5,6,7'-hexahydrospiro[pyran-4,2'-pyrrolo[3',2':5,6]pyrido[3,4-b]pyrazin]-3'(1'H)-one (200 mg, yield of 61%) as a yellow solid. ES-API: $[M+H]^+=399.1$ Step 3: 7'-(Phenylsulfonyl)-2,3,4',5,6,7'-hexahydrospiro [pyran-4,2'-pyrrolo[3',2':5,6]pyrido[3,4-b]pyrazin]-3'(1'H)-one (200 mg, 0.50 mmol) was dissolved in 10 mL of N,N-dimethylformamide, and anhydrous potassium carbonate (414 mg, 3.0 mmol) and iodomethane (352 mg, 2.5 mmol) were added thereto, and the reaction was stirred at 40° C. for 3 hours in a sealed tube. To the reaction solution, 100 mL of ethyl acetate was added for extraction. The organic phase was washed with water and saturated brine in turn, dried and then concentrated to obtain 4'-methyl-7'-(phenylsulfonyl)-2,3,4',5,6,7'-hexahydrospiro[pyran-4,2'-pyrrolo[3',2':5,6]pyrido[3,4-b]pyrazin]-3'(1'H)-one (180 mg, yield of 87%) as an off-white solid. ES-API: $[M+H]^+$= 413.1.

Step 4: 4'-Methyl-7'-(phenylsulfonyl)-2,3,4',5,6,7'-hexahydrospiro[pyran-4,2'-pyrrolo[3',2':5,6]pyrido[3,4-b] pyrazin]-3'(1'H)-one (180 mg, 0.43 mmol) was dissolved in 10 mL of methanol, 5 mL of tetrahydrofuran and 2 mL of water, and sodium hydroxide (86 mg, 2.15 mmol) was added thereto, and the reaction was stirred at 65° C. for 15 hours. To the reaction solution was added 15 mL of water and 4 mL of saturated ammonium chloride solution, and the mixture was extracted with 100 mL of ethyl acetate. The organic phase was washed with 20 mL of saturated sodium bicarbonate solution and 20 mL of saturated brine in turn, dried and then concentrated to obtain 4'-methyl-2,3,4',5,6,7'-hexahydrospiro[pyran-4,2'-pyrrolo[3',2':5,6]pyrido[3,4-b] pyrazin]-3'(1'H)-one (92 mg, yield of 42%) as an off-white solid. ES-API: $[M+H]^+$=273.1.

Step 5: 4'-Methyl-2,3,4',5,6,7'-hexahydrospiro[pyran-4, 2'-pyrrolo[3',2':5,6]pyrido[3,4-b]pyrazin]-3'(1'H)-one (92 mg, 0.34 mmol) and 2-chloro-4-phenoxybenzaldehyde (157 mg, 0.68 mmol) were dissolved in methanol (5 mL), and the reaction was cooled to 0° C., and potassium hydroxide (95 mg, 1.70 mmol) was added thereto. The reaction was stirred at room temperature for 3 hours. The reaction solution was poured into 60 mL of water, and the pH of the reaction solution was adjusted to 8 with 1.0 M dilute hydrochloric acid, and the reaction solution was extracted with 80 mL of ethyl acetate. The organic phase was washed with 25 mL of saturated brine, dried and then concentrated, and the crude product was purified by a thin-layer preparative plate (dichloromethane/methanol=10:1) to obtain 9'-((2-chloro-4-phenoxyphenyl)(hydroxy)methyl)-4'-methyl-2,3,4',5,6,7'-hexahydrospiro[pyran-4,2'-pyrrolo[3',2':5,6]pyrido[3,4-b] pyrazin]-3'(1'H)-one (110 mg, yield of 65%) as a pale yellow solid. ES-API: $[M+H]^+$=505.1.

Step 6: 9'-((2-Chloro-4-phenoxyphenyl)(hydroxy) methyl)-4'-methyl-2,3,4',5,6,7'-hexahydrospiro[pyran-4,2'-pyrrolo[3'2':5,6]pyrido[3,4-b]pyrazin]-3'(1'H)-one (110 mg, 0.218 mmol) was dissolved in 5 mL of 1,4-dioxane and 1 mL of water, and DDQ (99 mg, 0.436 mmol) was added thereto, and the reaction was stirred at room temperature for 30 minutes. To the reaction solution was added 5 mL of saturated sodium thiosulfate solution and 20 mL of saturated sodium bicarbonate solution, and the mixture was extracted with 60 mL of ethyl acetate. The mixture was concentrated, and the crude product was purified by preparative HPLC to obtain 9'-(2-chloro-4-phenoxybenzoyl)-4'-methyl-2,3,4',5,6,7'-hexahydrospiro[pyran-4,2'-pyrrolo[3',2':5,6]pyrido[3,4-b]pyrazin]-3'(1'H)-one (Z22, 28 mg, yield of 25%) as a white solid. $^1$H NMR (400 MHz, DMSO-$d_6$) δ 12.78 (s, 1H), 9.06 (s, 1H), 8.05 (s, 1H), 7.76 (s, 1H), 7.60 (d, J=8.5 Hz, 1H), 7.53-7.44 (m, 2H), 7.30-7.15 (m, 4H), 7.04 (dd, J=8.4, 2.4 Hz, 1H), 3.89-3.69 (m, 4H), 3.40 (s, 3H), 2.14-2.03 (m, 2H), 1.60 (d, J=13.4 Hz, 2H). ES-API: $[M+H]^+$=503.1.

Embodiment 22: Synthesis of Z55

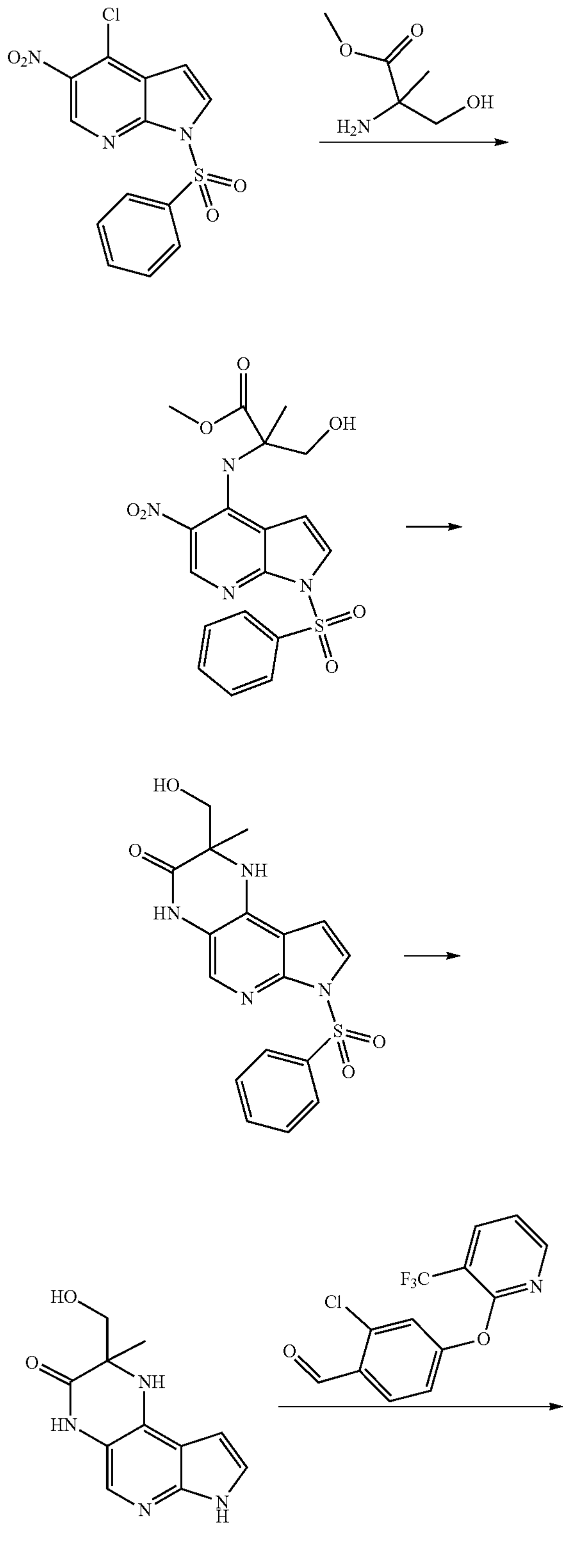

-continued

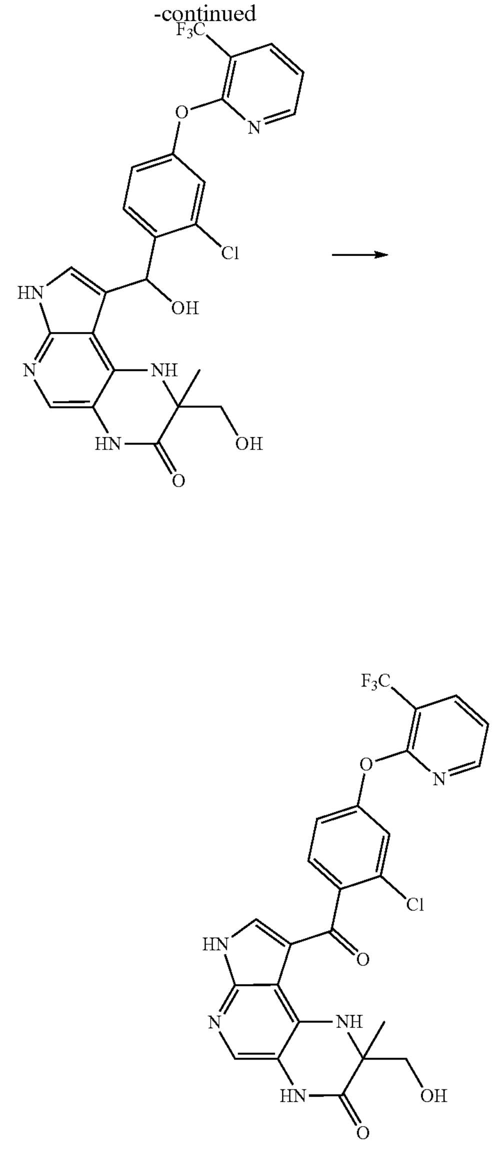

Z55

Step 1: 4-Chloro-5-nitro-1-(phenylsulfonyl)-1H-pyrrolo [2,3-b]pyridine (1.0 g, 2.96 mmol) and methyl 2-amino-3-hydroxy-2-methylpropanoate (472 mg, 3.56 mmol) were dissolved in N,N-dimethylacetamide (10 mL), and N,N-diisopropylethylamine (1.14 g, 8.88 mmol) was added thereto, and the reaction was stirred under microwave irradiation at 95° C. for 15 hours. The reaction solution was added with 100 mL of ethyl acetate, washed twice with 60 mL of water and 3 times with 30 mL of saturated brine, dried and concentrated, and the crude product was purified by a flash silica gel column (ethyl acetate/petroleum ether: 0-50%) to obtain 3-hydroxy-2-methyl-2-methyl-((5-nitro-1-(phenylsulfonyl)-1H-pyrrolo[2,3-b]pyridin-4-yl)amino)propanoate (770 mg, yield of 60%) as a yellow solid. ES-API: $[M+H]^+$=435.1.

Step 2: 3-Hydroxy-2-methyl-2-methyl-((5-nitro-1-(phenylsulfonyl)-1H-pyrrolo[2,3-b]pyridin-4-yl)amino)propanoate (770 mg, 1.77 mmol) was dissolved in acetic acid (10 mL), and iron powder (1.98 g, 35.4 mmol) was added thereto, and the reaction was stirred at 80° C. for 3 hours. The reaction solution was added with 100 mL of ethyl acetate, washed twice with 60 mL of water, twice with 40 mL of saturated sodium carbonate, twice with 40 mL of saturated sodium bicarbonate, and with 40 mL of saturated brine in turn, dried and concentrated, and the crude product was slurried with ethyl acetate to obtain 2-(hydroxymethyl)-2-methyl-7-(phenylsulfonyl)-4,7-dihydro-1H-pyrrolo[3',2':5,6]pyrido[3,4-b]pyrazin-3(2H)-one (462 mg, yield of 70%) as a yellow solid. ES-API: $[M+H]^+$=373.0.

Step 3: 2-(Hydroxymethyl)-2-methyl-7-(phenylsulfonyl)-4,7-dihydro-1H-pyrrolo[3',2':5,6]pyrido[3,4-b]pyrazin-3 (2H)-one (462 mg, 1.24 mmol) was dissolved in 30 mL of methanol, 5 mL of tetrahydrofuran and 3 mL of water, and sodium hydroxide (248 mg, 6.2 mmol) was added thereto, and the reaction was stirred at 65° C. for 6 hours. To the reaction solution was added 15 mL of water and 4 mL of saturated ammonium chloride solution, and the mixture was extracted with 100 mL of ethyl acetate. The organic phase was washed with 20 mL of saturated sodium bicarbonate solution and 20 mL of saturated brine in turn, dried and then concentrated to obtain 2-(hydroxymethyl)-2-methyl-4,7-dihydro-1H-pyrrolo[3',2':5,6]pyrido[3,4-b]pyrazin-3(2H)-one (110 mg, yield of 59%) as an off-white solid. ES-API: $[M+H]^+$=233.1.

Step 4: 2-(Hydroxymethyl)-2-methyl-4,7-dihydro-1H-pyrrolo[3',2':5,6]pyrido[3,4-b]pyrazin-3(2H)-one (110 mg, 0.474 mmol) and 2-chloro-4-((3-(trifluoromethyl)pyridin-2-yl)oxy)benzaldehyde (286 mg, 0.95 mmol) were dissolved in methanol (5 mL), and the reaction was cooled to 0° C., and potassium hydroxide (132 mg, 2.37 mmol) was added thereto. The reaction was stirred at room temperature for 3 hours. The reaction solution was poured into 60 mL of water, and the pH of the reaction solution was adjusted to 8 with 1.0 M dilute hydrochloric acid, and the reaction solution was extracted with 80 mL of ethyl acetate. The organic phase was washed with 25 mL of saturated brine, dried and then concentrated, and the crude product was purified by a thin-layer preparative plate (dichloromethane/methanol=10: 1) to obtain 9-((2-chloro-4-((3-(trifluoromethyl)pyridin-2-yl)oxy)phenyl)(hydroxy)methyl)-2-(hydroxymethyl)-2-methyl-4,7-dihydro-1H-pyrrolo[3',2':5,6]pyrido[3,4-b] pyrazin-3(2H)-one (110 mg, yield of 43%) as a pale yellow solid. ES-API: $[M+H]^+$=534.1.

Step 5: 9-((2-Chloro-4-((3-(trifluoromethyl)pyridin-2-yl) oxy)phenyl)(hydroxy)methyl)-2-(hydroxymethyl)-2-methyl-4,7-dihydro-1H-pyrrolo[3',2':5,6]pyrido[3,4-b] pyrazin-3(2H)-one (110 mg, 0.206 mmol) was dissolved in 5 mL of 1,4-dioxane and 1 mL of water, and DDQ (93 mg, 0.412 mmol) was added thereto, and the reaction was stirred at room temperature for 30 minutes. To the reaction solution was added 5 mL of saturated sodium thiosulfate solution and 20 mL of saturated sodium bicarbonate solution, and the mixture was extracted with 60 mL of ethyl acetate. The organic phase was concentrated, and the crude product was purified by preparative HPLC to obtain 9-(2-chloro-4-((3-(trifluoromethyl)pyridin-2-yl)oxy)benzoyl)-2-(hydroxymethyl)-2-methyl-4,7-dihydro-1H-pyrrolo[3',2':5,6]pyrido[3,4-b]pyrazin-3(2H)-one (55 mg, yield of 50%) as a white solid. $^1H$ NMR (400 MHz, $DMSO-d_6$) δ 10.43 (s, 1H), 9.03 (s, 1H), 8.48 (dd, J=5.0, 1.8 Hz, 1H), 8.33 (dd, J=7.8, 1.8 Hz, 1H), 8.24 (s, 1H), 7.68 (s, 1H), 7.61 (d, J=8.4 Hz, 1H), 7.57-7.48 (m, 2H), 7.42 (dd, J=7.6, 4.9 Hz, 1H), 7.29 (dd, J=8.4, 2.3 Hz, 1H), 5.25 (s, 1H), 3.70 (d, J=10.5 Hz, 1H), 3.49 (d, J=10.5 Hz, 1H), 1.37 (s, 3H). ES-API: $[M+H]^+$=532.1.

Embodiment 23: Synthesis of Z56

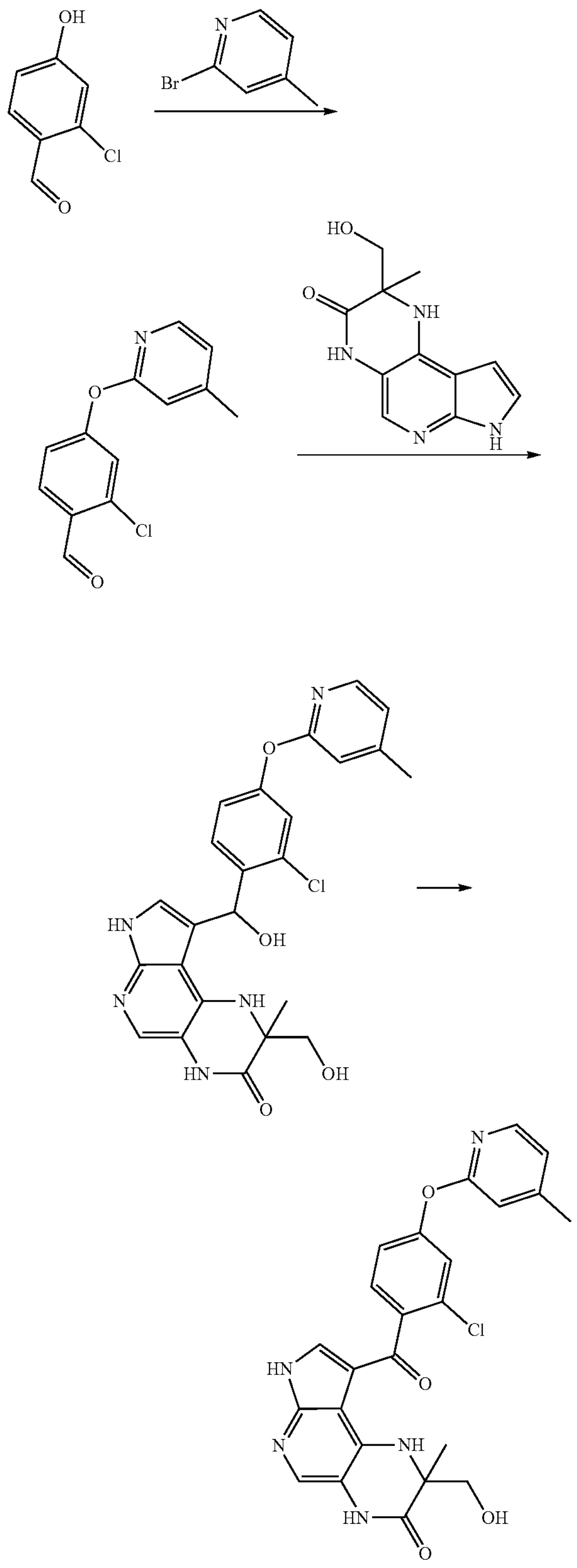

Z56

Step 1: Under nitrogen atmosphere, 2-chloro-4-hydroxybenzaldehyde (2.04 g, 13.081 mmol), 2-bromo-4-methylpyridine (1.5 g, 8.721 mmol), potassium phosphate (4.072 g, 19.186 mmol), cuprous iodide (166 mg, 0.872 mmol), and trans-N,N'-dimethyl-1,2-cyclohexanediamine (248 mg, 1.744 mmol) were dissolved in 45 mL of anhydrous N,N-dimethylformamide, and the reaction solution was heated to 110° C. and stirred overnight. LCMS detected the generation of product. The reaction solution was cooled to room temperature, filtered, and the filtrate was added with 50 mL of ethyl acetate and 50 mL of water, extracted with ethyl acetate (50 mL×3). The combined organic phases were washed with saturated brine (30 mL×3), then dried over anhydrous sodium sulfate, filtered, concentrated, and the crude product was purified by a flash silica gel column (ethyl acetate/petroleum ether: 0-50%) to obtain 2-chloro-4-((4-methylpyridin-2-yl)oxy)benzaldehyde (200 mg, yield of 9%) as a white solid. ES-API: $[M+H]^+=248.1$.

Step 2: To a solution of 2-chloro-4-((4-methylpyridin-2-yl)oxy)benzaldehyde (200 mg, 0.810 mmol) and 2-(hydroxymethyl)-2-methyl-1,2,4,7-tetrahydro-3H-pyrrolo[3',2':5,6]pyrido[3,4-b]pyrazin-3-one (94 mg, 0.405 mmol) in dichloromethane (8 mL) was added potassium hydroxide (113 mg, 2.025 mmol) under an ice-water bath, and the reaction solution was stirred at room temperature for 3 hours. LCMS detected the generation of product. The pH of the reaction solution was adjusted to about 7 by adding 1N HCl ($_{aq.}$), and the reaction solution was extracted with ethyl acetate (20 mL×3). The combined organic phases were washed with saturated brine (10 mL×2), and then dried over anhydrous sodium sulfate, filtered and concentrated to obtain 9-((2-chloro-4-((4-methylpyridin-2-yl)oxy)phenyl)(hydroxy)methyl)-2-(hydroxymethyl)-2-methyl-1,2,4,7-tetrahydro-3H-pyrrolo[3',2':5,6]pyrido[3,4-b]pyrazin-3-one (132 mg, yield of 68%) as an off-white solid. ES-API: $[M+H]^+=480.1$.

Step 3: To a solution of 9-((2-chloro-4-((4-methylpyridin-2-yl)oxy)phenyl)(hydroxy)methyl)-2-(hydroxymethyl)-2-methyl-1,2,4,7-tetrahydro-3H-pyrrolo[3',2':5,6]pyrido[3,4-b]pyrazin-3-one (132 mg, 0.276 mmol) in dichloromethane (15 mL) was added 2,3-dichloro-5,6-dicyano-1,4-benzoquinone (125 mg, 0.551 mmol) at room temperature, and the reaction solution was stirred at room temperature for 3 hours. LCMS detected the generation of product. The reaction solution was concentrated under reduced pressure, and the crude product was purified by preparative HPLC to obtain 9-(2-chloro-4-((4-methylpyridin-2-yl)oxy)benzoyl)-2-(hydroxymethyl)-2-methyl-1,2,4,7-tetrahydro-3H-pyrrolo[3',2':5,6]pyrido[3,4-b]pyrazin-3-one (Z56, 52.5 mg, yield of 40%) as an off-white solid. ES-API: $[M+H]^+=478.1$. $^1H$ NMR (500 MHz, DMSO-$d_6$) δ 8.25 (s, 1H), 8.09 (d, J=6.5 Hz, 1H), 7.67 (s, 1H), 7.56 (d, J=10.5 Hz, 1H), 7.52 (s, 1H), 7.38 (d, J=3.0 Hz, 1H), 7.19 (dd, J1=2.5 Hz, J2=10.5 Hz, 1H), 7.06 (d, J=5.5 Hz, 1H), 6.99 (s, 1H), 6.06 (bs, 1H), 3.69 (d, J=13.5 Hz, 1H), 3.48 (d, J=13.0 Hz, 1H), 2.37 (s, 3H), 1.36 (m 3H).

With reference to the preparation methods of Embodiments 1 to 23, the following compounds were prepared by changing some raw materials:

| Embodiment | Compound No. | Structure | MS [M + H]+ |
|---|---|---|---|
| 24 | Z20 | 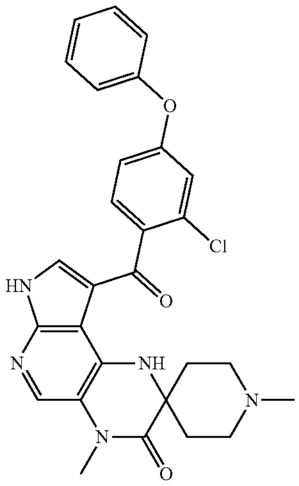 [SMILES: CN1CCC2(CC1)Nc1c(cnc3[nH]cc(C(=O)c4ccc(Oc5ccccc5)cc4Cl)c13)N(C)C2=O] | 516.2 |
| 25 | Z21 | 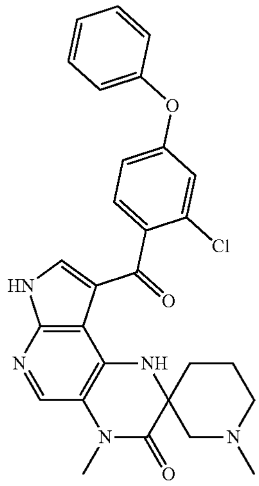 [SMILES: CN1CCCC2(C1)Nc1c(cnc3[nH]cc(C(=O)c4ccc(Oc5ccccc5)cc4Cl)c13)N(C)C2=O] | 516.2 |
| 26 | Z23 | 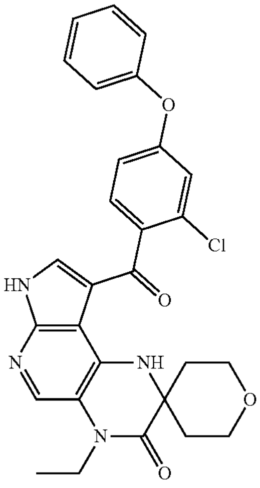 [SMILES: CCN1C(=O)C2(CCOCC2)Nc2c1cnc1[nH]cc(C(=O)c3ccc(Oc4ccccc4)cc3Cl)c21] | 517.2 |
-continued
| Embodiment | Compound No. | Structure | MS [M + H]+ |
|---|---|---|---|
| 30 | Z27 | 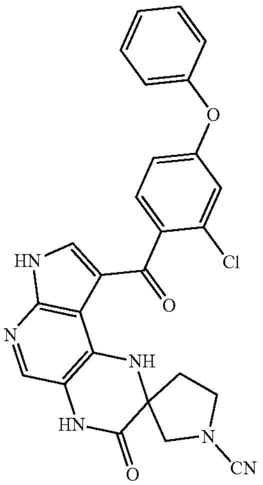 [SMILES: N#CN1CCC2(C1)Nc1c(cnc3[nH]cc(C(=O)c4ccc(Oc5ccccc5)cc4Cl)c13)NC2=O] | 499.1 |
| 31 | Z28 | 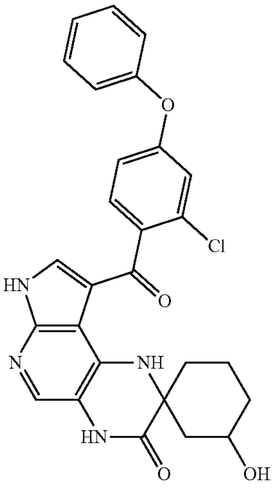 [SMILES: O=C(c1ccc(Oc2ccccc2)cc1Cl)c1c[nH]c2ncc3c(c12)NC1(CCCC(O)C1)C(=O)N3] | 503.1 |
| 32 | Z29 | 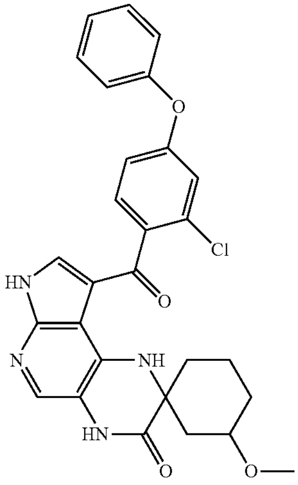 [SMILES: COC1CCCC2(C1)Nc1c(cnc3[nH]cc(C(=O)c4ccc(Oc5ccccc5)cc4Cl)c13)NC2=O] | 517.2 |

-continued
| Embodiment | Compound No. | Structure | MS [M + H]+ |
|---|---|---|---|
| 33 | Z30 | 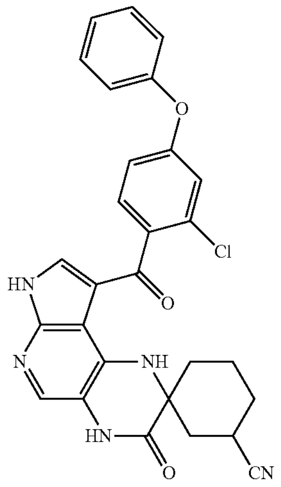 [SMILES: N#CC1CCCC2(C1)Nc1c(cnc3[nH]cc(C(=O)c4ccc(Oc5ccccc5)cc4Cl)c13)NC2=O] | 512.1 |
| 34 | Z31 | 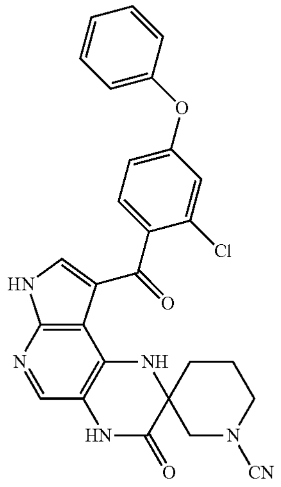 [SMILES: N#CN1CCCC2(C1)Nc1c(cnc3[nH]cc(C(=O)c4ccc(Oc5ccccc5)cc4Cl)c13)NC2=O] | 513.1 |
| 35 | Z32 | 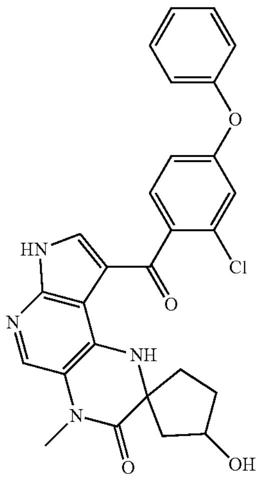 [SMILES: CN1C(=O)C2(CCC(O)C2)Nc2c1cnc1[nH]cc(C(=O)c3ccc(Oc4ccccc4)cc3Cl)c21] | 503.1 |
-continued
| Embodiment | Compound No. | Structure | MS [M + H]+ |
|---|---|---|---|
| 36 | Z33 | 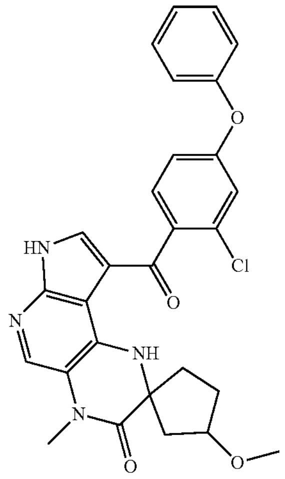 [SMILES: COC1CCC2(C1)Nc1c(cnc3[nH]cc(C(=O)c4ccc(Oc5ccccc5)cc4Cl)c13)N(C)C2=O] | 517.2 |
| 37 | Z34 | 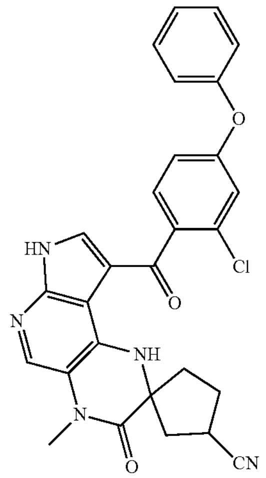 [SMILES: CN1C(=O)C2(CCC(C#N)C2)Nc2c1cnc1[nH]cc(C(=O)c3ccc(Oc4ccccc4)cc3Cl)c21] | 512.1 |
| 38 | Z35 | 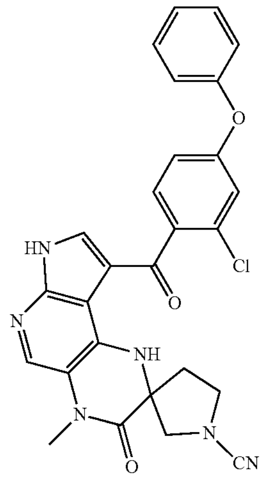 [SMILES: CN1C(=O)C2(CCN(C#N)C2)Nc2c1cnc1[nH]cc(C(=O)c3ccc(Oc4ccccc4)cc3Cl)c21] | 513.1 |

-continued
| Embodiment | Compound No. | Structure | MS [M + H]+ |
|---|---|---|---|
| 39 | Z36 | 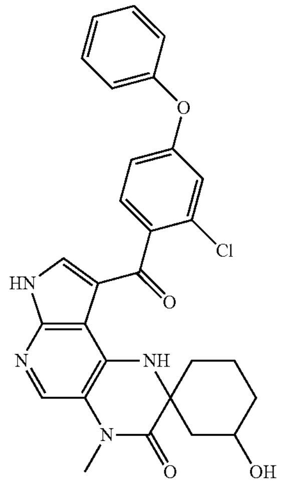 [SMILES: CN1C(=O)C2(CCCC(O)C2)Nc2c1cnc1[nH]cc(C(=O)c3ccc(Oc4ccccc4)cc3Cl)c21] | 517.2 |
| 40 | Z37 | 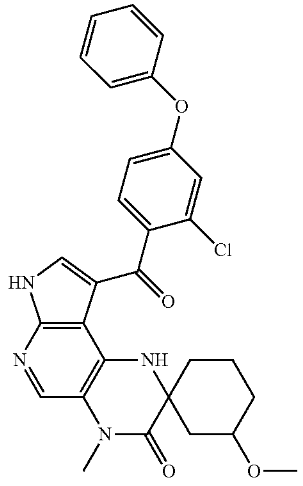 [SMILES: COC1CCCC2(C1)Nc1c(cnc3[nH]cc(C(=O)c4ccc(Oc5ccccc5)cc4Cl)c13)N(C)C2=O] | 531.2 |
| 41 | Z38 | 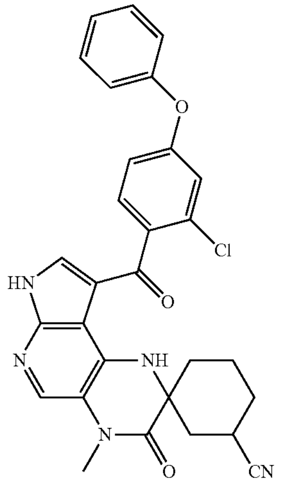 [SMILES: CN1C(=O)C2(CCCC(C#N)C2)Nc2c1cnc1[nH]cc(C(=O)c3ccc(Oc4ccccc4)cc3Cl)c21] | 526.2 |
-continued
| Embodiment | Compound No. | Structure | MS [M + H]+ |
|---|---|---|---|
| 42 | Z39 | 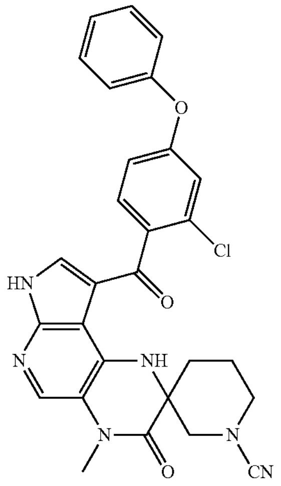 [SMILES: CN1C(=O)C2(CCCN(C#N)C2)Nc2c1cnc1[nH]cc(C(=O)c3ccc(Oc4ccccc4)cc3Cl)c21] | 527.2 |
| 43 | Z40 | 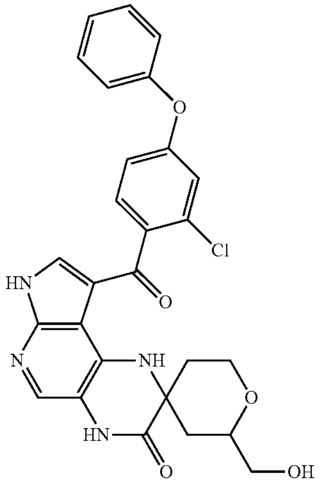 [SMILES: O=C(c1ccc(Oc2ccccc2)cc1Cl)c1c[nH]c2ncc3c(c12)NC1(CCOC(CO)C1)C(=O)N3] | 519.1 |
| 45 | Z42 | 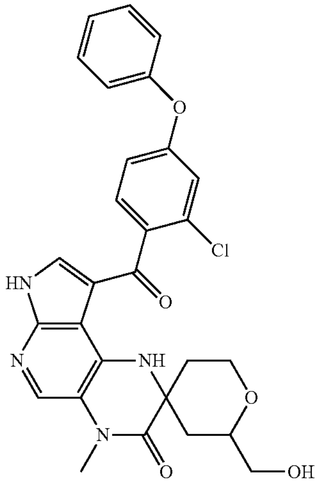 [SMILES: CN1C(=O)C2(CCOC(CO)C2)Nc2c1cnc1[nH]cc(C(=O)c3ccc(Oc4ccccc4)cc3Cl)c21] | 533.2 |

-continued
| Embodiment | Compound No. | Structure | MS [M + H]+ |
|---|---|---|---|
| 46 | Z43 | 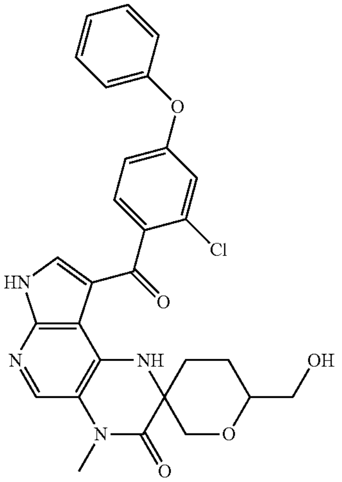 [SMILES: CN1C(=O)C2(CCC(CO)OC2)Nc2c1cnc1[nH]cc(C(=O)c3ccc(Oc4ccccc4)cc3Cl)c21] | 533.2 |
| 47 | Z44 | 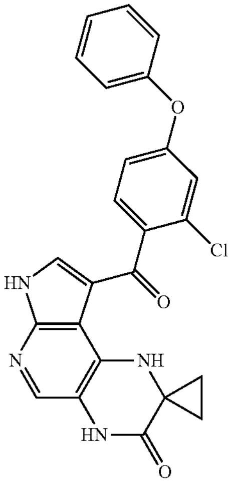 [SMILES: O=C(c1ccc(Oc2ccccc2)cc1Cl)c1c[nH]c2ncc3c(c12)NC1(CC1)C(=O)N3] | 445.1 |
| 48 | Z45 | 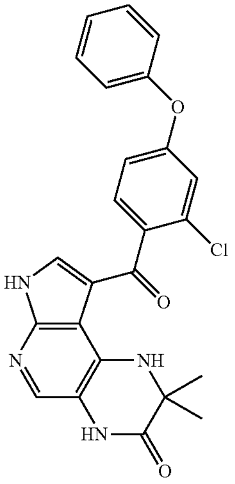 [SMILES: CC1(C)Nc2c(cnc3[nH]cc(C(=O)c4ccc(Oc5ccccc5)cc4Cl)c23)NC1=O] | 447.1 |
| 49 | Z46 | 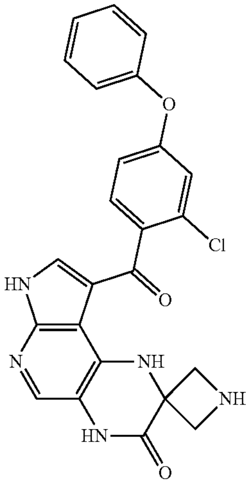 [SMILES: O=C(c1ccc(Oc2ccccc2)cc1Cl)c1c[nH]c2ncc3c(c12)NC1(CNC1)C(=O)N3] | 460.1 |
| 50 | Z47 | 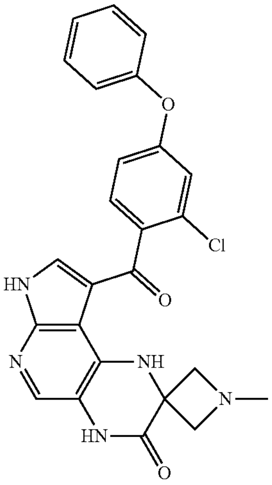 [SMILES: CN1CC2(C1)Nc1c(cnc3[nH]cc(C(=O)c4ccc(Oc5ccccc5)cc4Cl)c13)NC2=O] | 474.1 |
| 51 | Z48 | 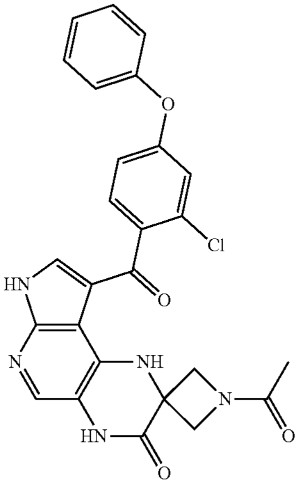 [SMILES: CC(=O)N1CC2(C1)Nc1c(cnc3[nH]cc(C(=O)c4ccc(Oc5ccccc5)cc4Cl)c13)NC2=O] | 502.1 |

-continued
| Embodiment | Compound No. | Structure | MS $[M + H]^+$ |
|---|---|---|---|
| 52 | Z49 | 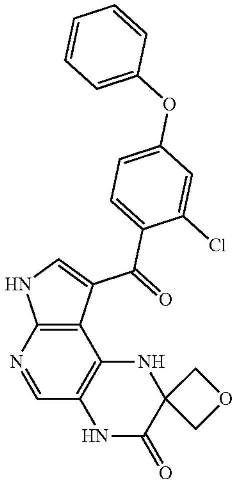 [SMILES: O=C(c1ccc(Oc2ccccc2)cc1Cl)c1c[nH]c2ncc3c(c12)NC1(COC1)C(=O)N3] | 461.1 |
| 53 | Z50 | 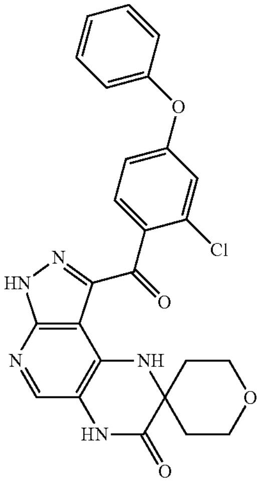 [SMILES: O=C(c1ccc(Oc2ccccc2)cc1Cl)c1n[nH]c2ncc3c(c12)NC1(CCOCC1)C(=O)N3] | 490.1 |
| 54 | Z51 | 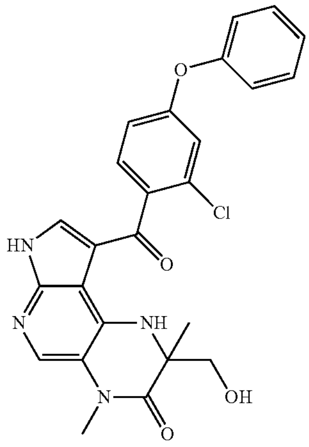 [SMILES: CN1C(=O)C(C)(CO)Nc2c1cnc1[nH]cc(C(=O)c3ccc(Oc4ccccc4)cc3Cl)c21] | 477.1 |
-continued
| Embodiment | Compound No. | Structure | MS $[M + H]^+$ |
|---|---|---|---|
| 57 | Z53-1 | 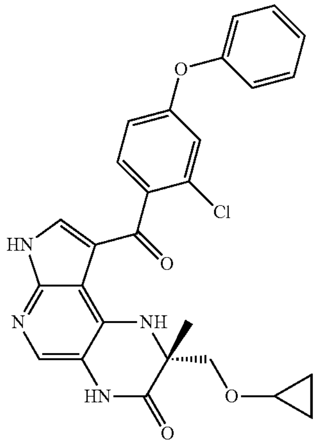 [SMILES: C[C@]1(COC2CC2)Nc2c(cnc3[nH]cc(C(=O)c4ccc(Oc5ccccc5)cc4Cl)c23)NC1=O] | 503.1 |
| 58 | Z54-1 | 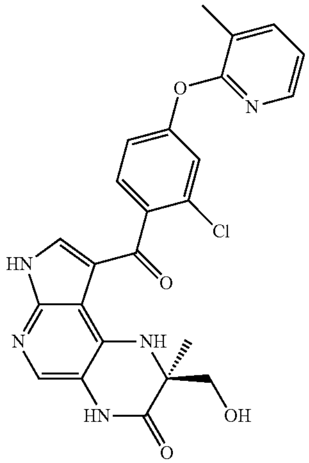 [SMILES: Cc1cccnc1Oc1ccc(C(=O)c2c[nH]c3ncc4c(c23)N[C@@](C)(CO)C(=O)N4)c(Cl)c1] | 478.1 |
| 59 | Z57 | 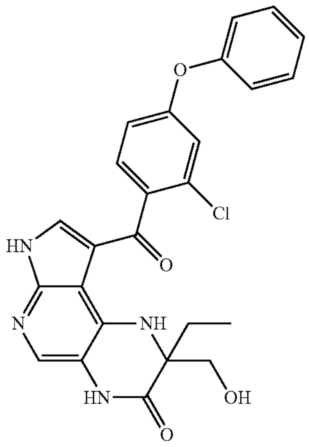 [SMILES: CCC1(CO)Nc2c(cnc3[nH]cc(C(=O)c4ccc(Oc5ccccc5)cc4Cl)c23)NC1=O] | 477.1 |

-continued
| Embodiment | Compound No. | Structure | MS [M + H]+ |
|---|---|---|---|
| 60 | Z58 | 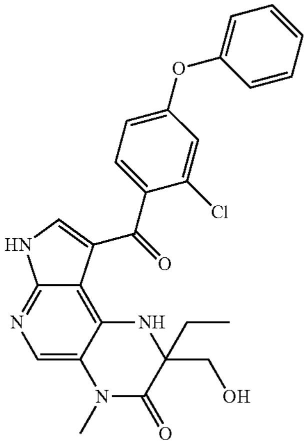 [SMILES: CCC1(CO)Nc2c(cnc3[nH]cc(C(=O)c4ccc(Oc5ccccc5)cc4Cl)c23)N(C)C1=O] | 491.1 |
| 61 | Z59 | 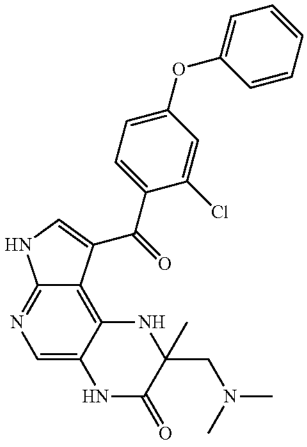 [SMILES: CN(C)CC1(C)Nc2c(cnc3[nH]cc(C(=O)c4ccc(Oc5ccccc5)cc4Cl)c23)NC1=O] | 490.2 |
| 62 | Z60 | 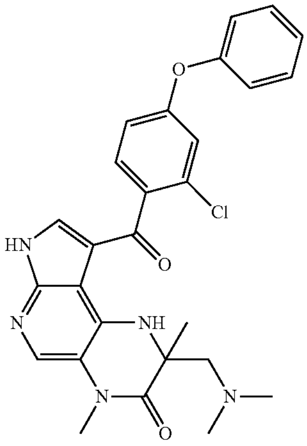 [SMILES: CN(C)CC1(C)Nc2c(cnc3[nH]cc(C(=O)c4ccc(Oc5ccccc5)cc4Cl)c23)N(C)C1=O] | 504.2 |
-continued
| Embodiment | Compound No. | Structure | MS [M + H]+ |
|---|---|---|---|
| 63 | Z61 | 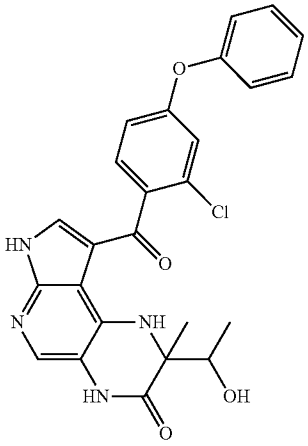 [SMILES: CC(O)C1(C)Nc2c(cnc3[nH]cc(C(=O)c4ccc(Oc5ccccc5)cc4Cl)c23)NC1=O] | 477.1 |
| 64 | Z62 | 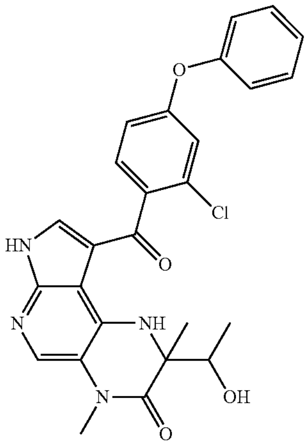 [SMILES: CC(O)C1(C)Nc2c(cnc3[nH]cc(C(=O)c4ccc(Oc5ccccc5)cc4Cl)c23)N(C)C1=O] | 491.1 |
| 66 | Z65 | 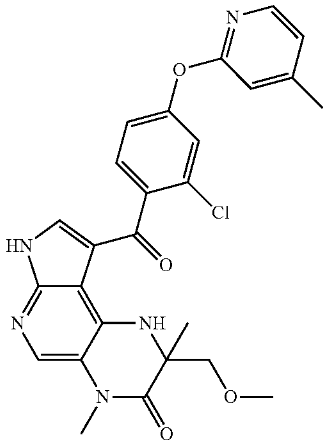 [SMILES: COCC1(C)Nc2c(cnc3[nH]cc(C(=O)c4ccc(Oc5cc(C)ccn5)cc4Cl)c23)N(C)C1=O] | 506.2 |

-continued
| Embodiment | Compound No. | Structure | MS [M + H]+ |
|---|---|---|---|
| 69 | Z68 | 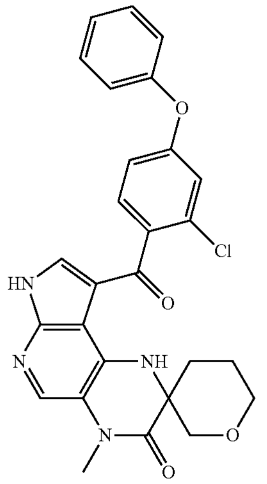 [SMILES: CN1C(=O)C2(CCCOC2)Nc2c1cnc1[nH]cc(C(=O)c3ccc(Oc4ccccc4)cc3Cl)c21] | 503.1 |
| 71 | Z70 | 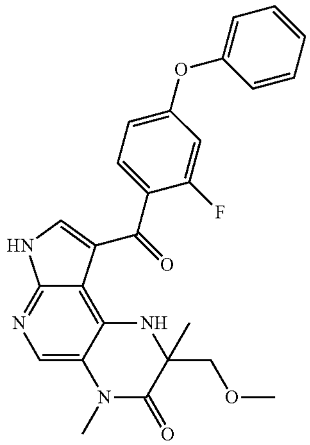 [SMILES: COCC1(C)Nc2c(cnc3[nH]cc(C(=O)c4ccc(Oc5ccccc5)cc4F)c23)N(C)C1=O] | 475.2 |
| 73 | Z72 | 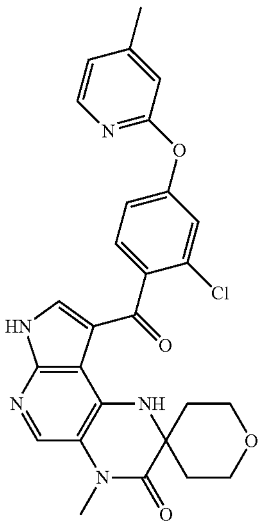 [SMILES: Cc1ccnc(Oc2ccc(C(=O)c3c[nH]c4ncc5c(c34)NC3(CCOCC3)C(=O)N5C)c(Cl)c2)c1] | 518.2 |
-continued
| Embodiment | Compound No. | Structure | MS [M + H]+ |
|---|---|---|---|
| 76 | Z75 | 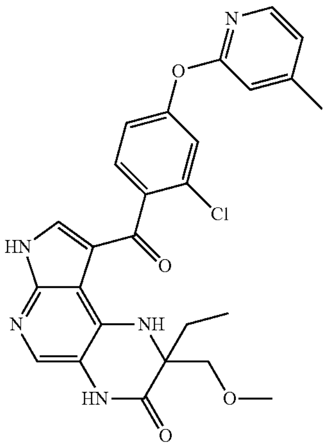 [SMILES: CCC1(COC)Nc2c(cnc3[nH]cc(C(=O)c4ccc(Oc5cc(C)ccn5)cc4Cl)c23)NC1=O] | 506.2 |
| 77 | Z76 | 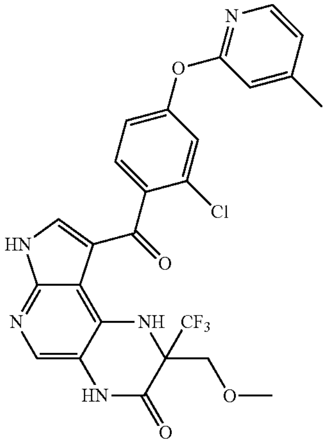 [SMILES: COCC1(C(F)(F)F)Nc2c(cnc3[nH]cc(C(=O)c4ccc(Oc5cc(C)ccn5)cc4Cl)c23)NC1=O] | 546.1 |
| 78 | Z77 | 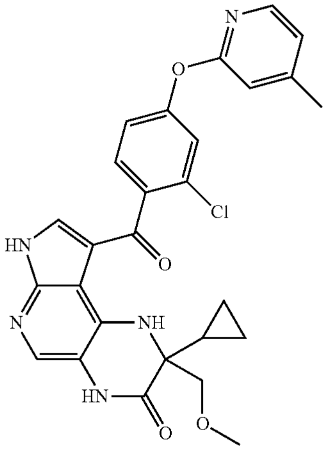 [SMILES: COCC1(C2CC2)Nc2c(cnc3[nH]cc(C(=O)c4ccc(Oc5cc(C)ccn5)cc4Cl)c23)NC1=O] | 518.2 |

Embodiment 27: Synthesis of Z24-1 and Isomers Thereof, Z24-2 and Isomers Thereof

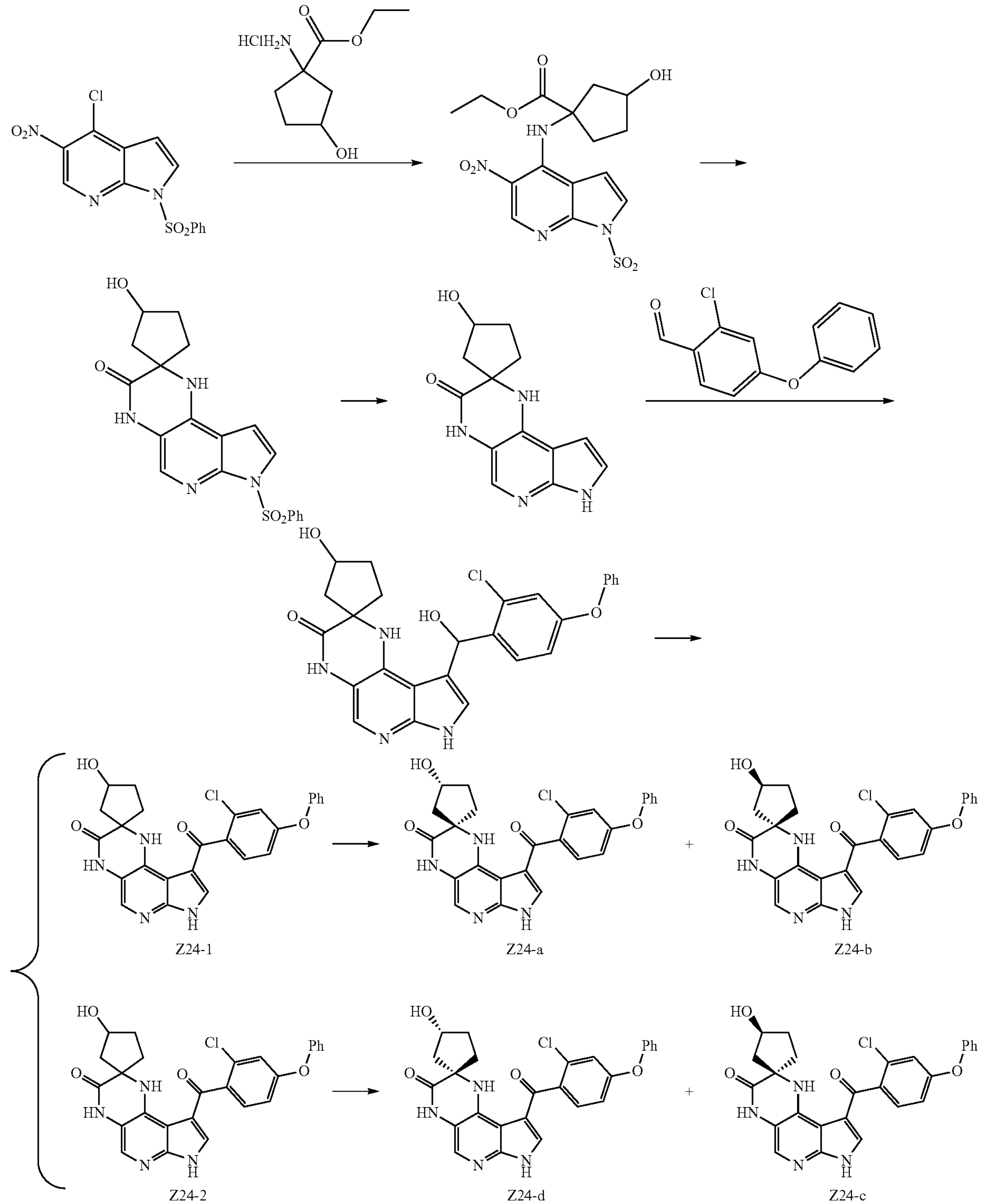

Z24-1 Z24-a Z24-b

Z24-2 Z24-d Z24-c

Step 1: 4-Chloro-5-nitro-1-(phenylsulfonyl)-1H-pyrrolo [2,3-b]pyridine (1.28 g, 3.79 mmol) and ethyl 1-amino-3-hydroxycyclopentane-1-carboxylate hydrochloride (662 mg, 3.16 mmol) were dissolved in N,N-dimethylacetamide (20 mL), and N,N-diisopropylethylamine (1.225 g, 9.48 mmol) was added thereto, and the reaction was stirred at 95° C. for 16 hours. The reaction solution was added with 120 mL of ethyl acetate, washed 4 times with 40 mL of dilute brine and washed with 40 mL of saturated brine in turn, dried and concentrated, and the crude product was purified by a flash silica gel column (ethyl acetate/petroleum ether: 0-60%) to obtain ethyl 3-hydroxy-1-((5-nitro-1-(phenylsulfonyl)-1H-pyrrolo[2,3-b]pyridin-4-yl)amino)cyclopentane-1-carboxylate (1.1 g, yield of 71%) as a yellow liquid. ES-API: $[M+H]^+$=475.1.

Step 2: Ethyl 3-hydroxy-1-((5-nitro-1-(phenylsulfonyl)-1H-pyrrolo[2,3-b]pyridin-4-yl)amino)cyclopentane-1-carboxylate (550 mg, 1.16 mmol) was dissolved in acetic acid (7 mL), and iron powder (649 mg, 11.6 mmol) was added thereto, and the reaction was stirred at 85° C. for 3 hours. The reaction solution was added with 100 mL of ethyl acetate, washed twice with 30 mL of water, twice with 40 mL of saturated sodium carbonate, twice with 40 mL of saturated sodium bicarbonate, and with 40 mL of saturated brine in turn, dried and concentrated, and the crude product was purified by a flash silica gel column (methanol/dichloromethane: 0-10%) to obtain 3-hydroxy-7'-(phenylsulfonyl)-4',7'-dihydrospiro[cyclopentane-1,2'-pyrrolo[3',2':5,6]pyrido[3,4-b]pyrazin]-3'(1'H)-one (410 mg, yield of 88.8%) as a yellow liquid. ES-API: $[M+H]^+$=399.1.

Step 3: 3-Hydroxy-7'-(phenylsulfonyl)-4',7'-dihydrospiro[cyclopentane-1,2'-pyrrolo[3',2':5,6]pyrido[3,4-b]pyrazin]-3'(1'H)-one (410 mg, 1.03 mmol) was dissolved in 10 mL of methanol, 4 mL of tetrahydrofuran and 2 mL of water, and sodium hydroxide (206 mg, 5.15 mmol) was added thereto, and the reaction was stirred at 65° C. for 6 hours. The reaction solution was concentrated under reduced pressure to obtain a crude product. ES-API: $[M+H]^+$=259.1.

Step 4: The above crude product and 2-chloro-4-phenoxybenzaldehyde (719 mg, 3.09 mmol) were dissolved in methanol (8 mL), and the reaction was cooled to 0° C., and potassium hydroxide (404 mg, 7.21 mmol) was added thereto. The reaction was stirred at room temperature for 12 hours. The pH of the reaction solution was adjusted to 8 with 1.0 M dilute hydrochloric acid, and the reaction solution was added with 2 mL of water and extracted with 60 mL of ethyl acetate. The organic phase was washed with 25 mL of saturated brine, dried and then concentrated, and subjected to flash column chromatography (methanol/dichloromethane=0-10%) to obtain 9'-((2-chloro-4-phenoxyphenyl)(hydroxy)methyl)-3-hydroxy-4',7'-dihydrospiro[cyclopentane-1,2'-pyrrolo[3',2':5,6]pyrido[3,4-b]pyrazin]-3'(1'H)-one (180 mg, yield of 36.7%) as a colorless liquid. ES-API: $[M+H]^+$ 471.1.

Step 5: 9'-((2-Chloro-4-phenoxyphenyl)(hydroxy)methyl)-3-hydroxy-4',7'-dihydrospiro[cyclopentane-1,2'-pyrrolo[3',2':5,6]pyrido[3,4-b]pyrazin]-3'(1'H)-one (180 mg, 0.367 mmol) was dissolved in 10 mL of tetrahydrofuran, and 2,3-dichloro-5,6-dicyano-1,4-benzoquinone (166 mg, 0.733 mmol) was added thereto, and the reaction was stirred at room temperature for 30 minutes. The reaction solution was quenched by adding 20 mL of saturated $NaHSO_3$ solution, extracted with 80 mL of ethyl acetate, and the organic phase was washed with 30 mL of saturated sodium bicarbonate solution and 30 mL of saturated brine, dried over anhydrous sodium sulfate and then concentrated, and the crude product was purified by preparative HPLC to obtain two enantiomers. One enantiomer was Z24-1 (81 mg, peak 1, retention time of 7.412 min, yield of 45%) as a white solid, ES-API: $[M+H]^+$=489.1. The other enantiomer was Z24-2 (32 mg, peak 2, retention time of 7.611 min, yield of 18%) as a white solid. ES-API: $[M+H]^+$=489.1.

Step 6: The enantiomer Z24-1 (78 mg) was resolved by chiral preparation (separation column: IC 150 mm*4.6 mm*5 μm, mobile phase: n-hexane:ethanol:trifluoroacetic acid=70:30:0.2, flow rate: 1 mL/min, column temperature: 30° C.) to obtain two isomers with single configuration. One single isomer with a structure arbitrarily designated as Z24-a (32 mg, peak 1, retention time of 10.259 min, yield of 41%) was a white solid. ES-API: $[M+H]^+$=489.1. The other single isomer with a structure arbitrarily designated as Z24-b (32 mg, peak 2, retention time of 17.062 min, yield of 41%) was a white solid. ES-API: $[M+H]^+$=489.1.

Step 7: The enantiomer Z24-2 (30 mg) was resolved by chiral preparation (separation column: IC 150 mm*4.6 mm*5 μm, mobile phase: n-hexane:ethanol=70:30, flow rate: 1 mL/min, column temperature: 30° C.) to obtain two isomers with single configuration. One single isomer with a structure arbitrarily designated as Z24-c (12 mg, peak 1, retention time of 8.805 min, yield of 40%) was a pale white solid. ES-API: $[M+H]^+$=489.1. The other single isomer with a structure arbitrarily designated as Z24-d (12 mg, peak 2, retention time of 11.458 min, yield of 40%) was a pale white solid. ES-API: $[M+H]^+$=489.1.

Embodiment 28: Synthesis of Z25 and Isomers Thereof

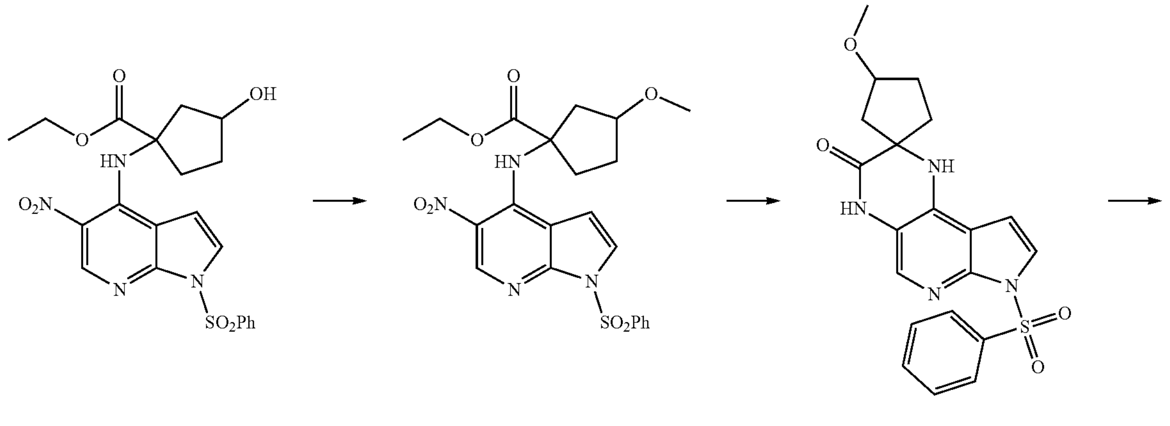

-continued

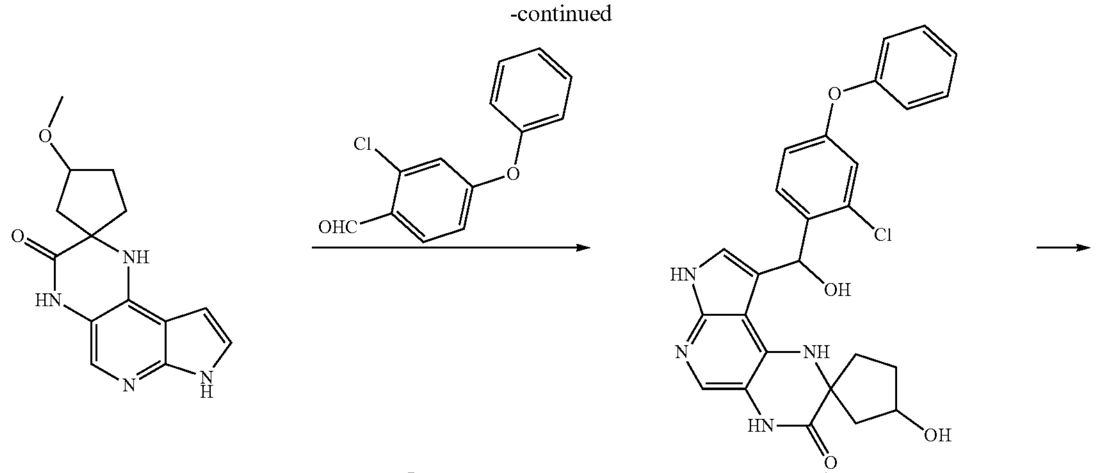

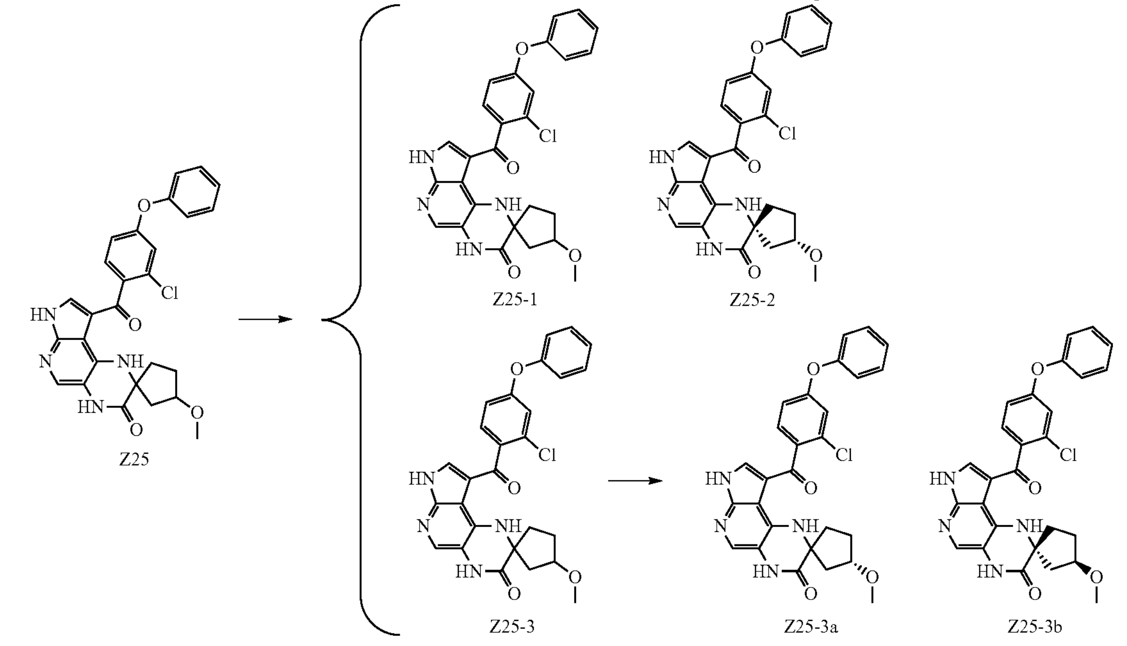

Z25 Z25-1 Z25-2 Z25-3 Z25-3a Z25-3b

Step 1: Ethyl 3-hydroxy-1-((5-nitro-1-(phenylsulfonyl)-1H-pyrrolo[2,3-b]pyridin-4-yl)amino)cyclopentane-1-carboxylate (550 mg, 1.16 mmol), silver oxide (5.3 g, 23 mmol) and iodomethane (3.3 g, 23 mmol) were dissolved in acetonitrile (50 mL), and the reaction was stirred at 35° C. in the dark for 3 days. The reaction solution was filtered through diatomite, and the filter cake was washed three times with 50 mL of ethyl acetate, and the filtrate was concentrated to obtain ethyl 3-methoxy-1-((5-nitro-1-(phenylsulfonyl)-1H-pyrrolo[2,3-b]pyridin-4-yl)amino)cyclopentane-1-carboxylate (354 mg, yield of 63%) as a yellow oil. ES-API: $[M+H]^+$=489.1.

Step 2: Ethyl 3-methoxy-1-((5-nitro-1-(phenylsulfonyl)-1H-pyrrolo[2,3-b]pyridin-4-yl)amino)cyclopentane-1-carboxylate (354 mg, 0.72 mmol) was dissolved in acetic acid (20 mL), and iron powder (286 mg, 5.11 mmol) was added thereto, and the reaction was stirred at 85° C. for 3 hours. The reaction solution was added with 100 mL of ethyl acetate, washed twice with 60 mL of water, twice with 40 mL of saturated sodium bicarbonate and twice with 40 mL of saturated brine in turn, dried and concentrated to obtain 3-methoxy-7'-(phenylsulfonyl)-4',7'-dihydrospiro[cyclopentane-1,2'-pyrrolo[3',2':5,6]pyrido[3,4-b]pyrazin]-3'(1'H)-one (360 mg, crude product) as a yellow solid. ES-API: $[M+H]^+$=413.1.

Step 3: 3-Methoxy-7'-(phenylsulfonyl)-4',7'-dihydrospiro[cyclopentane-1,2'-pyrrolo[3',2':5,6]pyrido[3,4-b]pyrazin]-3'(1'H)-one (360 mg, 0.87 mmol) was dissolved in 10 mL of methanol, 5 mL of tetrahydrofuran and 2 mL of water, and sodium hydroxide (244 mg, 6.09 mmol) was added thereto, and the reaction was stirred at 65° C. for 7 hours. To the reaction solution was added 15 mL of water and 4 mL of saturated ammonium chloride solution, and the mixture was extracted with 100 mL of ethyl acetate. The organic phase was washed with 20 mL of saturated sodium bicarbonate solution and 20 mL of saturated brine in turn, dried and then concentrated to obtain 3-methoxy-4',7'-dihydrospiro[cyclopentane-1,2'-pyrrolo[3',2':5,6]pyrido[3,4-b]pyrazin]-3'(1'H)-one (160 mg, yield of 67%) as an off-white solid. ES-API: $[M+H]^+$=273.1.

Step 4: 3-Methoxy-4',7'-dihydrospiro[cyclopentane-1,2'-pyrrolo[3',2':5,6]pyrido[3,4-b]pyrazin]-3'(1'H)-one (100 mg, 0.37 mmol) and 2-chloro-4-phenoxybenzaldehyde (172 mg, 0.74 mmol) were dissolved in methanol (20 mL), and the reaction was cooled to 0° C., and potassium hydroxide (145 mg, 2.59 mmol) was added thereto. The reaction was stirred at room temperature for 16 hours. The reaction solution was poured into 60 mL of water, and the pH of the reaction solution was adjusted to 8 with 1.0 M dilute hydrochloric acid, and the reaction solution was extracted with 80 mL of ethyl acetate. The organic phase was washed with 25 mL of saturated brine, dried and then concentrated, and the crude product was purified by a thin-layer preparative plate (dichloromethane/7M ammonia methanol=100: 7.5) to obtain 9'-((2-chloro-4-phenoxyphenyl)(hydroxy) methyl)-3-methoxy-4',7'-dihydrospiro[cyclopentane-1,2'-pyrrolo[3',2':5,6]pyrido[3,4-b]pyrazin]-3'(1'H)-one (121 mg, yield of 65%) as a pale yellow solid. ES-API: $[M+H]^+$=505.1.

Step 5: 9'-((2-Chloro-4-phenoxyphenyl)(hydroxy) methyl)-3-methoxy-4',7'-dihydrospiro[cyclopentane-1,2'-pyrrolo[3',2':5,6]pyrido[3,4-b]pyrazin]-3'(1'H)-one (121 mg, 0.24 mmol) was dissolved in 20 mL of tetrahydrofuran and 2 mL of water, and 2,3-dichloro-5,6-dicyano-p-benzoquinone (109 mg, 0.48 mmol) was added thereto, and the reaction was stirred at room temperature for 1 hour. The reaction solution was washed with 20 mL of saturated sodium thiosulfate solution and 20 mL of saturated sodium bicarbonate solution, and the mixture was extracted with 60 mL of ethyl acetate. The organic phase was washed with 15 mL of saturated brine, dried and then concentrated, and the crude product was purified by preparative HPLC (column: xbridge C18 19*150 mm, 5 μm; system: 10 mmol/L, aqueous $NH_4HCO_3$ solution; flow rate: 15 mL/min; gradient: 20 to 45% $CH_3CN—NH_4HCO_3$; column temperature: room temperature) to obtain 9'-(2-chloro-4-phenoxybenzoyl)-3-methoxy-4',7'-dihydrospiro[cyclopentane-1,2'-pyrrolo[3',2':5,6]pyrido[3,4-b]pyrazin]-3'(1'H)-one (Z25, 45 mg, yield of 53%) as a white solid. ES-API: $[M+H]^+$=503.1.

Step 6: The compound Z25 (45 mg) prepared in the above steps was resolved by chiral preparation (separation column IA, 250 mm*4.6 mm*5 μm, mobile phase: n-hexane:ethanol=40:60, flow rate: 1 mL/min, column temperature: 30° C.) to obtain multiple isomer compounds. One single isomer with a structure arbitrarily designated as Z25-1 (10 mg, peak 1, retention time of 5.211 min) was a white solid. ES-API: $[M+H]^+$=503.1. Another single isomer with a structure arbitrarily designated as Z25-2 (10 mg, peak 2, retention time of 7.713 min) was a white solid. ES-API: $[M+H]^+$=503.1. One enantiomer with a structure arbitrarily designated as Z25-3 (28 mg, peak 3, retention time of 12.324 min) was a white solid. ES-API: $[M+H]^+$=503.1.

The enantiomer Z25-3 was resolved by chiral preparation (separation column IG, 250 mm*4.6 mm*5 μm, mobile phase: acetonitrile:isopropanol=80:20, flow rate: 1 mL/min, column temperature: 30° C.) to obtain two single isomers. One single isomer with a structure arbitrarily designated as Z25-3a (5 mg, peak 3, retention time of 10.321 min) was a white solid. ES-API: $[M+H]^+$=503.1. The other single isomer with a structure arbitrarily designated as Z25-3b (4 mg, peak 4, retention time of 12.944 min) was a white solid. ES-API: $[M+H]^+$=503.1.

Embodiment 29: Synthesis of Z26 and Isomers Thereof

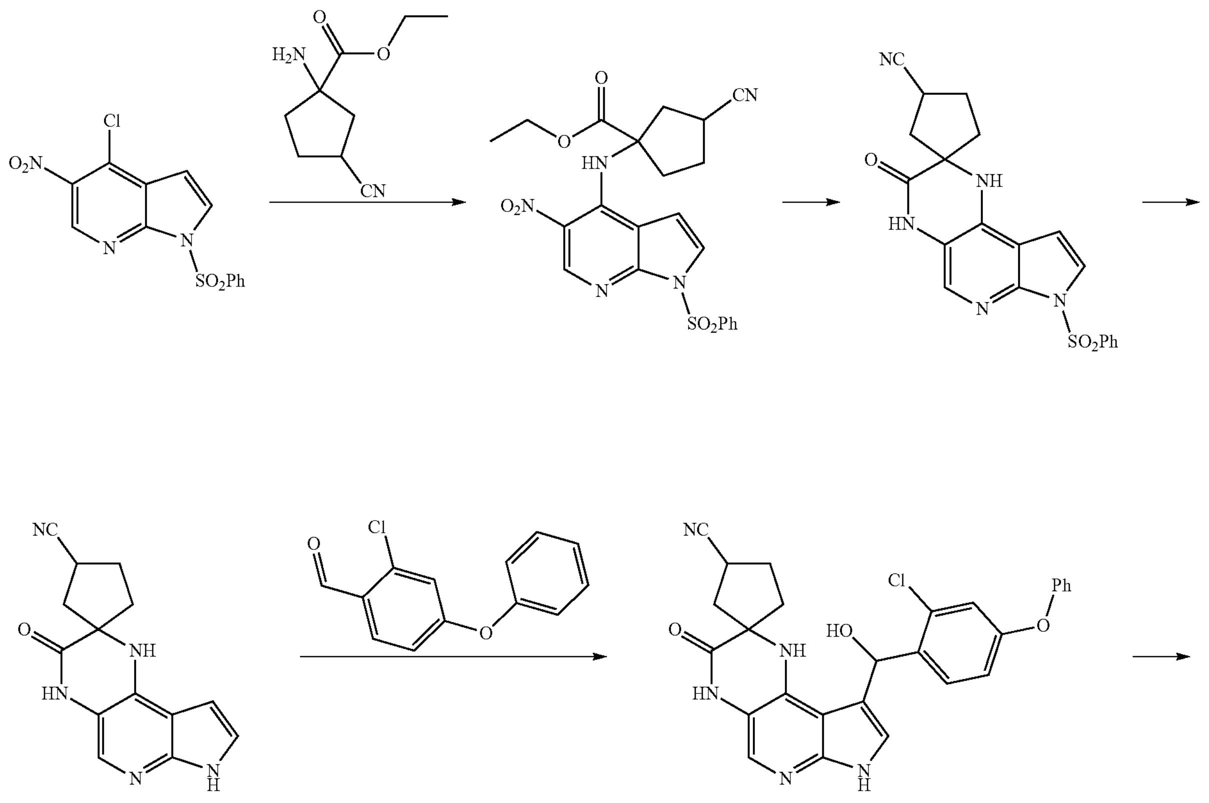

-continued

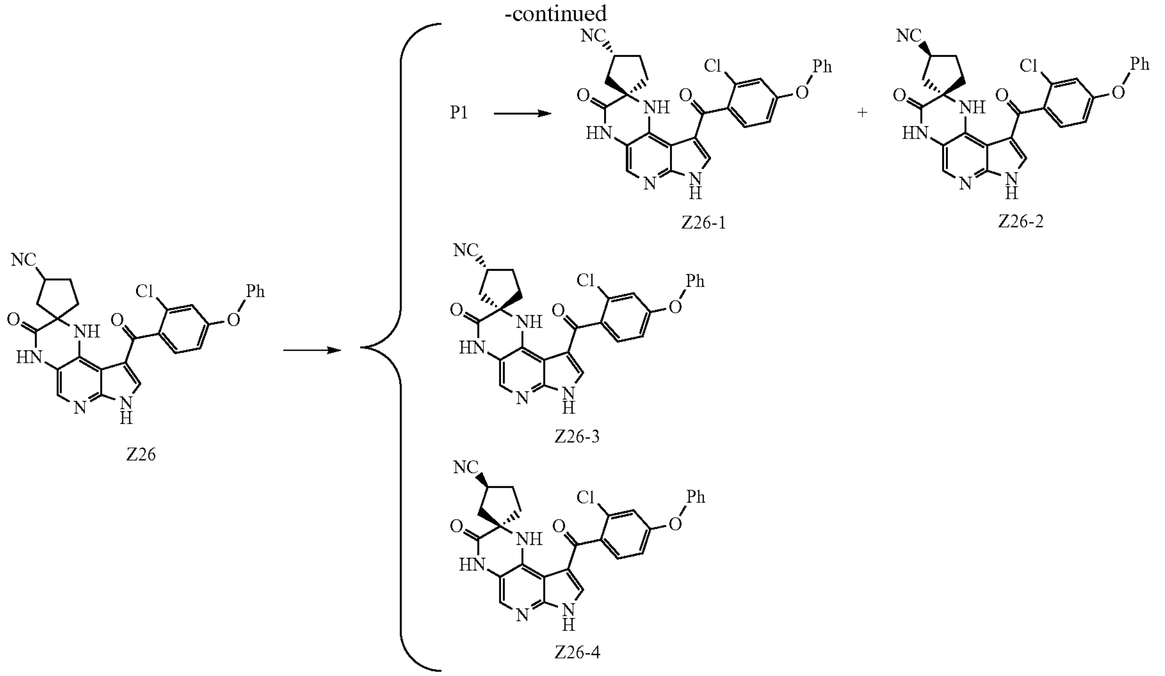

P1

Z26

Z26-1

Z26-2

Z26-3

Z26-4

Step 1:4-Chloro-5-nitro-1-(phenylsulfonyl)-1H-pyrrolo[2,3-b]pyridine (1.06 g, 3.14 mmol) and ethyl 1-amino-3-cyanocyclopentane-1-carboxylate (520 mg, 2.85 mmol) were dissolved in N,N-dimethylacetamide (20 mL), and N,N-diisopropylethylamine (11 g, 8.55 mmol) was added thereto, and the reaction was stirred at 100° C. for 16 hours. The reaction solution was added with 120 mL of ethyl acetate, washed 4 times with 40 mL of dilute brine and washed with 40 mL of saturated brine in turn, dried and concentrated, and the crude product was purified by a flash silica gel column (ethyl acetate/petroleum ether: 0-60%) to obtain ethyl 3-cyano-1-((5-nitro-1-(phenylsulfonyl)-1H-pyrrolo[2,3-b]pyridin-4-yl)amino)cyclopentane-1-carboxylate (973 mg, yield of 71%) as a yellow liquid. ES-API: $[M+H]^+$=484.1.

Step 2: Ethyl 3-cyano-1-((5-nitro-1-(phenylsulfonyl)-1H-pyrrolo[2,3-b]pyridin-4-yl)amino)cyclopentane-1-carboxylate (973 mg, 2.01 mmol) was dissolved in acetic acid (7 mL), and iron powder (1.126 g, 20.1 mmol) was added thereto, and the reaction was stirred at 80° C. for 3 hours. The reaction solution was added with 100 mL of ethyl acetate, washed twice with 30 mL of water, twice with 40 mL of saturated sodium carbonate, twice with 40 mL of saturated sodium bicarbonate, and with 40 mL of saturated brine in turn, dried and concentrated, and the crude product was purified by a flash silica gel column (ethyl acetate/petroleum ether: 0-100%) to obtain 3'-oxo-7'-(phenylsulfonyl)-1',3',4',7'-tetrahydrospiro[cyclopentane-1,2'-pyrrolo[3',2':5,6]pyrido[3,4-b]pyrazine]-3-carbonitrile (780 mg, yield of 95%) as a yellow liquid. ES-API: $[M+H]^+$=408.1.

Step 3: 3'-Oxo-7'-(phenylsulfonyl)-1',3',4',7'-tetrahydrospiro[cyclopentane-1,2'-pyrrolo[3',2':5,6]pyrido[3,4-b]pyrazine]-3-carbonitrile (390 mg, 0.96 mmol) was dissolved in 10 mL of methanol, 4 mL of tetrahydrofuran and 2 mL of water, and sodium hydroxide (192 mg, 4.8 mmol) was added thereto, and the reaction was stirred at 60° C. for 3 hours. The reaction solution was concentrated under reduced pressure to obtain a crude product. ES-API: $[M+H]^+$=268.1.

Step 4: The above crude product and 2-chloro-4-phenoxybenzaldehyde (670 mg, 2.88 mmol) were dissolved in methanol (8 mL), and the reaction was cooled to 0° C., and potassium hydroxide (376 mg, 6.72 mmol) was added thereto. The reaction was stirred at room temperature for 12 hours. The pH of the reaction solution was adjusted to 8 with 1.0 M dilute hydrochloric acid, and the reaction solution was added with 2 mL of water and extracted with 60 mL of ethyl acetate. The organic phase was washed with 25 mL of saturated brine, dried and then concentrated, and subjected to flash column chromatography (methanol/dichloromethane=0-20%) to obtain 9'-((2-chloro-4-phenoxyphenyl)(hydroxy)methyl)-3-isocyano-4',7'-dihydrospiro[cyclopentane-1,2'-pyrrolo[3',2':5,6]pyrido[3,4-b]pyrazin]-3'(1'H)-one (230 mg, yield of 48%) as a yellow liquid. ES-API: $[M+H]^+$ 500.1.

Step 5: 9'-((2-Chloro-4-phenoxyphenyl)(hydroxy)methyl)-3-isocyano-4',7'-dihydrospiro[cyclopentane-1,2'-pyrrolo[3',2':5,6]pyrido[3,4-b]pyrazin]-3'(1'H)-one (230 mg, 0.46 mmol) was dissolved in 10 mL of tetrahydrofuran, and Dess-Martin periodinane (390 mg, 0.92 mmol) was added thereto at 0° C., and the reaction was stirred at room temperature for 30 minutes. The reaction solution was quenched by adding 20 mL of saturated $NaHSO_3$ solution, extracted with 80 mL of ethyl acetate, and the organic phase was washed with 30 mL of saturated sodium bicarbonate solution and 30 mL of saturated brine, dried over anhydrous sodium sulfate and then concentrated, and the crude product was purified by preparative HPLC to obtain a target product (Z26, 148 mg, yield of 64%) as a white solid. ES-API: $[M+H]^+$=498.1. $^1H$ NMR (400 MHz, DMSO-$d_6$) δ 8.33 (s, 1H), 7.78 (s, 1H), 7.68 (d, J=1.8 Hz, 1H), 7.56 (dd, J=8.5, 5.7 Hz, 1H), 7.48 (dd, J=8.4, 7.2 Hz, 2H), 7.25 (td, J=7.4, 1.3 Hz, 1H), 7.22-7.15 (m, 3H), 7.03 (ddd, J=8.4, 3.9, 2.3 Hz, 1H), 2.36-2.19 (m, 3H), 2.18-1.98 (m, 2H), 1.91 (dd, J=13.5, 7.6 Hz, 1H), 1.81 (dd, J=12.7, 5.8 Hz, 1H).

Step 6: The compound Z26 (145 mg, 0.291 mmol) prepared in the above steps was resolved by chiral preparation (separation column: IC 150 mm*4.6 mm*5 μm, mobile phase: n-hexane:isopropanol:diethylamine=60:40:0.2, flow rate: 1 mL/min, column temperature: 30° C.) to obtain multiple isomer compounds. A mixture P1 of two isomers (15 mg, peak 1, retention time of 9.094 min, yield of 10%) was a white solid. One single isomer with a structure arbitrarily designated as Z26-3 (44.44 mg, peak 2, retention time of 13.578 min, yield of 31%) was a pale white solid. ES-API: $[M+H]^+$=498.1. The other single isomer with a structure arbitrarily designated as Z26-4 (45.18 mg, peak 3, retention time of 16.941 min, yield of 31%) was a pale white solid. ES-API: $[M+H]^+$=498.1.

Step 7: The mixture P1 (15 mg) of two isomers was resolved by chiral preparation (separation column: IA 150 mm*4.6 mm*5 μm, mobile phase: n-hexane:ethanol=60:40, flow rate: 1 mL/min, column temperature: 30° C.) to obtain two single isomer compounds. One single isomer with a structure arbitrarily designated as Z26-1 (5.25 mg, peak 1, retention time of 7.995 min, yield of 35%) was a white solid. ES-API: $[M+H]^+$=498.1. The other single isomer with a structure arbitrarily designated as Z26-2 (4.45 mg, peak 2, retention time of 14.713 min, yield of 30%) was a white solid. ES-API: $[M+H]^+$=498.1.

Embodiment 44: Synthesis of Z41-2 and Isomers Thereof

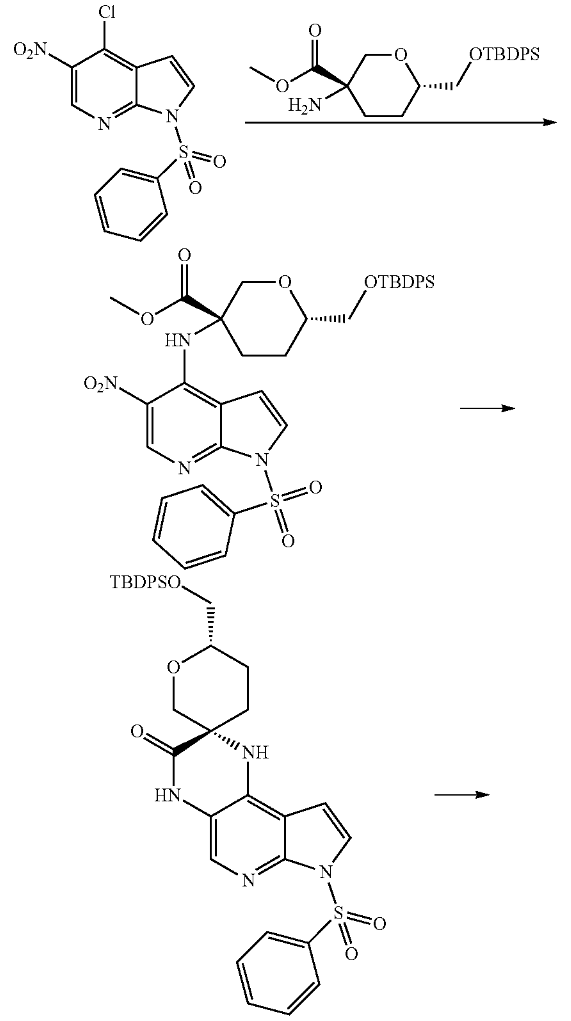

-continued

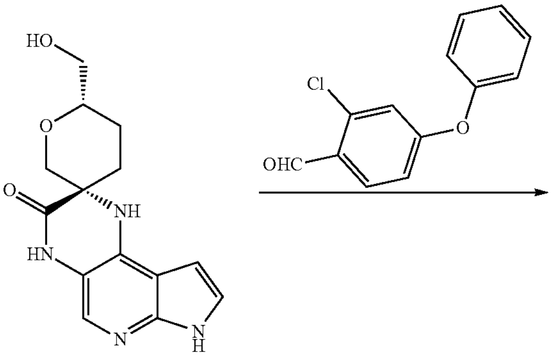

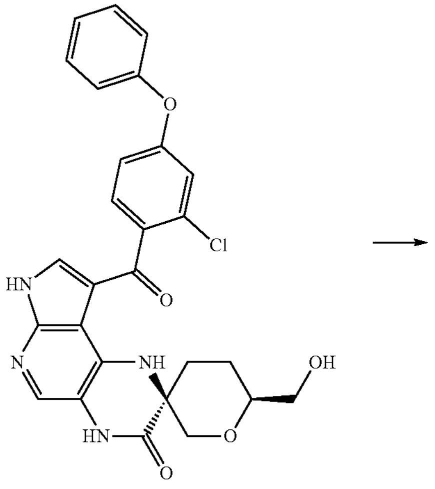

Z41-2

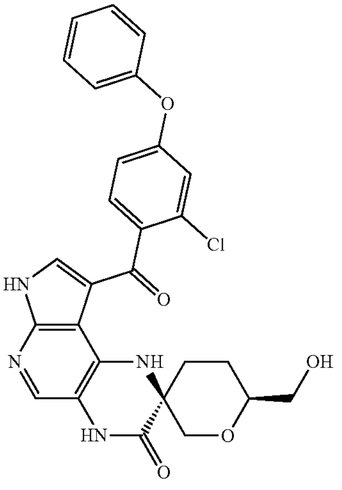

+

Z41-2a

-continued

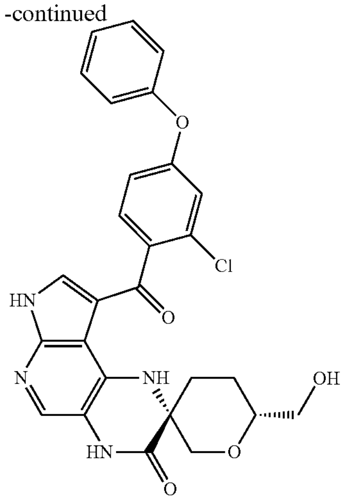

Z41-2b

Step 1: 4-Chloro-5-nitro-1-(phenylsulfonyl)-1H-pyrrolo[2,3-b]pyridine (687 mg, 2.03 mmol) and methyl trans-3-amino-6-(((tert-butyldiphenylsilyl)oxy)methyl)tetrahydro-2H-pyran-3-carboxylate (580 mg, 1.36 mmol) were dissolved in N,N-dimethylacetamide (10 mL), and N,N-diisopropylethylamine (877 mg, 6.80 mmol) was added thereto, and the reaction was stirred at 95° C. for 16 hours. The reaction solution was added with 80 mL of ethyl acetate, washed 4 times with 30 mL of dilute brine and 30 mL of saturated brine in turn, dried and concentrated, and the crude product was purified by a flash silica gel column (ethyl acetate/petroleum ether: 0-20%) to obtain methyl trans-6-(((tert-butyldiphenylsilyl)oxy)methyl)-3-((5-nitro-1-(phenylsulfonyl)-1H-pyrrolo[2,3-b]pyridin-4-yl)amino)tetrahydro-2H-pyran-3-carboxylate (420 mg, yield of 42%) as a yellow solid. ES-API: $[M+H]^+$=729.1.

Step 2: Methyl trans-6-(((tert-butyldiphenylsilyl)oxy)methyl)-3-((5-nitro-1-(phenylsulfonyl)-1H-pyrrolo[2,3-b]pyridin-4-yl)amino)tetrahydro-2H-pyran-3-carboxylate (420 mg, 0.58 mmol) was dissolved in acetic acid (10 mL), and iron powder (325 mg, 5.80 mmol) was added thereto, and the reaction was stirred at 85° C. for 2 hours. The reaction solution was added with 100 mL of ethyl acetate, washed twice with 30 mL of water, twice with 40 mL of saturated sodium carbonate, twice with 40 mL of saturated sodium bicarbonate, and with 40 mL of saturated brine in turn, dried and concentrated to obtain trans-6-(((tert-butyldiphenylsilyl)oxy)methyl)-7'-(phenylsulfonyl)-4',5,6,7'-tetrahydro-2H,4H-spiro[pyran-3,2'-pyrrolo[3',2':5,6]pyrido[3,4-b]pyrazin]-3'(1'H)-one (350 mg, yield of 91%) as a light brown solid. ES-API: $[M+H]^+$=667.2

Step 3: trans-6-(((tert-Butyldiphenylsilyl)oxy)methyl)-7'-(phenylsulfonyl)-4',5,6,7'-tetrahydro-2H,4H-spiro[pyran-3,2'-pyrrolo[3',2':5,6]pyrido[3,4-b]pyrazin]-3'(1'H)-one (330 mg, 0.49 mmol) was dissolved in 10 mL of methanol, 3 mL of tetrahydrofuran and 2 mL of water, and sodium hydroxide (119 mg, 2.97 mmol) was added thereto, and the reaction was stirred at 65° C. for 20 hours. The pH of the reaction solution was adjusted to 8 with 1.0 M dilute hydrochloric acid, and the reaction solution was extracted with 100 mL of ethyl acetate. The organic phase was dried, then concentrated, and slurried with 10 mL of petroleum ether to obtain trans-6-(hydroxymethyl)-4',5,6,7'-tetrahydro-2H,4H-spiro[pyran-3,2'-pyrrolo[3',2':5,6]pyrido[3,4-b]pyrazin]-3'(1'H)-one (240 mg, crude product) as a light brown solid. ES-API: $[M+H]^+$=289.1.

Step 4: trans-6-(Hydroxymethyl)-4',5,6,7'-tetrahydro-2H,4H-spiro[pyran-3,2'-pyrrolo[3',2':5,6]pyrido[3,4-b]pyrazin]-3'(1'H)-one (220 mg, crude product) and 2-chloro-4-phenoxybenzaldehyde (531 mg, 2.29 mmol) were dissolved in methanol (12 mL), and the reaction was cooled to 0° C., and potassium hydroxide (300 mg, 5.34 mmol) was added thereto. The reaction was stirred at room temperature for 16 hours. The pH of the reaction solution was adjusted to 8 with 1.0 M dilute hydrochloric acid, and the reaction solution was added with 2 mL of water and extracted with 80 mL of ethyl acetate. The organic phase was washed with 25 mL of saturated brine, dried and then concentrated, and the crude product was purified by a thin-layer preparative plate (dichloromethane/7M ammonia methanol=10:1) to obtain trans-9'-((2-chloro-4-phenoxyphenyl)(hydroxy)methyl)-6-(hydroxymethyl)-4',5,6,7'-tetrahydro-2H,4H-spiro[pyran-3,2'-pyrrolo[3',2':5,6]pyrido[3,4-b]pyrazin]-3'(1'H)-one (165 mg, 2-step yield of 64%) as a light brown solid. ES-API: $[M+H]^+$=521.2.

Step 5: trans-9'-((2-Chloro-4-phenoxyphenyl)(hydroxy)methyl)-6-(hydroxymethyl)-4',5,6,7'-tetrahydro-2H,4H-spiro[pyran-3,2'-pyrrolo[3',2':5,6]pyrido[3,4-b]pyrazin]-3'(1'H)-one (165 mg, 0.32 mmol) was dissolved in 1,4-dioxane (7 mL) and water (0.7 mL), and 2,3-dichloro-5,6-dicyano-p-benzoquinone (144 mg, 0.64 mmol) was added thereto, and the reaction was stirred at room temperature for 1 hour. To the reaction solution was added 6 mL of saturated sodium thiosulfate solution and 6 mL of saturated sodium bicarbonate solution, and the mixture was extracted with 60 mL of ethyl acetate. The organic phase was washed with 15 mL saturated sodium bicarbonate solution and 15 mL saturated brine in turn, dried and concentrated, and the crude product was purified by preparative HPLC, and then resolved by chiral preparation (separation column: IC 250 mm*4.6 mm*5 μm, mobile phase: n-hexane:ethanol=70:30, flow rate: 1 mL/min, column temperature: 30° C.) to obtain two single isomer compounds. One single isomer with a structure arbitrarily designated as Z41-2a (64 mg, peak 1, retention time of 13.441 min, yield of 39%) was a pale yellow solid. $^1H$ NMR (400 MHz, DMSO-$d_6$) δ 12.54 (s, 1H), 10.48 (s, 1H), 8.38 (s, 1H), 7.75 (s, 1H), 7.66 (s, 1H), 7.58 (d, J=8.4 Hz, 1H), 7.48 (t, J=7.6 Hz, 2H), 7.25 (t, J=7.6 Hz, 1H), 7.22-7.16 (m, 3H), 7.03 (dd, J=8.4, 2.4 Hz, 1H), 4.71-4.66 (m, 1H), 4.04 (d, J=11.6 Hz, 1H), 3.61-3.50 (m, 2H), 3.45-3.36 (m, 1H), 3.29 (d, J=12.0 Hz, 1H), 2.24-2.14 (m, 1H), 1.91-1.76 (m, 2H), 1.66-1.56 (m, 1H). ES-API: $[M+H]^+$=519.1. The other single isomer with a structure arbitrarily designated as Z41-2b (61 mg, peak 2, retention time of 15.881 min, yield of 37%) was a pale yellow solid. $^1H$ NMR (400 MHz, DMSO-$d_6$) δ 12.53 (s, 1H), 10.48 (s, 1H), 8.37 (s, 1H), 7.75 (s, 1H), 7.66 (s, 1H), 7.57 (d, J=8.4 Hz, 1H), 7.48 (t, J=7.6 Hz, 2H), 7.25 (t, J=7.6 Hz, 1H), 7.22-7.15 (m, 3H), 7.02 (dd, J=8.4, 2.4 Hz, 1H), 4.71-4.66 (m, 1H), 4.04 (d, J=11.2 Hz, 1H), 3.63-3.50 (m, 2H), 3.45-3.36 (m, 1H), 3.29 (d, J=11.6 Hz, 1H), 2.24-2.14 (m, 1H), 1.91-1.76 (m, 2H), 1.66-1.56 (m, 1H). ES-API: $[M+H]^+$=519.1.

Embodiment 55: Synthesis of Z52 and Isomers Thereof
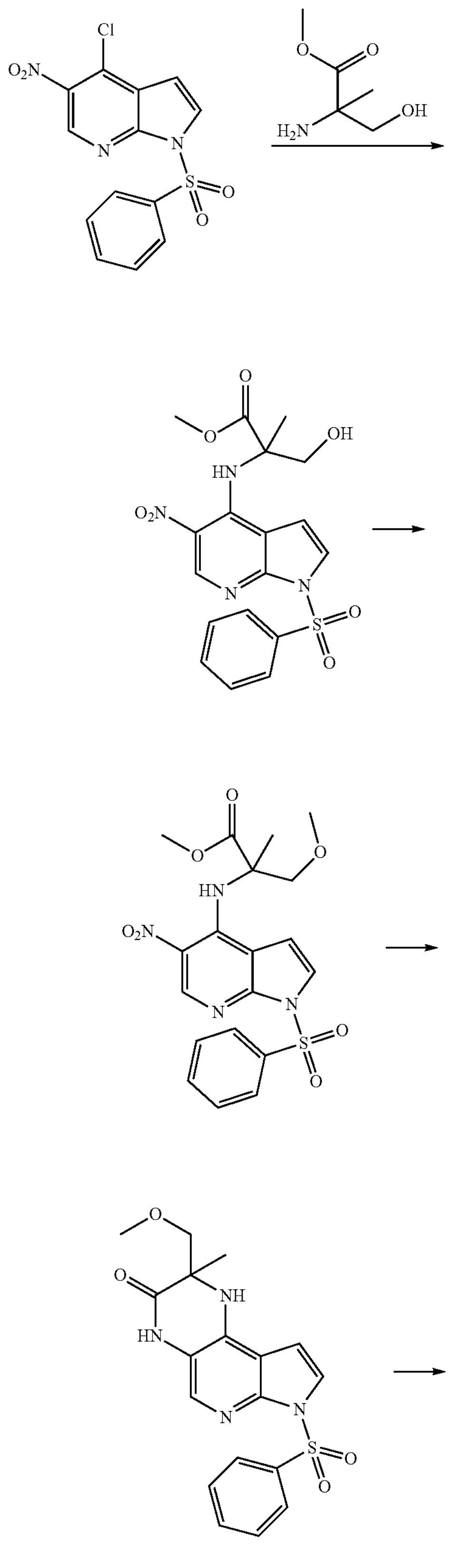
-continued
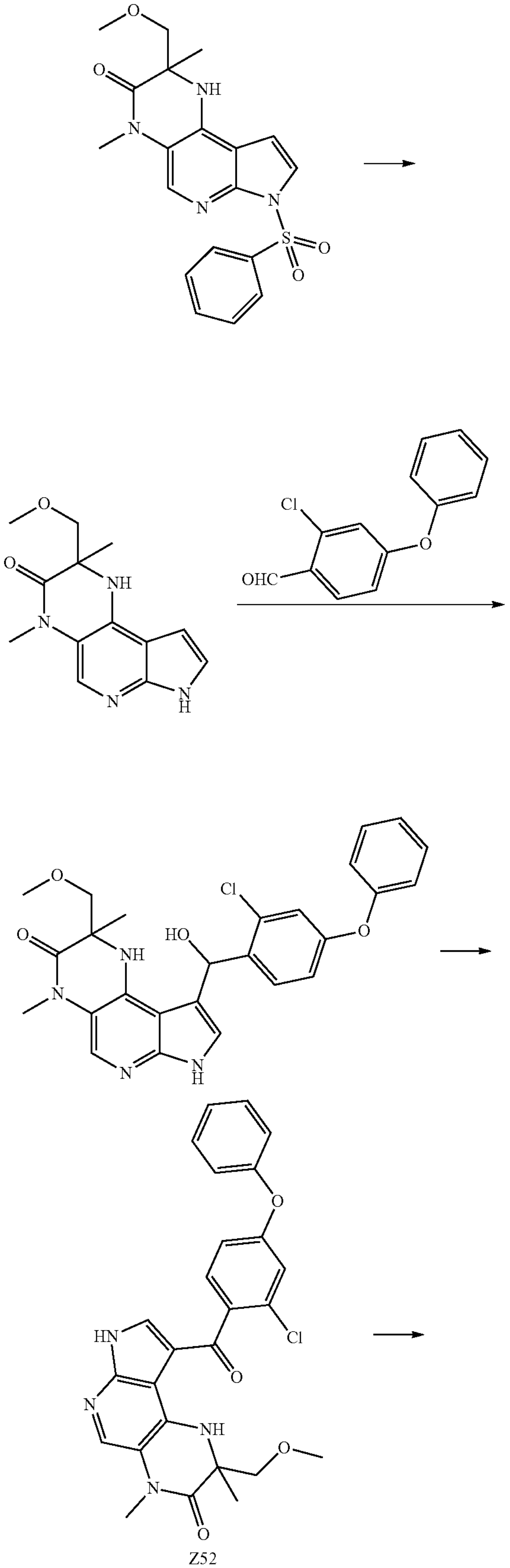
Z52

-continued

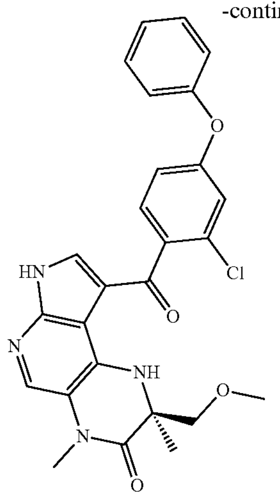

Z52-1

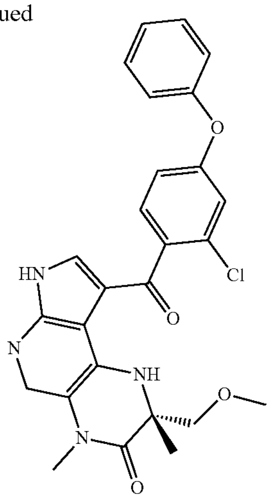

Z52-2

Step 1: 4-Chloro-5-nitro-1-(phenylsulfonyl)-1H-pyrrolo[2,3-b]pyridine (1.0 g, 2.967 mmol) and methyl 2-amino-3-hydroxy-2-methylpropanoate hydrochloride (0.6 g, 3.550 mmol) were dissolved in N,N-dimethylacetamide (30 mL), and N,N-diisopropylethylamine (7.64 g, 59.15 mmol) was added thereto, and the reaction was stirred at 95° C. for 16 hours. The reaction solution was added with 100 mL of ethyl acetate, washed twice with 60 mL of water and 3 times with 30 mL of saturated brine, dried and concentrated, and the crude product was purified by a flash silica gel column (ethyl acetate/petroleum ether: 0-50%) to obtain methyl 3-hydroxy-2-methyl-2-((5-nitro-1-(phenylsulfonyl)-1H-pyrrolo[2,3-b]pyridin-4-yl)amino)propanoate (0.6 g, yield of 46%) as a pale yellow solid. ES-API: $[M+H]^+$=435.1.

Step 2: Methyl 3-hydroxy-2-methyl-2-((5-nitro-1-(phenylsulfonyl)-1H-pyrrolo[2,3-b]pyridin-4-yl)amino)propanoate (600 mg, 1.382 mmol) was dissolved in acetonitrile (30 mL), and silver oxide (3.70 g, 15.96 mmol) and iodomethane (1 mL, 16.05 mmol) were added thereto in turn, and the reaction was stirred in the dark at room temperature for 48 hours under nitrogen atmosphere. After the reaction was completed, the reaction solution was filtered through diatomite, and the filtrate was evaporated to dryness by rotary evaporation under reduced pressure. The crude product was purified by a flash silica gel column (ethyl acetate/petroleum ether: 0-50%) to obtain methyl 3-methoxy-2-methyl-2-((5-nitro-1-(phenylsulfonyl)-1H-pyrrolo[2,3-b]pyridin-4-yl)amino)propanoate (520 mg, yield of 83%) as a yellow solid. ES-API: $[M+H]^+$=449.0.

Step 3: Methyl 3-methoxy-2-methyl-2-((5-nitro-1-(phenylsulfonyl)-1H-pyrrolo[2,3-b]pyridin-4-yl)amino)propanoate (520 mg, 1.272 mmol) was dissolved in acetic acid (20 mL), and iron powder (1.42 g, 25.44 mmol) was added thereto. The mixture was gradually heated to 80° C. and stirred for 1 hour. After the reaction was completed, the solvent was evaporated to dryness by rotary evaporation under reduced pressure, then 200 mL of ethyl acetate was added thereto. The mixture was washed twice with 80 mL of water, twice with 60 mL of saturated sodium carbonate, twice with 82 mL of saturated sodium bicarbonate, and with 80 mL of saturated brine in turn, dried and concentrated, and the crude product was slurried with ethyl acetate to obtain 2-(methoxymethyl)-2-methyl-7-(phenylsulfonyl)-1,2,4,7-tetrahydro-3H-pyrrolo[3',2':5,6]pyrido[3,4-b]pyrazin-3-one (260 mg, yield of 52%) as a yellow solid. ES-API: $[M+H]^+$=387.2

Step 4: 2-(Methoxymethyl)-2-methyl-7-(phenylsulfonyl)-1,2,4,7-tetrahydro-3H-pyrrolo[3',2':5,6]pyrido[3,4-b]pyrazin-3-one (260 mg, 0.69734 mmol) was dissolved in a mixed solution of acetone/N,N-dimethylformamide (10 mL:2 mL), and iodomethane (957 mg, 6.734 mmol) and potassium carbonate (465 mg, 3.367 mmol) were added thereto in turn, stirred in a sealed tube at 40° C. for 12 hours. After the reaction was completed, 200 mL of ethyl acetate was added thereto. The mixture was washed twice with 80 mL of water, twice with 60 mL of saturated sodium carbonate, twice with 82 mL of saturated sodium bicarbonate, and with 80 mL of saturated brine in turn, dried and concentrated, and the crude product was slurried with ethyl acetate to obtain 2-(methoxymethyl)-2,4-dimethyl-7-(phenylsulfonyl)-1,2,4,7-tetrahydro-3H-pyrrolo[3',2':5,6]pyrido[3,4-b]pyrazin-3-one (200 mg, yield of 74%) as a yellow solid. ES-API: $[M+H]^+$=401.2

Step 5: 2-(Methoxymethyl)-2,4-dimethyl-7-(phenylsulfonyl)-1,2,4,7-tetrahydro-3H-pyrrolo[3',2':5,6]pyrido[3,4-b]pyrazin-3-one (200 mg, 0.4997 mmol) was dissolved in 12 mL of methanol, 3 mL of tetrahydrofuran and 2 mL of water, and sodium hydroxide (7140.0 mg, 3.498 mmol) was added thereto, and the reaction was stirred at 65° C. for 7 hours. To the reaction solution was added 20 mL of water and 15 mL of saturated ammonium chloride solution, and the mixture was extracted with 150 mL of ethyl acetate. The organic phase was washed with 20 mL of saturated sodium bicarbonate solution and 60 mL of saturated brine in turn, dried over anhydrous sodium sulfate and then concentrated to obtain 2-(methoxymethyl)-2,4-dimethyl-1,2,4,7-tetrahydro-3H-pyrrolo[3',2':5,6]pyrido[3,4-b]pyrazin-3-one (253 mg, crude product) as a pale white solid. ES-API: $[M+H]^+$=261.1.

Step 6: 2-(Methoxymethyl)-2,4-dimethyl-1,2,4,7-tetrahydro-3H-pyrrolo[3',2':5,6]pyrido[3,4-b]pyrazin-3-one (253 mg, crude product) and 2-chloro-4-phenoxybenzaldehyde (230 mg, 0.9913 mmol) were dissolved in methanol (20.0 mL), and the reaction was cooled to 0° C., and potassium hydroxide (200 mg, 3.5710 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 150 mL of ethyl acetate. The organic phase was washed with 70 mL of saturated brine, dried and then concentrated to obtain a crude product 9-((2-chloro-4-phenoxyphenyl)(hydroxy)methyl)-2-(methoxymethyl)-2,4-dimethyl-1,2,4,7-tetrahydro-3H-pyrrolo[3',2':5,6]pyrido[3,4-b]pyrazin-3-one (380 mg, crude product) as a pale yellow solid. ES-API: $[M+H]^+$=545.2.

Step 7: 9-((2-Chloro-4-phenoxyphenyl)(hydroxy)methyl)-2-(methoxymethyl)-2,4-dimethyl-1,2,4,7-tetrahydro-3H-pyrrolo[3',2':5,6]pyrido[3,4-b]pyrazin-3-one (380 mg, crude product) was dissolved in 20 mL of tetrahydrofuran, and 2,3-dichloro-5,6-dicyano-1,4-benzoquinone (380 mg, 1.674 mmol) was added thereto, and the reaction was stirred at room temperature for 2 hours. To the reaction solution was added 60 mL of saturated sodium bicarbonate solution, and the mixture was extracted with 80 mL of ethyl acetate. The organic phase was washed with 60 mL of saturated brine, dried over anhydrous sodium sulfate and then concentrated, and the crude product was purified by preparative HPLC to obtain 9-(2-chloro-4-phenoxybenzoyl)-2-(methoxymethyl)-2,4-dimethyl-1,2,4,7-tetrahydro- 3H-pyrrolo[3',2':5,6]pyrido[3,4-b]pyrazin-3-one (Z52, 18 mg, 3-step yield of 7.3%) as a pale yellow solid, ES-API: $[M+H]^+=491.1$.

Step 8: The compound Z52 (18.0 mg) prepared in the above steps was resolved by chiral preparation (separation column: IC, 150 mm*4.6 mm*5 μm, mobile phase: n-hexane:ethanol:diethylamine=70:30:0.2, flow rate: 1 mL/min, column temperature: 30° C.) to obtain two single isomer compounds. One single isomer with a structure arbitrarily designated as Z52-1 (2.52 mg, peak 1, retention time of 15.908 min, yield of 14%) was a pale white solid. ES-API: $[M+H]^+=491.1$. The other single isomer with a structure arbitrarily designated as Z52-2 (1.98 mg, peak 2, retention time of 20.198 min, yield of 11%) was a pale white solid. ES-API: $[M+H]^+=491.1$.

Embodiment 65: Synthesis of Z64 and Isomers Thereof

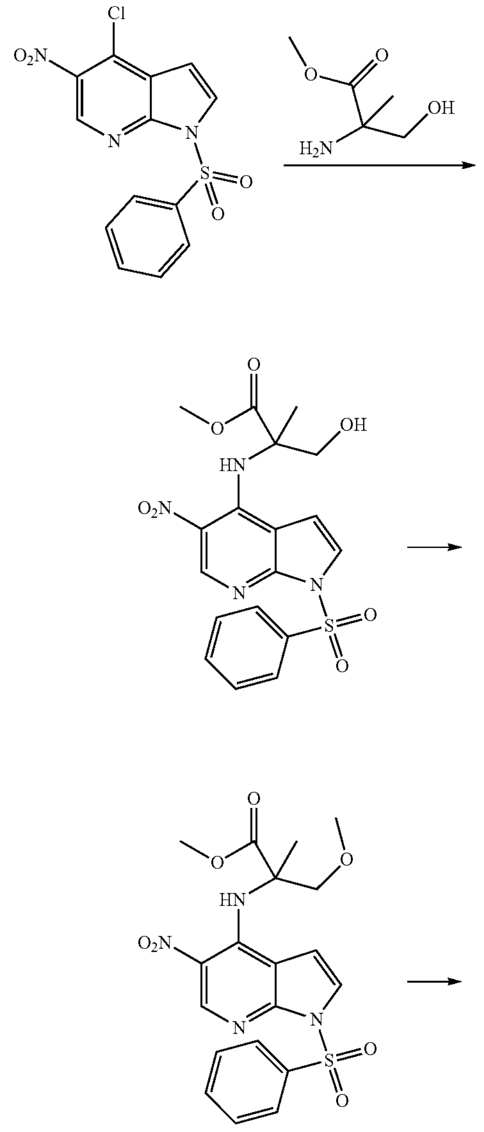

-continued

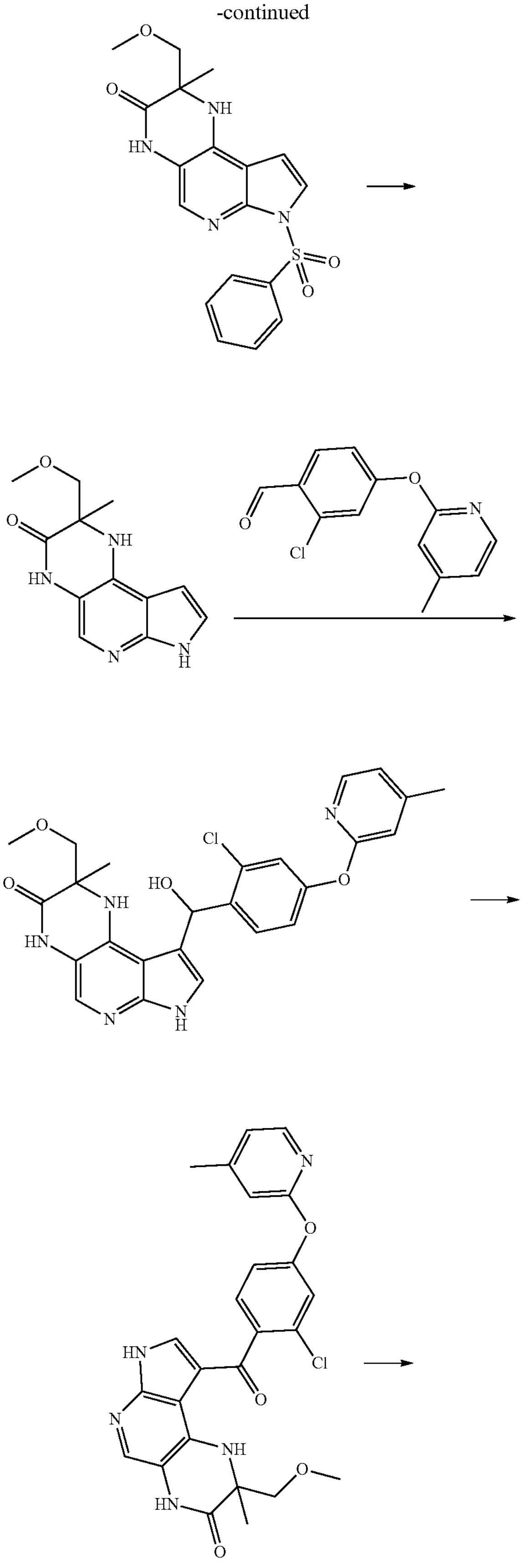

Z64

-continued

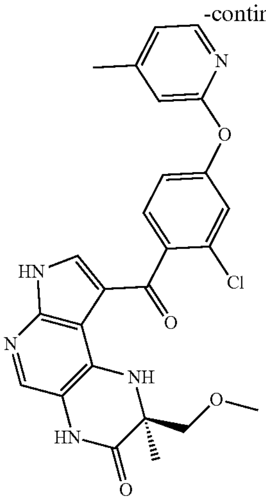

Z64-1

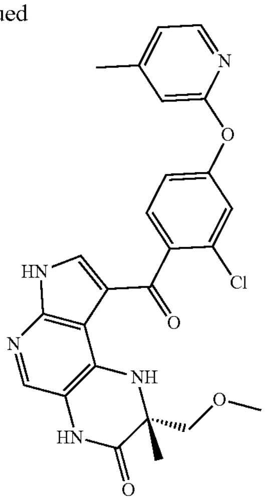

Z64-2

Step 1: 4-Chloro-5-nitro-1-(phenylsulfonyl)-1H-pyrrolo[2,3-b]pyridine (4.5 g, 13.35 mmol) and methyl 2-amino-3-hydroxy-2-methylpropanoate hydrochloride (4.0 g, 8.902 mmol) were dissolved in N,N-dimethylacetamide (80 mL), and N,N-diisopropylethylamine (7.64 g, 59.15 mmol) was added thereto, and the reaction was stirred at 95° C. for 16 hours. The reaction solution was added with 200 mL of ethyl acetate, washed twice with 60 mL of water and 3 times with 80 mL of saturated brine, dried and concentrated, and the crude product was purified by a flash silica gel column (ethyl acetate/petroleum ether: 0-50%) to obtain methyl 3-hydroxy-2-methyl-2-((5-nitro-1-(phenylsulfonyl)-1H-pyrrolo[2,3-b]pyridin-4-yl)amino)propanoate (3.3 g, yield of 57%) as a pale yellow solid. ES-API: $[M+H]^+$=435.1.

Step 2: Methyl 3-hydroxy-2-methyl-2-((5-nitro-1-(phenylsulfonyl)-1H-pyrrolo[2,3-b]pyridin-4-yl)amino)propanoate (2.60 g, 5.990 mmol) was dissolved in acetonitrile (100 mL), and silver oxide (20.82 g, 89.86 mmol) and iodomethane (21.26 g, 149.5 mmol) were added thereto in turn, and the mixture was stirred in the dark at room temperature for 48 hours under nitrogen atmosphere. After the reaction was completed, the reaction solution was filtered through diatomite, and the filtrate was evaporated to dryness by rotary evaporation under reduced pressure. The crude product was purified by a flash silica gel column (ethyl acetate/petroleum ether: 0-50%) to obtain methyl 3-methoxy-2-methyl-2-((5-nitro-1-(phenylsulfonyl)-1H-pyrrolo[2,3-b]pyridin-4-yl)amino)propanoate (2.20 g, yield of 82%) as a yellow solid. ES-API: $[M+H]^+$=449.0.

Step 3: Methyl 3-methoxy-2-methyl-2-((5-nitro-1-(phenylsulfonyl)-1H-pyrrolo[2,3-b]pyridin-4-yl)amino)propanoate (1.05 g, 2.343 mmol) was dissolved in acetic acid (30 mL), and iron powder (2.62 g, 46.87 mmol) was added thereto. The mixture was gradually heated to 80° C. and stirred for 1 hour. After the reaction was completed, the solvent was evaporated to dryness by rotary evaporation under reduced pressure, then 200 mL of ethyl acetate was added thereto. The mixture was washed twice with 80 mL of water, twice with 60 mL of saturated sodium carbonate, twice with 80 mL of saturated sodium bicarbonate, and with 80 mL of saturated brine in turn, dried and concentrated, and the crude product was slurried with ethyl acetate to obtain 2-(methoxymethyl)-2-methyl-7-(phenylsulfonyl)-1,2,4,7-tetrahydro-3H-pyrrolo[3',2':5,6]pyrido[3,4-b]pyrazin-3-one (650 mg, yield of 72%) as a yellow solid. ES-API: $[M+H]^+$=387.2

Step 4: 2-(Methoxymethyl)-2-methyl-7-(phenylsulfonyl)-1,2,4,7-tetrahydro-3H-pyrrolo[3',2':5,6]pyrido[3,4-b]pyrazin-3-one (200 mg, 0.5180 mmol) was dissolved in 12 mL of methanol, 3 mL of tetrahydrofuran and 2 mL of water, and sodium hydroxide (150 mg, 3.626 mmol) was added thereto, and the reaction was stirred at 65° C. for 7 hours. To the reaction solution was added 20 mL of water and 30 mL of saturated ammonium chloride solution, and the mixture was extracted with 100 mL of ethyl acetate. The organic phase was washed with 30 mL of saturated sodium bicarbonate solution and 80 mL of saturated brine in turn, dried over anhydrous sodium sulfate and then concentrated to obtain 2-(methoxymethyl)-2-methyl-1,2,4,7-tetrahydro-3H-pyrrolo[3',2':5,6]pyrido[3,4-b]pyrazin-3-one (246 mg, crude product) as a pale white solid. ES-API: $[M+H]^+$=247.1.

Step 5: 2-(Methoxymethyl)-2-methyl-1,2,4,7-tetrahydro-3H-pyrrolo[3',2':5,6]pyrido[3,4-b]pyrazin-3-one (246 mg, crude product) and 2-chloro-4-((4-methylpyridin-2-yl)oxy)benzaldehyde (230 mg, 0.9310 mmol) were dissolved in methanol (20.0 mL), and the reaction was cooled to 0° C., and potassium hydroxide (205 mg, 3.626 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and then concentrated to obtain a crude target product 9-((2-chloro-4-((4-methylpyridin-2-yl)oxy)phenyl)(hydroxyl)methyl)-2-(methoxymethyl)-2-methyl-1,2,4,7-tetrahydro-3H-pyrrolo[3',2':5,6]pyrido[3,4-b]pyrazin-3-one (310 mg, crude product) as a pale yellow solid. ES-API: $[M+H]^+$=494.2.

Step 6: 9-((2-Chloro-4-((4-methylpyridin-2-yl)oxy)phenyl)(hydroxyl)methyl)-2-(methoxymethyl)-2-methyl-1,2,4,7-tetrahydro-3H-pyrrolo[3',2':5,6]pyrido[3,4-b]pyrazin-3-one (380 mg, crude product) was dissolved in 30 mL of tetrahydrofuran, and 2,3-dichloro-5,6-dicyano-1,4-benzoquinone (310 mg, 1.3656 mmol) was added thereto, and the reaction was stirred at room temperature for 2 hours. To the reaction solution was added 60 mL of saturated sodium bicarbonate solution, and the mixture was extracted with 80 mL of ethyl acetate. The organic phase was washed with 60 mL of saturated brine, dried over anhydrous sodium sulfate and then concentrated, and the crude product was purified by preparative HPLC to obtain 9-(2-chloro-4-((4-methylpyridin-2-yl)oxy)benzoyl)-2-(methoxymethyl)-2-methyl-1,2,4,7-tetrahydro-3H-pyrrolo[3',2':5,6]pyrido[3,4-b]pyrazin-3-one (Z64, 30 mg, 3-step yield of 15.7%) as a pale yellow solid, ES-API: $[M+H]^+$=492.1. $^1$H NMR (400 MHz, DMSO-$d_6$) δ 12.46 (s, 1H), 10.49 (s, 1H), 8.28 (s, 1H), 8.09 (d, J=5.1 Hz, 1H), 7.70 (s, 1H), 7.64-7.53 (m, 2H), 7.38 (d, J=2.2 Hz, 1H), 7.19 (dd, J=8.4, 2.3 Hz, 1H), 7.06 (d, J=5.0 Hz, 1H), 6.99 (s, 1H), 3.65 (d, J=9.5 Hz, 1H), 3.48 (d, J=9.6 Hz, 1H), 3.30 (s, 3H), 2.37 (s, 3H), 1.39 (s, 3H).

Step 7: The compound Z64 (30 mg) prepared in the above steps was resolved by chiral preparation (separation column: IC 150 mm*4.6 mm*5 μm, mobile phase: n-hexane:ethanol:diethylamine=40:60:0.2, flow rate: 1 mL/min, column temperature: 30° C.) to obtain two single isomer compounds. One single isomer with a structure arbitrarily designated as Z64-1 (7.0 mg, peak 1, retention time of 18.717 min, yield of 23%) was a pale white solid. ES-API: $[M+H]^+$=492.1. The other single isomer with a structure arbitrarily designated as Z64-2 (12 mg, peak 2, retention time of 22.80 min, yield of 40%) was a pale white solid. ES-API: [M+H]+= 492.1.
Embodiment 67: Synthesis of Z66 and Isomers Thereof
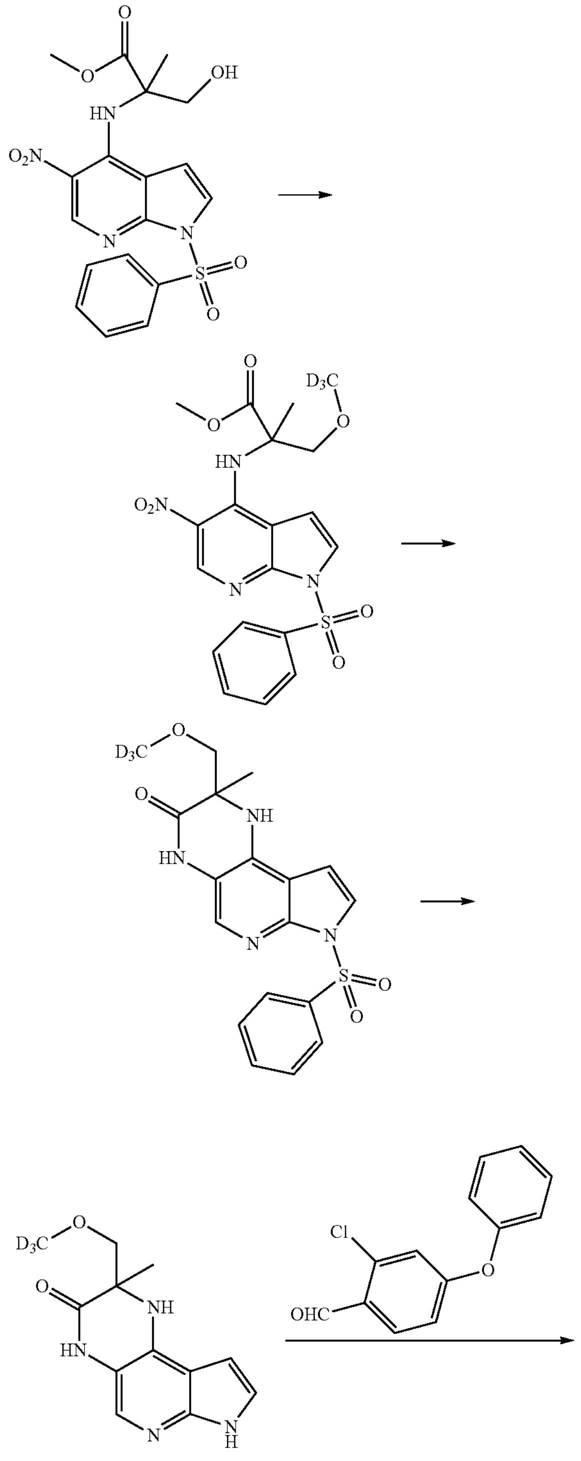
-continued
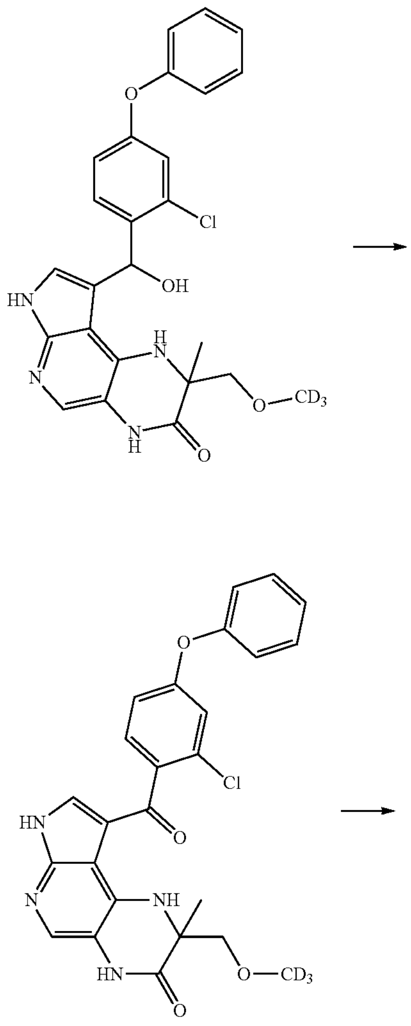
Z66
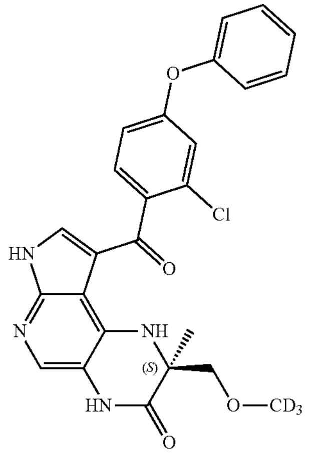
Z66-1
+

-continued

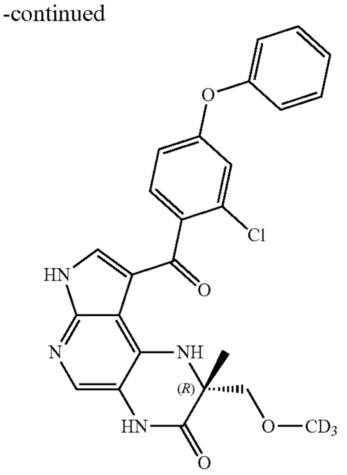

Z66-2

Step 1: 3-Hydroxy-2-methyl-2-methyl((5-nitro-1-(phenylsulfonyl)-1H-pyrrolo[2,3-b]pyridin-4-yl)amino)propionate (1.0 g, 2.3 mmol), silver oxide (5.3 g, 23 mmol) and deuterated iodomethane (3.34 g, 23 mmol) were dissolved in acetonitrile (50 mL), and the reaction was stirred at 35° C. in the dark for 2 days. The reaction solution was filtered through diatomite, and the filter cake was washed three times with 50 mL of ethyl acetate, and the filtrate was concentrated to obtain methyl 3-(methoxy-$d_3$)-2-methyl-2-((5-nitro-1-(phenylsulfonyl)-1H-pyrrolo[2,3-b]pyridin-4-yl)amino)propanoate (1.1 g, crude product) as a yellow oil. ES-API: $[M+H]^+$=452.1.

Step 2: Methyl 3-(methoxy-$d_3$)-2-methyl-2-((5-nitro-1-(phenylsulfonyl)-1H-pyrrolo[2,3-b]pyridin-4-yl)amino)propanoate (330 mg, 0.73 mmol) was dissolved in acetic acid (15 mL), and iron powder (286 mg, 5.11 mmol) was added thereto, and the reaction was stirred at 85° C. for 3 hours. The reaction solution was added with 100 mL of ethyl acetate, washed twice with 60 mL of water, with 40 mL of saturated sodium bicarbonate, and twice with 40 mL of saturated brine in turn, dried and concentrated, and the crude product was slurried with ethyl acetate to obtain 2-((methoxy-$d_3$)methyl)-2-methyl-7-(phenylsulfonyl)-1,2,4,7-tetrahydro-3H-pyrrolo[3',2':5,6]pyrido[3,4-b]pyrazin-3-one (270 mg, yield of 95%) as a yellow solid. ES-API: $[M+H]^+$=390.1

Step 3: 2-((Methoxy-$d_3$)methyl)-2-methyl-7-(phenylsulfonyl)-1,2,4,7-tetrahydro-3H-pyrrolo[3',2':5,6]pyrido[3,4-b]pyrazin-3-one (270 mg, 0.69 mmol) was dissolved in 10 mL of methanol, 5 mL of tetrahydrofuran and 2 mL of water, and sodium hydroxide (270 mg, 4.83 mmol) was added thereto, and the reaction was stirred at 65° C. for 7 hours. To the reaction solution was added 15 mL of water and 4 mL of saturated ammonium chloride solution, and the mixture was extracted with 100 mL of ethyl acetate. The organic phase was washed with 20 mL of saturated sodium bicarbonate solution and 20 mL of saturated brine in turn, dried and then concentrated to obtain 2-((methoxy-$d_3$)methyl)-2-methyl-1,2,4,7-tetrahydro-3H-pyrrolo[3',2':5,6]pyrido[3,4-b]pyrazin-3-one (120 mg, yield of 70%) as an off-white solid. ES-API: $[M+H]^+$=250.1.

Step 4: 2-((Methoxy-$d_3$)methyl)-2-methyl-1,2,4,7-tetrahydro-3H-pyrrolo[3',2':5,6]pyrido[3,4-b]pyrazin-3-one (120 mg, 0.48 mmol) and 2-chloro-4-phenoxybenzaldehyde (222 mg, 0.96 mmol) were dissolved in methanol (20 mL), and the reaction was cooled to 0° C., and potassium hydroxide (168 mg, 3.01 mmol) was added thereto. The reaction was stirred at room temperature for 48 hours. The reaction solution was poured into 60 mL of water, and the pH of the reaction solution was adjusted to 8 with 1.0 M dilute hydrochloric acid, and the reaction solution was extracted with 80 mL of ethyl acetate. The organic phase was washed with 25 mL of saturated brine, dried and then concentrated, and the crude product was purified by a thin-layer preparative plate (dichloromethane/7M ammonia methanol=100:7.5) to obtain 9-((2-chloro-4-phenoxyphenyl)(hydroxy)methyl)-2-((methoxy-$d_3$)methyl)-2-methyl-1,2,4,7-tetrahydro-3H-pyrrolo[3',2':5,6]pyrido[3,4-b]pyrazin-3-one (120 mg, yield of 52%) as a pale yellow solid. ES-API: $[M+H]^+$=482.1.

Step 5: 9-((2-Chloro-4-phenoxyphenyl)(hydroxy)methyl)-2-((methoxy-$d_3$)methyl)-2-methyl-1,2,4,7-tetrahydro-3H-pyrrolo[3',2':5,6]pyrido[3,4-b]pyrazin-3-one (120 mg, 0.26 mmol) was dissolved in 20 mL of tetrahydrofuran and 2 mL of water, and 2,3-dichloro-5,6-dicyano-p-benzoquinone (118 mg, 0.52 mmol) was added thereto, and the reaction was stirred at room temperature for 1 hour. The reaction solution was added with 20 mL of saturated sodium thiosulfate solution, extracted with 60 mL of ethyl acetate, and the organic phase was washed twice with 20 mL of saturated sodium bicarbonate solution, dried and then concentrated, and the crude product was purified by preparative HPLC (column: xbridge C18 19*150 mm, 5 μm; system: 10 mmol/L, aqueous $NH_4HCO_3$ solution; flow rate: 15 mL/min; gradient: 20 to 45% $CH_3CN$—$NH_4HCO_3$; column temperature: room temperature) to obtain 9-(2-chloro-4-phenoxybenzoyl)-2-((methoxy-$d_3$)methyl)-2-methyl-1,2,4,7-tetrahydro-3H-pyrrolo[3',2':5,6]pyrido[3,4-b]pyrazin-3-one (Z66, 80 mg, yield of 64%) as a white solid. ES-API: $[M+H]^+$=480.1. $^1H$ NMR (400 MHz, DMSO-$d_6$) δ 12.45 (s, 1H), 10.48 (s, 1H), 8.27 (s, 1H), 7.69 (s, 1H), 7.60 (s, 1H), 7.56 (d, J=8.4 Hz, 1H), 7.51-7.44 (m, 2H), 7.26-7.23 (m, 1H), 7.21-7.15 (m, 3H), 7.02 (dd, J=8.4, 2.4 Hz, 1H), 3.64 (d, J=9.6 Hz, 1H), 3.47 (d, J=9.6 Hz, 1H), 1.38 (s, 3H).

Step 6: The compound Z66 (80 mg) prepared in the above steps was resolved by chiral preparation (column: IE, 250 mm*4.6 mm*5 μm, mobile phase: n-hexane:ethanol=70:30, flow rate: 1 mL/min, column temperature: 30° C.) to obtain two single isomer compounds. One single isomer with a structure arbitrarily designated as Z66-1, (S)-9-(2-chloro-4-phenoxybenzoyl)-2-((methoxy-$d_3$)methyl)-2-methyl-1,2,4,7-tetrahydro-3H-pyrrolo[3',2':5,6]pyrido[3,4-b]pyrazin-3-one (32 mg, peak 1, retention time of 10.837 min), was a white solid. ES-API: $[M+H]^+$=480.1. The other single isomer with a structure arbitrarily designated as Z66-2, (R)-9-(2-chloro-4-phenoxybenzoyl)-2-((methoxy-$d_3$)methyl)-2-methyl-1,2,4,7-tetrahydro-3H-pyrrolo[3',2':5,6]pyrido[3,4-b]pyrazin-3-one (31 mg, peak 2, retention time of 12.802 min), was a white solid. ES-API: $[M+H]^+$=480.1.

Embodiment 68: Synthesis of Z67 and Isomers Thereof
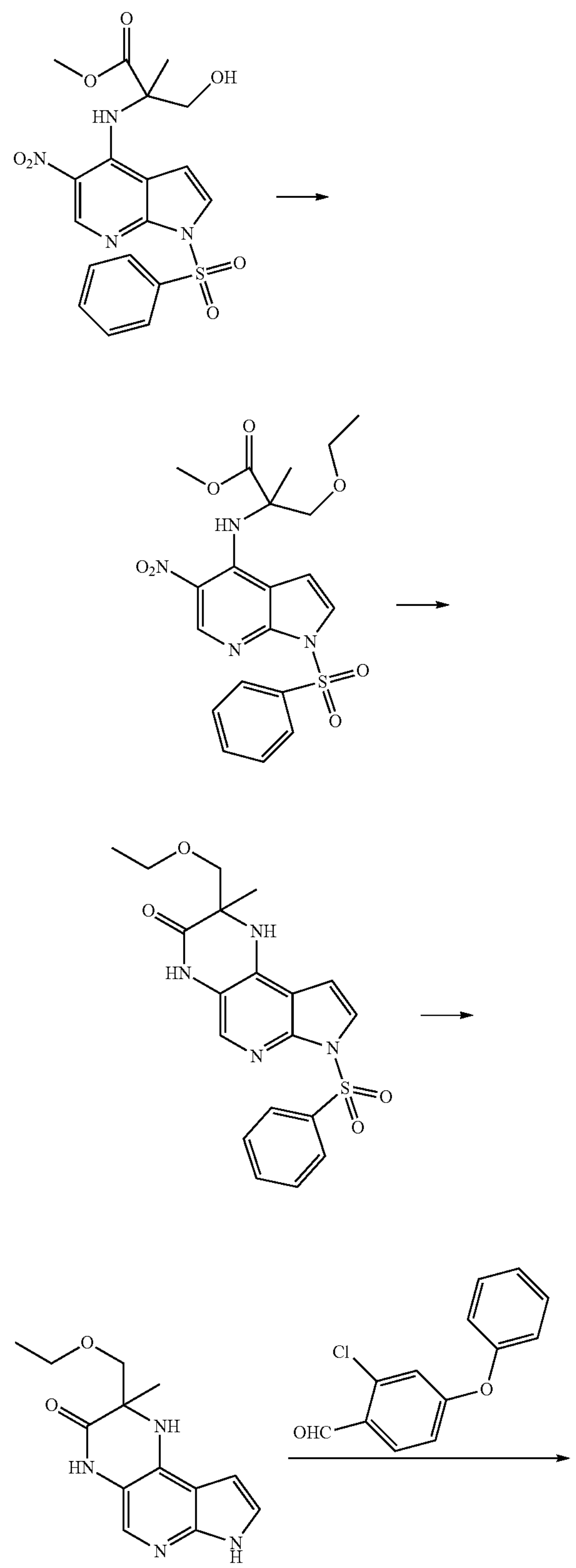
-continued
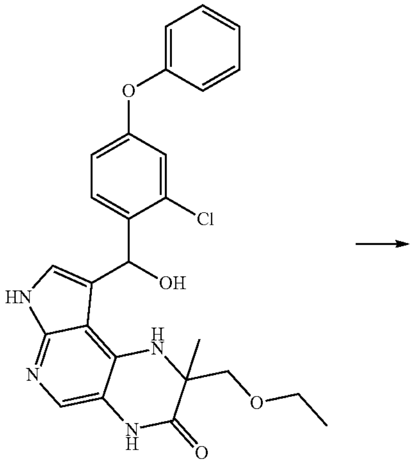
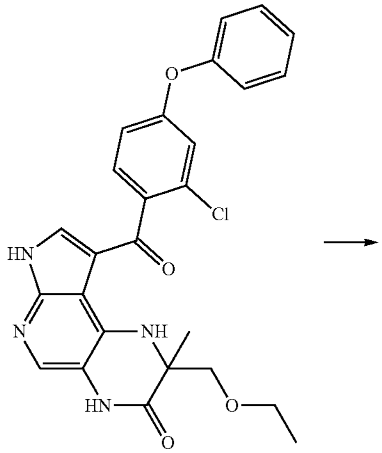
Z67
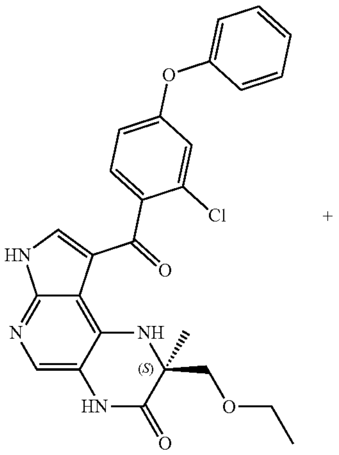
Z67-1

-continued

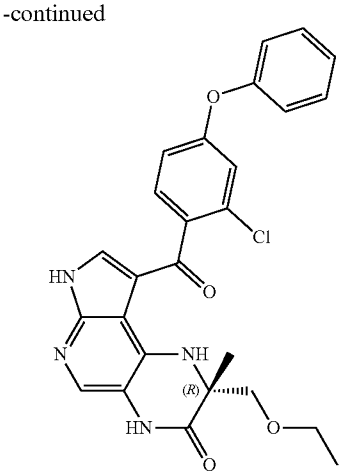

Z67-2

Step 1: 3-Hydroxy-2-methyl-2-methyl ((5-nitro-1-(phenylsulfonyl)-1H-pyrrolo[2,3-b]pyridin-4-yl)amino) propionate (1.0 g, 2.3 mmol), silver oxide (5.3 g, 23 mmol) and iodoethane (3.6 g, 23 mmol) were dissolved in acetonitrile (50 mL), and the reaction was stirred at 35° C. in the dark for 3 days. The reaction solution was filtered through diatomite, and the filter cake was washed three times with 50 mL of ethyl acetate, and the filtrate was concentrated to obtain methyl 3-ethoxy-2-methyl-2-((5-nitro-1-(phenylsulfonyl)-1H-pyrrolo[2,3-b]pyridin-4-yl)amino)propanoate (1.2 g, crude product) as a yellow oil. ES-API: $[M+H]^+$=463.1.

Step 2: Methyl 3-ethoxy-2-methyl-2-((5-nitro-1-(phenylsulfonyl)-1H-pyrrolo[2,3-b]pyridin-4-yl)amino)propanoate (250 mg, 0.54 mmol) was dissolved in acetic acid (15 mL), and iron powder (212 mg, 3.78 mmol) was added thereto, and the reaction was stirred at 85° C. for 3 hours. The reaction solution was added with 100 mL of ethyl acetate, washed twice with 60 mL of water, twice with 40 mL of saturated sodium bicarbonate solution and with 40 mL of saturated brine in turn, dried and concentrated to obtain 2-(ethoxymethyl)-2-methyl-7-(phenylsulfonyl)-1,2,4,7-tetrahydro-3H-pyrrolo[3',2':5,6]pyrido[3,4-b]pyrazin-3-one (170 mg, yield of 79%) as a yellow solid. ES-API: $[M+H]^+$=401.1.

Step 3: 2-(Ethoxymethyl)-2-methyl-7-(phenylsulfonyl)-1,2,4,7-tetrahydro-3H-pyrrolo[3',2':5,6]pyrido[3,4-b]pyrazin-3-one (170 mg, 0.43 mmol) was dissolved in 10 mL of methanol, 5 mL of tetrahydrofuran and 2 mL of water, and sodium hydroxide (119 mg, 2.98 mmol) was added thereto, and the reaction was stirred at 65° C. for 7 hours. To the reaction solution was added 15 mL of water and 4 mL of saturated ammonium chloride solution, and the mixture was extracted with 50 mL of ethyl acetate. The organic phase was washed with 20 mL of saturated sodium bicarbonate solution and 20 mL of saturated brine in turn, dried and then concentrated to obtain 2-(ethoxymethyl)-2-methyl-1,2,4,7-tetrahydro-3H-pyrrolo[3',2':5,6]pyrido[3,4-b]pyrazin-3-one (130 mg, yield of 100%) as an off-white solid. ES-API: $[M+H]^+$=261.1.

Step 4: 2-(Ethoxymethyl)-2-methyl-1,2,4,7-tetrahydro-3H-pyrrolo[3',2':5,6]pyrido[3,4-b]pyrazin-3-one (130 mg, 0.5 mmol) and 2-chloro-4-phenoxybenzaldehyde (232 mg, 1.00 mmol) were dissolved in methanol (20 mL), and the reaction was cooled to 0° C., and potassium hydroxide (196 mg, 3.5 mmol) was added thereto. The reaction was stirred at room temperature for 16 hours. The reaction solution was poured into 60 mL of water, and the pH of the reaction solution was adjusted to 8 with 1.0 M dilute hydrochloric acid, and the reaction solution was extracted with 80 mL of ethyl acetate. The organic phase was washed with 25 mL of saturated brine, dried and then concentrated, and the crude product was purified by a thin-layer preparative plate (dichloromethane/7M ammonia methanol=100:7.5) to obtain 9-((2-chloro-4-phenoxyphenyl)(hydroxy)methyl)-2-(ethoxymethyl)-2-methyl-1,2,4,7-tetrahydro-3H-pyrrolo[3',2':5,6]pyrido[3,4-b]pyrazin-3-one (135 mg, yield of 55%) as a pale yellow solid. ES-API: $[M+H]^+$=493.1.

Step 5: 9-((2-Chloro-4-phenoxyphenyl)(hydroxy)methyl)-2-(ethoxymethyl)-2-methyl-1,2,4,7-tetrahydro-3H-pyrrolo[3',2':5,6]pyrido[3,4-b]pyrazin-3-one (135 mg, 0.27 mmol) was dissolved in 20 mL of tetrahydrofuran and 2 mL of water, and 2,3-dichloro-5,6-dicyano-p-benzoquinone (123 mg, 0.56 mmol) was added thereto, and the reaction was stirred at room temperature for 1 hour. To the reaction solution was added 20 mL of saturated sodium thiosulfate solution, and the mixture was extracted with 50 mL of ethyl acetate. The organic phase was washed with 20 mL of saturated sodium bicarbonate solution and 20 mL of saturated brine in turn, dried and then concentrated, and the crude product was purified by preparative HPLC (column: xbridge C18 19*150 mm, 5 μm; system: 10 mmol/L, aqueous $NH_4HCO_3$ solution; flow rate: 15 mL/min; gradient: 20 to 45% $CH_3CN—NH_4HCO_3$; column temperature: room temperature) to obtain 9-(2-chloro-4-phenoxybenzoyl)-2-(ethoxymethyl)-2-methyl-1,2,4,7-tetrahydro-3H-pyrrolo[3',2':5,6]pyrido[3,4-b]pyrazin-3-one (Z67, 70 mg, yield of 53%) as a white solid. ES-API: $[M+H]^+$=491.1. $^1$H NMR (400 MHz, DMSO-$d_6$) δ 12.44 (s, 1H), 10.47 (s, 1H), 8.30 (s, 1H), 7.70 (s, 1H), 7.59 (s, 1H), 7.56-7.53 (m, 1H), 7.51-7.44 (m, 2H), 7.28-7.22 (m, 1H), 7.19-7.16 (m, 3H), 7.02 (dd, J=8.4, 2.4 Hz, 1H), 3.65 (d, J=9.8 Hz, 1H), 3.55-3.43 (m, 4H), 1.39 (s, 3H), 1.03 (t, J=7.0 Hz, 3H).

Step 6: The compound Z67 (70 mg) prepared in the above steps was resolved by chiral preparation (separation column IE, 250 mm*4.6 mm*5 μm, mobile phase: n-hexane:ethanol=70:30, flow rate: 1 mL/min, column temperature: 30° C.) to obtain two single isomer compounds. One single isomer with a structure arbitrarily designated as Z67-1, (S)-9-(2-chloro-4-phenoxybenzoyl)-2-(ethoxymethyl)-2-methyl-1,2,4,7-tetrahydro-3H-pyrrolo[3',2':5,6]pyrido[3,4-b]pyrazin-3-one (26 mg, peak 1, retention time of 8.852 min), was a white solid. ES-API: $[M+H]^+$=491.1. The other single isomer with a structure arbitrarily designated as Z67-2, (R)-9-(2-chloro-4-phenoxybenzoyl)-2-(ethoxymethyl)-2-methyl-1,2,4,7-tetrahydro-3H-pyrrolo[3',2':5,6]pyrido[3,4-b]pyrazin-3-one (25 mg, peak 2, retention time of 11.215 min), was a white solid. ES-API: $[M+H]^+$=491.1.

Embodiment 70: Synthesis of Z69 and Isomers Thereof

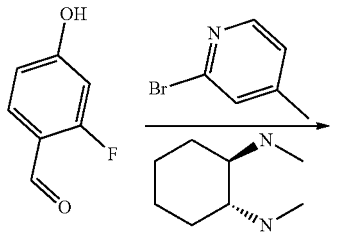

-continued

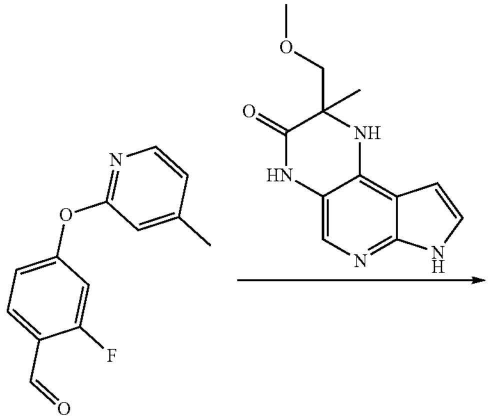

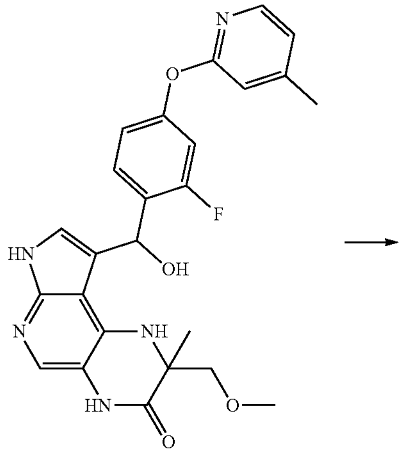

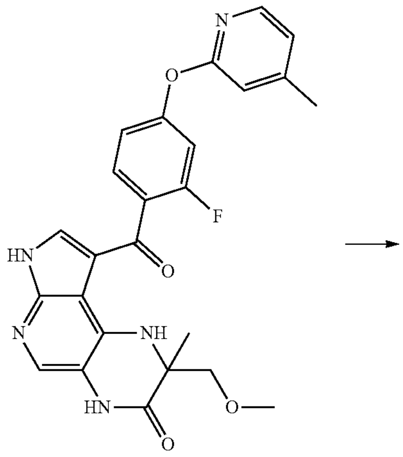

Z69

-continued

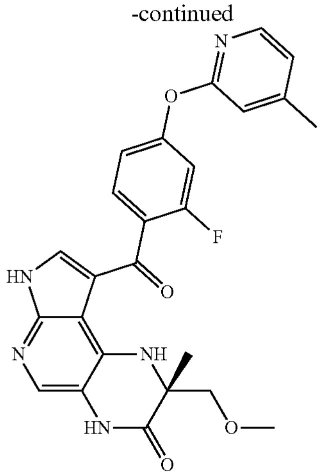

Z69-1

+

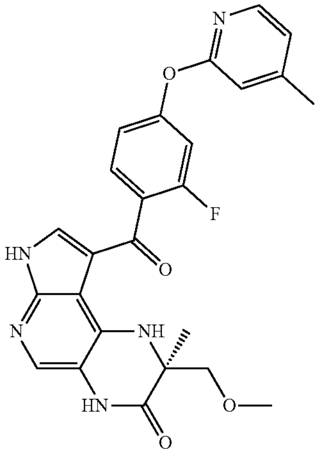

Z69-2

Step 1: Under nitrogen atmosphere, 2-fluoro-4-hydroxybenzaldehyde (1.652 g, 11.628 mmol), 2-bromo-4-methylpyridine (2 g, 11.628 mmol), potassium phosphate (5.43 g, 25.582 mmol), cuprous iodide (220 mg), and (1R,2R)-(−)-N,N'-dimethyl-1,2-cyclohexanediamine (330 mg, 2.326 mmol) were dissolved in N,N'-dimethylformamide (20 mL), and the reaction solution was stirred under microwave irradiation at 110° C. for 1 hour. LCMS detected that the reaction was complete. The reaction solution was cooled to room temperature, added with 30 mL of ethyl acetate, washed once with 30 mL of water, washed with saturated brine (25 mL×3), and the organic phase was dried over anhydrous sodium sulfate, filtered, and the filtrate was concentrated to dryness under reduced pressure to obtain 2-fluoro-4-((4-methylpyridin-2-yl)oxy)benzaldehyde (215 mg, yield of 8%) as a pale yellow liquid. ES-API: $[M+H]^+$= 232.1.

Step 2: 2-(Methoxymethyl)-2-methyl-1,2,4,7-tetrahydro-3H-pyrrolo[3',2':5,6]pyrido[3,4-b]pyrazin-3-one (68 mg, 0.275 mmol) and 2-fluoro-4-((4-methylpyridin-2-yl)oxy)benzaldehyde (160 mg, 0.693 mmol) were dissolved in methanol (10 mL), and the reaction solution was cooled to 0° C., and potassium hydroxide (108 mg, 1.925 mmol) was added thereto. The reaction solution was slowly raised to room temperature and stirred for 4 hours. LCMS detected that the reaction was complete. The reaction was quenched by adding 20 mL of saturated ammonium chloride solution, extracted with ethyl acetate (15 mL×3). The organic phase was washed with 20 mL of saturated brine, dried over anhydrous sodium sulfate and then concentrated to obtain compound 9-((2-fluoro-4-((4-methylpyridin-2-yl)oxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (62 mg, yield of 47%). ES-API: $[M+H]^+$=478.1.

Step 3: 9-((2-Fluoro-4-((4-methylpyridin-2-yl)oxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (62 mg, 0.130 mmol) was dissolved in 10 mL of tetrahydrofuran, and 2,3-dichloro-5,6-dicyano-p-benzoquinone (59 mg, 0.260 mmol) was added thereto, and the reaction solution was stirred at room temperature for 3 hours. LCMS detected that the reaction was complete. To the reaction solution was added 20 mL of saturated sodium thiosulfate solution and 20 mL of saturated sodium bicarbonate solution, and the mixture was extracted with 30 mL of ethyl acetate. The organic phase was washed with 15 mL of saturated brine, dried and concentrated, and the crude product was prepared by preparative HPLC (column: xbridge C18 19*150 mm, 5 μm; system: 10 mmol/L, aqueous $NH_4HCO_3$ solution; flow rate: 15 mL/min; gradient: 20 to 45% $CH_3CN—NH_4HCO_3$; column temperature: room temperature) to obtain 9-(2-fluoro-4-((4-methylpyridin-2-yl)oxy)benzoyl)-2-(methoxymethyl)-2-methyl-1,2,4,7-tetrahydro-3H-pyrrolo[3',2':5,6]pyrido[3,4-b]pyrazin-3-one (Z69, 22 mg, yield of 35%) as a white solid. ES-API: $[M+H]^+$=476.1

Step 4: The compound Z69 obtained in the above steps was chirally resolved by SFC (chromatographic column: Daicel CHIRALPAK IE 250*4.6 mm, 5 μm; mobile phase: hexane/ethanol=50:50 (V/V); flow rate: 1 mL/min; column temperature: room temperature) to obtain two single isomer compounds. One single isomer was a compound with a structure arbitrarily designated as Z69-1 (peak 1, retention time: 11.371 min, 5.59 mg). ES-API: $[M+H]^+$=476.1. The other single isomer was a compound with a structure arbitrarily designated as Z69-2 (peak 2, retention time: 14.824 min, 6.63 mg). ES-API: $[M+H]^+$=476.1.

Embodiment 72: Synthesis of Z71 and Isomers Thereof

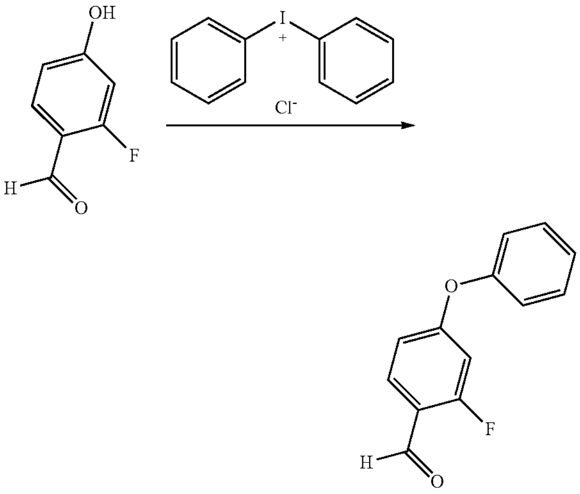

-continued

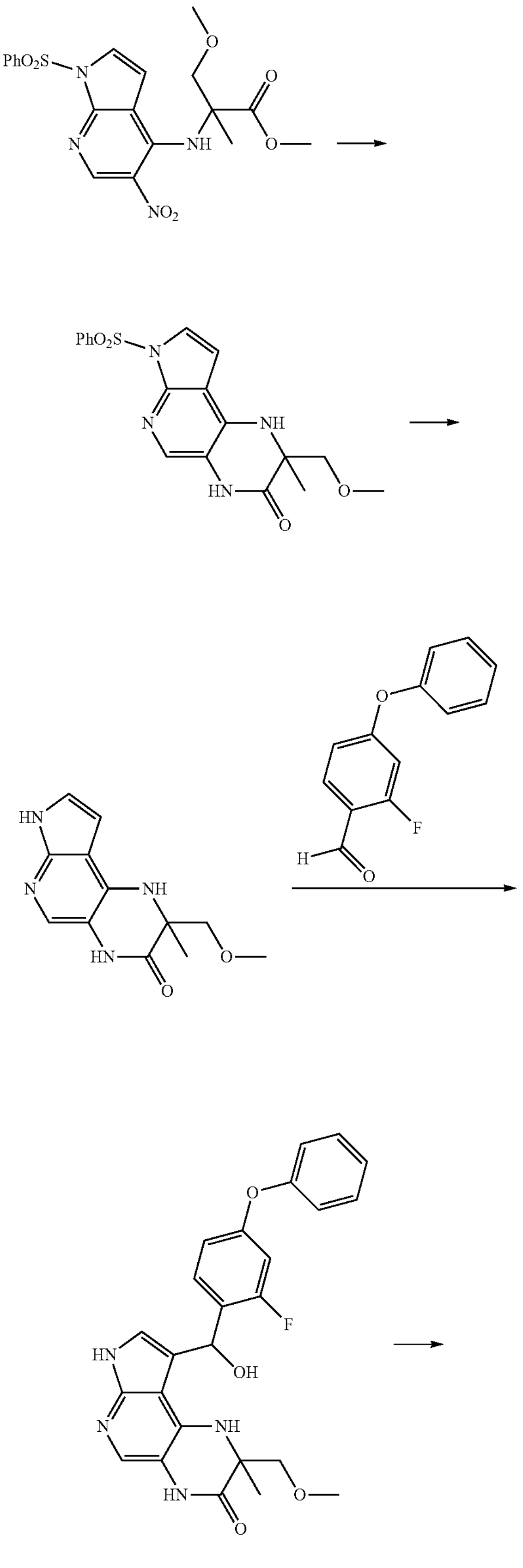

-continued

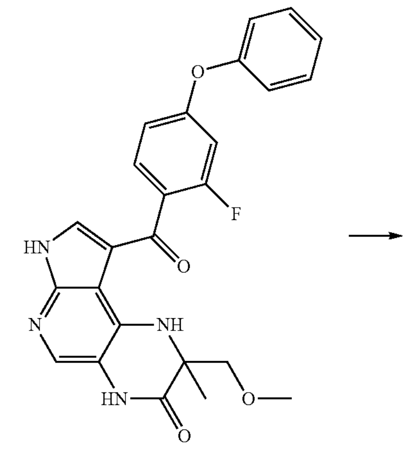

Z71

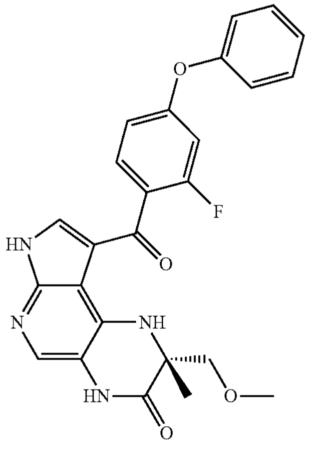

Z71-1

+

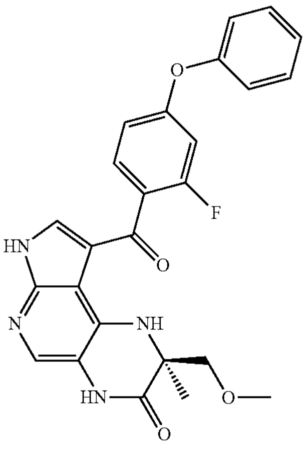

Z71-2

Step 1: A mixed solution of 2-fluoro-4-hydroxybenzaldehyde (500 mg, 3.57 mmol), diphenyliodonium chloride (1.24 g, 3.93 mmol) and potassium carbonate (1.48 g, 10.71 mmol) in N,N-dimethylformamide (20 mL) was stirred overnight at 80° C. After the reaction was completed, the reaction solution was dissolved in 50 mL of ethyl acetate, washed three times with 50 mL of saturated brine, and the organic phase was dried and concentrated, and purified by a flash silica gel column (0-30% of ethyl acetate/petroleum ether) to obtain a white solid 2-fluoro-4-phenoxybenzaldehyde (600 mg) with a purity of 100% and a yield of 78%.

Step 2: To a solution of methyl 3-methoxy-2-methyl-2-((5-nitro-1-(phenylsulfonyl)-1H-pyrrolo[2,3-b]pyridin-4-yl)amino)propanoate (700 mg, 1.56 mmol) in acetic acid (30 mL) was added iron powder (1.74 g, 31.2 mmol). The reaction solution was stirred at 80° C. for 2 hours. The reaction solution was filtered through diatomite, washed with 50 mL of ethyl acetate, and the filtrate was washed three times with 30 mL of water, three times with 30 mL of saturated sodium bicarbonate, and the organic phase was dried, and concentrated under reduced pressure to obtain a crude product 2-(methoxymethyl)-2-methyl-7-(phenylsulfonyl)-1,2,4,7-tetrahydro-3H-pyrrolo[3',2':5,6]pyrido[3,4-b]pyrazin-3-one (500 mg). ES-API $[M+H]^+$=387.1.

Step 3: To a mixed solvent of methanol/water (5 mL/1 mL) was added 2-(methoxymethyl)-2-methyl-7-(phenylsulfonyl)-1,2,4,7-tetrahydro-3H-pyrrolo[3',2':5,6]pyrido[3,4-b]pyrazin-3-one (250 mg, 0.65 mmol) and sodium hydroxide (130 mg, 3.23 mmol), and stirred at 60° C. for 2 hours. The reaction solution was concentrated to obtain a crude product 2-(methoxymethyl)-2-methyl-1,2,4,7-tetrahydro-3H-pyrrolo[3',2':5,6]pyrido[3,4-b]pyrazin-3-one (200 mg). ES-API: $[M+H]^+$=247.1.

Step 4: To a solution of the above crude product 2-(methoxymethyl)-2-methyl-1,2,4,7-tetrahydro-3H-pyrrolo[3',2':5,6]pyrido[3,4-b]pyrazin-3-one (160 mg, 0.65 mmol) in methanol (5 mL) was added 2-fluoro-4-phenoxybenzaldehyde (421 mg, 1.95 mmol) and potassium hydroxide (255 mg, 4.55 mmol), stirred at room temperature for 2 hours. After the reaction was completed, the pH of the reaction solution was adjusted to 7 with 1 M hydrochloric acid solution, and the mixture was added with 20 mL of ethyl acetate and extracted three times. The organic phases were combined, dried, concentrated and purified by a flash silica gel column (0-20% of methanol/dichloromethane) to obtain a yellow solid 9-((2-fluoro-4-phenoxyphenyl)(hydroxy)methyl)-2-(methoxymethyl)-2-methyl-1,2,4,7-tetrahydro-3H-pyrrolo[3',2':5,6]pyrido[3,4-b]pyrazin-3-one (120 mg) with a purity of 100% and a yield of 40%. ES-API: $[M+H]^+$=463.1.

Step 5: To a mixed solution of 9-((2-fluoro-4-phenoxyphenyl)(hydroxy)methyl)-2-(methoxymethyl)-2-methyl-1,2,4,7-tetrahydro-3H-pyrrolo[3',2':5,6]pyrido[3,4-b]pyrazin-3-one (120 mg, 0.26 mmol) in 1,4-dioxane/water (5 mL/0.5 mL) was added 2,3-dichloro-5,6-dicyano-p-benzoquinone (118 mg, 0.52 mmol), stirred at room temperature for 30 minutes. The reaction was completed, quenched by adding 2 mL of aqueous sodium thiosulfate solution, added with 20 mL of ethyl acetate, washed with 20 mL of saturated aqueous sodium bicarbonate solution and 20 mL of saturated brine in turn, dried over anhydrous sodium sulfate, filtered, concentrated and purified by preparative HPLC to obtain an off-white solid (Z71, 32 mg) with a purity of 100% and a yield of 27%. ES-API: $[M+H]^+$=461.2.

Step 6: The compound Z71 (32 mg, 0.07 mmol) obtained in the above steps was resolved by chiral preparation (separation column: IA 250 mm*4.6 mm*5 μm, mobile phase: n-hexane:isopropanol:dimethylamine=60:40:2, flow rate: 1 mL/min, column temperature: 30° C.) to obtain two single isomer compounds. One single isomer with a structure arbitrarily designated as Z71-1 (10 mg, peak 1, retention time of 9.71 min, yield of 31%, de %=100%) was a white solid. ES-API: $[M+H]^+$=461.2. The other single isomer with a structure arbitrarily designated as Z71-2 (10 mg, peak 2, retention time of 14.40 min, yield of 31%, de %=100%) was a white solid. ES-API: $[M+H]^+$=461.2.

Embodiment 74: Synthesis of Z73 and Isomers Thereof

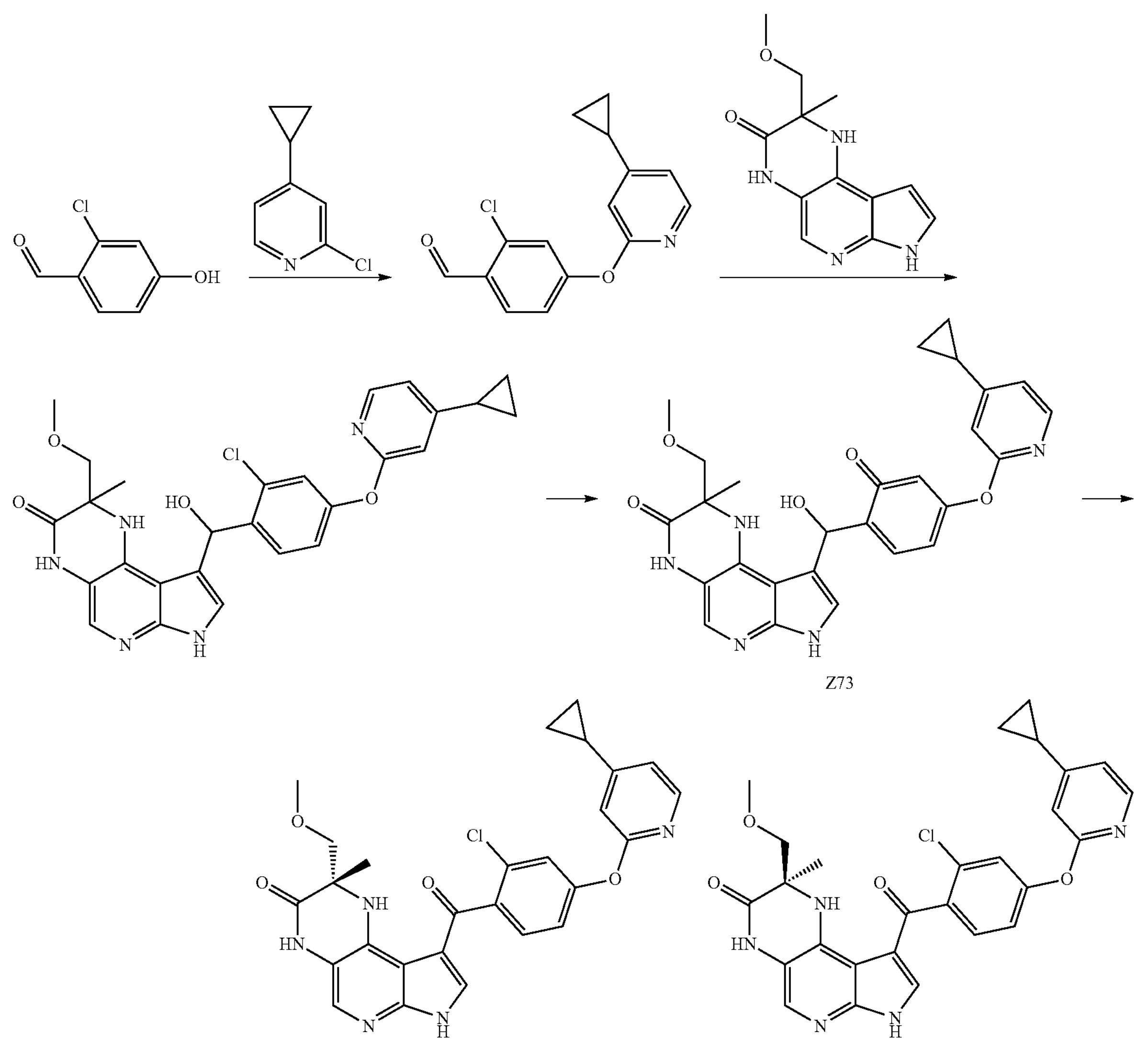

Z73

Z73-1

Z73-2

Step 1: 2-Chloro-4-hydroxybenzaldehyde (400 mg, 2.6 mmol), 2-chloro-4-cyclopropylpyridine (486 mg, 3.12 mmol), L-proline (60 mg, 0.52 mmol), cuprous iodide (98 mg, 0.52 mmol), anhydrous potassium carbonate (896 mg, 6.5 mmol) and N,N'-dimethylacetamide (8 mL) were added to a 20 mL microwave tube, replaced with nitrogen, and heated to 130° C. and reacted for 3 hours. The mixture was extracted with ethyl acetate, washed with water and saturated brine in turn, dried over anhydrous sodium sulfate, filtered, concentrated, and purified by a silica gel column to obtain a product 2-chloro-4-((4-cyclopropylpyridin-2-yl)oxy)benzaldehyde (50 mg, yield of 7%). ES-API: $[M+H]^+$=274.0.

Step 2: 2-Chloro-4-((4-cyclopropylpyridin-2-yl)oxy)benzaldehyde (50 mg, 0.183 mmol), 2-(methoxymethyl)-2-methyl-4,7-dihydro-1H-pyrrolo[3',2':5,6]pyrido[3,4-b]pyrazin-3(2H)-one (100 mg, 0.40 mmol) and potassium hydroxide (112 mg, 2 mmol) were added to 8 mL of methanol and stirred at room temperature for 5 hours. The reaction was completed, quenched with saturated ammonium chloride, extracted with ethyl acetate, and concentrated to obtain 9-((2-chloro-4-((4-cyclopropylpyridin-2-yl)oxy)phenyl)(hydroxy)methyl)-2-(methoxymethyl)-2-methyl-4,7-dihydro-1H-pyrrolo[3',2':5,6]pyrido[3,4-b]pyrazin-3(2H)-one (60 mg, crude product). ES-API: $[M+H]^+$=520.1.

Step 3: To a mixed solution of 1,4-dioxane/water (5 mL/1 mL) was added 9-((2-chloro-4-((4-cyclopropylpyridin-2-yl)oxy)phenyl)(hydroxy)methyl)-2-(methoxymethyl)-2-methyl-4,7-dihydro-1H-pyrrolo[3',2':5,6]pyrido[3,4-b]pyrazin-3(2H)-one (60 mg, 0.115 mmol), and then 2,3-dichloro-5,6-dicyano-p-benzoquinone (52 mg, 0.231 mmol) was added thereto in batches, stirred at room temperature for 30 minutes, and the reaction was completed. The reaction was quenched by adding 2 mL of aqueous sodium thiosulfate solution, washed with saturated aqueous sodium bicarbonate solution and saturated brine in turn, dried over anhydrous sodium sulfate, filtered, concentrated and purified by preparative HPLC to obtain 9-(2-chloro-4-((4-cyclopropylpyridin-2-yl)oxy)benzoyl)-2-(methoxymethyl)-2-methyl-4,7-dihydro-1H-pyrrolo[3',2':5,6]pyrido[3,4-b]pyrazin-3(2H)-one (Z73, 30 mg, 2-step yield of 31.5%). ES-API: $[M+H]^+=518.1$.

Step 4: The compound Z73 (30 mg) obtained in the above steps was resolved and purified by reverse phase HPLC (column: IG 250 mm*4.6 mm*5 μm; mobile phase: n-hexane:ethanol=60:40; flow rate: 1 mL/min; column temperature: 30° C.) to obtain two single isomer compounds. One isomer was a compound with a structure arbitrarily designated as Z73-1 (peak 1, retention time of 24.62 min, 12 mg, yield of 40%, purity of 100%); ES-API: $[M+H]^+=518.1$. $^1H$ NMR (400 MHz, DMSO-$d_6$) δ 12.47 (s, 1H), 10.50 (s, 1H), 8.28 (s, 1H), 8.03 (d, J=5.3 Hz, 1H), 7.70 (s, 1H), 7.64-7.52 (m, 2H), 7.37 (d, J=2.3 Hz, 1H), 7.18 (dd, J=8.4, 2.3 Hz, 1H), 6.97-6.86 (m, 2H), 3.65 (d, J=9.5 Hz, 1H), 3.48 (d, J=9.6 Hz, 1H), 3.30 (s, 3H), 2.05-1.97 (m, 1H), 1.39 (s, 3H), 1.12-1.07 (m, 2H), 0.89-0.85 (m, 2H). The other single isomer was a compound with a structure arbitrarily designated as Z73-2 (peak 2, retention time of 30.46 min, 12 mg, yield of 40%, purity of 100%). ES-API: $[M+H]^+=518.1$. $^1H$ NMR (400 MHz, DMSO-$d_6$) δ 12.47 (s, 1H), 10.50 (s, 1H), 8.28 (s, 1H), 8.03 (d, J=5.3 Hz, 1H), 7.70 (s, 1H), 7.63-7.49 (m, 2H), 7.37 (d, J=2.3 Hz, 1H), 7.18 (dd, J=8.4, 2.3 Hz, 1H), 6.94-6.87 (m, 2H), 3.65 (d, J=9.5 Hz, 1H), 3.48 (d, J=9.5 Hz, 1H), 3.30 (s, 3H), 2.01 (td, J=8.6, 4.3 Hz, 1H), 1.39 (s, 3H), 1.13-1.07 (m, 2H), 0.89-0.85 (m, 2H).

Embodiment 75: Synthesis of Z74

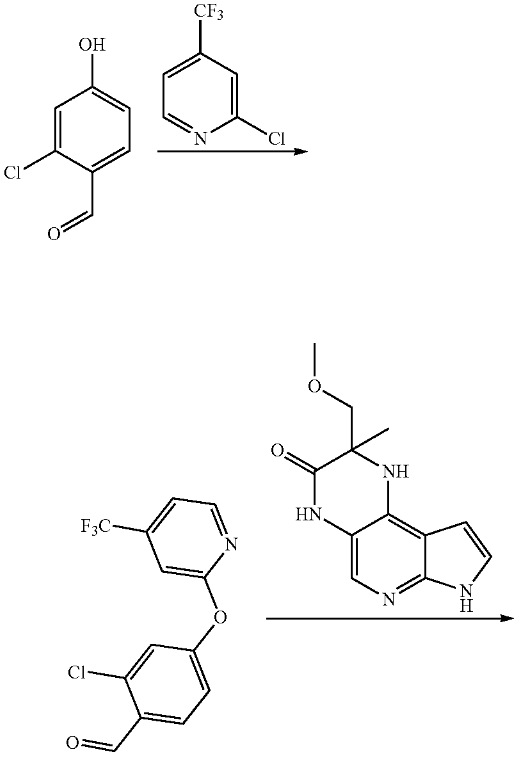

-continued

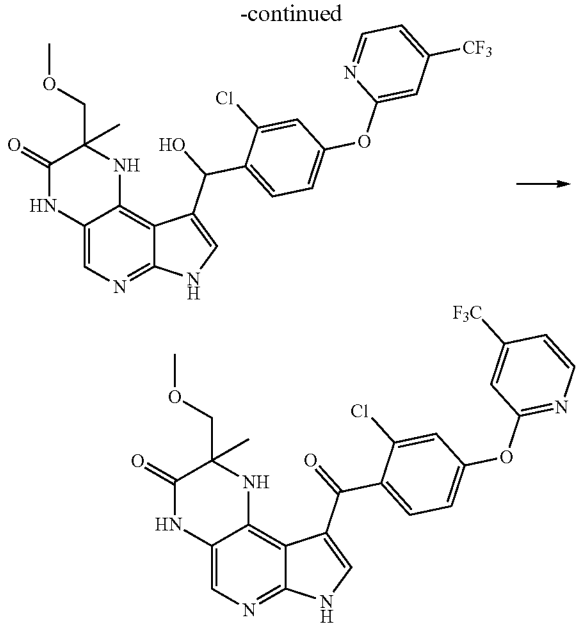

Z74

Step 1: To a 50 mL microwave tube was added 2-chloro-4-hydroxybenzaldehyde (1.23 g, 7.9 mmol), 2-chloro-4-trifluoromethylpyridine (870 mg, 5.27 mmol), anhydrous potassium carbonate (2.18 g, 15.8 mmol) and N,N'-dimethylformamide (10 mL), replaced with nitrogen, heated to 80° C. and reacted for 18 hours. The mixture was extracted with ethyl acetate, washed with water and saturated brine in turn, dried over anhydrous sodium sulfate, filtered, concentrated, and purified by a silica gel column to obtain a product 2-chloro-4-((4-trifluoromethylpyridin-2-yl)oxy)benzaldehyde (300 mg, yield of 20%). ES-API: $[M+H]^+=302.0$.

Step 2: To 8 mL of methanol was added 2-chloro-4-((4-trifluoromethylpyridin-2-yl)oxy)benzaldehyde (300 mg, 0.99 mmol), 2-(methoxymethyl)-2-methyl-4,7-dihydro-1H-pyrrolo[3',2':5,6]pyrido[3,4-b]pyrazin-3(2H)-one (150 mg, 0.61 mmol) and potassium hydroxide (170 mg, 3.04 mmol), stirred at room temperature for 3 hours. The reaction was completed, quenched with saturated ammonium chloride, extracted with ethyl acetate, and concentrated to obtain 9-((2-chloro-4-((4-trifluoromethylpyridin-2-yl)oxy)phenyl)(hydroxy)methyl)-2-(methoxymethyl)-2-methyl-4,7-dihydro-1H-pyrrolo[3',2':5,6]pyrido[3,4-b]pyrazin-3(2H)-one (160 mg, crude product). ES-API $[M+H]^+=548.1$.

Step 3: To a mixed solution of 1,4-dioxane/water (5 mL/1 mL) was added 9-((2-chloro-4-((4-trifluoromethylpyridin-2-yl)oxy)phenyl)(hydroxy)methyl)-2-(methoxymethyl)-2-methyl-4,7-dihydro-1H-pyrrolo[3',2':5,6]pyrido[3,4-b]pyrazin-3 (2H)-one (160 mg, 0.29 mmol), and then 2,3-dichloro-5,6-dicyano-p-benzoquinone (132 mg, 0.58 mmol) was added thereto in batches, stirred at room temperature for 30 minutes, and the reaction was completed. The reaction was quenched by adding 2 mL of aqueous sodium thiosulfate solution, washed with saturated aqueous sodium bicarbonate solution and saturated brine in turn, dried over anhydrous sodium sulfate, filtered, concentrated and purified by preparative HPLC to obtain 9-(2-chloro-4-((4-trifluoromethylpyridin-2-yl)oxy)benzoyl)-2-(methoxymethyl)-2-methyl-4,7-dihydro-1H-pyrrolo[3',2':5,6]pyrido[3,4-b]pyrazin-3 (2H)-one (Z74, 65 mg, 2-step yield of 19.5%). ES-API: $[M+H]^+=546.1$. $^1H$ NMR (400 MHz, DMSO-$d_6$) δ

12.49 (s, 1H), 10.51 (s, 1H), 8.49 (dd, J=5.3, 0.9 Hz, 1H), 8.28 (s, 1H), 7.70 (s, 1H), 7.64 (d, J=8.4 Hz, 1H), 7.62-7.56 (m, 3H), 7.54 (d, J=2.3 Hz, 1H), 7.31 (dd, J=8.4, 2.3 Hz, 1H), 3.65 (d, J=9.5 Hz, 1H), 3.49 (d, J=9.5 Hz, 1H), 3.30 (s, 3H), 1.39 (s, 3H).

Embodiment 79: Synthesis of Z78-1 and Z78-2

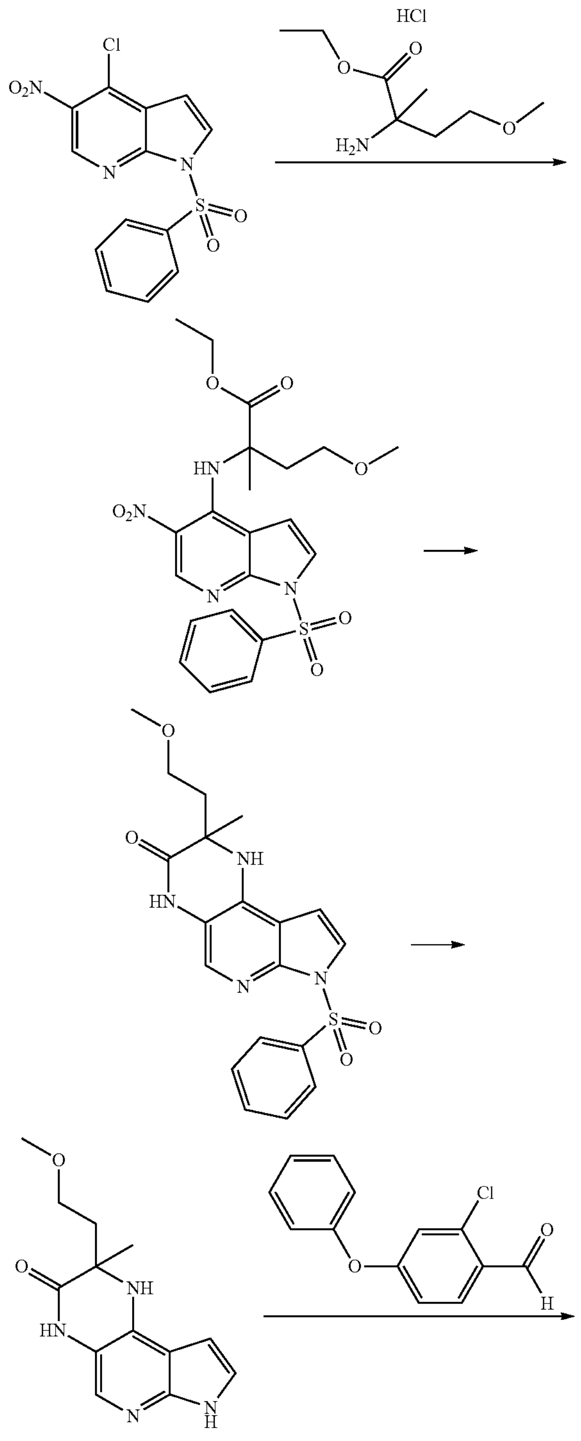

-continued

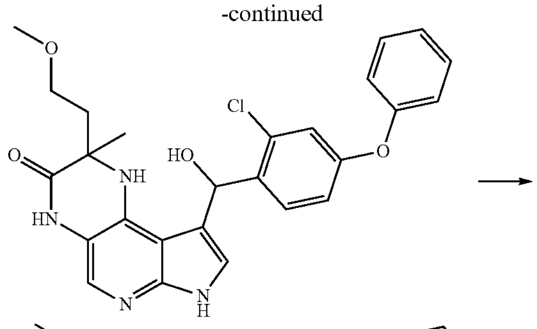

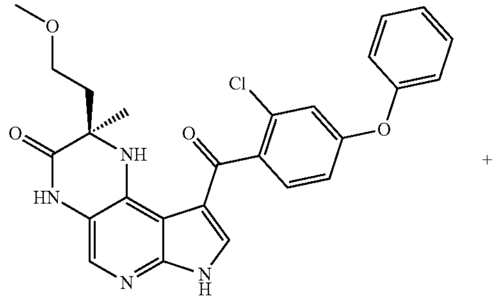

Z78-1

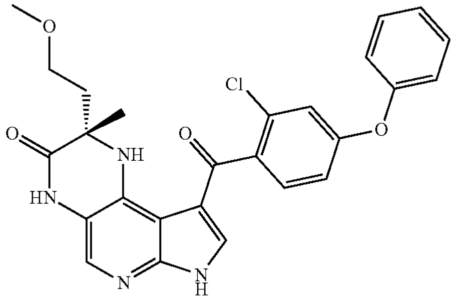

Z78-2

Step 1: 4-Chloro-5-nitro-1-(phenylsulfonyl)-1H-pyrrolo[2,3-b]pyridine (3.0 g, 8.90 mmol) and ethyl 2-amino-4-methoxy-2-methylbutanoate hydrochloride (2.4 g, 11.57 mmol) were dissolved in N,N-dimethylacetamide (30 mL), and N,N-diisopropylethylamine (9.3 mL, 53.40 mmol) was added thereto, and the reaction was stirred at 95° C. for 16 hours. The reaction solution was added with 200 mL of ethyl acetate, washed 3 times with 70 mL of dilute brine and with 70 mL of saturated brine in turn, dried and concentrated, and the crude product was purified by a flash silica gel column (ethyl acetate/petroleum ether: 0-30%) to obtain ethyl 4-methoxy-2-methyl-2-((5-nitro-1-(phenylsulfonyl)-1H-pyrrolo[2,3-b]pyridin-4-yl)amino)butanoate (2.6 g, yield of 61%) as a yellow solid. ES-API: $[M+H]^+$=477.1.

Step 2: Ethyl 4-methoxy-2-methyl-2-((5-nitro-1-(phenylsulfonyl)-1H-pyrrolo[2,3-b]pyridin-4-yl)amino)butanoate (2.5 g, 5.25 mmol) was dissolved in acetic acid (40 mL), and iron powder (2.06 g, 36.75 mmol) was added thereto, and the reaction was stirred at 85° C. for 2 hours. The reaction solution was added with 300 mL of ethyl acetate, washed twice with 80 mL of water, with 80 mL of saturated potassium carbonate, twice with 80 mL of saturated sodium bicarbonate, and with 80 mL of saturated brine in turn, dried and concentrated to obtain 2-(2-methoxyethyl)-2-methyl-7-(phenylsulfonyl)-1,2,4,7-tetrahydro-3H-pyrrolo[3',2':5,6]pyrido[3,4-b]pyrazin-3-one (2.0 g, yield of 95%) as a white solid. ES-API: $[M+H]^+$=401.2

Step 3: 2-(2-Methoxyethyl)-2-methyl-7-(phenylsulfonyl)-1,2,4,7-tetrahydro-3H-pyrrolo[3',2':5,6]pyrido[3,4-b]pyrazin-3-one (1.0 g, 2.50 mmol) was dissolved in 25 mL of methanol, 10 mL of tetrahydrofuran and 5 mL of water, and sodium hydroxide (400 mg, 10.0 mmol) was added thereto, and the reaction was stirred at 55° C. for 16 hours. The pH of the reaction solution was adjusted to 8 with 1.0 M dilute hydrochloric acid, after the reaction solution was concentrated, the crude product was purified by a flash silica gel column (methanol/dichloromethane: 0-10%) to obtain 2-(2-methoxyethyl)-2-methyl-1,2,4,7-tetrahydro-3H-pyrrolo[3',2':5,6]pyrido[3,4-b]pyrazin-3-one (580 mg, yield of 89%) as a light brown solid. ES-API: $[M+H]^+=261.3$.

Step 4: 2-(2-Methoxyethyl)-2-methyl-1,2,4,7-tetrahydro-3H-pyrrolo[3',2':5,6]pyrido[3,4-b]pyrazin-3-one (550 mg, 2.11 mmol) and 2-chloro-4-phenoxybenzaldehyde (1.47 g, 6.33 mmol) were dissolved in methanol (20 mL), and the reaction was cooled to 0° C., and potassium hydroxide (827 mg, 14.77 mmol) was added thereto. The reaction was stirred at room temperature for 2 hours. The pH of the reaction solution was adjusted to 8 with 4.0 M dilute hydrochloric acid, after the reaction solution was concentrated, the crude product was purified by a flash silica gel column (methanol/dichloromethane: 0-10%) to obtain 9-((2-chloro-4-phenoxyphenyl)(hydroxy)methyl)-2-(2-methoxyethyl)-2-methyl-1,2,4,7-tetrahydro-3H-pyrrolo[3',2':5,6]pyrido[3,4-b]pyrazin-3-one (825 mg, yield of 79%) as a light brown solid. ES-API: $[M+H]^+=493.2$.

Step 5: 9-((2-Chloro-4-phenoxyphenyl)(hydroxy)methyl)-2-(2-methoxyethyl)-2-methyl-1,2,4,7-tetrahydro-3H-pyrrolo[3',2':5,6]pyrido[3,4-b]pyrazin-3-one (800 mg, 1.63 mmol) was dissolved in 1,4-dioxane (20 mL) and water (2 mL), and 2,3-dichloro-5,6-dicyano-p-benzoquinone (474 mg, 2.09 mmol) was added thereto, and the reaction was stirred at room temperature for 1 hour. To the reaction solution was added 25 mL of saturated sodium thiosulfate solution and 25 mL of saturated sodium bicarbonate solution, and the mixture was extracted twice with 80 mL of ethyl acetate. The organic phase was washed with 30 mL saturated sodium bicarbonate solution and 30 mL saturated brine in turn, dried and then concentrated, and the crude product was resolved by chiral preparation (separation column IG 250 mm*4.6 mm*5 μm, mobile phase: n-hexane: ethanol=50:50, flow rate: 1 mL/min, column temperature: 30° C.) to obtain two single isomer compounds. One single isomer with a structure arbitrarily designated as Z78-1 (205 mg, peak 1, retention time of 10.078 min, yield of 26%) was a pale yellow solid. $^1H$ NMR (400 MHz, DMSO-$d_6$) δ 12.50 (s, 1H), 10.44 (s, 1H), 8.19 (s, 1H), 7.72 (s, 1H), 7.63 (s, 1H), 7.56 (d, J=8.4 Hz, 1H), 7.53-7.42 (m, 2H), 7.25 (t, J=7.6 Hz, 1H), 7.21-7.15 (m, 3H), 7.02 (dd, J=8.4, 2.4 Hz, 1H), 3.54-3.42 (m, 2H), 3.15 (s, 3H), 2.10-2.03 (m, 1H), 1.89-1.78 (m, 1H), 1.43 (s, 3H). ES-API: $[M+H]^+=491.1$. The other single isomer with a structure arbitrarily designated as Z78-2 (185 mg, peak 2, retention time of 22.662 min, yield of 23%) was a pale yellow solid. $^1H$ NMR (400 MHz, DMSO-$d_6$) δ 12.50 (s, 1H), 10.44 (s, 1H), 8.18 (s, 1H), 7.72 (s, 1H), 7.63 (s, 1H), 7.57 (d, J=8.4 Hz, 1H), 7.52-7.42 (m, 2H), 7.25 (t, J=7.6 Hz, 1H), 7.21-7.15 (m, 3H), 7.02 (dd, J=8.4, 2.4 Hz, 1H), 3.54-3.42 (m, 2H), 3.15 (s, 3H), 2.10-2.03 (m, 1H), 1.89-1.77 (m, 1H), 1.43 (s, 3H). ES-API: $[M+H]^+=491.1$.

Embodiment 80: Synthesis of Z79

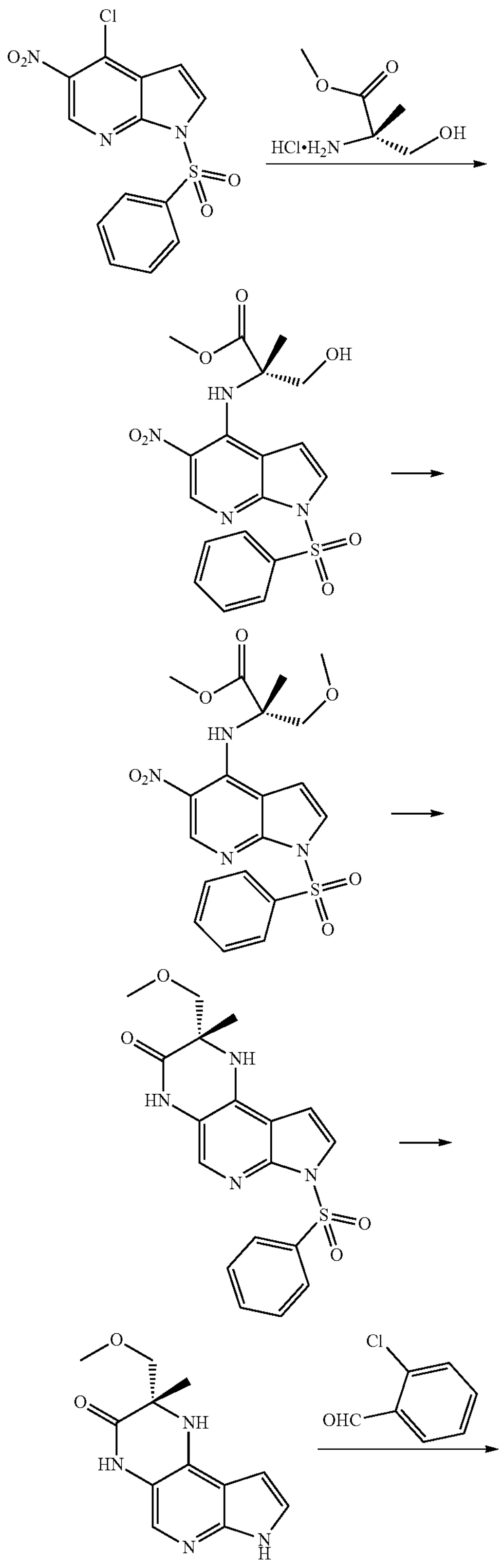

-continued

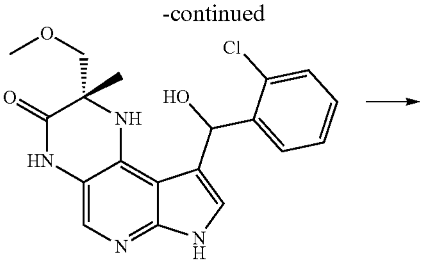

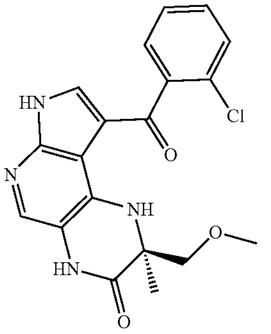

Z79

Step 1: 4-Chloro-5-nitro-1-(phenylsulfonyl)-1H-pyrrolo[2,3-b]pyridine (1.5 g, 4.451 mmol) and methyl (S)-2-amino-3-hydroxy-2-methylpropanoate hydrochloride (1.5 g, 8.902 mmol) were dissolved in N,N-dimethylacetamide (30 mL), and N,N-diisopropylethylamine (7.64 g, 59.15 mmol) was added thereto, and the reaction was stirred at 95° C. for 16 hours. The reaction solution was added with 100 mL of ethyl acetate, washed twice with 60 mL of water and 3 times with 30 mL of saturated brine, dried and concentrated, and the crude product was purified by a flash silica gel column (ethyl acetate/petroleum ether: 0-50%) to obtain methyl (S)-3-hydroxy-2-methyl-2-((5-nitro-1-(phenylsulfonyl)-1H-pyrrolo[2,3-b]pyridin-4-yl)amino)propanoate (1.3 g, yield of 67%) as a pale yellow solid. ES-API: $[M+H]^+$=435.1.

Step 2: Methyl (S)-3-hydroxy-2-methyl-2-((5-nitro-1-(phenylsulfonyl)-1H-pyrrolo[2,3-b]pyridin-4-yl)amino)propanoate (1.30 g, 2.9947 mmol) was dissolved in acetonitrile (40 mL), and silver oxide (10.41 g, 44.92 mmol) and iodomethane (6.38 g, 44.92 mmol) were added thereto in turn, and the mixture was stirred in the dark at room temperature for 48 hours under nitrogen atmosphere. After the reaction was completed, the reaction solution was filtered through diatomite, and the filtrate was evaporated to dryness by rotary evaporation under reduced pressure. The crude product was purified by a flash silica gel column (ethyl acetate/petroleum ether: 0-50%) to obtain methyl (S)-3-methoxy-2-methyl-2-((5-nitro-1-(phenylsulfonyl)-1H-pyrrolo[2,3-b]pyridin-4-yl)amino)propanoate (1.41 g, crude product) as a yellow solid. ES-API: $[M+H]^+$ 449.0.

Step 3: Methyl (S)-3-methoxy-2-methyl-2-((5-nitro-1-(phenylsulfonyl)-1H-pyrrolo[2,3-b]pyridin-4-yl)amino)propanoate (1.41 g, crude product) was dissolved in acetic acid (40 mL), and iron powder (2.52 g, 44.99 mmol) was added thereto. The mixture was gradually heated to 80° C. and stirred for 1 hour. After the reaction was completed, the solvent was evaporated to dryness by rotary evaporation under reduced pressure, then 200 mL of ethyl acetate was added thereto. The mixture was washed twice with 80 mL of water, twice with 60 mL of saturated sodium carbonate, twice with 80 mL of saturated sodium bicarbonate, and with 80 mL of saturated brine in turn, dried and concentrated, and the crude product was slurried with ethyl acetate to obtain (S)-2-(methoxymethyl)-2-methyl-7-(phenylsulfonyl)-1,2,4,7-tetrahydro-3H-pyrrolo[3',2':5,6]pyrido[3,4-b]pyrazin-3-one (1.05 g, yield of 90.8%) as a yellow solid. ES-API: $[M+H]^+$=387.2

Step 4: (S)-2-(Methoxymethyl)-2-methyl-7-(phenylsulfonyl)-1,2,4,7-tetrahydro-3H-pyrrolo[3',2':5,6]pyrido[3,4-b]pyrazin-3-one (1.05 g, 2.7187 mmol) was dissolved in 36 mL of methanol, 9 mL of tetrahydrofuran and 6 mL of water, and sodium hydroxide (761.0 mg, 19.03 mmol) was added thereto, and the reaction was stirred at 65° C. for 7 hours. To the reaction solution was added 20 mL of water and 15 mL of saturated ammonium chloride solution, and the mixture was extracted with 150 mL of ethyl acetate. The organic phase was washed with 30 mL of saturated sodium bicarbonate solution and 80 mL of saturated brine in turn, dried over anhydrous sodium sulfate and then concentrated to obtain (S)-2-(methoxymethyl)-2-methyl-1,2,4,7-tetrahydro-3H-pyrrolo[3',2':5,6]pyrido[3,4-b]pyrazin-3-one (2.20 g, crude product) as a pale white solid. ES-API: $[M+H]^+$=247.1.

Step 5: (S)-2-(Methoxymethyl)-2-methyl-1,2,4,7-tetrahydro-3H-pyrrolo[3',2':5,6]pyrido[3,4-b]pyrazin-3-one (209 mg, crude product) and 2-chlorobenzaldehyde (80 mg, 0.5181 mmol) were dissolved in methanol (10.0 mL), and the reaction was cooled to 0° C., and potassium hydroxide (100 mg, 1.785 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and then concentrated to obtain a crude target product (2S)-9-((2-chlorophenyl)(hydroxyl)methyl)-2-(methoxymethyl)-2-methyl-1,2,4,7-tetrahydro-3H-pyrrolo[3',2':5,6]pyrido[3,4-b]pyrazin-3-one (80 mg, 2-step yield of 80%) as a pale yellow solid. ES-API: $[M+H]^+$=387.3.

Step 6: (2S)-9-((2-Chlorophenyl)(hydroxyl)methyl)-2-(methoxymethyl)-2-methyl-1,2,4,7-tetrahydro-3H-pyrrolo[3',2':5,6]pyrido[3,4-b]pyrazin-3-one (80 mg, 0.2071 mmol) was dissolved in 10 mL of tetrahydrofuran, and 2,3-dichloro-5,6-dicyano-1,4-benzoquinone (94 mg, 0.4142 mmol) was added thereto, and the reaction was stirred at room temperature for 2 hours. To the reaction solution was added 60 mL of saturated sodium bicarbonate solution, and the mixture was extracted with 80 mL of ethyl acetate. The organic phase was washed with 60 mL of saturated brine, dried over anhydrous sodium sulfate and then concentrated, and the crude product was purified by preparative HPLC to obtain (S)-9-(2-chlorobenzoyl)-2-(methoxymethyl)-2-methyl-1,2,4,7-tetrahydro-3H-pyrrolo[3',2':5,6]pyrido[3,4-b]pyrazin-3-one (Z79, 22 mg, yield of 28%) as a pale yellow solid, ES-API: $[M+H]^+$=385.1. $^1H$ NMR (500 MHz, DMSO-$d_6$) δ 12.43 (s, 1H), 10.49 (s, 1H), 8.29 (s, 1H), 7.70 (s, 1H), 7.56 (dt, J=26.0, 6.7 Hz, 3H), 7.49-7.42 (m, 2H), 3.65 (d, J=9.5 Hz, 1H), 3.48 (d, J=9.6 Hz, 1H), 3.30 (s, 3H), 1.39 (s, 3H).

Embodiment 81: Synthesis of Z122

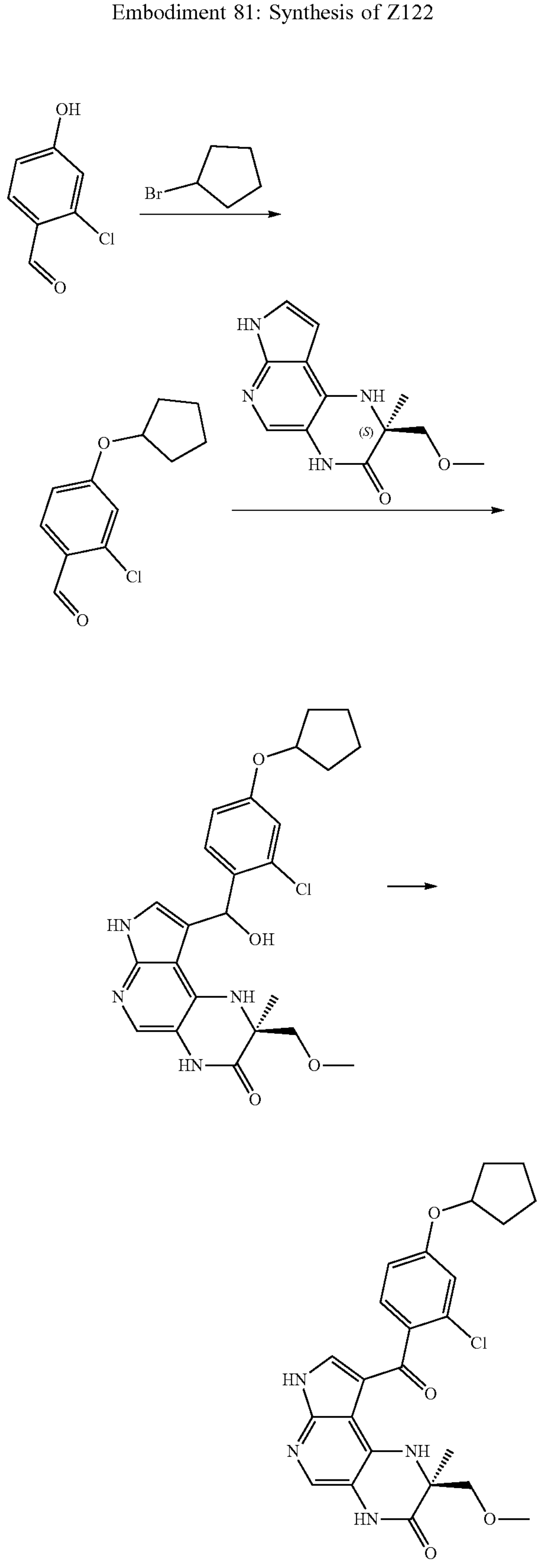

Z122

Step 1: 2-Chloro-4-hydroxybenzaldehyde (500 mg, 3.193 mmol), bromocyclopentane (476 mg, 3.193 mmol) and potassium carbonate (883 mg, 6.383 mmol) were dissolved in N,N-dimethylformamide (15 mL), and the reaction was stirred at 90° C. for 3 hours, and LCMS detected that the reaction was complete. The reaction solution was cooled to room temperature, added with 30 mL of ethyl acetate, washed once with 30 mL of water and washed with saturated brine (25 mL×3) respectively, and the organic phase was dried over anhydrous sodium sulfate, filtered, and the filtrate was concentrated to dryness under reduced pressure to obtain 2-chloro-4-(cyclopentyloxy)benzaldehyde (560 mg, yield of 78%) as a pale yellow liquid. ES-API: $[M+H]^+$=225.1

Step 2: (S)-2-(Methoxymethyl)-2-methyl-1,2,4,7-tetrahydro-3H-pyrrolo[3',2':5,6]pyrido[3,4-b]pyrazin-3-one (36.5 mg, 0.148 mmol) and 2-chloro-4-(cyclopentyloxy)benzaldehyde (83 mg, 0.371 mmol) were dissolved in methanol (6 mL), and the reaction solution was cooled to 0° C., and potassium hydroxide (58 mg, 1.036 mmol) was added thereto. The reaction was stirred at room temperature for 24 hours. LCMS detected that the reaction was complete. The reaction was quenched by adding 20 mL of saturated ammonium chloride solution, extracted with ethyl acetate (15 mL×3). The organic phase was washed with 20 mL of saturated brine, dried over anhydrous sodium sulfate and then concentrated to obtain a crude product (2S)-9-((2-chloro-4-(cyclopentyloxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (70 mg, yield of 100%). ES-API: $[M+H]^+$=471.3

Step 3: (2S)-9-((2-Chloro-4-(cyclopentyloxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (70 mg, 0.149 mmol) was dissolved in 10 mL of tetrahydrofuran, and 2,3-dichloro-5,6-dicyano-p-benzoquinone (78 mg, 0.346 mmol) was added thereto, and the reaction was stirred at room temperature for 2 hours. To the reaction solution was added 20 mL of saturated sodium thiosulfate solution and 20 mL of saturated sodium bicarbonate solution, and the mixture was extracted with 30 mL of ethyl acetate. The organic phase was washed with 15 mL of saturated brine, dried and then concentrated, and the crude product was purified by preparative HPLC to obtain a pale yellow solid (S)-9-(2-chloro-4-(cyclopentyloxy)benzoyl)-2-(methoxymethyl)-2-methyl-1,2,4,7-tetrahydro-3H-pyrrolo[3',2':5,6]pyrido[3,4-b]pyrazin-3-one (Z122, 17.88 mg, yield of 26%). ES-API: $[M+H]^+$=469.1. $^1H$ NMR (500 MHz, DMSO-$d_6$) δ 10.48 (bs, 1H), 8.30 (s, 1H), 7.68 (s, 1H), 7.50 (s, 1H), 7.45 (d, J=8.5 Hz, 1H), 7.08 (d, J=2.5 Hz, 1H), 6.96 (dd, J1=3.0 Hz, J2=8.5 Hz, 1H), 4.96-4.92 (m, 1H), 3.64 (d, J=9.5 Hz, 1H), 3.46 (d, J=9.0 Hz, 1H), 3.29 (s, 3H), 1.99-1.92 (m, 2H), 1.78-1.68 (m, 4H), 1.65-1.58 (m, 2H), 1.38 (s, 3H).

With reference to the preparation method of Embodiment 80 or 81, the following compounds were prepared by changing some raw materials:

| Embodiment | Compound No. | Structure | MS [M + H]+ |
|---|---|---|---|
| 82 | Z80 | 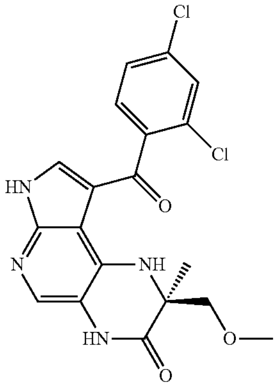 | 419.1 |
| 83 | Z81 | 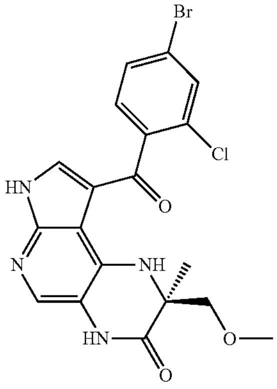 [SMILES: COC[C@]1(C)Nc2c(cnc3[nH]cc(C(=O)c4ccc(Br)cc4Cl)c23)NC1=O] | 463.0 |
| 84 | Z82 | 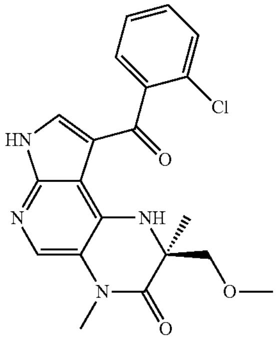 [SMILES: COC[C@]1(C)Nc2c(cnc3[nH]cc(C(=O)c4ccccc4Cl)c23)N(C)C1=O] | 399.1 |
| 85 | Z83 | 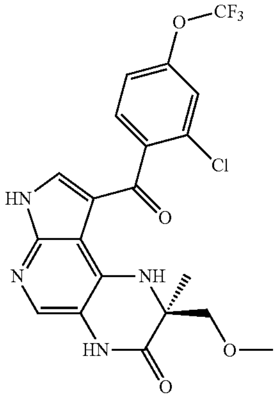 [SMILES: COC[C@]1(C)Nc2c(cnc3[nH]cc(C(=O)c4ccc(OC(F)(F)F)cc4Cl)c23)NC1=O] | 469.1 |
-continued
| Embodiment | Compound No. | Structure | MS [M + H]+ |
|---|---|---|---|
| 86 | Z84 | 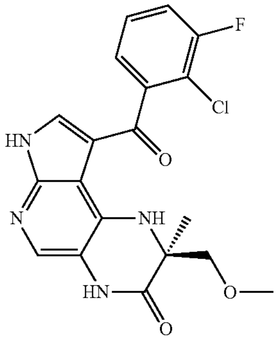 [SMILES: COC[C@]1(C)Nc2c(cnc3[nH]cc(C(=O)c4cccc(F)c4Cl)c23)NC1=O] | 403.1 |
| 87 | Z85 | 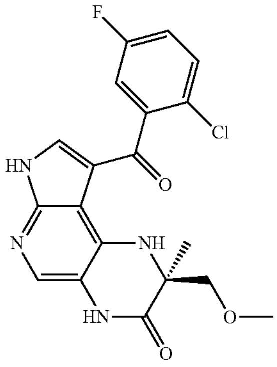 [SMILES: COC[C@]1(C)Nc2c(cnc3[nH]cc(C(=O)c4cc(F)ccc4Cl)c23)NC1=O] | 403.1 |
| 88 | Z86 | 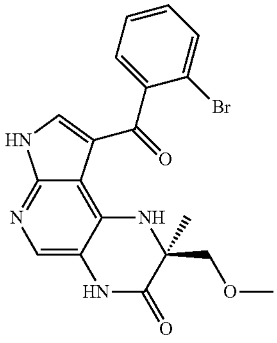 [SMILES: COC[C@]1(C)Nc2c(cnc3[nH]cc(C(=O)c4ccccc4Br)c23)NC1=O] | 429.0 |
| 89 | Z87 | 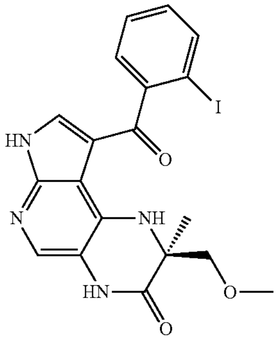 [SMILES: COC[C@]1(C)Nc2c(cnc3[nH]cc(C(=O)c4ccccc4I)c23)NC1=O] | 477.0 |

-continued
| Embodiment | Compound No. | Structure | MS [M + H]+ |
|---|---|---|---|
| 90 | Z88 | 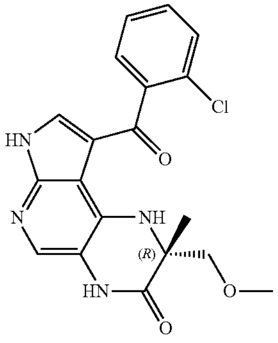 | 385.1 |
| 91 | Z89 | 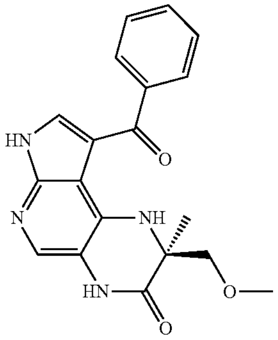 [SMILES: COC[C@]1(C)Nc2c(cnc3[nH]cc(C(=O)c4ccccc4)c23)NC1=O] | 351.1 |
| 92 | Z90 | 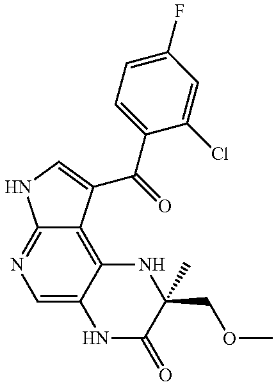 [SMILES: COC[C@]1(C)Nc2c(cnc3[nH]cc(C(=O)c4ccc(F)cc4Cl)c23)NC1=O] | 403.1 |
| 93 | Z91 | 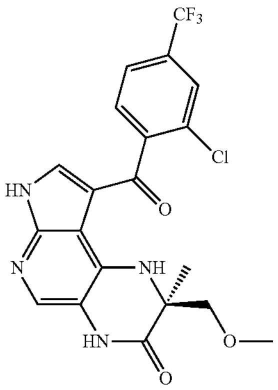 | 453.1 |
-continued
| Embodiment | Compound No. | Structure | MS [M + H]+ |
|---|---|---|---|
| 94 | Z92 | 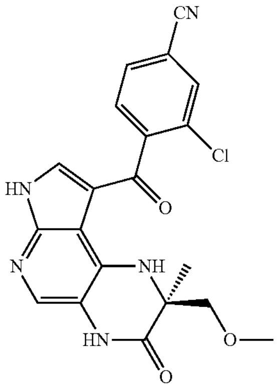 [SMILES: COC[C@]1(C)Nc2c(cnc3[nH]cc(C(=O)c4ccc(C#N)cc4Cl)c23)NC1=O] | 410.1 |
| 95 | Z93 | 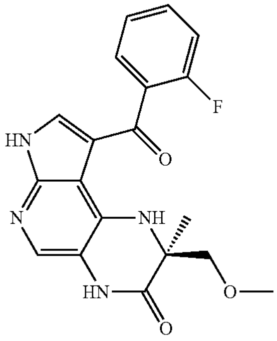 [SMILES: COC[C@]1(C)Nc2c(cnc3[nH]cc(C(=O)c4ccccc4F)c23)NC1=O] | 369.1 |
| 96 | Z94 | 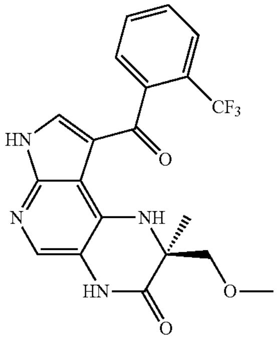 [SMILES: COC[C@]1(C)Nc2c(cnc3[nH]cc(C(=O)c4ccccc4C(F)(F)F)c23)NC1=O] | 419.1 |
| 97 | Z95 | 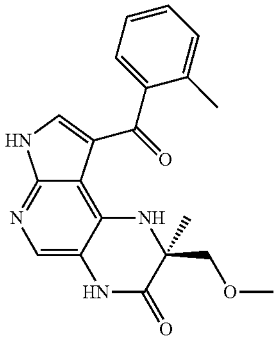 [SMILES: COC[C@]1(C)Nc2c(cnc3[nH]cc(C(=O)c4ccccc4C)c23)NC1=O] | 365.2 |

-continued
| Embodiment | Compound No. | Structure | MS [M + H]+ |
|---|---|---|---|
| 98 | Z96 | 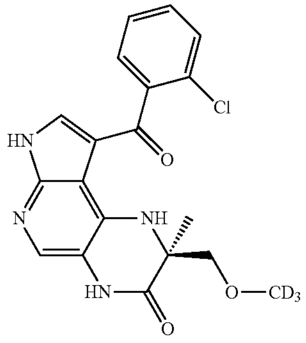 [SMILES: [2H]C([2H])([2H])OC[C@]1(C)Nc2c(cnc3[nH]cc(C(=O)c4ccccc4Cl)c23)NC1=O] | 388.1 |
| 99 | Z97 | 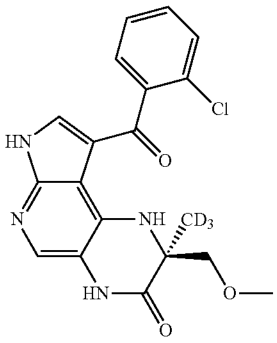 [SMILES: [2H]C([2H])([2H])[C@@]1(COC)Nc2c(cnc3[nH]cc(C(=O)c4ccccc4Cl)c23)NC1=O] | 388.1 |
| 100 | Z98 | 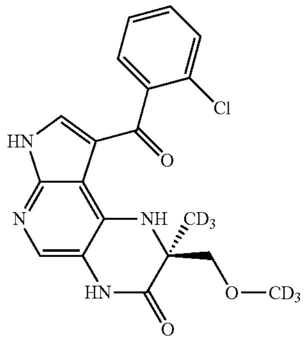 [SMILES: [2H]C([2H])([2H])OC[C@]1(C([2H])([2H])[2H])Nc2c(cnc3[nH]cc(C(=O)c4ccccc4Cl)c23)NC1=O] | 391.1 |
| 101 | Z99 | 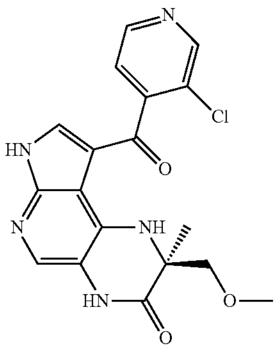 [SMILES: COC[C@]1(C)Nc2c(cnc3[nH]cc(C(=O)c4ccncc4Cl)c23)NC1=O] | 386.1 |
-continued
| Embodiment | Compound No. | Structure | MS [M + H]+ |
|---|---|---|---|
| 102 | Z100 | 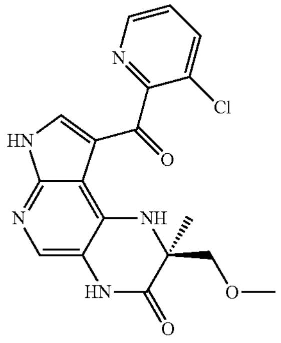 [SMILES: COC[C@]1(C)Nc2c(cnc3[nH]cc(C(=O)c4ncccc4Cl)c23)NC1=O] | 386.1 |
| 103 | Z101 | 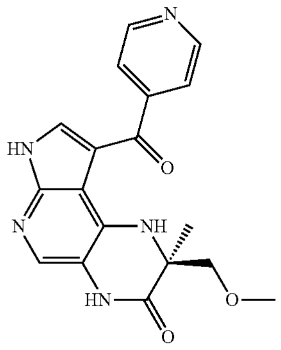 [SMILES: COC[C@]1(C)Nc2c(cnc3[nH]cc(C(=O)c4ccncc4)c23)NC1=O] | 352.1 |
| 104 | Z102 | 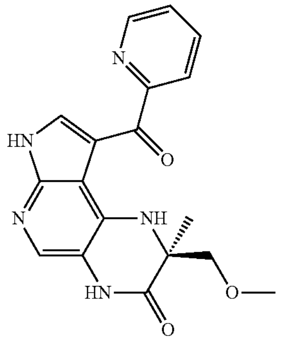 [SMILES: COC[C@]1(C)Nc2c(cnc3[nH]cc(C(=O)c4ccccn4)c23)NC1=O] | 352.1 |
| 105 | Z103 | 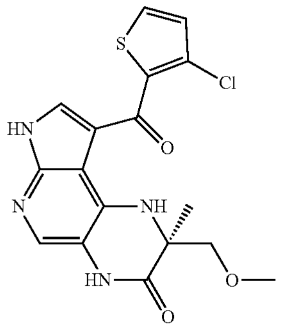 [SMILES: COC[C@]1(C)Nc2c(cnc3[nH]cc(C(=O)c4sccc4Cl)c23)NC1=O] | 391.1 |

-continued
| Embodiment | Compound No. | Structure | MS [M + H]+ |
|---|---|---|---|
| 106 | Z104 | 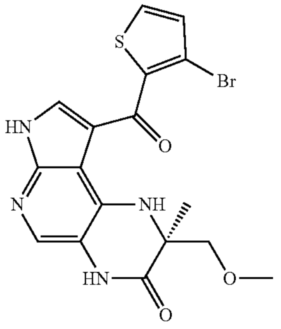 [SMILES: COC[C@]1(C)Nc2c(cnc3[nH]cc(C(=O)c4sccc4Br)c23)NC1=O] | 435.0 |
| 107 | Z105 | 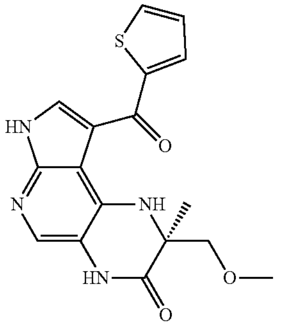 [SMILES: COC[C@]1(C)Nc2c(cnc3[nH]cc(C(=O)c4cccs4)c23)NC1=O] | 357.1 |
| 108 | Z106 | 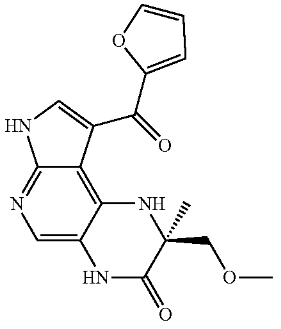 [SMILES: COC[C@]1(C)Nc2c(cnc3[nH]cc(C(=O)c4ccco4)c23)NC1=O] | 341.1 |
| 109 | Z107 | 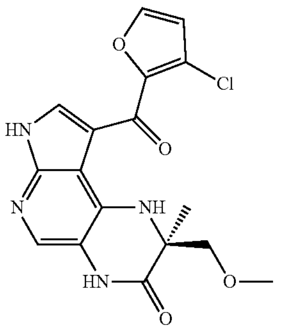 [SMILES: COC[C@]1(C)Nc2c(cnc3[nH]cc(C(=O)c4occc4Cl)c23)NC1=O] | 375.1 |
-continued
| Embodiment | Compound No. | Structure | MS [M + H]+ |
|---|---|---|---|
| 110 | Z108 | 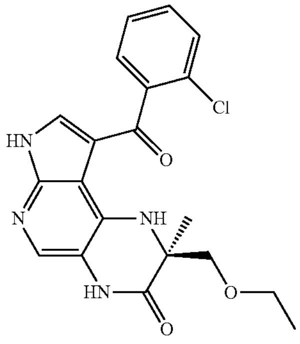 [SMILES: CCOC[C@]1(C)Nc2c(cnc3[nH]cc(C(=O)c4ccccc4Cl)c23)NC1=O] | 399.1 |
| 111 | Z109 | 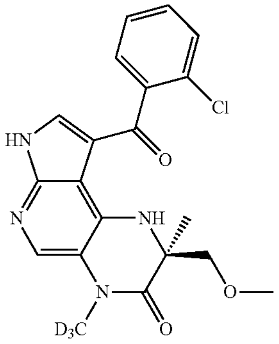 [SMILES: [2H]C([2H])([2H])N1C(=O)[C@](C)(COC)Nc2c1cnc1[nH]cc(C(=O)c3ccccc3Cl)c21] | 402.1 |
| 112 | Z110 | 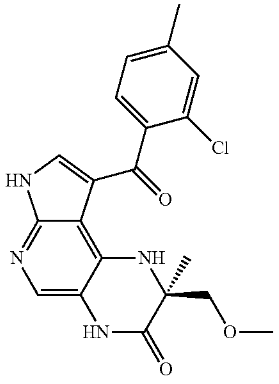 [SMILES: COC[C@]1(C)Nc2c(cnc3[nH]cc(C(=O)c4ccc(C)cc4Cl)c23)NC1=O] | 399.1 |
| 113 | Z111 | 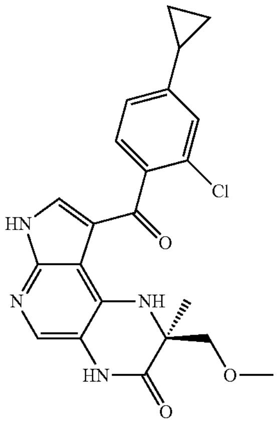 [SMILES: COC[C@]1(C)Nc2c(cnc3[nH]cc(C(=O)c4ccc(C5CC5)cc4Cl)c23)NC1=O] | 425.1 |

-continued
| Embodiment | Compound No. | Structure | MS [M + H]+ |
| --- | --- | --- | --- |
| 114 | Z112 | 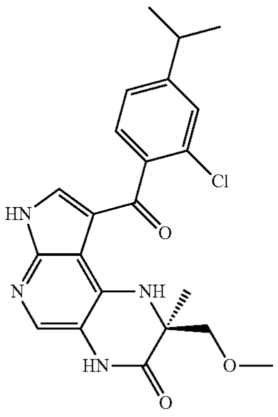 [SMILES: COC[C@]1(C)Nc2c(cnc3[nH]cc(C(=O)c4ccc(C(C)C)cc4Cl)c23)NC1=O] | 427.1 |
| 115 | Z113 | 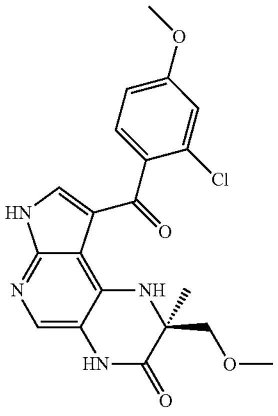 [SMILES: COC[C@]1(C)Nc2c(cnc3[nH]cc(C(=O)c4ccc(OC)cc4Cl)c23)NC1=O] | 415.1 |
| 116 | Z114 | 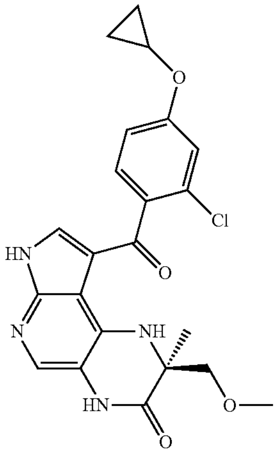 [SMILES: COC[C@]1(C)Nc2c(cnc3[nH]cc(C(=O)c4ccc(OC5CC5)cc4Cl)c23)NC1=O] | 441.1 |
-continued
| Embodiment | Compound No. | Structure | MS [M + H]+ |
| --- | --- | --- | --- |
| 117 | Z115 | 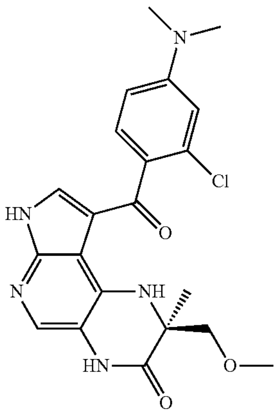 [SMILES: COC[C@]1(C)Nc2c(cnc3[nH]cc(C(=O)c4ccc(N(C)C)cc4Cl)c23)NC1=O] | 428.1 |
| 118 | Z116 | 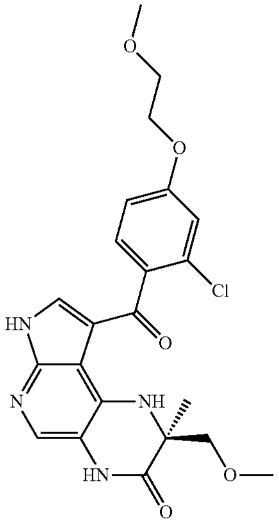 [SMILES: COCCOc1ccc(C(=O)c2c[nH]c3ncc4c(c23)N[C@@](C)(COC)C(=O)N4)c(Cl)c1] | 459.1 |
| 119 | Z117 | 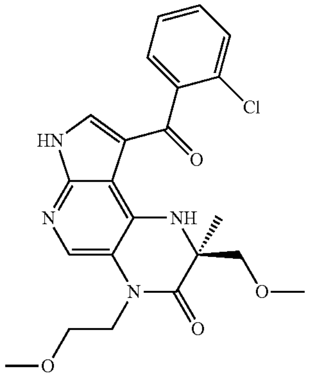 | 443.1 |

-continued
| Embodiment | Compound No. | Structure | MS [M + H]+ |
|---|---|---|---|
| 120 | Z118 | 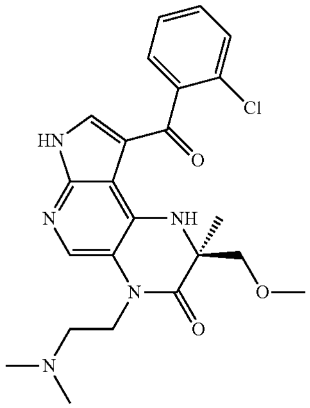 | 456.2 |
| 121 | Z119 | 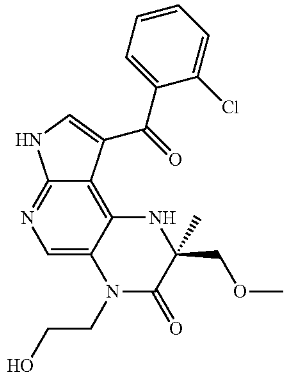 [SMILES: COC[C@]1(C)Nc2c(cnc3[nH]cc(C(=O)c4ccccc4Cl)c23)N(CCO)C1=O] | 429.1 |
| 122 | Z120 | 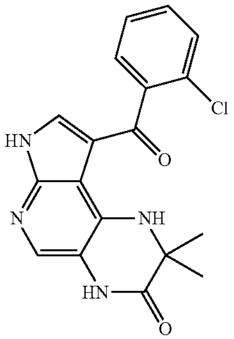 [SMILES: CC1(C)Nc2c(cnc3[nH]cc(C(=O)c4ccccc4Cl)c23)NC1=O] | 355.1 |
| 123 | Z121 | 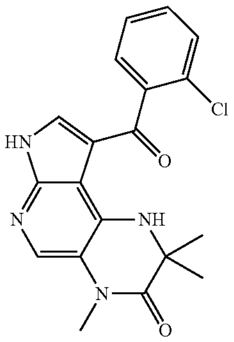 [SMILES: CN1C(=O)C(C)(C)Nc2c1cnc1[nH]cc(C(=O)c3ccccc3Cl)c21] | 369.1 |
Embodiment 124: Synthesis of Z124-1
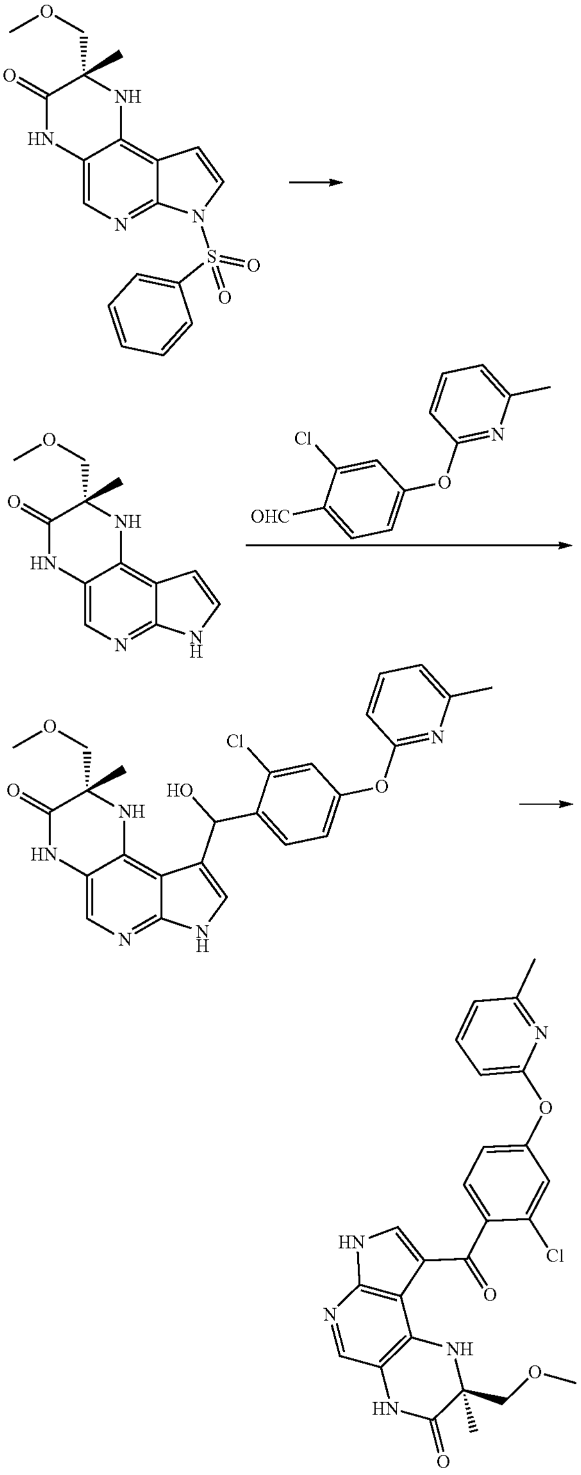
Z124-1
Step 1: (S)-2-(Methoxymethyl)-2-methyl-7-(phenylsulfonyl)-1,2,4,7-tetrahydro-3H-pyrrolo[3',2':5,6]pyrido[3,4-b]pyrazin-3-one (1.40 g, 3.570 mmol) was dissolved in 36 mL of methanol, 9 mL of tetrahydrofuran and 6 mL of water, and sodium hydroxide (1.01 g, 24.99 mmol) was added thereto, and the reaction was stirred at 65° C. for 7 hours. To the reaction solution was added 20 mL of water and 15 mL of saturated ammonium chloride solution, and the mixture was extracted with 200 mL of ethyl acetate. The organic phase was washed with 30 mL of saturated sodium bicarbonate solution and 80 mL of saturated brine in turn, dried over anhydrous sodium sulfate and then concentrated to obtain (S)-2-(methoxymethyl)-2-methyl-1,2,4,7-tetrahydro-3H-pyrrolo[3',2':5,6]pyrido[3,4-b]pyrazin-3-one (0.58 g, crude yield of 66%) as a pale white solid. ES-API: $[M+H]^+=247.1$.

Step 2: (S)-2-(Methoxymethyl)-2-methyl-1,2,4,7-tetrahydro-3H-pyrrolo[3',2':5,6]pyrido[3,4-b]pyrazin-3-one (480 mg, 1.950 mmol) and 2-chloro-4-((6-methylpyridin-2-yl)oxy)benzaldehyde (750 mg, 3.036 mmol) were dissolved in methanol (20.0 mL), and the reaction was cooled to 0° C., and potassium hydroxide (152 mg, 2.720 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and then concentrated to obtain a crude target product (2S)-9-((2-chloro-4-((6-methylpyridin-2-yl)oxy)phenyl)(hydroxyl)methyl)-2-(methoxymethyl)-2-methyl-1,2,4,7-tetrahydro-3H-pyrrolo[3',2':5,6]pyrido[3,4-b]pyrazin-3-one (1.10 g, crude product) as a pale yellow solid. ES-API: $[M+H]^+=494.2$.

Step 3: (2S)-9-((2-Chloro-4-((6-methylpyridin-2-yl)oxy)phenyl)(hydroxyl)methyl)-2-(methoxymethyl)-2-methyl-1,2,4,7-tetrahydro-3H-pyrrolo[3',2':5,6]pyrido[3,4-b]pyrazin-3-one (400 mg, crude product) was dissolved in 10 mL of tetrahydrofuran, and 2,3-dichloro-5,6-dicyano-1,4-benzoquinone (400 mg, 1.762 mmol) was added thereto, and the reaction was stirred at room temperature for 2 hours. To the reaction solution was added 60 mL of saturated sodium bicarbonate solution, and the mixture was extracted with 80 mL of ethyl acetate. The organic phase was washed with 60 mL of saturated brine, dried over anhydrous sodium sulfate and then concentrated, and the crude product was purified by preparative HPLC to obtain (S)-9-(2-chloro-4-((6-methylpyridin-2-yl)oxy)benzoyl)-2-(methoxymethyl)-2-methyl-1,2,4,7-tetrahydro-3H-pyrrolo[3',2':5,6]pyrido[3,4-b]pyrazin-3-one (Z124-1, 12 mg, 2-step yield of 6%) as a pale yellow solid, ES-API: $[M+H]^+=492.1$. $^1H$ NMR (400 MHz, DMSO-$d_6$)[1] δ 8.29 (s, 1H), 7.80 (t, J=7.7 Hz, 1H), 7.70 (s, 1H), 7.59 (d, J=7.1 Hz, 2H), 7.38 (d, J=2.1 Hz, 1H), 7.22-7.17 (m, 1H), 7.09 (d, J=7.3 Hz, 1H), 6.92 (d, J=8.1 Hz, 1H), 3.65 (d, J=9.4 Hz, 1H), 3.48 (d, J=9.5 Hz, 1H), 3.30 (s, 3H), 2.38 (s, 3H), 1.39 (s, 3H).

Embodiment 125: Synthesis of Z125-1

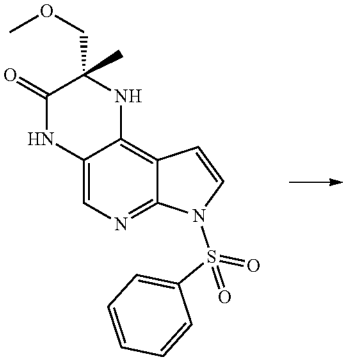

-continued

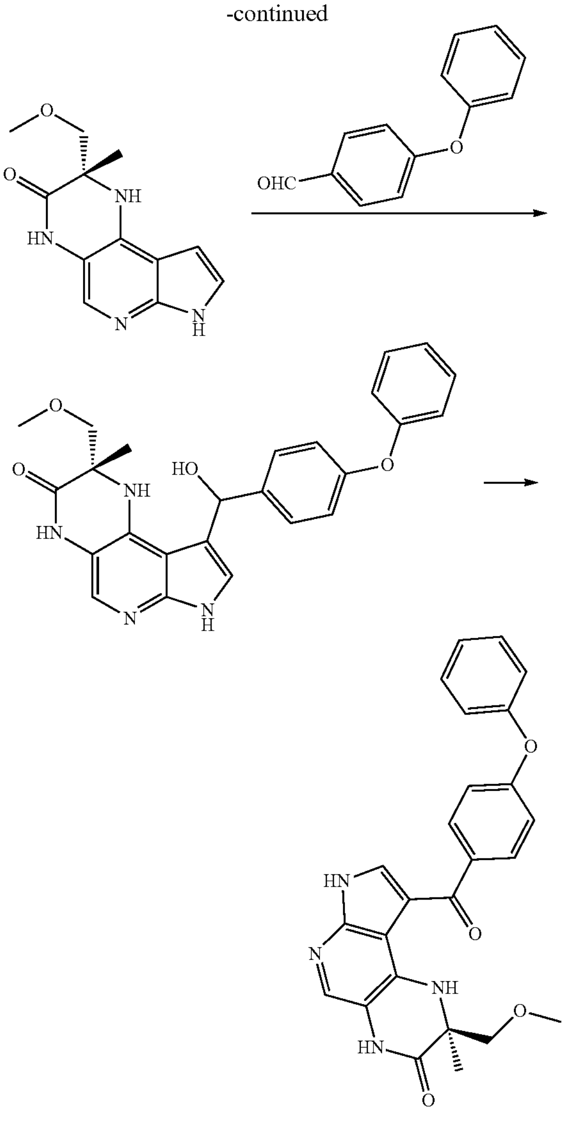

Z125-1

Step 1: (S)-2-(Methoxymethyl)-2-methyl-7-(phenylsulfonyl)-1,2,4,7-tetrahydro-3H-pyrrolo[3',2':5,6]pyrido[3,4-b]pyrazin-3-one (0.40 g, 2.7187 mmol) was dissolved in 12 mL of methanol, 3 mL of tetrahydrofuran and 2 mL of water, and sodium hydroxide (290.0 mg, 7.252 mmol) was added thereto, and the reaction was stirred at 65° C. for 7 hours. To the reaction solution was added 20 mL of water and 15 mL of saturated ammonium chloride solution, and the mixture was extracted with 150 mL of ethyl acetate. The organic phase was washed with 30 mL of saturated sodium bicarbonate solution and 80 mL of saturated brine in turn, dried over anhydrous sodium sulfate and then concentrated to obtain (S)-2-(methoxymethyl)-2-methyl-1,2,4,7-tetrahydro-3H-pyrrolo[3',2':5,6]pyrido[3,4-b]pyrazin-3-one (0.70 g, crude product) as a pale white solid. ES-API: $[M+H]^+=247.1$.

Step 2: (S)-2-(Methoxymethyl)-2-methyl-1,2,4,7-tetrahydro-3H-pyrrolo[3',2':5,6]pyrido[3,4-b]pyrazin-3-one (209 mg, crude product) and 4-phenoxybenzaldehyde (410 mg, 2.072 mmol) were dissolved in methanol (20.0 mL), and the reaction was cooled to 0° C., and potassium hydroxide (406 mg, 7.252 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and then concentrated to obtain a crude target product (2S)-9-(hydroxy(4-phenoxyphenyl)methyl)-2-(methoxymethyl)-2-methyl-1,2,4,7-tetrahydro-3H-pyrrolo[3',2':5,6]pyrido[3,4-b]pyrazin-3-one (300 mg, 2-step yield of 67%) as a pale yellow solid. ES-API: $[M+H]^+$=445.1.1.

Step 3: (2S)-9-(Hydroxy(4-phenoxyphenyl)methyl)-2-(methoxymethyl)-2-methyl-1,2,4,7-tetrahydro-3H-pyrrolo[3',2':5,6]pyrido[3,4-b]pyrazin-3-one (300 mg, 0.6548 mmol) was dissolved in 20 mL of tetrahydrofuran, and 2,3-dichloro-5,6-dicyano-1,4-benzoquinone (300 mg, 1.321 mmol) was added thereto, and the reaction was stirred at room temperature for 2 hours. To the reaction solution was added 60 mL of saturated sodium bicarbonate solution, and the mixture was extracted with 80 mL of ethyl acetate. The organic phase was washed with 60 mL of saturated brine, dried over anhydrous sodium sulfate and then concentrated, and the crude product was purified by preparative HPLC to obtain (S)-2-(methoxymethyl)-2-methyl-9-(4-phenoxybenzoyl)-1,2,4,7-tetrahydro-3H-pyrrolo[3',2':5,6]pyrido[3,4-b]pyrazin-3-one (Z125-1, 20 mg, yield of 7%) as a pale yellow solid, ES-API: $[M+H]^+$=443.2. $^1H$ NMR (400 MHz, DMSO-d6) δ 12.39 (s, 1H), 10.46 (s, 1H), 8.30 (s, 1H), 7.82 (d, J=8.8 Hz, 3H), 7.69 (s, 1H), 7.56-7.43 (m, 2H), 7.25 (d, J=7.4 Hz, 1H), 7.19-7.14 (m, 2H), 7.08 (d, J=8.7 Hz, 2H), 3.64 (d, J=9.4 Hz, 1H), 3.46 (d, J=9.5 Hz, 1H), 3.28 (s, 3H), 1.37 (s, 3H).

Embodiment 126: Synthesis of Z126

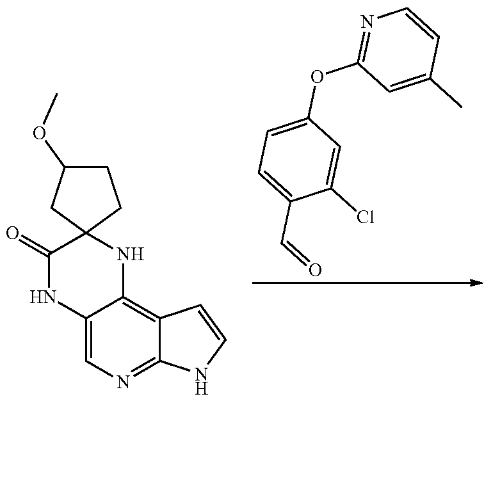

-continued

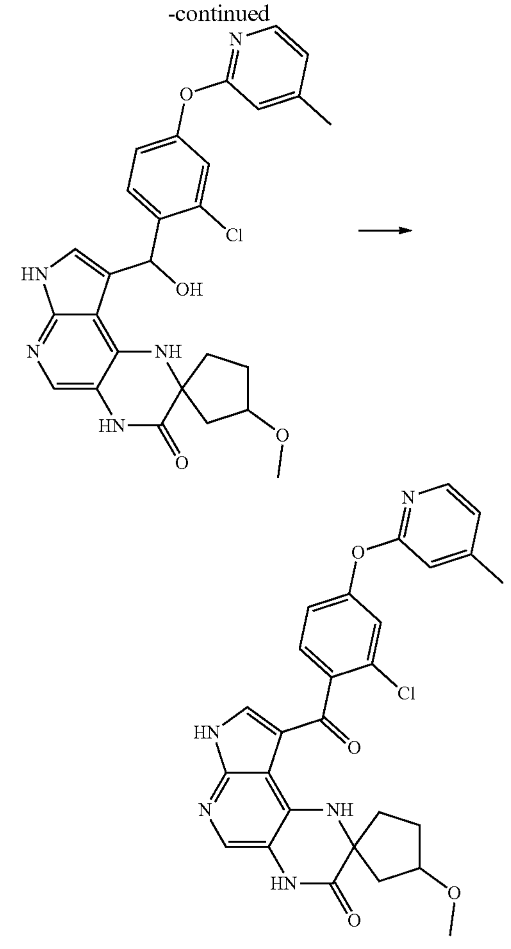

Z126

Step 1: 3-Methoxy-4',7'-dihydrospiro[cyclopentane-1,2'-pyrrolo[3',2':5,6]pyrido[3,4-b]pyrazin]-3'(1'H)-one (50 mg, 0.18 mmol) and 2-chloro-4-((4-methylpyridin-2-yl)oxy)benzaldehyde (89 mg, 0.36 mmol) were dissolved in methanol (20 mL), and the reaction was cooled to 0° C., and potassium hydroxide (71 mg, 1.26 mmol) was added thereto. The reaction was stirred at room temperature for 16 hours. The reaction solution was poured into 30 mL of water, and the pH of the reaction solution was adjusted to 8 with 1.0 M dilute hydrochloric acid, and the reaction solution was extracted with 50 mL of ethyl acetate. The organic phase was washed with 25 mL of saturated brine, dried and then concentrated, and the crude product was purified by a thin-layer preparative plate (dichloromethane/7M ammonia methanol=100:8) to obtain 9'-((2-chloro-4-((4-methylpyridin-2-yl)oxy)phenyl)(hydroxy)methyl)-3-methoxy-4',7'-dihydrospiro[cyclopentane-1,2'-pyrrolo[3',2':5,6]pyrido[3,4-b]pyrazin]-3'(1'H)-one (72 mg, yield of 77%) as a pale yellow solid. ES-API: $[M+H]^+$=520.1.

Step 2: 9'-((2-Chloro-4-((4-methylpyridin-2-yl)oxy)phenyl)(hydroxy)methyl)-3-methoxy-4',7'-dihydrospiro[cyclopentane-1,2'-pyrrolo[3',2':5,6]pyrido[3,4-b]pyrazin]-3'(1'H)-one (72 mg, 0.14 mmol) was dissolved in 20 mL of tetrahydrofuran and 2 mL of water, and 2,3-dichloro-5,6-dicyano-p-benzoquinone (79 mg, 0.35 mmol) was added thereto, and the reaction was stirred at room temperature for 1 hour. To the reaction solution was added 20 mL of saturated sodium thiosulfate solution and 20 mL of saturated sodium bicarbonate solution, and the mixture was extracted with 60 mL of ethyl acetate. The organic phase was washed with 15 mL of saturated brine, dried and then concentrated, and the crude product was purified by preparative HPLC (column: xbridge C18 19*150 mm, 5 μm; system: 10 mmol/L, aqueous $NH_4HCO_3$ solution; flow rate: 15 mL/min; gradient: 20 to 45% $CH_3CN$—$NH_4HCO_3$; column temperature: room temperature) to obtain 9'-(2-chloro-4-((4-methylpyridin-2-yl)oxy)benzoyl)-3-methoxy-4',7'-dihydrospiro [cyclopentane-1,2'-pyrrolo[3',2':5,6]pyrido[3,4-b]pyrazin]-3'(1'H)-one (Z126, 19 mg, yield of 26%) as a white solid. ES-API: $[M+H]^+$=518.1. $^1H$ NMR (400 MHz, DMSO-$d_6$) δ 12.56-12.47 (m, 1H), 10.54-10.50 (m, 1H), 8.33-8.31 (m, 1H), 8.09 (d, J=5.2 Hz, 1H), 7.76 (d, J=10.0 Hz, 1H), 7.66-7.49 (m, 2H), 7.44-7.33 (m, 1H), 7.19 (dd, J=8.4, 2.0 Hz, 1H), 7.06 (d, J=5.0 Hz, 1H), 6.99 (s, 1H), 4.07-3.94 (m, 1H), 3.21 (s, 3H), 2.37 (s, 3H), 2.35-2.32 (m, 1H), 2.32-2.06 (m, 2H), 1.98-1.78 (m, 3H).

Embodiment 127: Synthesis of Z127-1

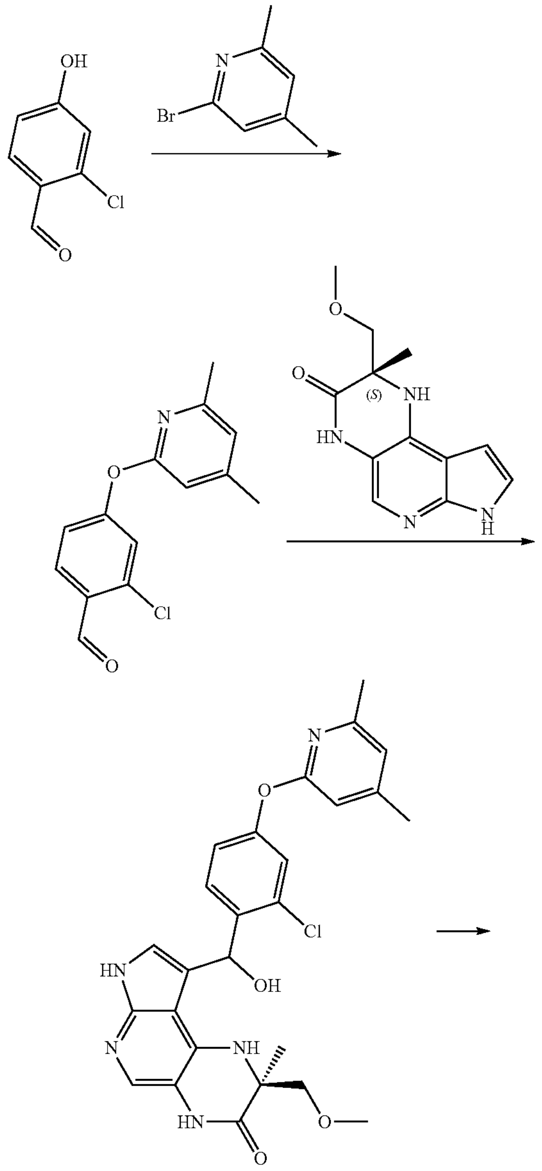

-continued

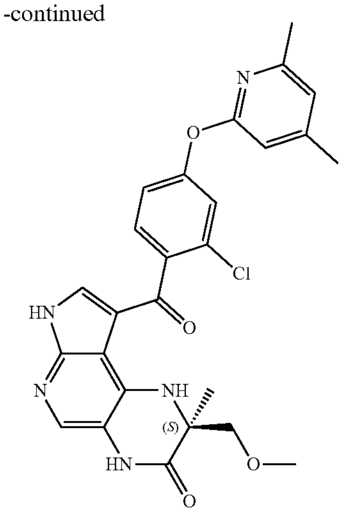

Z127-1

Step 1: Under nitrogen atmosphere, 2-chloro-4-hydroxybenzaldehyde (2.520 g, 16.124 mmol), 2-bromo-4,6-dimethylpyridine (2 g, 10.750 mmol), potassium phosphate (5.0 g, 23.650 mmol), cuprous iodide (204 mg, 1.075 mmol) and L-proline (247 mg, 2.150 mmol) were dissolved in N,N'-dimethylformamide (20 mL), and the reaction solution was stirred under microwave irradiation at 115° C. for 2 hours. LCMS detected that the reaction was complete. The reaction solution was cooled to room temperature, added with 30 mL of ethyl acetate, washed once with 30 mL of water, washed with saturated brine (25 mL×3) respectively, and the organic phase was dried over anhydrous sodium sulfate, filtered, and the filtrate was concentrated to dryness under reduced pressure to obtain 2-chloro-4-((4,6-dimethylpyridin-2-yl)oxy) benzaldehyde (185 mg, yield of 7%) as a pale yellow liquid. ES-API: $[M+H]^+$=262.1

Step 2: (S)-2-(Methoxymethyl)-2-methyl-1,2,4,7-tetrahydro-3H-pyrrolo[3',2':5,6]pyrido[3,4-b]pyrazin-3-one (87 mg, 0.354 mmol) and 2-chloro-4-((4,6-dimethylpyridin-2-yl)oxy)benzaldehyde (185 mg, 0.709 mmol) were dissolved in methanol (6 mL), and the reaction solution was cooled to 0° C., and potassium hydroxide (139 mg, 2.478 mmol) was added thereto. The reaction was stirred at room temperature for 24 hours. LCMS detected that the reaction was complete. The reaction was quenched by adding 20 mL of saturated ammonium chloride solution, extracted with ethyl acetate (15 mL×3). The organic phase was washed with 20 mL of saturated brine, dried over anhydrous sodium sulfate and then concentrated to obtain a crude product (2S)-9-((2-chloro-4-((4,6-dimethylpyridin-2-yl)oxy)phenyl)(hydroxyl) methyl)-2-(methoxymethyl)-2-methyl-1,2,4,7-tetrahydro-3H-pyrrolo[3',2':5,6]pyrido[3,4-b]pyrazin-3-one (179 mg, yield of 100%). ES-API: $[M+H]^+$=508.1

Step 3: (2S)-9-((2-Chloro-4-((4,6-dimethylpyridin-2-yl) oxy)phenyl)(hydroxyl)methyl)-2-(methoxymethyl)-2-methyl-1,2,4,7-tetrahydro-3H-pyrrolo[3',2':5,6]pyrido[3,4-b]pyrazin-3-one (179 mg, 0.354 mmol) was dissolved in 20 mL of tetrahydrofuran, and 2,3-dichloro-5,6-dicyano-p-benzoquinone (179 mg, 0.789 mmol) was added thereto, and the reaction was stirred at room temperature for 2 hours. To the reaction solution was added 20 mL of saturated sodium thiosulfate solution and 20 mL of saturated sodium bicarbonate solution, and the mixture was extracted with 30 mL of ethyl acetate. The organic phase was washed with 15 mL of saturated brine, dried and then concentrated, and the crude product was prepared by preparative HPLC (column: xbridge C18 19*150 mm, 5 μm; system: 10 mmol/L, aqueous $NH_4HCO_3$ solution; flow rate: 15 mL/min; gradient: 20 to 45% $CH_3CN—NH_4HCO_3$; column temperature: room temperature) to obtain (S)-9-(2-chloro-4-((4,6-dimethylpyridin-2-yl)oxy)benzoyl)-2-(methoxymethyl)-2-methyl-1,2,4,7-tetrahydro-3H-pyrrolo[3',2':5,6]pyrido[3,4-b]pyrazin-3-one (Z127-1, 53.68 mg, yield of 30%) as a white solid. ES-API: $[M+H]^+$=506.1. $^1H$ NMR (500 MHz, DMSO-$d_6$) δ 10.32 (s, 1H), 8.10 (s, 1H), 7.52 (s, 1H), 7.40-7.38 (m, 2H), 7.15 (d, J=2.0 Hz, 1H), 6.97 (dd, J1=2.5 Hz, J2=8.0 Hz, 1H), 6.75 (s, 1H), 6.57 (s, 1H), 3.47 (d, J=9.5 Hz, 2H), 3.11 (s, 3H), 2.14 (s, 3H), 2.13 (s, 3H), 1.20 (s, 3H).

Embodiment 128: Synthesis of Z189-1

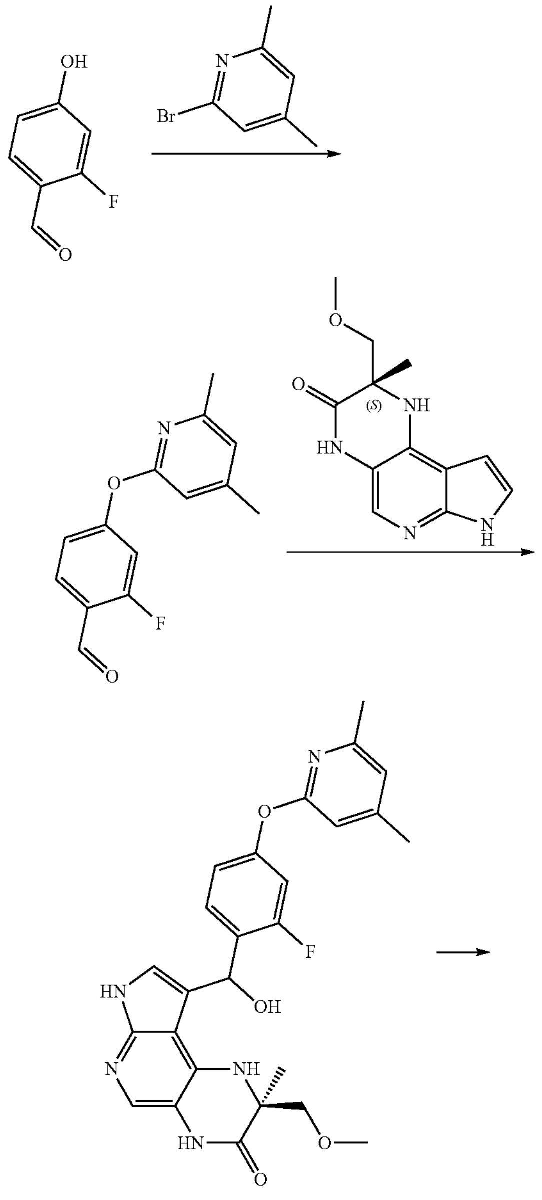

-continued

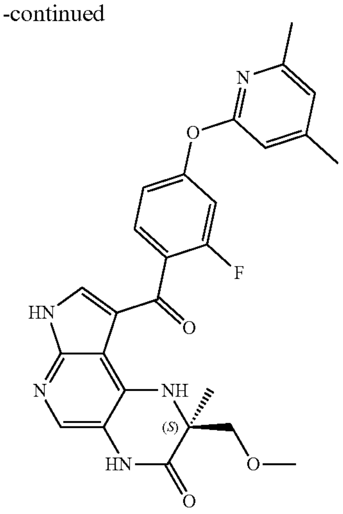

Z189-1

Step 1: Under nitrogen atmosphere, 2-fluoro-4-hydroxybenzaldehyde (2.256 g, 16.124 mmol), 2-bromo-4,6-dimethylpyridine (2 g, 10.750 mmol), potassium phosphate (5.0 g, 23.650 mmol), cuprous iodide (204 mg, 1.075 mmol) and L-proline (247 mg, 2.150 mmol) were dissolved in N,N'-dimethylformamide (20 mL), and the reaction solution was stirred under microwave irradiation at 115° C. for 2 hours. LCMS detected that the reaction was complete. The reaction solution was cooled to room temperature, added with 30 mL of ethyl acetate, washed once with 30 mL of water, washed with saturated brine (25 mL×3) respectively, and the organic phase was dried over anhydrous sodium sulfate, filtered, and the filtrate was concentrated to dryness under reduced pressure to obtain 4-((4,6-dimethylpyridin-2-yl)oxy)-2-fluorobenzaldehyde (274 mg, yield of 10%) as a pale yellow liquid. ES-API: $[M+H]^+$=246.2

Step 2: (S)-2-(Methoxymethyl)-2-methyl-1,2,4,7-tetrahydro-3H-pyrrolo[3',2':5,6]pyrido[3,4-b]pyrazin-3-one (85 mg, 0.346 mmol) and 4-((4,6-dimethylpyridin-2-yl)oxy)-2-fluorobenzaldehyde (220 mg, 0.898 mmol) were dissolved in methanol (6 mL), and the reaction solution was cooled to 0° C., and potassium hydroxide (136 mg, 2.422 mmol) was added thereto. The reaction was stirred at room temperature for 24 hours. LCMS detected that the reaction was complete. The reaction was quenched by adding 20 mL of saturated ammonium chloride solution, extracted with ethyl acetate (15 mL×3). The organic phase was washed with 20 mL of saturated brine, dried over anhydrous sodium sulfate and then concentrated to obtain a crude product (2S)-9-((4-((4,6-dimethylpyridin-2-yl)oxy)-2-fluorophenyl)(hydroxyl)methyl)-2-(methoxymethyl)-2-methyl-1,2,4,7-tetrahydro-3H-pyrrolo[3',2':5,6]pyrido[3,4-b]pyrazin-3-one (170 mg, yield of 100%). ES-API: $[M+H]^+$=492.3

Step 3: (2S)-9-((4-((4,6-Dimethylpyridin-2-yl)oxy)-2-fluorophenyl)(hydroxyl)methyl)-2-(methoxymethyl)-2-methyl-1,2,4,7-tetrahydro-3H-pyrrolo[3',2':5,6]pyrido[3,4-b]pyrazin-3-one (170 mg, 0.346 mmol) was dissolved in 20 mL of tetrahydrofuran, and 2,3-dichloro-5,6-dicyano-p-benzoquinone (170 mg, 0.747 mmol) was added thereto, and the reaction was stirred at room temperature for 2 hours. To the reaction solution was added 20 mL of saturated sodium thiosulfate solution and 20 mL of saturated sodium bicarbonate solution, and the mixture was extracted with 30 mL of ethyl acetate. The organic phase was washed with 15 mL of saturated brine, dried and concentrated, and the crude product was purified by preparative HPLC (column: xbridge C18 19*150 mm, 5 μm; system: 10 mmol/L, aqueous $NH_4HCO_3$ solution; flow rate: 15 mL/min; gradient: 20 to 45% $CH_3CN$—$NH_4HCO_3$; column temperature: room temperature) to obtain (S)-9-(4-((4,6-dimethylpyridin-2-yl)oxy)-2-fluorobenzoyl)-2-(methoxymethyl)-2-methyl-1,2,4,7-tetrahydro-3H-pyrrolo[3',2':5,6]pyrido[3,4-b]pyrazin-3-one (Z189-1, 39 mg, yield of 23%) as a white solid. ES-API: $[M+H]^+$=490.1. $^1$H NMR (500 MHz, DMSO-$d_6$) δ 12.46 (s, 1H), 10.48 (s, 1H), 8.26 (s, 1H), 7.75 (s, 1H), 7.69 (s, 1H), 7.63 (t, J=8.0 Hz, 1H), 7.15 (dd, J1=2.5 Hz, J2=11.0 Hz, 1H), 7.02 (dd, J1=2.5 Hz, J2=8.5 Hz, 1H), 6.95 (s, 1H), 6.77 (s, 1H), 3.65 (d, J=9.0 Hz, 1H), 3.47 (d, J=9.5 Hz, 1H), 3.30 (s, 3H), 2.34 (s, 3H), 2.32 (s, 3H), 1.38 (s, 3H).

Embodiment 129: Synthesis of Z131

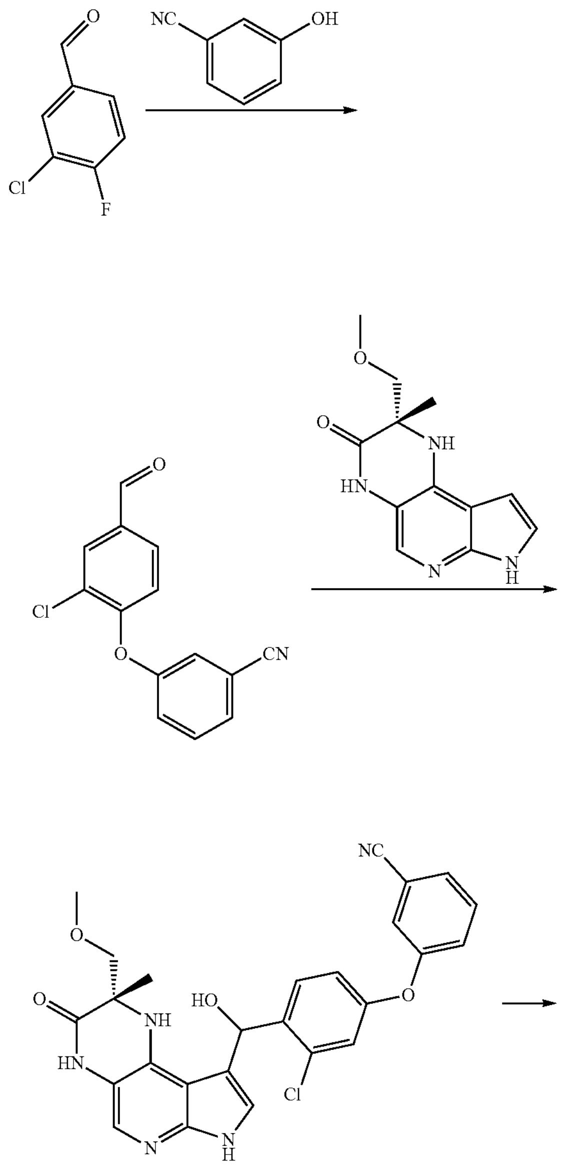

-continued

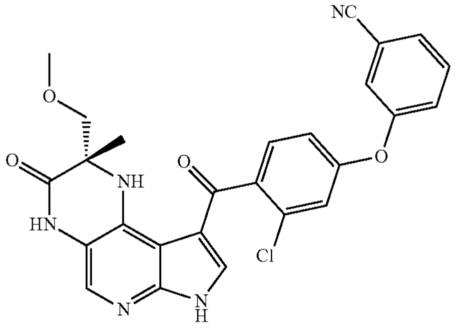

Z131

Step 1: To a 50 mL reaction flask was added 2-chloro-4-fluorobenzaldehyde (1 g, 6.31 mmol), 3-cyanophenol (1.12 g, 9.46 mmol), anhydrous potassium carbonate (3.06 g, 22.2 mmol) and N,N'-dimethylformamide (10 mL), replaced with nitrogen, heated to 90° C. and reacted for 3 hours. The mixture was extracted with ethyl acetate, washed with water and saturated brine in turn, dried over anhydrous sodium sulfate, filtered, concentrated, and purified by a silica gel column to obtain a product 3-(2-chloro-4-formylphenoxy)benzonitrile (1 g, yield of 62%). ES-API: $[M+H]^+$=258.0.

Step 2: 3-(2-Chloro-4-formylphenoxy)benzonitrile (470 mg, 1.83 mmol), (S)-2-(methoxymethyl)-2-methyl-4,7-dihydro-1H-pyrrolo[3',2':5,6]pyrido[3,4-b]pyrazin-3(2H)-one (150 mg, 0.61 mmol) and potassium hydroxide (170 mg, 3.05 mmol) were added to 10 mL of methanol and stirred at room temperature for 3 hours. The reaction was completed, quenched with saturated ammonium chloride, extracted with ethyl acetate, and concentrated to obtain 3-(3-chloro-4-(hydroxy((S)-2-(methoxymethyl)-2-methyl-3-oxo-2,3,4,7-tetrahydro-1H-pyrrolo[3',2':5,6]pyrido[3,4-b]pyrazin-9-yl)methyl)phenoxy)benzonitrile (20 mg, yield of 6.5%). ES-API: $[M+H]^+$=504.1.

Step 3: To a mixed solution of 1,4-dioxane/water (5 mL/1 mL) was added 3-(3-chloro-4-(hydroxy((S)-2-(methoxymethyl)-2-methyl-3-oxo-2,3,4,7-tetrahydro-1H-pyrrolo[3',2':5,6]pyrido[3,4-b]pyrazin-9-yl)methyl)phenoxy)benzonitrile (20 mg, 0.039 mmol), and then 2,3-dichloro-5,6-dicyano-p-benzoquinone (18 mg, 0.079 mmol) was added thereto in batches, stirred at room temperature for 30 minutes, and the reaction was completed. The reaction was quenched by adding 2 mL of aqueous sodium thiosulfate solution, washed with saturated aqueous sodium bicarbonate solution and saturated brine in turn, dried over anhydrous sodium sulfate, filtered, concentrated and purified by preparative HPLC to obtain (S)-3-(3-chloro-4-(2-(methoxymethyl)-2-methyl-3-oxo-2,3,4,7-tetrahydro-1H-pyrrolo[3',2':5,6]pyrido[3,4-b]pyrazine-9-carbonyl)phenoxy)benzonitrile (Z131, 5 mg, yield of 25.6%). ES-API: $[M+H]^+$=502.1. $^1$H NMR (400 MHz, DMSO-$d_6$) δ 10.46 (s, 1H), 8.29 (s, 1H), 7.75-7.62 (m, 4H), 7.62-7.49 (m, 2H), 7.34 (d, J=2.4 Hz, 1H), 7.12 (dd, J=8.4, 2.4 Hz, 1H), 3.64 (d, J=9.6 Hz, 1H), 3.47 (d, J=9.6 Hz, 1H), 3.30 (s, 3H), 1.38 (s, 3H).

Embodiment 130: Synthesis of Z132

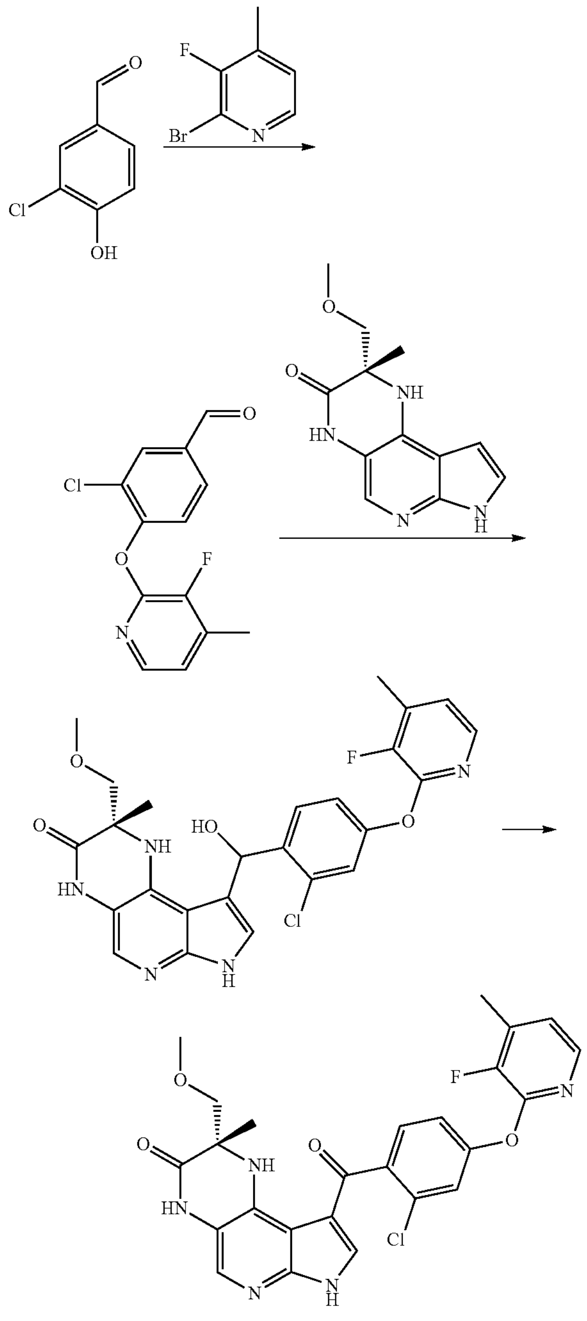

Z132

Step 1: To a 20 mL microwave tube was added 2-chloro-4-hydroxybenzaldehyde (1.16 g, 7.4 mmol), 2-bromo-3-fluoro-4-methylpyridine (1.67 g, 8.9 mmol), L-proline (85 mg, 0.74 mmol), cuprous iodide (280 mg, 1.48 mmol), anhydrous potassium carbonate (3.06 g, 22.2 mmol) and N,N'-dimethylacetamide (8 mL), replaced with nitrogen, and heated to 140° C. and reacted for 3 hours. The mixture was extracted with ethyl acetate, washed with water and saturated brine in turn, dried over anhydrous sodium sulfate, filtered, concentrated, and purified by a silica gel column to obtain a product 2-chloro-4-((3-fluoro-4-methylpyridin-2-yl)oxy)benzaldehyde (157 mg, yield of 8%). ES-API: [M+H]$^+$=266.0.

Step 2: To 10 mL of methanol was added 2-chloro-4-((3-fluoro-4-methylpyridin-2-yl)oxy)benzaldehyde (157 mg, 0.592 mmol), (S)-2-(methoxymethyl)-2-methyl-4,7-dihydro-1H-pyrrolo[3',2':5,6]pyrido[3,4-b]pyrazin-3(2H)-one (145 mg, 0.59 mmol) and potassium hydroxide (165 mg, 2.95 mmol), stirred at room temperature for 8 hours. The reaction was completed, quenched with saturated ammonium chloride, extracted with ethyl acetate, and concentrated to obtain 9-((2-chloro-4-((3-fluoro-4-methylpyridin-2-yl)oxy)phenyl)(hydroxy)methyl)-2-(methoxymethyl)-2-methyl-4,7-dihydro-1H-pyrrolo[3',2':5,6]pyrido[3,4-b]pyrazin-3(2H)-one (100 mg, yield of 33%). ES-API [M+H]$^+$= 512.1.

Step 3: To a mixed solution of 1,4-dioxane/water (5 mL/1 mL) was added 9-((2-chloro-4-((3-fluoro-4-methylpyridin-2-yl)oxy)phenyl)(hydroxy)methyl)-2-(methoxymethyl)-2-methyl-4,7-dihydro-1H-pyrrolo[3',2':5,6]pyrido[3,4-b]pyrazin-3(2H)-one (100 mg, 0.195 mmol), and then 2,3-dichloro-5,6-dicyano-p-benzoquinone (85.5 mg, 0.39 mmol) was added thereto in batches, stirred at room temperature for 30 minutes, and the reaction was completed. The reaction was quenched by adding 2 mL of aqueous sodium thiosulfate solution, washed with saturated aqueous sodium bicarbonate solution and saturated brine in turn, dried over anhydrous sodium sulfate, filtered, concentrated and purified by preparative HPLC to obtain 9-(2-chloro-4-((3-fluoro-4-methylpyridin-2-yl)oxy)benzoyl)-2-(methoxymethyl)-2-methyl-4,7-dihydro-1H-pyrrolo[3',2':5,6]pyrido[3,4-b]pyrazin-3(2H)-one (Z132, 50 mg, 2-step yield of 50.4%). ES-API: [M+H]$^+$=510.1. 1H NMR (400 MHz, DMSO-$d_6$) δ 10.50 (s, 1H), 8.28 (s, 1H), 7.90 (d, J=5.0 Hz, 1H), 7.69 (s, 1H), 7.60 (d, J=8.4 Hz, 1H), 7.54 (s, 1H), 7.47 (d, J=2.3 Hz, 1H), 7.25 (dd, J=8.4, 2.3 Hz, 1H), 7.20 (t, J=5.0 Hz, 1H), 3.65 (d, J=9.5 Hz, 1H), 3.48 (d, J=9.6 Hz, 1H), 3.30 (s, 3H), 2.37 (d, J=1.9 Hz, 3H), 1.39 (s, 3H).

Embodiment 131: Synthesis of Z133

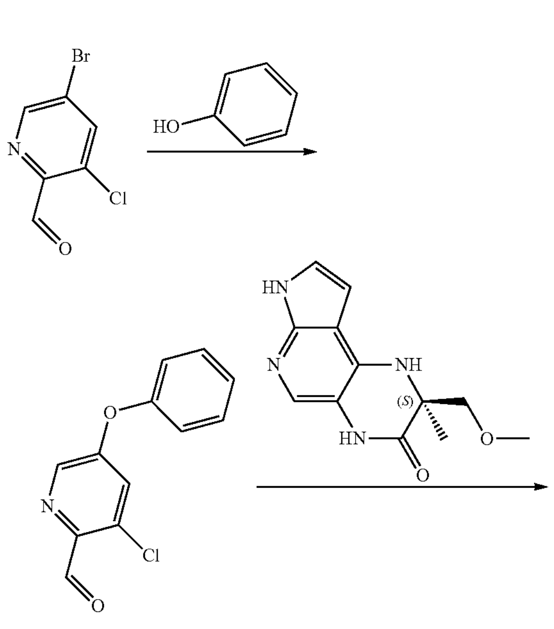

-continued

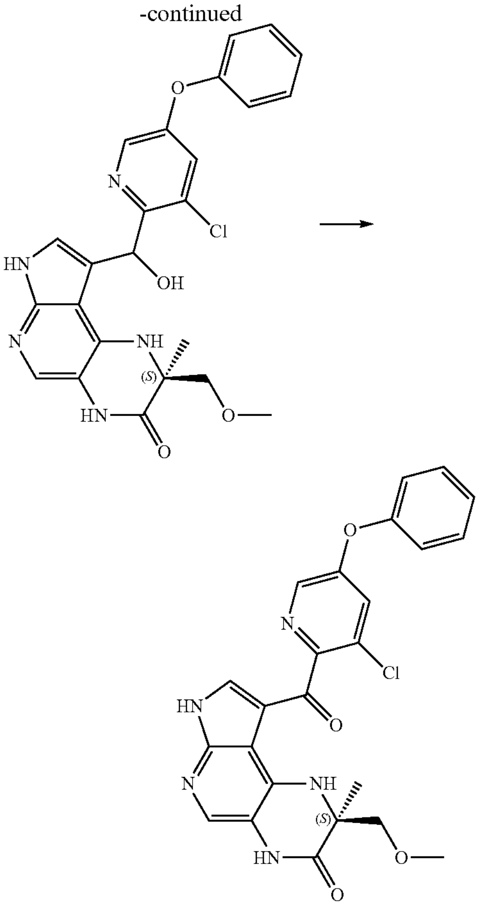

Z133

Step 1: Under nitrogen atmosphere, a mixture of phenol (100 mg, 1.06 mmol), 5-bromo-3-chloropicolinaldehyde (234 mg, 1.06 mmol), 2,2,6,6-tetramethyl-3,5-heptanedione (20 mg, 0.11 mmol), cuprous iodide (10 mg, 0.05 mmol) and cesium carbonate (346 mg, 1.06 mmol) in N,N-dimethylacetamide (3 mL) was reacted under microwave irradiation at 80° C. for 30 minutes. The reaction solution was dissolved in 30 mL of ethyl acetate, washed with 30 mL of saturated brine and 30 mL of water in turn, and the organic phase was dried and concentrated, and then purified by a flash silica gel column (0-10% of ethyl acetate/petroleum ether) to obtain a colorless liquid 3-chloro-5-phenoxypicolinaldehyde (100 mg) with a purity of 95% and a yield of 40%. ES-API: $[M+H]^+$=234.1.

Step 2: To a solution of(S)-2-(methoxymethyl)-2-methyl-1,2,4,7-tetrahydro-3H-pyrrolo[3',2':5,6]pyrido[3,4-b]pyrazin-3-one (100 mg, 0.41 mmol) in methanol (5 mL) was added 3-chloro-5-phenoxypicolinaldehyde (100 mg, 0.43 mmol) and potassium hydroxide (160 mg, 2.84 mmol), stirred at room temperature for 2 hours. After the reaction was completed, the pH of the reaction solution was adjusted to 7 with 1 M hydrochloric acid solution, and the mixture was extracted three times with 20 mL of ethyl acetate. The organic phases were combined, dried, concentrated and purified by a flash silica gel column (0-10% of methanol/dichloromethane) to obtain a yellow solid (2S)-9-((3-chloro-5-phenoxypyridin-2-yl)(hydroxy)methyl)-2-(methoxymethyl)-2-methyl-1,2,4,7-tetrahydro-3H-pyrrolo[3',2':5,6]pyrido[3,4-b]pyrazin-3-one (80 mg) with a purity of 100% and a yield of 41%. ES-API: $[M+H]^+$=480.2.

Step 3: To a mixed solution of (2S)-9-((3-chloro-5-phenoxypyridin-2-yl)(hydroxy)methyl)-2-(methoxymethyl)-2-methyl-1,2,4,7-tetrahydro-3H-pyrrolo[3',2':5,6]pyrido[3,4-b]pyrazin-3-one (80 mg, 0.16 mmol) in 1,4-dioxane/water (2 mL/0.2 mL) was added 2,3-dichloro-5,6-dicyano-p-benzoquinone (76 mg, 0.33 mmol), stirred at room temperature for 30 minutes. The reaction was completed, quenched by adding 2 mL of aqueous sodium thiosulfate solution, added with 20 mL of ethyl acetate, washed with 20 mL of saturated aqueous sodium bicarbonate solution and 20 mL of saturated brine in turn, dried over anhydrous sodium sulfate, filtered, concentrated and purified by preparative HPLC to obtain an off-white solid (Z133, 17 mg, purity of 100%, yield of 21%). $^1H$ NMR (400 MHz, DMSO-$d_6$) δ 12.54 (s, 1H), 10.51 (s, 1H), 8.39 (d, J=2.4 Hz, 1H), 8.23 (s, 1H), 7.77 (s, 1H), 7.75 (d, J=2.4 Hz, 1H), 7.70 (s, 1H), 7.53-7.47 (m, 2H), 7.31-7.23 (m, 3H), 3.65 (d, J=9.6 Hz, 1H), 3.46 (d, J=9.6 Hz, 1H), 3.29 (s, 3H), 1.39 (s, 3H). ES-API: $[M+H]^+$=478.1.

Embodiment 132: Synthesis of Z134 and Z135

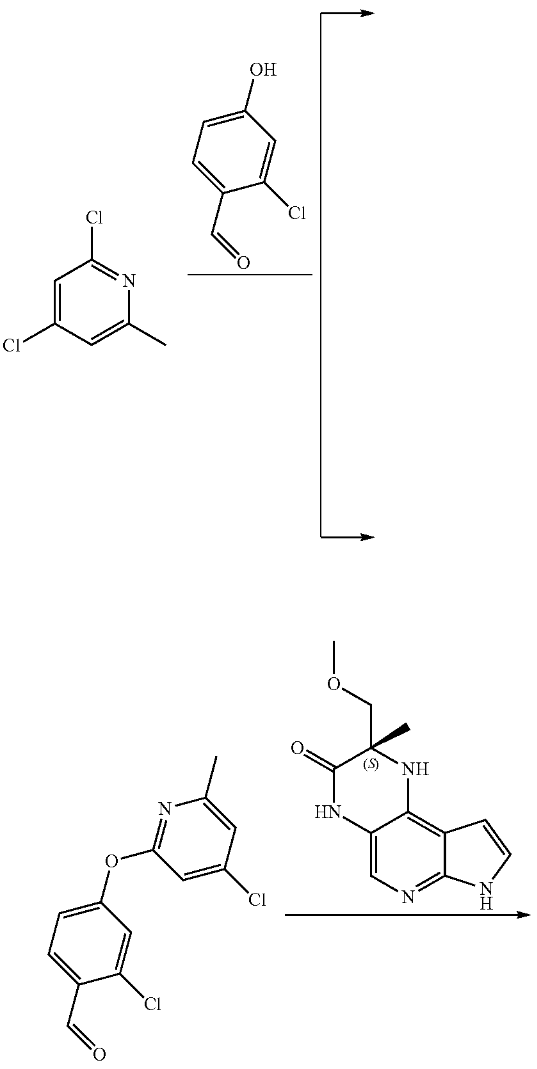

-continued

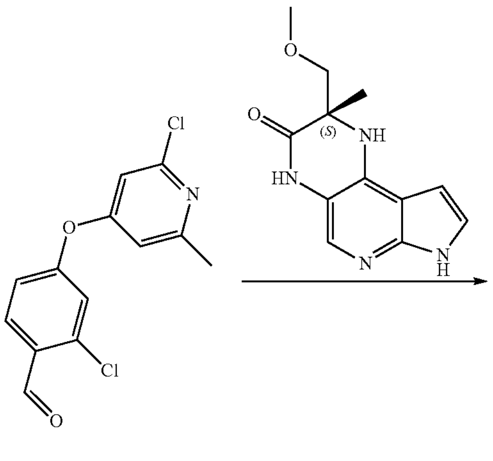

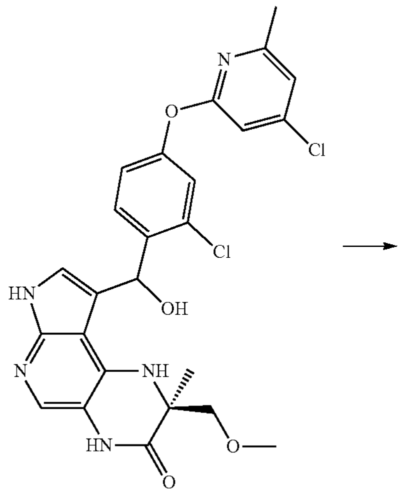

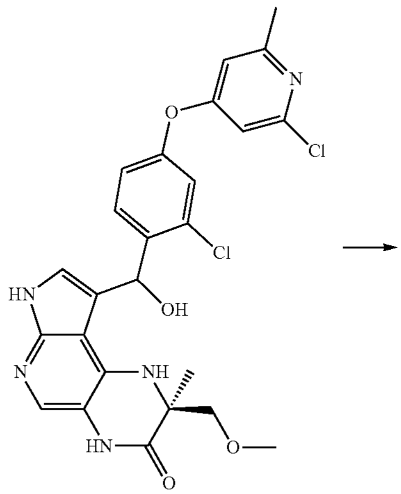

-continued

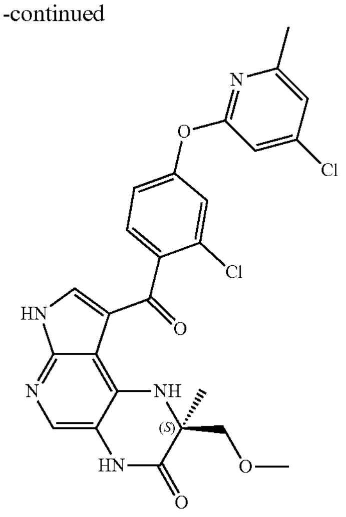

Z134

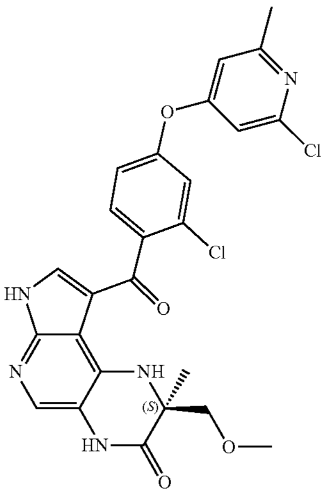

Z135

Step 1: 2-Chloro-4-hydroxybenzaldehyde (1 g, 6.387 mmol), 2,4-dichloro-6-methylpyridine (1.034 g, 6.387 mmol) and potassium carbonate (1.765 g, 12.744 mmol) were dissolved in dimethyl sulfoxide (10 mL), and the reaction mixture was stirred under microwave irradiation at 130° C. for 8 hours. LCMS detected that the reaction was complete. The reaction solution was cooled to room temperature, added with 50 mL of ethyl acetate, washed once with 30 mL of water and washed with saturated brine (25 mL×3) respectively. The organic phase was dried over anhydrous sodium sulfate, filtered, and the filtrate was concentrated to dryness under reduced pressure, and the residue was purified by combiflash to obtain 2-chloro-4-((4-chloro-6-methylpyridin-2-yl)oxy)benzaldehyde (133 mg, yield of 7.4%) and 2-chloro-4-((2-chloro-6-methylpyridin-4-yl)oxy)benzaldehyde (167 mg, yield of 9.3%). ES-API: $[M+H]^+$=282.1

Step 2: (S)-2-(Methoxymethyl)-2-methyl-1,2,4,7-tetrahydro-3H-pyrrolo[3',2':5,6]pyrido[3,4-b]pyrazin-3-one (65 mg, 0.264 mmol) and 2-chloro-4-((4-chloro-6-methylpyridin-2-yl)oxy)benzaldehyde (133 mg, 0.473 mmol) were dissolved in methanol (6 mL), and the reaction solution was cooled to 0° C., and potassium hydroxide (103 mg, 1.848 mmol) was added thereto. The reaction was stirred at room temperature for 24 hours. LCMS detected that the reaction was complete. The reaction was quenched by adding 20 mL of saturated ammonium chloride solution, extracted with ethyl acetate (15 mL×3). The organic phase was washed with 20 mL of saturated brine, dried over anhydrous sodium sulfate and then concentrated to obtain a crude product (2S)-9-((2-chloro-4-((4-chloro-6-methylpyridin-2-yl)oxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (139 mg, yield of 100%). ES-API: $[M+H]^+=528.1$ Step 3: (2S)-9-((2-Chloro-4-((4-chloro-6-methylpyridin-2-yl)oxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (139 mg, 0.264 mmol) was dissolved in 10 mL of tetrahydrofuran, and 2,3-dichloro-5,6-dicyano-p-benzoquinone (139 mg, 0.612 mmol) was added thereto, and the reaction was stirred at room temperature for 2 hours. To the reaction solution was added 20 mL of saturated sodium thiosulfate solution and 20 mL of saturated sodium bicarbonate solution, and the mixture was extracted with 30 mL of ethyl acetate. The organic phase was washed with 15 mL of saturated brine, dried and concentrated, and the crude product was purified by preparative HPLC (column: xbridge C18 19*150 mm, 5 μm; system: 10 mmol/L, aqueous $NH_4HCO_3$ solution; flow rate: 15 mL/min; gradient: 20 to 45% $CH_3CN—NH_4HCO_3$; column temperature: room temperature) to obtain a light red solid (S)-9-(2-chloro-4-((4-chloro-6-methylpyridin-2-yl)oxy)benzoyl)-2-(methoxymethyl)-2-methyl-1,2,4,7-tetrahydro-3H-pyrrolo[3',2':5,6]pyrido[3,4-b]pyrazin-3-one (Z134, 29.63 mg, yield of 21%). ES-API: $[M+H]^+=526.2$. $^1H$ NMR (500 MHz, DMSO-$d_6$) δ 12.47 (s, 1H), 10.49 (s, 1H), 8.28 (s, 1H), 7.70 (s, 1H), 7.61-7.60 (m, 2H), 7.45 (d, J=1.5 Hz, 1H), 7.25-7.23 (m, 2H), 7.12 (s, 1H), 3.65 (d, J=9.0 Hz, 1H), 3.48 (d, J=9.5 Hz, 1H), 3.30 (s, 3H), 2.37 (s, 3H), 1.39 (s, 3H).

Step 4: (S)-2-(Methoxymethyl)-2-methyl-1,2,4,7-tetrahydro-3H-pyrrolo[3',2':5,6]pyrido[3,4-b]pyrazin-3-one (65 mg, 0.264 mmol) and 2-chloro-4-((2-chloro-6-methylpyridin-4-yl)oxy)benzaldehyde (167 mg, 0.594 mmol) were dissolved in methanol (6 mL), and the reaction solution was cooled to 0° C., and potassium hydroxide (103 mg, 1.848 mmol) was added thereto. The reaction was stirred at room temperature for 24 hours. LCMS detected that the reaction was complete. The reaction was quenched by adding 20 mL of saturated ammonium chloride solution, extracted with ethyl acetate (15 mL×3). The organic phase was washed with 20 mL of saturated brine, dried over anhydrous sodium sulfate and then concentrated to obtain a crude product (2S)-9-((2-chloro-4-((2-chloro-6-methylpyridin-4-yl)oxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (139 mg, yield of 100%). ES-API: $[M+H]^+=528.1$ Step 5: (2S)-9-((2-Chloro-4-((2-chloro-6-methylpyridin-4-yl)oxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (139 mg, 0.264 mmol) was dissolved in 10 mL of tetrahydrofuran, and 2,3-dichloro-5,6-dicyano-p-benzoquinone (139 mg, 0.612 mmol) was added thereto, and the reaction was stirred at room temperature for 2 hours. To the reaction solution was added 20 mL of saturated sodium thiosulfate solution and 20 mL of saturated sodium bicarbonate solution, and the mixture was extracted with 30 mL of ethyl acetate. The organic phase was washed with 15 mL of saturated brine, dried and concentrated, and the crude product was purified by preparative HPLC (column: xbridge C18 19*150 mm, 5 μm; system: 10 mmol/L, aqueous $NH_4HCO_3$ solution; flow rate: 15 mL/min; gradient: 20 to 45% $CH_3CN—NH_4HCO_3$; column temperature: room temperature) to obtain a pale yellow solid (S)-9-(2-chloro-4-((2-chloro-6-methylpyridin-4-yl)oxy)benzoyl)-2-(methoxymethyl)-2-methyl-1,2,4,7-tetrahydro-3H-pyrrolo[3',2':5,6]pyrido[3,4-b]pyrazin-3-one (Z135, 24.97 mg, yield of 18%). ES-API: $[M+H]^+=528.0$. $^1H$ NMR (500 MHz, DMSO-$d_6$) δ 12.51 (s, 1H), 10.50 (s, 1H), 8.27 (s, 1H), 7.77 (s, 1H), 7.70 (s, 1H), 7.65 (d, J=8.0 Hz, 1H), 7.53 (d, J=2.5 Hz, 1H), 7.28 (dd, J1=2.5 Hz, J2=9.0 Hz, 1H), 7.07 (d, J=2.0 Hz, 1H), 7.01 (d, J=2.0 Hz, 1H), 3.65 (d, J=10.0 Hz, 1H), 3.49 (d, J=10.0 Hz, 1H), 3.31 (s, 3H), 2.44 (s, 3H), 1.39 (s, 3H).

Embodiment 133: Synthesis of Z136

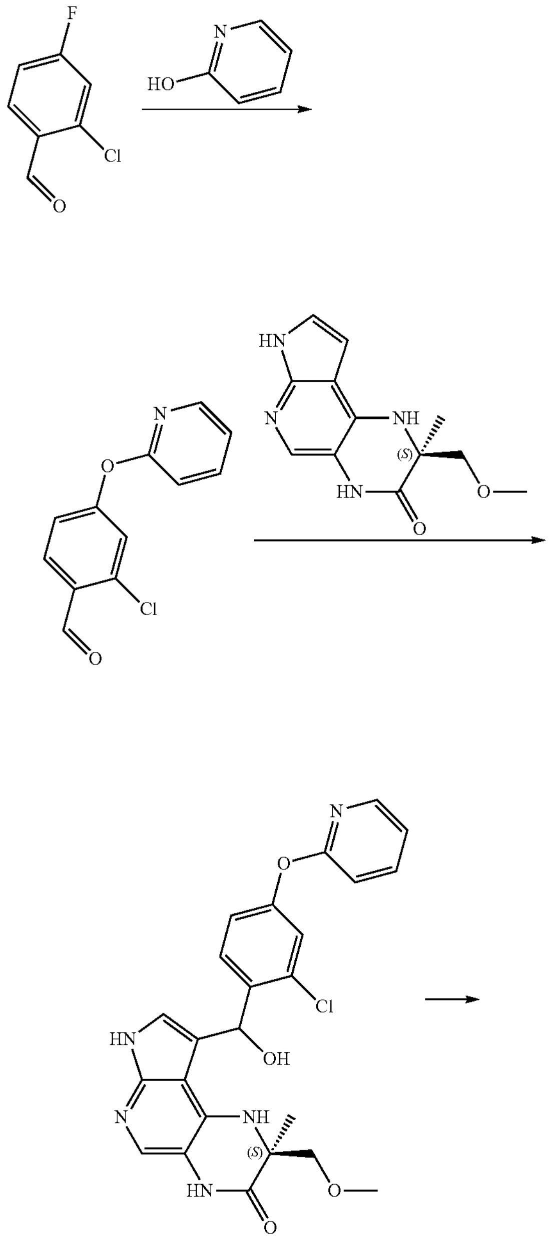

-continued

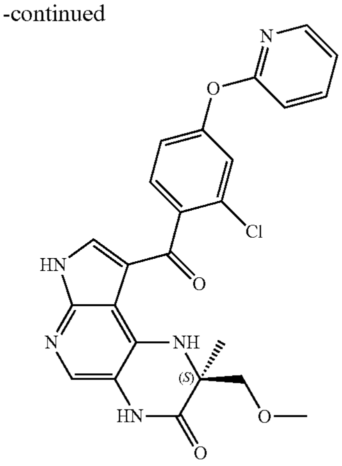

Z136

Step 1:2-Chloro-4-fluorobenzaldehyde (1 g, 6.4 mmol), pyridin-2-ol (1.1 g, 7.04 mmol) and potassium carbonate (1.3 g, 9.6 mmol) were dissolved in N,N'-dimethylformamide (30 mL), and the reaction was stirred at 130° C. overnight. The reaction was cooled to 0° C., added with 50 mL of ethyl acetate, and the organic phase was wash three times with 50 mL of water, washed with 50 mL of saturated brine respectively, dried and then concentrated, and purified by column chromatography (petroleum ether:ethyl acetate=20:1) to obtain a product 2-chloro-4-(pyridin-2-yloxy)benzaldehyde (442 mg, yield of 30%) as a pale yellow solid. ES-API: $[M+H]^+$=234.0.

Step 2: (S)-2-(Methoxymethyl)-2-methyl-1,2,4,7-tetrahydro-3H-pyrrolo[3',2':5,6]pyrido[3,4-b]pyrazin-3-one (150 mg, 0.61 mmol) and 2-chloro-4-(pyridin-2-yloxy)benzaldehyde (308 mg, 1.32 mmol) were dissolved in methanol (20 mL), and the reaction was cooled to 0° C., and potassium hydroxide (137 mg, 2.44 mmol) was added thereto. The reaction was stirred at room temperature for 16 hours. The reaction solution was poured into 15 mL of water, and the pH of the reaction solution was adjusted to 8 with 1.0 M dilute hydrochloric acid, and the reaction solution was extracted with 50 mL of ethyl acetate. The organic phase was washed with 25 mL of saturated brine, dried and then concentrated, and the crude product was purified by a thin-layer preparative plate (dichloromethane/7M ammonia methanol=100:8) to obtain (2S)-9-((2-chloro-4-(pyridin-2-yloxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (101 mg, yield of 35%) as a pale yellow solid. ES-API: $[M+H]^+$=480.1.

Step 3: (2S)-9-((2-Chloro-4-(pyridin-2-yloxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (101 mg, 0.21 mmol) was dissolved in 20 mL of tetrahydrofuran and 2 mL of water, and 2,3-dichloro-5,6-dicyano-p-benzoquinone (95 mg, 0.42 mmol) was added thereto, and the reaction was stirred at room temperature for 1 hour. To the reaction solution was added 20 mL of saturated sodium thiosulfate solution and 20 mL of saturated sodium bicarbonate solution, and the mixture was extracted with 60 mL of ethyl acetate. The organic phase was washed with 15 mL of saturated brine, dried and concentrated, and the crude product was purified by preparative HPLC (column: xbridge C18 19*150 mm, 5 μm; system: 10 mmol/L, aqueous $NH_4HCO_3$ solution; flow rate: 15 mL/min; gradient: 20 to 45% $CH_3CN$—$NH_4HCO_3$; column temperature: room temperature) to obtain (S)-9-(2-chloro-4-(pyridin-2-yloxy)benzoyl)-2-(methoxymethyl)-2-methyl-1,2,4,7-tetrahydro-3H-pyrrolo[3',2':5,6]pyrido[3,4-b]pyrazin-3-one (Z136, 30 mg, yield of 30%) as a white solid. ES-API: $[M+H]^+$=478.1. $^1H$ NMR (400 MHz, DMSO-$d_6$) δ 12.48 (s, 1H), 10.51 (s, 1H), 8.38-8.16 (m, 2H), 8.03-7.78 (m, 1H), 7.70 (s, 1H), 7.63-7.54 (m, 2H), 7.42 (d, J=2.2 Hz, 1H), 7.29-7.20 (m, 2H), 7.16 (d, J=8.4 Hz, 1H), 3.65 (d, J=9.6 Hz, 1H), 3.48 (d, J=9.6 Hz, 1H), 3.30 (s, 3H), 1.39 (s, 3H).

Embodiment 134: Synthesis of Z137

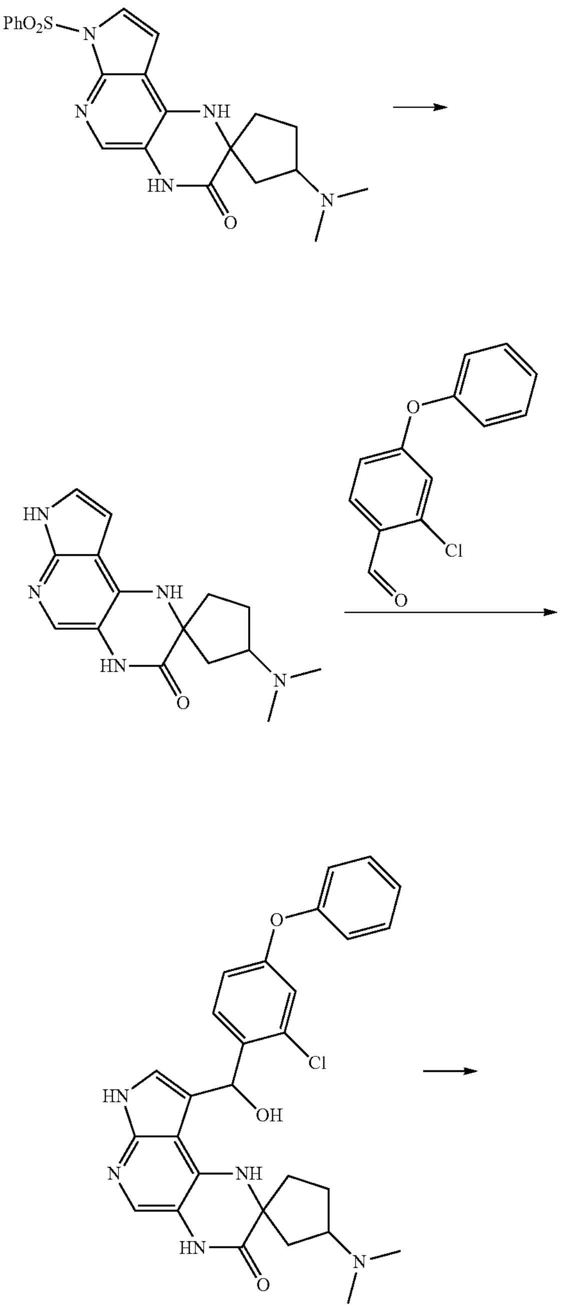

-continued

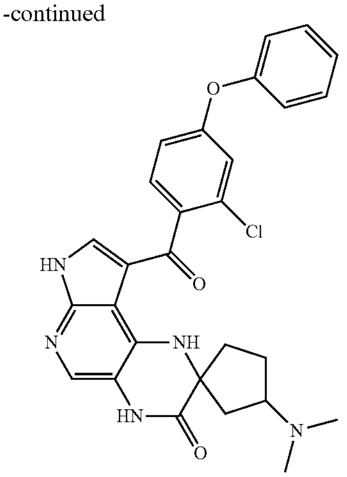

Z137

Step 1: To a mixed solvent of methanol/water (4 mL/0.8 mL) was added 3-(dimethylamino)-7'-(phenylsulfonyl)-4',7'-dihydrospiro[cyclopentane-1,2'-pyrrolo[3',2':5,6]pyrido[3,4-b]pyrazin]-3'(1'H)-one (200 mg, 0.47 mmol) and sodium hydroxide (94 mg, 2.35 mmol), stirred at 60° C. for 8 hours. The reaction solution was concentrated to obtain a crude product 3-(dimethylamino)-4',7'-dihydrospiro[cyclopentane-1,2'-pyrrolo[3',2':5,6]pyrido[3,4-b]pyrazin]-3'(1'H)-one (134 mg). ES-API: $[M+H]^+$=286.2.

Step 2: To a solution of the above crude product 3-(dimethylamino)-4',7'-dihydrospiro[cyclopentane-1,2'-pyrrolo[3',2':5,6]pyrido[3,4-b]pyrazin]-3'(1'H)-one (134 mg, 0.47 mmol) in methanol (5 mL) was added 2-chloro-4-phenoxybenzaldehyde (328 mg, 1.41 mmol) and potassium hydroxide (184 mg, 3.29 mmol), stirred at room temperature for 2 hours. After the reaction was completed, the pH of the mixture was adjusted to 7 with 1 M hydrochloric acid solution, and the mixture was extracted three times with 20 mL of ethyl acetate. The organic phases were combined, dried, concentrated to obtain a yellow solid 9'-((2-chloro-4-phenoxyphenyl)(hydroxy)methyl)-3-(dimethylamino)-4',7'-dihydrospiro[cyclopentane-1,2'-pyrrolo[3',2':5,6]pyrido[3,4-b]pyrazin]-3'(1'H)-one (400 mg). ES-API: $[M+H]^+$=518.2.

Step 3: To a mixed solution of 9'-((2-chloro-4-phenoxyphenyl)(hydroxy)methyl)-3-(dimethylamino)-4',7'-dihydrospiro[cyclopentane-1,2'-pyrrolo[3',2':5,6]pyrido[3,4-b]pyrazin]-3'(1'H)-one (400 mg, 0.77 mmol) in 1,4-dioxane/water (5 mL/0.5 mL) was added 2,3-dichloro-5,6-dicyano-p-benzoquinone (175 mg, 0.77 mmol), stirred at room temperature for 30 minutes. The reaction was completed, quenched by adding 2 mL of aqueous sodium thiosulfate solution, added with 20 mL of ethyl acetate, washed with 20 mL of saturated aqueous sodium bicarbonate solution and 20 mL of saturated brine in turn, dried over anhydrous sodium sulfate, filtered, concentrated and purified by preparative HPLC to obtain an off-white solid (Z137, 54 mg, purity of 100%, 3-step yield of 22%). $^1H$ NMR (400 MHz, DMSO-$d_6$) δ 12.55 (s, 1H), 10.52 (s, 1H), 8.34 (s, 1H), 7.76 (s, 1H), 7.66 (s, 1H), 7.58 (d, J=8.4 Hz, 1H), 7.53-7.45 (m, 2H), 7.29-7.22 (m, 1H), 7.21-7.15 (m, 3H), 7.08-7.00 (m, 1H), 2.88-2.75 (m, 1H), 2.38-2.29 (m, 1H), 2.12 (s, 6H), 2.06-1.99 (m, 1H), 1.99-1.95 (m, 2H), 1.76-1.57 (m, 2H). ES-API: $[M+H]^+$=516.1.

Embodiment 135: Synthesis of Z139

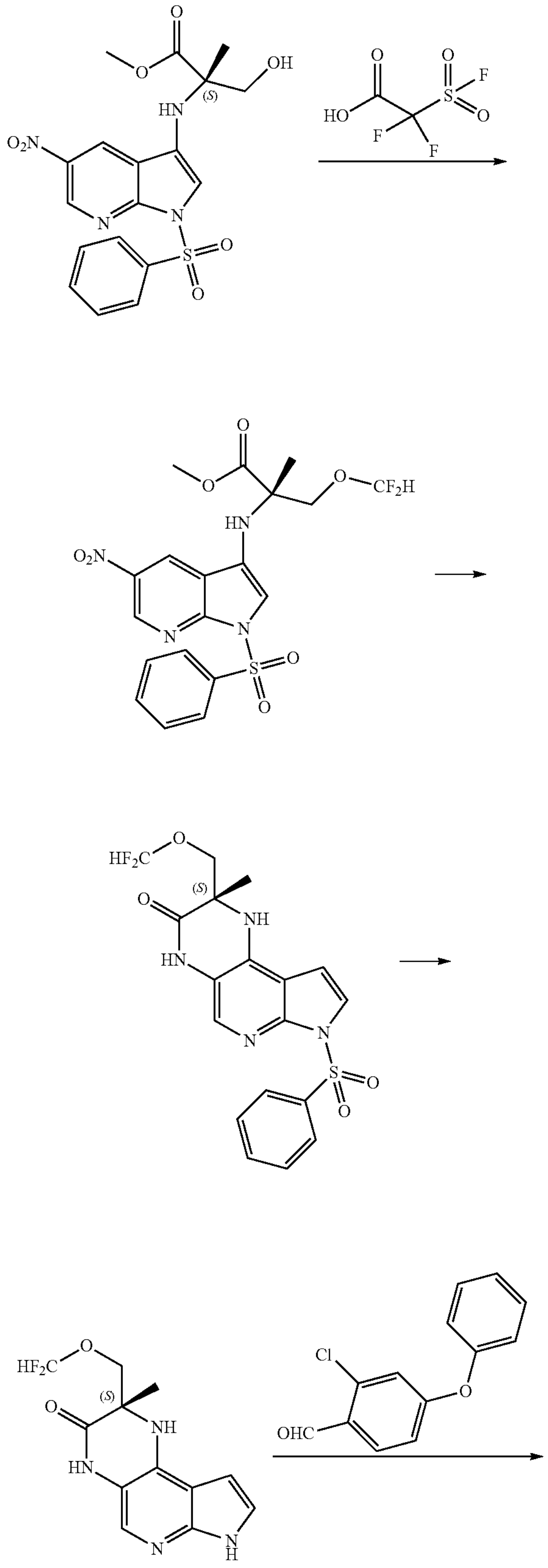

-continued

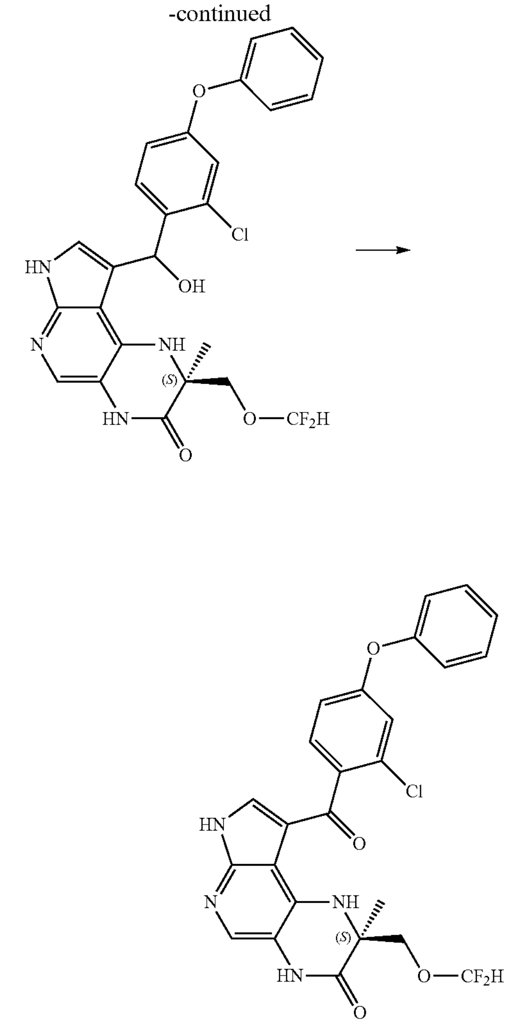

Z139

Step 1: Methyl (S)-3-hydroxy-2-methyl-2-((5-nitro-1-(phenylsulfonyl)-1H-pyrrolo[2,3-b]pyridin-4-yl)amino)propanoate (1.0 g, 2.3 mmol) and cuprous iodide (437 mg, 2.3 mmol) were dissolved in acetonitrile (50 mL), and the reaction was added dropwise with 2,2-difluoro-2-(fluorosulfonyl)acetic acid (2.05 g, 11.5 mmol) at 85° C. under nitrogen atmosphere. To the reaction was added 50 mL of saturated sodium bicarbonate solution, and the mixture was extracted with 60 mL of ethyl acetate. The organic phase was washed with 15 mL of saturated brine, dried and then concentrated, and the crude product was separated by column chromatography (petroleum ether:ethyl acetate=20:1) to obtain methyl (S)-3-(difluoromethoxy)-2-methyl-2-((5-nitro-1-(phenylsulfonyl)-1H-pyrrolo[2,3-b]pyridin-4-yl)amino)propanoate (200 mg, yield of 18%) as a yellow solid. ES-API: $[M+H]^+$=485.0.

Step 2: Methyl (S)-3-(difluoromethoxy)-2-methyl-2-((5-nitro-1-(phenylsulfonyl)-1H-pyrrolo[2,3-b]pyridin-4-yl)amino)propanoate (156 mg, 0.32 mmol) was dissolved in acetic acid (15 mL), and iron powder (125 mg, 2.24 mmol) was added thereto, and the reaction was stirred at 85° C. for 3 hours. The reaction solution was added with 100 mL of ethyl acetate, washed twice with 60 mL of water, twice with 40 mL of saturated sodium bicarbonate and with mL of saturated brine in turn, dried and concentrated to obtain (S)-2-((difluoromethoxy)methyl)-2-methyl-7-(phenylsulfonyl)-1,2,4,7-tetrahydro-3H-pyrrolo[3',2':5,6]pyrido[3,4-b]pyrazin-3-one (126 mg, yield of 93%) as a yellow solid. ES-API: $[M+H]^+$=423.0

Step 3: (S)-2-((Difluoromethoxy)methyl)-2-methyl-7-(phenylsulfonyl)-1,2,4,7-tetrahydro-3H-pyrrolo[3',2':5,6]pyrido[3,4-b]pyrazin-3-one (126 mg, 0.29 mmol) was dissolved in 10 mL of methanol, 5 mL of tetrahydrofuran and 2 mL of water, and sodium hydroxide (81 mg, 2.03 mmol) was added thereto, and the reaction was stirred at 65° C. for 7 hours. To the reaction solution was added 15 mL of water and 4 mL of saturated ammonium chloride solution, and the mixture was extracted with 50 mL of ethyl acetate. The organic phase was washed with 20 mL of saturated sodium bicarbonate solution and 20 mL of saturated brine in turn, dried and then concentrated to obtain (S)-2-((difluoromethoxy)methyl)-2-methyl-1,2,4,7-tetrahydro-3H-pyrrolo[3',2':5,6]pyrido[3,4-b]pyrazin-3-one (72 mg, yield of 88%) as an off-white solid. ES-API: $[M+H]^+$=283.0.

Step 4: (S)-2-((Difluoromethoxy)methyl)-2-methyl-1,2,4,7-tetrahydro-3H-pyrrolo[3',2':5,6]pyrido[3,4-b]pyrazin-3-one (72 mg, 0.26 mmol) and 2-chloro-4-phenoxybenzaldehyde (121 mg, 0.52 mmol) were dissolved in methanol (20 mL), and the reaction was cooled to 0° C., and potassium hydroxide (114 mg, 2.03 mmol) was added thereto. The reaction was stirred at room temperature for 18 hours. The reaction solution was poured into 60 mL of water, and the pH of the reaction solution was adjusted to 8 with 1.0 M dilute hydrochloric acid, and the reaction solution was extracted with 80 mL of ethyl acetate. The organic phase was washed with 25 mL of saturated brine, dried and then concentrated, and the crude product was purified by a thin-layer preparative plate (dichloromethane/7M ammonia methanol=100:7.5) to obtain (2S)-9-((2-chloro-4-phenoxyphenyl)(hydroxy)methyl)-2-((difluoromethoxy)methyl)-2-methyl-1,2,4,7-tetrahydro-3H-pyrrolo[3',2':5,6]pyrido[3,4-b]pyrazin-3-one (110 mg, yield of 82%) as a pale yellow solid. ES-API: $[M+H]^+$=515.0.

Step 5: (2S)-9-((2-Chloro-4-phenoxyphenyl)(hydroxy)methyl)-2-((difluoromethoxy)methyl)-2-methyl-1,2,4,7-tetrahydro-3H-pyrrolo[3',2':5,6]pyrido[3,4-b]pyrazin-3-one (110 mg, 0.21 mmol) was dissolved in 20 mL of tetrahydrofuran and 2 mL of water, and 2,3-dichloro-5,6-dicyano-p-benzoquinone (118 mg, 0.52 mmol) was added thereto, and the reaction was stirred at room temperature for 1 hour. To the reaction solution was added 20 mL of saturated sodium thiosulfate solution, and the mixture was extracted with 60 mL of ethyl acetate. The organic phase was washed twice with 20 mL of saturated sodium bicarbonate solution and 15 mL of saturated brine in turn, dried and then concentrated, and the crude product was purified by preparative HPLC (column: xbridge C18 19*150 mm, 5 μm; system: 10 mmol/L, aqueous $NH_4HCO_3$ solution; flow rate: 15 mL/min; gradient: 20 to 45% $CH_3CN$—$NH_4HCO_3$; column temperature: room temperature) to obtain (S)-9-(2-chloro-4-phenoxybenzoyl)-2-((difluoromethoxy)methyl)-2-methyl-1,2,4,7-tetrahydro-3H-pyrrolo[3',2':5,6]pyrido[3,4-b]pyrazin-3-one (Z139, 38 mg, yield of 64%) as a white solid. ES-API: $[M+H]^+$=513.0. $^1H$ NMR (400 MHz, DMSO-$d_6$) δ 12.50 (s, 1H), 10.65 (s, 1H), 8.35 (s, 1H), 7.73 (s, 1H), 7.63 (s, 1H), 7.55 (d, J=8.4 Hz, 1H), 7.48 (t, J=8.0 Hz, 2H), 7.26-7.23 (m, 1H), 7.19-7.13 (m, 3H), 7.02 (dd, J=8.4, 2.2 Hz, 1H), 6.90-6.53 (m, 1H), 4.17 (d, J=10.0 Hz, 1H), 3.97 (d, J=10.0 Hz, 1H), 1.43 (s, 3H).

Embodiment 136: Synthesis of Z140

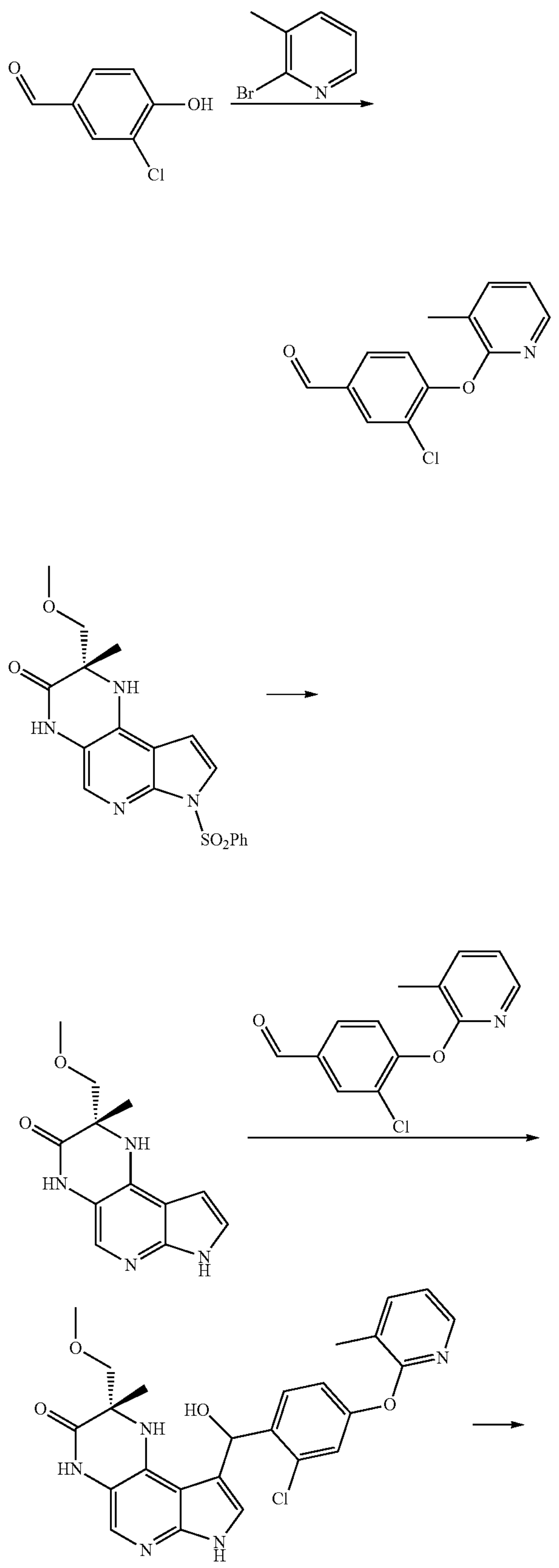

-continued

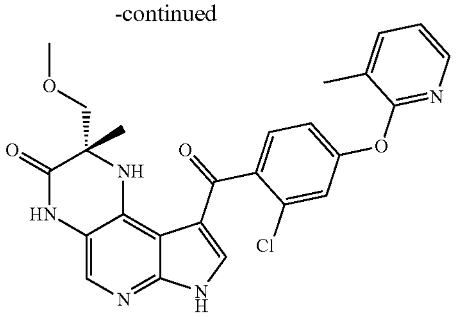

Z140

Step 1: 3-Chloro-4-hydroxybenzaldehyde (1.16 g, 7.4 mmol), 2-bromo-3-methylpyridine (1.53 g, 8.9 mmol), CuI (280 mg, 1.48 mmol), L-Proline (85 mg, 0.74 mmol), potassium carbonate (3.06 g, 22.2 mmol) were dissolved in 1,4 dioxane (30 mL) under $N_2$ atmosphere and stirred in an oil bath at 110° C. for 12 hours. After the reaction was completed, the reaction solution was filtered through diatomite, and after the filtrate was evaporated to dryness by rotary evaporation under reduced pressure, subjected to column chromatography (ethyl acetate/petroleum ether=0-30%) to obtain 3-chloro-4-((3-methylpyridin-2-yl)oxy)benzaldehyde (1.3 g, yield of 71%) as a colorless liquid. ES-API: $[M+H]^+$=248.1;

Step 2: 2-(Methoxymethyl)-2-methyl-7-(phenylsulfonyl)-1,2,4,7-tetrahydro-3H-pyrrolo[3',2':5,6]pyrido[3,4-b]pyrazin-3-one (193 mg, 0.5 mmol) was dissolved in 12 mL of methanol, 3 mL of tetrahydrofuran and 2 mL of water, and sodium hydroxide (290 mg, 7.264 mmol) was added thereto, and the reaction was stirred at 65° C. for 7 hours. The reaction solution was concentrated under reduced pressure to obtain a crude product as a brown solid. ES-API: $[M+H]^+$= 247.1;

Step 3: The crude product from the previous step and 3-chloro-4-((3-methylpyridin-2-yl)oxy)benzaldehyde (247 mg, 1 mmol) were dissolved in methanol (10.0 mL), and the reaction was cooled to 0° C., and potassium hydroxide (140 mg, 2.5 mmol) was added thereto. The reaction was transferred to 30° C. and stirred for 1 hour. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and then concentrated, and subjected to column chromatography (methanol/dichloromethane=0-10%) to obtain (2S)-9-((2-chloro-4-((3-methylpyridin-2-yl)oxy)phenyl)(hydroxyl)methyl)-2-(methoxymethyl)-2-methyl-1,2,4,7-tetrahydro-3H-pyrrolo[3',2':5,6]pyrido[3,4-b]pyrazin-3-one (137 mg, yield of 55%) as a brown solid. ES-API: $[M+H]^+$=494.2;

Step 4: (2S)-9-((2-Chloro-4-((3-methylpyridin-2-yl)oxy)phenyl)(hydroxyl)methyl)-2-(methoxymethyl)-2-methyl-1,2,4,7-tetrahydro-3H-pyrrolo[3',2':5,6]pyrido[3,4-b]pyrazin-3-one (137 mg, 0.277 mmol) was dissolved in 10 mL of tetrahydrofuran, and 2,3-dichloro-5,6-dicyano-1,4-benzoquinone (125 mg, 0.554 mmol) was added thereto, and the reaction was stirred at room temperature for 30 minutes. The reaction solution was quenched by adding 20 mL of saturated $NaHSO_3$ solution, extracted with 80 mL of ethyl acetate. The organic phase was washed with 30 mL of saturated sodium bicarbonate solution and 30 mL of saturated brine, dried over anhydrous sodium sulfate and then concentrated, and the crude product was purified by preparative HPLC to obtain (S)-9-(2-chloro-4-((3-methylpyridin-2-yl)oxy)benzoyl)-2-(methoxymethyl)-2-methyl-1,2,4,7-tetrahydro-3H-pyrrolo[3',2':5,6]pyrido[3,4-b]pyrazin-3-one (Z140, 9.65 mg, yield of 7%) as a white solid, ES-API: $[M+H]^+$=492.1.

Embodiment 137: Synthesis of Z141

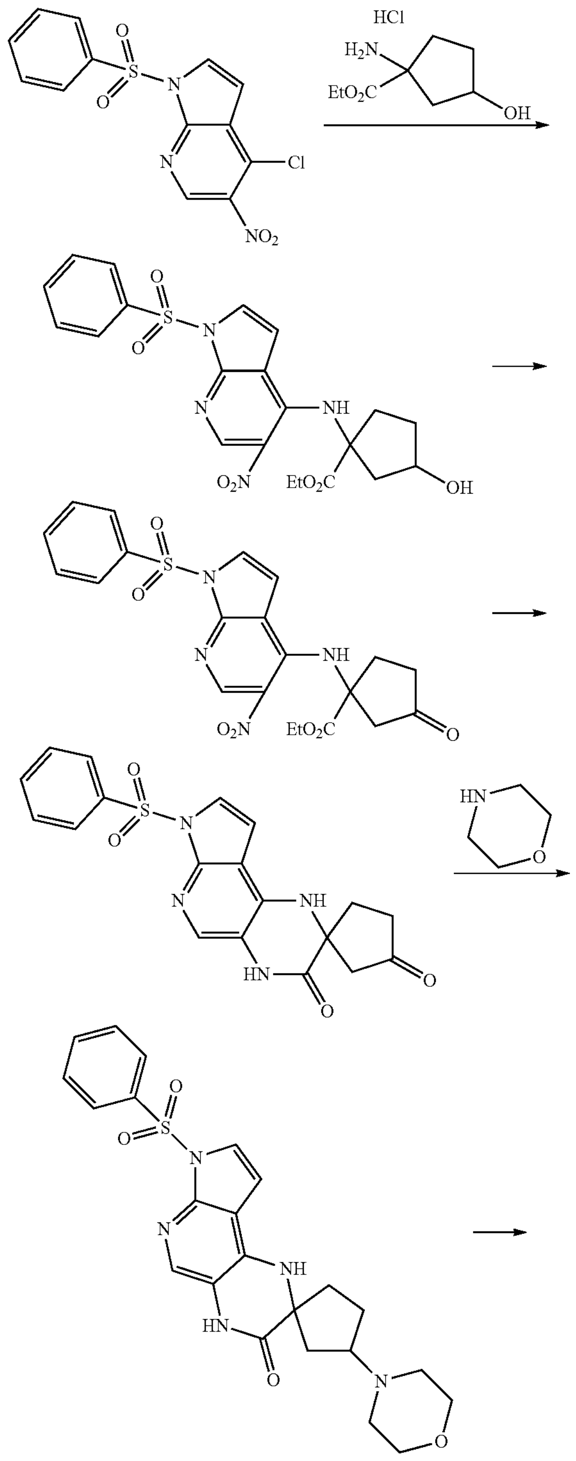

-continued

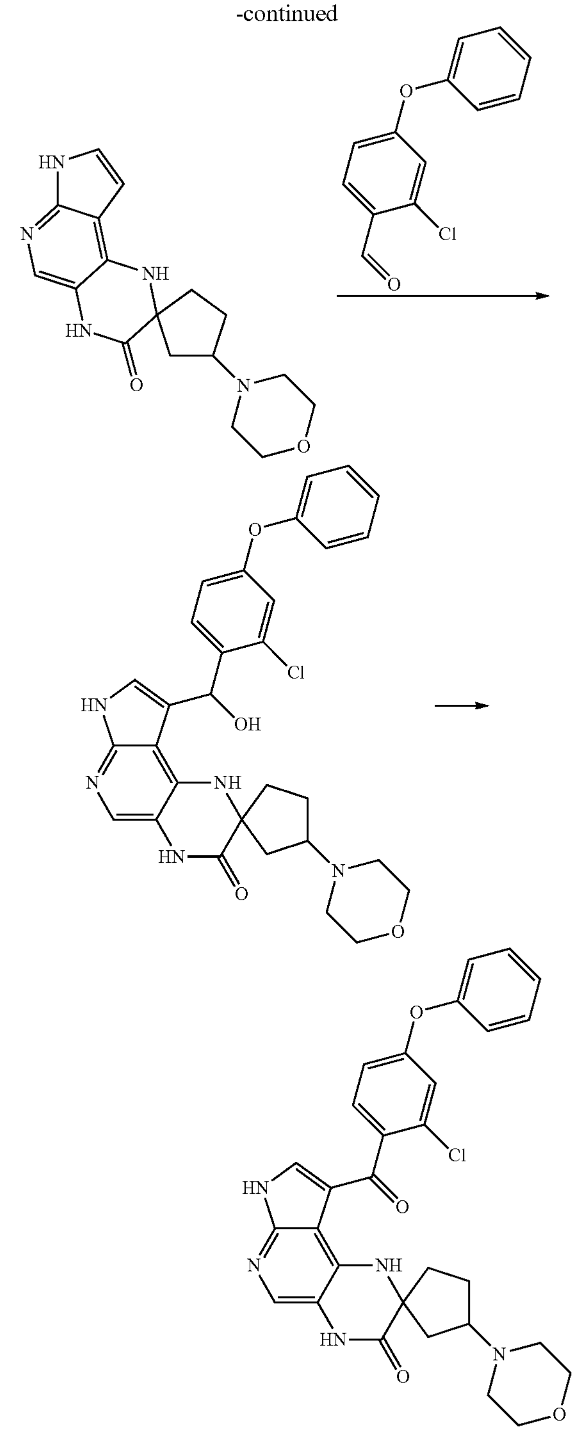

Z141

Step 1: To a 100 mL round-bottom flask was added ethyl 1-amino-3-hydroxycyclopentane-1-carboxylate hydrochloride (1.1 g, 5.24 mmol), 4-chloro-5-nitro-1-(phenylsulfonyl)-1H-pyrrolo[2,3-b]pyridine (1.7 g, 5.24 mmol), N,N-diisopropylethylamine (2 g, 15.72 mmol) and DMF (20 mL). The reaction was stirred at 100° C. for 16 hours. The reaction solution was poured into ice-water, and extracted with ethyl acetate. The organic phase was dried and then concentrated, and the crude product was subjected to column chromatography (0-50% of ethyl acetate/petroleum ether) to obtain ethyl 3-hydroxy-1-((5-nitro-1-(phenylsulfonyl)-1H-pyrrolo[2,3-b]pyridin-4-yl)amino)cyclopentane-1-carboxylate (600 mg, 24%) as a yellow solid. ES-API: $[M+H]^+$=475.1

Step 2: To a 100 mL reaction flask was added ethyl 3-hydroxy-1-((5-nitro-1-(phenylsulfonyl)-1H-pyrrolo[2,3-b]pyridin-4-yl)amino)cyclopentane-1-carboxylate (600 mg, 1.26 mmol), Dess-Martin periodinane (1.07 g, 2.52 mmol) and 10 mL of dichloromethane at 0° C. The reaction was stirred at room temperature for 16 hours, and the reaction was stopped. To the reaction solution was added 50 mL of saturated sodium bicarbonate, extracted three times with ethyl acetate, and the organic phase was dried and concentrated and then purified by a flash silica gel column (0-80% of ethyl acetate/petroleum ether) to obtain ethyl 1-((5-nitro-1-(phenylsulfonyl)-1H-pyrrolo[2,3-b]pyridin-4-yl)amino)-3-oxocyclopentane-1-carboxylate (450 mg, 75%) as a yellow solid. ES-API: $[M+H]^+$=473.2

Step 3: To a 100 mL round-bottom flask was added ethyl 1-((5-nitro-1-(phenylsulfonyl)-1H-pyrrolo[2,3-b]pyridin-4-yl)amino)-3-oxocyclopentane-1-carboxylate (450 mg, 0.95 mmol), iron powder (1.06 g, 19.0 mmol) and acetic acid (15 mL). The reaction was stirred at 80° C. for 2 hours. The reaction was quenched with water and extracted with ethyl acetate. The organic phase was dried over anhydrous sodium sulfate. The organic phase was concentrated to obtain a crude product 7'-(phenylsulfonyl)-4',7'-dihydrospiro[cyclopentane-1,2'-pyrrolo[3',2':5,6]pyrido[3,4-b]pyrazin]-3,3'(1'H)-dione (240 mg, 64%). ES-API: $[M+H]^+$=397.1

Step 4: To a 100 mL round-bottom flask was added 7'-(phenylsulfonyl)-4',7'-dihydrospiro[cyclopentane-1,2'-pyrrolo[3',2':5,6]pyrido[3,4-b]pyrazin]-3,3'(1'H)-dione (240 mg, 0.61 mmol), morpholine (422 mg, 4.85 mmol), acetic acid (73 mg, 1.22 mmol) and 1,2-dichloroethane (10 mL). To the reaction solution was added $NaBH(OAc)_3$ (647 mg, 3.05 mmol). The reaction was stirred at room temperature for 2 hours. The reaction was quenched with water and extracted with dichloromethane. The organic phase was dried over anhydrous sodium sulfate. The organic phase was concentrated to obtain a crude product, and the crude product was purified by a flash silica gel column (0-20% of methanol/ethyl acetate) to obtain 3-morpholino-7'-(phenylsulfonyl)-4',7'-dihydrospiro[cyclopentane-1,2'-pyrrolo[3',2':5,6]pyrido[3,4-b]pyrazin]-3'(1'H)-one (210 mg, 73%). ES-API: $[M+H]^+$=468.2

Step 5: To a 100 mL round-bottom flask was added 3-morpholino-7'-(phenylsulfonyl)-4',7'-dihydrospiro[cyclopentane-1,2'-pyrrolo[3',2':5,6]pyrido[3,4-b]pyrazin]-3'(1'H)-one (210 mg, 0.45 mmol), sodium hydroxide (89 mg, 2.24 mmol), water (5 mL) and methanol (1 mL). The reaction was stirred at 65° C. for 4 hours. The reaction was quenched with saturated aqueous ammonium chloride solution and concentrated to dryness to obtain a crude product 3-morpholino-4',7'-dihydrospiro[cyclopentane-1,2'-pyrrolo[3',2':5,6]pyrido[3,4-b]pyrazin]-3'(1'H)-one (147 mg). ES-API: $[M+H]^+$=328.1

Step 6: To a 100 mL round-bottom flask was added 3-morpholino-4',7'-dihydrospiro[cyclopentane-1,2'-pyrrolo[3',2':5,6]pyrido[3,4-b]pyrazin]-3'(1'H)-one (147 mg, crude product), 2-chloro-4-phenoxybenzaldehyde (260 mg, 1.12 mmol), potassium hydroxide (252 mg, 4.5 mmol) and methanol (6 mL). The reaction was stirred at 30° C. for 5 hours. The reaction was quenched with 2 N hydrochloric acid and extracted with ethyl acetate. The organic phase was dried over anhydrous sodium sulfate. The organic phase was concentrated to obtain a crude product 9'-((2-chloro-4-phenoxyphenyl)(hydroxy)methyl)-3-morpholino-4',7'-dihydrospiro[cyclopentane-1,2'-pyrrolo[3',2':5,6]pyrido[3,4-b]pyrazin]-3'(1'H)-one (250 mg, crude product). ES-API: $[M+H]^+$=560.2.

Step 7: To a 100 mL round-bottom flask was added 9'-((2-chloro-4-phenoxyphenyl)(hydroxy)methyl)-3-morpholino-4',7'-dihydrospiro[cyclopentane-1,2'-pyrrolo[3',2':5,6]pyrido[3,4-b]pyrazin]-3'(1'H)-one (250 mg, crude product), dichloromethane (10 mL) and water (0.5 mL) at 0° C. To the reaction solution was added 2,3-dichloro-5,6-dicyano-p-benzoquinone (227 mg, 0.54 mmol). The reaction was stirred at room temperature for 1 hour. The reaction was quenched with saturated aqueous sodium bicarbonate solution and extracted with dichloromethane. The organic phase was dried over anhydrous sodium sulfate. After the organic phase was concentrated, the crude product was purified by preparative HPLC to obtain 9'-(2-chloro-4-phenoxybenzoyl)-3-morpholino-4',7'-dihydrospiro[cyclopentane-1,2'-pyrrolo[3',2':5,6]pyrido[3,4-b]pyrazin]-3'(1'H)-one (Z141, 50 mg, 3-step yield of 20%). ES-API: $[M+H]^+$=558.1

Embodiment 138: Synthesis of Z142

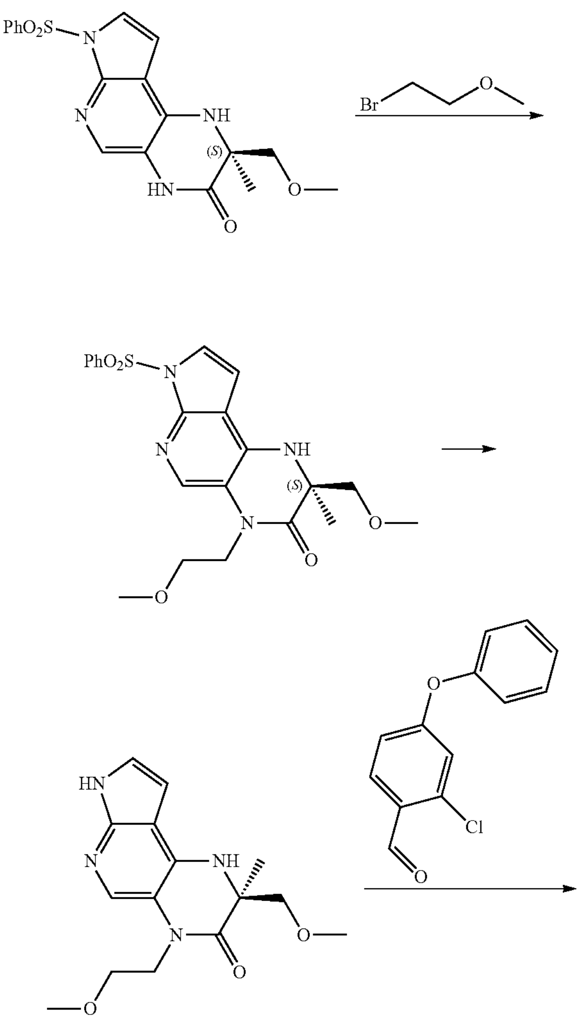

-continued

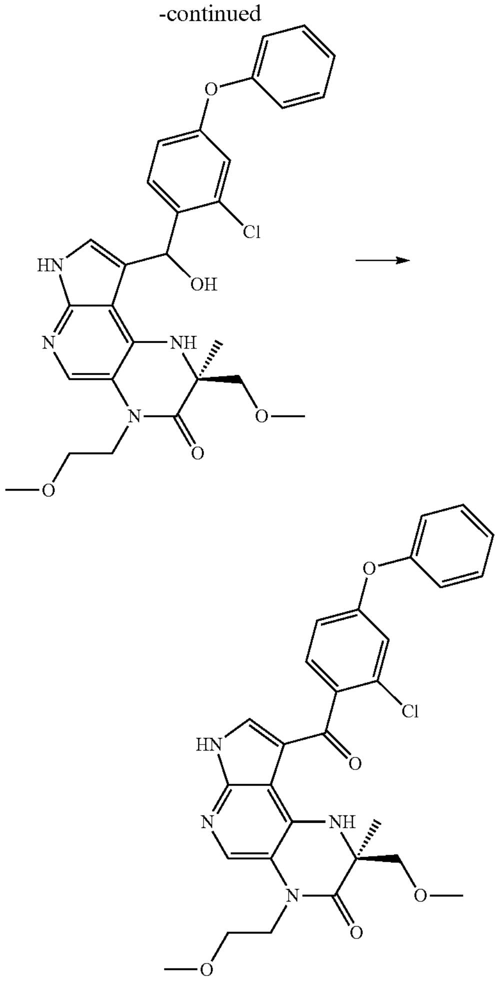

Z142

Step 1: (S)-2-(Methoxymethyl)-2-methyl-7-(phenylsulfonyl)-1,2,4,7-tetrahydro-3H-pyrrolo[3',2':5,6]pyrido[3,4-b]pyrazin-3-one (250 mg, 0.65 mmol) was dissolved in 6 mL of N,N-dimethylformamide, then anhydrous potassium carbonate (359 mg, 2.60 mmol) and 1-bromo-2-methoxyethane (271 mg, 1.95 mmol) were added thereto, and the reaction was stirred at 70° C. for 3 days. The reaction solution was poured into 20 mL of water and extracted with 60 mL of ethyl acetate. The organic phase was washed 3 times with 25 mL of saturated brine, dried and concentrated, and the crude product was purified by a flash silica gel column (methanol/dichloromethane: 0-3%) to obtain (S)-4-(2-methoxyethyl)-2-(methoxymethyl)-2-methyl-7-(phenylsulfonyl)-1,2,4,7-tetrahydro-3H-pyrrolo[3',2':5,6]pyrido[3,4-b]pyrazin-3-one (260 mg, yield of 90%) as a yellow solid. ES-API: $[M+H]^+$=445.1.

Step 2: (S)-4-(2-Methoxyethyl)-2-(methoxymethyl)-2-methyl-7-(phenylsulfonyl)-1,2,4,7-tetrahydro-3H-pyrrolo[3',2':5,6]pyrido[3,4-b]pyrazin-3-one (260 mg, 0.58 mmol) was dissolved in 10 mL of methanol, 4 mL of tetrahydrofuran and 2 mL of water, and sodium hydroxide (116 mg, 2.90 mmol) was added thereto, and the reaction was stirred at 60° C. for 5 hours. The pH of the reaction solution was adjusted to 8 with 1.0 M dilute hydrochloric acid, and the reaction solution was dried and then concentrated, and the crude product was purified by a flash silica gel column (methanol/dichloromethane: 0-5%) to obtain (S)-4-(2-methoxyethyl)-2-(methoxymethyl)-2-methyl-1,2,4,7-tetrahydro-3H-pyrrolo[3',2':5,6]pyrido[3,4-b]pyrazin-3-one (150 mg, yield of 84%) as a pale yellow solid. ES-API: $[M+H]^+$=305.2.

Step 3: (S)-4-(2-Methoxyethyl)-2-(methoxymethyl)-2-methyl-1,2,4,7-tetrahydro-3H-pyrrolo[3',2':5,6]pyrido[3,4-b]pyrazin-3-one (75 mg, 0.25 mmol) and 2-chloro-4-phenoxybenzaldehyde (172 mg, 0.75 mmol) were dissolved in methanol (6 mL), and the reaction was cooled to 0° C., and potassium hydroxide (98 mg, 1.75 mmol) was added thereto. The reaction was stirred at room temperature for 6 hours. The pH of the reaction solution was adjusted to 8 with 1.0 M dilute hydrochloric acid, and the reaction solution was added with 3 mL of water and extracted with 60 mL of ethyl acetate. The reaction solution was dried and then concentrated, and the crude product was purified by a flash silica gel column (methanol/dichloromethane: 0-5%) to obtain (2S)-9-((2-chloro-4-phenoxyphenyl)(hydroxy)methyl)-4-(2-methoxyethyl)-2-(methoxymethyl)-2-methyl-1,2,4,7-tetrahydro-3H-pyrrolo[3',2':5,6]pyrido[3,4-b]pyrazin-3-one (110 mg, yield of 83%) as a pale yellow solid. ES-API: $[M+H]^+$=537.3.

Step 4: (2S)-9-((2-Chloro-4-phenoxyphenyl)(hydroxy)methyl)-4-(2-methoxyethyl)-2-(methoxymethyl)-2-methyl-1,2,4,7-tetrahydro-3H-pyrrolo[3',2':5,6]pyrido[3,4-b]pyrazin-3-one (110 mg, 0.20 mmol) was dissolved in 1,4-dioxane (5 mL) and water (0.5 mL), and 2,3-dichloro-5,6-dicyano-p-benzoquinone (91 mg, 0.40 mmol) was added thereto at room temperature, and the reaction was stirred at room temperature for 2 hours. To the reaction solution was added 6 mL of saturated sodium thiosulfate solution and 10 mL of saturated sodium bicarbonate solution, and the mixture was extracted 3 times with 50 mL of ethyl acetate. The combined organic phases were washed with 20 mL of saturated sodium bicarbonate solution and 20 mL of saturated brine in turn, dried and then concentrated, and the crude product was purified by preparative HPLC to obtain a white solid (Z142, 95 mg, yield of 87%). $^1H$ NMR (400 MHz, DMSO-$d_6$) δ 12.25 (s, 1H), 8.54 (s, 1H), 8.06 (s, 1H), 7.66 (s, 1H), 7.56 (d, J=8.4 Hz, 1H), 7.48 (t, J=7.6 Hz, 2H), 7.25 (t, J=7.6 Hz, 1H), 7.22-7.15 (m, 3H), 7.03 (dd, J=8.4, 2.4 Hz, 1H), 4.29-4.11 (m, 2H), 3.62-3.50 (m, 4H), 3.29 (s, 3H), 3.26 (s, 3H), 1.36 (s, 3H). ES-API: $[M+H]^+$=535.1.

Embodiment 139: Synthesis of Z143

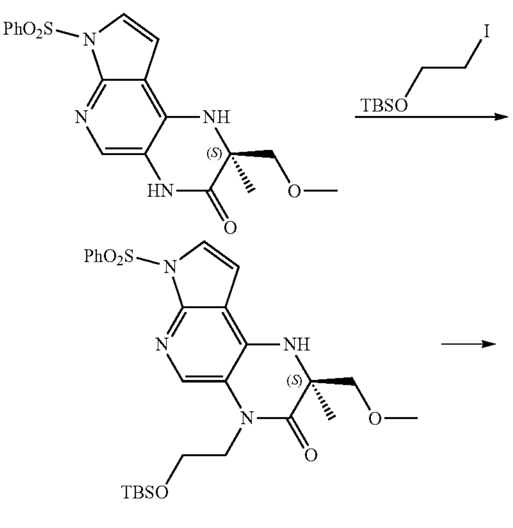

-continued

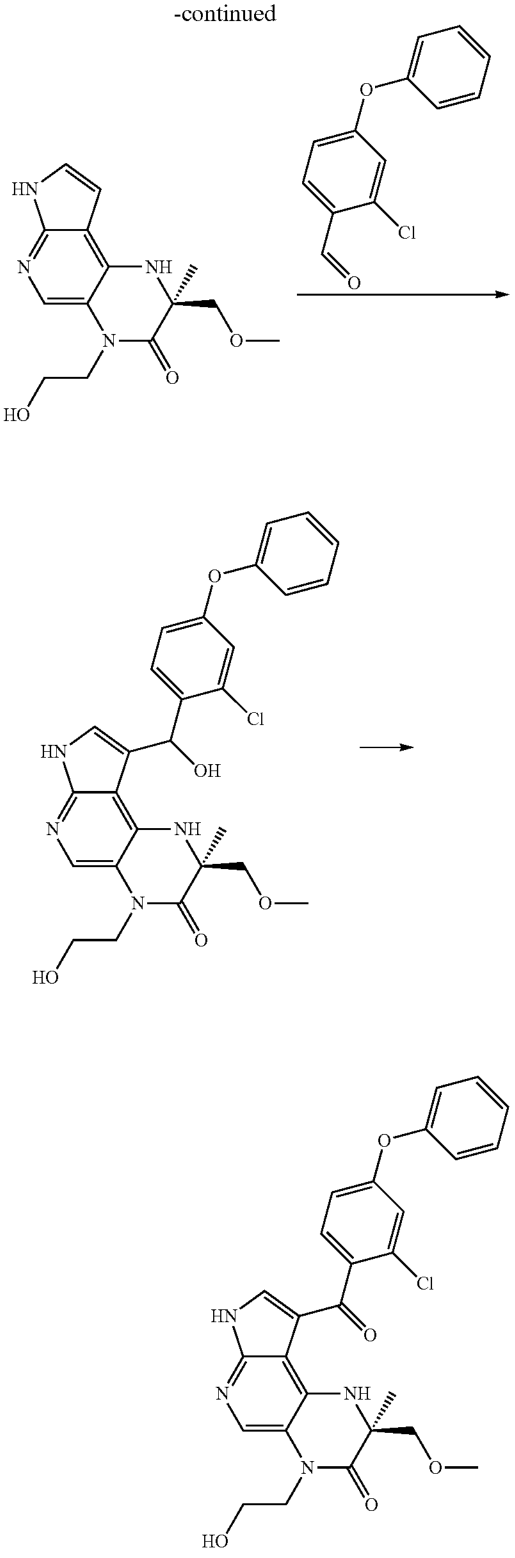

Z143

Step 1: (S)-2-(Methoxymethyl)-2-methyl-7-(phenylsulfonyl)-1,2,4,7-tetrahydro-3H-pyrrolo[3',2':5,6]pyrido[3,4-b]pyrazin-3-one (250 mg, 0.65 mmol) was dissolved in 6 mL of N,N-dimethylformamide, then anhydrous potassium carbonate (359 mg, 2.60 mmol) and tert-butyl (2-iodoethoxy) dimethylsilane (555 mg, 1.95 mmol) were added thereto, and the reaction was stirred at 60° C. for 3 days. The reaction solution was poured into 20 mL of water and extracted with 60 mL of ethyl acetate. The organic phase was washed 3 times with 25 mL of saturated brine, dried and concentrated, and the crude product was purified by a flash silica gel column (methanol/dichloromethane: 0-3%) to obtain (S)-4-(2-((tert-butyldimethylsilyl)oxy)ethyl)-2-(methoxymethyl)-2-methyl-7-(phenylsulfonyl)-1,2,4,7-tetrahydro-3H-pyrrolo[3',2':5,6]pyrido[3,4-b]pyrazin-3-one (330 mg, yield of 93%) as a pale yellow solid. ES-API: $[M+H]^+$=545.1.

Step 2: (S)-4-(2-((tert-Butyldimethylsilyl)oxy)ethyl)-2-(methoxymethyl)-2-methyl-7-(phenylsulfonyl)-1,2,4,7-tetrahydro-3H-pyrrolo[3',2':5,6]pyrido[3,4-b]pyrazin-3-one (300 mg, 0.55 mmol) was dissolved in 10 mL of methanol, 4 mL of tetrahydrofuran and 2 mL of water, and sodium hydroxide (110 mg, 2.75 mmol) was added thereto, and the reaction was stirred at 65° C. for 16 hours. The pH of the reaction solution was adjusted to 8 with 1.0 M dilute hydrochloric acid, and the reaction solution was dried and then concentrated, and the crude product was purified by a flash silica gel column (methanol/dichloromethane: 0-10%) to obtain (S)-4-(2-hydroxyethyl)-2-(methoxymethyl)-2-methyl-1,2,4,7-tetrahydro-3H-pyrrolo[3',2':5,6]pyrido[3,4-b]pyrazin-3-one (140 mg, yield of 87%) as a pale yellow solid. ES-API: $[M+H]^+$=291.3.

Step 3: (S)-4-(2-Hydroxyethyl)-2-(methoxymethyl)-2-methyl-1,2,4,7-tetrahydro-3H-pyrrolo[3',2':5,6]pyrido[3,4-b]pyrazin-3-one (75 mg, 0.26 mmol) and 2-chloro-4-phenoxybenzaldehyde (180 mg, 0.78 mmol) were dissolved in methanol (6 mL), and the reaction was cooled to 0° C., and potassium hydroxide (102 mg, 1.85 mmol) was added thereto. The reaction was stirred at room temperature for 6 hours. The pH of the reaction solution was adjusted to 8 with 1.0 M dilute hydrochloric acid, and the reaction solution was added with 3 mL of water and extracted with 60 mL of ethyl acetate. The reaction solution was dried and then concentrated, and the crude product was prepared by a thin-layer preparative plate (methanol/dichloromethane=10:1) to obtain (2S)-9-((2-chloro-4-phenoxyphenyl)(hydroxy)methyl)-4-(2-hydroxyethyl)-2-(methoxymethyl)-2-methyl-1,2,4,7-tetrahydro-3H-pyrrolo[3',2':5,6]pyrido[3,4-b]pyrazin-3-one (100 mg, yield of 74%) as a pale yellow solid. ES-API: $[M+H]^+$=523.2.

Step 4: (2S)-9-((2-Chloro-4-phenoxyphenyl)(hydroxy)methyl)-4-(2-hydroxyethyl)-2-(methoxymethyl)-2-methyl-1,2,4,7-tetrahydro-3H-pyrrolo[3',2':5,6]pyrido[3,4-b]pyrazin-3-one (100 mg, 0.19 mmol) was dissolved in 1,4-dioxane (5 mL) and water (0.5 mL), and 2,3-dichloro-5,6-dicyano-p-benzoquinone (86 mg, 0.38 mmol) was added thereto at room temperature, and the reaction was stirred at room temperature for 30 minutes. To the reaction solution was added 6 mL of saturated sodium thiosulfate solution and 6 mL of saturated sodium bicarbonate solution, and the mixture was extracted with 60 mL of ethyl acetate. The organic phase was washed with 15 mL of saturated sodium bicarbonate solution and 15 mL of saturated brine in turn, dried and then concentrated, and the crude product was purified by preparative HPLC to obtain a target product (Z143, 90 mg, yield of 90%) as a white solid. $^1$H NMR (400 MHz, DMSO-$d_6$) δ 12.56 (s, 1H), 8.53 (s, 1H), 8.09 (s, 1H), 7.65 (s, 1H), 7.55 (d, J=8.4 Hz, 1H), 7.51-7.42 (m, 2H), 7.25 (t, J=7.2 Hz, 1H), 7.21-7.14 (m, 3H), 7.02 (dd, J=8.4, 2.4 Hz, 1H), 4.90 (s, 1H), 4.10-3.98 (m, 2H), 3.63-3.55 (m, 3H), 3.51 (d, J=9.6 Hz, 1H), 3.29 (s, 3H), 1.36 (s, 3H). ES-API: $[M+H]^+$=521.2.

Embodiment 140: Synthesis of Z144

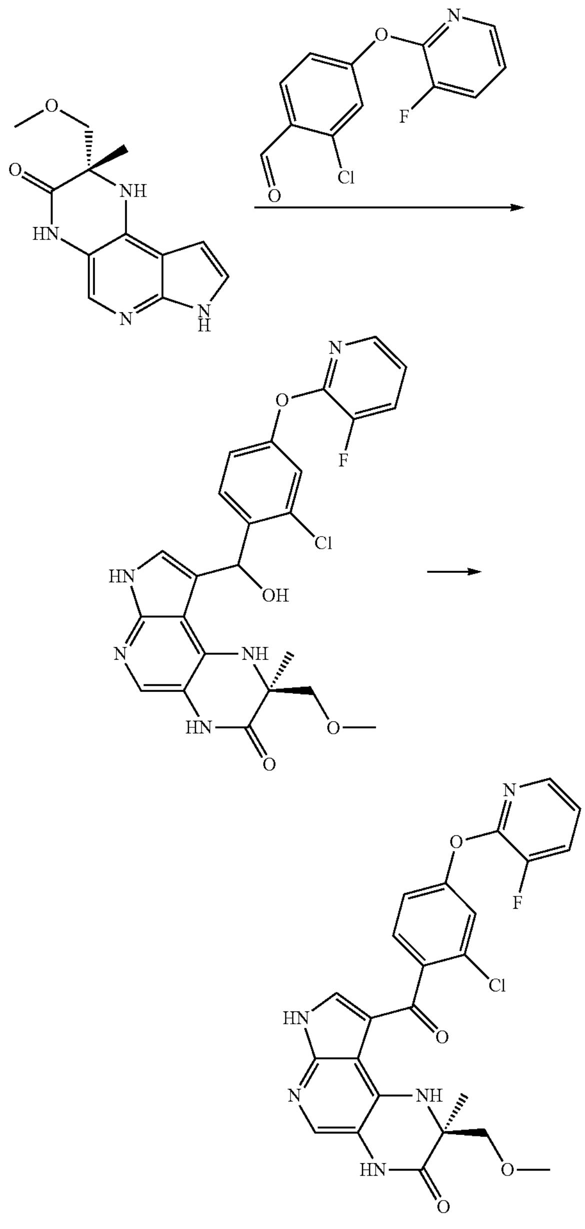

Z144

Step 1: (S)-2-(Methoxymethyl)-2-methyl-1,2,4,7-tetrahydro-3H-pyrrolo[3',2':5,6]pyrido[3,4-b]pyrazin-3-one (50 mg, 0.203 mmol) and 2-chloro-4-((3-fluoropyridin-2-yl)oxy)benzaldehyde (102 mg, 0.406 mmol) were dissolved in methanol (3 mL), and the reaction was cooled to 0° C., and potassium hydroxide (80 mg, 1.42 mmol) was added thereto. The reaction was stirred at room temperature for 16 hours. The pH of the reaction solution was adjusted to 8 with dilute hydrochloric acid (1.0 M), and the reaction solution was extracted with ethyl acetate (40 mL). The organic phase was washed with saturated brine (20 mL), dried and concentrated, and the crude product was purified by a flash silica gel column (methanol/dichloromethane: 0-8%) to obtain (2S)-9-((2-chloro-4-((3-fluoropyridin-2-yl)oxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (25 mg, 0.05 mmol, yield of 25%) as a pale yellow solid. ES-API: $[M+H]^+=498.1$.

Step 2: (2S)-9-((2-Chloro-4-((3-fluoropyridin-2-yl)oxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (25 mg, 0.05 mmol) was dissolved in tetrahydrofuran (1 mL) and water (0.1 mL), and 2,3-dichloro-5,6-dicyano-p-benzoquinone (34 mg, 0.151 mmol) was added thereto at room temperature, and the reaction was stirred at room temperature for 2 hours. To the reaction solution was added saturated sodium sulfite solution (5 mL) and saturated sodium bicarbonate solution (5 mL) to quench the reaction, and then extracted with ethyl acetate (20 mL). The organic phase was washed with saturated sodium bicarbonate solution (10 mL) and saturated brine (10 mL) in turn, dried and then concentrated, and the crude product was purified by preparative HPLC to obtain (S)-9-(2-chloro-4-((3-fluoropyridin-2-yl)oxy)benzoyl)-2-(methoxymethyl)-2-methyl-1,2,4,7-tetrahydro-3H-pyrrolo[3',2':5,6]pyrido[3,4-b]pyrazin-3-one (Z144, 8 mg, 0.016 mmol, yield of 33%) as a white solid. $^1H$ NMR (500 MHz, DMSO-$d_6$) δ 12.48 (s, 1H), 10.50 (s, 1H), 8.28 (s, 1H), 8.05 (s, 1H), 7.98-7.90 (m, 1H), 7.70 (s, 1H), 7.62 (d, J=8.5 Hz, 1H), 7.58-7.50 (m, 2H), 7.32-7.27 (m, 2H), 3.65 (d, J=10.0 Hz, 1H), 3.48 (d, J=10.0 Hz, 1H), 3.30 (s, 3H), 1.39 (s, 3H). ES-API: $[M+H]^+=496.1$.

Embodiment 141: Synthesis of Z145

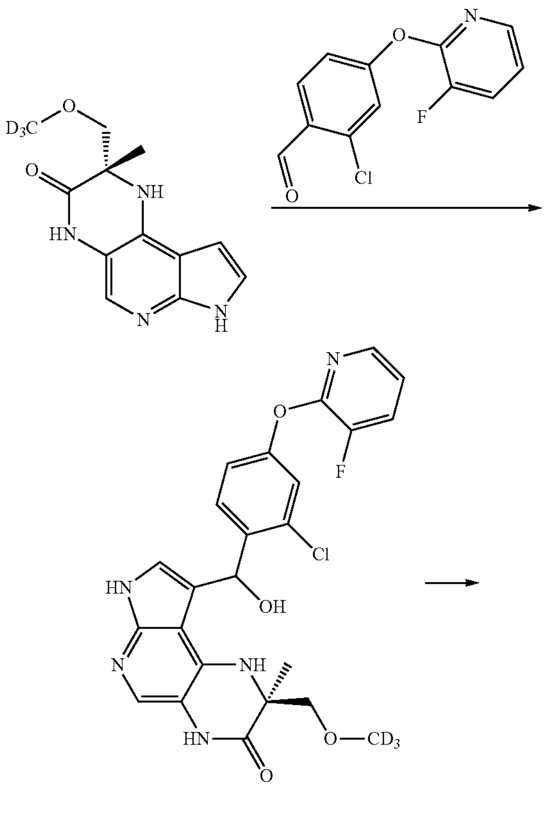

-continued

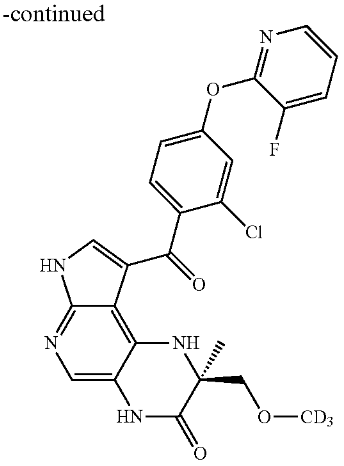

Z145

Step 1: (S)-2-((Methoxy-$d_3$)methyl)-2-methyl-1,2,4,7-tetrahydro-3H-pyrrolo[3',2':5,6]pyrido[3,4-b]pyrazin-3-one (50 mg, 0.203 mmol) and 2-chloro-4-((3-fluoropyridin-2-yl)oxy)benzaldehyde (102 mg, 0.406 mmol) were dissolved in methanol (3 mL), and the reaction was cooled to 0° C., and potassium hydroxide (80 mg, 1.42 mmol) was added thereto. The reaction was stirred at room temperature for 16 hours. The pH of the reaction solution was adjusted to 8 with dilute hydrochloric acid (1.0 M), and the reaction solution was extracted with ethyl acetate (40 mL). The organic phase was washed with saturated brine (20 mL), dried and concentrated, and the crude product was purified by a flash silica gel column (methanol/dichloromethane: 0-8%) to obtain (2S)-9-((2-chloro-4-((3-fluoropyridin-2-yl)oxy)phenyl)(hydroxy)methyl)-2-((methoxy-$d_3$)methyl)-2-methyl-1,2,4,7-tetrahydro-3H-pyrrolo[3',2':5,6]pyrido[3,4-b]pyrazin-3-one (25 mg, 0.05 mmol, yield of 25%) as a pale yellow solid. ES-API: $[M+H]^+$=501.1.

Step 2: (2S)-9-((2-Chloro-4-((3-fluoropyridin-2-yl)oxy)phenyl)(hydroxy)methyl)-2-((methoxy-$d_3$)methyl)-2-methyl-1,2,4,7-tetrahydro-3H-pyrrolo[3',2':5,6]pyrido[3,4-b]pyrazin-3-one (25 mg, 0.05 mmol) was dissolved in tetrahydrofuran (1 mL) and water (0.1 mL), and 2,3-dichloro-5,6-dicyano-p-benzoquinone (34 mg, 0.151 mmol) was added thereto at room temperature, and the reaction was stirred at room temperature for 2 hours. To the reaction solution was added saturated sodium sulfite solution (5 mL) and saturated sodium bicarbonate solution (5 mL) to quench the reaction, and then extracted with ethyl acetate (20 mL). The organic phase was washed with saturated sodium bicarbonate solution (10 mL) and saturated brine (10 mL) in turn, dried and then concentrated, and the crude product was purified by preparative HPLC to obtain (S)-9-(2-chloro-4-((3-fluoropyridin-2-yl)oxy)benzoyl)-2-((methoxy-$d_3$)methyl)-2-methyl-1,2,4,7-tetrahydro-3H-pyrrolo[3',2':5,6]pyrido[3,4-b]pyrazin-3-one (Z145, 8 mg, 0.016 mmol, yield of 33%) as a white solid. $^1H$ NMR (500 MHz, DMSO-$d_6$) δ 12.48 (s, 1H), 10.50 (s, 1H), 8.28 (s, 1H), 8.05 (s, 1H), 7.98-7.90 (m, 1H), 7.70 (s, 1H), 7.62 (d, J=8.5 Hz, 1H), 7.58-7.50 (m, 2H), 7.32-7.27 (m, 2H), 3.65 (d, J=10.0 Hz, 1H), 3.48 (d, J=10.0 Hz, 1H), 1.39 (s, 3H). ES-API: $[M+H]^+$= 499.1.

Embodiment 142: Synthesis of Z146

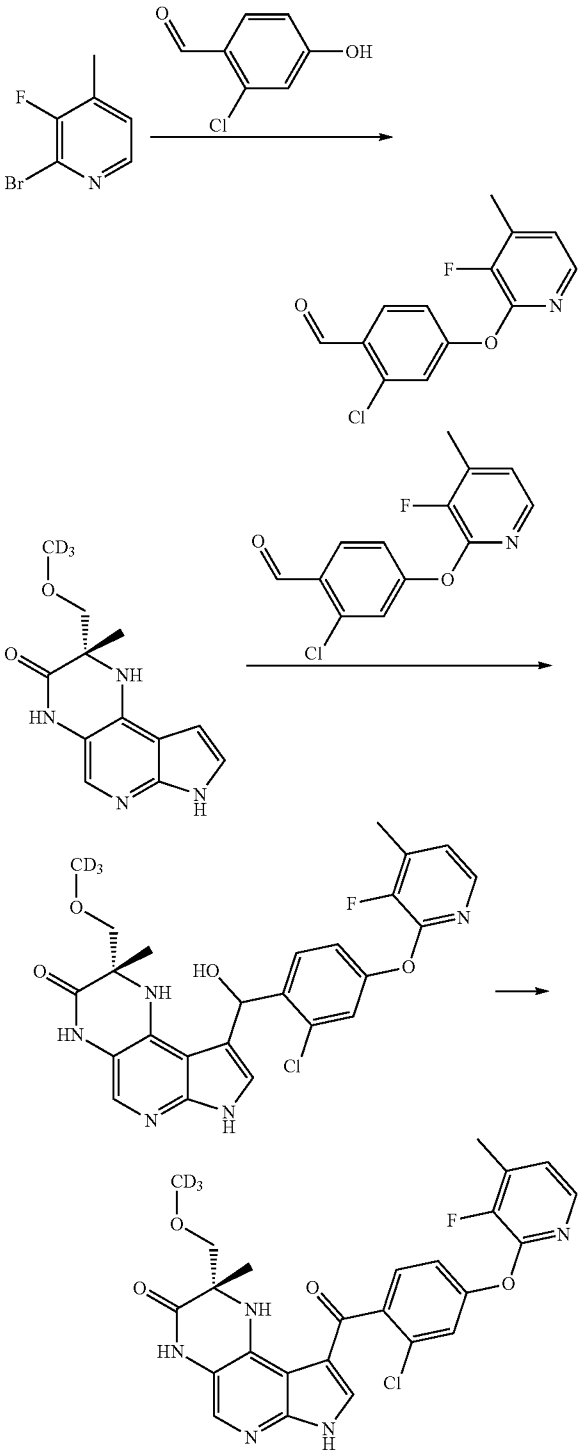

Z146

Step 1: 2-Bromo-3-fluoro-4-methylpyridine (7.0 g, 36.84 mmol) and 2-chloro-4-hydroxybenzaldehyde (8.65 g, 55.26 mmol) were dissolved in 1,4-dioxane (300 mL), then copper iodide (702 mg, 3.68 mmol), L-proline (848 mg, 7.37 mmol) and potassium carbonate (15.27 g, 110.52 mmol) were added thereto, and the reaction was stirred at 110° C. under nitrogen atmosphere for 24 hours. The reaction solution was cooled to room temperature and then filtered through diatomite, and the filter cake was washed with ethyl acetate (300 mL). After the filtrate was concentrated, the crude product was purified by a flash silica gel column (ethyl acetate/petroleum ether: 0-20%) to obtain 2-chloro-4-((3-fluoro-4-methylpyridin-2-yl)oxy)benzaldehyde (1.8 g, 6.78 mmol, yield of 18.4%) as a white solid. ES-API: $[M+H]^+=266.1$.

Step 2: (S)-2-((Methoxy-$d_3$)methyl)-2-methyl-1,2,4,7-tetrahydro-3H-pyrrolo[3',2':5,6]pyrido[3,4-b]pyrazin-3-one (50 mg, 0.201 mmol) and 2-chloro-4-((3-fluoro-4-methylpyridin-2-yl)oxy)benzaldehyde (160 mg, 0.602 mmol) were dissolved in methanol (3 mL), and the reaction was cooled to 0° C., and potassium hydroxide (79 mg, 1.40 mmol) was added thereto. The reaction was stirred at room temperature for 16 hours. The pH of the reaction solution was adjusted to 8 with dilute hydrochloric acid (1.0 M), and the reaction solution was extracted with ethyl acetate (40 mL). The organic phase was washed with saturated brine (20 mL), dried and concentrated, and the crude product was purified by a flash silica gel column (methanol/dichloromethane: 0-8%) to obtain (2S)-9-((2-chloro-4-((3-fluoro-4-methylpyridin-2-yl)oxy)phenyl)(hydroxy)methyl)-2-((methoxy-$d_3$)methyl)-2-methyl-1,2,4,7-tetrahydro-3H-pyrrolo[3',2':5,6]pyrido[3,4-b]pyrazin-3-one (20 mg, 0.038 mmol, yield of 19.3%) as a pale yellow solid. ES-API: $[M+H]^+=515.1$.

Step 3: (2S)-9-((2-Chloro-4-((3-fluoro-4-methylpyridin-2-yl)oxy)phenyl)(hydroxy)methyl)-2-((methoxy-$d_3$)methyl)-2-methyl-1,2,4,7-tetrahydro-3H-pyrrolo[3',2':5,6]pyrido[3,4-b]pyrazin-3-one (20 mg, 0.038 mmol) was dissolved in tetrahydrofuran (1 mL) and water (0.1 mL), and 2,3-dichloro-5,6-dicyano-p-benzoquinone (26 mg, 0.117 mmol) was added thereto at room temperature, and the reaction was stirred at room temperature for 2 hours. To the reaction solution was added with saturated sodium sulfite solution (5 mL) and saturated sodium bicarbonate solution (5 mL) to quench the reaction, and then extracted with ethyl acetate (20 mL). The organic phase was washed with saturated sodium bicarbonate solution (10 mL) and saturated brine (10 mL) in turn, dried and then concentrated, and the crude product was purified by preparative HPLC to obtain (S)-9-(2-chloro-4-((3-fluoro-4-methylpyridin-2-yl)oxy)benzoyl)-2-((methoxy-$d_3$)methyl)-2-methyl-1,2,4,7-tetrahydro-3H-pyrrolo[3',2':5,6]pyrido[3,4-b]pyrazin-3-one (Z146, 8 mg, 0.016 mmol, yield of 40%) as a white solid. $^1H$ NMR (500 MHz, DMSO-$d_6$) δ 12.47 (s, 1H), 10.50 (s, 1H), 8.28 (s, 1H), 7.90 (d, J=5.0 Hz, 1H), 7.70 (s, 1H), 7.61 (d, J=8.5 Hz, 1H), 7.55 (s, 1H), 7.48 (d, J=2.5 Hz, 1H), 7.26 (dd, J=8.5, 2.5 Hz, 1H), 7.20 (t, J=5.0 Hz, 1H), 3.65 (d, J=9.5 Hz, 1H), 3.48 (d, J=9.5 Hz, 1H), 2.37 (s, 3H), 1.40 (s, 3H). ES-API: $[M+H]^+=513.1$.

-continued

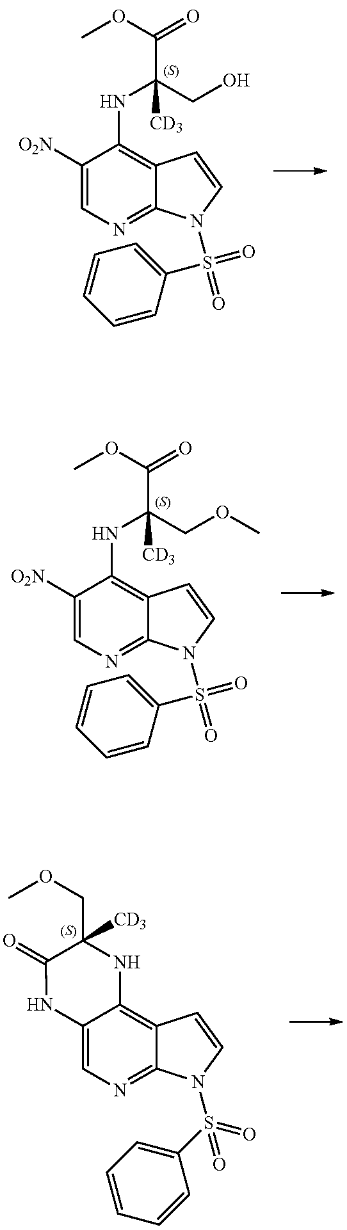

Embodiment 143: Synthesis of Z149

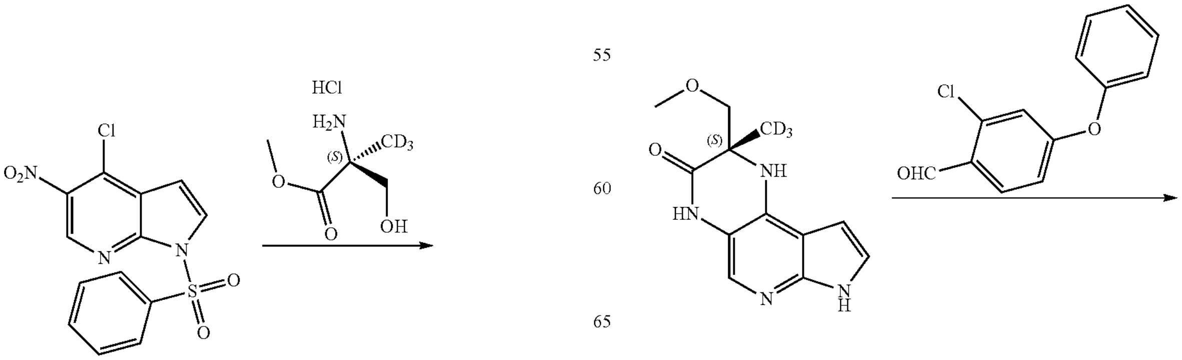

-continued

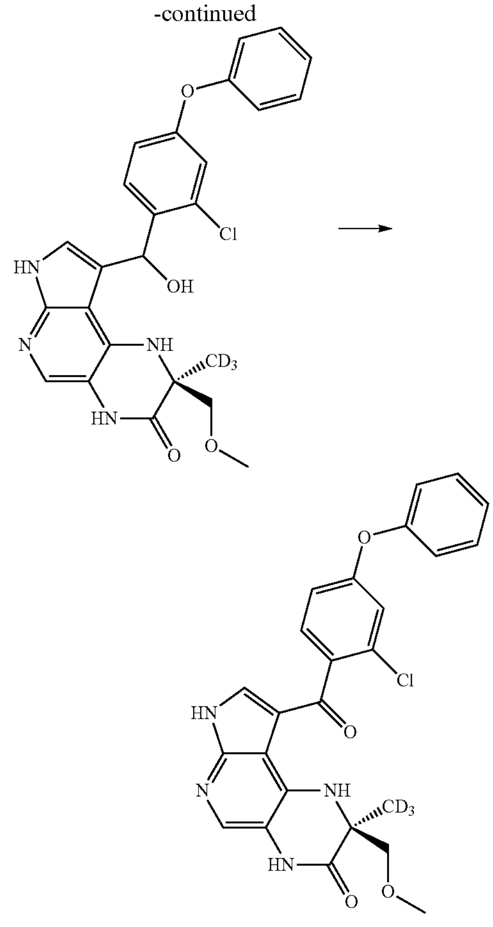

Z149

Step 1: 4-Chloro-5-nitro-1-(phenylsulfonyl)-1H-pyrrolo[2,3-b]pyridine (5.4 g, 15.96 mmol), methyl (S)-2-amino-2-(hydroxymethyl)propanoate-3,3,3-$d_3$ hydrochloride (2.3 g, 13.3 mmol) and DIEA (6.6 mL) were dissolved in anhydrous DMA (40 mL), and the reaction was stirred overnight at 95° C. and returned to room temperature. The reaction solution was added with 100 mL of ethyl acetate, washed 3 times with 60 mL of water and once with 50 mL of saturated brine in turn, dried and concentrated, and the crude product was purified by column chromatography (petroleum ether:ethyl acetate=30:1) to obtain compound methyl (S)-2-(hydroxymethyl)-2-((5-nitro-1-(phenylsulfonyl)-1H-pyrrolo[2,3-b]pyridin-4-yl)amino)propanoate-3,3,3-$d_3$ (3.1 g, yield of 44%). ES-API: $[M+H]^+$=438.1.

Step 2: Methyl (S)-2-(hydroxymethyl)-2-((5-nitro-1-(phenylsulfonyl)-1H-pyrrolo[2,3-b]pyridin-4-yl)amino)propanoate-3,3,3-$d_3$ (1.0 g, 2.3 mmol), silver oxide (11 g, 45.8 mmol) and iodomethane (6.5 g, 45.8 mmol) were dissolved in acetonitrile (50 mL), and the reaction was stirred at 35° C. in the dark for 2 days. The reaction solution was filtered through diatomite, and the filter cake was washed three times with 50 mL of ethyl acetate, and the filtrate was concentrated to obtain methyl (S)-2-(methoxymethyl)-2-((5-nitro-1-(phenylsulfonyl)-1H-pyrrolo[2,3-b]pyridin-4-yl)amino)propanoate-3,3,3-$d_3$ (1.1 g, crude product) as a yellow oil. ES-API: $[M+H]^+$=452.2.

Step 3: Methyl (S)-2-(methoxymethyl)-2-((5-nitro-1-(phenylsulfonyl)-1H-pyrrolo[2,3-b]pyridin-4-yl)amino)propanoate-3,3,3-$d_3$ (1.1 g, 2.4 mmol) was dissolved in acetic acid (30 mL), and iron powder (941 mg, 16.8 mmol) was added thereto, and the reaction was stirred at 85° C. for 3 hours. The reaction solution was added with 100 mL of ethyl acetate, washed twice with 60 mL of water, twice with 40 mL of saturated sodium carbonate, twice with 40 mL of saturated sodium bicarbonate, and with 40 mL of saturated brine in turn, dried and concentrated to obtain (S)-2-(methoxymethyl)-2-(methyl-$d_3$)-7-(phenylsulfonyl)-1,2,4,7-tetrahydro-3H-pyrrolo[3',2':5,6]pyrido[3,4-b]pyrazin-3-one (950 mg, crude product 100%) as a yellow solid. ES-API: $[M+H]^+$=390.1

Step 4: (S)-2-(Methoxymethyl)-2-(methyl-$d_3$)-7-(phenylsulfonyl)-1,2,4,7-tetrahydro-3H-pyrrolo[3',2':5,6]pyrido[3,4-b]pyrazin-3-one (950 mg, 2.44 mmol) was dissolved in 20 mL of methanol, 4 mL of tetrahydrofuran and 2 mL of water, and sodium hydroxide (683 mg, 17.08 mmol) was added thereto, and the reaction was stirred at 65° C. for 6 hours. To the reaction solution was added 15 mL of water and 4 mL of saturated ammonium chloride solution, and the mixture was extracted with 100 mL of ethyl acetate. The organic phase was washed with 20 mL of saturated sodium bicarbonate solution and 20 mL of saturated brine in turn, dried and then concentrated to obtain (S)-2-(methoxymethyl)-2-(methyl-$d_3$)-1,2,4,7-tetrahydro-3H-pyrrolo[3',2':5,6]pyrido[3,4-b]pyrazin-3-one (650 mg, crude product 100%) as a pale yellow solid, ES-API: $[M+H]^+$=250.1.

Step 5: (S)-2-(Methoxymethyl)-2-(methyl-$d_3$)-1,2,4,7-tetrahydro-3H-pyrrolo[3',2':5,6]pyrido[3,4-b]pyrazin-3-one (650 mg, 2.61 mmol) and 2-chloro-4-phenoxybenzaldehyde (1.21 g, 5.22 mmol) were dissolved in methanol (20 mL), and the reaction was cooled to 0° C., and potassium hydroxide (1.02 g, 18.27 mmol) was added thereto. The reaction was stirred at room temperature for 16 hours. The reaction solution was poured into 60 mL of water, and the pH of the reaction solution was adjusted to 8 with 1.0 M dilute hydrochloric acid, and the reaction solution was extracted with 80 mL of ethyl acetate. The organic phase was washed with 25 mL of saturated brine, dried and then concentrated, and the crude product was purified by a thin-layer preparative plate (dichloromethane/7M ammonia methanol=100:7.5) to obtain (2S)-9-((2-chloro-4-phenoxyphenyl)(hydroxy)methyl)-2-(methoxymethyl)-2-(methyl-$d_3$)-1,2,4,7-tetrahydro-3H-pyrrolo[3',2':5,6]pyrido[3,4-b]pyrazin-3-one (850 mg, yield of 68%) as a pale yellow solid. ES-API: $[M+H]^+$=482.2.

Step 6: (2S)-9-((2-Chloro-4-phenoxyphenyl)(hydroxy)methyl)-2-(methoxymethyl)-2-(methyl-$d_3$)-1,2,4,7-tetrahydro-3H-pyrrolo[3',2':5,6]pyrido[3,4-b]pyrazin-3-one (850 mg, 1.77 mmol) was dissolved in 20 mL of tetrahydrofuran and 2 mL of water, and 2,3-dichloro-5,6-dicyano-p-benzoquinone (804 mg, 3.54 mmol) was added thereto, and the reaction was stirred at room temperature for 1 hour. To the reaction solution was added 20 mL of saturated sodium thiosulfate solution and 20 mL of saturated sodium bicarbonate solution, and the mixture was extracted with 60 mL of ethyl acetate. The organic phase was washed with 15 mL of saturated brine, dried and then concentrated, and the crude product was purified by preparative HPLC to obtain (S)-9-(2-chloro-4-phenoxybenzoyl)-2-(methoxymethyl)-2-(methyl-$d_3$)-1,2,4,7-tetrahydro-3H-pyrrolo[3',2':5,6]pyrido[3,4-b]pyrazin-3-one (Z149, 350 mg, yield of 41%) as a white solid. ES-API: $[M+H]^+$=480.1. $^1H$ NMR (400 MHz, DMSO-$d_6$) δ 12.48 (s, 1H), 10.50 (s, 1H), 8.27 (s, 1H), 7.69 (s, 1H), 7.61 (s, 1H), 7.56 (d, J=8.4 Hz, 1H), 7.51-7.36 (m, 2H), 7.25 (t, J=7.4 Hz, 1H), 7.19-7.17 (m, 3H), 7.02 (dd, J=8.4, 2.4 Hz, 1H), 3.64 (d, J=9.6 Hz, 1H), 3.47 (d, J=9.6 Hz, 1H), 3.29 (s, 3H).

Embodiment 144: Synthesis of Z150

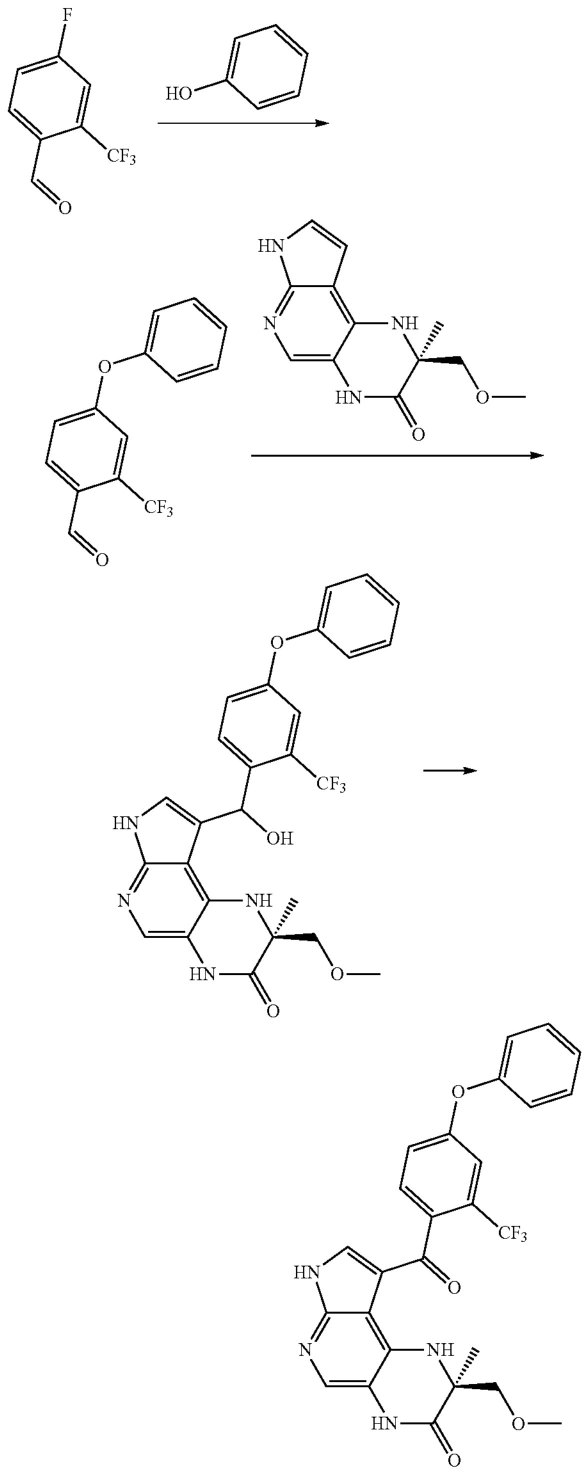

Z150

Step 1: 4-Fluoro-2-(trifluoromethyl)benzaldehyde (500 mg, 2.6 mmol), phenol (221 mg, 2.34 mmol) and cesium carbonate (929 mg, 2.86 mmol) were dissolved in N,N'-dimethylformamide (30 mL), and the reaction was stirred at 65° C. for two hours. The reaction was cooled to 0° C., added with 50 mL of ethyl acetate, added with 50 mL of water to wash three times respectively, and the organic phase was washed with 50 mL of saturated brine, dried and then concentrated, and purified by column chromatography (petroleum ether:ethyl acetate=30:1) to obtain a product 4-phenoxy-2-(trifluoromethyl)benzaldehyde (330 mg, yield of 48%) as a pale yellow solid. ES-API: $[M+H]^+=267.0$.

Step 2: (S)-2-(Methoxymethyl)-2-methyl-1,2,4,7-tetrahydro-3H-pyrrolo[3',2':5,6]pyrido[3,4-b]pyrazin-3-one (100 mg, 0.41 mmol) and 4-phenoxy-2-(trifluoromethyl)benzaldehyde (218 mg, 0.82 mmol) were dissolved in methanol (20 mL), and the reaction was cooled to 0° C., and potassium hydroxide (161 mg, 2.87 mmol) was added thereto. The reaction was stirred at room temperature for 16 hours. The reaction solution was poured into 30 mL of water, and the pH of the reaction solution was adjusted to 8 with 1.0 M dilute hydrochloric acid, and the reaction solution was extracted with 50 mL of ethyl acetate. The organic phase was washed with 25 mL of saturated brine, dried and then concentrated, and the crude product was purified by a thin-layer preparative plate (dichloromethane/7M ammonia methanol=100:8) to obtain (2S)-9-(hydroxy(4-phenoxy-2-(trifluoromethyl)phenyl)methyl)-2-(methoxymethyl)-2-methyl-1,2,4,7-tetrahydro-3H-pyrrolo[3',2':5,6]pyrido[3,4-b]pyrazin-3-one (121 mg, yield of 58%) as a pale yellow solid. ES-API: $[M+H]^+=513.2$.

Step 3: (2S)-9-(Hydroxy(4-phenoxy-2-(trifluoromethyl)phenyl)methyl)-2-(methoxymethyl)-2-methyl-1,2,4,7-tetrahydro-3H-pyrrolo[3',2':5,6]pyrido[3,4-b]pyrazin-3-one (121 mg, 0.24 mmol) was dissolved in 20 mL of tetrahydrofuran and 2 mL of water, and 2,3-dichloro-5,6-dicyano-p-benzoquinone (109 mg, 0.48 mmol) was added thereto, and the reaction was stirred at room temperature for 1 hour. To the reaction solution was added 20 mL of saturated sodium thiosulfate solution, and the mixture was extracted with 60 mL of ethyl acetate. The organic phase was washed twice with 20 mL of saturated sodium bicarbonate solution and 15 mL of saturated brine in turn, dried and then concentrated, and the crude product was purified by preparative HPLC (column: xbridge C18 19*150 mm, 5 μm; system: 10 mmol/L, aqueous $NH_4HCO_3$ solution; flow rate: 15 mL/min; gradient: 20 to 45% $CH_3CN—NH_4HCO_3$; column temperature: room temperature) to obtain (S)-2-(methoxymethyl)-2-methyl-9-(4-phenoxy-2-(trifluoromethyl)benzoyl)-1,2,4,7-tetrahydro-3H-pyrrolo[3',2':5,6]pyrido[3,4-b]pyrazin-3-one (Z150, 50 mg, yield of 30%) as a white solid. ES-API: $[M+H]^+=511.1$. $^1H$ NMR (400 MHz, DMSO-$d_6$) δ 12.48 (s, 1H), 10.51 (s, 1H), 8.22 (s, 1H), 7.78-7.61 (m, 2H), 7.60 (s, 1H), 7.52-7.48 (m, 2H), 7.43 (s, 1H), 7.29-7.25 (m, 2H), 7.22-7.20 (m, 2H), 3.63 (d, J=12.5 Hz, 1H), 3.44 (d, J=12.5 Hz, 1H), 3.28 (s, 3H), 1.38 (s, 3H).

Embodiment 145: Synthesis of Z153 and Isomers Thereof

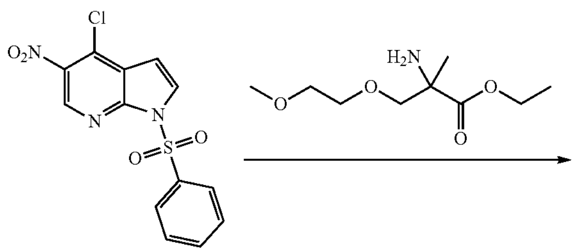

-continued
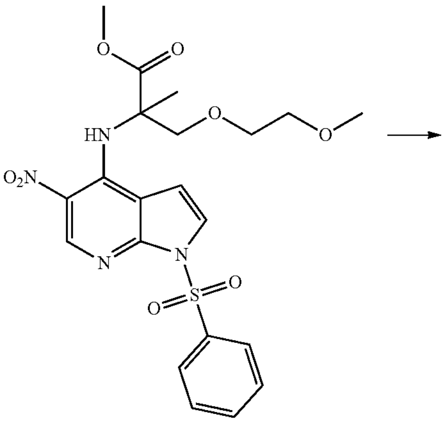
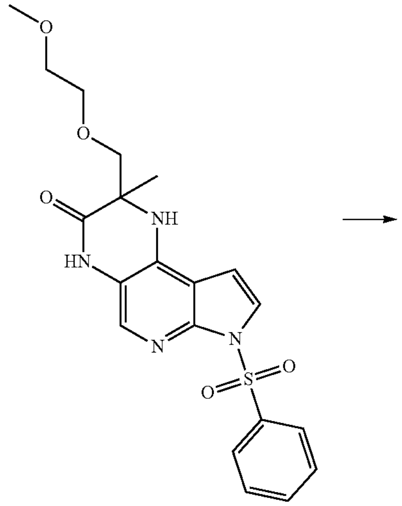
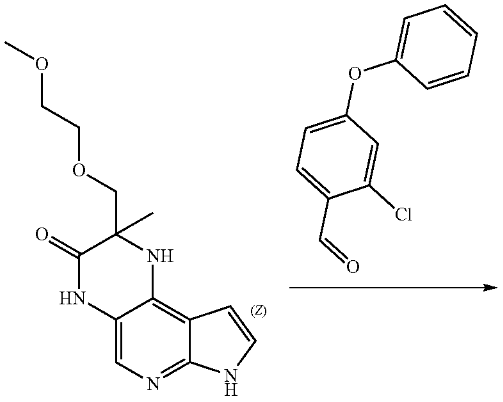
-continued
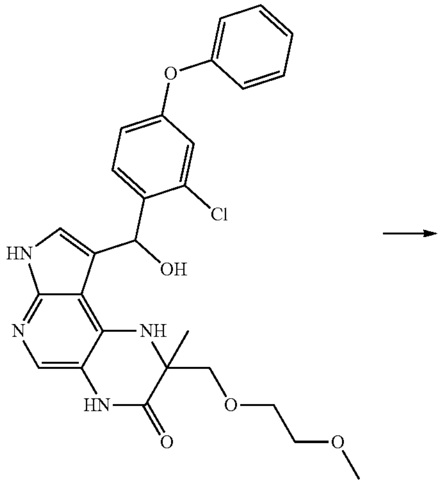
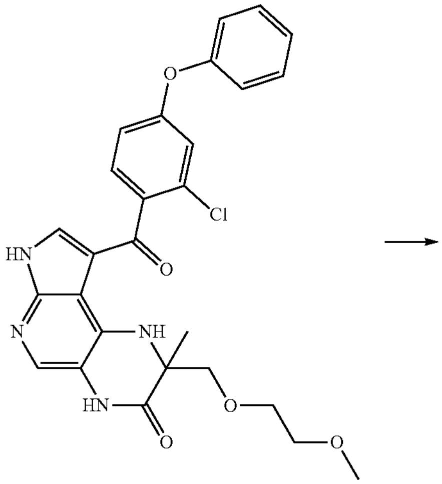
Z153
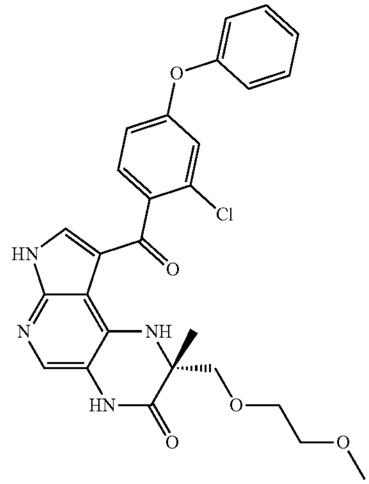
+
Z153-1

-continued

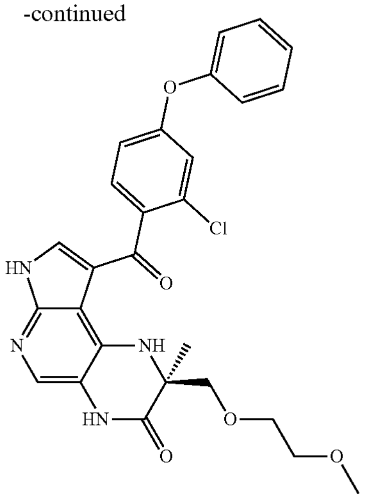

Z153-2

Step 1: 4-Chloro-5-nitro-1-(phenylsulfonyl)-1H-pyrrolo[2,3-b]pyridine (1 g, 2.967 mmol), ethyl 2-amino-3-(2-methoxyethoxy)-2-methylpropanoate (791 mg, 3.858 mmol) and N,N-diisopropylethylamine (1.914 g, 14.835 mmol) were dissolved in anhydrous N,N-dimethylacetamide (20 mL), and the reaction mixture was heated to 95° C. and reacted for 6 hours in a sealed tube. LCMS detected that the reaction was complete, and the reaction solution was cooled to room temperature, diluted with 50 mL of ethyl acetate, then washed once with 30 mL of water, washed with saturated brine (25 mL×3). The organic phase was dried over anhydrous sodium sulfate, filtered, and the filtrate was concentrated under reduced pressure, and the crude product was purified by combiflash (petroleum ether/ethyl acetate=0-80%) to obtain compound methyl 3-(2-methoxyethoxy)-2-methyl-2-((5-nitro-1-(phenylsulfonyl)-1H-pyrrolo[2,3-b]pyridin-4-yl)amino)propanoate (900 mg, yield of 60%). ES-API: $[M+H]^+$=507.1

Step 2: Under nitrogen atmosphere, methyl 3-(2-methoxyethoxy)-2-methyl-2-((5-nitro-1-(phenylsulfonyl)-1H-pyrrolo[2,3-b]pyridin-4-yl)amino)propanoate (800 mg, 1.581 mmol) was dissolved in acetic acid (30 mL), and iron powder (2.656 g, 47.431 mmol) was added thereto, and the reaction mixture was heated to 80° C. and stirred for 1 hour. LCMS detected that the reaction was complete, and the reaction solution was cooled to room temperature, diluted with 100 mL of ethyl acetate, washed with water (30 mL×3) and saturated aqueous sodium carbonate solution (30 mL×3) in turn. The organic phase was dried over anhydrous sodium sulfate, filtered, and the filtrate was concentrated under reduced pressure, and the crude product was purified by combiflash (petroleum ether/ethyl acetate=0-80%) to obtain a yellow solid 2-((2-methoxyethoxy)methyl)-2-methyl-7-(phenylsulfonyl)-1,2,4,7-tetrahydro-3H-pyrrolo[3',2':5,6]pyrido[3,4-b]pyrazin-3-one (545 mg, yield of 80%). ES-API: $[M+H]^+$=431.2

Step 3: 2-((2-Methoxyethoxy)methyl)-2-methyl-7-(phenylsulfonyl)-1,2,4,7-tetrahydro-3H-pyrrolo[3',2':5,6]pyrido[3,4-b]pyrazin-3-one (300 mg, 0.698 mmol) was dissolved in 5 mL of methanol, 2.5 mL of tetrahydrofuran and 0.5 mL of water, and sodium hydroxide (140 mg, 3.488 mmol) was added thereto, and the reaction mixture was heated to 60° C. and stirred for 6 hours in a sealed tube. LCMS detected that the reaction was complete, and the reaction solution was cooled to room temperature. The pH of the reaction solution was adjusted to 7.0 by adding 2 mol/L dilute hydrochloric acid, then the reaction solution was concentrated under reduced pressure and the residue was purified by combiflash (dichloromethane/methanol=0-9.5%) to obtain compound 2-((2-methoxyethoxy)methyl)-2-methyl-1,2,4,7-tetrahydro-3H-pyrrolo[3',2':5,6]pyrido[3,4-b]pyrazin-3-one (167 mg, yield of 83%). ES-API: $[M+H]^+$=291.3

Step 4: 2-((2-Methoxyethoxy)methyl)-2-methyl-1,2,4,7-tetrahydro-3H-pyrrolo[3',2':5,6]pyrido[3,4-b]pyrazin-3-one (167 mg, 0.576 mmol) and 2-chloro-4-phenoxybenzaldehyde (267 mg, 1.152 mmol) were dissolved in methanol (15 mL), and the reaction solution was cooled to 0° C., and potassium hydroxide (226 mg, 4.032 mmol) was added thereto. The reaction solution was slowly raised to room temperature and stirred for 18 hours. LCMS detected that the reaction was complete. The reaction was quenched by adding 20 mL of saturated ammonium chloride solution, extracted with ethyl acetate (15 mL×3). The organic phase was washed with 20 mL of saturated brine, dried over anhydrous sodium sulfate and then concentrated to obtain a crude product 9-((2-chloro-4-phenoxyphenyl)(hydroxy)methyl)-2-((2-methoxyethoxy)methyl)-2-methyl-1,2,4,7-tetrahydro-3H-pyrrolo[3',2':5,6]pyrido[3,4-b]pyrazin-3-one (310 mg). ES-API: $[M+H]^+$=523.2

Step 5: The crude product 9-((2-chloro-4-phenoxyphenyl)(hydroxy)methyl)-2-((2-methoxyethoxy)methyl)-2-methyl-1,2,4,7-tetrahydro-3H-pyrrolo[3',2':5,6]pyrido[3,4-b]pyrazin-3-one (310 mg) was dissolved in 30 mL of tetrahydrofuran, and 2,3-dichloro-5,6-dicyano-p-benzoquinone (310 mg, 1.366 mmol) was added thereto, and the reaction was stirred at room temperature for 2 hours. LCMS detected that the reaction was complete. To the reaction solution was added 20 mL of saturated sodium thiosulfate solution and 20 mL of saturated sodium bicarbonate solution, and the mixture was extracted with 30 mL of ethyl acetate. The organic phase was washed with 15 mL of saturated brine, dried and concentrated, and the crude product was purified by preparative HPLC (column: xbridge C18 19*150 mm, 5 μm; system: 10 mmol/L, aqueous $NH_4HCO_3$ solution; flow rate: 15 mL/min; gradient: 20 to 45% $CH_3CN$—$NH_4HCO_3$; column temperature: room temperature) to obtain a pale yellow solid 9-(2-chloro-4-phenoxybenzoyl)-2-((2-methoxyethoxy)methyl)-2-methyl-1,2,4,7-tetrahydro-3H-pyrrolo[3',2':5,6]pyrido[3,4-b]pyrazin-3-one (Z153, 182 mg, yield of 59%). ES-API: $[M+H]^+$=521.2.

Step 6: The above obtained compound Z153 was chirally resolved by SFC (chromatographic column: Daicel CHIRALPAK IE 250*4.6 mm, 5 μm; mobile phase: HEX (0.1% DEA)/ETOH (0.1% DEA)=60:40 (V/V); flow rate: 1 mL/min; column temperature: room temperature) to obtain two single isomer compounds. One single isomer with a structure arbitrarily designated as Z153-1 (retention time: 8.790 min, 74.07 mg). ES-API: $[M+H]^+$=521.2. The other single isomer with a structure arbitrarily designated as Z153-2 (retention time: 10.732 min, 75.05 mg). ES-API: $[M+H]^+$=521.2.

Embodiment 146: Synthesis of Z155

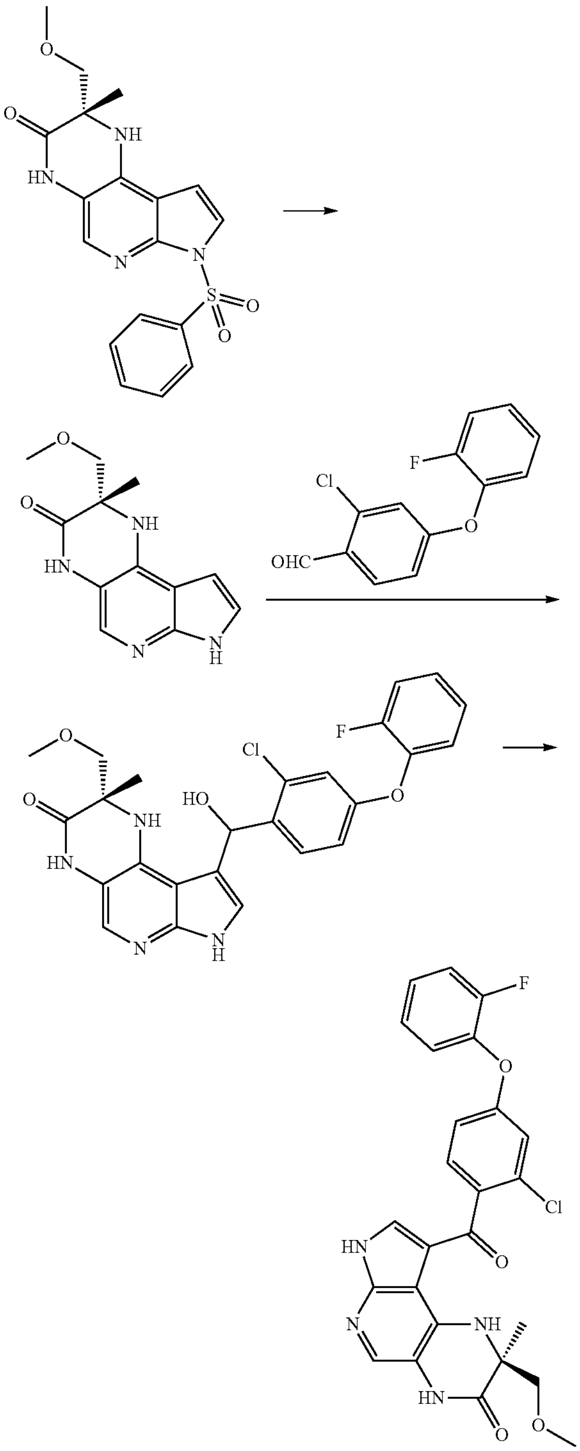

Z155

Step 1: (S)-2-(Methoxymethyl)-2-methyl-7-(phenylsulfonyl)-1,2,4,7-tetrahydro-3H-pyrrolo[3',2':5,6]pyrido[3,4-b]pyrazin-3-one (1.40 g, 3.570 mmol) was dissolved in 36 mL of methanol, 9 mL of tetrahydrofuran and 6 mL of water, and sodium hydroxide (1.01 g, 24.99 mmol) was added thereto, and the reaction was stirred at 65° C. for 7 hours. To the reaction solution was added 20 mL of water and 15 mL of saturated ammonium chloride solution, and the mixture was extracted with 200 mL of ethyl acetate. The organic phase was washed with 30 mL of saturated sodium bicarbonate solution and 80 mL of saturated brine in turn, dried over anhydrous sodium sulfate and then concentrated to obtain (S)-2-(methoxymethyl)-2-methyl-1,2,4,7-tetrahydro-3H-pyrrolo[3',2':5,6]pyrido[3,4-b]pyrazin-3-one (0.58 g, crude yield of 66%) as a pale white solid. ES-API: $[M+H]^+=247.1$.

Step 2: (S)-2-(Methoxymethyl)-2-methyl-1,2,4,7-tetrahydro-3H-pyrrolo[3',2':5,6]pyrido[3,4-b]pyrazin-3-one (213 mg, 0.8667 mmol) and 2-chloro-4-(2-fluorophenoxy)benzaldehyde (433 mg, 1.733 mmol) were dissolved in methanol (20.0 mL), and the reaction was cooled to 0° C., and potassium hydroxide (340 mg, 6.067 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and then concentrated to obtain a crude target product (2S)-9-((2-chloro-4-(2-fluorophenoxy)phenyl)(hydroxyl)methyl)-2-(methoxymethyl)-2-methyl-1,2,4,7-tetrahydro-3H-pyrrolo[3',2':5,6]pyrido[3,4-b]pyrazin-3-one (0.250 g, yield of 58%) as a pale yellow solid. ES-API: $[M+H]^+=497.2$.

Step 3: (2S)-9-((2-Chloro-4-(2-fluorophenoxy)phenyl)(hydroxyl)methyl)-2-(methoxymethyl)-2-methyl-1,2,4,7-tetrahydro-3H-pyrrolo[3',2':5,6]pyrido[3,4-b]pyrazin-3-one (250 mg, 0.5038 mmol) was dissolved in 25 mL of tetrahydrofuran, and 2,3-dichloro-5,6-dicyano-1,4-benzoquinone (228 mg, 1.007 mmol) was added thereto, and the reaction was stirred at room temperature for 2 hours. To the reaction solution was added 60 mL of saturated sodium bicarbonate solution, and the mixture was extracted with 80 mL of ethyl acetate. The organic phase was washed with 60 mL of saturated brine, dried over anhydrous sodium sulfate and then concentrated, and the crude product was purified by preparative HPLC to obtain (S)-9-(2-chloro-4-(2-fluorophenoxy)benzoyl)-2-(methoxymethyl)-2-methyl-1,2,4,7-tetrahydro-3H-pyrrolo[3',2':5,6]pyrido[3,4-b]pyrazin-3-one (Z155, 115 mg, yield of 46%) as a pale yellow solid, ES-API: $[M+H]^+=495.1$. $^1H$ NMR (400 MHz, DMSO-d6) δ 12.45 (s, 1H), 10.49 (s, 1H), 8.27 (s, 1H), 7.69 (s, 1H), 7.63-7.54 (m, 2H), 7.53-7.43 (m, 1H), 7.43-7.28 (m, 3H), 7.21 (d, J=2.3 Hz, 1H), 7.00 (dd, J=8.4, 2.3 Hz, 1H), 3.64 (d, J=9.5 Hz, 1H), 3.47 (d, J=9.5 Hz, 1H), 3.29 (s, 3H), 1.38 (s, 3H).

Embodiment 147: Synthesis of Z156

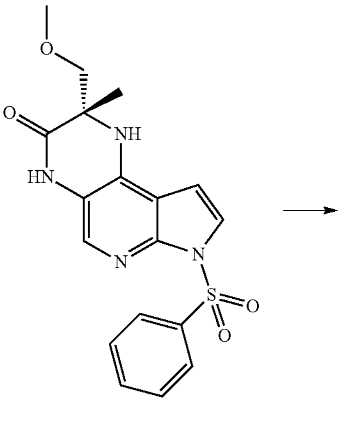

-continued

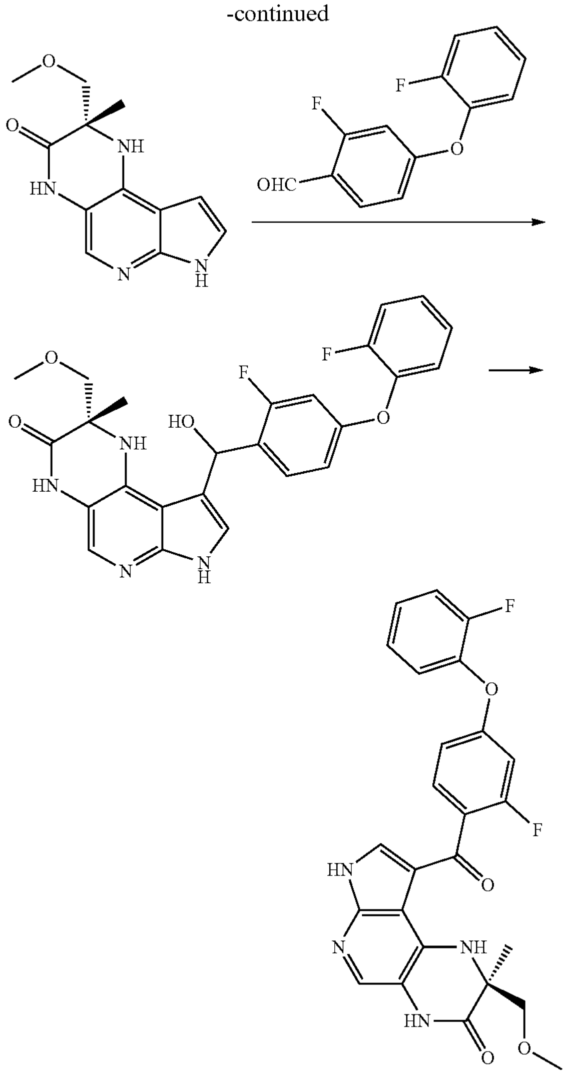

Z156

Step 1: (S)-2-(Methoxymethyl)-2-methyl-7-(phenylsulfonyl)-1,2,4,7-tetrahydro-3H-pyrrolo[3',2':5,6]pyrido[3,4-b]pyrazin-3-one (1.40 g, 3.570 mmol) was dissolved in 36 mL of methanol, 9 mL of tetrahydrofuran and 6 mL of water, and sodium hydroxide (1.01 g, 24.99 mmol) was added thereto, and the reaction was stirred at 65° C. for 7 hours. To the reaction solution was added 20 mL of water and 15 mL of saturated ammonium chloride solution, and the mixture was extracted with 200 mL of ethyl acetate. The organic phase was washed with 30 mL of saturated sodium bicarbonate solution and 80 mL of saturated brine in turn, dried over anhydrous sodium sulfate and then concentrated to obtain (S)-2-(methoxymethyl)-2-methyl-1,2,4,7-tetrahydro-3H-pyrrolo[3',2':5,6]pyrido[3,4-b]pyrazin-3-one (0.58 g, crude yield of 66%) as a pale white solid. ES-API: $[M+H]^+=247.1$.

Step 2: (S)-2-(Methoxymethyl)-2-methyl-1,2,4,7-tetrahydro-3H-pyrrolo[3',2':5,6]pyrido[3,4-b]pyrazin-3-one (213 mg, 0.8667 mmol) and 2-fluoro-4-(2-fluorophenoxy)benzaldehyde (405 mg, 1.733 mmol) were dissolved in methanol (20.0 mL), and the reaction was cooled to 0° C., and potassium hydroxide (340 mg, 6.067 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and then concentrated to obtain a crude target product (2S)-9-((2-fluoro-4-(2-fluorophenoxy)phenyl)(hydroxyl)methyl)-2-(methoxymethyl)-2-methyl-1,2,4,7-tetrahydro-3H-pyrrolo[3',2':5,6]pyrido[3,4-b]pyrazin-3-one (237 mg, yield of 57%) as a pale yellow solid. ES-API: $[M+H]^+=481.3$.

Step 3: (2S)-9-((2-Fluoro-4-(2-fluorophenoxy)phenyl)(hydroxyl)methyl)-2-(methoxymethyl)-2-methyl-1,2,4,7-tetrahydro-3H-pyrrolo[3',2':5,6]pyrido[3,4-b]pyrazin-3-one (237 mg, 0.4934 mmol) was dissolved in 25 mL of tetrahydrofuran, and 2,3-dichloro-5,6-dicyano-1,4-benzoquinone (224 mg, 0.9869 mmol) was added thereto, and the reaction was stirred at room temperature for 2 hours. To the reaction solution was added 60 mL of saturated sodium bicarbonate solution, and the mixture was extracted with 80 mL of ethyl acetate. The organic phase was washed with 60 mL of saturated brine, dried over anhydrous sodium sulfate and then concentrated, and the crude product was purified by preparative HPLC to obtain (S)-9-(2-fluoro-4-(2-fluorophenoxy)benzoyl)-2-(methoxymethyl)-2-methyl-1,2,4,7-tetrahydro-3H-pyrrolo[3',2':5,6]pyrido[3,4-b]pyrazin-3-one (Z156, 73 mg, yield of 31%) as a pale yellow solid, ES-API: $[M+H]^+=479.2$. $^1H$ NMR (400 MHz, DMSO-d6) δ 8.24 (s, 1H), 7.74 (s, 1H), 7.68 (s, 1H), 7.62 (t, J=8.3 Hz, 1H), 7.47 (dd, J=11.1, 8.0 Hz, 1H), 7.34 (tdd, J=13.7, 10.8, 7.0 Hz, 3H), 7.02 (dd, J=11.1, 2.2 Hz, 1H), 6.91-6.84 (m, 1H), 6.07 (s, OH), 3.64 (d, J=9.5 Hz, 1H), 3.47 (d, J=9.5 Hz, 2H), 3.29 (s, 3H), 1.37 (s, 3H).

Embodiment 148: Synthesis of Z157

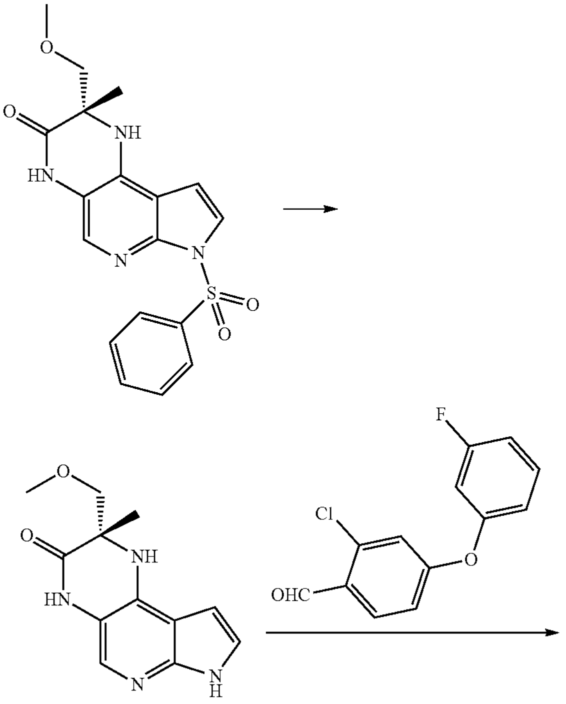

-continued

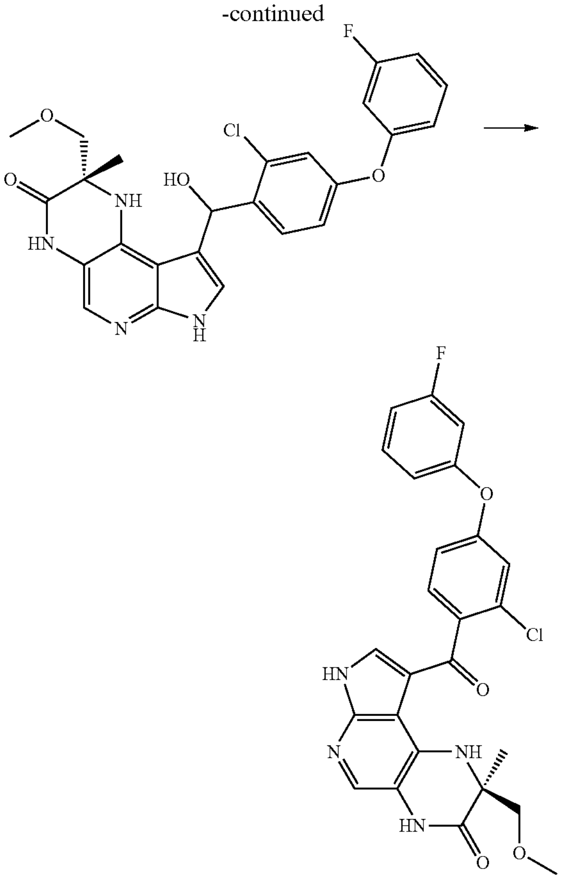

Z157

Step 1: (S)-2-(Methoxymethyl)-2-methyl-7-(phenylsulfonyl)-1,2,4,7-tetrahydro-3H-pyrrolo[3',2':5,6]pyrido[3,4-b]pyrazin-3-one (1.40 g, 3.570 mmol) was dissolved in 36 mL of methanol, 9 mL of tetrahydrofuran and 6 mL of water, and sodium hydroxide (1.01 g, 24.99 mmol) was added thereto, and the reaction was stirred at 65° C. for 7 hours. To the reaction solution was added 20 mL of water and 15 mL of saturated ammonium chloride solution, and the mixture was extracted with 200 mL of ethyl acetate. The organic phase was washed with 30 mL of saturated sodium bicarbonate solution and 80 mL of saturated brine in turn, dried over anhydrous sodium sulfate and then concentrated to obtain (S)-2-(methoxymethyl)-2-methyl-1,2,4,7-tetrahydro-3H-pyrrolo[3',2':5,6]pyrido[3,4-b]pyrazin-3-one (0.58 g, crude yield of 66%) as a pale white solid. ES-API: $[M+H]^+$=247.1.

Step 2: (S)-2-(Methoxymethyl)-2-methyl-1,2,4,7-tetrahydro-3H-pyrrolo[3',2':5,6]pyrido[3,4-b]pyrazin-3-one (213 mg, 0.8667 mmol) and 2-chloro-4-(3-fluorophenoxy)benzaldehyde (433 mg, 1.733 mmol) were dissolved in methanol (20.0 mL), and the reaction was cooled to 0° C., and potassium hydroxide (340 mg, 6.067 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and then concentrated to obtain a crude target product (2S)-9-((2-chloro-4-(3-fluorophenoxy)phenyl)(hydroxyl)methyl)-2-(methoxymethyl)-2-methyl-1,2,4,7-tetrahydro-3H-pyrrolo[3',2':5,6]pyrido[3,4-b]pyrazin-3-one (305 mg, yield of 70%) as a pale yellow solid. ES-API: $[M+H]^+$=497.2.

Step 3: (2S)-9-((2-Chloro-4-(3-fluorophenoxy)phenyl)(hydroxyl)methyl)-2-(methoxymethyl)-2-methyl-1,2,4,7-tetrahydro-3H-pyrrolo[3',2':5,6]pyrido[3,4-b]pyrazin-3-one (305 mg, 0.6146 mmol) was dissolved in 20 mL of tetrahydrofuran, and 2,3-dichloro-5,6-dicyano-1,4-benzoquinone (280 mg, 1.230 mmol) was added thereto, and the reaction was stirred at room temperature for 2 hours. To the reaction solution was added 63 mL of saturated sodium bicarbonate solution, and the mixture was extracted with 88 mL of ethyl acetate. The organic phase was washed with 60 mL of saturated brine, dried over anhydrous sodium sulfate and then concentrated, and the crude product was purified by preparative HPLC to obtain (S)-9-(2-chloro-4-(3-fluorophenoxy)benzoyl)-2-(methoxymethyl)-2-methyl-1,2,4,7-tetrahydro-3H-pyrrolo[3',2':5,6]pyrido[3,4-b]pyrazin-3-one (Z157, 100 mg, yield of 33%) as a pale yellow solid, ES-API: $[M+H]^+$=495.1. $^1H$ NMR (400 MHz, DMSO-$d_6$) δ 12.48 (s, 1H), 10.50 (s, 1H), 8.27 (s, 1H), 7.70 (s, 1H), 7.65 (s, 1H), 7.58 (d, J=8.4 Hz, 1H), 7.49 (dd, J=15.2, 8.2 Hz, 1H), 7.29 (d, J=2.3 Hz, 1H), 7.15-7.05 (m, 3H), 7.02 (dd, J=8.2, 2.0 Hz, 1H), 3.65 (d, J=9.5 Hz, 1H), 3.48 (d, J=9.6 Hz, 1H), 3.30 (s, 3H), 1.39 (s, 3H).

Embodiment 149: Synthesis of Z160

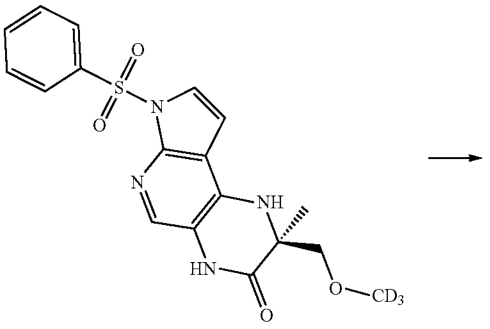

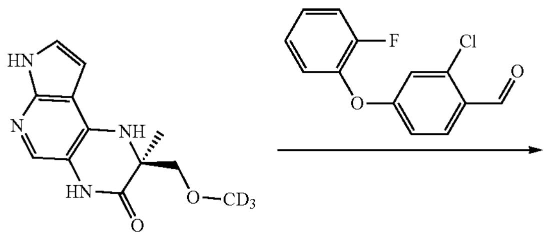

-continued

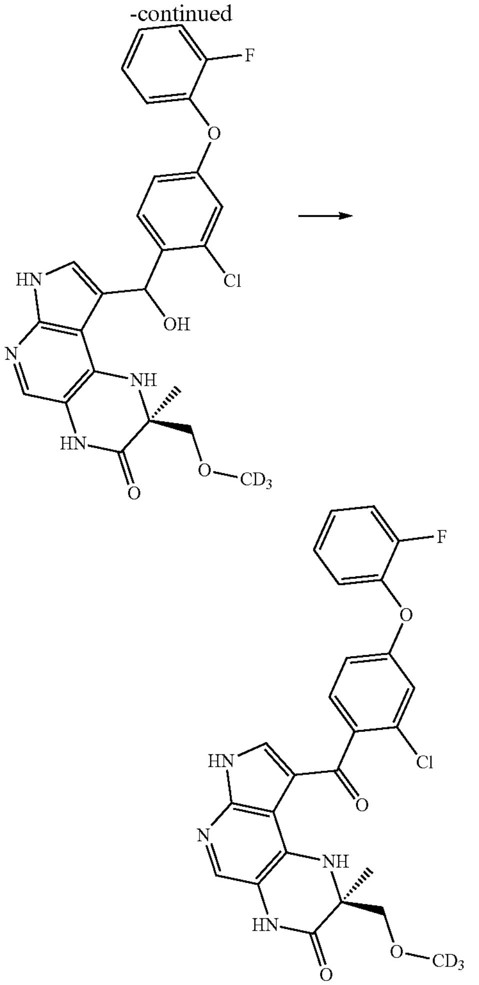

Z160

Step 1: (S)-2-((Methoxy-$d_3$)methyl)-2-methyl-7-(phenylsulfonyl)-1,2,4,7-tetrahydro-3H-pyrrolo[3',2':5,6]pyrido[3,4-b]pyrazin-3-one (500 mg, 1.28 mmol) was dissolved in methanol (6 mL), tetrahydrofuran (3 mL) and water (1 mL), and sodium hydroxide (359 mg, 8.99 mmol) was added thereto, and the reaction was stirred at 60° C. for 16 hours. After the reaction solution was cooled to room temperature, the pH of the reaction solution was adjusted to 8 with dilute hydrochloric acid (1.0 M), then 30 mL of saturated sodium bicarbonate solution was added thereto, and the mixture was extracted with ethyl acetate (100 mL). The organic phase was washed once with saturated sodium bicarbonate solution (30 mL), washed twice with saturated brine (30 mL) in turn, dried and concentrated to obtain (S)-2-((methoxy-$d_3$)methyl)-2-methyl-1,2,4,7-tetrahydro-3H-pyrrolo[3',2':5,6]pyrido[3,4-b]pyrazin-3-one (320 mg, 1.28 mmol, yield of 100%) as a white solid. ES-API: $[M+H]^+$=250.1.

Step 2: (S)-2-((Methoxy-$d_3$)methyl)-2-methyl-1,2,4,7-tetrahydro-3H-pyrrolo[3',2':5,6]pyrido[3,4-b]pyrazin-3-one (320 mg, 1.28 mmol) and 2-chloro-4-(2-fluorophenoxy)benzaldehyde (644 mg, 2.57 mmol) were dissolved in methanol (10 mL), and the reaction was cooled to 0° C., and potassium hydroxide (504 mg, 8.99 mmol) was added thereto. The reaction was stirred at room temperature for 16 hours. The pH of the reaction solution was adjusted to 8 with dilute hydrochloric acid (1.0 M), and the reaction solution was extracted with ethyl acetate (100 mL). The organic phase was washed with saturated brine (30 mL), dried and concentrated, and the crude product was purified by a flash silica gel column (methanol/dichloromethane: 0-8%) to obtain (2S)-9-((2-chloro-4-(2-fluorophenoxy)phenyl)(hydroxy)methyl)-2-((methoxy-$d_3$)methyl)-2-methyl-tetrahydro-3H-pyrrolo[3',2':5,6]pyrido[3,4-b]pyrazin-3-one (460 mg, 0.92 mmol, yield of 72%) as a pale yellow solid. ES-API: $[M+H]^+$=500.1.

Step 3: (2S)-9-((2-Chloro-4-(2-fluorophenoxy)phenyl)(hydroxy)methyl)-2-((methoxy-$d_3$)methyl)-2-methyl-tetrahydro-3H-pyrrolo[3',2':5,6]pyrido[3,4-b]pyrazin-3-one (460 mg, 0.92 mmol) was dissolved in tetrahydrofuran (10 mL) and water (1 mL), and 2,3-dichloro-5,6-dicyano-p-benzoquinone (538 mg, 2.36 mmol) was added thereto at room temperature, and the reaction was stirred at room temperature for 2 hours. To the reaction solution was added saturated sodium sulfite solution (10 mL) and saturated sodium bicarbonate solution (10 mL) to quench the reaction, and then extracted with ethyl acetate (50 mL). The organic phase was washed with saturated sodium bicarbonate solution (20 mL) and saturated brine (20 mL) in turn, dried and then concentrated, and the crude product was purified by preparative HPLC to obtain (S)-9-(2-chloro-4-(2-fluorophenoxy)benzoyl)-2-((methoxy-$d_3$)methyl)-2-methyl-1,2,4,7-tetrahydro-3H-pyrrolo[3',2':5,6]pyrido[3,4-b]pyrazin-3-one (Z160, 170 mg, 0.341 mmol, yield of 37%) as a white solid. $^1H$ NMR (500 MHz, DMSO-$d_6$) δ 12.45 (s, 1H), 10.48 (s, 1H), 8.26 (s, 1H), 7.69 (s, 1H), 7.59-7.54 (m, 2H), 7.50-7.43 (m, 1H), 7.39-7.28 (m, 3H), 7.20 (d, J=2.4 Hz, 1H), 7.00 (dd, J=8.5, 2.5 Hz, 1H), 3.64 (d, J=9.5 Hz, 1H), 3.47 (d, J=9.5 Hz, 1H), 1.38 (s, 3H). ES-API: $[M+H]^+$=498.1.

Embodiment 150: Synthesis of Z161

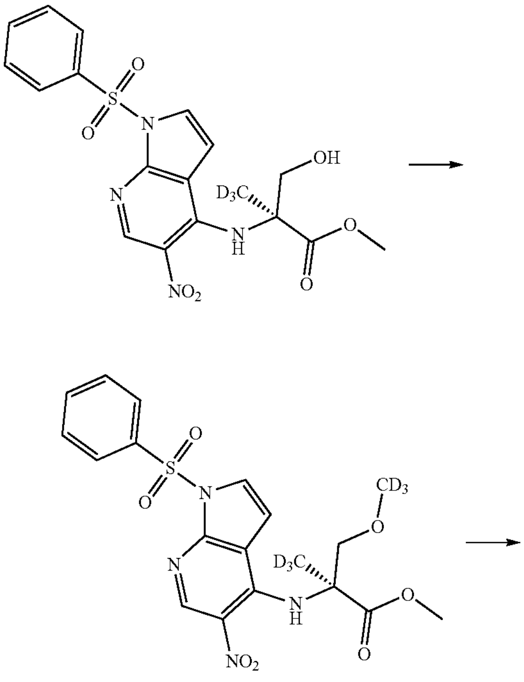

-continued

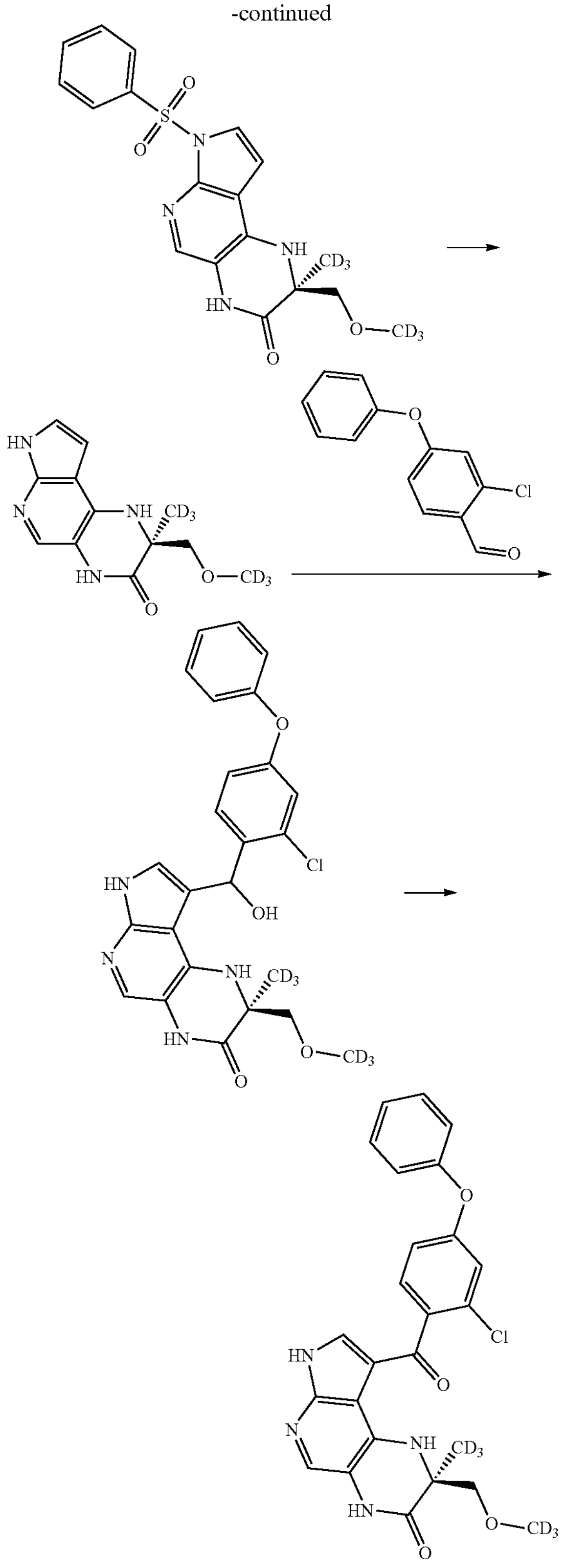

Z161

Step 1: Deuteromethyl (S)-2-(hydroxymethyl)-2-((5-nitro-1-(phenylsulfonyl)-1H-pyrrolo[2,3-b]pyridin-4-yl) amino)propanoate (500 mg, 1.14 mmol) was dissolved in acetonitrile (15 mL), and silver (II) oxide (3.97 g, 17.15 mmol) and deuterated iodomethane (2.49 g, 17.15 mmol) were added thereto, and the reaction was stirred at 35° C. for 48 hours. The reaction solution was cooled to room temperature and then filtered through diatomite, and the filter cake was washed with ethyl acetate (20 mL). The resulting filtrate was concentrated under vacuum to obtain deuteromethyl (S)-2-((methoxy-$d_3$)methyl)-2-((5-nitro-1-(phenylsulfonyl)-1H-pyrrolo[2,3-b]pyridin-4-yl)amino)propanoate (520 mg, 1.14 mmol, yield of 100%) as a yellow solid. ES-API: $[M+H]^+$=455.1.

Step 2: Deuteromethyl (S)-2-((methoxy-$d_3$)methyl)-2-((5-nitro-1-(phenylsulfonyl)-1H-pyrrolo[2,3-b]pyridin-4-yl) amino)propanoate (520 mg, 1.14 mmol) was dissolved in acetic acid (10 mL), and iron powder (447 mg, 8.01 mmol) was added thereto, and the reaction was stirred at 90° C. for 2 hours. The reaction solution was cooled to room temperature and then filtered through diatomite, and the filter cake was washed with ethyl acetate (20 mL). The filtrate was concentrated under vacuum and the resulting crude product was purified by a flash silica gel column (ethyl acetate/petroleum ether: 0-100%) to obtain (S)-2-((methoxy-ds) methyl)-2-(methyl-$d_3$)-7-(phenylsulfonyl)-1,2,4,7-tetrahydro-3H-pyrrolo[3',2':5,6]pyrido[3,4-b]pyrazin-3-one (350 mg, 0.87 mmol, yield of 78%) as a pale yellow solid. ES-API: $[M+H]^+$=393.2.

Step 3: (S)-2-((Methoxy-$d_3$)methyl)-2-(methyl-$d_3$)-7-(phenylsulfonyl)-1,2,4,7-tetrahydro-3H-pyrrolo[3',2':5,6] pyrido[3,4-b]pyrazin-3-one (350 mg, 0.87 mmol) was dissolved in methanol (3 mL), tetrahydrofuran (2 mL) and water (0.8 mL), and sodium hydroxide (250 mg, 6.24 mmol) was added thereto, and the reaction was stirred at 65° C. for 6 hours. After the reaction solution was cooled to room temperature, the pH of the reaction solution was adjusted to 8 with dilute hydrochloric acid (1.0 M), then 20 mL of saturated sodium bicarbonate solution was added thereto, and the mixture was extracted with ethyl acetate (100 mL). The organic phase was washed once with saturated sodium bicarbonate solution (20 mL), washed twice with saturated brine (20 mL), dried and concentrated to obtain (S)-2-((methoxy-$d_3$)methyl)-2-(methyl-$d_3$)-1,2,4,7-tetrahydro-3H-pyrrolo[3',2':5,6]pyrido[3,4-b]pyrazin-3-one (225 mg, 0.89 mmol, yield of 100%) as a white solid. ES-API: $[M+H]^+$=253.1.

Step 4: (S)-2-((Methoxy-$d_3$)methyl)-2-(methyl-$d_3$)-1,2,4,7-tetrahydro-3H-pyrrolo[3',2':5,6]pyrido[3,4-b]pyrazin-3-one (225 mg, 0.89 mmol) and 2-chloro-4-phenoxybenzaldehyde (622 mg, 2.68 mmol) were dissolved in methanol (10 mL), and the reaction was cooled to 0° C., and potassium hydroxide (350 mg, 6.24 mmol) was added thereto. The reaction was stirred at room temperature for 16 hours. The pH of the reaction solution was adjusted to 8 with dilute hydrochloric acid (1.0 M), and the reaction solution was extracted with ethyl acetate (100 mL). The organic phase was washed with saturated brine (30 mL), dried and concentrated, and the crude product was purified by a flash silica gel column (methanol/dichloromethane: 0-8%) to obtain (2S)-9-((2-chloro-4-phenoxyphenyl)(hydroxy)methyl)-2-((methoxy-$d_3$)methyl)-2-(methyl-$d_3$)-1,2,4,7-tetrahydro-3H-pyrrolo[3',2':5,6]pyrido[3,4-b]pyrazin-3-one (200 mg, 0.412 mmol, yield of 46%) as a pale yellow solid. ES-API: $[M+H]^+$=485.1.

Step 5: (2S)-9-((2-Chloro-4-phenoxyphenyl)(hydroxy) methyl)-2-((methoxy-$d_3$)methyl)-2-(methyl-$d_3$)-1,2,4,7-tetrahydro-3H-pyrrolo[3',2':5,6]pyrido[3,4-b]pyrazin-3-one (200 mg, 0.412 mmol) was dissolved in tetrahydrofuran (5 mL) and water (0.5 mL), and 2,3-dichloro-5,6-dicyano-p-benzoquinone (281 mg, 1.24 mmol) was added thereto at room temperature, and the reaction was stirred at room temperature for 2 hours. To the reaction solution was added saturated sodium sulfite solution (10 mL) and saturated sodium bicarbonate solution (10 mL) to quench the reaction, and then extracted with ethyl acetate (50 mL). The organic phase was washed with saturated sodium bicarbonate solution (20 mL) and saturated brine (20 mL) in turn, dried and then concentrated, and the crude product was purified by preparative HPLC to obtain (S)-9-(2-chloro-4-phenoxybenzoyl)-2-((methoxy-$d_3$)methyl)-2-(methyl-$d_3$)-1,2,4,7-tetrahydro-3H-pyrrolo[3',2':5,6]pyrido[3,4-b]pyrazin-3-one (Z161, 76 mg, 0.157 mmol, yield of 38%) as a white solid. $^1$H NMR (500 MHz, DMSO-$d_6$) δ 12.46 (s, 1H), 10.48 (s, 1H), 8.27 (s, 1H), 7.69 (s, 1H), 7.60 (s, 1H), 7.56 (d, J=8.5 Hz, 1H), 7.48 (t, J=8.5 Hz, 2H), 7.25 (t, J=7.5 Hz, 1H), 7.20-7.16 (m, 3H), 7.02 (dd, J=8.5, 2.5 Hz, 1H), 3.64 (d, J=9.5 Hz, 1H), 3.47 (d, J=9.5 Hz, 1H). ES-API: $[M+H]^+$=483.1.

Embodiment 151: Synthesis of Z162

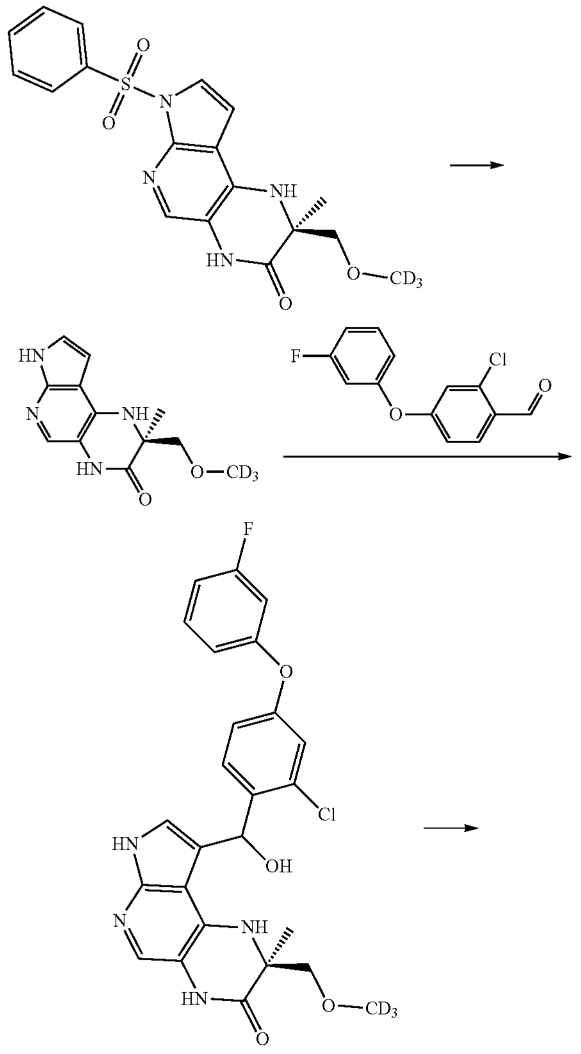

-continued

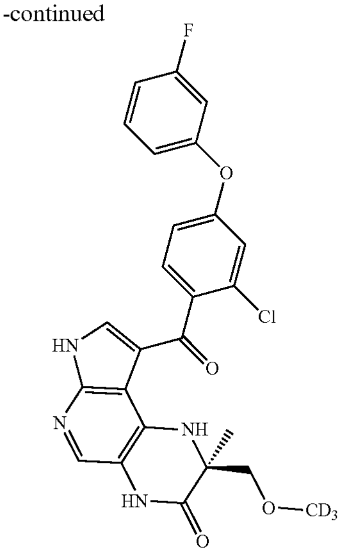

Z162

Step 1: (S)-2-((Methoxy-$d_3$)methyl)-2-methyl-7-(phenylsulfonyl)-1,2,4,7-tetrahydro-3H-pyrrolo[3',2':5,6]pyrido[3,4-b]pyrazin-3-one (300 mg, 0.776 mmol) was dissolved in methanol (3 mL), tetrahydrofuran (2 mL) and water (1 mL), and sodium hydroxide (217 mg, 5.43 mmol) was added thereto, and the reaction was stirred at 60° C. for 16 hours. After the reaction solution was cooled to room temperature, the pH of the reaction solution was adjusted to 8 with dilute hydrochloric acid (1.0 M), then 20 mL of saturated sodium bicarbonate solution was added thereto, and the mixture was extracted with ethyl acetate (100 mL). The organic phase was washed once with saturated sodium bicarbonate solution (20 mL), washed twice with saturated brine (20 mL) in turn, dried and concentrated to obtain (S)-2-((methoxy-$d_3$)methyl)-2-methyl-1,2,4,7-tetrahydro-3H-pyrrolo[3',2':5,6]pyrido[3,4-b]pyrazin-3-one (192 mg, 0.770 mmol, yield of 100%) as a white solid. ES-API: $[M+H]^+$=250.1.

Step 2: (S)-2-((Methoxy-$d_3$)methyl)-2-methyl-1,2,4,7-tetrahydro-3H-pyrrolo[3',2':5,6]pyrido[3,4-b]pyrazin-3-one (191 mg, 0.776 mmol) and 2-chloro-4-(3-fluorophenoxy)benzaldehyde (579 mg, 2.31 mmol) were dissolved in methanol (8 mL), and the reaction was cooled to 0° C., and potassium hydroxide (302 mg, 5.39 mmol) was added thereto. The reaction was stirred at room temperature for 16 hours. The pH of the reaction solution was adjusted to 8 with dilute hydrochloric acid (1.0 M), and the reaction solution was extracted with ethyl acetate (100 mL). The organic phase was washed with saturated brine (30 mL), dried and concentrated, and the crude product was purified by a flash silica gel column (methanol/dichloromethane: 0-8%) to obtain (2S)-9-((2-chloro-4-(3-fluorophenoxy)phenyl)(hydroxy)methyl)-2-((methoxy-$d_3$)methyl)-2-methyl-tetrahydro-3H-pyrrolo[3',2':5,6]pyrido[3,4-b]pyrazin-3-one (200 mg, 0.402 mmol, yield of 52%) as a pale yellow solid. ES-API: $[M+H]^+$=500.1.

Step 3: (2S)-9-((2-Chloro-4-(3-fluorophenoxy)phenyl)(hydroxy)methyl)-2-((methoxy-$d_3$)methyl)-2-methyl-tetrahydro-3H-pyrrolo[3',2':5,6]pyrido[3,4-b]pyrazin-3-one (200 mg, 0.402 mmol) was dissolved in tetrahydrofuran (5 mL) and water (0.5 mL), and 2,3-dichloro-5,6-dicyano-p-benzoquinone (269 mg, 1.18 mmol) was added thereto at room temperature, and the reaction was stirred at room temperature for 2 hours. To the reaction solution was added saturated sodium sulfite solution (10 mL) and saturated sodium bicarbonate solution (10 mL) to quench the reaction, and then extracted with ethyl acetate (50 mL). The organic phase was washed with saturated sodium bicarbonate solution (20 mL) and saturated brine (20 mL) in turn, dried and then concentrated, and the crude product was purified by preparative HPLC to obtain (S)-9-(2-chloro-4-(3-fluorophenoxy)benzoyl)-2-((methoxy-$d_3$)methyl)-2-methyl-1,2,4,7-tetrahydro-3H-pyrrolo[3',2':5,6]pyrido[3,4-b]pyrazin-3-one (Z162, 70 mg, 0.181 mmol, yield of 45%) as a white solid. $^1$H NMR (500 MHz, DMSO-$d_6$) δ 10.48 (s, 1H), 8.27 (s, 1H), 7.70 (s, 1H), 7.64 (s, 1H), 7.58 (d, J=8.5 Hz, 1H), 7.49 (dd, J=15.0, 8.5 Hz, 1H), 7.29 (d, J=2.5 Hz, 1H), 7.12-7.05 (m, 3H), 7.02 (dd, J=8.5, 2.5 Hz, 1H), 3.64 (d, J=9.5 Hz, 1H), 3.47 (d, J=9.5 Hz, 1H), 1.39 (s, 3H). ES-API: $[M+H]^+$=498.1.

Embodiment 152: Synthesis of Z163

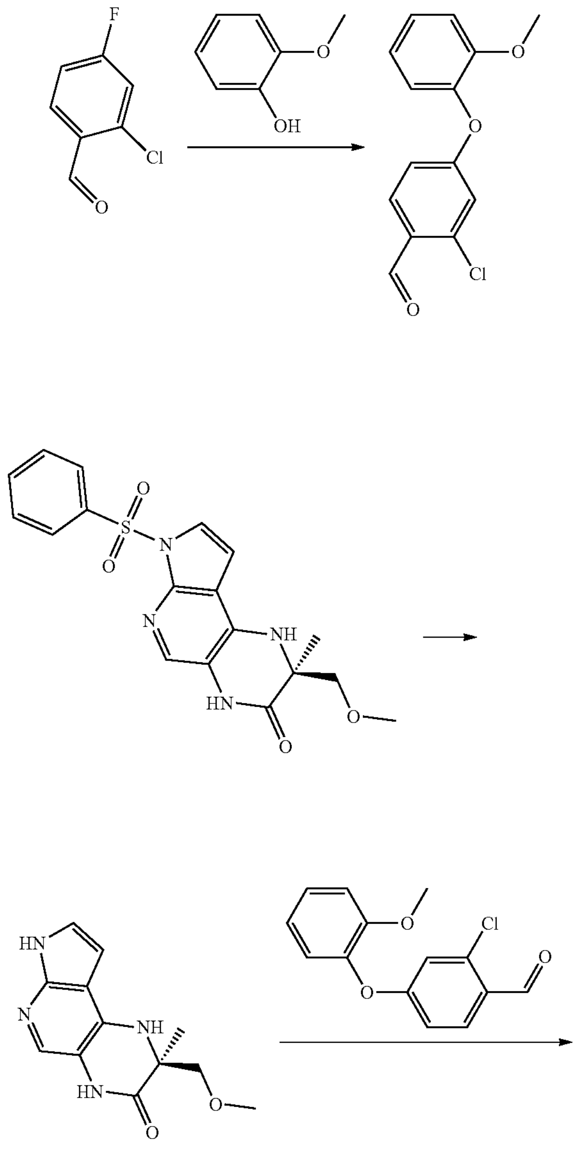

-continued

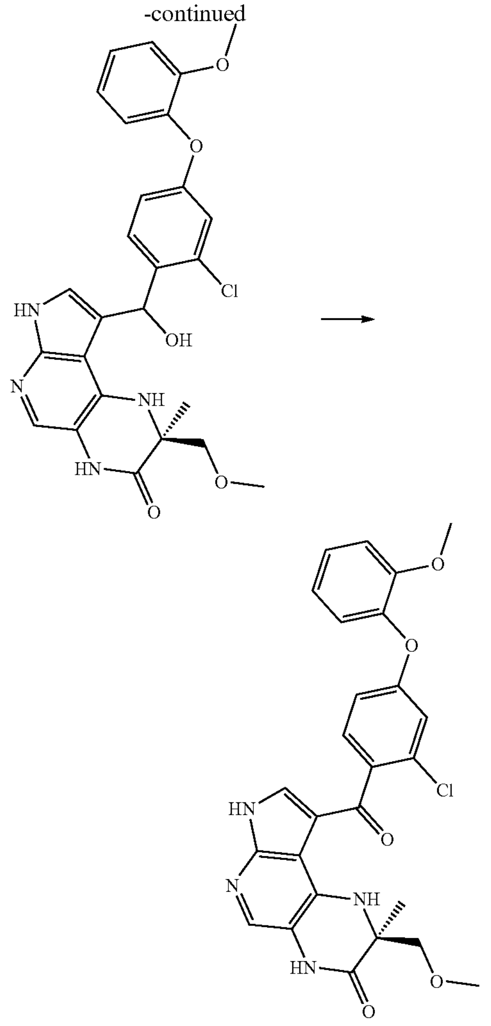

Z163

Step 1: 2-Chloro-4-fluorobenzaldehyde (2 g, 12.61 mmol) and 2-methoxyphenol (1.57 g, 12.61 mmol) were dissolved in anhydrous N,N-dimethylformamide (50 mL), and anhydrous potassium carbonate (3.49 g, 25.32 mmol) was added thereto, and the reaction was stirred at 90° C. for 3 hours. The reaction solution was cooled to room temperature, poured into 500 mL of water, and extracted with ethyl acetate (250 mL). The organic phase was washed 3 times with saturated brine (80 mL), dried over anhydrous sodium sulfate and concentrated to obtain 2-chloro-4-(2-methoxyphenoxy)benzaldehyde (3 g, 11.42 mmol, yield of 90%) as a white solid. ES-API: $[M+H]^+$=263.1.

Step 2: (S)-2-(Methoxymethyl)-2-methyl-7-(phenylsulfonyl)-1,2,4,7-tetrahydro-3H-pyrrolo[3',2':5,6]pyrido[3,4-b]pyrazin-3-one (300 mg, 0.776 mmol) was dissolved in methanol (3 mL), tetrahydrofuran (2 mL) and water (0.8 mL), and sodium hydroxide (217 mg, 5.43 mmol) was added thereto, and the reaction was stirred at 60° C. for 16 hours. After the reaction solution was cooled to room temperature, the pH of the reaction solution was adjusted to 8 with dilute hydrochloric acid (1.0 M), then 20 mL of saturated sodium bicarbonate solution was added thereto, and the mixture was extracted with ethyl acetate (100 mL). The organic phase was washed once with saturated sodium bicarbonate solution (20 mL), washed twice with saturated brine (20 mL) in turn, dried and concentrated to obtain (S)-2-(methoxymethyl)-2-methyl-1,2,4,7-tetrahydro-3H-pyrrolo[3',2':5,6]pyrido[3,4-b]pyrazin-3-one (191 mg, 0.776 mmol, yield of 100%) as a white solid. ES-API: $[M+H]^+$=247.1.

Step 3: (S)-2-(Methoxymethyl)-2-methyl-1,2,4,7-tetrahydro-3H-pyrrolo[3',2':5,6]pyrido[3,4-b]pyrazin-3-one (191 mg, 0.776 mmol) and 2-chloro-4-(2-methoxyphenoxy)benzaldehyde (611 mg, 2.33 mmol) were dissolved in methanol (8 mL), and the reaction was cooled to 0° C., and potassium hydroxide (305 mg, 5.43 mmol) was added thereto. The reaction was stirred at room temperature for 16 hours. The pH of the reaction solution was adjusted to 8 with dilute hydrochloric acid (1.0 M), and the reaction solution was extracted with ethyl acetate (100 mL). The organic phase was washed with saturated brine (30 mL), dried and concentrated, and the crude product was purified by a flash silica gel column (methanol/dichloromethane: 0-8%) to obtain (2S)-9-((2-chloro-4-(2-methoxyphenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (250 mg, 0.497 mmol, yield of 60%) as a pale yellow solid. ES-API: $[M+H]^+$=509.1.

Step 4: (2S)-9-((2-Chloro-4-(2-methoxyphenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (250 mg, 0.497 mmol) was dissolved in tetrahydrofuran (5 mL) and water (0.5 mL), and 2,3-dichloro-5,6-dicyano-p-benzoquinone (269 mg, 1.18 mmol) was added thereto at room temperature, and the reaction was stirred at room temperature for 2 hours. To the reaction solution was added saturated sodium sulfite solution (10 mL) and saturated sodium bicarbonate solution (10 mL) to quench the reaction, and then and the mixture was extracted with ethyl acetate (50 mL). The organic phase was washed with saturated sodium bicarbonate solution (20 mL) and saturated brine (20 mL) in turn, dried and then concentrated, and the crude product was purified by preparative HPLC to obtain (S)-9-(2-chloro-4-(2-methoxyphenoxy)benzoyl)-2-(methoxymethyl)-2-methyl-1,2,4,7-tetrahydro-3H-pyrrolo[3',2':5,6]pyrido[3,4-b]pyrazin-3-one (Z163, 162 mg, 0.320 mmol, yield of 65%) as a white solid. $^1H$ NMR (500 MHz, DMSO-$d_6$) δ 12.42 (s, 1H), 10.47 (s, 1H), 8.28 (s, 1H), 7.69 (s, 1H), 7.53 (s, 1H), 7.50 (d, J=8.5 Hz, 1H), 7.32-7.27 (m, 1H), 7.26-7.22 (m, 1H), 7.20 (dd, J=8.5, 1.5 Hz, 1H), 7.07-7.02 (m, 1H), 7.00 (d, J=2.5 Hz, 1H), 6.85 (dd, J=8.5, 2.5 Hz, 1H), 3.78 (s, 3H), 3.64 (d, J=9.5 Hz, 1H), 3.47 (d, J=9.5 Hz, 1H), 3.29 (3, 2H), 1.38 (s, 3H). ES-API: $[M+H]^+$=507.1.

Embodiment 153: Synthesis of Z164

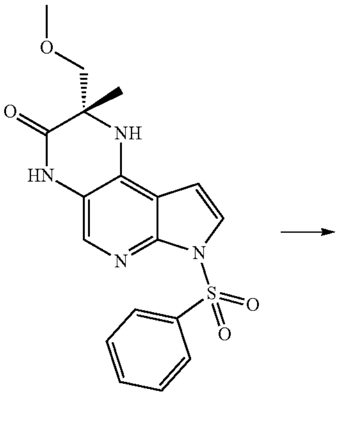

-continued

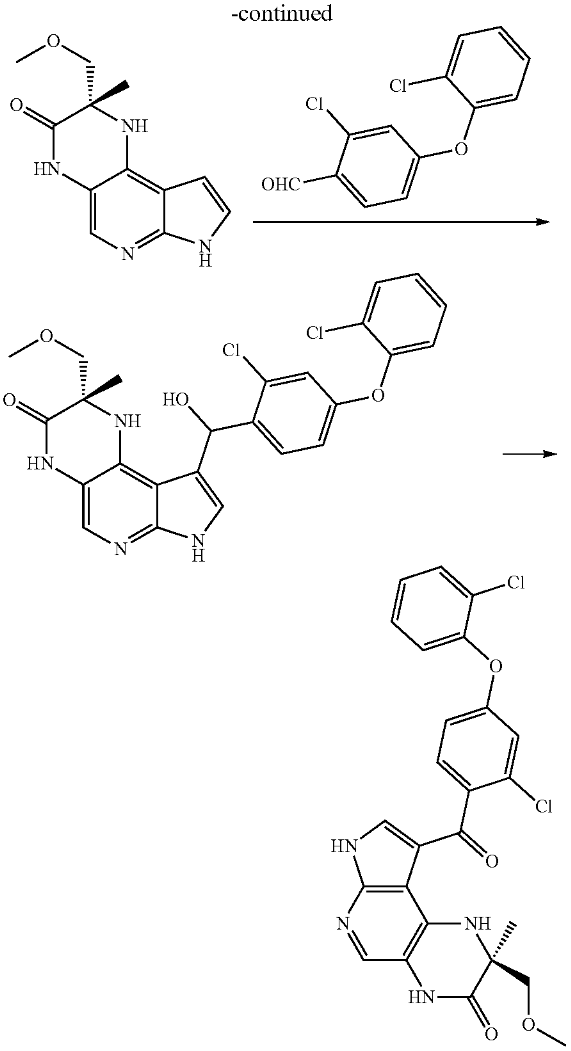

Z164

Step 1: (S)-2-(Methoxymethyl)-2-methyl-7-(phenylsulfonyl)-1,2,4,7-tetrahydro-3H-pyrrolo[3',2':5,6]pyrido[3,4-b]pyrazin-3-one (1.40 g, 3.570 mmol) was dissolved in 36 mL of methanol, 9 mL of tetrahydrofuran and 6 mL of water, and sodium hydroxide (1.01 g, 24.99 mmol) was added thereto, and the reaction was stirred at 65° C. for 7 hours. To the reaction solution was added 20 mL of water and 15 mL of saturated ammonium chloride solution, and the mixture was extracted with 200 mL of ethyl acetate. The organic phase was washed with 30 mL of saturated sodium bicarbonate solution and 80 mL of saturated brine in turn, dried over anhydrous sodium sulfate and then concentrated to obtain (S)-2-(methoxymethyl)-2-methyl-1,2,4,7-tetrahydro-3H-pyrrolo[3',2':5,6]pyrido[3,4-b]pyrazin-3-one (0.58 g, crude yield of 66%) as a pale white solid. ES-API: $[M+H]^+$=247.1.

Step 2: (S)-2-(Methoxymethyl)-2-methyl-1,2,4,7-tetrahydro-3H-pyrrolo[3',2':5,6]pyrido[3,4-b]pyrazin-3-one (223 mg, 0.9065 mmol) and 2-chloro-4-(2-chlorophenoxy)benzaldehyde (484 mg, 1.8127 mmol) were dissolved in methanol (25.0 mL), and the reaction was cooled to 0° C., and potassium hydroxide (350 mg, 6.250 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and then concentrated to obtain a crude target product (2S)-9-((2-chloro-4-(2-chlorophenoxy)phenyl)(hydroxyl) methyl)-2-(methoxymethyl)-2-methyl-1,2,4,7-tetrahydro-3H-pyrrolo[3',2':5,6]pyrido[3,4-b]pyrazin-3-one (190 mg, yield of 41%) as a pale yellow solid. ES-API: $[M+H]^+$=513.1/515.0.

Step 3: (2S)-9-((2-Chloro-4-(2-chlorophenoxy)phenyl)(hydroxyl)methyl)-2-(methoxymethyl)-2-methyl-1,2,4,7-tetrahydro-3H-pyrrolo[3',2':5,6]pyrido[3,4-b]pyrazin-3-one (190 mg, 0.3711 mmol) was dissolved in 20 mL of tetrahydrofuran, and 2,3-dichloro-5,6-dicyano-1,4-benzoquinone (170 mg, 0.7422 mmol) was added thereto, and the reaction was stirred at room temperature for 2 hours. To the reaction solution was added 63 mL of saturated sodium bicarbonate solution, and the mixture was extracted with 88 mL of ethyl acetate. The organic phase was washed with 60 mL of saturated brine, dried over anhydrous sodium sulfate and then concentrated, and the crude product was purified by preparative HPLC to obtain (S)-9-(2-chloro-4-(2-chlorophenoxy)benzoyl)-2-(methoxymethyl)-2-methyl-1,2,4,7-tetrahydro-3H-pyrrolo[3',2':5,6]pyrido[3,4-b]pyrazin-3-one (Z164, 80.5 mg, yield of 42%) as a pale yellow solid, ES-API: $[M+H]^+$=511.1/513.2. $^1H$ NMR (500 MHz, DMSO-$d_6$) δ 12.46 (s, 1H), 10.49 (s, 1H), 8.27 (s, 1H), 7.76-7.64 (m, 2H), 7.62-7.54 (m, 2H), 7.46 (t, J=7.7 Hz, 1H), 7.32 (dd, J=16.2, 7.4 Hz, 2H), 7.18 (d, J=2.2 Hz, 1H), 6.96 (dd, J=8.4, 2.2 Hz, 1H), 3.64 (d, J=9.5 Hz, 1H), 3.47 (d, J=9.5 Hz, 1H), 3.29 (s, 3H), 1.38 (s, 3H).

Embodiment 154: Synthesis of Z166

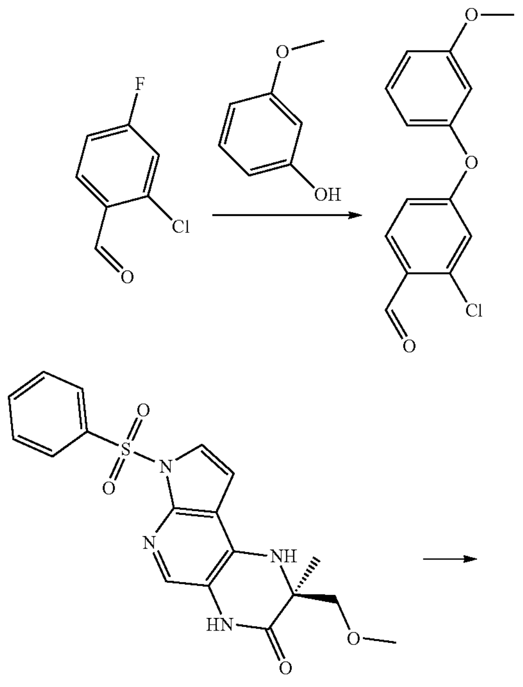

-continued

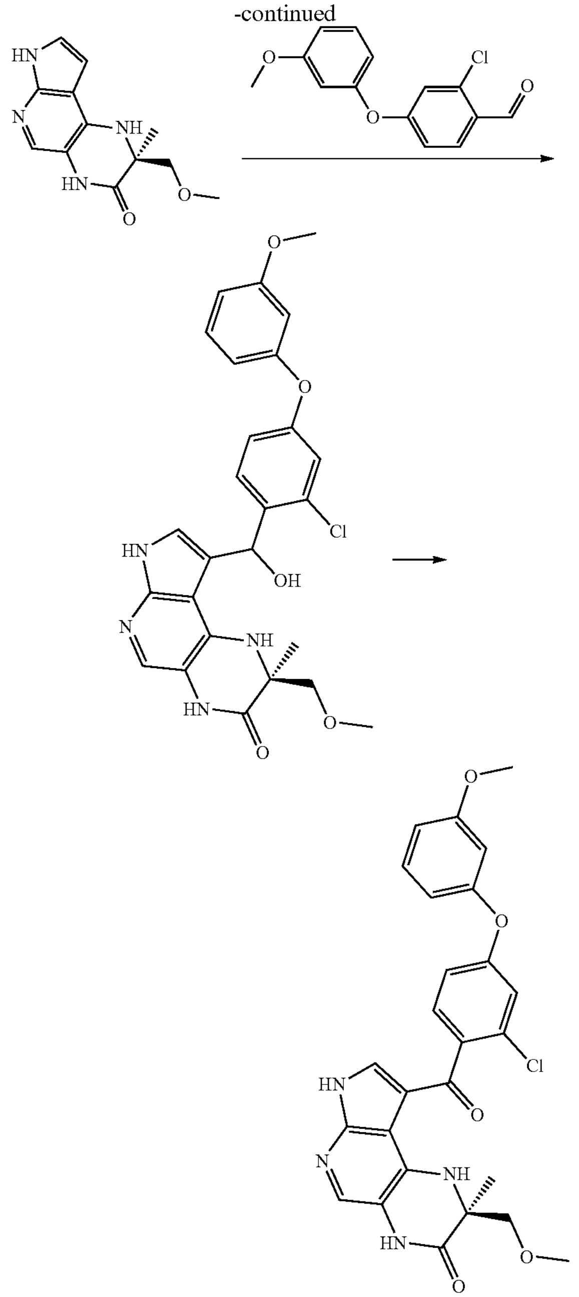

Z166

Step 1: 2-Chloro-4-fluorobenzaldehyde (2 g, 12.61 mmol) and 3-methoxyphenol (1.57 g, 12.61 mmol) were dissolved in anhydrous N,N-dimethylformamide (50 mL), and anhydrous potassium carbonate (3.49 g, 25.32 mmol) was added thereto, and the reaction was stirred at 90° C. for 3 hours. The reaction solution was cooled to room temperature, poured into 500 mL of water, and extracted with ethyl acetate (250 mL). The organic phase was washed 3 times with saturated brine (80 mL), dried over anhydrous sodium sulfate and concentrated to obtain 2-chloro-4-(3-methoxyphenoxy)benzaldehyde (2.5 g, 9.52 mmol, yield of 75%) as a white solid. ES-API: $[M+H]^+$=263.1.

Step 2: (S)-2-(Methoxymethyl)-2-methyl-7-(phenylsulfonyl)-1,2,4,7-tetrahydro-3H-pyrrolo[3',2':5,6]pyrido[3,4-b]pyrazin-3-one (300 mg, 0.776 mmol) was dissolved in methanol (3 mL), tetrahydrofuran (2 mL) and water (0.8 mL), and sodium hydroxide (217 mg, 5.43 mmol) was added thereto, and the reaction was stirred at 60° C. for 16 hours. After the reaction solution was cooled to room temperature, the pH of the reaction solution was adjusted to 8 with dilute hydrochloric acid (1.0 M), then 20 mL of saturated sodium bicarbonate solution was added thereto, and the mixture was extracted with ethyl acetate (100 mL). The organic phase was washed once with saturated sodium bicarbonate solution (20 mL), washed twice with saturated brine (20 mL), dried and concentrated to obtain (S)-2-(methoxymethyl)-2-methyl-1,2,4,7-tetrahydro-3H-pyrrolo[3',2':5,6]pyrido[3,4-b]pyrazin-3-one (191 mg, 0.776 mmol, yield of 100%) as a white solid. ES-API: $[M+H]^+$=247.1.

Step 3: (S)-2-(Methoxymethyl)-2-methyl-1,2,4,7-tetrahydro-3H-pyrrolo[3',2':5,6]pyrido[3,4-b]pyrazin-3-one (191 mg, 0.776 mmol) and 2-chloro-4-(3-methoxyphenoxy)benzaldehyde (611 mg, 2.33 mmol) were dissolved in methanol (8 mL), and the reaction was cooled to 0° C., and potassium hydroxide (305 mg, 5.43 mmol) was added thereto. The reaction was stirred at room temperature for 16 hours. The pH of the reaction solution was adjusted to 8 with dilute hydrochloric acid (1.0 M), and the reaction solution was extracted with ethyl acetate (100 mL). The organic phase was washed with saturated brine (30 mL), dried and concentrated, and the crude product was purified by a flash silica gel column (methanol/dichloromethane: 0-8%) to obtain (2S)-9-((2-chloro-4-(3-methoxyphenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (200 mg, 0.395 mmol, yield of 51%) as a pale yellow solid. ES-API: $[M+H]^+$=509.1.

Step 4: (2S)-9-((2-Chloro-4-(3-methoxyphenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (200 mg, 0.395 mmol) was dissolved in tetrahydrofuran (5 mL) and water (0.5 mL), and 2,3-dichloro-5,6-dicyano-p-benzoquinone (269 mg, 1.18 mmol) was added thereto at room temperature, and the reaction was stirred at room temperature for 2 hours. To the reaction solution was added saturated sodium sulfite solution (10 mL) and saturated sodium bicarbonate solution (10 mL) to quench the reaction, and then the mixture was extracted with ethyl acetate (50 mL). The organic phase was washed with saturated sodium bicarbonate solution (20 mL) and saturated brine (20 mL) in turn, dried and then concentrated, and the crude product was purified by preparative HPLC to obtain (S)-9-(2-chloro-4-(3-methoxyphenoxy)benzoyl)-2-(methoxymethyl)-2-methyl-1,2,4,7-tetrahydro-3H-pyrrolo[3',2':5,6]pyrido[3,4-b]pyrazin-3-one (Z166, 70 mg, 0.138 mmol, yield of 35%) as a white solid. $^1$H NMR (500 MHz, DMSO-$d_6$) δ 12.44 (s, 1H), 10.48 (s, 1H), 8.27 (s, 1H), 7.69 (s, 1H), 7.60 (s, 1H), 7.55 (d, J=8.5 Hz, 1H), 7.37 (t, J=8.5 Hz, 1H), 7.19 (d, J=2.5 Hz, 1H), 7.03 (dd, J=8.5, 2.5 Hz, 1H), 6.83 (dd, J=8.5, 2.5 Hz, 1H), 6.76 (t, J=2.5 Hz, 1H), 6.75-6.70 (m, 1H), 3.78 (s, 3H), 3.64 (d, J=9.5 Hz, 1H), 3.47 (d, J=9.5 Hz, 1H), 3.29 (s, 3H), 1.38 (s, 3H). ES-API: $[M+H]^+$=507.1.

Embodiment 155: Synthesis of Z167

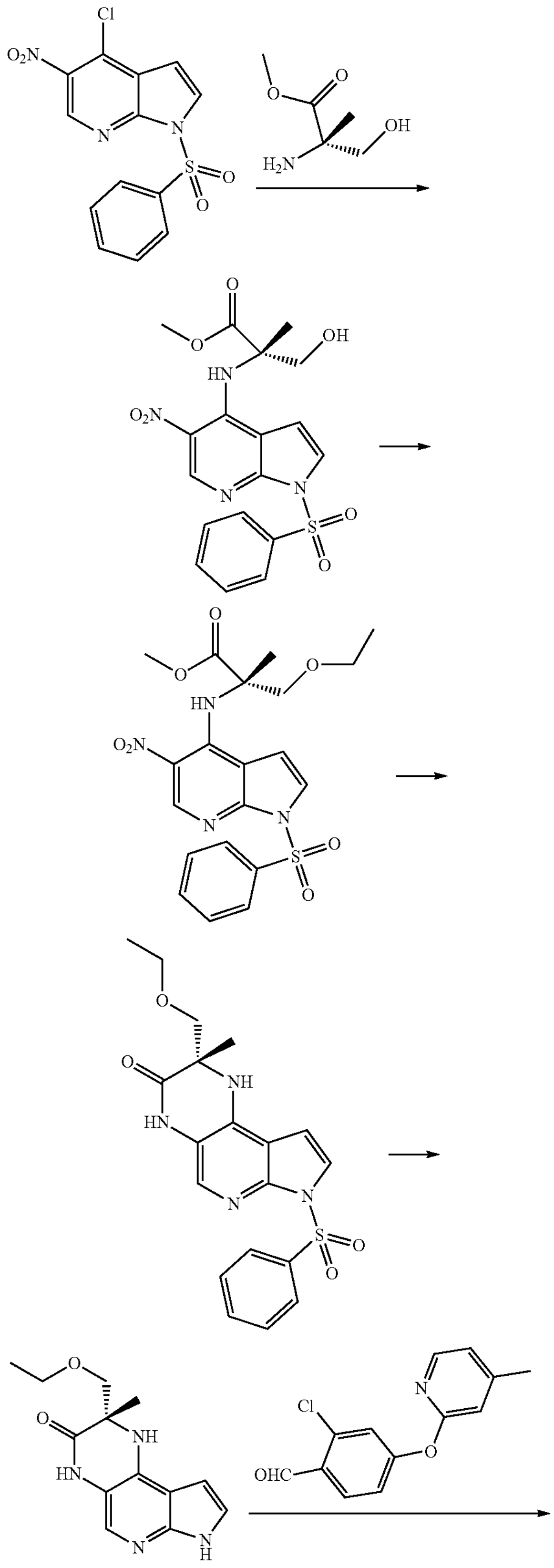

-continued

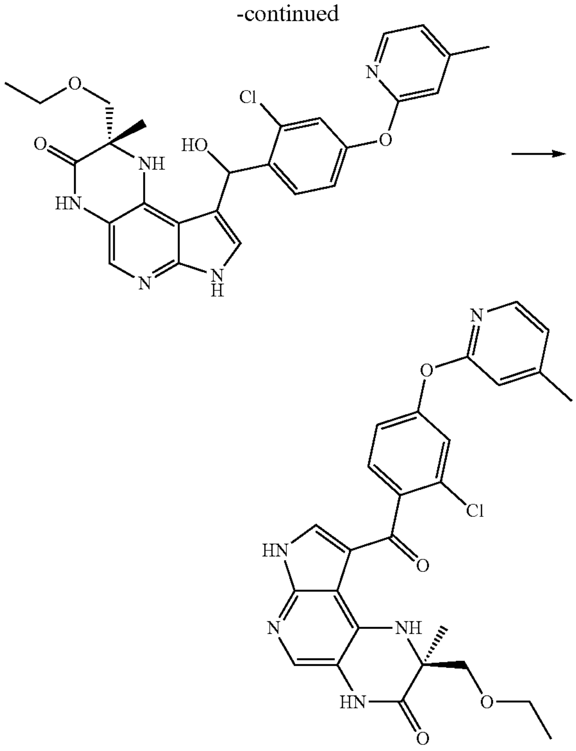

Z167

Step 1: 4-Chloro-5-nitro-1-(phenylsulfonyl)-1H-pyrrolo[2,3-b]pyridine (1.5 g, 4.451 mmol) and methyl (S)-2-amino-3-hydroxy-2-methylpropanoate hydrochloride (1.5 g, 8.902 mmol) were dissolved in N,N-dimethylacetamide (30 mL), and N,N-diisopropylethylamine (7.64 g, 59.15 mmol) was added thereto, and the reaction was stirred at 95° C. for 16 hours. The reaction solution was added with 100 mL of ethyl acetate, washed twice with 60 mL of water and 3 times with 30 mL of saturated brine, dried and concentrated, and the crude product was purified by a flash silica gel column (ethyl acetate/petroleum ether: 0-50%) to obtain methyl (S)-3-hydroxy-2-methyl-2-((5-nitro-1-(phenylsulfonyl)-1H-pyrrolo[2,3-b]pyridin-4-yl)amino)propanoate (1.3 g, yield of 72%) as a pale yellow solid. ES-API: $[M+H]^+$=435.1.

Step 2: Methyl (S)-3-hydroxy-2-methyl-2-((5-nitro-1-(phenylsulfonyl)-1H-pyrrolo[2,3-b]pyridin-4-yl)amino)propanoate (300 mg, 0.6911 mmol) was dissolved in acetonitrile (40 mL), and silver oxide (1.60 g, 6.911 mmol) and iodoethane (1.078 g, 6.911 mmol) were added thereto in turn, and the mixture was stirred in the dark at room temperature for 48 hours under nitrogen atmosphere. After the reaction was completed, the reaction solution was filtered through diatomite, and the filtrate was evaporated to dryness by rotary evaporation under reduced pressure. The crude product was purified by a flash silica gel column (ethyl acetate/petroleum ether: 0-50%) to obtain methyl (S)-3-ethoxy-2-methyl-2-((5-nitro-1-(phenylsulfonyl)-1H-pyrrolo[2,3-b]pyridin-4-yl)amino)propanoate (223 mg, yield of 70%) as a yellow solid. ES-API: $[M+H]^+$=463.1.

Step 3: Methyl (S)-3-ethoxy-2-methyl-2-((5-nitro-1-(phenylsulfonyl)-1H-pyrrolo[2,3-b]pyridin-4-yl)amino)propanoate (223 mg, 0.4827 mmol) was dissolved in acetic acid (20 mL), and iron powder (405 mg, 7.240 mmol) was added thereto. The mixture was gradually heated to 80° C. and stirred for 1 hour. After the reaction was completed, the solvent was evaporated to dryness by rotary evaporation under reduced pressure, then 200 mL of ethyl acetate was added thereto. The mixture was washed twice with 80 mL of water, twice with 60 mL of saturated sodium carbonate, twice with 80 mL of saturated sodium bicarbonate, and with 80 mL of saturated brine in turn, dried and concentrated, and the crude product was slurried with ethyl acetate to obtain (S)-2-(ethoxymethyl)-2-methyl-7-(phenylsulfonyl)-1,2,4,7-tetrahydro-3H-pyrrolo[3',2':5,6]pyrido[3,4-b]pyrazin-3-one (220 mg, crude product) as a yellow solid. ES-API: $[M+H]^+$= 401.2

Step 4: (S)-2-(Ethoxymethyl)-2-methyl-7-(phenylsulfonyl)-1,2,4,7-tetrahydro-3H-pyrrolo[3',2':5,6]pyrido[3,4-b]pyrazin-3-one (220 mg, crude product) was dissolved in 12 mL of methanol, 3 mL of tetrahydrofuran and 2 mL of water, and sodium hydroxide (135 mg, 3.378 mmol) was added thereto, and the reaction was stirred at 65° C. for 7 hours. To the reaction solution was added 20 mL of water and 15 mL of saturated ammonium chloride solution, and the mixture was extracted with 150 mL of ethyl acetate. The organic phase was washed with 30 mL of saturated sodium bicarbonate solution and 80 mL of saturated brine in turn, dried over anhydrous sodium sulfate and then concentrated to obtain (S)-2-(ethoxymethyl)-2-methyl-1,2,4,7-tetrahydro-3H-pyrrolo[3',2':5,6]pyrido[3,4-b]pyrazin-3-one (240 mg, crude product) as a pale white solid. ES-API: $[M+H]^+$= 261.1.

Step 5: (S)-2-(Ethoxymethyl)-2-methyl-1,2,4,7-tetrahydro-3H-pyrrolo[3',2':5,6]pyrido[3,4-b]pyrazin-3-one (240 mg, crude product) and 2-chloro-4-((4-methylpyridin-2-yl)oxy)benzaldehyde (240 mg, 0.9654 mmol) were dissolved in methanol (20.0 mL), and the reaction was cooled to 0° C., and potassium hydroxide (190 mg, 3.379 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and then concentrated to obtain a crude target product (2S)-9-((2-chloro-4-((4-methylpyridin-2-yl)oxy)phenyl)(hydroxyl)methyl)-2-(ethoxymethyl)-2-methyl-1,2,4,7-tetrahydro-3H-pyrrolo[3',2':5,6]pyrido[3,4-b]pyrazin-3-one (160 mg, 3-step yield of 65%) as a pale yellow solid. ES-API: $[M+H]^+$=508.1.

Step 6: (2S)-9-((2-Chloro-4-((4-methylpyridin-2-yl)oxy)phenyl)(hydroxyl)methyl)-2-(ethoxymethyl)-2-methyl-1,2,4,7-tetrahydro-3H-pyrrolo[3',2':5,6]pyrido[3,4-b]pyrazin-3-one (160 mg, 0.3155 mmol) was dissolved in 20 mL of tetrahydrofuran, and 2,3-dichloro-5,6-dicyano-1,4-benzoquinone (145 mg, 0.6310 mmol) was added thereto, and the reaction was stirred at room temperature for 2 hours. To the reaction solution was added 65 mL of saturated sodium bicarbonate solution, and the mixture was extracted with 83 mL of ethyl acetate. The organic phase was washed with 70 mL of saturated brine, dried over anhydrous sodium sulfate and then concentrated, and the crude product was purified by preparative HPLC to obtain (S)-9-(2-chloro-4-((4-methylpyridin-2-yl)oxy)benzoyl)-2-(ethoxymethyl)-2-methyl-1,2,4,7-tetrahydro-3H-pyrrolo[3',2':5,6]pyrido[3,4-b]pyrazin-3-one (Z167, 65 mg, yield of 40%) as a pale yellow solid, ES-API: $[M+H]^+$=506.1. $^1H$ NMR (500 MHz, DMSO-$d_6$) δ 10.39 (s, 1H), 8.32 (s, 1H), 8.09 (d, J=5.1 Hz, 1H), 7.70 (s, 1H), 7.58-7.47 (m, 2H), 7.37 (d, J=2.2 Hz, 1H), 7.19 (dd, J=8.3, 2.3 Hz, 1H), 7.06 (d, J=5.1 Hz, 1H), 6.99 (s, 1H), 3.65 (d, J=9.7 Hz, 1H), 3.53-3.43 (m, 3H), 2.37 (s, 3H), 1.40 (s, 3H), 1.04 (t, J=7.0 Hz, 3H).

Embodiment 156: Synthesis of Z168

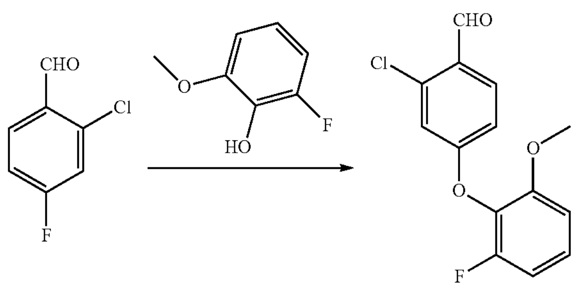

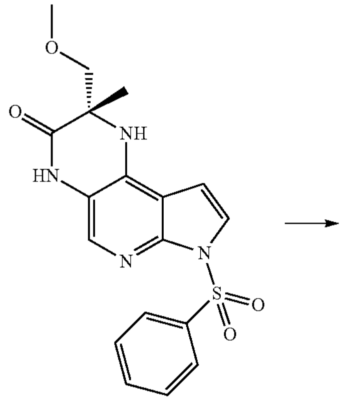

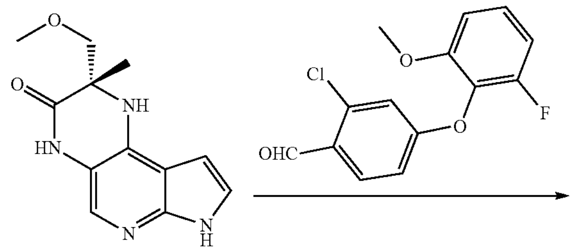

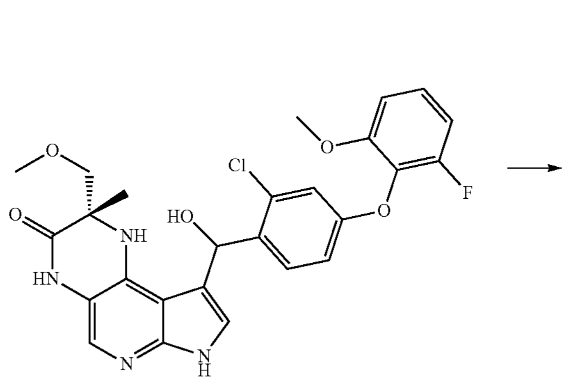

-continued

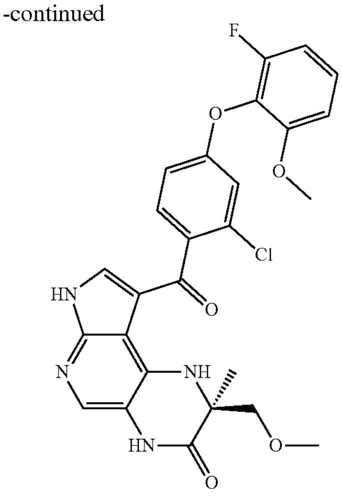

Z168

Step 1: 2-Chloro-4-fluorobenzaldehyde (1.58 g, 10.0 mmol) and 2-fluoro-6-methoxyphenol (1.42 g, 10.0 mmol) were dissolved in dry N,N-dimethylacetamide (30 mL), and finally cesium carbonate (9.60 g, 30.0 mmol) was added thereto, and the mixture was heated to 90° C. and reacted for 2 hours under nitrogen atmosphere. After the reaction was completed, the cooling solution was added with ethyl acetate (200 mL), and washed 3 times with saturated brine (3*80 mL). The ethyl acetate phase was dried with anhydrous sodium sulfate, filtered and evaporated to dryness by rotary evaporation under reduced pressure to obtain 2-chloro-4-(2-fluoro-6-methoxyphenoxy)benzaldehyde (2.40 g, yield 85%). ES-API $[M+H]^+$=281.0.

Step 2: (S)-2-(Methoxymethyl)-2-methyl-7-(phenylsulfonyl)-1,2,4,7-tetrahydro-3H-pyrrolo[3',2':5,6]pyrido[3,4-b] pyrazin-3-one (1.05 g, 2.7187 mmol) was dissolved in 36 mL of methanol, 9 mL of tetrahydrofuran and 6 mL of water, and sodium hydroxide (761.0 mg, 19.03 mmol) was added thereto, and the reaction was stirred at 65° C. for 7 hours. To the reaction solution was added 20 mL of water and 15 mL of saturated ammonium chloride solution, and the mixture was extracted with 150 mL of ethyl acetate. The organic phase was washed with 30 mL of saturated sodium bicarbonate solution and 80 mL of saturated brine in turn, dried over anhydrous sodium sulfate and then concentrated to obtain (S)-2-(methoxymethyl)-2-methyl-1,2,4,7-tetrahydro-3H-pyrrolo[3',2':5,6]pyrido[3,4-b]pyrazin-3-one (2.20 g, crude product) as a pale white solid. ES-API: $[M+H]^+$=247.1.

Step 3: (S)-2-(Methoxymethyl)-2-methyl-1,2,4,7-tetrahydro-3H-pyrrolo[3',2':5,6]pyrido[3,4-b]pyrazin-3-one (200 mg, 0.8130 mmol) and 2-chloro-4-(2-fluoro-6-methoxyphenoxy)benzaldehyde (300 mg, 1.070 mmol) were dissolved in methanol (15.0 mL), and the reaction was cooled to 0° C., and potassium hydroxide (318 mg, 5.690 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and then concentrated to obtain a crude target product (2S)-9-((2-chloro-4-(2-fluoro-6-methoxyphenoxy)phenyl) (hydroxy)methyl)-2-(methoxymethyl)-2-methyl-1,2,4,7-tetrahydro-3H-pyrrolo[3',2':5,6]pyrido[3,4-b]pyrazin-3-one (240 mg, 2-step yield of 56%) as a pale yellow solid. ES-API: $[M+H]^+$=527.2.

Step 4: (2S)-9-((2-Chloro-4-(2-fluoro-6-methoxyphenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (240 mg, 0.4561 mmol) was dissolved in 20 mL of tetrahydrofuran, and 2,3-dichloro-5,6-dicyano-1,4-benzoquinone (240 mg, 1.057 mmol) was added thereto, and the reaction was stirred at room temperature for 2 hours. To the reaction solution was added 60 mL of saturated sodium bicarbonate solution, and the mixture was extracted with 80 mL of ethyl acetate. The organic phase was washed with 60 mL of saturated brine, dried over anhydrous sodium sulfate and then concentrated, and the crude product was purified by preparative HPLC to obtain (S)-9-(2-chloro-4-(2-fluoro-6-methoxyphenoxy)benzoyl)-2-(methoxymethyl)-2-methyl-1,2,4,7-tetrahydro-3H-pyrrolo[3',2':5,6]pyrido[3,4-b]pyrazin-3-one (Z168, 67.8 mg, yield of 28%) as a pale yellow solid, ES-API: $[M+H]^+$=525.1. $^1H$ NMR (500 MHz, DMSO-$d_6$) δ 12.45 (s, 1H), 10.50 (s, 1H), 8.27 (s, 1H), 7.68 (s, 1H), 7.61-7.49 (m, 2H), 7.40-7.24 (m, 1H), 7.19-7.04 (m, 3H), 6.86 (d, J=8.0 Hz, 1H), 3.82 (s, 3H), 3.64 (d, J=9.4 Hz, 1H), 3.47 (d, J=9.6 Hz, 1H), 3.29 (s, 3H), 1.38 (s, 3H).

Embodiment 157: Synthesis of Z170

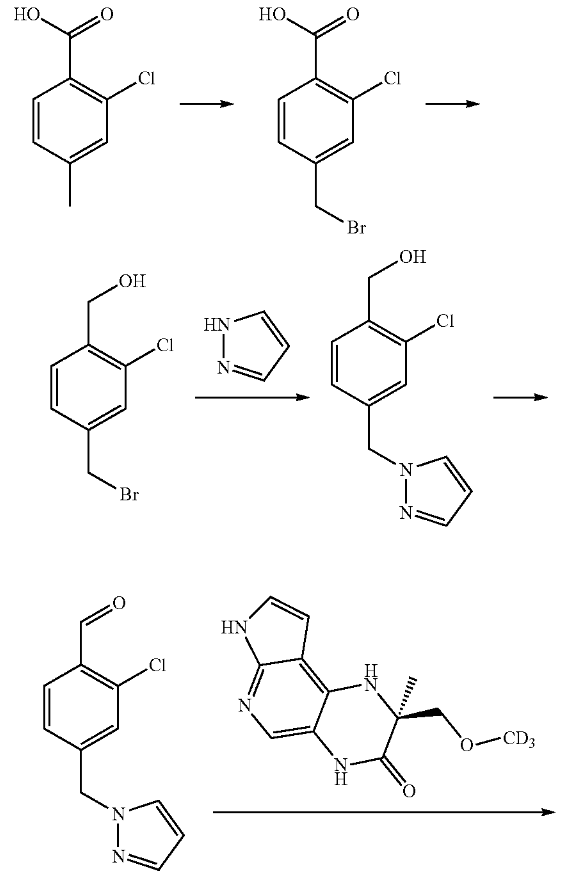

-continued

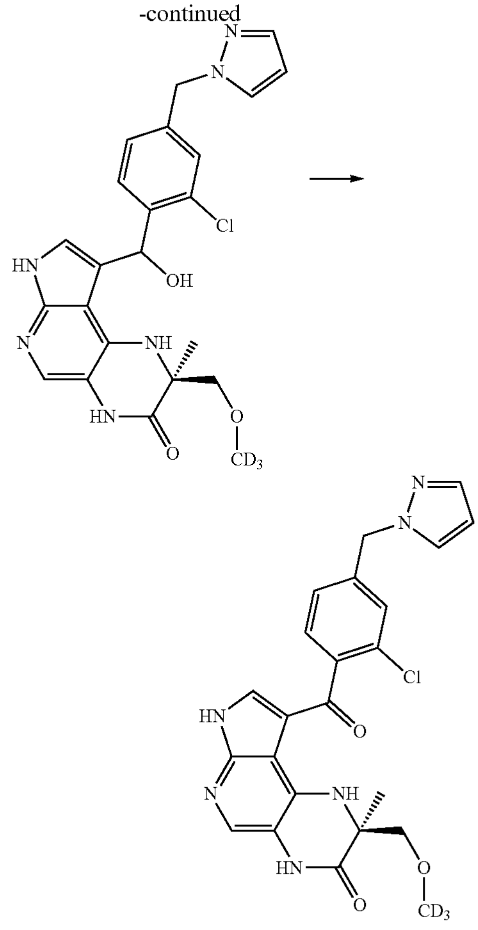

Z170

Step 1: 2-Chloro-4-methylbenzoic acid (2 g, 11.72 mmol) and benzoyl peroxide (284 mg, 1.17 mmol) were dissolved in carbon tetrachloride (60 mL). The reaction was stirred at 90° C. for one hour, then bromosuccinimide (2.13 g, 11.96 mmol) was added thereto, and the reaction was stirred at 90° C. for another five hours. The reaction was cooled to room temperature, then poured into water (200 mL), and extracted with dichloromethane (300 mL). The organic phase was washed 3 times with saturated brine (80 mL), dried over anhydrous sodium sulfate and concentrated to obtain 4-(bromomethyl)-2-chlorobenzoic acid (2.8 g, 11.22 mmol, yield of 96%) as a white solid. ES-API: $[M+H]^+$=249.1.

Step 2: 4-(Bromomethyl)-2-chlorobenzoic acid (2 g, 8.02 mmol) was dissolved in anhydrous tetrahydrofuran (30 mL), and the reaction was cooled to 0° C., and borane tetrahydrofuran complex (1 M, 24.05 mL, 24.05 mmol) was slowly added dropwise thereto. After the dropwise addition was completed, the reaction was continued to stir for one hour at 0° C. The reaction solution was quenched with anhydrous methanol (20 mL) and concentrated to obtain (4-(bromomethyl)-2-chlorophenyl)methanol (1.89 g, 8.02 mmol, yield of 100%) as a white solid. ES-API: $[M+H]^+$=235.1.

Step 3: Pyrazole (52 mg, 0.763 mmol) was dissolved in N,N-dimethylformamide (2 mL), and the reaction was cooled to 0° C., and potassium tert-butoxide solid (107 mg, 0.955 mmol) was added thereto. The reaction was stirred at 0° C. for half an hour and then 4-(bromomethyl)-2-chlorobenzoic acid (150 mg, 0.637 mmol) was added thereto. The reaction was continued to stir at 0° C. for one hour. The reaction solution was poured into water (20 mL), and extracted with ethyl acetate (10 mL). The organic phase was washed 3 times with saturated brine (10 mL), dried over anhydrous sodium sulfate and concentrated to obtain (4-((1H-pyrazol-1-yl)methyl)-2-chlorophenyl)methanol (140 mg, 0.629 mmol, yield of 98%) as a white solid. ES-API: $[M+H]^+$=223.1.

Step 4: (4-((1H-Pyrazol-1-yl)methyl)-2-chlorophenyl) methanol (140 mg, 0.629 mmol) was dissolved in ethyl acetate (5 mL) and ethanol (5 mL), and active manganese dioxide (328 mg, 3.77 mmol) was added thereto, and the reaction was stirred at room temperature for 17 hours. After the reaction solution was filtered through diatomite, the filtrate was concentrated to obtain 4-((1H-pyrazol-1-yl) methyl)-2-chlorobenzaldehyde (120 mg, 0.543 mmol, yield of 86%) as a yellow oily liquid. ES-API: $[M+H]^+$=221.1.

Step 5: (S)-2-((Methoxy-$d_3$)methyl)-2-methyl-1,2,4,7-tetrahydro-3H-pyrrolo[3',2':5,6]pyrido[3,4-b]pyrazin-3-one (50 mg, 0.201 mmol) and 4-((1H-pyrazol-1-yl)methyl)-2-chlorobenzaldehyde (120 mg, 0.543 mmol) were dissolved in methanol (8 mL), and the reaction was cooled to 0° C., and potassium hydroxide (79 mg, 1.40 mmol) was added thereto. The reaction was stirred at room temperature for 16 hours. The pH of the reaction solution was adjusted to 8 with dilute hydrochloric acid (1.0 M), and the reaction solution was extracted with ethyl acetate (100 mL). The organic phase was washed with saturated brine (30 mL), dried and then concentrated, and the crude product was purified by a flash silica gel column (methanol/dichloromethane: 0-8%) to obtain (2S)-9-((4-((1H-pyrazol-1-yl)methyl)-2-chlorophenyl)(hydroxy)methyl)-2-((methoxy-$d_3$)methyl)-2-methyl-1,2,4,7-tetrahydro-3H-pyrrolo[3',2':5,6]pyrido[3,4-b]pyrazin-3-one (80 mg, 0.17 mmol, yield of 85%) as a pale yellow solid. ES-API: $[M+H]^+$=470.1.

Step 6: (2S)-9-((4-((1H-Pyrazol-1-yl)methyl)-2-chlorophenyl)(hydroxy)methyl)-2-((methoxy-$d_3$)methyl)-2-methyl-1,2,4,7-tetrahydro-3H-pyrrolo[3',2':5,6]pyrido[3,4-b]pyrazin-3-one (80 mg, 0.17 mmol) was dissolved in tetrahydrofuran (5 mL) and water (0.5 mL), and 2,3-dichloro-5,6-dicyano-p-benzoquinone (116 mg, 0.511 mmol) was added thereto at room temperature, and the reaction was stirred at room temperature for 2 hours. To the reaction solution was added saturated sodium sulfite solution (10 mL) and saturated sodium bicarbonate solution (10 mL) to quench the reaction, and then the mixture was extracted with ethyl acetate (50 mL). The organic phase was washed with saturated sodium bicarbonate solution (20 mL) and saturated brine (20 mL) in turn, dried and then concentrated, and the crude product was purified by preparative HPLC to obtain (S)-9-(4-((1H-pyrazol-1-yl)methyl)-2-chlorobenzoyl)-2-((methoxy-$d_3$)methyl)-2-methyl-1,2,4,7-tetrahydro-3H-pyrrolo[3',2':5,6]pyrido[3,4-b]pyrazin-3-one (Z170, 70 mg, 0.138 mmol, yield of 35%) as a white solid. $^1H$ NMR (500 MHz, DMSO-$d_6$) δ 12.76 (br s, 1H), 10.48 (s, 1H), 8.47 (s, 1H), 8.25 (s, 1H), 7.91 (d, J=2.5 Hz, 1H), 7.69 (s, 1H), 7.55-7.55 (m, 2H), 7.44 (s, 1H), 7.37 (s, 1H), 7.23 (d, J=8.0 Hz, 1H), 6.33 (t, J=2.5 Hz, 1H), 5.45 (s, 2H), 3.63 (d, J=9.5 Hz, 1H), 3.46 (d, J=9.5 Hz, 1H), 1.38 (s, 3H). ES-API: $[M+H]^+$=468.1.

Embodiment 158: Synthesis of Z171, Z174 and Z175

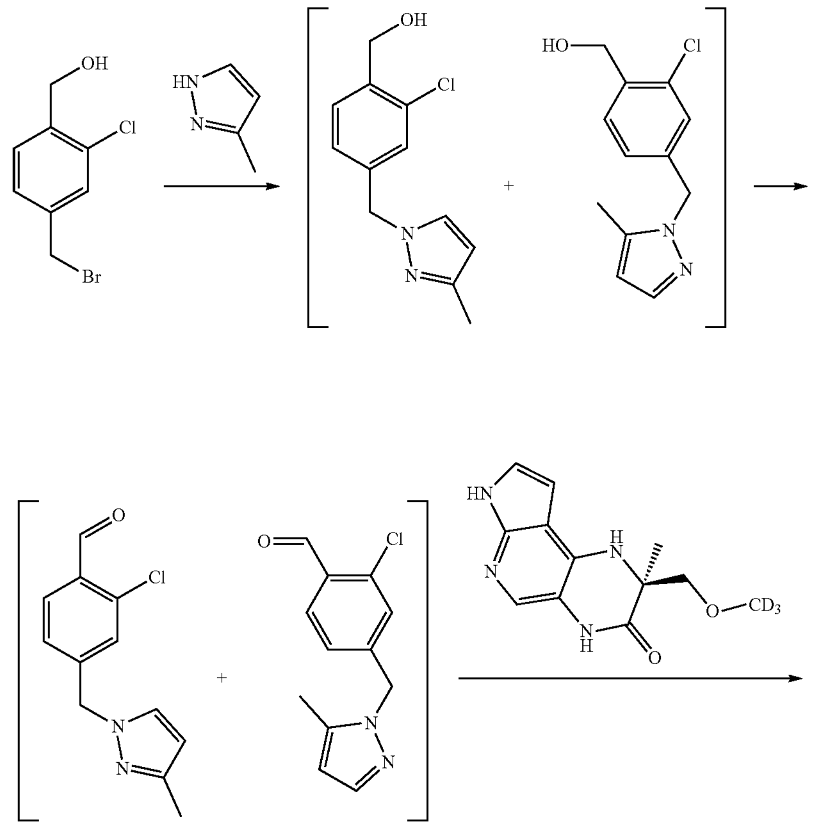

-continued

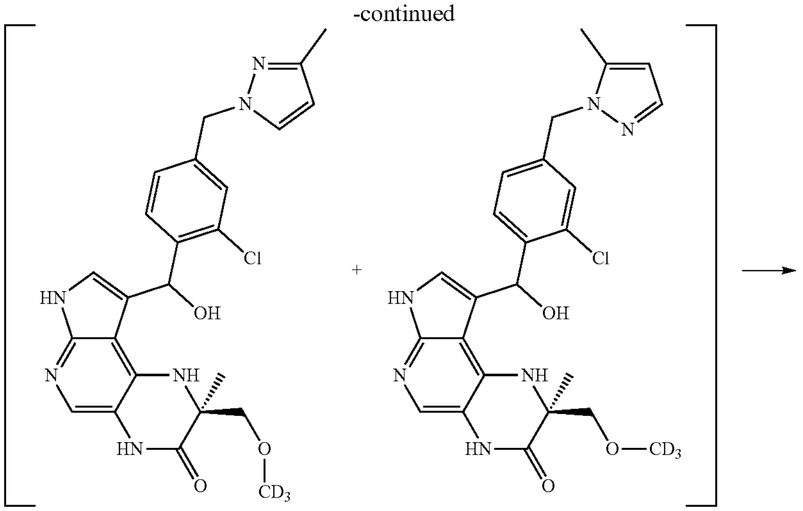

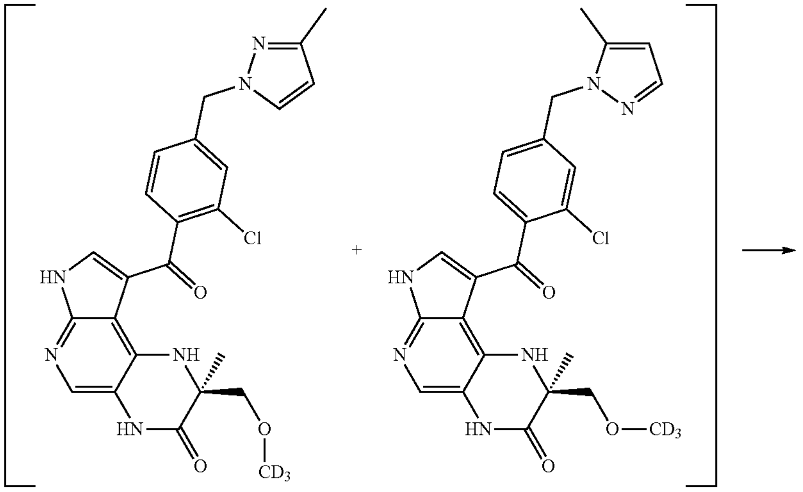

Z171

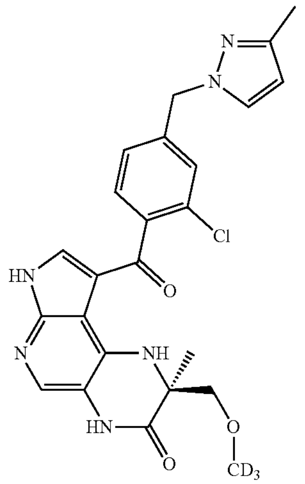

+

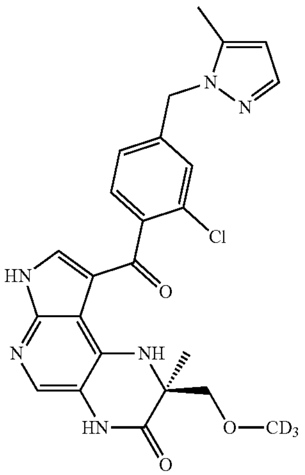

Z174 Z175

Step 1: 3-Methyl-1H-pyrazole (126 mg, 1.53 mmol) was dissolved in N,N-dimethylformamide (5 mL), and the reaction was cooled to 0° C., and potassium tert-butoxide solid (214 mg, 1.91 mmol) was added thereto. The reaction was stirred at 0° C. for half an hour and then 4-(bromomethyl)-2-chlorobenzoic acid (300 mg, 1.27 mmol) was added thereto. The reaction was continued to stir at 0° C. for one hour. The reaction solution was poured into water (20 mL), and extracted with ethyl acetate (10 mL). The organic phase was washed 3 times with saturated brine (10 mL), dried over anhydrous sodium sulfate and concentrated to obtain a mixture of (2-chloro-4-((3-methyl-1H-pyrazol-1-yl)methyl)

phenyl)methanol and (2-chloro-4-((5-methyl-1H-pyrazol-1-yl)methyl)phenyl)methanol (300 mg, 1.27 mmol in total, yield of 98%) as a white solid. ES-API: $[M+H]^+$=237.1.

Step 2: The mixture of (2-chloro-4-((3-methyl-1H-pyrazol-1-yl)methyl)phenyl)methanol and (2-chloro-4-((5-methyl-1H-pyrazol-1-yl)methyl)phenyl)methanol (300 mg, 1.27 mmol in total) was dissolved in ethyl acetate (8 mL) and ethanol (8 mL), and active manganese dioxide (771 mg, 8.89 mmol) was added thereto, and the reaction was stirred at room temperature for 17 hours. After the reaction solution was filtered through diatomite, the filtrate was concentrated to obtain a mixture of 2-chloro-4-((3-methyl-1H-pyrazol-1-yl)methyl)benzaldehyde and 2-chloro-4-((5-methyl-1H-pyrazol-1-yl)methyl)benzaldehyde (290 mg, 1.24 mmol, yield of 98%) as a yellow oily liquid. ES-API: $[M+H]^+$=235.1.

Step 3: The mixture of 2-chloro-4-((3-methyl-1H-pyrazol-1-yl)methyl)benzaldehyde and 2-chloro-4-((5-methyl-1H-pyrazol-1-yl)methyl)benzaldehyde (290 mg, 1.24 mmol) and (S)-2-((methoxy-$d_3$)methyl)-2-methyl-1,2,4,7-tetrahydro-3H-pyrrolo[3',2':5,6]pyrido[3,4-b]pyrazin-3-one (108 mg, 0.430 mmol) was dissolved in methanol (8 mL), and the reaction was cooled to 0° C., and potassium hydroxide (153 mg, 2.72 mmol) was added thereto. The reaction was stirred at room temperature for 16 hours. The pH of the reaction solution was adjusted to 8 with dilute hydrochloric acid (1.0 M), and the reaction solution was extracted with ethyl acetate (100 mL). The organic phase was washed with saturated brine (30 mL), dried and concentrated, and the crude product was purified by a flash silica gel column (methanol/dichloromethane: 0-8%) to obtain a mixture of (2S)-9-((2-chloro-4-((3-methyl-1H-pyrazol-1-yl)methyl)phenyl)(hydroxy)methyl)-2-((methoxy-$d_3$)methyl)-2-methyl-1,2,4,7-tetrahydro-3H-pyrrolo[3',2':5,6]pyrido[3,4-b]pyrazin-3-one and (2S)-9-((2-chloro-4-((5-methyl-1H-pyrazol-1-yl)methyl)phenyl)(hydroxy)methyl)-2-((methoxy-$d_3$)methyl)-2-methyl-1,2,4,7-tetrahydro-3H-pyrrolo[3',2':5,6]pyrido[3,4-b]pyrazin-3-one (120 mg, 0.248 mmol, yield of 20%) as a pale yellow solid. ES-API: $[M+H]^+$=484.1.

Step 4: The mixture of (2S)-9-((2-chloro-4-((3-methyl-1H-pyrazol-1-yl)methyl)phenyl)(hydroxy)methyl)-2-((methoxy-$d_3$)methyl)-2-methyl-1,2,4,7-tetrahydro-3H-pyrrolo[3',2':5,6]pyrido[3,4-b]pyrazin-3-one and (2S)-9-((2-chloro-4-((5-methyl-1H-pyrazol-1-yl)methyl)phenyl)(hydroxy)methyl)-2-((methoxy-$d_3$)methyl)-2-methyl-1,2,4,7-tetrahydro-3H-pyrrolo[3',2':5,6]pyrido[3,4-b]pyrazin-3-one (120 mg, 0.248 mmol) was dissolved in tetrahydrofuran (5 mL) and water (0.5 mL), and 2,3-dichloro-5,6-dicyano-p-benzoquinone (169 mg, 0.744 mmol) was added thereto at room temperature, and the reaction was stirred at room temperature for 2 hours. To the reaction solution was added saturated sodium sulfite solution (10 mL) and saturated sodium bicarbonate solution (10 mL) to quench the reaction, and then the mixture was extracted with ethyl acetate (50 mL). The organic phase was washed with saturated sodium bicarbonate solution (20 mL) and saturated brine (20 mL) in turn, dried and then concentrated, and the crude product was purified by preparative HPLC to obtain a mixture of (S)-9-(2-chloro-4-((3-methyl-1H-pyrazol-1-yl)methyl)benzoyl)-2-((methoxy-$d_3$)methyl)-2-methyl-1,2,4,7-tetrahydro-3H-pyrrolo[3',2':5,6]pyrido[3,4-b]pyrazin-3-one and (S)-9-(2-chloro-4-((5-methyl-1H-pyrazol-1-yl)methyl)benzoyl)-2-((methoxy-$d_3$)methyl)-2-methyl-1,2,4,7-tetrahydro-3H-pyrrolo[3',2':5,6]pyrido[3,4-b]pyrazin-3-one (Z171, 16 mg, 0.248 mmol, yield of 14%) as a white solid.

The resulting mixture Z171 was subjected to chiral resolution to obtain two compounds:

One was compound Z174: (S)-9-(2-chloro-4-((3-methyl-1H-pyrazol-1-yl)methyl)benzoyl)-2-((methoxy-$d_3$)methyl)-2-methyl-1,2,4,7-tetrahydro-3H-pyrrolo[3',2':5,6]pyrido[3,4-b]pyrazin-3-one (6 mg) (column type: IE 250 mm, 10 mm, 5 μm; mobile phase system: (A: n-hexane; B: ethanol); flow rate: 1 mL/min; B %=0-40%; column temperature: room temperature; peak 1, retention time: 10.996); a white solid; $^1$H NMR (500 MHz, DMSO-$d_6$) δ 12.43 (s, 1H), 10.48 (s, 1H), 8.25 (s, 1H), 7.76 (d, J=2.0 Hz, 1H), 7.69 (s, 1H), 7.52 (d, J=8.0 Hz, 1H), 7.46 (s, 1H), 7.38 (s, 1H), 7.23 (d, J=8.0 Hz, 1H), 6.09 (d, J=2.0 Hz, 1H), 5.33 (s, 2H), 3.63 (d, J=9.5 Hz, 1H), 3.46 (d, J=9.5 Hz, 1H), 2.17 (s, 3H), 1.38 (s, 3H). ES-API: $[M+H]^+$=482.1.

The other was compound Z175: (S)-9-(2-chloro-4-((5-methyl-1H-pyrazol-1-yl)methyl)benzoyl)-2-((methoxy-$d_3$)methyl)-2-methyl-1,2,4,7-tetrahydro-3H-pyrrolo[3',2':5,6]pyrido[3,4-b]pyrazin-3-one (3 mg) (column type: IE 250 mm, 10 mm, 5 μm; mobile phase system: (A: n-hexane; B: ethanol); flow rate: 1 mL/min; B %=0-30%; column temperature: room temperature; peak 2, retention time: 13.181); a white solid. $^1$H NMR (500 MHz, DMSO-$d_6$) δ 12.43 (s, 1H), 10.48 (s, 1H), 8.25 (s, 1H), 7.69 (s, 1H), 7.51 (d, J=7.5 Hz, 1H), 7.47 (s, 1H), 7.42 (s, 1H), 7.25 (s, 1H), 7.09 (d, J=7.5 Hz, 1H), 6.13 (s, 1H), 5.40 (s, 2H), 3.63 (d, J=9.5 Hz, 1H), 3.46 (d, J=9.5 Hz, 1H), 2.25 (s, 3H), 1.38 (s, 3H). ES-API: $[M+H]^+$=482.1.

Embodiment 159: Synthesis of Z173

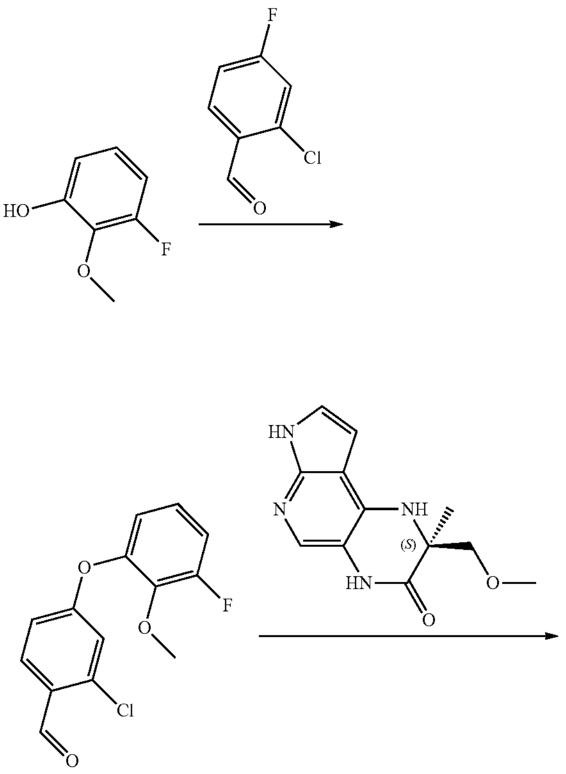

-continued

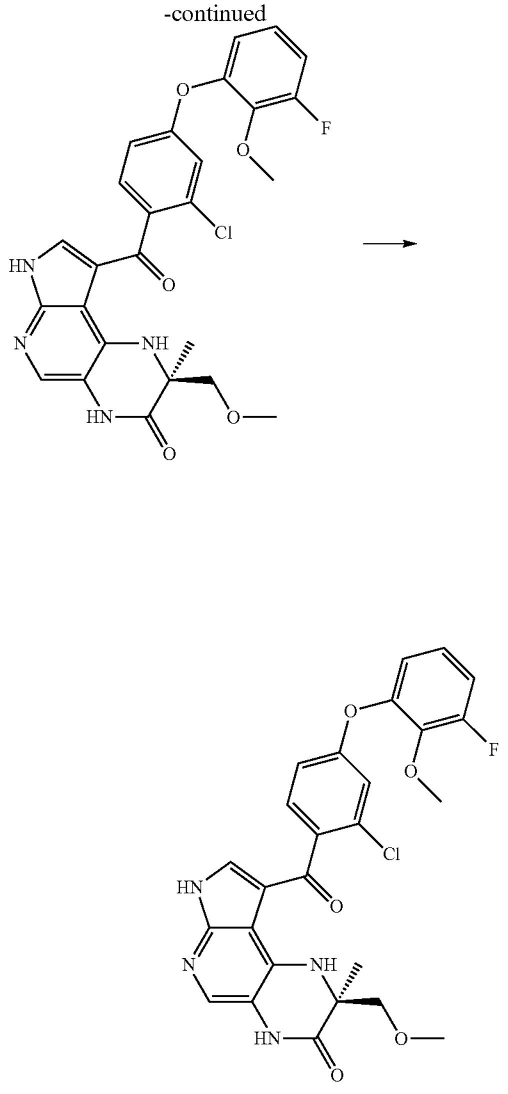

Z173

Step 1: 2-Chloro-4-fluorobenzaldehyde (972 mg, 6.127 mmol), 3-fluoro-2-methoxyphenol (870 mg, 6.127 mmol) and potassium carbonate (2.540 g, 18.381 mmol) were dissolved in N,N'-dimethylformamide (30 mL), and the reaction was stirred at 90° C. for 3 hours. LCMS detected that the reaction was complete. The reaction solution was cooled to room temperature, added with 30 mL of ethyl acetate, washed once with 30 mL of water and washed with saturated brine (25 mL×3) respectively. The organic phase was dried over anhydrous sodium sulfate, filtered, and the filtrate was concentrated to dryness under reduced pressure to obtain a pale yellow liquid 2-chloro-4-(3-fluoro-2-methoxyphenoxy)benzaldehyde (1314 mg, yield of 77%). ES-API: $[M+H]^+$=281.0

Step 2: (S)-2-(Methoxymethyl)-2-methyl-1,2,4,7-tetrahydro-3H-pyrrolo[3',2':5,6]pyrido[3,4-b]pyrazin-3-one (36.5 mg, 0.148 mmol) and 2-chloro-4-(3-fluoro-2-methoxyphenoxy)benzaldehyde (104 mg, 0.371 mmol) were dissolved in methanol (6 mL), and the reaction solution was cooled to 0° C., and potassium hydroxide (58 mg, 1.036 mmol) was added thereto. The reaction was stirred at room temperature for 24 hours. LCMS detected that the reaction was complete. The reaction was quenched by adding 20 mL of saturated ammonium chloride solution, extracted with ethyl acetate (15 mL×3). The organic phase was washed with 20 mL of saturated brine, dried over anhydrous sodium sulfate and then concentrated to obtain a crude product (2S)-9-((2-chloro-4-(3-fluoro-2-methoxyphenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (78 mg, yield of 100%). ES-API: $[M+H]^+$=527.2

Step 3: (2S)-9-((2-Chloro-4-(3-fluoro-2-methoxyphenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (78 mg, 0.148 mmol) was dissolved in 10 mL of tetrahydrofuran, and 2,3-dichloro-5,6-dicyano-p-benzoquinone (78 mg, 0.344 mmol) was added thereto, and the reaction was stirred at room temperature for 2 hours. To the reaction solution was added 20 mL of saturated sodium thiosulfate solution and 20 mL of saturated sodium bicarbonate solution, and the mixture was extracted with 30 mL of ethyl acetate. The organic phase was washed with 15 mL of saturated brine, dried and concentrated, and the crude product was prepared by preparative HPLC (column: xbridge C18 19*150 mm, 5 μm; system: 10 mmol/L, aqueous $NH_4HCO_3$ solution; flow rate: 15 mL/min; gradient: 20 to 45% $CH_3CN—NH_4HCO_3$; column temperature: room temperature) to obtain a pale yellow solid (S)-9-(2-chloro-4-(3-fluoro-2-methoxyphenoxy)benzoyl)-2-(methoxymethyl)-2-methyl-1,2,4,7-tetrahydro-3H-pyrrolo[3',2':5,6]pyrido[3,4-b]pyrazin-3-one (Z173, 12 mg, yield of 15%). ES-API: $[M+H]^+$=525.3. $^1H$ NMR (500 MHz, DMSO-$d_6$) δ 12.43 (s, 1H), 10.48 (s, 1H), 8.27 (s, 1H), 7.69 (s, 1H), 7.56-7.54 (m, 2H), 7.24-7.16 (m, 3H), 7.05 (d, J=7.5 Hz, 1H), 6.99 (dd, J1=2.0 Hz, J2=8.0 Hz, 1H), 3.83 (s, 3H), 3.64 (d, J=9.5 Hz, 1H), 3.47 (d, J=9.0 Hz, 1H), 3.29 (s, 3H), 1.38 (s, 3H).

Embodiment 160: Synthesis of Z177

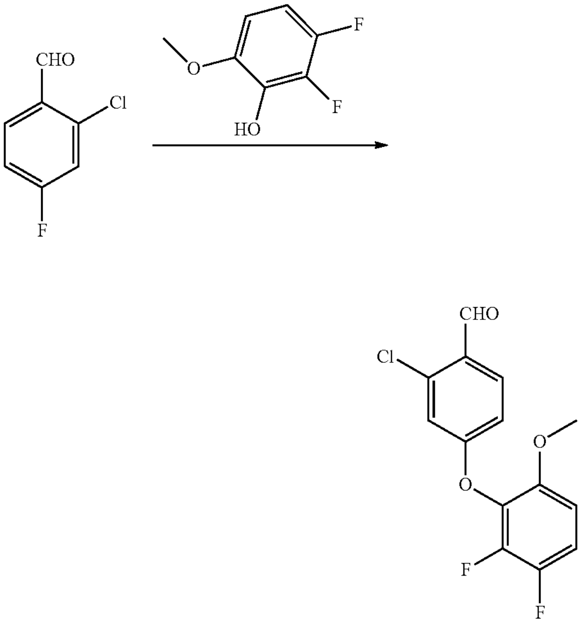

-continued

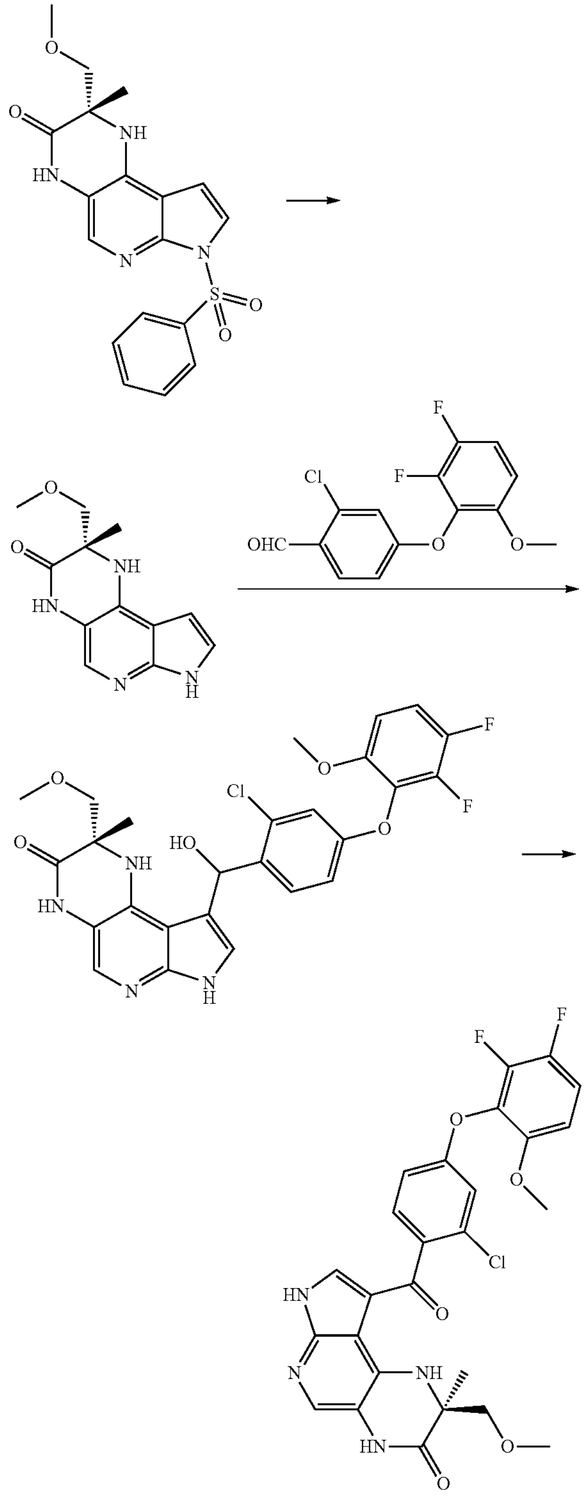

Z177

Step 1: 2-Chloro-4-fluorobenzaldehyde (1.0 g, 6.329 mmol) and 2,3-difluoro-6-methoxyphenol (1.06 g, 6.250 mmol) were dissolved in dry N,N-dimethylacetamide (30 mL), and finally cesium carbonate (5.0 g, 15.34 mmol) was added thereto, and the mixture was heated to 90° C. and reacted for 2 hours under nitrogen atmosphere. After the reaction was completed, the cooling solution was added with ethyl acetate (200 mL), and washed 3 times with saturated brine (3*80 mL). The ethyl acetate phase was dried with anhydrous sodium sulfate, filtered and evaporated to dryness by rotary evaporation under reduced pressure to obtain 2-chloro-4-(2,3-difluoro-6-methoxyphenoxy)benzaldehyde (1.20 g, yield 63%). ES-API: $[M+H]^+$=299.0.

Step 2: (S)-2-(Methoxymethyl)-2-methyl-7-(phenylsulfonyl)-1,2,4,7-tetrahydro-3H-pyrrolo[3',2':5,6]pyrido[3,4-b]pyrazin-3-one (1.05 g, 2.7187 mmol) was dissolved in 36 mL of methanol, 9 mL of tetrahydrofuran and 6 mL of water, and sodium hydroxide (761.0 mg, 19.03 mmol) was added thereto, and the reaction was stirred at 65° C. for 7 hours. To the reaction solution was added 20 mL of water and 15 mL of saturated ammonium chloride solution, and the mixture was extracted with 150 mL of ethyl acetate. The organic phase was washed with 30 mL of saturated sodium bicarbonate solution and 80 mL of saturated brine in turn, dried over anhydrous sodium sulfate and then concentrated to obtain (S)-2-(methoxymethyl)-2-methyl-1,2,4,7-tetrahydro-3H-pyrrolo[3',2':5,6]pyrido[3,4-b]pyrazin-3-one (2.20 g, crude product) as a pale white solid. ES-API: $[M+H]^+$=247.1.

Step 3: (S)-2-(Methoxymethyl)-2-methyl-1,2,4,7-tetrahydro-3H-pyrrolo[3',2':5,6]pyrido[3,4-b]pyrazin-3-one (209 mg, crude product) and 2-chloro-4-(2,3-difluoro-6-methoxyphenoxy)benzaldehyde (237 mg, 0.7953 mmol) were dissolved in methanol (20.0 mL), and the reaction was cooled to 0° C., and potassium hydroxide (152 mg, 2.720 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and then concentrated to obtain a crude target product (2S)-9-((2-chloro-4-(2,3-difluoro-6-methoxyphenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (60 mg, 2-step yield of 28%) as a pale yellow solid. ES-API: $[M+H]^+$=545.2.

Step 4: (2S)-9-((2-Chloro-4-(2,3-difluoro-6-methoxyphenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (60 mg, 0.1102 mmol) was dissolved in 10 mL of tetrahydrofuran, and 2,3-dichloro-5,6-dicyano-1,4-benzoquinone (50 mg, 0.2205 mmol) was added thereto, and the reaction was stirred at room temperature for 2 hours. To the reaction solution was added 60 mL of saturated sodium bicarbonate solution, and the mixture was extracted with 80 mL of ethyl acetate. The organic phase was washed with 60 mL of saturated brine, dried over anhydrous sodium sulfate and then concentrated, and the crude product was purified by preparative HPLC to obtain (S)-9-(2-chloro-4-(2,3-difluoro-6-methoxyphenoxy)benzoyl)-2-(methoxymethyl)-2-methyl-1,2,4,7-tetrahydro-3H-pyrrolo[3',2':5,6]pyrido[3,4-b]pyrazin-3-one (Z177, 13 mg, yield of 22%) as a pale yellow solid, ES-API: $[M+H]^+$=543.2. $^1$H NMR (500 MHz, DMSO-$d_6$) δ 12.43 (s, 1H), 10.48 (s, 1H), 8.27 (s, 1H), 7.69 (s, 1H), 7.59-7.50 (m, 2H), 7.43 (dd, J=19.1, 9.5 Hz, 1H), 7.17 (d, J=2.4 Hz, 1H), 7.15-7.05 (m, 1H), 6.94 (dd, J=8.5, 2.3 Hz, 1H), 3.80 (s, 3H), 3.64 (d, J=9.5 Hz, 1H), 3.47 (d, J=9.6 Hz, 1H), 3.29 (s, 3H), 1.38 (s, 3H).

Embodiment 161: Synthesis of Z187

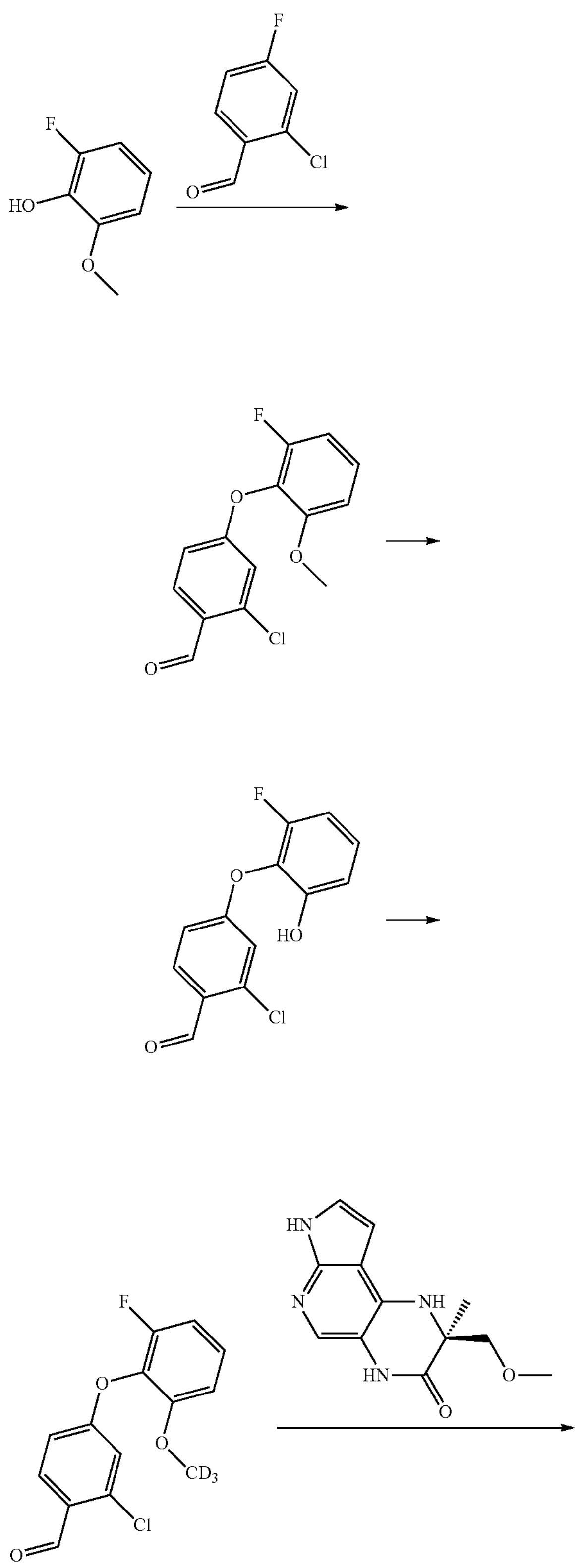

-continued

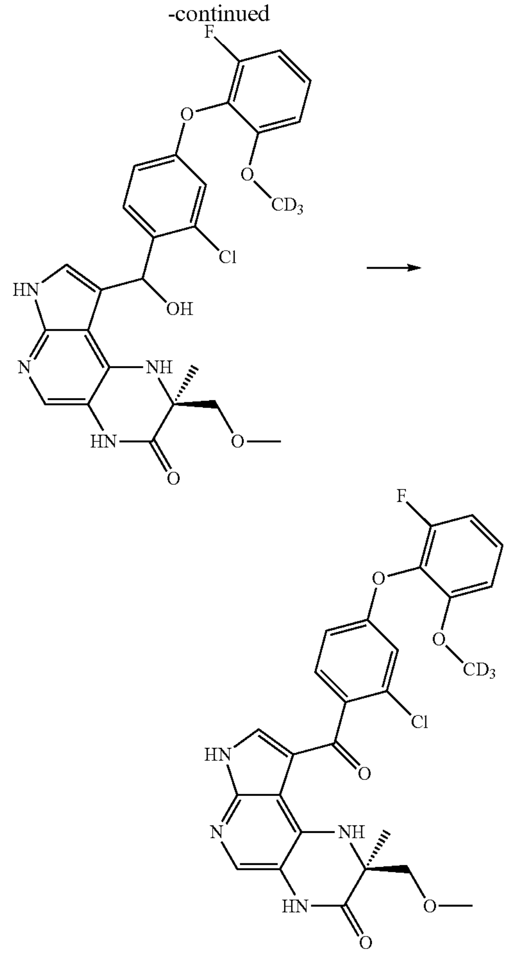

Z187

Step 1: To a 100 mL round-bottom flask was added 2-fluoro-6-methoxyphenol (880 mg, 6.19 mmol), 2-chloro-4-fluorobenzaldehyde (982 mg, 6.19 mmol), potassium carbonate (2.56 g, 18.57 mmol) and DMF (15 mL). The reaction was stirred at 95° C. for 3 hours. The reaction solution was poured into ice-water, and extracted with ethyl acetate. The organic phase was dried and concentrated to obtain a crude product 2-chloro-4-(2-fluoro-6-methoxyphenoxy)benzaldehyde (1.5 g, 86%) as a yellow solid. ES-API: $[M+H]^+=281.0$ Step 2: To a 100 mL reaction flask was added 2-chloro-4-(2-fluoro-6-methoxyphenoxy)benzaldehyde (800 mg, 2.86 mmol) and 10 mL of dichloromethane. The system was cooled to 0° C., a dichloromethane solution of boron tribromide (8.6 mL, 8.6 mmol, 1 M) was added dropwise thereto. The reaction was stirred at room temperature for 2 hours, and the reaction was stopped. To the reaction solution was added 50 mL of ice saturated sodium bicarbonate, and the mixture was extracted three times with dichloromethane, and the organic phase was dried and concentrated and then purified by a flash silica gel column (0-20% of ethyl acetate/petroleum ether) to obtain 2-chloro-4-(2-fluoro-6-hydroxyphenoxy)benzaldehyde (500 mg, 65%) as a yellow solid. ES-API: $[M+H]^+=267.1$ Step 3: To a 100 mL round-bottom flask was added 2-chloro-4-(2-fluoro-6-hydroxyphenoxy)benzaldehyde (400 mg, 1.5 mmol), deuterated iodomethane (654 mg, 14.5 mmol), potassium carbonate (414 mg, 3.05 mmol) and DMF (16 mL). The reaction was stirred at 40° C. for 3 hours. The reaction was quenched with water and extracted with ethyl acetate. The organic phase was dried over anhydrous sodium sulfate. After the organic phase was concentrated, the crude product was obtained, and purified by a flash silica gel column (0-20% of ethyl acetate/petroleum ether) to obtain 2-chloro-4-(2-fluoro-6-(methoxy-$d_3$)phenoxy)benzaldehyde (130 mg, 30%). $^1$HNMR (500 MHz, DMSO-$d_6$): 10.21 (s, 1H), 7.86 (d, J=9.0 Hz, 1H), 7.37-7.34 (m, 1H), 7.11-7.03 (m, 3H), 6.97 (dd, J=9.0, 2.0 Hz, 1H), 7.65 (d, J=1.2, 1H), 6.35 (s, 1H), 3.89 (s, 3H), 2.44 (s, 3H). ES-API: $[M+H]^+$= 284.1

Step 4: To a 100 mL round bottom flask was added 2-chloro-4-(2-fluoro-6-(methoxy-$d_3$)phenoxy)benzaldehyde (130 mg, 0.46 mmol), (S)-2-(methoxymethyl)-2-methyl-1,2,4,7-tetrahydro-3H-pyrrolo[3',2':5,6]pyrido[3,4-b]pyrazin-3-one (113 mg, 0.46 mmol), potassium hydroxide (180 mg, 3.22 mmol) and methanol (6 mL). The reaction was stirred at room temperature for 24 hour. The reaction was quenched with 2 N hydrochloric acid and extracted with ethyl acetate. The organic phase was dried over anhydrous sodium sulfate. The organic phase was concentrated to obtain a crude product (2S)-9-((2-chloro-4-(2-fluoro-6-(methoxy-$d_3$)phenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (130 mg, crude product). ES-API: $[M+H]^+$= 530.2

Step 5: To a 100 mL round-bottom flask was added (2S)-9-((2-chloro-4-(2-fluoro-6-(methoxy-$d_3$)phenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (130 mg, crude product) and tetrahydrofuran (5 mL) at 0° C. To the reaction solution was added 2,3-dichloro-5,6-dicyano-p-benzoquinone (111 mg, 0.48 mmol). The reaction was stirred at room temperature for 30 minutes. The reaction was quenched with saturated aqueous sodium bicarbonate solution and extracted with dichloromethane. The organic phase was dried over anhydrous sodium sulfate. After concentration, the crude product was purified by preparative HPLC to obtain a target product (Z187, 43 mg, 2-step yield of 34%). ES-API: $[M+H]^+$=528.2.

With reference to the preparation methods of Embodiments 1 to 23, the following compounds were prepared by changing some raw materials:

| Embodiment | Compound No. | Structure | MS $[M + H]^+$ |
|---|---|---|---|
| 162 | Z190 | 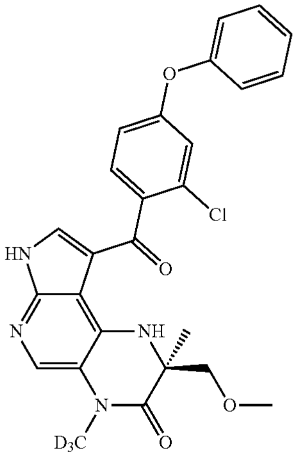 [SMILES: [2H]C([2H])([2H])N1C(=O)[C@](C)(COC)Nc2c1cnc1[nH]cc(C(=O)c3ccc(Oc4ccccc4)cc3Cl)c21] | 494.2 |

-continued

| Embodiment | Compound No. | Structure | MS $[M + H]^+$ |
|---|---|---|---|
| 163 | Z191 | 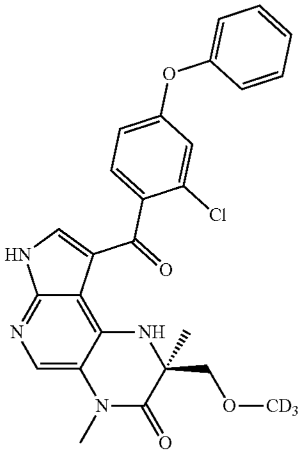 [SMILES: [2H]C([2H])([2H])OC[C@]1(C)Nc2c(cnc3[nH]cc(C(=O)c4ccc(Oc5ccccc5)cc4Cl)c23)N(C)C1=O] | 494.2 |
| 164 | Z192 | 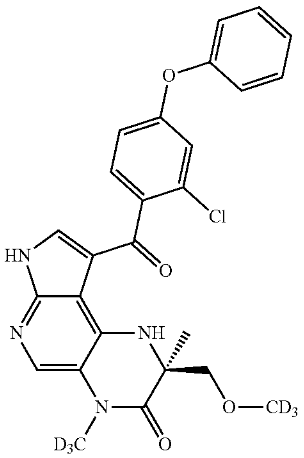 [SMILES: [2H]C([2H])([2H])OC[C@]1(C)Nc2c(cnc3[nH]cc(C(=O)c4ccc(Oc5ccccc5)cc4Cl)c23)N(C([2H])([2H])[2H])C1=O] | 497.2 |

Embodiment 165: Synthesis of Z85

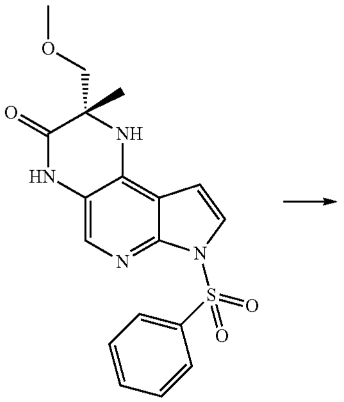

-continued

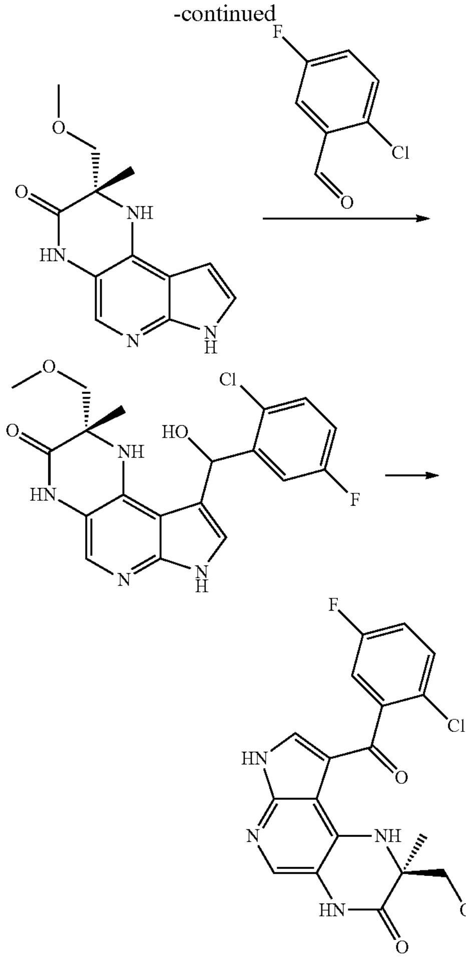

Z85

Step 1: (S)-2-(Methoxymethyl)-2-methyl-7-(phenylsulfonyl)-1,2,4,7-tetrahydro-3H-pyrrolo[3',2':5,6]pyrido[3,4-b]pyrazin-3-one (1.40 g, 3.570 mmol) was dissolved in 36 mL of methanol, 9 mL of tetrahydrofuran and 6 mL of water, and sodium hydroxide (1.01 g, 24.99 mmol) was added thereto, and the reaction was stirred at 65° C. for 7 hours. To the reaction solution was added 20 mL of water and 15 mL of saturated ammonium chloride solution, and the mixture was extracted with 200 mL of ethyl acetate. The organic phase was washed with 30 mL of saturated sodium bicarbonate solution and 80 mL of saturated brine in turn, dried over anhydrous sodium sulfate and then concentrated to obtain (S)-2-(methoxymethyl)-2-methyl-1,2,4,7-tetrahydro-3H-pyrrolo[3',2':5,6]pyrido[3,4-b]pyrazin-3-one (377 mg, yield of 43%) as a pale white solid. ES-API: $[M+H]^+$=247.1.

Step 2: (S)-2-(Methoxymethyl)-2-methyl-1,2,4,7-tetrahydro-3H-pyrrolo[3',2':5,6]pyrido[3,4-b]pyrazin-3-one (160 mg, 0.6501 mmol) and 2-chloro-5-fluorobenzaldehyde (210 mg, 1.324 mmol) were dissolved in methanol (20.0 mL), and the reaction was cooled to 0° C., and potassium hydroxide (253 mg, 4.517 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried over anhydrous sodium sulfate, and concentrated to obtain (2S)-9-((2-chloro-5-fluorophenyl)(hydroxy)methyl)-2-(methoxymethyl)-2-methyl-1,2,4,7-tetrahydro-3H-pyrrolo[3',2':5,6]pyrido[3,4-b]pyrazin-3-one (270 mg, crude product) as a pale yellow solid. ES-API: $[M+H]^+$=405.1.

Step 3: (2S)-9-((2-Chloro-5-fluorophenyl)(hydroxy)methyl)-2-(methoxymethyl)-2-methyl-1,2,4,7-tetrahydro-3H-pyrrolo[3',2':5,6]pyrido[3,4-b]pyrazin-3-one (270 mg, crude product) was dissolved in 20 mL of tetrahydrofuran, and 2,3-dichloro-5,6-dicyano-1,4-benzoquinone (303 mg, 1.335 mmol) was added thereto, and the reaction was stirred at room temperature for 2 hours. To the reaction solution was added 63 mL of saturated sodium bicarbonate solution, and the mixture was extracted with 88 mL of ethyl acetate. The organic phase was washed with 60 mL of saturated brine, dried over anhydrous sodium sulfate and then concentrated, and the crude product was purified by preparative HPLC to obtain (S)-9-(2-chloro-5-fluorobenzoyl)-2-(methoxymethyl)-2-methyl-1,2,4,7-tetrahydro-3H-pyrrolo[3',2':5,6]pyrido[3,4-b]pyrazin-3-one (Z85, 115 mg, 2-step yield of 44%) as a pale yellow solid. ES-API: $[M+H]^+$=403.1. $^1H$ NMR (500 MHz, DMSO-$d_6$) δ 11.90 (s, 1H), 10.49 (s, 1H), 8.22 (s, 1H), 7.70 (s, 1H), 7.66-7.58 (m, 2H), 7.51 (dd, J=8.3, 3.0 Hz, 1H), 7.41 (td, J=8.6, 3.1 Hz, 1H), 3.65 (d, J=9.6 Hz, 1H), 3.48 (d, J=9.6 Hz, 1H), 3.30 (s, 3H), 1.39 (s, 3H).

Embodiment 166: Synthesis of Z86

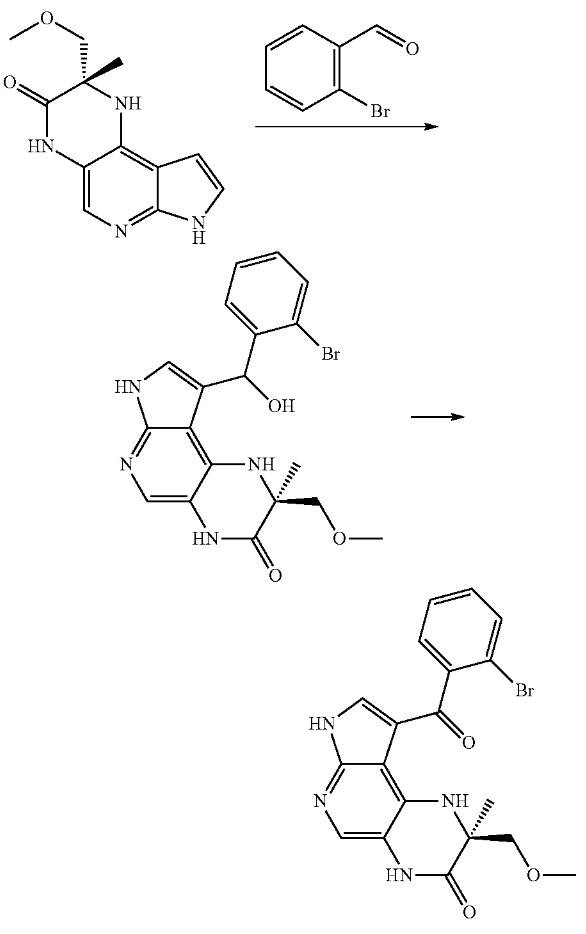

Z86

Step 1: (S)-2-(Methoxymethyl)-2-methyl-1,2,4,7-tetrahydro-3H-pyrrolo[3',2':5,6]pyrido[3,4-b]pyrazin-3-one (200 mg, 0.8 mmol) and 2-bromobenzaldehyde (293 mg, 1.6 mmol) were dissolved in methanol (10 mL), and the reaction was cooled to 0° C., and potassium hydroxide (314 mg, 5.6 mmol) was added thereto. The reaction was stirred at room temperature for 16 hours. The reaction solution was poured into 30 mL of water, and the pH of the reaction solution was adjusted to 8 with 1.0 M dilute hydrochloric acid, and the reaction solution was extracted with 50 mL of ethyl acetate. The organic phase was washed with 25 mL of saturated brine, dried over anhydrous sodium sulfate and concentrated, and the crude product was purified by a thin-layer preparative plate (dichloromethane/7M ammonia methanol=100:8) to obtain (2S)-9-((2-bromophenyl)(hydroxy)methyl)-2-(methoxymethyl)-2-methyl-1,2,4,7-tetrahydro-3H-pyrrolo[3',2':5,6]pyrido[3,4-b]pyrazin-3-one (227 mg, yield of 66%) as a pale yellow solid. ES-API: $[M+H]^+$=433.1.

Step 2: (2S)-9-((2-Bromophenyl)(hydroxy)methyl)-2-(methoxymethyl)-2-methyl-1,2,4,7-tetrahydro-3H-pyrrolo[3',2':5,6]pyrido[3,4-b]pyrazin-3-one (227 mg, 0.53 mmol) was dissolved in 20 mL of tetrahydrofuran and 2 mL of water, and 2,3-dichloro-5,6-dicyano-p-benzoquinone (301 mg, 1.33 mmol) was added thereto, and the reaction was stirred at room temperature for 2 hours. To the reaction solution was added 20 mL of saturated sodium thiosulfate solution, and the mixture was extracted with 60 mL of ethyl acetate. The organic phase was washed twice with 20 mL of saturated sodium bicarbonate solution and 15 mL of saturated brine in turn, dried over anhydrous sodium sulfate and concentrated, and the crude product was purified by preparative HPLC (column model: xbridge C18 19*150 mm, 5 μm; system: 10 mmol/L, aqueous $NH_4HCO_3$ solution; flow rate: 15 mL/min; gradient: 20 to 45% $CH_3CN—NH_4HCO_3$; column temperature: room temperature) to obtain a target product (S)-9-(2-bromobenzoyl)-2-(methoxymethyl)-2-methyl-1,2,4,7-tetrahydro-3H-pyrrolo[3',2':5,6]pyrido[3,4-b]pyrazin-3-one (Z86, 130 mg, yield of 57%) as a white solid. ES-API: $[M+H]^+$=431.0. $^1$H NMR (500 MHz, DMSO) δ 12.43 (s, 1H), 10.49 (s, 1H), 8.29 (s, 1H), 7.74 (d, J=7.5 Hz, 1H), 7.70 (s, 1H), 7.54-0.48 (m, 2H), 7.48-0.43 (m, 1H), 7.41 (s, 1H), 3.65 (d, J=9.5 Hz, 1H), 3.45 (d, J=9.5, 1H), 3.30 (s, 3H), 1.39 (s, 3H).

Embodiment 167: Synthesis of Z89

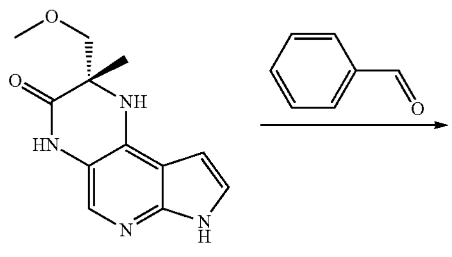

-continued

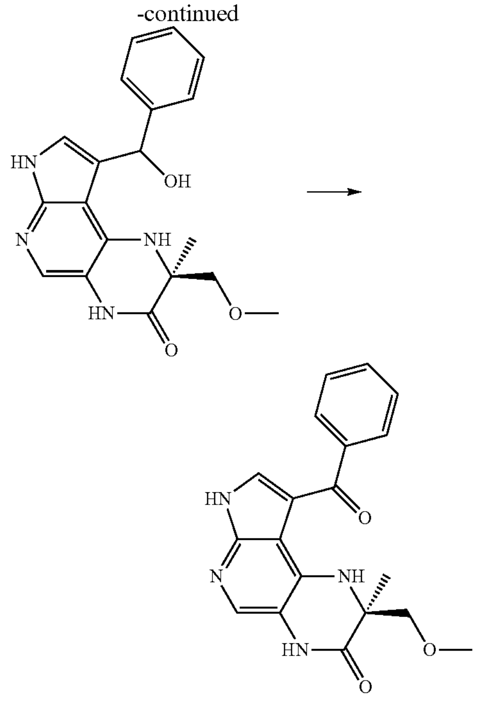

Z89

Step 1: (S)-2-(Methoxymethyl)-2-methyl-1,2,4,7-tetrahydro-3H-pyrrolo[3',2':5,6]pyrido[3,4-b]pyrazin-3-one (200 mg, 0.8 mmol) and benzaldehyde (170 mg, 1.6 mmol) were dissolved in methanol (10 mL), and the reaction was cooled to 0° C., and potassium hydroxide (314 mg, 5.6 mmol) was added thereto. The reaction was stirred at room temperature for 16 hours. The reaction solution was poured into 30 mL of water, and the pH of the reaction solution was adjusted to 8 with 1.0 M dilute hydrochloric acid, and the reaction solution was extracted with 50 mL of ethyl acetate. The organic phase was washed with 25 mL of saturated brine, dried over anhydrous sodium sulfate and concentrated, and the crude product was purified by a thin-layer preparative plate (dichloromethane/7M ammonia methanol=100:5) to obtain (2S)-9-(hydroxy(phenyl)methyl)-2-(methoxymethyl)-2-methyl-1,2,4,7-tetrahydro-3H-pyrrolo[3',2':5,6]pyrido[3,4-b]pyrazin-3-one (197 mg, yield of 70%) as a pale yellow solid. ES-API: $[M+H]^+$=353.1.

Step 2: (2S)-9-(Hydroxy(phenyl)methyl)-2-(methoxymethyl)-2-methyl-1,2,4,7-tetrahydro-3H-pyrrolo[3',2':5,6]pyrido[3,4-b]pyrazin-3-one (197 mg, 0.53 mmol) was dissolved in 20 mL of tetrahydrofuran and 2 mL of water, and 2,3-dichloro-5,6-dicyano-p-benzoquinone (301 mg, 1.33 mmol) was added thereto, and the reaction was stirred at room temperature for 2 hours. To the reaction solution was added 20 mL of saturated sodium thiosulfate solution, and the mixture was extracted with 60 mL of ethyl acetate. The organic phase was washed twice with 20 mL of saturated sodium bicarbonate solution and 15 mL of saturated brine in turn, dried over anhydrous sodium sulfate and concentrated, and the crude product was purified by preparative HPLC (column model: xbridge C18 19*150 mm, 5 μm; system: 10 mmol/L, aqueous $NH_4HCO_3$ solution; flow rate: 15 mL/min; gradient: 20 to 45% $CH_3CN—NH_4HCO_3$; column temperature: room temperature) to obtain a target product (S)-9-benzoyl-2-(methoxymethyl)-2-methyl-1,2,4,7-tetrahydro-3H-pyrrolo[3',2':5,6]pyrido[3,4-b]pyrazin-3-one (Z89, 109 mg, yield of 59%) as a white solid. ES-API: $[M+H]^+$=351.1. $^1H$ NMR (500 MHz, DMSO) δ 10.61-10.41 (m, 1H), 8.35 (s, 1H), 7.76 (d, J=7.5 Hz, 2H), 7.73 (s, 1H), 7.69 (s, 1H), 7.62 (t, J=7.5 Hz, 1H), 7.54 (t, J=7.5 Hz, 2H), 7.04-6.71 (m, 1H), 3.65 (d, J=9.5 Hz, 1H), 3.45 (t, J=9.4 Hz, 1H), 3.32 (s, 3H), 1.38 (s, 3H).

Embodiment 168: Synthesis of Z113

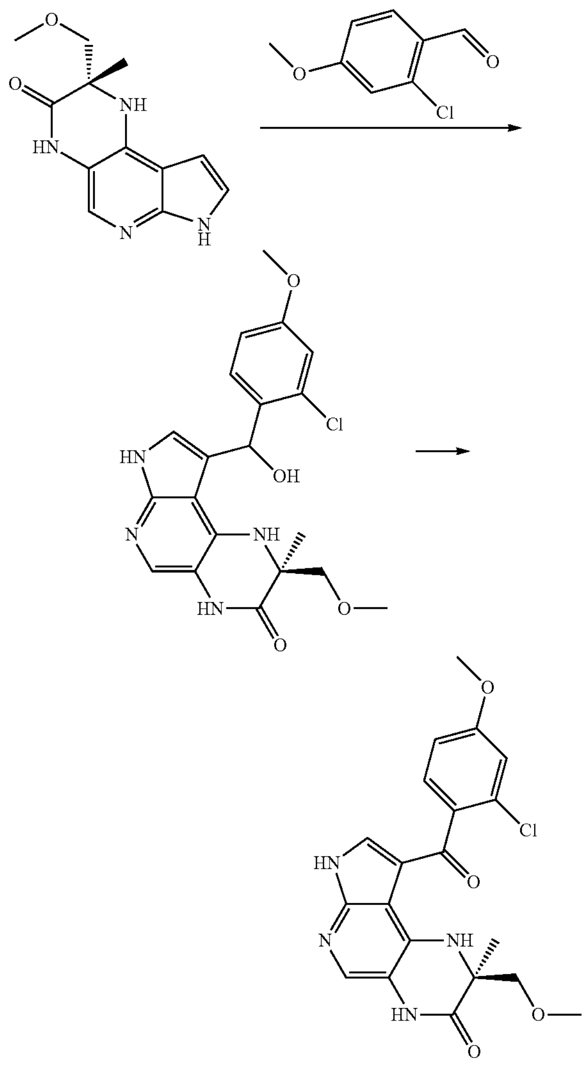

Z113

Step 1: (S)-2-(Methoxymethyl)-2-methyl-1,2,4,7-tetrahydro-3H-pyrrolo[3',2':5,6]pyrido[3,4-b]pyrazin-3-one (200 mg, 0.8 mmol) and 2-chloro-4-methoxybenzaldehyde (272 mg, 1.6 mmol) were dissolved in methanol (10 mL), and the reaction was cooled to 0° C., and potassium hydroxide (314 mg, 5.6 mmol) was added thereto. The reaction was stirred at room temperature for 16 hours. The reaction solution was poured into 30 mL of water, and the pH of the reaction solution was adjusted to 8 with 1.0 M dilute hydrochloric acid, and the reaction solution was extracted with 50 mL of ethyl acetate. The organic phase was washed with 25 mL of saturated brine, dried over anhydrous sodium sulfate and concentrated, and the crude product was purified by a thin-layer preparative plate (dichloromethane/7M ammonia methanol=100:8) to obtain a target product (2S)-9-((2-chloro-4-methoxyphenyl)(hydroxy)methyl)-2-(methoxymethyl)-2-methyl-1,2,4,7-tetrahydro-3H-pyrrolo[3',2':5,6]pyrido[3,4-b]pyrazin-3-one (171 mg, yield of 51%) as a pale yellow solid. ES-API: $[M+H]^+$=417.2.

Step 2: (2S)-9-((2-Chloro-4-methoxyphenyl)(hydroxy)methyl)-2-(methoxymethyl)-2-methyl-1,2,4,7-tetrahydro-3H-pyrrolo[3',2':5,6]pyrido[3,4-b]pyrazin-3-one (171 mg, 0.41 mmol) was dissolved in 20 mL of tetrahydrofuran and 2 mL of water, and 2,3-dichloro-5,6-dicyano-p-benzoquinone (227 mg, 1.0 mmol) was added thereto, and the reaction was stirred at room temperature for 2 hours. To the reaction solution was added 20 mL of saturated sodium thiosulfate solution, and the mixture was extracted with 60 mL of ethyl acetate. The organic phase was washed twice with 20 mL of saturated sodium bicarbonate solution and 15 mL of saturated brine in turn, dried over anhydrous sodium sulfate and concentrated, and the crude product was purified by preparative HPLC (column model: xbridge C18 19*150 mm, 5 μm; system: 10 mmol/L, aqueous $NH_4HCO_3$ solution; flow rate: 15 mL/min; gradient: 20 to 45% $CH_3CN$—$NH_4HCO_3$; column temperature: room temperature) to obtain a target product (S)-9-(2-chloro-4-methoxybenzoyl)-2-(methoxymethyl)-2-methyl-1,2,4,7-tetrahydro-3H-pyrrolo[3',2':5,6]pyrido[3,4-b]pyrazin-3-one (Z113, 77 mg, yield of 45.4%) as a white solid. ES-API: $[M+H]^+$=415.1. $^1H$ NMR (500 MHz, DMSO) δ 12.36 (s, 1H), 10.47 (s, 1H), 8.29 (s, 1H), 7.69 (s, 1H), 7.49 (d, J=10.0 Hz, 2H), 7.15 (d, J=2.0 Hz, 1H), 7.01 (dd, J=8.5, 2.5 Hz, 1H), 3.85 (s, 3H), 3.64 (d, J=9.6 Hz, 1H), 3.47 (d, J=9.6 Hz, 1H), 3.29 (s, 3H), 1.38 (s, 3H).

Embodiment 169: Synthesis of Z120

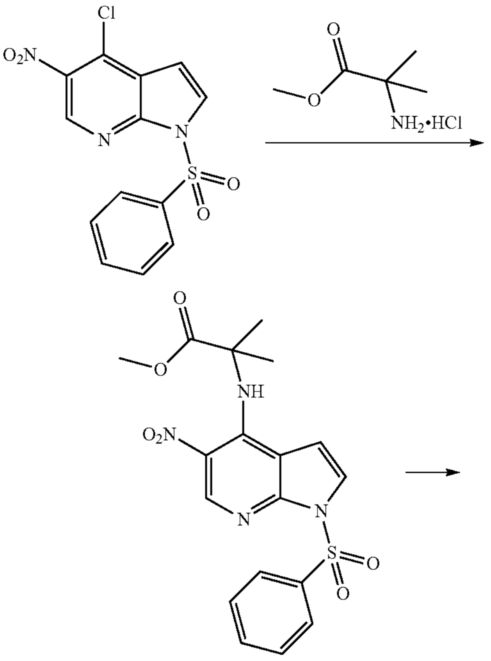

-continued

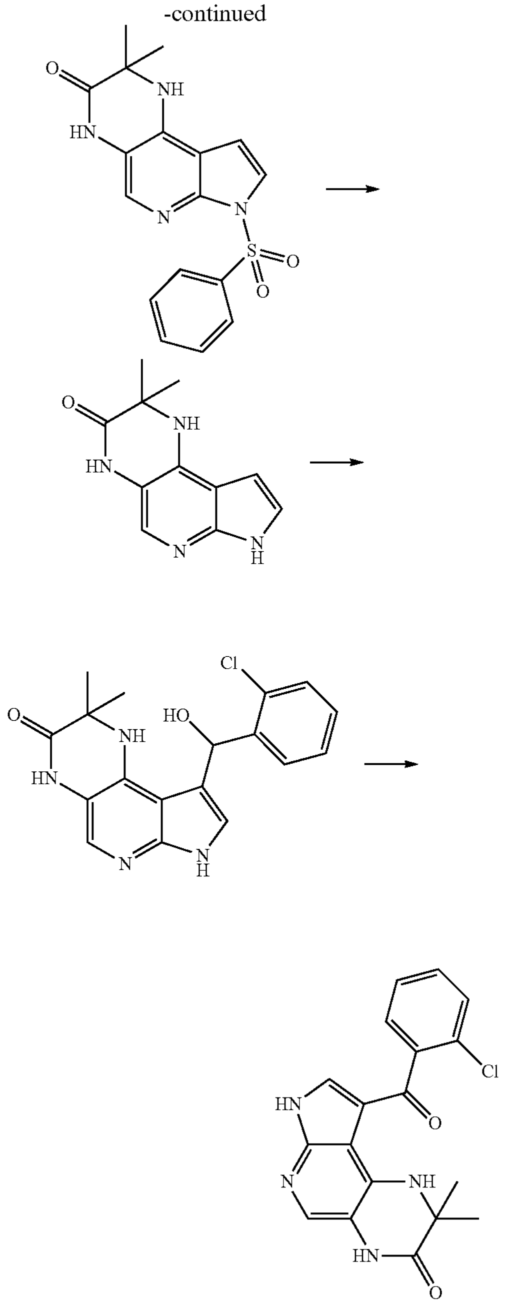

Z120

Step 1: 4-Chloro-5-nitro-1-(phenylsulfonyl)-1H-pyrrolo[2,3-b]pyridine (1.0 g, 2.967 mmol) and methyl 2-amino-2-methylpropanoate hydrochloride (1.0 g, 6.509 mmol) were dissolved in N,N-dimethylacetamide (30 mL), and N,N-diisopropylethylamine (7.64 g, 59.15 mmol) was added thereto, and the reaction was stirred at 85° C. for 12 hours. The reaction solution was added with 100 mL of ethyl acetate, washed with water (2×60 mL), washed with saturated brine (3×30 mL), dried over anhydrous sodium sulfate and concentrated, and the crude product was purified by a flash silica gel column (ethyl acetate/petroleum ether: 0-50%) to obtain methyl 2-methyl-2-((5-nitro-1-(phenylsulfonyl)-1H-pyrrolo[2,3-b]pyridin-4-yl)amino)propanoate (1.1 g, yield of 88%) as a pale yellow solid. ES-API: $[M+H]^+$=419.1.

Step 2: Methyl 2-methyl-2-((5-nitro-1-(phenylsulfonyl)-1H-pyrrolo[2,3-b]pyridin-4-yl)amino)propanoate (1.10 g, 2.63 mmol) was dissolved in acetic acid (30 mL), and iron powder (1.50 g, 26.31 mmol) was added thereto. The mixture was gradually heated to 80° C. and stirred for 1 hour. After the reaction was completed, the solvent was evaporated to dryness by rotary evaporation under reduced pressure, then the residue was added with 200 mL of ethyl acetate, washed with water (2×80 mL), saturated sodium carbonate (2×60 mL), saturated brine (2×80 mL) in turn. The organic phase was dried over anhydrous sodium sulfate, concentrated, and the crude product was slurried with ethyl acetate (20 mL) to obtain 2,2-dimethyl-7-(phenylsulfonyl)-1,2,4,7-tetrahydro-3H-pyrrolo[3',2':5,6]pyrido[3,4-b]pyrazin-3-one (240 mg, yield of 25%) as a yellow solid. ES-API: $[M+H]^+$=357.1.

Step 3: 2,2-Dimethyl-7-(phenylsulfonyl)-1,2,4,7-tetrahydro-3H-pyrrolo[3',2':5,6]pyrido[3,4-b]pyrazin-3-one (240 mg, 0.6739 mmol) was dissolved in 20 mL of methanol, 6 mL of tetrahydrofuran and 4 mL of water, and sodium hydroxide (188.0 mg, 4.717 mmol) was added thereto, and the reaction was stirred at 65° C. for 12 hours. To the reaction solution was added 20 mL of water and 15 mL of saturated ammonium chloride solution, and the mixture was extracted with 150 mL of ethyl acetate. The organic phase was washed with 30 mL of saturated sodium bicarbonate solution and 80 mL of saturated brine in turn, dried over anhydrous sodium sulfate and then concentrated to obtain 2,2-dimethyl-1,2,4,7-tetrahydro-3H-pyrrolo[3',2':5,6]pyrido[3,4-b]pyrazin-3-one (300 mg, crude product) as a pale white solid. ES-API: $[M+H]^+$=217.1.

Step 4: 2,2-Dimethyl-1,2,4,7-tetrahydro-3H-pyrrolo[3',2':5,6]pyrido[3,4-b]pyrazin-3-one (300 mg, crude product) and 2-chloro-benzaldehyde (188 mg, 1.342 mmol) were dissolved in methanol (25.0 mL), and the reaction was cooled to 0° C., and potassium hydroxide (264 mg, 4.714 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried over anhydrous sodium sulfate, and concentrated to obtain a crude product 9-((2-chlorophenyl)(hydroxy)methyl)-2,2-dimethyl-1,2,4,7-tetrahydro-3H-pyrrolo[3',2':5,6]pyrido[3,4-b]pyrazin-3-one (210 mg, 2-step yield of 87%) as a pale yellow solid. ES-API: $[M+H]^+$=357.2.

Step 5: 9-((2-Chlorophenyl)(hydroxy)methyl)-2,2-dimethyl-1,2,4,7-tetrahydro-3H-pyrrolo[3',2':5,6]pyrido[3,4-b]pyrazin-3-one (210 mg, 0.5898 mmol) was dissolved in 20 mL of tetrahydrofuran, and 2,3-dichloro-5,6-dicyano-1,4-benzoquinone (267 mg, 1.176 mmol) was added thereto, and the reaction was stirred at room temperature for 2 hours. To the reaction solution was added 60 mL of saturated sodium bicarbonate solution, and the mixture was extracted with 80 mL of ethyl acetate. The organic phase was washed with 60 mL of saturated brine, dried over anhydrous sodium sulfate and then concentrated, and the crude product was purified by preparative HPLC to obtain a target product 9-(2-chlorobenzoyl)-2,2-dimethyl-1,2,4,7-tetrahydro-3H-pyrrolo[3',2':5,6]pyrido[3,4-b]pyrazin-3-one (Z120, 95 mg, yield of 45%) as a pale yellow solid. ES-API: $[M+H]^+$=355.1. $^1$H NMR (500 MHz, DMSO-$d_6$) δ 10.67 (d, J=236.9 Hz, 2H), 8.10 (s, 1H), 7.76 (s, 1H), 7.63-7.51 (m, 3H), 7.51-7.37 (m, 2H), 1.41 (s, 6H).

Embodiment 170: Synthesis of Z190

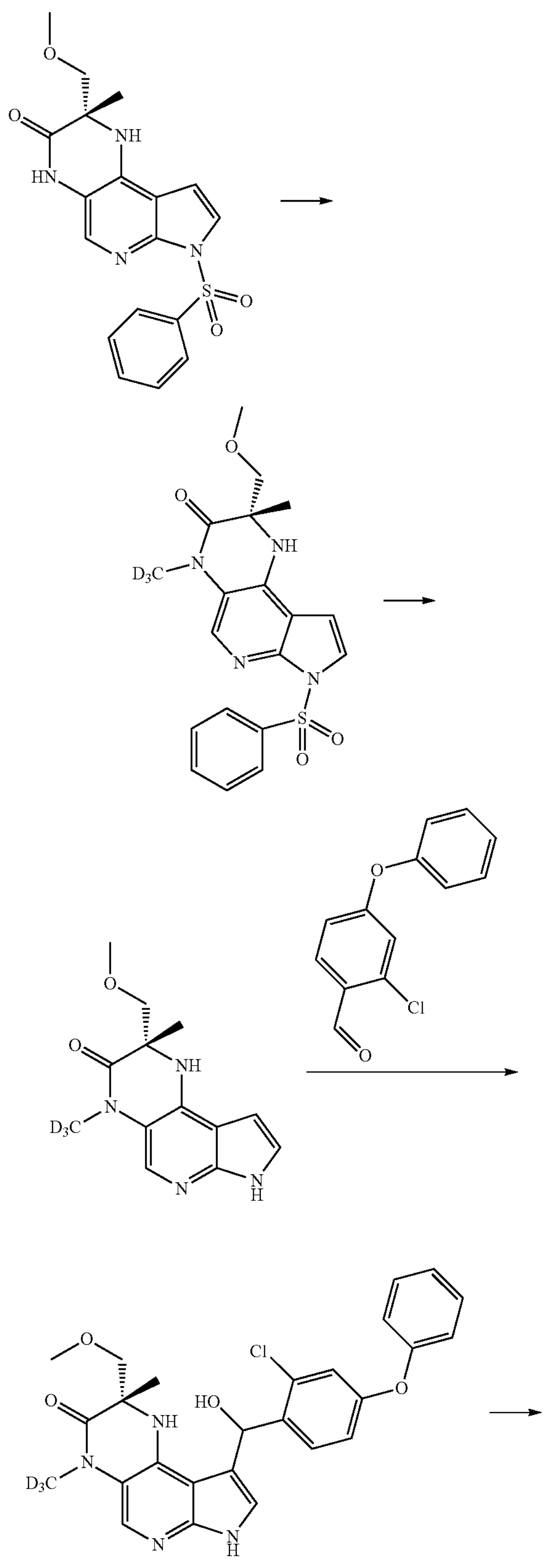

-continued

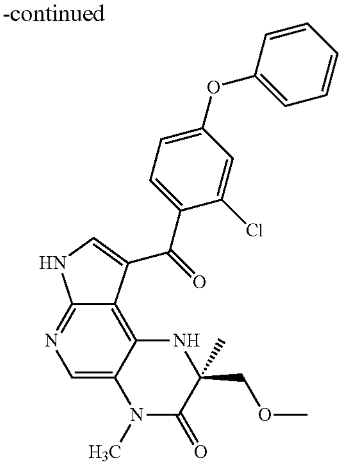

Z190

Step 1: To a sealed tube was added (S)-2-(methoxymethyl)-2-methyl-7-(phenylsulfonyl)-1,2,4,7-tetrahydro-3H-pyrrolo[3',2':5,6]pyrido[3,4-b]pyrazin-3-one (400 mg, 1.036 mmol), deuterated iodomethane (1.50 g, 10.36 mmol), potassium carbonate (430 mg, 3.108 mmol) and a mixture of acetone/N,N-dimethylformamide (20 mL/4.0 mL), reacted at 40° C. for 12 hours. The reaction was completed, cooled to room temperature, added with ethyl acetate (1×200 mL) for extraction, washed with saturated brine (3×100 mL), and the organic phase was dried over anhydrous sodium sulfate, filtered, and the solvent was evaporated to dryness by rotary evaporation under reduced pressure to obtain a crude product (S)-2-(methoxymethyl)-2-methyl-4-(methyl-$d_3$)-7-(phenylsulfonyl)-1,2,4,7-tetrahydro-3H-pyrrolo[3',2':5,6]pyrido[3,4-b]pyrazin-3-one (530 mg, crude product). ES-API: $[M+H]^+$=404.2.

Step 2: (S)-2-(Methoxymethyl)-2-methyl-4-(methyl-$d_3$)-7-(phenylsulfonyl)-1,2,4,7-tetrahydro-3H-pyrrolo[3',2':5,6]pyrido[3,4-b]pyrazin-3-one (530 mg, crude product) was dissolved in 30 mL of methanol, 7.5 mL of tetrahydrofuran and 5 mL of water, and sodium hydroxide (290 mg, 7.252 mmol) was added thereto, and the reaction was stirred at 65° C. for 16 hours. The reaction was completed, then cooled to room temperature. To the reaction solution was added 20 mL of water and 15 mL of saturated ammonium chloride solution, and the mixture was extracted with 200 mL of ethyl acetate. The organic phase was washed with 30 mL of saturated sodium bicarbonate solution and 80 mL of saturated brine in turn, dried over anhydrous sodium sulfate and then concentrated to obtain (S)-2-(methoxymethyl)-2-methyl-4-(methyl-$d_3$)-1,2,4,7-tetrahydro-3H-pyrrolo[3',2':5,6]pyrido[3,4-b]pyrazin-3-one (0.60 g, crude product) as a pale white solid. ES-API: $[M+H]^+$=264.3.

Step 3: (S)-2-(Methoxymethyl)-2-methyl-4-(methyl-$d_3$)-1,2,4,7-tetrahydro-3H-pyrrolo[3',2':5,6]pyrido[3,4-b]pyrazin-3-one (0.60 g, crude product) and 2-chloro-4-phenoxybenzaldehyde (480 mg, 2.069 mmol) were dissolved in methanol (25.0 mL), and the reaction was cooled to 0° C., and potassium hydroxide (406 mg, 7.25 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried over anhydrous sodium sulfate, and concentrated to obtain a crude product (2S)-9-((2-chloro-4-phenoxyphenyl)(hydroxy)methyl)-2-(methoxymethyl)-2-methyl-4-(methyl-$d_3$)-1,2,4,7-tetrahydro-3H-pyrrolo[3',2':5,6]pyrido[3,4-b]pyrazin-3-one (300 mg, 3-step yield of 58%) as a pale yellow solid. ES-API: $[M+H]^+$=496.3.

Step 4: (2S)-9-((2-Chloro-4-phenoxyphenyl)(hydroxy)methyl)-2-(methoxymethyl)-2-methyl-4-(methyl-$d_3$)-1,2,4,7-tetrahydro-3H-pyrrolo[3',2':5,6]pyrido[3,4-b]pyrazin-3-one (300 mg, 0.6057 mmol) was dissolved in 20 mL of tetrahydrofuran, and 2,3-dichloro-5,6-dicyano-1,4-benzoquinone (275 mg, 1.211 mmol) was added thereto, and the reaction was stirred at room temperature for 2 hours. To the reaction solution was added 63 mL of saturated sodium bicarbonate solution, and the mixture was extracted with 88 mL of ethyl acetate. The organic phase was washed with 60 mL of saturated brine, dried over anhydrous sodium sulfate and then concentrated, and the crude product was purified by preparative HPLC to obtain a target product (S)-9-(2-chloro-4-phenoxybenzoyl)-2-(methoxymethyl)-2-methyl-4-(methyl-$d_3$)-1,2,4,7-tetrahydro-3H-pyrrolo[3',2':5,6]pyrido[3,4-b]pyrazin-3-one (Z190, 136 mg, yield of 45%) as a pale yellow solid. ES-API: $[M+H]^+$=494.2. $^1H$ NMR (500 MHz, DMSO-$d_6$) δ 12.55 (s, 1H), 8.53 (s, 1H), 7.95 (s, 1H), 7.66 (s, 1H), 7.56 (d, J=8.4 Hz, 1H), 7.48 (t, J=8.0 Hz, 2H), 7.25 (t, J=7.4 Hz, 1H), 7.19 (dd, J=5.1, 2.6 Hz, 3H), 7.03 (dd, J=8.4, 2.3 Hz, 1H), 3.64 (d, J=9.6 Hz, 1H), 3.50 (d, J=9.6 Hz, 1H), 3.28 (s, 3H), 1.38 (s, 3H).

Embodiment 171: Synthesis of Z193

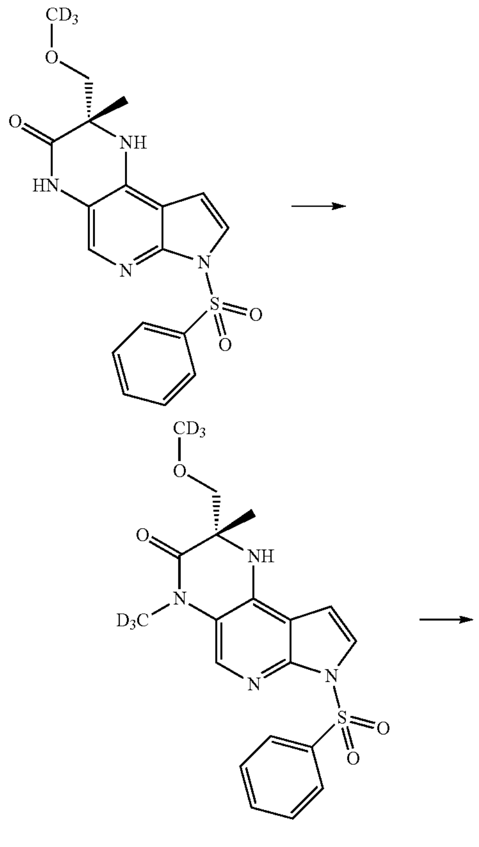

-continued

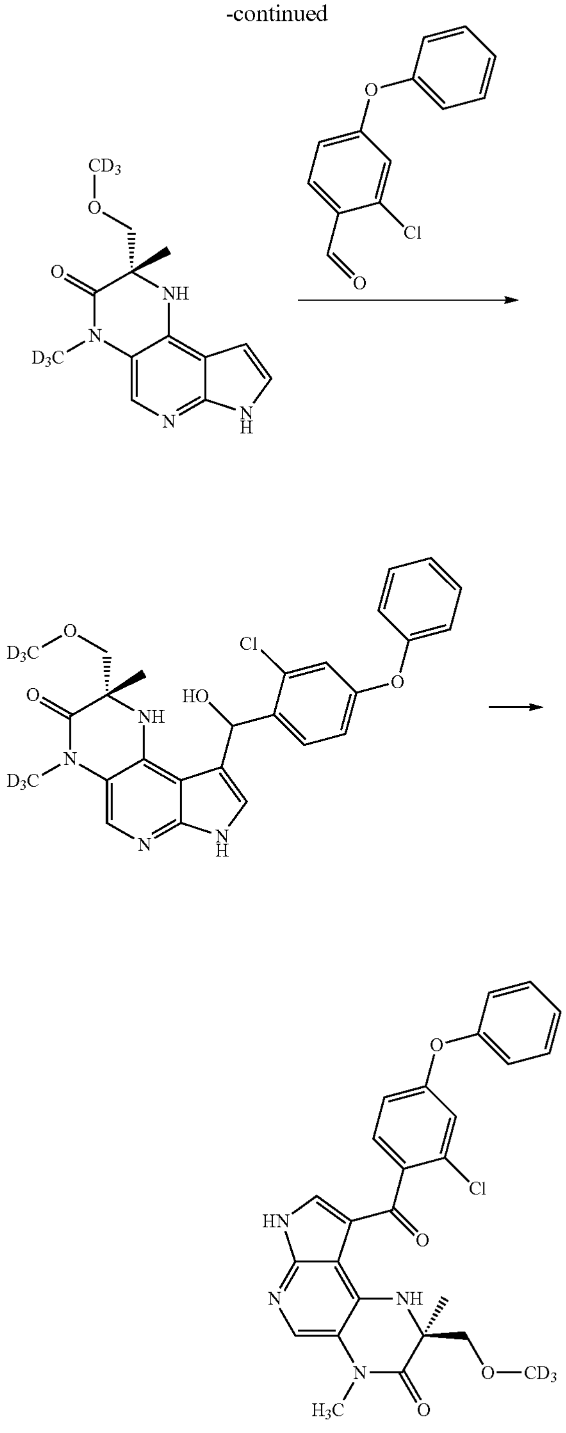

Z193

Step 1: To a sealed tube was added (S)-2-((methoxy-$d_3$)methyl)-2-methyl-7-(phenylsulfonyl)-1,2,4,7-tetrahydro-3H-pyrrolo[3',2':5,6]pyrido[3,4-b]pyrazin-3-one (350 mg, 0.8995 mmol), deuterated iodomethane (1.30 g, 8.995 mmol), potassium carbonate (372 mg, 2.698 mmol) and a mixture of acetone/N,N-dimethylformamide (20 mL/4.0 mL), reacted at 40° C. for 12 hours. The reaction was completed, cooled to room temperature, added with ethyl acetate (1×200 mL) for extraction, washed with saturated brine (3×100 mL), and the organic phase was dried over anhydrous sodium sulfate, filtered, and the solvent was evaporated to dryness by rotary evaporation under reduced pressure to obtain (S)-2-((methoxy-$d_3$)methyl)-2-methyl-4-(methyl-$d_3$)-7-(phenylsulfonyl)-1,2,4,7-tetrahydro-3H-pyrrolo[3',2':5,6]pyrido[3,4-b]pyrazin-3-one (340 mg, yield of 93%). ES-API: $[M+H]^+$=407.2.

Step 2: (S)-2-((Methoxy-$d_3$)methyl)-2-methyl-4-(methyl-$d_3$)-7-(phenylsulfonyl)-1,2,4,7-tetrahydro-3H-pyrrolo[3',2':5,6]pyrido[3,4-b]pyrazin-3-one (340 mg, 0.8370 mmol) was dissolved in 24 mL of methanol, 6 mL of tetrahydrofuran and 4 mL of water, and sodium hydroxide (234 mg, 5.859 mmol) was added thereto, and the reaction was stirred at 65° C. for 16 hours. The reaction was completed, then cooled to room temperature. To the reaction solution was added 20 mL of water and 15 mL of saturated ammonium chloride solution, and the mixture was extracted with 200 mL of ethyl acetate. The organic phase was washed with 30 mL of saturated sodium bicarbonate solution and 80 mL of saturated brine in turn, dried over anhydrous sodium sulfate and then concentrated to obtain (S)-2-((methoxy-$d_3$)methyl)-2-methyl-4-(methyl-$d_3$)-1,2,4,7-tetrahydro-3H-pyrrolo[3',2':5,6]pyrido[3,4-b]pyrazin-3-one (400 mg, crude product) as a pale white solid. ES-API: $[M+H]^+$=267.3.

Step 3: (S)-2-((Methoxy-$d_3$)methyl)-2-methyl-4-(methyl-$d_3$)-1,2,4,7-tetrahydro-3H-pyrrolo[3',2':5,6]pyrido[3,4-b]pyrazin-3-one (400 mg, crude product) and 2-chloro-4-phenoxybenzaldehyde (420 mg, 1.810 mmol) were dissolved in methanol (20.0 mL), and the reaction was cooled to 0° C., and potassium hydroxide (355 mg, 6.34 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried over anhydrous sodium sulfate, and concentrated to obtain (2S)-9-((2-chloro-4-phenoxyphenyl)(hydroxy)methyl)-2-((methoxy-$d_3$)methyl)-2-methyl-4-(methyl-$d_3$)-1,2,4,7-tetrahydro-3H-pyrrolo[3',2':5,6]pyrido[3,4-b]pyrazin-3-one (265 mg, 2-step yield of 63%) as a pale yellow solid. ES-API: $[M+H]^+$=499.3.

Step 4: (2S)-9-((2-Chloro-4-phenoxyphenyl)(hydroxy)methyl)-2-((methoxy-$d_3$)methyl)-2-methyl-4-(methyl-$d_3$)-1,2,4,7-tetrahydro-3H-pyrrolo[3',2':5,6]pyrido[3,4-b]pyrazin-3-one (300 mg, 0.6057 mmol) was dissolved in 20 mL of tetrahydrofuran, and 2,3-dichloro-5,6-dicyano-1,4-benzoquinone (265 mg, 0.5318 mmol) was added thereto, and the reaction was stirred at room temperature for 2 hours. To the reaction solution was added 63 mL of saturated sodium bicarbonate solution, and the mixture was extracted with 88 mL of ethyl acetate. The organic phase was washed with 60 mL of saturated brine, dried over anhydrous sodium sulfate and then concentrated, and the crude product was purified by preparative HPLC to obtain a target product (S)-9-(2-chloro-4-phenoxybenzoyl)-2-((methoxy-$d_3$)methyl)-2-methyl-4-(methyl-$d_3$)-1,2,4,7-tetrahydro-3H-pyrrolo[3',2':5,6]pyrido[3,4-b]pyrazin-3-one (Z193, 102 mg, yield of 38%) as a pale yellow solid. ES-API $[M+H]^+$=497.2. $^1H$ NMR (500 MHz, DMSO-$d_6$) δ 8.53 (s, 1H), 7.94 (s, 1H), 7.65 (s, 1H), 7.56 (d, J=8.4 Hz, 1H), 7.48 (t, J=8.0 Hz, 2H), 7.25 (t, J=7.4 Hz, 1H), 7.18 (dd, J=5.0, 2.6 Hz, 3H), 7.02 (dd, J=8.4, 2.3 Hz, 1H), 3.63 (d, J=9.6 Hz, 1H), 3.50 (d, J=9.6 Hz, 1H), 1.38 (s, 3H).

Embodiment 172: Synthesis of Z194

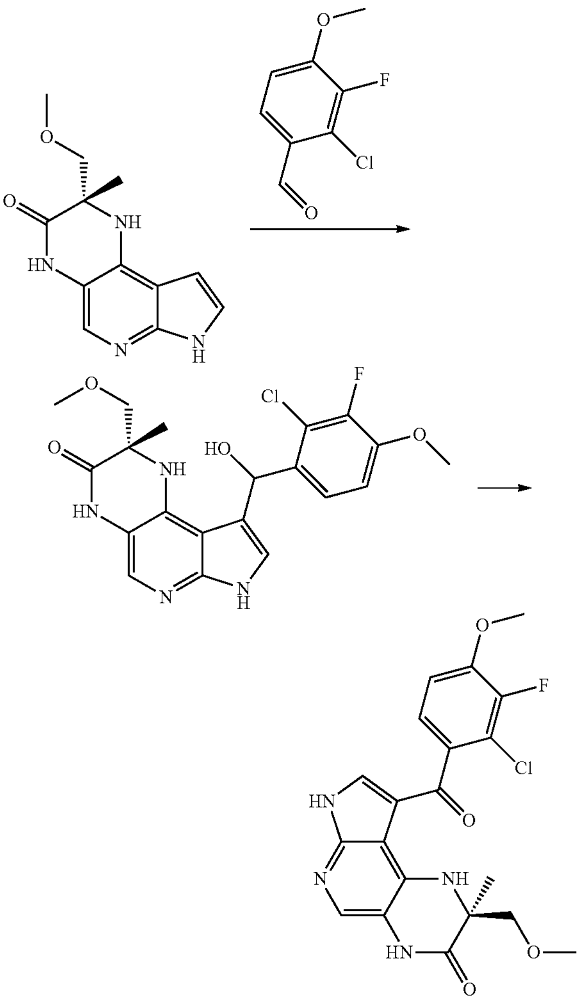

Z194

Step 1: (S)-2-(Methoxymethyl)-2-methyl-1,2,4,7-tetrahydro-3H-pyrrolo[3',2':5,6]pyrido[3,4-b]pyrazin-3-one (160 mg, 0.6501 mmol) and 2-chloro-3-fluoro-4-methoxybenzaldehyde (232 mg, 1.298 mmol) were dissolved in methanol (20.0 mL), and the reaction was cooled to 0° C., and potassium hydroxide (253 mg, 4.517 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried over anhydrous sodium sulfate and concentrated to obtain a crude product (2S)-9-((2-chloro-3-fluoro-4-methoxyphenyl)(hydroxy)methyl)-2-(methoxymethyl)-2-methyl-1,2,4,7-tetrahydro-3H-pyrrolo[3',2':5,6]pyrido[3,4-b]pyrazin-3-one (250 mg, crude product) as a pale yellow solid. ES-API: $[M+H]^+$=435.1.

Step 2: (2S)-9-((2-Chloro-3-fluoro-4-methoxyphenyl)(hydroxy)methyl)-2-(methoxymethyl)-2-methyl-1,2,4,7-tetrahydro-3H-pyrrolo[3',2':5,6]pyrido[3,4-b]pyrazin-3-one (250 mg, crude product) was dissolved in 20 mL of tetrahydrofuran, and 2,3-dichloro-5,6-dicyano-1,4-benzoquinone (295 mg, 1.300 mmol) was added thereto, and the reaction was stirred at room temperature for 2 hours. To the reaction solution was added 63 mL of saturated sodium bicarbonate solution, and the mixture was extracted with 88 mL of ethyl acetate. The organic phase was washed with 60 mL of saturated brine, dried over anhydrous sodium sulfate and then concentrated, and the crude product was purified by preparative HPLC to obtain a target product (S)-9-(2-chloro-3-fluoro-4-methoxybenzoyl)-2-(methoxymethyl)-2-methyl-1,2,4,7-tetrahydro-3H-pyrrolo[3',2':5,6]pyrido[3,4-b]pyrazin-3-one (Z194, 70.9 mg, 2-step yield of 25%) as a pale yellow solid. ES-API: $[M+H]^+$=433.1. $^1$H NMR (500 MHz, DMSO-$d_6$) δ 8.24 (s, 1H), 7.69 (s, 1H), 7.60 (s, 1H), 7.38 (dd, J=8.5, 1.4 Hz, 1H), 7.26 (t, J=8.2 Hz, 1H), 3.95 (s, 3H), 3.64 (d, J=9.5 Hz, 1H), 3.47 (d, J=9.6 Hz, 1H), 3.29 (s, 4H), 1.39 (s, 3H).

Embodiment 173: Synthesis of Z195

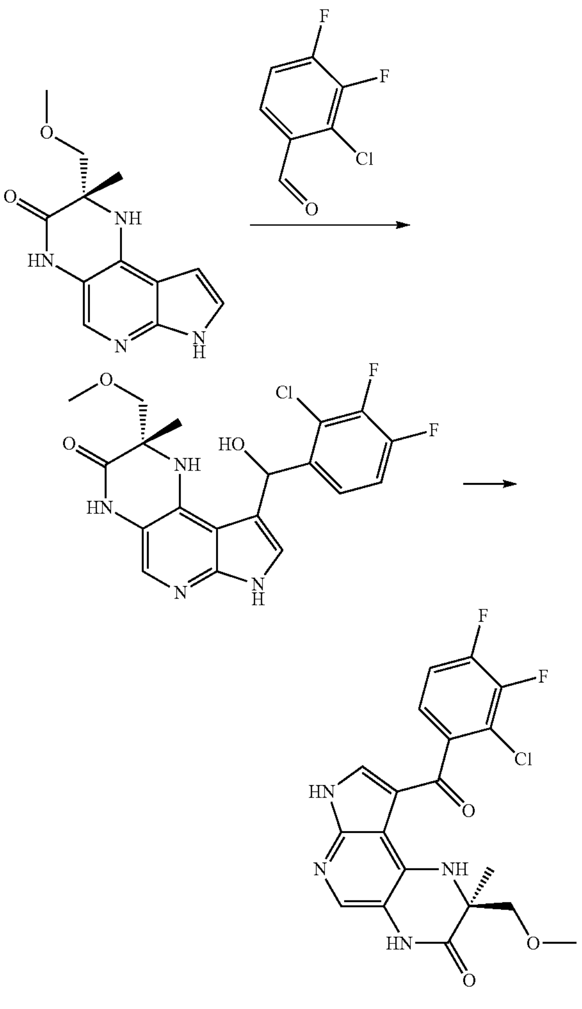

Z195

Step 1: (S)-2-(Methoxymethyl)-2-methyl-1,2,4,7-tetrahydro-3H-pyrrolo[3',2':5,6]pyrido[3,4-b]pyrazin-3-one (160 mg, 0.6501 mmol) and 2-chloro-3,4-difluorobenzaldehyde (232 mg, 1.298 mmol) were dissolved in methanol (20.0 mL), and the reaction was cooled to 0° C., and potassium hydroxide (253 mg, 4.517 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried over anhydrous sodium sulfate, and concentrated to obtain (2S)-9-((2-chloro-3,4-difluorophenyl)(hydroxy)methyl)-2-(methoxymethyl)-2-methyl-1,2,4,7-tetrahydro-3H-pyrrolo[3',2':5,6]pyrido[3,4-b]pyrazin-3-one (250 mg, crude product) as a pale yellow solid. ES-API: $[M+H]^+$=423.1.

Step 2: (2S)-9-((2-Chloro-3,4-difluorophenyl)(hydroxy)methyl)-2-(methoxymethyl)-2-methyl-1,2,4,7-tetrahydro-3H-pyrrolo[3',2':5,6]pyrido[3,4-b]pyrazin-3-one (120 mg, crude product) was dissolved in 15.0 mL of tetrahydrofuran, and 2,3-dichloro-5,6-dicyano-1,4-benzoquinone (230 mg, 1.013 mmol) was added thereto, and the reaction was stirred at room temperature for 2 hours. To the reaction solution was added 63 mL of saturated sodium bicarbonate solution, and the mixture was extracted with 88 mL of ethyl acetate. The organic phase was washed with 60 mL of saturated brine, dried over anhydrous sodium sulfate and then concentrated, and the crude product was purified by preparative HPLC to obtain a target product (S)-9-(2-chloro-3,4-difluorobenzoyl)-2-(methoxymethyl)-2-methyl-1,2,4,7-tetrahydro-3H-pyrrolo[3',2':5,6]pyrido[3,4-b]pyrazin-3-one (Z195, 42 mg, 2-step yield of 35%) as a pale yellow solid. ES-API: $[M+H]^+$=421.1.1. $^1$H NMR (500 MHz, DMSO-$d_6$) δ 12.53 (s, 1H), 10.49 (s, 1H), 8.18 (s, 1H), 7.70 (d, J=3.4 Hz, 2H), 7.58 (dd, J=17.2, 8.7 Hz, 1H), 7.50-7.36 (m, 1H), 3.65 (d, J=9.5 Hz, 1H), 3.48 (d, J=9.6 Hz, 1H), 3.30 (s, 3H), 1.38 (s, 3H).

Embodiment 174: Synthesis of Z103

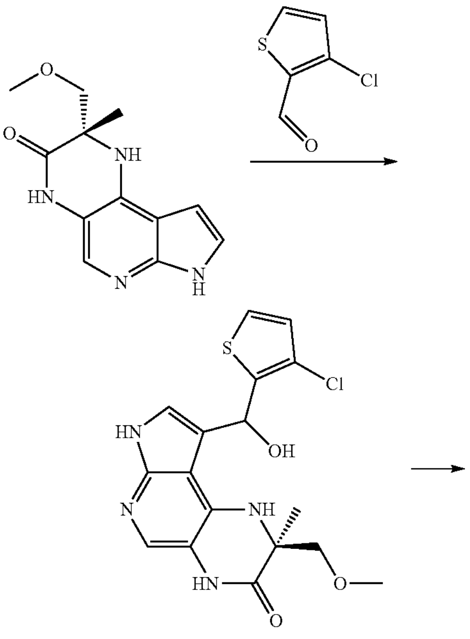

-continued

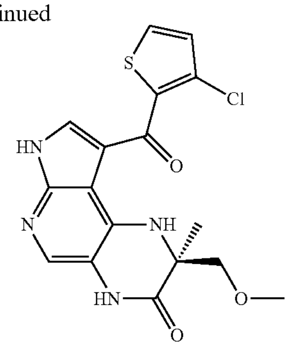

Z103

Step 1: (S)-2-(Methoxymethyl)-2-methyl-1,2,4,7-tetrahydro-3H-pyrrolo[3',2':5,6]pyrido[3,4-b]pyrazin-3-one (50 mg, 0.2 mmol) and 3-chlorothiophene-2-carbaldehyde (88 mg, 0.6 mmol) were dissolved in methanol (10 mL), and the reaction was cooled to 0° C., and potassium hydroxide (56 mg, 1 mmol) was added thereto. The reaction was stirred at room temperature for 16 hours. The reaction solution was poured into 30 mL of water, and the pH of the reaction solution was adjusted to 8 with 1.0 M dilute hydrochloric acid, and the reaction solution was extracted with 50 mL of ethyl acetate. The organic phase was washed with 25 mL of saturated brine, dried over anhydrous sodium sulfate and concentrated, and the crude product was purified by a thin-layer preparative plate (dichloromethane/7M ammonia methanol=100:8) to obtain (2S)-9-((3-chlorothiophen-2-yl)(hydroxy)methyl)-2-(methoxymethyl)-2-methyl-1,2,4,7-tetrahydro-3H-pyrrolo[3',2':5,6]pyrido[3,4-b]pyrazin-3-one (49 mg, yield of 61%) as a pale yellow solid. ES-API: $[M+H]^+$=393.1.

Step 2: (2S)-9-((3-chlorothiophen-2-yl)(hydroxy)methyl)-2-(methoxymethyl)-2-methyl-1,2,4,7-tetrahydro-3H-pyrrolo[3',2':5,6]pyrido[3,4-b]pyrazin-3-one (49 mg, 0.125 mmol) was dissolved in 10 mL of tetrahydrofuran and 2 mL of water, and 2,3-dichloro-5,6-dicyano-p-benzoquinone (57 mg, 0.25 mmol) was added thereto, and the reaction was stirred at room temperature for 1 hour. To the reaction solution was added 20 mL of saturated sodium thiosulfate solution, and the mixture was extracted with 60 mL of ethyl acetate. The organic phase was washed twice with 20 mL of saturated sodium bicarbonate solution and 15 mL of saturated brine in turn, dried over anhydrous sodium sulfate and concentrated, and the crude product was purified by preparative HPLC (column model: xbridge C18 19*150 mm, 5 μm; system: 10 mmol/L, aqueous $NH_4HCO_3$ solution; flow rate: 15 mL/min; gradient: 20 to 45% $CH_3CN$—$NH_4HCO_3$; column temperature: room temperature) to obtain a target product (S)-9-(3-chlorothiophene-2-carbonyl)-2-(methoxymethyl)-2-methyl-1,2,4,7-tetrahydro-3H-pyrrolo[3',2':5,6]pyrido[3,4-b]pyrazin-3-one (Z103, 28 mg, yield of 57%) as a pale yellow solid. ES-API: $[M+H]^+$=v391.1.

Embodiment 175: Synthesis of Z196

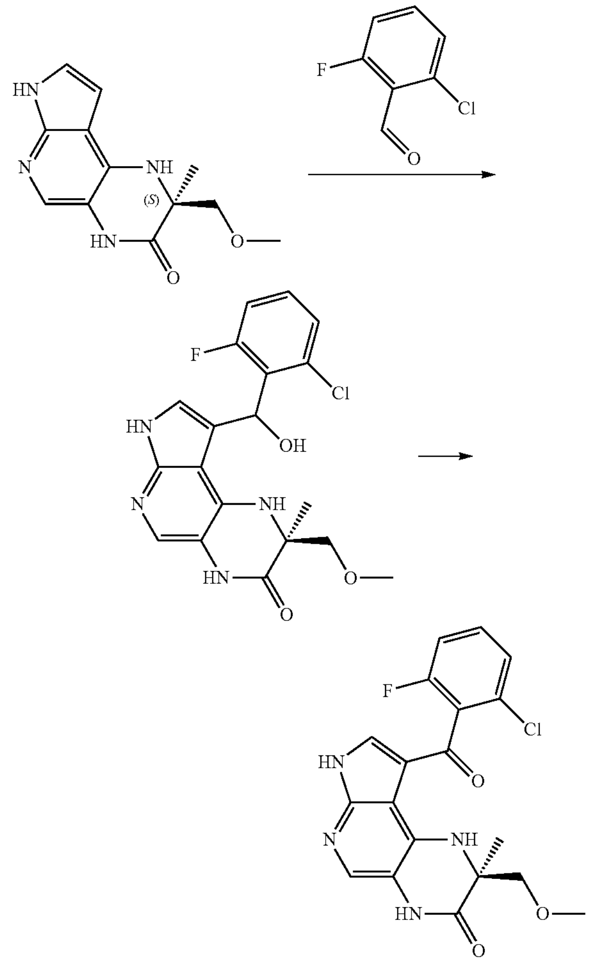

Z196

Step 1: (S)-2-(Methoxymethyl)-2-methyl-1,2,4,7-tetrahydro-3H-pyrrolo[3',2':5,6]pyrido[3,4-b]pyrazin-3-one (20 mg, 0.081 mmol) and 2-chloro-6-fluorobenzaldehyde (26 mg, 0.162 mmol) were dissolved in methanol (5 mL), and the reaction solution was cooled to 0° C., and potassium hydroxide (32 mg, 0.567 mmol) was added thereto. The reaction was stirred at room temperature for 24 hours. LCMS detected that the reaction was complete. The reaction was quenched by adding 20 mL of saturated ammonium chloride solution, extracted with ethyl acetate (15 mL×3). The organic phase was washed with 20 mL of saturated brine, dried over anhydrous sodium sulfate and then concentrated to obtain a crude product (2S)-9-((2-chloro-6-fluorophenyl)(hydroxy)methyl)-2-(methoxymethyl)-2-methyl-1,2,4,7-tetrahydro-3H-pyrrolo[3',2':5,6]pyrido[3,4-b]pyrazin-3-one (32 mg, yield of 100%). ES-API: $[M+H]^+$=405.1.

Step 2: The above crude product (2S)-9-((2-chloro-6-fluorophenyl)(hydroxy)methyl)-2-(methoxymethyl)-2-methyl-1,2,4,7-tetrahydro-3H-pyrrolo[3',2':5,6]pyrido[3,4-b]pyrazin-3-one (32 mg, 0.081 mmol) was dissolved in 5 mL of tetrahydrofuran, and 2,3-dichloro-5,6-dicyano-p-benzoquinone (32 mg, 0.141 mmol) was added thereto, and the reaction was stirred at room temperature for 2 hours. To the reaction solution was added 20 mL of saturated sodium thiosulfate solution and 20 mL of saturated sodium bicarbonate solution, and the mixture was extracted with 30 mL of ethyl acetate. The organic phase was washed with 15 mL of saturated brine, dried over anhydrous sodium sulfate and concentrated, and the crude product was purified by preparative HPLC (column model: xbridge C18 19*150 mm, 5 μm; system: 10 mmol/L, aqueous $NH_4HCO_3$ solution; flow rate: 15 mL/min; gradient: 20 to 45% $CH_3CN—NH_4HCO_3$; column temperature: room temperature) to obtain an off-white solid (S)-9-(2-chloro-6-fluorobenzoyl)-2-(methoxymethyl)-2-methyl-1,2,4,7-tetrahydro-3H-pyrrolo[3',2':5,6]pyrido[3,4-b]pyrazin-3-one (Z196, 3.02 mg, yield of 9%). ES-API: $[M+H]^+=403.1$. $^1H$ NMR (500 MHz, DMSO) δ 12.58 (bs, 1H), 10.50 (s, 1H), 8.11 (s, 1H), 7.70 (d, J=9.5 Hz, 2H), 7.60-7.56 (m, 1H), 7.46 (d, J=8.0 Hz, 1H), 7.41-7.37 (m, 1H), 3.64 (d, J=9.5 Hz, 1H), 3.47 (d, J=9.0 Hz, 1H), 3.32 (s, 3H), 1.39 (d, J=3.0 Hz, 3H).

Embodiment 176: Synthesis of Z197

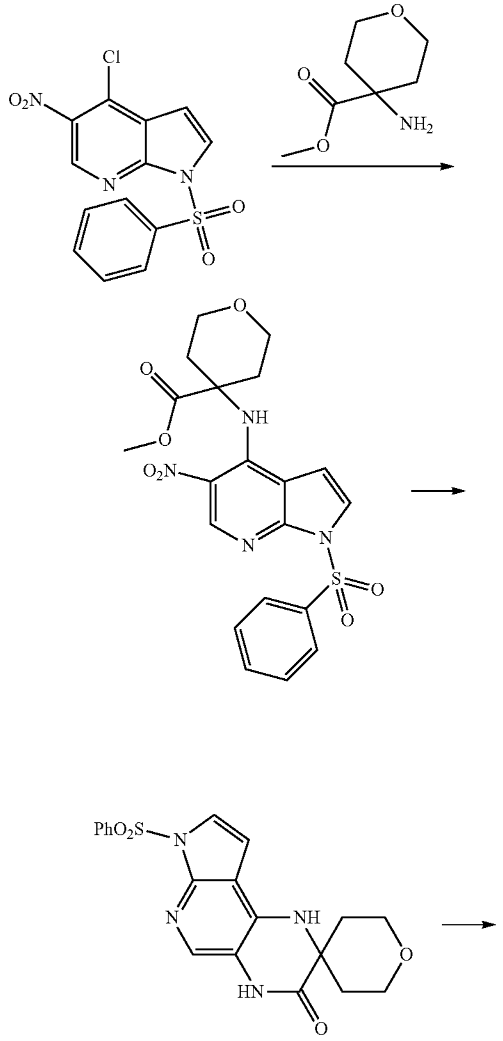

-continued

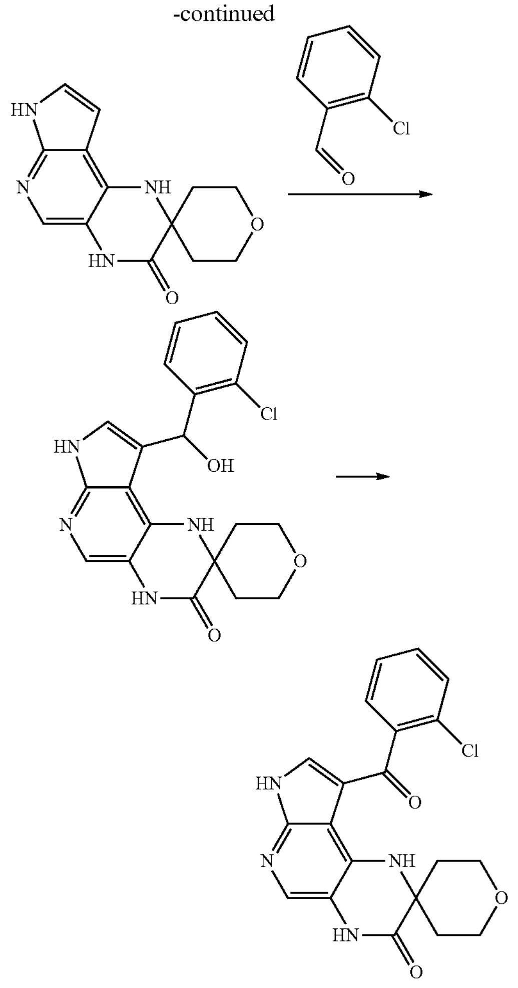

Z197

Step 1: 4-Chloro-5-nitro-1-(phenylsulfonyl)-1H-pyrrolo[2,3-b]pyridine (1.60 g, 4.7477 mmol) and methyl 4-aminotetrahydro-2H-pyran-4-carboxylate (0.5 g, 3.141 mmol) were dissolved in N,N-dimethylacetamide (30 mL), and N,N-diisopropylethylamine (2.35 g, 18.18 mmol) was added thereto, and the reaction was stirred at 115° C. for 12 hours. The reaction solution was added with 100 mL of ethyl acetate, washed with water (2×60 mL), washed with saturated brine (3×30 mL), dried over anhydrous sodium sulfate and concentrated, and the crude product was purified by a flash silica gel column (ethyl acetate/petroleum ether: 0-50%) to obtain methyl 4-((5-nitro-1-(phenylsulfonyl)-1H-pyrrolo[2,3-b]pyridin-4-yl)amino)tetrahydro-2H-pyran-4-carboxylate (560 mg, yield of 38%) as a pale yellow solid. ES-API: $[M+H]^+=461.2$.

Step 2: Methyl 4-((5-nitro-1-(phenylsulfonyl)-1H-pyrrolo[2,3-b]pyridin-4-yl)amino)tetrahydro-2H-pyran-4-carboxylate (560 mg, 1.217 mmol) was dissolved in acetic acid (20 mL), and iron powder (1.36 g, 24.34 mmol) was added thereto. The mixture was gradually heated to 80° C. and stirred for 1 hour. After the reaction was completed, the solvent was evaporated to dryness by rotary evaporation under reduced pressure, then the residue was added with 200 mL of ethyl acetate, washed with water (2×80 mL), saturated sodium carbonate (2×60 mL), saturated brine (2×80 mL) in turn. The organic phase was dried over anhydrous sodium sulfate, concentrated, and the crude product was slurried with ethyl acetate (20 mL) to obtain 7'-(phenylsulfonyl)-2,3,4',5,6,7'-hexahydrospiro[pyran-4,2'-pyrrolo[3',2':5,6]pyrido[3,4-b]pyrazin]-3'(1'H)-one (336 mg, yield of 69%) as a yellow solid. ES-API: $[M+H]^+$=399.1.

Step 3: 7'-(Phenylsulfonyl)-2,3,4',5,6,7'-hexahydrospiro[pyran-4,2'-pyrrolo[3',2':5,6]pyrido[3,4-b]pyrazin]-3'(1'H)-one (336.0 mg, 0.844 mmol) was dissolved in 15 mL of methanol, 4 mL of tetrahydrofuran and 3 mL of water, and sodium hydroxide (236.0 mg, 5.908 mmol) was added thereto, and the reaction was stirred at 65° C. for 12 hours. To the reaction solution was added 20 mL of water and 15 mL of saturated ammonium chloride solution, and the mixture was extracted with 150 mL of ethyl acetate. The organic phase was washed with 30 mL of saturated sodium bicarbonate solution and 80 mL of saturated brine in turn, dried over anhydrous sodium sulfate and then concentrated to obtain 2,3,4',5,6,7'-hexahydrospiro[pyran-4,2'-pyrrolo[3',2':5,6]pyrido[3,4-b]pyrazin]-3'(1'H)-one (358 mg, crude product) as a pale white solid. ES-API: $[M+H]^+$=259.1.

Step 4: 2,3,4',5,6,7'-Hexahydrospiro[pyran-4,2'-pyrrolo[3',2':5,6]pyrido[3,4-b]pyrazin]-3'(1'H)-one (358.0 mg, crude product) and 2-chlorobenzaldehyde (240.0 mg, 1.707 mmol) were dissolved in methanol (15.0 mL), and the reaction was cooled to 0° C., and potassium hydroxide (331.0 mg, 5.909 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried and concentrated to obtain 9'-((2-chlorophenyl)(hydroxy)methyl)-2,3,4',5,6,7'-hexahydrospiro[pyran-4,2'-pyrrolo[3',2':5,6]pyrido[3,4-b]pyrazin]-3'(1'H)-one (150 mg, 2-step yield of 44%) as a pale yellow solid. ES-API: $[M+H]^+$=399.1.

Step 5: 9'-((2-Chlorophenyl)(hydroxy)methyl)-2,3,4',5,6,7'-hexahydrospiro[pyran-4,2'-pyrrolo[3',2':5,6]pyrido[3,4-b]pyrazin]-3'(1'H)-one (150 mg, 0.3768 mmol) was dissolved in 15.0 mL of tetrahydrofuran, and 2,3-dichloro-5,6-dicyano-1,4-benzoquinone (171.0 mg, 0.7533 mmol) was added thereto, and the reaction was stirred at room temperature for 2 hours. To the reaction solution was added 60 mL of saturated sodium bicarbonate solution, and the mixture was extracted with 80 mL of ethyl acetate. The organic phase was washed with 60 mL of saturated brine, dried over anhydrous sodium sulfate and then concentrated, and the crude product was purified by preparative HPLC to obtain 9'-(2-chlorobenzoyl)-2,3,4',5,6,7'-hexahydrospiro[pyran-4,2'-pyrrolo[3',2':5,6]pyrido[3,4-b]pyrazin]-3'(1'H)-one (Z197, 44 mg, yield of 29%) as a pale yellow solid, ES-API: $[M+H]^+$=397.1. $^1H$ NMR (500 MHz, DMSO-$d_6$) δ 12.58 (s, 1H), 10.54 (s, 1H), 8.86 (s, 1H), 7.79 (s, 1H), 7.65-7.53 (m, 4H), 7.48 (td, J=7.4, 1.1 Hz, 1H), 3.96-3.81 (m, 2H), 3.75 (dd, J=11.9, 10.3 Hz, 2H), 2.16-2.02 (m, 2H), 1.62 (d, J=12.4 Hz, 2H).

Embodiment 177: Synthesis of Z198

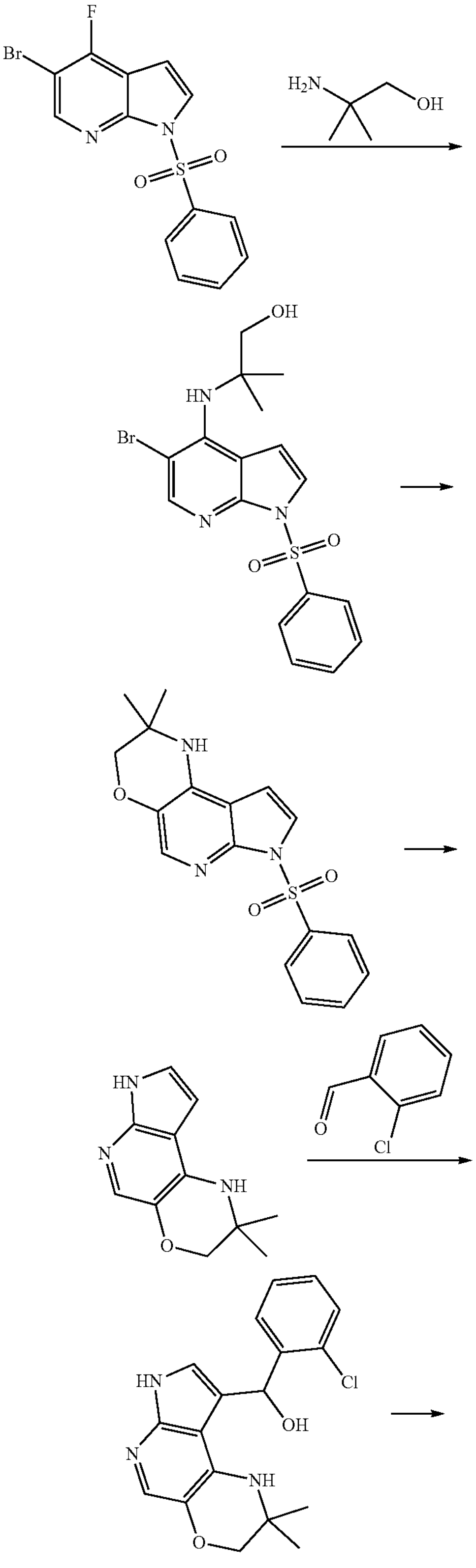

-continued

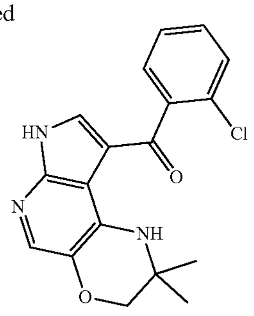

Z198

Step 1: To a 20 mL microwave tube was added 5-bromo-4-fluoro-1-(phenylsulfonyl)-1H-pyrrolo[2,3-b]pyridine (500 mg, 1.41 mmol), 2-amino-2-methylpropan-1-ol (376 mg, 4.23 mmol), N,N-dimethylacetamide (8 mL) and N,N-diisopropylethylamine (364 mg, 2.82 mmol), reacted in a microwave reactor at 150° C. for 2 hours. The reaction solution was added with ethyl acetate (80 mL), washed with dilute brine (30 mL×3), washed with saturated brine (30 mL), dried over anhydrous sodium sulfate and concentrated, and the crude product was purified by a thin-layer chromatography preparative plate (dichloromethane/methanol=30:1) to obtain a target product 2-((5-bromo-1-(phenylsulfonyl)-1H-pyrrolo[2,3-b]pyridin-4-yl)amino)-2-methylpropan-1-ol (280 mg, yield of 46%) as an off-white solid. ES-API: $[M+H]^+$-424.1, 426.1.

Step 2: To a 5 mL microwave tube was added 2-((5-bromo-1-(phenylsulfonyl)-1H-pyrrolo[2,3-b]pyridin-4-yl)amino)-2-methylpropan-1-ol (140 mg, 0.33 mmol), palladium acetate (8 mg, 0.033 mmol), 2-(di-tert-butylphosphino)-1,1'-binaphthyl (20 mg, 0.05 mmol), cesium carbonate (162 mg, 0.50 mmol) and toluene (4 mL), and the mixture was blown with nitrogen for 2 minutes and reacted at 115° C. for 1 hour in a microwave reactor. The reaction solution was filtered, washed with dichloromethane, and the filtrate was concentrated, and the crude product was purified by a flash silica gel column (ethyl acetate/petroleum ether: 0-40%) to obtain 2,2-dimethyl-7-(phenylsulfonyl)-1,2,3,7-tetrahydropyrrolo[3',2':5,6]pyrido[3,4-b][1,4]oxazine (95 mg, yield of 83%) as an off-white solid. ES-API: $[M+H]^+$=344.2

Step 3: 2,2-Dimethyl-7-(phenylsulfonyl)-1,2,3,7-tetrahydropyrrolo[3',2':5,6]pyrido[3,4-b][1,4]oxazine (190 mg, 0.55 mmol) was dissolved in methanol (8 mL), tetrahydrofuran (2 mL) and water (2 mL), and sodium hydroxide (88 mg, 2.2 mmol) was added thereto, and the reaction was stirred at 65° C. for 18 hours. The pH of the reaction solution was adjusted to 8 with 1.0 M dilute hydrochloric acid, and the reaction solution was added with ethyl acetate (80 mL), washed with saturated sodium bicarbonate solution (25 mL×2) and saturated brine (25 mL) in turn, dried over anhydrous sodium sulfate and concentrated to obtain 2,2-dimethyl-1,2,3,7-tetrahydropyrrolo[3',2':5,6]pyrido[3,4-b][1,4]oxazine (113 mg, yield of 100%) as a pale yellow solid. ES-API: $[M+H]^+$=204.1.

Step 4: 2,2-Dimethyl-1,2,3,7-tetrahydropyrrolo[3',2':5,6]pyrido[3,4-b][1,4]oxazine (107 mg, 0.53 mmol) and 2-chlorobenzaldehyde (223 mg, 1.59 mmol) were dissolved in methanol (8 mL), and the reaction was cooled to 0° C., and potassium hydroxide (208 mg, 3.71 mmol) was added thereto. The reaction was stirred at room temperature for 16 hours. The pH of the reaction solution was adjusted to 8 with 1.0 M dilute hydrochloric acid, and the reaction solution was extracted with ethyl acetate (80 mL). The organic phase was washed with saturated brine (30 mL), dried over anhydrous sodium sulfate and concentrated, and the crude product was purified by a flash silica gel column (methanol/dichloromethane: 0-5%) to obtain (2-chlorophenyl)(2,2-dimethyl-1,2,3,7-tetrahydropyrrolo[3',2':5,6]pyrido[3,4-b][1,4]oxazin-9-yl)methanol (160 mg, yield of 88%) as an off-white solid. ES-API: $[M+H]^+$=344.2.

Step 5: (2-Chlorophenyl)(2,2-dimethyl-1,2,3,7-tetrahydropyrrolo[3',2':5,6]pyrido[3,4-b][1,4]oxazin-9-yl)methanol (160 mg, 0.47 mmol) was dissolved in 1,4-dioxane (7 mL) and water (0.7 mL), and 2,3-dichloro-5,6-dicyano-p-benzoquinone (160 mg, 0.70 mmol) was added thereto at room temperature, and the reaction was stirred at room temperature for 1 hour. To the reaction solution was added 5 mL of saturated sodium thiosulfate solution (6 mL) and saturated sodium bicarbonate solution (6 mL), and the mixture was extracted with ethyl acetate (70 mL). The organic phase was washed with saturated sodium bicarbonate solution (20 mL×2) and saturated brine (20 mL) in turn, dried over anhydrous sodium sulfate and concentrated, and the crude product was purified by preparative HPLC to obtain a target product (2-chlorophenyl)(2,2-dimethyl-1,2,3,7-tetrahydropyrrolo[3',2':5,6]pyrido[3,4-b][1,4]oxazin-9-yl)methanone (Z198, 75 mg, yield of 47%) as a pale yellow solid. $^1H$ NMR (500 MHz, DMSO-$d_6$) δ12.33 (s, 1H), 8.07 (s, 1H), 7.73 (s, 1H), 7.60-7.55 (m, 1H), 7.55-7.49 (m, 2H), 7.48-7.42 (m, 1H), 7.35 (s, 1H), 3.83 (s, 2H), 1.29 (s, 6H). ES-API: $[M+H]^+$=341.1.

Embodiment 178: Synthesis of Z199

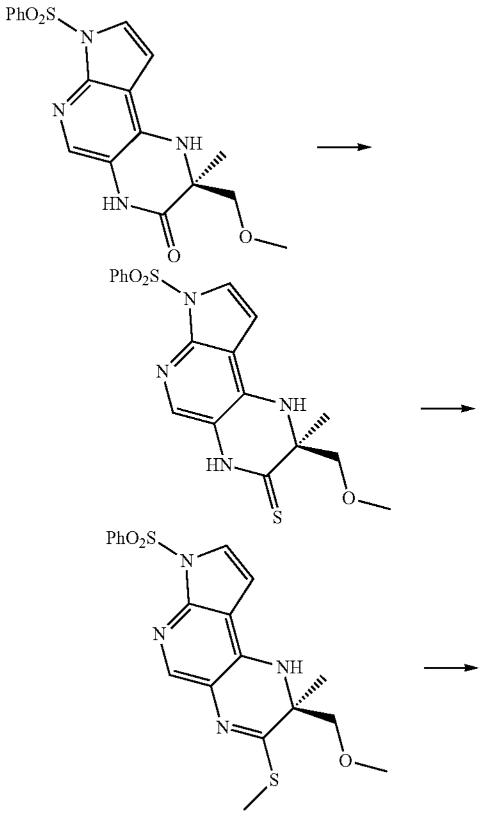

-continued

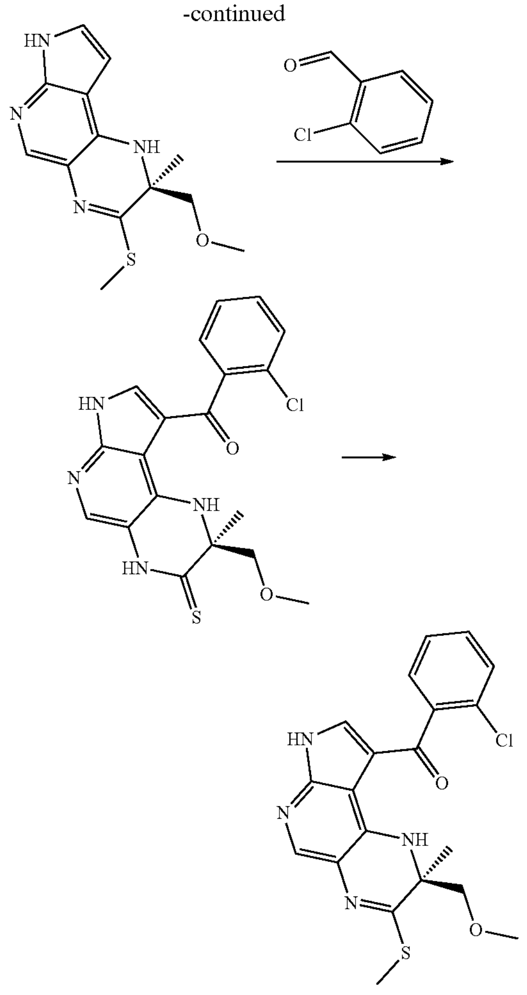

Z199

Step 1: To a solution of (S)-2-(methoxymethyl)-2-methyl-7-(phenylsulfonyl)-1,2,4,7-tetrahydro-3H-pyrrolo[3',2':5,6]pyrido[3,4-b]pyrazin-3-one (500 mg, 1.298 mmol) in toluene (20 mL) was added Lawesson's reagent (577.5 mg, 1.427 mmol), and reacted at 90° C. for 3 hours under nitrogen atmosphere. After the reaction was completed, the solvent was evaporated to dryness by rotary evaporation under reduced pressure, and the crude product was purified by a silica gel column [petroleum ether:ethyl acetate=100:0 to 20:80 (v/v)] to obtain a target compound (S)-2-(methoxymethyl)-2-methyl-7-(phenylsulfonyl)-1,2,4,7-tetrahydro-3H-pyrrolo[3',2':5,6]pyrido[3,4-b]pyrazine-3-thione (283 mg, yield of 54%). $[M+H]^+$=403.1.

Step 2: To a solution of (S)-2-(methoxymethyl)-2-methyl-7-(phenylsulfonyl)-1,2,4,7-tetrahydro-3H-pyrrolo[3',2':5,6]pyrido[3,4-b]pyrazine-3-thione (50 mg, 0.1243 mmol) in N,N-dimethylformamide (0.5 mL) was added iodomethane (20 mg, 0.1408 mmol) and sodium carbonate (20 mg, 0.1886 mmol), reacted for 1 hour at room temperature. The reaction was completed, cooled to room temperature, extracted by adding ethyl acetate (1×80 mL), washed with saturated brine (3×30 mL), and the organic phase was dried over anhydrous sodium sulfate, filtered, and the solvent evaporated to dryness by rotary evaporation under reduced pressure, and the crude product was purified by a silica gel column [petroleum ether:ethyl acetate=100:0 to 20:80 (v/v)] to obtain a target compound (S)-2-(methoxymethyl)-2-methyl-3-(methylthio)-7-(phenylsulfonyl)-2,7-dihydro-1H-pyrrolo[3',2':5,6]pyrido[3,4-b]pyrazine (48 mg, yield of 93%). ES-API: $[M+H]^+$=417.1.

Step 3: (S)-2-(Methoxymethyl)-2-methyl-3-(methylthio)-7-(phenylsulfonyl)-2,7-dihydro-1H-pyrrolo[3',2':5,6]pyrido[3,4-b]pyrazine (210 mg, 0.5047 mmol) was dissolved in 18 mL of methanol, 5.0 mL of tetrahydrofuran and 3.0 mL of water, and sodium hydroxide (141.0 mg, 3.533 mmol) was added thereto, and the reaction was stirred at 65° C. for 16 hours. The reaction was completed, then cooled to room temperature. To the reaction solution was added 20 mL of water and 15 mL of saturated ammonium chloride solution, and the mixture was extracted with 200 mL of ethyl acetate. The organic phase was washed with 30 mL of saturated sodium bicarbonate solution and 80 mL of saturated brine in turn, dried over anhydrous sodium sulfate and then concentrated to obtain (S)-2-(methoxymethyl)-2-methyl-3-(methylthio)-2,7-dihydro-1H-pyrrolo[3',2':5,6]pyrido[3,4-b]pyrazine (264.0 g, crude product) as a pale white solid. ES-API: $[M+H]^+$=277.1.

Step 4: (S)-2-(Methoxymethyl)-2-methyl-3-(methylthio)-2,7-dihydro-1H-pyrrolo[3',2':5,6]pyrido[3,4-b]pyrazine (264.0 g, crude product) and 2-benzaldehyde (141.3 mg, 1.010 mmol) were dissolved in methanol (20.0 mL), and the reaction was cooled to 0° C., and potassium hydroxide (198 mg, 3.530 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried over anhydrous sodium sulfate, and concentrated to obtain a crude product (2S)-9-((2-chlorophenyl)(hydroxy)methyl)-2-(methoxymethyl)-2-methyl-1,2,4,7-tetrahydro-3H-pyrrolo[3',2':5,6]pyrido[3,4-b]pyrazine-3-thione (180 mg, 2-step yield of 85%) as a pale yellow solid. ES-API: $[M+H]^+$=417.1.

Step 5: (2S)-9-((2-Chlorophenyl)(hydroxy)methyl)-2-(methoxymethyl)-2-methyl-1,2,4,7-tetrahydro-3H-pyrrolo[3',2':5,6]pyrido[3,4-b]pyrazine-3-thione (180 mg, 0.4326 mmol) was dissolved in 12 mL of tetrahydrofuran, and 2,3-dichloro-5,6-dicyano-1,4-benzoquinone (196 mg, 0.8652 mmol) was added thereto, and the reaction was stirred at room temperature for 2 hours. To the reaction solution was added 63 mL of saturated sodium bicarbonate solution, and the mixture was extracted with 88 mL of ethyl acetate. The organic phase was washed with 60 mL of saturated brine, dried over anhydrous sodium sulfate and then concentrated, and the crude product was purified by preparative HPLC to obtain a target product (S)-(2-chlorophenyl)(2-(methoxymethyl)-2-methyl-3-(methylthio)-2,7-dihydro-1H-pyrrolo[3',2':5,6]pyrido[3,4-b]pyrazin-9-yl)methanone (Z199, 47 mg, yield of 26%) as a pale yellow solid. ES-API: $[M+H]^+$=415.1. $^1H$ NMR (500 MHz, DMSO-$d_6$) δ 10.59 (s, 1H), 8.30 (s, 1H), 7.95 (s, 1H), 7.56 (dt, J=26.2, 7.2 Hz, 3H), 7.51-7.33 (m, 2H), 3.59 (d, J=9.8 Hz, 1H), 3.48 (d, J=9.8 Hz, 1H), 3.30 (s, 3H), 2.44 (s, 3H), 1.48 (s, 3H).

Embodiment 179: Synthesis of Z200

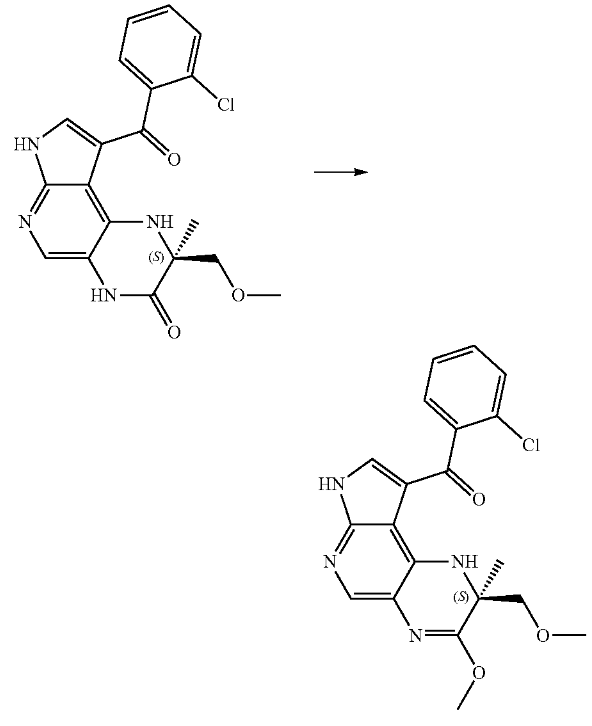

Z200

Step 1: (S)-9-(2-Chlorobenzoyl)-2-(methoxymethyl)-2-methyl-1,2,4,7-tetrahydro-3H-pyrrolo[3',2':5,6]pyrido[3,4-b]pyrazin-3-one (100 mg, 0.26 mmol) was dissolved in dichloromethane (25 mL), and trimethyloxonium tetrafluoroborate (115 mg, 0.78 mmol) was added thereto, and the reaction was stirred at room temperature for 18 hours. The reaction solution was added with saturated sodium bicarbonate (15 mL) and extracted with dichloromethane (30 mL). The organic layer was washed with saturated brine (15 mL), dried over anhydrous sodium sulfate and concentrated, and the crude product was purified by preparative HPLC to obtain a target product (S)-(2-chlorophenyl)(3-methoxy-2-(methoxymethyl)-2-methyl-2,7-dihydro-1H-pyrrolo[3',2':5,6]pyrido[3,4-b]pyrazin-9-yl)methanone (Z200, 40 mg, yield of 38%) as a yellow solid. $^1$H NMR (500 MHz, DMSO-$d_6$) δ 12.40 (s, 1H), 8.35 (s, 1H), 7.80 (s, 1H), 7.60-7.56 (m, 1H), 7.55-7.51 (m, 2H), 7.49-7.43 (m, 1H), 7.41 (s, 1H), 3.82 (s, 3H), 3.64 (d, J=10.0 Hz, 1H), 3.42 (d, J=10.0 Hz, 1H), 3.30 (s, 3H), 1.42 (s, 3H). ES-API: $[M+H]^+$=399.1.

Embodiment 180: Synthesis of Z201

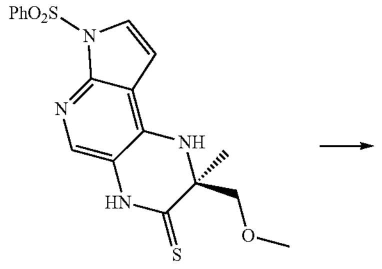

-continued

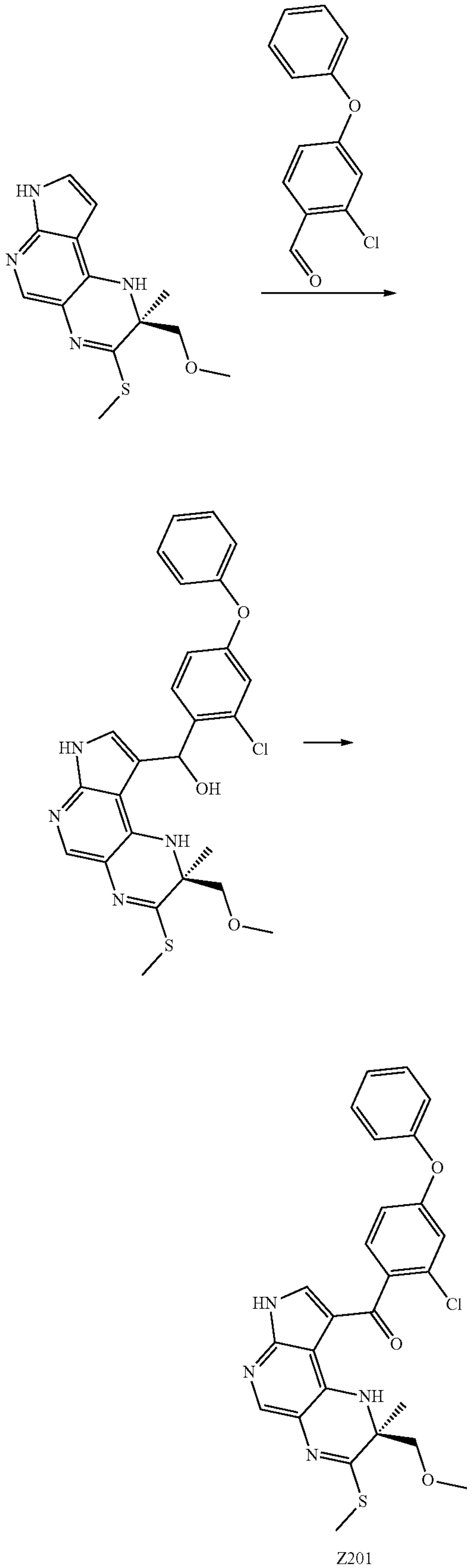

Z201

Step 1: (S)-2-(Methoxymethyl)-2-methyl-7-(phenylsulfonyl)-1,2,4,7-tetrahydro-3H-pyrrolo[3',2':5,6]pyrido[3,4-b]pyrazine-3-thione (280 mg, 0.6965 mmol) was dissolved in 15 mL of methanol, 5 mL of tetrahydrofuran and 3.0 mL of water, and sodium hydroxide (195.0 mg, 4.875 mmol) was added thereto, and the reaction was stirred at 65° C. for 16 hours. The reaction was completed, then cooled to room temperature. To the reaction solution was added 20 mL of water and 15 mL of saturated ammonium chloride solution, and the mixture was extracted with 200 mL of ethyl acetate. The organic phase was washed with 30 mL of saturated sodium bicarbonate solution and 80 mL of saturated brine in turn, dried over anhydrous sodium sulfate and then concentrated to obtain (S)-2-(methoxymethyl)-2-methyl-3-(methylthio)-2,7-dihydro-1H-pyrrolo[3',2':5,6]pyrido[3,4-b]pyrazine (308 g, crude product) as a pale white solid. ES-API: $[M+H]^+$=277.1.

Step 2: (S)-2-(Methoxymethyl)-2-methyl-3-(methylthio)-2,7-dihydro-1H-pyrrolo[3',2':5,6]pyrido[3,4-b]pyrazine (308 g, crude product) and 2-chloro-4-phenoxybenzaldehyde (352.0 mg, 1.517 mmol) were dissolved in methanol (15.0 mL), and the reaction was cooled to 0° C., and potassium hydroxide (272 mg, 4.857 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried over anhydrous sodium sulfate and then concentrated, and the crude product was purified by a silica gel column [dichloromethane:methanol=100:0 to 10:1 (v/v)] to obtain (2-chloro-4-phenoxyphenyl)((S)-2-(methoxymethyl)-2-methyl-3-(methylthio)-2,7-dihydro-1H-pyrrolo[3',2':5,6]pyrido[3,4-b]pyrazin-9-yl)methanol (175 mg, 2-step yield of 50%) as a pale yellow solid. ES-API: $[M+H]^+$=509.0.

Step 3: (2-Chloro-4-phenoxyphenyl)((S)-2-(methoxymethyl)-2-methyl-3-(methylthio)-2,7-dihydro-1H-pyrrolo[3',2':5,6]pyrido[3,4-b]pyrazin-9-yl)methanol (175 mg, 0.3493 mmol) was dissolved in 12 mL of tetrahydrofuran, and 2,3-dichloro-5,6-dicyano-1,4-benzoquinone (160 mg, 0.6986 mmol) was added thereto, and the reaction was stirred at room temperature for 2 hours. To the reaction solution was added 63 mL of saturated sodium bicarbonate solution, and the mixture was extracted with 88 mL of ethyl acetate. The organic phase was washed with 60 mL of saturated brine, dried over anhydrous sodium sulfate and then concentrated, and the crude product was purified by preparative HPLC to obtain a target product (S)-(2-chloro-4-phenoxyphenyl)(2-(methoxymethyl)-2-methyl-3-(methylthio)-2,7-dihydro-1H-pyrrolo[3',2':5,6]pyrido[3,4-b]pyrazin-9-yl)methanone (Z201, 22 mg, yield of 12.4%) as a pale yellow solid. ES-API: $[M+H]^+$=507.1. $^1H$ NMR (500 MHz, DMSO-$d_6$) δ 12.51 (s, 1H), 8.29 (s, 1H), 7.95 (s, 1H), 7.48 (t, J=7.9 Hz, 2H), 7.25 (t, J=7.3 Hz, 1H), 7.22-7.14 (m, 3H), 7.02 (dd, J=8.4, 2.2 Hz, 1H), 3.59 (d, J=9.9 Hz, 1H), 3.47 (d, J=9.8 Hz, 1H), 3.30 (s, 3H), 2.44 (s, 3H), 1.47 (s, 3H).

Embodiment 181: Synthesis of Z202

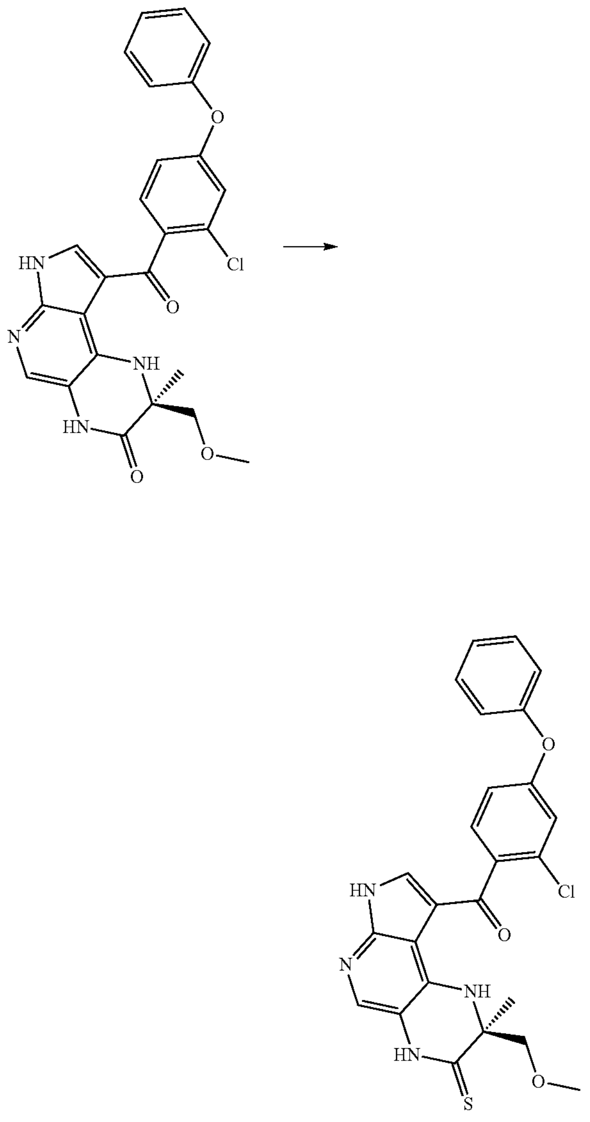

Z202

Step 1: To a solution of (S)-9-(2-chloro-4-phenoxybenzoyl)-2-(methoxymethyl)-2-methyl-1,2,4,7-tetrahydro-3H-pyrrolo[3',2':5,6]pyrido[3,4-b]pyrazin-3-one (50 mg, 0.1050 mmol) in toluene (3.0 mL) was added Lawesson's reagent (84.0 mg, 0.2100 mmol), reacted at 115° C. for 2 hours under nitrogen atmosphere. After the reaction was completed, the solvent was evaporated to dryness by rotary evaporation under reduced pressure, and the crude product was purified by preparative HPLC to obtain a target compound (S)-(2-chloro-4-phenoxyphenyl)(2-(methoxymethyl)-2-methyl-3-thioxo-2,3,4,7-tetrahydro-1H-pyrrolo[3',2':5,6]pyrido[3,4-b]pyrazin-9-yl)methanone (Z202, 22 mg, yield of 42%). $[M+H]^+$=493.1. $^1H$ NMR (500 MHz, DMSO-$d_6$) δ 12.38 (s, 2H), 8.33 (s, 1H), 7.94 (s, 1H), 7.65 (s, 1H), 7.57 (d, J=8.4 Hz, 1H), 7.48 (t, J=7.8 Hz, 2H), 7.25 (t, J=7.3 Hz, 1H), 7.18 (d, J=6.7 Hz, 3H), 7.02 (dd, J=8.4, 2.0 Hz, 1H), 3.74 (dd, J=25.0, 9.4 Hz, 2H), 3.35 (s, 3H), 1.51 (s, 3H).

Embodiment 182: Synthesis of Z203

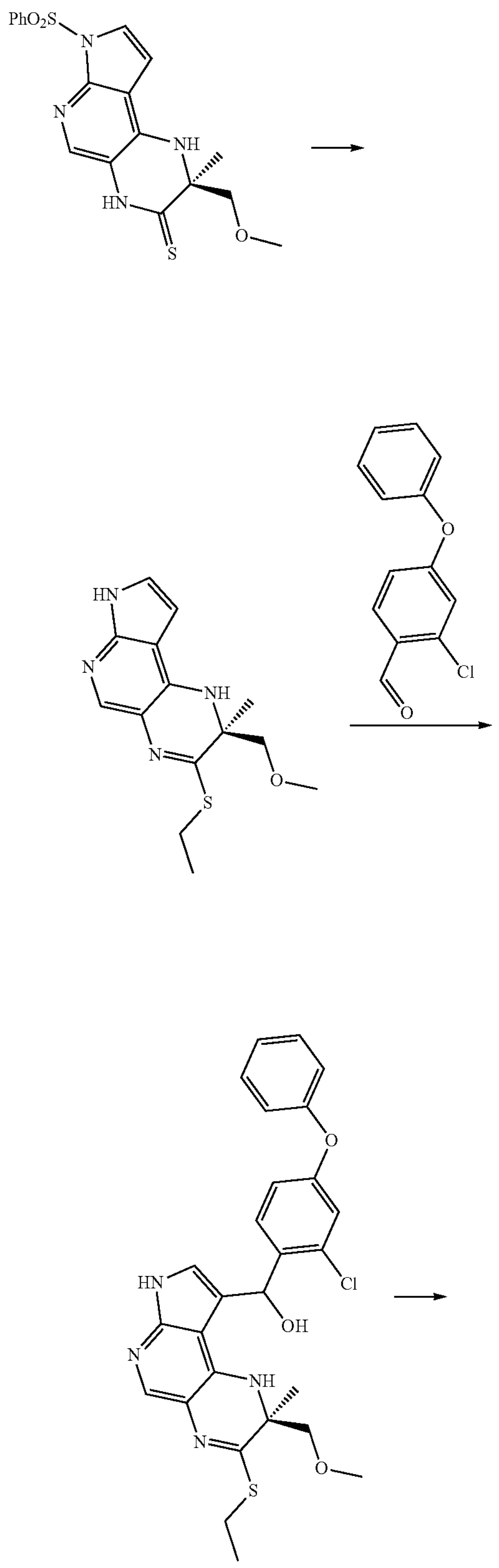

-continued

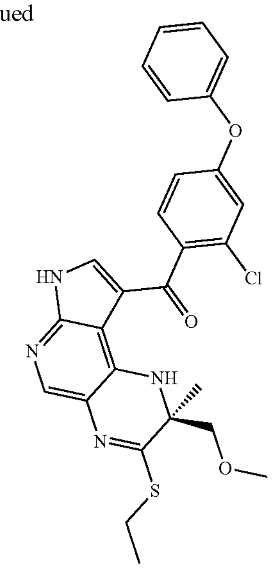

Z203

Step 1: (S)-2-(Methoxymethyl)-2-methyl-7-(phenylsulfonyl)-1,2,4,7-tetrahydro-3H-pyrrolo[3',2':5,6]pyrido[3,4-b]pyrazine-3-thione (430 mg, 1.069 mmol) was dissolved in 15 mL of methanol, 5 mL of tetrahydrofuran and 3.0 mL of water, and sodium hydroxide (300 mg, 7.487 mmol) was added thereto, and the reaction was stirred at 65° C. for 16 hours. The reaction was completed, then cooled to room temperature. To the reaction solution was added 20 mL of water and 15 mL of saturated ammonium chloride solution, and the mixture was extracted with 200 mL of ethyl acetate. The organic phase was washed with 30 mL of saturated sodium bicarbonate solution and 80 mL of saturated brine in turn, dried over anhydrous sodium sulfate and then concentrated to obtain (S)-3-(ethylthio)-2-(methoxymethyl)-2-methyl-2,7-dihydro-1H-pyrrolo[3',2':5,6]pyrido[3,4-b]pyrazine (412 g, crude product) as a pale white solid. ES-API: $[M+H]^+=291.1$.

Step 2: (S)-3-(Ethylthio)-2-(methoxymethyl)-2-methyl-2,7-dihydro-1H-pyrrolo[3',2':5,6]pyrido[3,4-b]pyrazine (412 g, crude product) and 2-chloro-4-phenoxybenzaldehyde (496 mg, 2.138 mmol) were dissolved in methanol (12.0 mL), and the reaction was cooled to 0° C., and potassium hydroxide (420 mg, 7.483 mmol) was added thereto. The reaction was stirred at room temperature for 6 hours. The reaction solution was poured into 30 mL of saturated aqueous ammonium chloride solution, and the pH of the reaction solution was adjusted to 8, and the reaction solution was extracted with 100 mL of ethyl acetate. The organic phase was washed with 60 mL of saturated brine, dried over anhydrous sodium sulfate and then concentrated, and the crude product was purified by a silica gel column [dichloromethane:methanol=100:0 to 10:1 (v/v)] to obtain (2-chloro-4-phenoxyphenyl)((S)-3-(ethylthio)-2-(methoxymethyl)-2-methyl-2,7-dihydro-1H-pyrrolo[3',2':5,6]pyrido[3,4-b]pyrazin-9-yl)methanol (320 mg, 2-step yield of 60%) as a pale yellow solid. ES-API: $[M+H]^+=523.2$.

Step 3: (2-Chloro-4-phenoxyphenyl)((S)-3-(ethylthio)-2-(methoxymethyl)-2-methyl-2,7-dihydro-1H-pyrrolo[3',2':5,6]pyrido[3,4-b]pyrazin-9-yl)methanol (320 mg, 0.6299 mmol) was dissolved in 15 mL of tetrahydrofuran, and 2,3-dichloro-5,6-dicyano-1,4-benzoquinone (286 mg, 1.2598 mmol) was added thereto, and the reaction was stirred at room temperature for 2 hours. To the reaction solution was added 63 mL of saturated sodium bicarbonate solution, and the mixture was extracted with 88 mL of ethyl acetate. The organic phase was washed with 60 mL of saturated brine, dried over anhydrous sodium sulfate and then concentrated, and the crude product was purified by preparative HPLC to obtain a target product (S)-(2-chloro-4-phenoxyphenyl)(3-(ethylthio)-2-(methoxymethyl)-2-methyl-2,7-dihydro-1H-pyrrolo[3',2':5,6]pyrido[3,4-b]pyrazin-9-yl)methanone (Z203, 82 mg, yield of 25%) as a pale yellow solid. ES-API: $[M+H]^+$=521.2. $^1$H NMR (500 MHz, DMSO-$d_6$) δ 8.96 (s, 1H), 8.04 (s, 1H), 7.73 (s, 1H), 7.60 (d, J=8.5 Hz, 1H), 7.49 (t, J=7.9 Hz, 2H), 7.27 (t, J=7.4 Hz, 1H), 7.20 (dd, J=8.7, 5.1 Hz, 3H), 7.04 (dd, J=8.4, 2.3 Hz, 1H), 3.68 (d, J=10.0 Hz, 1H), 3.52 (d, J=10.1 Hz, 1H), 3.11 (q, J=7.3 Hz, 2H), 1.54 (s, 3H), 1.31 (t, J=7.3 Hz, 3H).

Embodiment 183: Synthesis of Z204

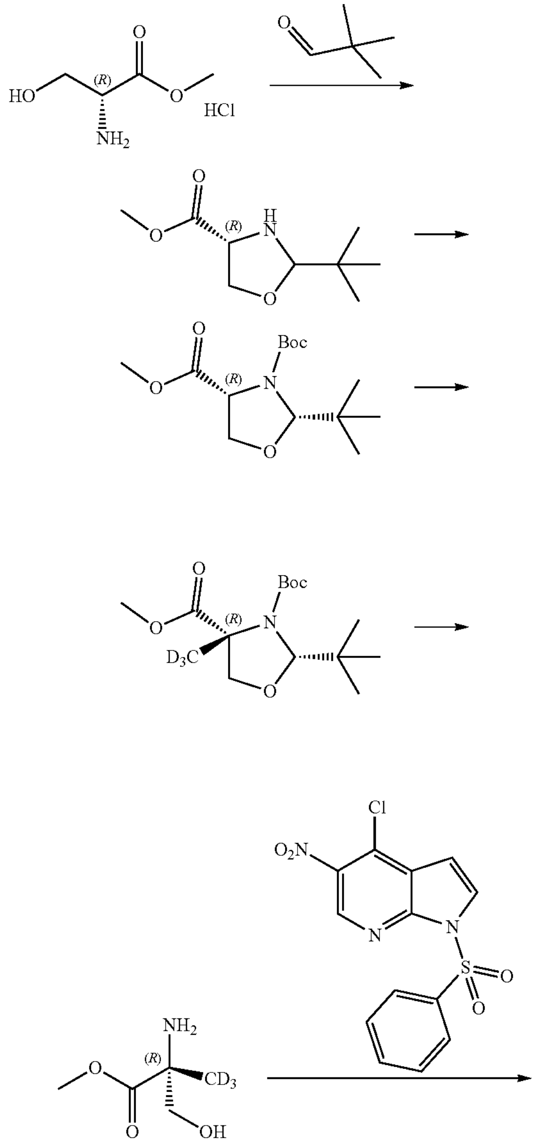

-continued

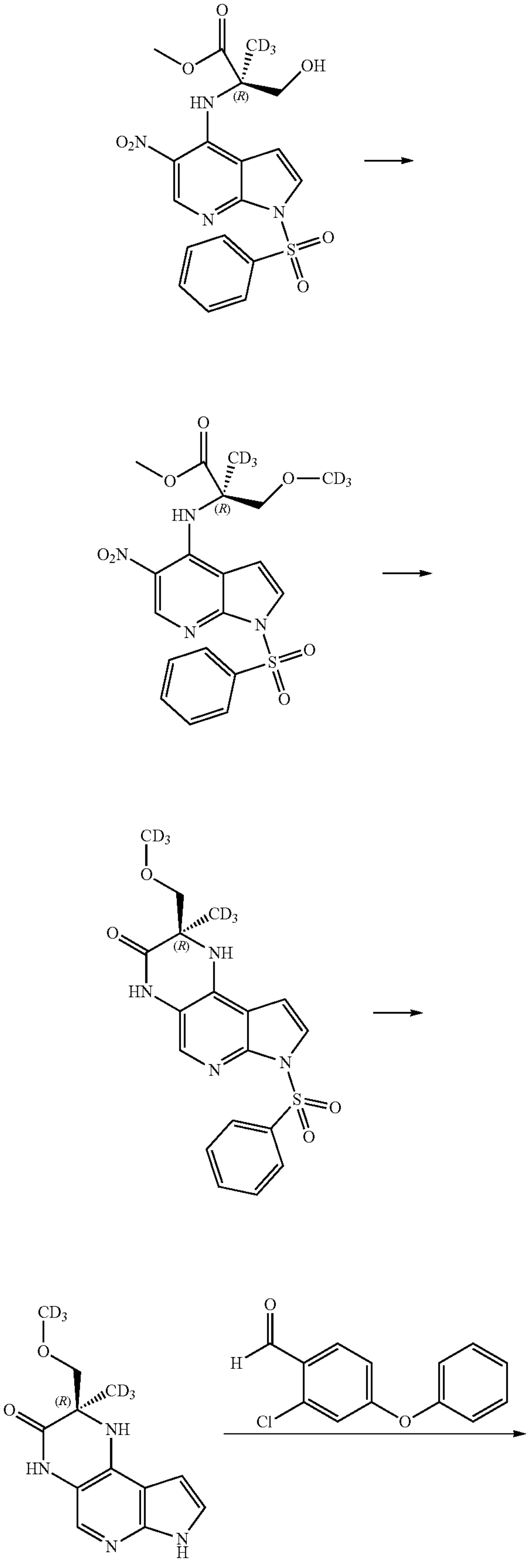

-continued

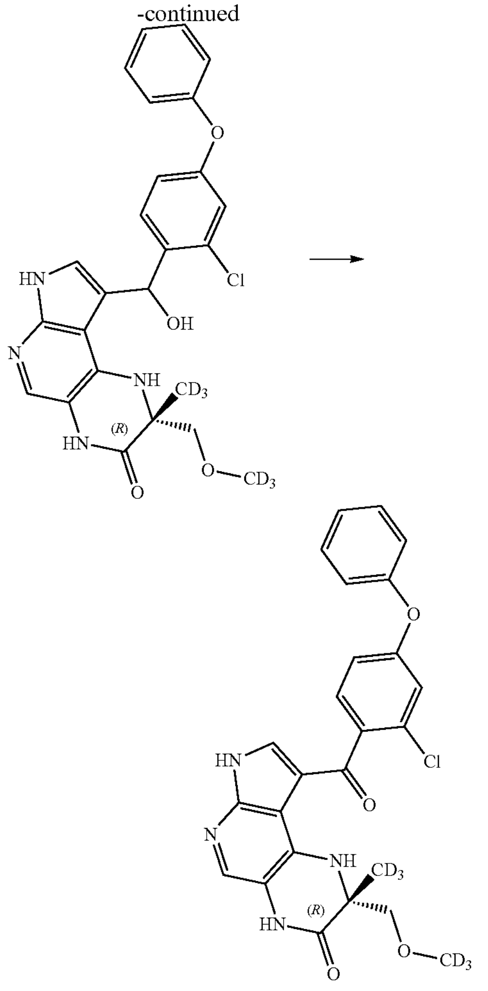

Z204

Step 1: Methyl (R)-2-amino-3-hydroxypropionate hydrochloride (23 g, 193 mmol) was dissolved in tetrahydrofuran (300 mL), then pivaldehyde (19.96 g, 231 mmol) and triethylamine (23.45 g, 231 mmol) were added thereto, and the mixture was reacted at 70° C. for 4 hours, cooled to room temperature, and the reaction solution was directly used for next step of reaction without treatment.

Step 2: To the reaction solution of the previous step was added potassium carbonate solution (28.74 g, 208.3 mmol) and di-tert-butyl dicarbonate (30.27 g, 138.86 mmol), and the mixture was reacted at room temperature for 16 hours, then water (500 mL), ethyl acetate (500 mL) were added to separate the phases. The organic phase was washed with saturated brine (500 mL×1) and N-methylpiperazine (50 mL), dried over anhydrous sodium sulfate, and concentrated to obtain 3-(tert-butyl) 4-methyl (2S,4R)-2-(tert-butyl)oxazolidine-3,4-dicarboxylate (26 g, yield: 65.16%). ES-API: $[M-Boc+1]^+$=188.1.

Step 3: 3-(tert-Butyl) 4-methyl (2S,4R)-2-(tert-butyl)oxazolidine-3,4-dicarboxylate (26 g, 90.48 mmol) was dissolved in tetrahydrofuran (300 mL), cooled to −78° C., and lithium bis(trimethylsilyl)amide tetrahydrofuran solution (104 mL, 1 M) was added thereto, reacted for 0.5 hours, and deuterated iodomethane (65.60 g, 452 mmol) was added thereto, and reacted at −78° C. for 1 hour. The reaction was quenched with ammonium chloride (500 mL), extracted with ethyl acetate (300 mL×2), and the organic phase was washed with dilute hydrochloric acid (500 mL×1), sodium bicarbonate (500 mL×1), and saturated brine (500 mL×1), dried over anhydrous sodium sulfate, concentrated, and the crude product was purified by column chromatography (petroleum ether/ethyl acetate=5/1) to obtain a product 3-(tert-butyl) 4-methyl (2S,4R)-2-(tert-butyl)-4-(methyl-$d_3$) oxazolidine-3,4-dicarboxylate (8.6 g, yield: 31.2%). ES-API: $[M-55]^+$=249.2.

Step 4: 3-(tert-Butyl) 4-methyl (2S,4R)-2-(tert-butyl)-4-(methyl-$d_3$)oxazolidine-3,4-dicarboxylate (8.6 g, 28.25 mmol) was dissolved in dioxane (25 mL), and concentrated hydrochloric acid (25 mL) was added thereto, and the mixture was reacted at 50° C. for 2 hours, concentrated. The crude product was dissolved in 1M hydrochloric acid (100 mL), and back-extraction was performed with ethyl acetate (50 mL×2), and the aqueous phase was concentrated to obtain a product methyl (R)-2-amino-2-(hydroxymethyl) propanoate-3,3,3-$d_3$ hydrochloride (3 g, yield: 77.9%). ES-API: $[M+H]^+$=137.1.

Step 5: Methyl (R)-2-amino-2-(hydroxymethyl)propanoate-3,3,3-$d_3$ hydrochloride (3 g, 22.03 mmol) was dissolved in N,N-dimethylacetamide (30 mL), and N,N-diisopropylethylamine (8.54 g, 66.10 mmol) and 4-chloro-5-nitro-1-(phenylsulfonyl)-1H-pyrrolo[2,3-b]pyridine (7.44 g, 22.03 mmol) were added thereto. The mixture was reacted at 100° C. for 16 hours, cooled, added with water (100 mL), ethyl acetate (50 mL) to separate the phases. The organic phase was washed with brine (50 mL×1), dried, concentrated, and the crude product was purified by column chromatography (petroleum ether/ethyl acetate=3/1) to obtain a product methyl (R)-2-(hydroxymethyl)-2-((5-nitro-1-(phenylsulfonyl)-1H-pyrrolo[2,3-b]pyridin-4-yl)amino)propanoate-3,3,3-ds (3 g, yield: 31.13%). ES-API: $[M+H]^+$=438.1.

Step 6: Methyl (R)-2-(hydroxymethyl)-2-((5-nitro-1-(phenylsulfonyl)-1H-pyrrolo[2,3-b]pyridin-4-yl)amino)propanoate-3,3,3-ds (2.5 g, 5.72 mmol) was dissolved in acetonitrile (40 mL), and silver oxide (10.6 g, 45.72 mmol) and deuterated-iodomethane (12.43 g, 85.73 mmol) were added thereto. The mixture was reacted at 35° C. for 16 hours, filtered, concentrated, and the crude product was purified by column chromatography (ethyl acetate/petroleum ether=0-35%) to obtain methyl (R)-2-((methoxy-$d_3$)methyl)-2-((5-nitro-1-(phenylsulfonyl)-1H-pyrrolo[2,3-b]pyridin-4-yl)amino)propanoate-3,3,3-$d_3$ (620 mg, yield: 23.87%). ES-API: $[M+H]^+$=455.2.

Step 7: Methyl (R)-2-((methoxy-$d_3$)methyl)-2-((5-nitro-1-(phenylsulfonyl)-1H-pyrrolo[2,3-b]pyridin-4-yl)amino)propanoate-3,3,3-$d_3$ (600 mg, 1.32 mmol) was dissolved in acetic acid (25 mL), and iron powder (737 mg, 13.2 mmol) was added thereto, and the mixture was reacted at 80° C. for 2 hours, filtered, concentrated, and the crude product was purified by column chromatography (petroleum ether/ethyl acetate=1/2) to obtain a product (R)-2-((methoxy-$d_3$)methyl)-2-(methyl-$d_3$)-7-(phenylsulfonyl)-1,2,4,7-tetrahydro-3H-pyrrolo[3',2':5,6]pyrido[3,4-b]pyrazin-3-one (400 mg, yield: 77.2%). ES-API: $[M+H]^+$=393.1.

Step 8: To a solution of (R)-2-((methoxy-$d_3$)methyl)-2-(methyl-$d_3$)-7-(phenylsulfonyl)-1,2,4,7-tetrahydro-3H-pyrrolo[3',2':5,6]pyrido[3,4-b]pyrazin-3-one (100 mg, 0.25 mmol) in methanol (5 mL) was slowly added dropwise an aqueous solution (1 mL) of sodium hydroxide (71.34 mg, 1.78 mmol) in an ice-water bath, stirred in an ice-water bath for 10 minutes, reacted at 60° C. for 2 hours, cooled to 0° C., slowly added dropwise with 6M hydrochloric acid solution until the pH of the system was 7, filtered, and the filtrate was concentrated to obtain (R)-2-((methoxy-$d_3$)methyl)-2-

(methyl-$d_3$)-1,2,4,7-tetrahydro-3H-pyrrolo[3',2':5,6]pyrido[3,4-b]pyrazin-3-one (200 mg, crude product). ES-API: $[M+H]^+$=253.1.

Step 9: (R)-2-((Methoxy-$d_3$)methyl)-2-(methyl-$d_3$)-1,2,4,7-tetrahydro-3H-pyrrolo[3',2':5,6]pyrido[3,4-b]pyrazin-3-one (200 mg, crude product) and 2-chloro-4-phenoxybenzaldehyde (368 mg, 1.59 mmol) were dissolved in anhydrous methanol (10 mL), and a solution of potassium hydroxide (133 mg, 2.38 mmol) in methanol (1 mL) was slowly added dropwise thereto under an ice bath. The mixture was reacted at room temperature for 3 hours, added with saturated ammonium chloride solution (5 mL), extracted with ethyl acetate (10 mL×3), concentrated, and the crude product was purified by column chromatography (dichloromethane/methanol=100:1-20:1) to obtain a product (2R)-9-((2-chloro-4-phenoxyphenyl)(hydroxy)methyl)-2-((methoxy-$d_3$)methyl)-2-(methyl-$d_3$)-1,2,4,7-tetrahydro-3H-pyrrolo[3',2':5,6]pyrido[3,4-b]pyrazin-3-one (250 mg, yield: 65.03%). ES-API $[M+H]^+$=485.2.

Step 10: (2R)-9-((2-Chloro-4-phenoxyphenyl)(hydroxy)methyl)-2-((methoxy-$d_3$)methyl)-2-(methyl-$d_3$)-1,2,4,7-tetrahydro-3H-pyrrolo[3',2':5,6]pyrido[3,4-b]pyrazin-3-one (150 mg, 3.09 mmol) was dissolved in a mixed solution of tetrahydrofuran (10 mL) and water (2 mL), and 2,3-dichloro-5,6-dicyanobenzoquinone (140 mg, 6.18 mmol) was added thereto, reacted at room temperature for 2 hours. LCMS detected that the reaction was complete, and the reaction solution was added with ethyl acetate (10 mL), then washed with saturated sodium sulfite solution (10 mL×2). The organic phase was washed with saturated sodium bicarbonate solution (10 mL×2), dried over anhydrous sodium sulfate, concentrated, and the crude product was purified by column chromatography (dichloromethane:methanol=100:1-20:1) to obtain compound (R)-9-(2-chloro-4-phenoxyphenyl)-2-((methoxy-$d_3$)methyl)-2-(methyl-$d_3$)-1,2,4,7-tetrahydro-3H-pyrrolo[3',2':5,6]pyrido[3,4-b]pyrazin-3-one (100 mg, yield: 6.7%), ES-API: $[M+H]^+$=483.2. $^1H$ NMR (400 MHz, $CDCl_3$) δ 8.65 (s, 1H), 8.05 (s, 1H), 7.41-7.45 (m, 4H), 7.23 (t, J=7.6 Hz, 1H), 7.09-7.11 (m, 3H), 6.96 (dd, J=8.4 Hz, 2.3 Hz, 1H), 3.89 (d, J=9.6 Hz, 1H), 3.59 (d, J=9.6 Hz, 1H).

-continued

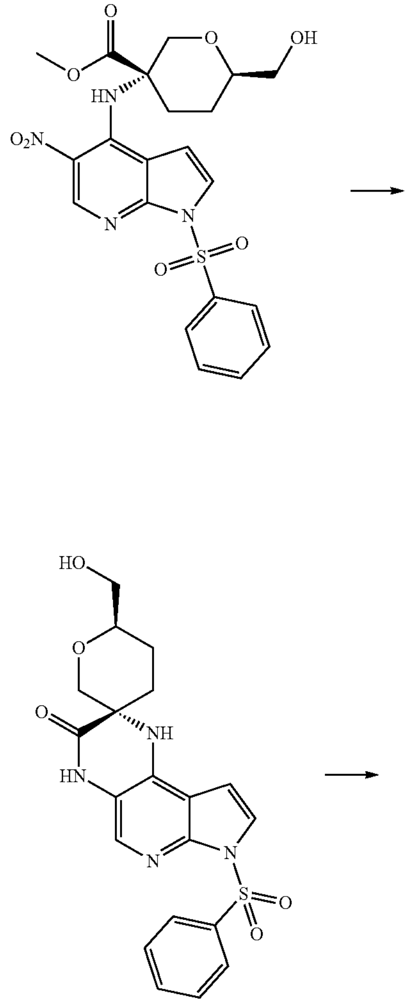

Embodiment 184: Synthesis of Z41-a and Z41-b

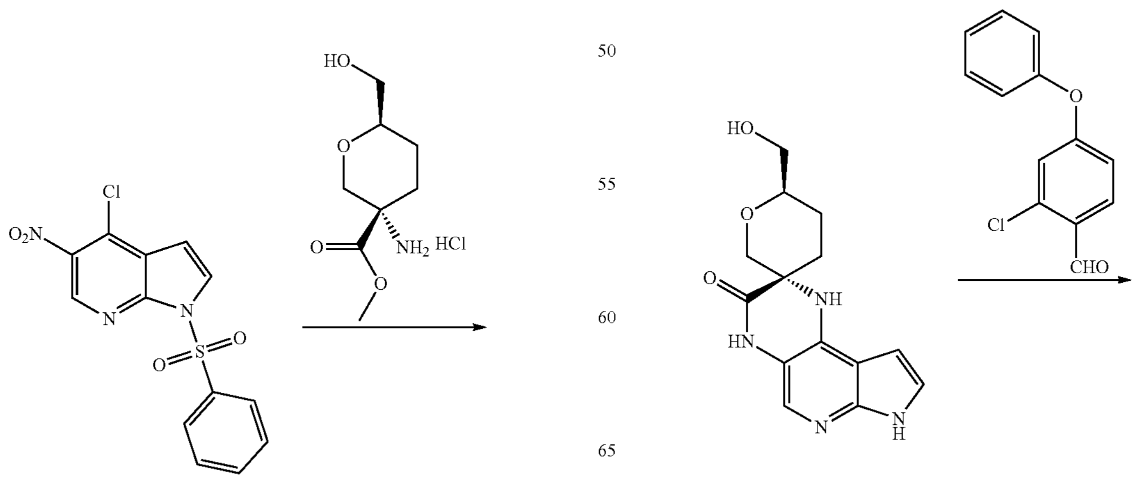

-continued

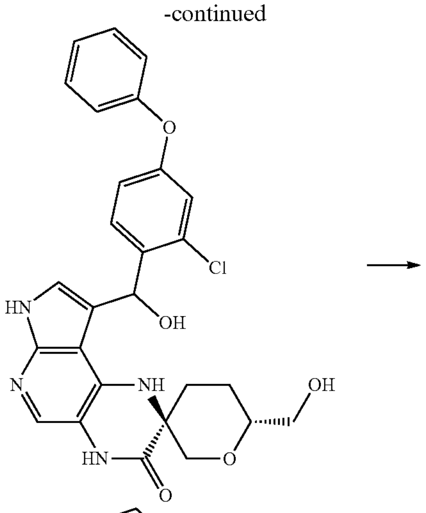

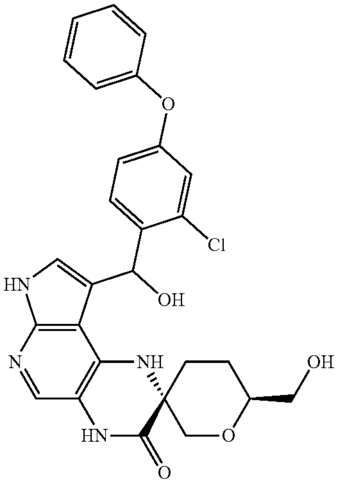

+

Z41-a

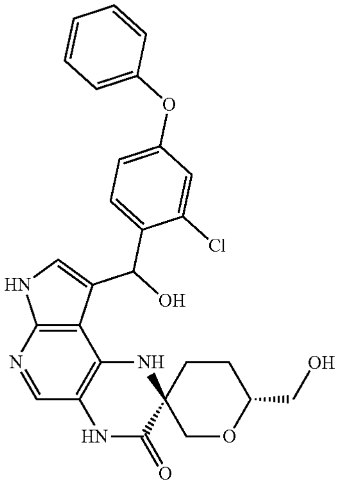

Z41-b

Step 1: 4-Chloro-5-nitro-1-(phenylsulfonyl)-1H-pyrrolo[2,3-b]pyridine (2.7 g, 8.01 mmol) and methyl cis-3-amino-6-(hydroxymethyl)tetrahydro-2H-pyran-3-carboxylate hydrochloride (600 mg, 2.67 mmol) were dissolved in N,N-dimethylacetamide (20 mL), and N,N-diisopropylethylamine (3.44 g, 26.70 mmol) was added thereto, and the reaction was stirred at 95° C. for 16 hours. The reaction solution was added with ethyl acetate (120 mL), washed with dilute brine (40 mL×4) and saturated brine (40 mL) in turn, dried over anhydrous sodium sulfate and concentrated. The crude product was purified by a flash silica gel column (ethyl acetate/petroleum ether: 0-60%) to obtain methyl cis-6-(hydroxymethyl)-3-((5-nitro-1-(phenylsulfonyl)-1H-pyrrolo[2,3-b]pyridin-4-yl)amino)tetrahydro-2H-pyran-3-carboxylate (220 mg, yield: 17%) as a light brown solid. ES-API: $[M+H]^+$=491.0.

Step 2: Methyl cis-6-(hydroxymethyl)-3-((5-nitro-1-(phenylsulfonyl)-1H-pyrrolo[2,3-b]pyridin-4-yl)amino)tetrahydro-2H-pyran-3-carboxylate (200 mg, 0.41 mmol) was dissolved in acetic acid (7 mL), and iron powder (230 mg, 4.10 mmol) was added thereto, and the reaction was stirred at 85° C. for 3 hours. The reaction solution was added with ethyl acetate (100 mL), washed with water (30 mL×2), saturated sodium carbonate (40 mL×2), saturated sodium bicarbonate (40 mL×2), and saturated brine (40 mL) in turn, dried over anhydrous sodium sulfate and concentrated to obtain cis-6-(hydroxymethyl)-7'-(phenylsulfonyl)-4',5,6,7'-tetrahydro-2H,4H-spiro[pyran-3,2'-pyrrolo[3',2':5,6]pyrido[3,4-b]pyrazin]-3'(1'H)-one (175 mg, yield: 100%) as alight brown solid. ES-API: $[M+H]^+$=429.1.

Step 3: cis-6-(Hydroxymethyl)-7'-(phenylsulfonyl)-4',5,6,7'-tetrahydro-2H,4H-spiro[pyran-3,2'-pyrrolo[3',2':5,6]pyrido[3,4-b]pyrazin]-3'(1'H)-one (155 mg, 0.36 mmol) was dissolved in methanol (10 mL), tetrahydrofuran (4 mL) and water (2 mL), and sodium hydroxide (72 mg, 1.80 mmol) was added thereto, and the reaction was stirred at 65° C. for 16 hours. The pH of the reaction solution was adjusted to 8 with 1.0 M dilute hydrochloric acid, and the reaction solution was extracted with ethyl acetate (100 mL). The organic phase was dried over anhydrous sodium sulfate and concentrated to obtain cis-6-(hydroxymethyl)-4',5,6,7'-tetrahydro-2H,4H-spiro[pyran-3,2'-pyrrolo[3',2':5,6]pyrido[3,4-b]pyrazin]-3'(1'H)-one (150 mg, crude product) as alight brown solid. ES-API: $[M+H]^+$=289.1.

Step 4: cis-6-(Hydroxymethyl)-4',5,6,7'-tetrahydro-2H,4H-spiro[pyran-3,2'-pyrrolo[3',2':5,6]pyrido[3,4-b]pyrazin]-3'(1'H)-one (150 mg, crude product) and 2-chloro-4-phenoxybenzaldehyde (314 mg, 1.35 mmol) were dissolved in methanol (8 mL), and the reaction was cooled to 0° C., and potassium hydroxide (177 mg, 3.16 mmol) was added thereto. The reaction was stirred at room temperature for 16 hours. The pH of the reaction solution was adjusted to 8 with 1.0 M dilute hydrochloric acid, and the reaction solution was added with water (2 mL) and extracted with ethyl acetate (60 mL). The organic phase was washed with saturated brine (25 mL), dried over anhydrous sodium sulfate and then concentrated, and the crude product was purified by a thin-layer chromatography preparative plate (dichloromethane/methanol=10:1) to obtain cis-9'-((2-chloro-4-phenoxyphenyl)(hydroxy)methyl)-6-(hydroxymethyl)-4',5,6,7'-tetrahydro-2H,4H-spiro[pyran-3,2'-pyrrolo[3',2':5,6]pyrido[3,4-b]pyrazin]-3'(1'H)-one (115 mg, 2-step yield: 61%) as alight brown solid. ES-API: $[M+H]^+$=521.2.

Step 5: cis-9'-((2-Chloro-4-phenoxyphenyl)(hydroxy)methyl)-6-(hydroxymethyl)-4',5,6,7'-tetrahydro-2H,4H-spiro[pyran-3,2'-pyrrolo[3',2':5,6]pyrido[3,4-b]pyrazin]-3'(1'H)-one (105 mg, 0.20 mmol) was dissolved in 1,4-dioxane (5 mL) and water (0.5 mL), and 2,3-dichloro-5,6-dicyano-p-benzoquinone (91 mg, 0.40 mmol) was added thereto, and the reaction was stirred at room temperature for 1 hour. To the reaction solution was added saturated sodium thiosulfate solution (6 mL) and saturated sodium bicarbonate solution (6 mL), and the mixture was extracted with ethyl acetate (60 mL). The organic phase was washed with saturated sodium bicarbonate solution (15 mL) and saturated brine (15 mL) in turn, dried over anhydrous sodium sulfate and then concentrated. The crude product was purified by preparative HPLC, then resolved by chiral preparative HPLC (separation column: IE 250 mm*4.6 mm*5 μM, mobile phase: n-hexane:ethanol:diethylamine=60:40:2, flow rate: 1 mL/min, column temperature: 30° C.) to obtain (3R,6S)-9'-(2-chloro-4-phenoxybenzoyl)-6-(hydroxymethyl)-4',5,6,7'-tetrahydro-2H,4H-spiro[pyran-3,2'-pyrrolo[3',2':5,6]pyrido[3,4-b]pyrazin]-3'(1'H)-one (Z41-a, 35 mg, peak 1, retention time of 11.479 min, yield: 33%) as a pale yellow solid. ES-API: $[M+H]^+$=519.1. $^1$H NMR (400 MHz, DMSO-$d_6$) δ 12.51 (s, 1H), 10.54 (s, 1H), 8.78 (s, 1H), 7.74 (s, 1H), 7.65 (s, 1H), 7.57 (d, J=8.4 Hz, 1H), 7.51-7.43 (m, 2H), 7.25 (t, J=7.6 Hz, 1H), 7.22-7.16 (m, 3H), 7.03 (dd, J=8.4, 2.4 Hz, 1H), 4.68 (t, J=5.6 Hz, 1H), 3.87 (dd, J=11.2 Hz, 2.0 Hz, 1H), 3.80 (d, J=11.2 Hz, 1H), 3.57-3.50 (m, 1H), 3.48-3.40 (m, 1H), 3.37-3.30 (m, 1H), 1.98-1.82 (m, 2H), 1.61-1.49 (m, 2H); (3S,6R)-9'-(2-chloro-4-phenoxybenzoyl)-6-(hydroxymethyl)-4',5,6,7'-tetrahydro-2H,4H-spiro[pyran-3,2'-pyrrolo[3',2':5,6]pyrido[3,4-b]pyrazin]-3'(1'H)-one (Z41-b, 35 mg, peak 2, retention time of 13.649 min, yield of 33%) as a pale yellow solid. ES-API: $[M+H]^+$=519.1. $^1$H NMR (400 MHz, DMSO-$d_6$) δ 12.51 (s, 1H), 10.54 (s, 1H), 8.78 (s, 1H), 7.75 (s, 1H), 7.65 (s, 1H), 7.57 (d, J=8.4 Hz, 1H), 7.52-7.44 (m, 2H), 7.25 (t, J=7.6 Hz, 1H), 7.22-7.16 (m, 3H), 7.03 (dd, J=8.4, 2.4 Hz, 1H), 4.68 (t, J=5.6 Hz, 1H), 3.87 (dd, J=11.2 Hz, 2.0 Hz, 1H), 3.80 (d, J=11.2 Hz, 1H), 3.57-3.50 (m, 1H), 3.48-3.40 (m, 1H), 3.37-3.30 (m, 1H), 1.98-1.82 (m, 2H), 1.61-1.49 (m, 2H).

Embodiment 185: Synthesis of Z51, Z51-1 and Z51-2

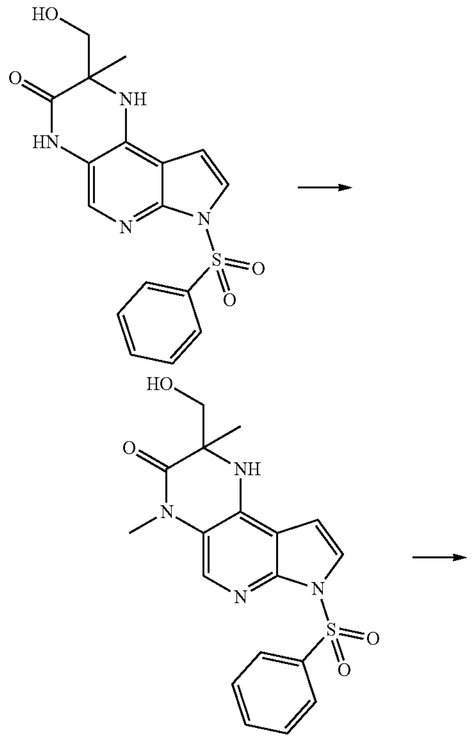

-continued

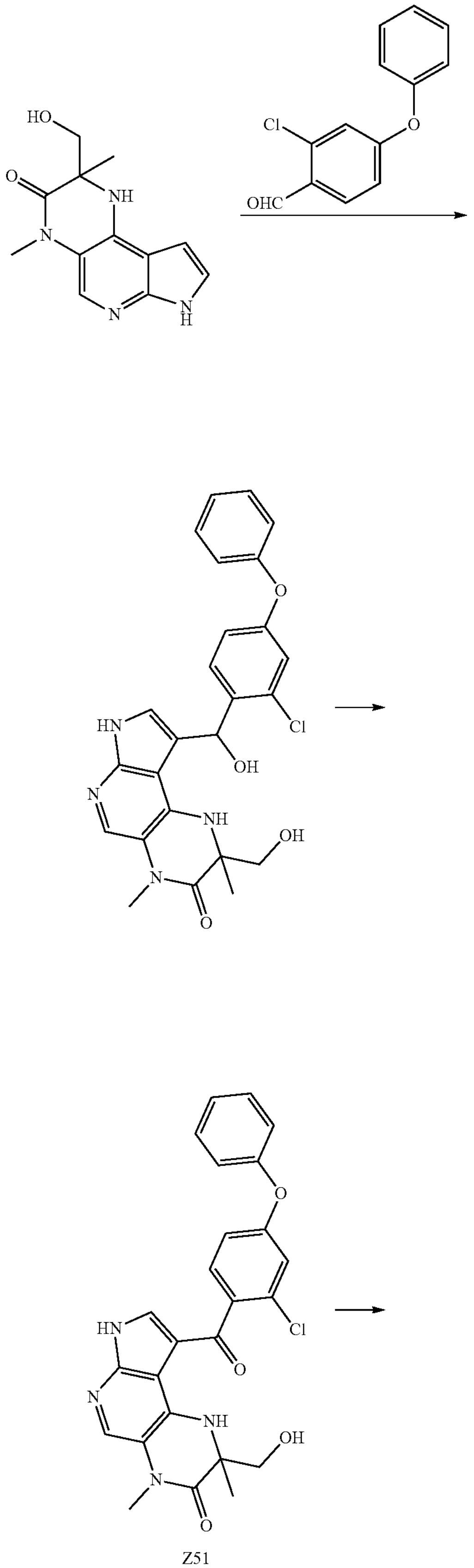

Z51

-continued

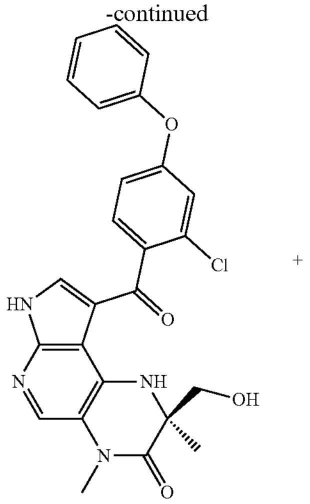

Z51-1

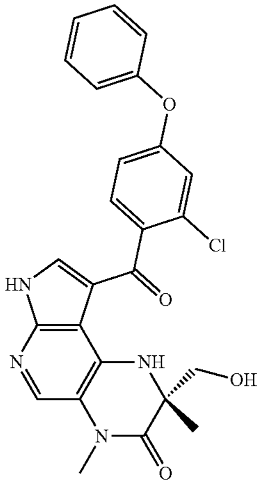

Z51-2

Step 1: 2-(Hydroxymethyl)-2-methyl-7-(phenylsulfonyl)-1,2,4,7-tetrahydro-3H-pyrrolo[3',2':5,6]pyrido[3,4-b]pyrazin-3-one (200 mg, 0.5375 mmol) was dissolved in a mixed solution of acetone/N,N-dimethylformamide (10 mL:2 mL), and iodomethane (764 mg, 5.375 mmol) and potassium carbonate (371 mg, 2.687 mmol) were added thereto in turn, stirred in a sealed tube at 40° C. for 12 hours. After the reaction was completed, ethyl acetate (200 mL) was added thereto. The mixture was washed with water (80 mL×2), saturated sodium carbonate (60 mL×2), saturated sodium bicarbonate (82 mL×2), saturated brine (80 mL) in turn, dried over anhydrous sodium sulfate, concentrated, and the crude product was slurried with ethyl acetate to obtain 2-(hydroxymethyl)-2,4-dimethyl-7-(phenylsulfonyl)-1,2,4,7-tetrahydro-3H-pyrrolo[3',2':5,6]pyrido[3,4-b]pyrazin-3-one (200 mg, yield: 96%) as a yellow solid. ES-API: $[M+H]^+$=387.1.

Step 2: 2-(Hydroxymethyl)-2,4-dimethyl-7-(phenylsulfonyl)-1,2,4,7-tetrahydro-3H-pyrrolo[3',2':5,6]pyrido[3,4-b]pyrazin-3-one (200 mg, 0.5180 mmol) was dissolved in methanol (12 mL), tetrahydrofuran (3 mL) and water (2 mL), and sodium hydroxide (150 mg, 3.750 mmol) was added thereto, stirred and reacted at 65° C. for 7 hours. To the reaction solution was added water (20 mL) and saturated ammonium chloride solution (15 mL), and the mixture was extracted with ethyl acetate (150 mL). The organic phase was washed with saturated sodium bicarbonate solution (20 mL), saturated brine (60 mL) in turn, dried over anhydrous sodium sulfate and concentrated to obtain 2-(hydroxymethyl)-2,4-dimethyl-1,2,4,7-tetrahydro-3H-pyrrolo[3',2':5,6]pyrido[3,4-b]pyrazin-3-one (237 mg, crude product) as a pale white solid. ES-API: $[M+H]^+$=247.1.

Step 3: 2-(Hydroxymethyl)-2,4-dimethyl-1,2,4,7-tetrahydro-3H-pyrrolo[3',2':5,6]pyrido[3,4-b]pyrazin-3-one (237 mg, crude product) and 2-chloro-4-phenoxybenzaldehyde (240 mg, 1.034 mmol) were dissolved in methanol (20.0 mL), and the reaction was cooled to 0° C., and potassium hydroxide (203 mg, 3.625 mmol) was added thereto. The reaction was stirred at room temperature for 6 hours. The reaction solution was poured into saturated aqueous ammonium chloride solution (30 mL), and the pH of the reaction solution was adjusted to 8, and the reaction solution was extracted with ethyl acetate (200 mL). The organic phase was washed with saturated brine (80 mL), dried over anhydrous sodium sulfate and concentrated to obtain 9-((2-chloro-4-phenoxyphenyl)(hydroxy)methyl)-2-(hydroxymethyl)-2,4-dimethyl-1,2,4,7-tetrahydro-3H-pyrrolo[3',2':5,6]pyrido[3,4-b]pyrazin-3-one (360 mg, crude product) as a pale yellow solid. ES-API: $[M+H]^+$=479.2.

Step 4: 9-((2-Chloro-4-phenoxyphenyl)(hydroxy)methyl)-2-(hydroxymethyl)-2,4-dimethyl-1,2,4,7-tetrahydro-3H-pyrrolo[3',2':5,6]pyrido[3,4-b]pyrazin-3-one (360 mg, crude product) was dissolved in tetrahydrofuran (20 mL), and 2,3-dichloro-5,6-dicyano-1,4-benzoquinone (360 mg, 1.586 mmol) was added thereto, and the reaction was stirred at room temperature for 2 hours. The reaction solution was added with saturated sodium bicarbonate solution (60 mL), and extracted with ethyl acetate (80 mL). The organic phase was washed with saturated brine (60 mL), dried over anhydrous sodium sulfate, concentrated, and the crude product was purified by preparative HPLC to obtain 9-(2-chloro-4-phenoxybenzoyl)-2-(hydroxymethyl)-2,4-dimethyl-1,2,4,7-tetrahydro-3H-pyrrolo[3',2':5,6]pyrido[3,4-b]pyrazin-3-one (Z51, 68 mg, 3-step yield: 27.5%) as a pale yellow solid, ES-API: $[M+H]^+$=477.1.

Step 5: 9-(2-Chloro-4-phenoxybenzoyl)-2-(hydroxymethyl)-2,4-dimethyl-1,2,4,7-tetrahydro-3H-pyrrolo[3',2':5,6]pyrido[3,4-b]pyrazin-3-one (Z51, 68 mg, 0.1424 mmol) was resolved by chiral preparation (separation column: IC 150 mm*4.6 mm*5 μM, mobile phase: n-hexane:ethanol:diethylamine=70:30:0.2, flow rate: 1 mL/min, column temperature: 30° C.) to obtain (Z51-1, 19.34 mg, peak 1, retention time of 10.161 min, yield: 28%) as a pale white solid. ES-API: $[M+H]^+$=477.1. $^1$H NMR (400 MHz, DMSO-$d_6$) δ 12.69-12.18 (m, 1H), 8.49 (s, 1H), 7.92 (s, 1H), 7.63 (s, 1H), 7.58-7.44 (m, 3H), 7.25 (t, J=7.4 Hz, 1H), 7.22-7.17 (m, 2H), 7.02 (dd, J=8.4, 2.4 Hz, 1H), 5.22 (t, J=5.5 Hz, 1H), 3.68 (dd, J=10.6, 6.0 Hz, 1H), 3.55-3.48 (m, 1H), 3.36 (s, 3H), 1.36 (s, 3H). (Z51-2, 21.07 mg, peak 2, retention time of 12.24 min, yield: 31%); a pale white solid. ES-API: $[M+H]^+$=477.1. $^1$H NMR (400 MHz, DMSO-$d_6$) δ 12.49 (s, 1H), 8.49 (s, 1H), 7.92 (s, 1H), 7.63 (s, 1H), 7.55 (d, J=8.4 Hz, 1H), 7.48 (dd, J=8.4, 7.5 Hz, 2H), 7.25 (t, J=7.4 Hz, 1H), 7.22-7.16 (m, 3H), 7.02 (dd, J=8.4, 2.4 Hz, 1H), 5.23 (t, J=5.4 Hz, 1H), 3.68 (dd, J=10.6, 6.0 Hz, 1H), 3.49 (dd, J=10.7, 5.0 Hz, 1H), 3.36 (s, 3H), 1.36 (s, 3H).

Embodiment 186: Synthesis of Z65
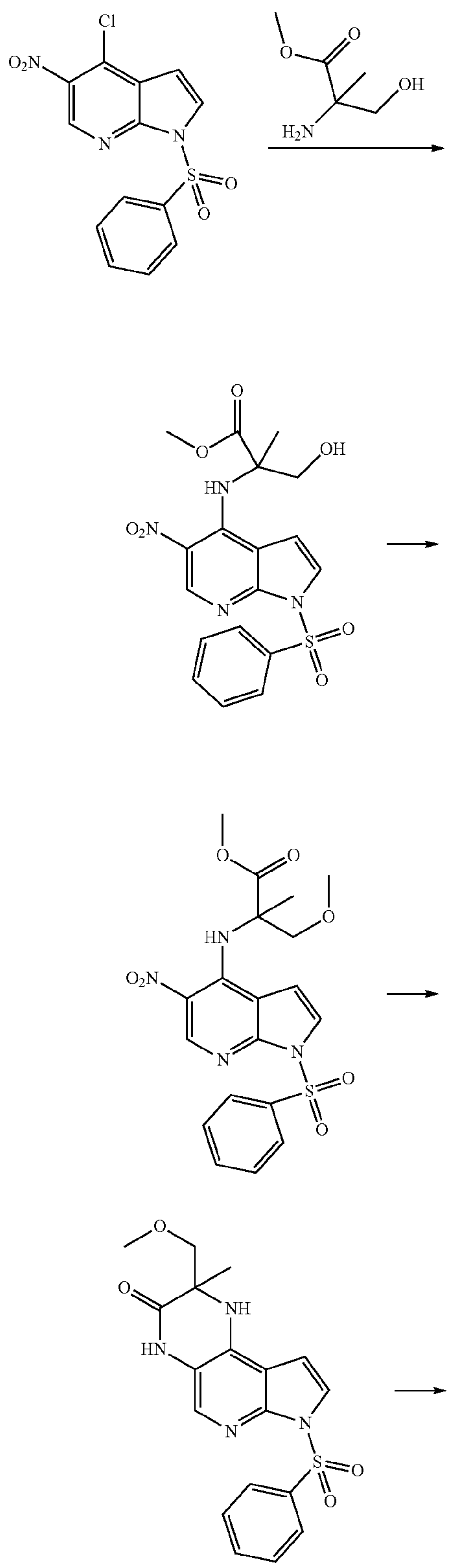
-continued
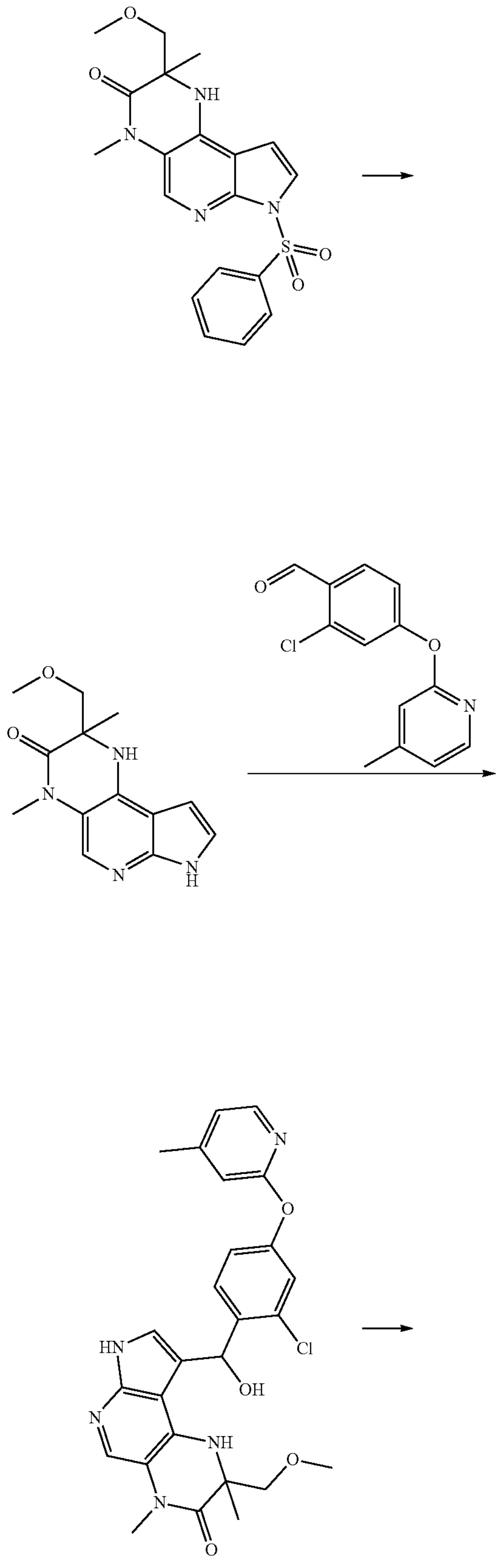

-continued

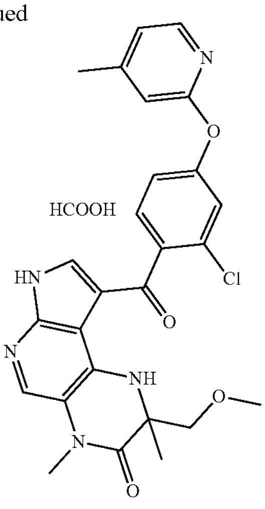

Z65

Step 1: 4-Chloro-5-nitro-1-(phenylsulfonyl)-1H-pyrrolo[2,3-b]pyridine (1.0 g, 2.967 mmol) and methyl 2-amino-3-hydroxy-2-methylpropanoate hydrochloride (4.5 g, 13.35 mmol) were dissolved in N,N-dimethylacetamide (80 mL), and N,N-diisopropylethylamine (11.75 g, 91 mmol) was added thereto, and the reaction was stirred at 95° C. for 16 hours. The reaction solution was added with ethyl acetate (300 mL), washed with water (100 mL×2), washed with saturated brine (150 mL×3), dried over anhydrous sodium sulfate and concentrated, and the crude product was purified by a flash silica gel column (ethyl acetate/petroleum ether: 0-50%) to obtain methyl 3-hydroxy-2-methyl-2-((5-nitro-1-(phenylsulfonyl)-1H-pyrrolo[2,3-b]pyridin-4-yl)amino)propanoate (0.735 g, yield: 57%) as a pale yellow solid. ES-API: $[M+H]^+$=435.1.

Step 2: Methyl 3-hydroxy-2-methyl-2-((5-nitro-1-(phenylsulfonyl)-1H-pyrrolo[2,3-b]pyridin-4-yl)amino)propanoate (2.60 g, 5.990 mmol) was dissolved in acetonitrile (100 mL), and silver oxide (20.82 g, 89.86 mmol) and iodomethane (21.26 g, 149.75 mmol) were added thereto in turn, and the mixture was stirred in the dark at room temperature for 48 hours under nitrogen atmosphere. After the reaction was completed, the reaction solution was filtered through diatomite, and the filtrate was evaporated to dryness by rotary evaporation under reduced pressure. The crude product was purified by a flash silica gel column (ethyl acetate/petroleum ether: 0-50%) to obtain methyl 3-methoxy-2-methyl-2-((5-nitro-1-(phenylsulfonyl)-1H-pyrrolo[2,3-b]pyridin-4-yl)amino)propanoate (2.20 g, yield: 82%) as a yellow solid. ES-API: $[M+H]^+$=449.0.

Step 3: Methyl 3-methoxy-2-methyl-2-((5-nitro-1-(phenylsulfonyl)-1H-pyrrolo[2,3-b]pyridin-4-yl)amino)propanoate (1.05 g, 2.343 mmol) was dissolved in acetic acid (30 mL), and iron powder (2.62 g, 46.87 mmol) was added thereto. The mixture was gradually heated to 80° C. and stirred for 1 hour. After the reaction was completed, the solvent was evaporated to dryness by rotary evaporation under reduced pressure, and ethyl acetate (200 mL) was added thereto. The mixture was washed with water (80 mL×2), saturated sodium carbonate (60 mL×2), saturated sodium bicarbonate (82 mL×2), saturated brine (80 mL) in turn, dried over anhydrous sodium sulfate, concentrated, and the crude product was slurried with ethyl acetate to obtain 2-(methoxymethyl)-2-methyl-7-(phenylsulfonyl)-1,2,4,7-tetrahydro-3H-pyrrolo[3',2':5,6]pyrido[3,4-b]pyrazin-3-one (650 mg, yield: 72%) as a yellow solid. ES-API: $[M+H]^+$=387.2.

Step 4: 2-(Methoxymethyl)-2-methyl-7-(phenylsulfonyl)-1,2,4,7-tetrahydro-3H-pyrrolo[3',2':5,6]pyrido[3,4-b]pyrazin-3-one (500 mg, 1.292 mmol) was dissolved in a mixed solution of acetone/N,N-dimethylformamide (20 mL:4 mL), and iodomethane (1.83 g, 12.92 mmol) and potassium carbonate (892 mg, 6.458 mmol) were added thereto in turn, stirred in a sealed tube at 40° C. for 12 hours. After the reaction was completed, ethyl acetate (200 mL) was added thereto. The mixture was washed with water (80 mL×2), saturated sodium carbonate (60 mL×2), saturated sodium bicarbonate (82 mL×2), saturated brine (80 mL) in turn, dried over anhydrous sodium sulfate, concentrated, and the crude product was slurried with ethyl acetate to obtain 2-(methoxymethyl)-2,4-dimethyl-7-(phenylsulfonyl)-1,2,4,7-tetrahydro-3H-pyrrolo[3',2':5,6]pyrido[3,4-b]pyrazin-3-one (450 mg, yield: 86.8%) as a yellow solid. ES-API: $[M+H]^+$=401.2.

Step 5: 2-(Methoxymethyl)-2,4-dimethyl-7-(phenylsulfonyl)-1,2,4,7-tetrahydro-3H-pyrrolo[3',2':5,6]pyrido[3,4-b]pyrazin-3-one (450 mg, 1.125 mmol) was dissolved in methanol (20 mL), tetrahydrofuran (5 mL) and water (4 mL), and sodium hydroxide (315 mg, 7.875 mmol) was added thereto, stirred and reacted at 65° C. for 7 hours. To the reaction solution was added water (20 mL) and saturated ammonium chloride solution (15 mL), and the mixture was extracted with ethyl acetate (200 mL). The organic phase was washed with saturated sodium bicarbonate solution (20 mL), saturated brine (60 mL) in turn, dried over anhydrous sodium sulfate and concentrated to obtain 2-(methoxymethyl)-2,4-dimethyl-1,2,4,7-tetrahydro-3H-pyrrolo[3',2':5,6]pyrido[3,4-b]pyrazin-3-one (500 mg, crude product) as a pale white solid. ES-API: $[M+H]^+$=261.2.

Step 6: 2-(Methoxymethyl)-2,4-dimethyl-1,2,4,7-tetrahydro-3H-pyrrolo[3',2':5,6]pyrido[3,4-b]pyrazin-3-one (250 mg, crude product) and 2-chloro-4-((4-methylpyridin-2-yl)oxy)benzaldehyde (250 mg, 1.012 mmol) were dissolved in methanol (20.0 mL), and the reaction was cooled to 0° C., and potassium hydroxide (220 mg, 3.937 mmol) was added thereto. The reaction was stirred at room temperature for 6 hours. The reaction solution was poured into saturated aqueous ammonium chloride solution (30 mL), and the pH of the reaction solution was adjusted to 8, and the reaction solution was extracted with ethyl acetate (150 mL). The organic phase was washed with saturated brine (70 mL), dried and concentrated to obtain 9-((2-chloro-4-((4-methylpyridin-2-yl)oxy)phenyl)(hydroxyl)methyl)-2-(methoxymethyl)-2,4-dimethyl-1,2,4,7-tetrahydro-3H-pyrrolo[3',2':5,6]pyrido[3,4-b]pyrazin-3-one (350 mg, crude product) as a pale yellow solid. ES-API: $[M+H]^+$=508.1.

Step 7: 9-((2-Chloro-4-((4-methylpyridin-2-yl)oxy)phenyl)(hydroxyl)methyl)-2-(methoxymethyl)-2,4-dimethyl-1,2,4,7-tetrahydro-3H-pyrrolo[3',2':5,6]pyrido[3,4-b]pyrazin-3-one (330 mg, crude product) was dissolved in tetrahydrofuran (20 mL), and 2,3-dichloro-5,6-dicyano-1,4-benzoquinone (350 mg, 1.542 mmol) was added thereto, and the reaction was stirred at room temperature for 2 hours. The reaction solution was added with saturated sodium bicarbonate solution (60 mL), and extracted with ethyl acetate (80 mL). The organic phase was washed with saturated brine (60 mL), dried over anhydrous sodium sulfate, concentrated, and the crude product was purified by preparative HPLC to obtain 9-(2-chloro-4-((4-methylpyridin-2-yl)oxy)benzoyl)-2-(methoxymethyl)-2,4-dimethyl-1,2,4,7-tetrahydro-3H-pyrrolo[3',2':5,6]pyrido[3,4-b]pyrazin-3-one formate (50 mg, 3-step yield: 17.6%) as a pale yellow solid, ES-API: $[M+H]^+=506.2$. $^1H$ NMR (400 MHz, DMSO-$d_6$) δ 12.60 (s, 1H), 8.61 (s, 1H), 8.09 (d, J=5.1 Hz, 1H), 7.96 (s, 1H), 7.75-7.57 (m, 2H), 7.39 (d, J=2.2 Hz, 1H), 7.20 (dd, J=8.4, 2.2 Hz, 1H), 7.07 (d, J=5.1 Hz, 1H), 6.99 (s, 1H), 3.65 (d, J=9.6 Hz, 1H), 3.51 (d, J=9.6 Hz, 1H), 3.38 (s, 4H), 3.29 (s, 3H), 2.37 (s, 3H), 1.39 (s, 3H).

Embodiment 187: Synthesis of Z72

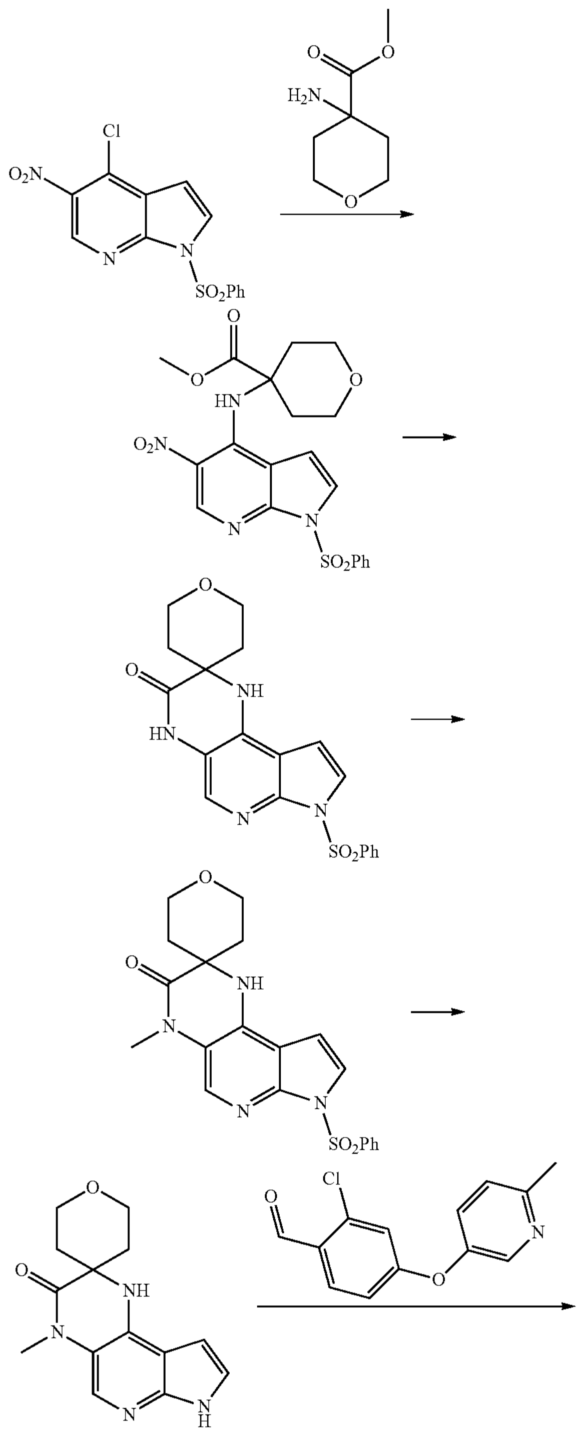

-continued

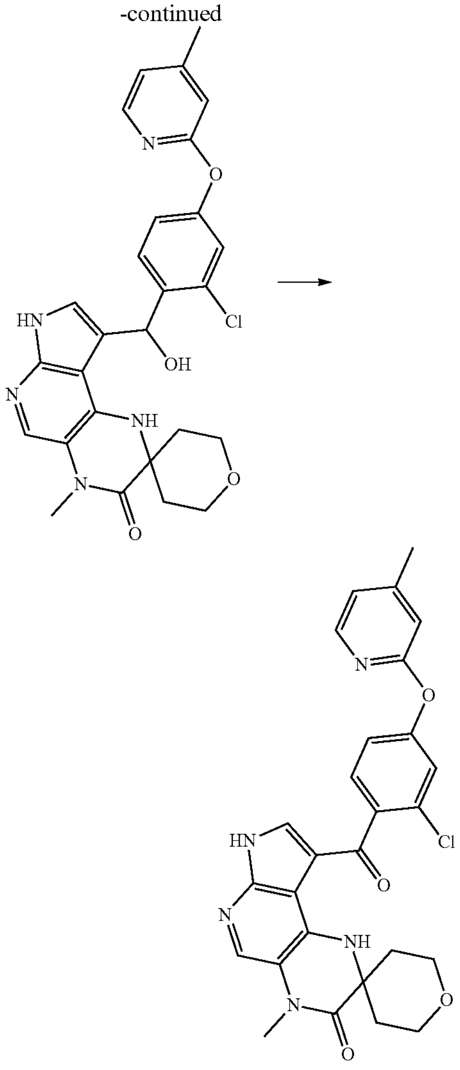

Z72

Step 1: To a microwave tube containing a mixture of 4-chloro-5-nitro-1-(phenylsulfonyl)-1H-pyrrolo[2,3-b]pyridine (500 mg, 1.48 mmol), methyl 4-aminotetrahydro-2H-pyran-4-carboxylate (353 mg, 2.22 mmol) and dry N,N-diisopropylethylamine (954 mg, 7.4 mmol) was added dry N,N-dimethylacetamide (8 mL), heated at 115° C. under microwave irradiation and reacted for 2 hours. The mixture was added with ethyl acetate (100 mL), washed with water (30 mL×2) and saturated brine (30 mL×1) in turn, dried over anhydrous sodium sulfate, concentrated, and the crude product was purified by a flash silica gel column (petroleum ether/ethyl acetate=40/60) to obtain methyl 4-((5-nitro-1-(phenylsulfonyl)-1H-pyrrolo[2,3-b]pyridin-4-yl)amino)tetrahydro-2H-pyran-4-carboxylate (560 mg, yield: 82%). ES-API: $[M+H]^+=461.1$.

Step 2: To a flask containing 4-((5-nitro-1-(phenylsulfonyl)-1H-pyrrolo[2,3-b]pyridin-4-yl)amino)tetrahydro-2H-pyran-4-carboxylate (500 mg, 1.08 mmol) was added iron powder (1.21 g, 21.7 mmol) and acetic acid (10 mL), and heated in an oil bath at 80° C. and reacted for 3 hours. The mixture was added with ethyl acetate (100 mL), washed with water (30 mL×2) and saturated brine (30 mL×1) in turn, dried over anhydrous sodium sulfate, concentrated, and the crude product was purified by a flash silica gel column (petroleum ether/ethyl acetate=10/90) to obtain 7'-(phenylsulfonyl)-2,3,4',5,6,7'-hexahydrospiro[pyran-4,2'-pyrrolo[3',2':5,6]pyrido[3,4-b]pyrazin]-3'(1'H)-one (300 mg, yield: 69.7%). ES-API: $[M+H]^+$=399.1.

Step 3: To a solution of N,N-dimethylformamide (8 mL) containing 7'-(phenylsulfonyl)-2,3,4',5,6,7'-hexahydrospiro[pyran-4,2'-pyrrolo[3',2':5,6]pyrido[3,4-b]pyrazin]-3'(1'H)-one (300 mg, 0.75 mmol) was added iodomethane (852 mg, 6.0 mmol) and potassium carbonate (621 mg, 4.5 mmol), and heated in an oil bath at 40° C. and reacted for 4 hours. The mixture was added with ethyl acetate (100 mL), washed with water (30 mL×2) and saturated brine (30 mL×1) in turn, dried over anhydrous sodium sulfate, concentrated, and the crude product was purified by a flash silica gel column (petroleum ether/ethyl acetate=10/90) to obtain 4'-methyl-7'-(phenylsulfonyl)-2,3,4',5,6,7'-hexahydrospiro[pyran-4,2'-pyrrolo[3',2':5,6]pyrido[3,4-b]pyrazin]-3'(1'H)-one (200 mg, yield: 64.7%). ES-API: $[M+H]^+$=413.1.

Step 4: To a flask containing 4'-methyl-7'-(phenylsulfonyl)-2,3,4',5,6,7'-hexahydrospiro[pyran-4,2'-pyrrolo[3',2':5,6]pyrido[3,4-b]pyrazin]-3'(1'H)-one (200 mg, 0.485 mmol) was added sodium hydroxide (136 mg, 3.39 mmol), methanol (12 mL) and water (3 mL), and heated in an oil bath at 65° C. and reacted for 15 hours. The mixture was added with ethyl acetate (30 mL), washed with water (1 mL×2) and saturated brine (10 mL×1) in turn, dried over anhydrous sodium sulfate, concentrated, and the crude product was purified by preparative thin-layer chromatography (dichloromethane/methanol=10/1) to obtain a product 4'-methyl-2,3,4',5,6,7'-hexahydrospiro[pyran-4,2'-pyrrolo[3',2':5,6]pyrido[3,4-b]pyrazin]-3'(1'H)-one (65 mg, yield: 49.2%). ES-API: $[M+H]^+$=273.3.

Step 5: To a solution of methanol (3 mL) containing 4'-methyl-2,3,4',5,6,7'-hexahydrospiro[pyran-4,2'-pyrrolo[3',2':5,6]pyrido[3,4-b]pyrazin]-3'(1'H)-one (65 mg, 0.239 mmol) was added 2-chloro-4-((6-methylpyridin-3-yl)oxy)benzaldehyde (117 mg, 0.478 mmol) and potassium hydroxide (67 mg, 1.19 mmol), and reacted at room temperature for 5 hours. 1M dilute hydrochloric acid was added dropwise to adjust the pH of the reaction mixture to 7-8. The mixture was added with ethyl acetate (100 mL), washed with water (30 mL×2) and saturated brine (30 mL×1) in turn, dried over anhydrous sodium sulfate, filtered and concentrated to obtain 9'-((2-chloro-4-((5-methylpyridin-2-yl)oxy)phenyl)(hydroxy)methyl)-4'-methyl-2,3,4',5,6,7'-hexahydrospiro[pyran-4,2'-pyrrolo[3',2':5,6]pyrido[3,4-b]pyrazin]-3'(1'H)-one (130 mg, crude product). ES-API: $[M+H]^+$=520.1.

Step 6: 9'-((2-Chloro-4-((5-methylpyridin-2-yl)oxy)phenyl)(hydroxy)methyl)-4'-methyl-2,3,4',5,6,7'-hexahydrospiro[pyran-4,2'-pyrrolo[3',2':5,6]pyrido[3,4-b]pyrazin]-3'(1'H)-one (130 mg, crude product) was dissolved in a solution of 1,4-dioxane (5 mL) and water (1 mL), and 2,3-dichloro-5,6-dicyanobenzoquinone (108 mg, 0.478 mmol) was slowly added thereto and reacted at room temperature for 0.5 hours. The reaction was quenched by dropping sodium bisulfite solution (5 mL). The mixture was added with ethyl acetate (20 mL), washed with water (10 mL×2) and saturated brine (10 mL×1) in turn, dried over anhydrous sodium sulfate, filtered and concentrated, and the crude product was purified by HPLC to obtain 9'-(2-chloro-4-((4-methylpyridin-2-yl)oxy)benzoyl)-4'-methyl-2,3,4',5,6,7'-hexahydrospiro[pyran-4,2'-pyrrolo[3',2':5,6]pyrido[3,4-b]pyrazin]-3'(1'H)-one (80 mg, 2-step yield: 65%). ES-API: $[M+H]^+$=518.1. $^1H$ NMR (400 MHz, DMSO-$d_6$) δ 12.70 (s, 1H), 9.07 (s, 1H), 8.09 (d, J=5.1 Hz, 1H), 8.06 (s, 1H), 7.72 (s, 1H), 7.64 (d, J=8.3 Hz, 1H), 7.41 (d, J=2.3 Hz, 1H), 7.22 (dd, J=8.3, 2.2 Hz, 1H), 7.07 (d, J=5.2 Hz, 1H), 7.00 (s, 1H), 3.84 (dt, J=11.4, 3.7 Hz, 2H), 3.81-3.70 (m, 2H), 3.41 (s, 3H), 2.37 (s, 3H), 2.09 (td, J=12.8, 5.1 Hz, 2H), 1.61 (d, J=13.4 Hz, 2H).

Embodiment 188: Synthesis of Z147

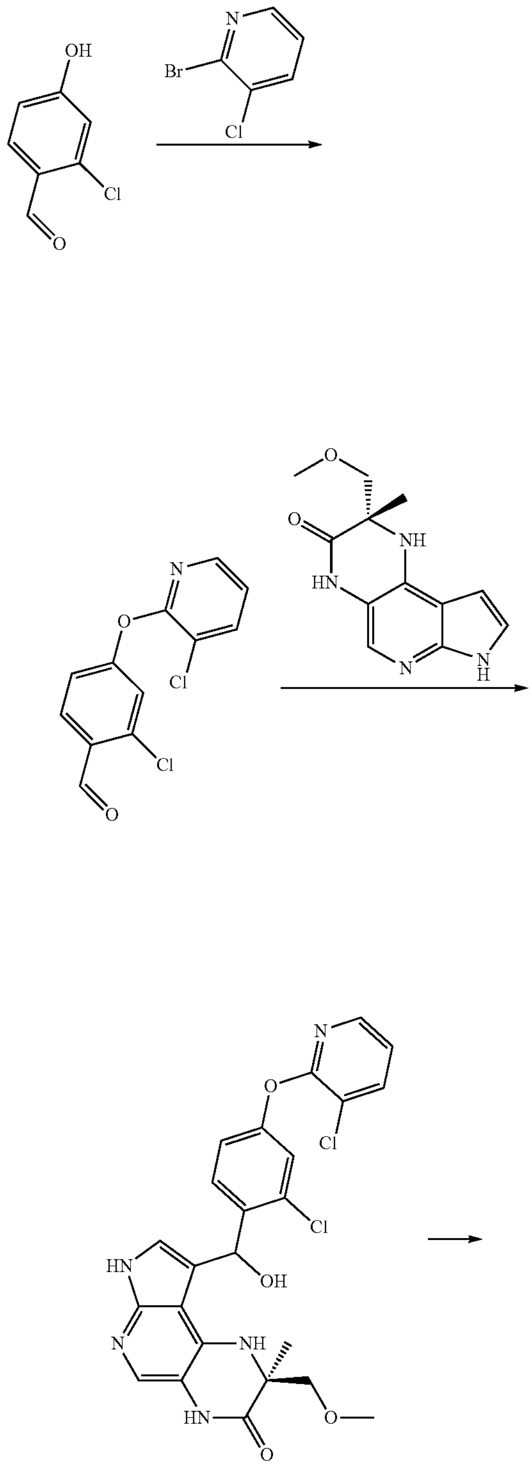

-continued

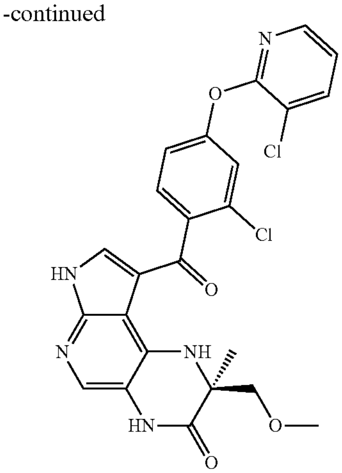

Z147

Step 1: 2-Chloro-4-hydroxybenzaldehyde (3.0 g, 19.23 mmol), 2-bromo-3-chloropyridine (2.40 g, 12.56 mmol), cuprous iodide (350 mg, 1.742 mmol), potassium phosphate (9.0 g, 42.45 mmol) and L-proline (0.50 g, 4.343 mmol) were dissolved in dry N,N-dimethylacetamide (70 mL), and heated to 115° C. under nitrogen atmosphere for 24 hours. After the reaction was completed, the cooling solution was added with ethyl acetate (200 mL), and washed with saturated brine (80 mL×3). The ethyl acetate phase was dried over anhydrous sodium sulfate, filtered and evaporated to dryness by rotary evaporation under reduced pressure. The crude product was purified by a flash silica gel column [PE:EA=100:0-70:30, (v/v)] to obtain 2-chloro-4-((3-chloropyridin-2-yl)oxy)benzaldehyde (675 mg, yield: 20%). ES-API: $[M+H]^+$=268.0.

Step 2: (S)-2-(Methoxymethyl)-2-methyl-1,2,4,7-tetrahydro-3H-pyrrolo[3',2':5,6]pyrido[3,4-b]pyrazin-3-one (550 mg, 0.6796 mmol) and 2-chloro-4-((3-chloropyridin-2-yl)oxy)benzaldehyde (400 mg, 1.498 mmol) were dissolved in methanol (25.0 mL), and the reaction was cooled to 0° C., and potassium hydroxide (266 mg, 4.757 mmol) was added thereto, and the reaction was stirred at room temperature for 6 hours. The reaction solution was poured into saturated aqueous ammonium chloride solution (30 mL), and the pH of the reaction solution was adjusted to 8, and the reaction solution was extracted with ethyl acetate (100 mL). The organic phase was washed with saturated brine (60 mL), dried over anhydrous sodium sulfate and concentrated to obtain (2S)-9-((2-chloro-4-((3-chloropyridin-2-yl)oxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (190 mg, yield: 54%) as apale yellow solid. ES-API: $[M+H]^+$=514.2.

Step 3: (2S)-9-((2-Chloro-4-((3-chloropyridin-2-yl)oxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (190 mg, 0.3702 mmol) was dissolved in tetrahydrofuran (20 mL), and 2,3-dichloro-5,6-dicyano-1,4-benzoquinone (170 mg, 0.7404 mmol) was added thereto, and the reaction was stirred at room temperature for 2 hours. The reaction solution was added with saturated sodium bicarbonate solution (63 mL), and extracted with ethyl acetate (88 mL). The organic phase was washed with saturated brine (60 mL), dried over anhydrous sodium sulfate, then concentrated, and the crude product was purified by preparative HPLC to obtain (S)-9-(2-chloro-4-((3-chloropyridin-2-yl)oxy)benzoyl)-2-(methoxymethyl)-2-methyl-1,2,4,7-tetrahydro-3H-pyrrolo[3',2':5,6]pyrido[3,4-b]pyrazin-3-one (110 mg, yield: 57%) as a pale yellow solid. ES-API: $[M+H]^+$=512.0. $^1H$ NMR (400 MHz, DMSO-$d_6$) δ 12.48 (s, 1H), 10.51 (s, 1H), 8.28 (s, 1H), 8.20-8.16 (m, 1H), 8.13 (dd, J=7.8, 1.6 Hz, 1H), 7.70 (s, 1H), 7.62 (d, J=8.4 Hz, 1H), 7.56 (s, 1H), 7.50 (d, J=2.2 Hz, 1H), 7.31-7.24 (m, 2H), 3.65 (d, J=9.5 Hz, 1H), 3.49 (d, J=9.6 Hz, 1H), 3.30 (s, 3H), 1.40 (s, 3H).

Embodiment 189: Synthesis of Z165

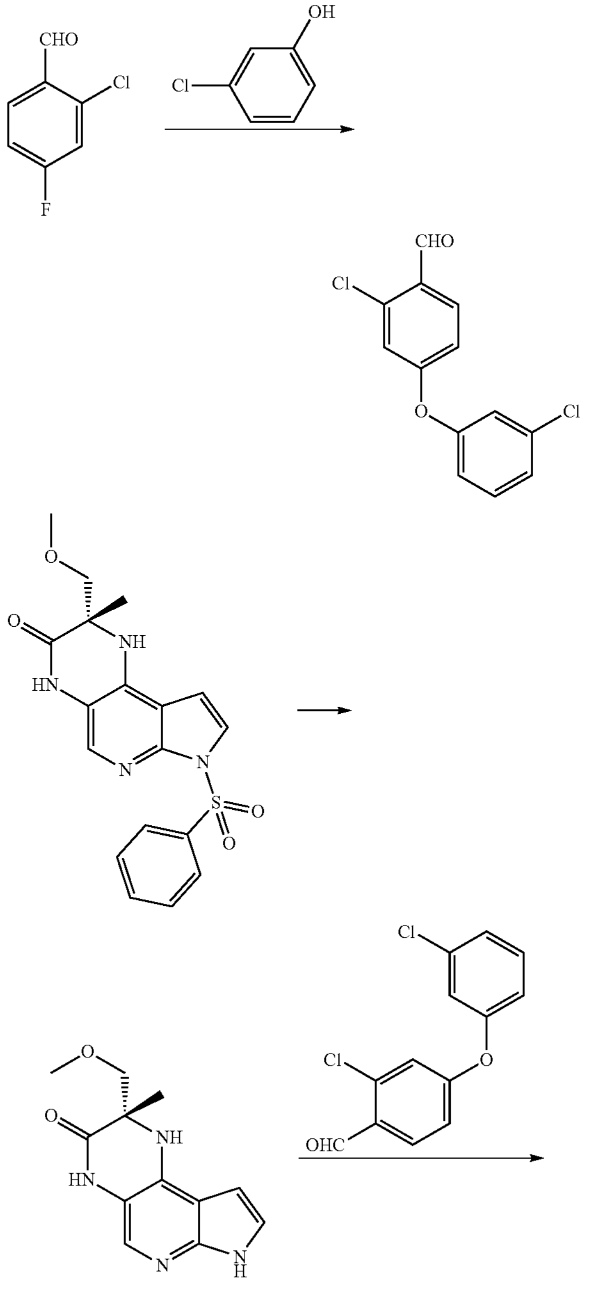

-continued

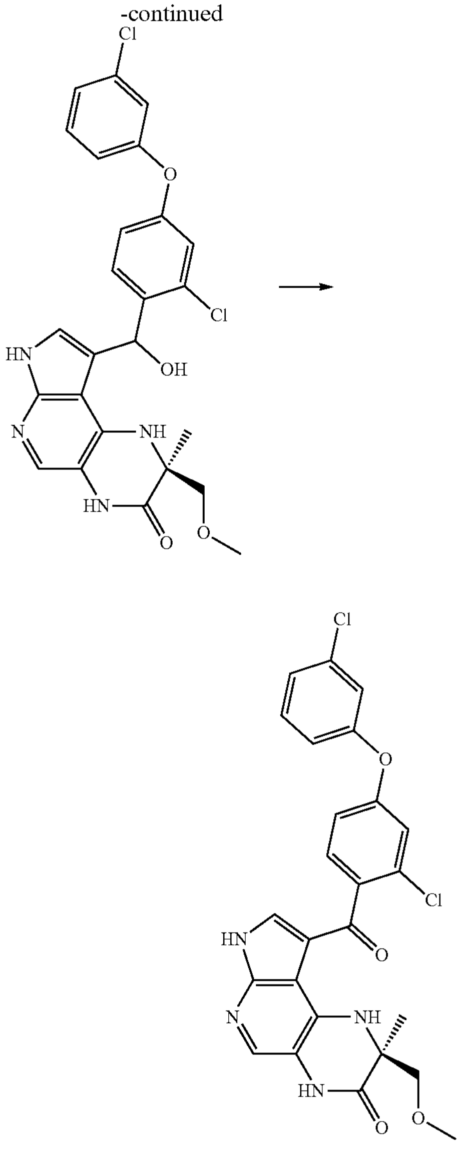

Z165

Step 1: 2-Chloro-4-fluorobenzaldehyde (1.58 g, 10.0 mmol) and 3-chlorophenol (1.20 g, 9.375 mmol) were dissolved in dry N,N-dimethylacetamide (20 mL), and cesium carbonate (10.0 g, 30.69 mmol) was added thereto, and the mixture was heated to 90° C. and reacted for 2 hours under nitrogen atmosphere. After the reaction was completed, the cooling solution was added with ethyl acetate (200 mL), and washed with saturated brine (80 mL×3). The ethyl acetate phase was dried with anhydrous sodium sulfate, filtered and evaporated to dryness by rotary evaporation under reduced pressure to obtain 2-chloro-4-(3-chlorophenoxy)benzaldehyde (2.60 g, crude product). ES-API: $[M+H]^+$=267.1/269.0.

Step 2: (S)-2-(Methoxymethyl)-2-methyl-7-(phenylsulfonyl)-1,2,4,7-tetrahydro-3H-pyrrolo[3',2':5,6]pyrido[3,4-b]pyrazin-3-one (1.40 g, 3.570 mmol) was dissolved in methanol (36 mL), tetrahydrofuran (9 mL) and water (6 mL), and sodium hydroxide (1.01 g, 24.99 mmol) was added thereto, stirred and reacted at 65° C. for 7 hours. To the reaction solution was added water (20 mL) and saturated ammonium chloride solution (15 mL), and the mixture was extracted with ethyl acetate (200 mL). The organic phase was washed with saturated sodium bicarbonate solution (30 mL), saturated brine (80 mL) in turn, dried over anhydrous sodium sulfate and concentrated to obtain (S)-2-(methoxymethyl)-2-methyl-1,2,4,7-tetrahydro-3H-pyrrolo[3',2':5,6]pyrido[3,4-b]pyrazin-3-one (0.58 g, yield: 66%) as a pale white solid. ES-API: $[M+H]^+$=247.1.

Step 3: (S)-2-(Methoxymethyl)-2-methyl-1,2,4,7-tetrahydro-3H-pyrrolo[3',2':5,6]pyrido[3,4-b]pyrazin-3-one (223 mg, 0.9065 mmol) and 2-chloro-4-(3-chlorophenoxy)benzaldehyde (484 mg, 1.8127 mmol) were dissolved in methanol (25.0 mL), and the reaction was cooled to 0° C., and potassium hydroxide (355 mg, 6.345 mmol) was added thereto. The reaction was stirred at room temperature for 6 hours. The reaction solution was poured into saturated aqueous ammonium chloride solution (30 mL), and the pH of the reaction solution was adjusted to 8, and the reaction solution was extracted with ethyl acetate (100 mL). The organic phase was washed with saturated brine (60 mL), dried over anhydrous sodium sulfate and concentrated to obtain (2S)-9-((2-chloro-4-(3-chlorophenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (215 mg, 2-step yield: 46%) as a pale yellow solid. ES-API: $[M+H]^+$=513.1/515.0.

Step 4: (2S)-9-((2-Chloro-4-(3-chlorophenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (213 mg, 0.4152 mmol) was dissolved in tetrahydrofuran (20 mL), and 2,3-dichloro-5,6-dicyano-1,4-benzoquinone (190 mg, 0.8304 mmol) was added thereto, and the reaction was stirred at room temperature for 2 hours. The reaction solution was added with saturated sodium bicarbonate solution (63 mL), and extracted with ethyl acetate (88 mL). The organic phase was washed with saturated brine (60 mL), dried over anhydrous sodium sulfate, then concentrated, and the crude product was purified by preparative HPLC to obtain (S)-9-(2-chloro-4-(3-chlorophenoxy)benzoyl)-2-(methoxymethyl)-2-methyl-1,2,4,7-tetrahydro-3H-pyrrolo[3',2':5,6]pyrido[3,4-b]pyrazin-3-one (80.8 mg, yield: 40%) as a pale yellow solid. ES-API: $[M+H]^+$=511.1/513.2. $^1H$ NMR (500 MHz, DMSO-$d_6$) δ 12.48 (s, 1H), 10.49 (s, 1H), 8.27 (s, 1H), 7.70 (s, 1H), 7.65 (s, 1H), 7.58 (d, J=8.3 Hz, 1H), 7.48 (t, J=8.2 Hz, 1H), 7.29 (s, 3H), 7.15 (d, J=7.8 Hz, 1H), 7.09 (d, J=7.9 Hz, 1H), 3.65 (d, J=9.5 Hz, 1H), 3.48 (d, J=9.6 Hz, 1H), 3.30 (s, 3H), 1.39 (s, 3H).

Embodiment 190: Synthesis of Z169

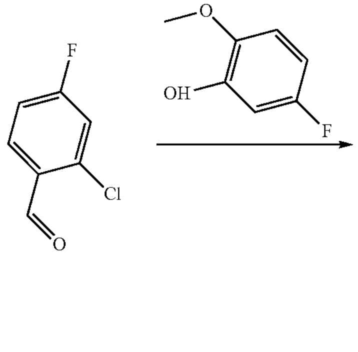

-continued

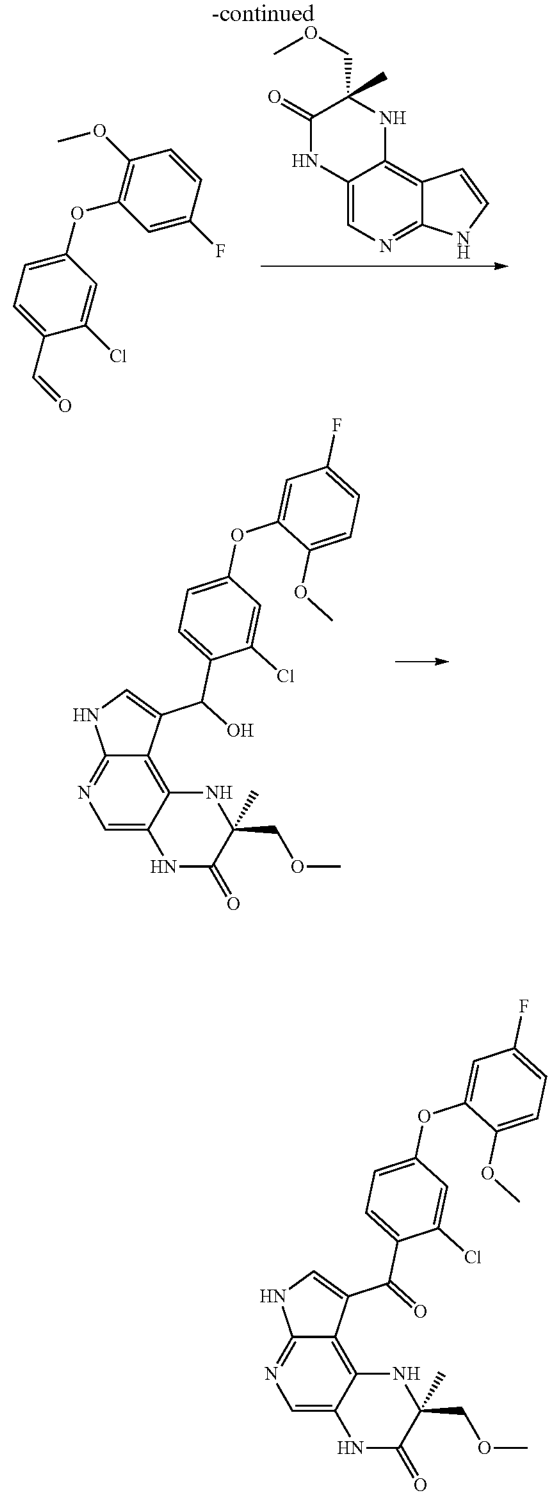

Z169

Step 1: 2-Chloro-4-fluorobenzaldehyde (1.58 g, 10.0 mmol), 5-fluoro-2-methoxyphenol (1.40 g, 9.856 mmol) and cesium carbonate (9.60 g, 29.46 mmol) were dissolved in dry N,N-dimethylacetamide (30.0 mL), heated to 95° C. and reacted for 2 hours under nitrogen atmosphere. After the reaction was completed, the cooling solution was added with ethyl acetate (200 mL), and the mixture was washed with saturated brine (80 mL×3). The ethyl acetate phase was dried over anhydrous sodium sulfate, filtered and evaporated to dryness by rotary evaporation under reduced pressure. The crude product was purified by a flash silica gel column [PE:EA=100:0-70:30, (v/v)] to obtain 2-chloro-4-(5-fluoro-2-methoxyphenoxy)benzaldehyde (2.60 g, yield: 94%). ES-API: $[M+H]^+$=281.0.

Step 2: (S)-2-(Methoxymethyl)-2-methyl-1,2,4,7-tetrahydro-3H-pyrrolo[3',2':5,6]pyrido[3,4-b]pyrazin-3-one (200 mg, 0.8130 mmol) and 2-chloro-4-(5-fluoro-2-methoxyphenoxy)benzaldehyde (300 mg, 1.070 mmol) were dissolved in methanol (25.0 mL), and the reaction was cooled to 0° C., and potassium hydroxide (318 mg, 5.691 mmol) was added thereto, and the reaction was stirred at room temperature for 6 hours. The reaction solution was poured into saturated aqueous ammonium chloride solution (30 mL), and the pH of the reaction solution was adjusted to 8, and the reaction solution was extracted with ethyl acetate (100 mL). The organic phase was washed with saturated brine (60 mL), dried over anhydrous sodium sulfate and concentrated to obtain (2S)-9-((2-chloro-4-(5-fluoro-2-methoxyphenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (260 mg, yield: 60%) as a pale yellow solid. ES-API: $[M+H]^+$=527.2.

Step 3: (2S)-9-((2-Chloro-4-(5-fluoro-2-methoxyphenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (260 mg, 0.4941 mmol) was dissolved in tetrahydrofuran (20 mL), and 2,3-dichloro-5,6-dicyano-1,4-benzoquinone (224 mg, 0.9882 mmol) was added thereto, and the reaction was stirred at room temperature for 2 hours. The reaction solution was added with saturated sodium bicarbonate solution (80 mL), and extracted with ethyl acetate (100 mL). The organic phase was washed with saturated brine (60 mL), dried over anhydrous sodium sulfate, then concentrated, and the crude product was purified by preparative HPLC to obtain (S)-9-(2-chloro-4-(5-fluoro-2-methoxyphenoxy)benzoyl)-2-(methoxymethyl)-2-methyl-1,2,4,7-tetrahydro-3H-pyrrolo[3',2':5,6]pyrido[3,4-b]pyrazin-3-one (54.03 mg, yield: 21%) as a pale yellow solid. ES-API: $[M+H]^+$=525.1. $^1H$ NMR (500 MHz, DMSO-$d_6$) δ 12.46 (s, 1H), 10.51 (s, 1H), 8.28 (s, 1H), 7.69 (s, 1H), 7.60-7.47 (m, 2H), 7.30-7.05 (m, 4H), 6.91 (dd, J=8.4, 2.3 Hz, 1H), 3.77 (s, 3H), 3.64 (d, J=9.5 Hz, 1H), 3.47 (d, J=9.5 Hz, 1H), 3.29 (s, 3H), 1.38 (s, 3H).

Embodiment 191: Synthesis of Z178

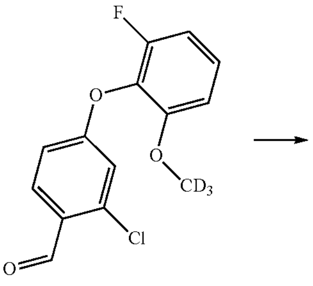

-continued

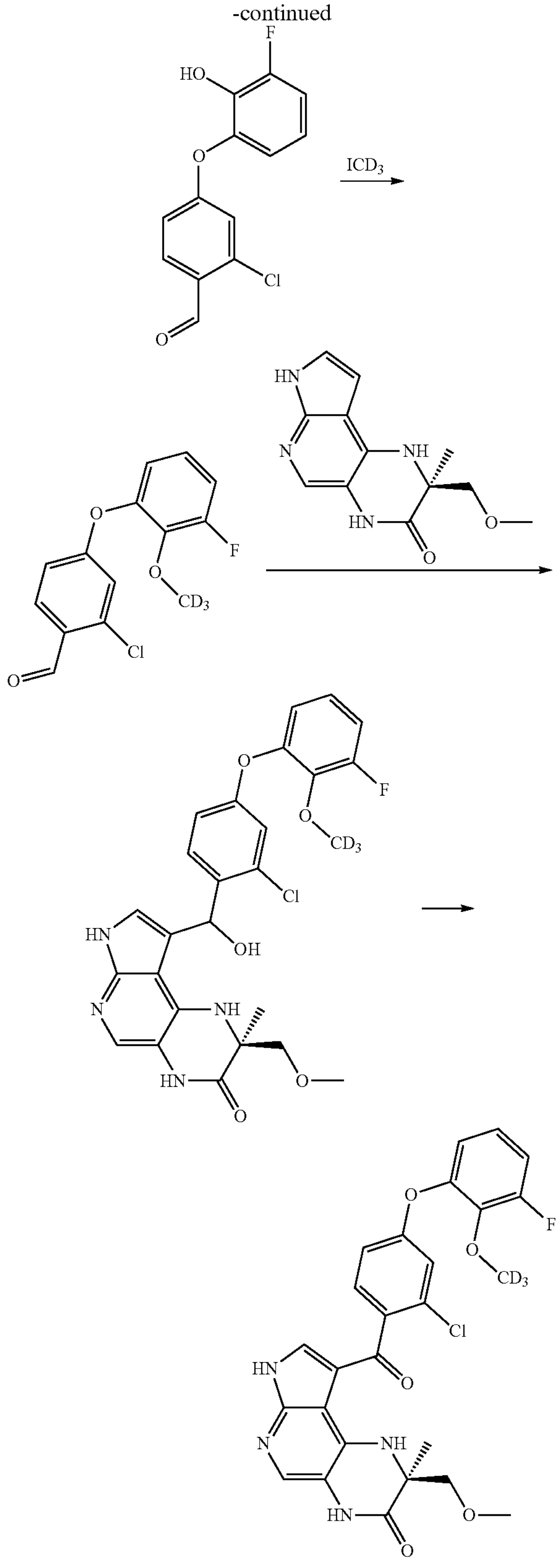

Z178

Step 1: To a 100 mL reaction flask was added 2-chloro-4-(2-fluoro-6-methoxyphenoxy)benzaldehyde (800 mg, 2.86 mmol) and dichloromethane (10 mL). The system was cooled to 0° C., and a dichloromethane solution of boron tribromide (8.6 mL, 8.6 mmol, 1 M) was added dropwise thereto. The reaction was stirred at room temperature for 2 hours. The reaction solution was poured into ice saturated sodium bicarbonate solution (50 mL), extracted with dichloromethane (50 mL×3), and the organic phase was dried over anhydrous sodium sulfate, concentrated, and the crude product was purified by a flash silica gel column (0-20% of ethyl acetate/petroleum ether) to obtain 2-chloro-4-(3-fluoro-2-hydroxyphenoxy)benzaldehyde (500 mg, crude product) as a yellow solid. ES-API: $[M+H]^+$=267.1.

Step 2: To a 100 mL round-bottom flask was added 2-chloro-4-(3-fluoro-2-hydroxyphenoxy)benzaldehyde (400 mg, 1.5 mmol), deuterated iodomethane (654 mg, 14.5 mmol), potassium carbonate (414 mg, 3.05 mmol) and N,N-dimethylformamide (16 mL). The reaction was stirred at 40° C. for 3 hours. The reaction was quenched with water (50 mL), extracted with ethyl acetate (50 mL×3). The organic phase was dried over anhydrous sodium sulfate, concentrated, and the crude product was purified by a flash silica gel column (0-20% of ethyl acetate/petroleum ether) to obtain 2-chloro-4-(3-fluoro-2-(methoxy-$d_3$)phenoxy)benzaldehyde (64 mg, yield: 15%) as a yellow solid. ES-API: $[M+H]^+$=284.1. $^1H$ NMR (500 MHz, DMSO-$d_6$): 10.21 (s, 1H), 7.87 (d, J=8.5 Hz, 1H), 7.30-7.27 (m, 1H), 7.23-7.20 (m, 1H), 7.17 (d, J=2.5 Hz, 1H), 7.11-7.09 (m, 1H), 7.02 (dd, J=9.0, 2.5 Hz, 1H).

Step 3: To a 100 mL round-bottom flask was added 2-chloro-4-(3-fluoro-2-(methoxy-$d_3$)phenoxy)benzaldehyde (64 mg, 0.22 mmol), (S)-2-(methoxymethyl)-2-methyl-1,2,4,7-tetrahydro-3H-pyrrolo[3',2':5,6]pyrido[3,4-b]pyrazin-3-one (113 mg, 0.46 mmol), potassium hydroxide (180 mg, 3.22 mmol) and methanol (6 mL). The reaction was stirred at room temperature for 24 hours. The reaction was quenched with 2 N hydrochloric acid (3 mL) and water (20 mL), extracted with ethyl acetate (50 mL×3). The organic phase was dried over anhydrous sodium sulfate and concentrated to obtain (2S)-9-((2-chloro-4-(3-fluoro-2-(methoxy-$d_3$)phenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (100 mg, crude product). ES-API: $[M+H]^+$=530.2.

Step 4: To a round-bottom flask was added (2S)-9-((2-chloro-4-(3-fluoro-2-(methoxy-$d_3$)phenoxy)phenyl)(hydroxy)methyl)-2-(methoxymethyl)-2-methyl-1,2,4,7-tetrahydro-3H-pyrrolo[3',2':5,6]pyrido[3,4-b]pyrazin-3-one (100 mg, crude product) and tetrahydrofuran (5 mL) at 0° C. To the reaction solution was added 2,3-dichloro-5,6-dicyanobenzoquinone (100 mg, 0.43 mmol). The reaction was stirred at room temperature for 30 minutes. The reaction was quenched with saturated aqueous sodium bicarbonate solution (20 mL), and extracted with dichloromethane (50 mL×3). The organic phase was dried over anhydrous sodium sulfate, concentrated, and the crude product was purified by preparative HPLC to obtain (S)-9-(2-chloro-4-(3-fluoro-2-(methoxy-$d_3$)phenoxy)benzoyl)-2-(methoxymethyl)-2-methyl-1,2,4,7-tetrahydro-3H-pyrrolo[3',2':5,6]pyrido[3,4-b]pyrazin-3-one (25 mg, 2-step yield: 21%). ES-API: $[M+H]^+$=528.2.

Test Embodiment 1: BTK and BTK C481S Enzyme Experiment

A 3-fold gradient concentration stock solution of 1000× compound was prepared using DMSO and diluted 100-fold to 10× compound stock solution using reaction buffer (50 mM HEPES, pH 7.5, 0.0015% Briji-35, 2 mM DTT, 10 mM $MgCl_2$), and the 10× compound stock solution was transferred to a 384-well plate. Enzyme reactions were set up with BTK Kinase Enzyme System (Promega Catalog #V2941) or BTK (C481S) Kinase Enzyme System (Promega Catalog #VA7033). First, a 2× enzyme solution containing 10 nM BTK or 10 nM BTK C481S was prepared with reaction buffer and added to the plate, and incubated with the compound for 10 minutes. Then, a 2.5× substrate solution containing ATP (125 μM) and Poly(Glu4, Tyr1) (0.05 μg/μL) was prepared with reaction buffer and added to the plate, and reacted at 20° C. for 90 minutes. Finally, the kinase activity was detected according to the experimental steps provided by ADP-Glo™ kinase Assay Kit (Promega, #V9101), and finally the luminescence chemiluminescence value was read. DMSO was used as the maximum signal value, and adding no enzyme was used as the minimum signal value. The inhibition rate of the compound (%)=(maximum signal value−compound signal value)/(maximum signal value−minimum signal value)×100% was calculated. The compound gradient dilution concentration and the corresponding inhibition rate of the enzyme activity were fit by using XLFit four-parameter method, and $IC_{50}$ value was calculated. As can be seen from the experimental results, the compounds of the present disclosure have a relatively high inhibitory activity to BTK or BTK (C481S) kinase, and the $IC_{50}$ values are less than 500 nM (such as 0.1 nM to 500 nM); the $IC_{50}$ values of some compounds are even less than 100 nM (such as 0.1 nM to 100 nM), or less than 50 nM (such as 0.1 nM to 50 nM), and even less than 10 nM (such as 0.1 nM to 10 nM). The experimental results of some of the compounds are shown in Table 1.

TABLE 1

| No. | BTK(WT) $IC_{50}$ (nM) | BTK(C481S) $IC_{50}$ (nM) |
|---|---|---|
| Z1 | 41.2 | 18.9 |
| Z1-1 | 67.1 | 23.6 |
| Z1-2 | 64.7 | 27.2 |
| Z2 | 19.4 | 12.3 |
| Z3 | 48.9 | 35.2 |
| Z2-1 | 19.0 | 9.2 |
| Z2-2 | 25.4 | 10.9 |
| Z4 | 17.1 | 10.3 |
| Z5 | 27.8 | 12.0 |
| Z6 | 19.3 | 14.1 |
| Z7 | 28.3 | 17.8 |
| Z8 | 73.6 | 27.9 |
| Z9 | 22.8 | 14.5 |
| Z4-1 | 17.0 | 6.8 |
| Z4-2 | 46.1 | 19.8 |
| Z10 | 70.2 | 25.4 |
| Z11 | 54.4 | 21.3 |
| Z9-1 | 20.0 | 20.0 |
| Z9-2 | 9.5 | 10.8 |
| Z12 | 26.4 | 45.8 |
| Z13-1 | 11.4 | 9.8 |
| Z13-2 | 40.0 | 23.2 |
| Z14 | 7.6 | 5.1 |
| Z15 | 57.4 | 71.7 |
| Z16-1 | 7.6 | 9.1 |
| Z16-2 | 5.0 | 5.6 |
| Z17 | 345.3 | 273.4 |
| Z63 | 185.1 | 128.6 |
| Z18 | 144.8 | 87.7 |
| Z19 | 23.1 | 12.6 |
| Z22 | 27.1 | 7.2 |
| Z55 | 142.0 | 120.3 |
| Z56 | 22.9 | 18.4 |
| Z74 | 36.0 | 34.8 |
| Z73 | 22.8 | 14.5 |
| Z69 | 34.8 | 28.0 |
| Z66 | 16.4 | 9.3 |

TABLE 1-continued

| No. | BTK(WT) $IC_{50}$ (nM) | BTK(C481S) $IC_{50}$ (nM) |
|---|---|---|
| Z67 | 40.0 | 18.3 |
| Z71 | 20.2 | 21.3 |
| Z24-1 | 3.5 | 3.7 |
| Z24-2 | 5.0 | 4.7 |
| Z52-1 | 23.8 | 24.2 |
| Z52-2 | 135.7 | 92.3 |
| Z64 | 6.5 | 13.3 |
| Z24-a | 5.5 | 8.4 |
| Z24-b | 4.2 | 5.8 |
| Z24-c | 3.2 | 3.0 |
| Z24-d | 3.4 | 3.1 |
| Z66-1 | 6.7 | 3.8 |
| Z66-2 | 12.7 | 8.6 |
| Z67-1 | 9.6 | 10.3 |
| Z67-2 | 20.4 | 17.8 |
| Z71-1 | 8.5 | 8.3 |
| Z71-2 | 23.5 | 19.2 |
| Z69-1 | 13.9 | 21.2 |
| Z69-2 | 17.5 | 28.3 |
| Z25 | 6.0 | 4.9 |
| Z26 | 7.0 | 6.5 |
| Z85 | 15.2 | 18.5 |
| Z89 | 23.4 | 7.5 |
| Z120 | 4.3 | 2.0 |
| Z193 | 19.1 | 21.9 |
| Z195 | 3.9 | 3.9 |
| Z196 | 26.4 | 25.8 |
| Z198 | 17.4 | 15.1 |
| Z200 | 18.8 | 9.9 |
| Z202 | 23.8 | 27.8 |
| Z64-1 | 6.3 | 10.7 |
| Z169 | 8.5 | 9.0 |
| Z147 | 11.1 | 19.8 |
| Z65 | 30.6 | 31.2 |
| Z72 | 40.0 | 37.2 |
| Z204 | 34.0 | 28.9 |
| Z64-2 | 8.4 | 17.2 |
| Z73-1 | 15.3 | 29.5 |
| Z73-2 | 34.3 | 60.8 |
| Z124-1 | 24.5 | 30.1 |
| Z125-1 | 28.2 | 29.1 |
| Z126 | 5.7 | 13.4 |
| Z26-1 | 15.6 | 15.4 |
| Z26-2 | 23.6 | 17.5 |
| Z26-3 | 34.0 | 20.6 |
| Z26-4 | 35.9 | 28.5 |
| Z41-2a | 4.3 | 3.4 |
| Z41-2b | 7.9 | 6.1 |
| Z127-1 | 29.1 | 31.5 |
| Z189-1 | 50.4 | 60.3 |
| Z25-1 | 32.0 | 19.8 |
| Z25-2 | 14.7 | 8.7 |
| Z25-3 | 22.4 | 16.4 |
| Z131 | 26.9 | 37.8 |
| Z132 | 11.8 | 15.5 |
| Z133 | 28.8 | 38.4 |
| Z134 | 14.9 | 11.4 |
| Z135 | 58.9 | 88.8 |
| Z136 | 6.7 | 7.6 |
| Z137 | 12.9 | 10.3 |
| Z25-3a | 15.4 | 7.6 |
| Z25-3b | 15.1 | 10.0 |
| Z139 | 37.1 | 22.1 |
| Z140 | 26.5 | 18.2 |
| Z141 | 11.5 | 5.1 |
| Z142 | 35.2 | 19.7 |
| Z143 | 35.6 | 23.2 |
| Z144 | 11.7 | 16.8 |
| Z145 | 9.3 | 13.1 |
| Z146 | 10.0 | 16.3 |
| Z78-1 | 27.6 | 28.8 |
| Z78-2 | 10.2 | 17.4 |
| Z149 | 23.5 | 13.2 |
| Z153-1 | 45.8 | 26.0 |
| Z153-2 | 114.5 | 51.1 |
| Z155 | 8.6 | 10.6 |
| Z156 | 20.0 | 10.5 |

TABLE 1-continued

| No. | BTK(WT) $IC_{50}$ (nM) | BTK(C481S) $IC_{50}$ (nM) |
|---|---|---|
| Z157 | 15.2 | 10.8 |
| Z160 | 16.8 | 21.5 |
| Z161 | 10.6 | 12.5 |
| Z162 | 25.6 | 36.0 |
| Z163 | 10.6 | 16.5 |
| Z164 | 22.4 | 30.1 |
| Z166 | 34.0 | 59.4 |
| Z167 | 11.2 | 12.1 |
| Z168 | 4.5 | 6.6 |
| Z170 | 28.4 | 36.5 |
| Z171 | 68.1 | 104.8 |
| Z173 | 26.5 | 18.4 |
| Z174 | 76.6 | 114.8 |
| Z175 | 74.4 | 76.5 |
| Z122 | 64.1 | 70.5 |
| Z79 | 5.8 | 3.2 |
| Z177 | 6.4 | 11.1 |
| Z86 | 16.0 | 9.7 |
| Z113 | 61.8 | 61.1 |
| Z190 | 16.3 | 20.1 |
| Z194 | 47.3 | 77.4 |
| Z103 | 20.1 | 9.8 |
| Z197 | 3.0 | 1.3 |
| Z199 | 42.6 | 23.2 |
| Z201 | 121.8 | 214.9 |
| Z203 | 75.1 | 142.0 |
| Z178 | 36.2 | 42.3 |
| Z165 | 54.2 | 73.9 |
| Z41-1a | 3.6 | 4.1 |
| Z41-1b | 5.5 | 4.8 |
| Z51 | 36.5 | 39.6 |
| Z51-1 | 52.3 | 34.3 |
| Z51-2 | 32.6 | 20.8 |

Test Embodiment 2: p-BTK Cell Experiment

Day 1: HEK293 cells (ADDEXBIO, T0011001) at logarithmic growth phase were taken, digested with enzyme EDTA, collected and counted, and 2E6 cells were inoculated in a 10 cm culture dish and cultured overnight. Day 2: A mixed solution containing 6 μg of WT-BTK/C481S-BTK plasmid and 18 μL of FuGENE HD transfection reagent was prepared by using 1000 μL of Opti-MEM. After standing at room temperature for 10 minutes, the mixed solution was slowly added to the culture dish with a pipettor and cultured overnight. Day 3: The culture dish was taken out, and the cells were digested with enzyme EDTA, collected and counted, and 1E4 cells were inoculated in a 96-well cell culture plate and cultured overnight. A 3.16-fold gradient concentration stock solution of 1000× compound was prepared using DMSO, and placed at room temperature. Day 4: A prepared 1000× compound stock solution was taken, and diluted 200-fold to 5× compound stock solution with culture medium. 5× compound stock solution was added to each cell culture well with a final concentration of 1× compound stock solution and a DMSO content of 0.1%. DMSO was used as an experimental control. After the compound was added and cultured for two hours, the residual culture medium was removed. 100 μL of cell lysis buffer was added to each well, stood on ice for 30 minutes, and ultrasonically lysed with ice water for 5 minutes. After diluting the cell lysate in proportion, 80 μL of the mixture was transfer to an ELISA plate, and 80 μL of cell lysis buffer was added to the blank well. After incubating in an incubator at 37° C. for 2 hours, the plate was taken and the antibody incubation and color development termination operation were completed according to the instructions of Pathscan P-BTK (Y223) Sandwich ELISA Kit (Cell Signaling #23843 CA), and finally the OD value was read. The inhibition rate of the compound (%)=$(OD_{control}-OD_{compound})/(OD_{control}-OD_{blank})\times 100\%$ was calculated. The compound gradient dilution concentration and the corresponding cell proliferation inhibition rate were fit by using Prism 8 four-parameter method, and $IC_{50}$ value was calculated. As can be seen from the experimental results, the compounds of the present disclosure have a relatively high inhibitory activity to BTK or BTK (C481S) phosphorylation level, and the $IC_{50}$ values are less than 500 nM (such as 0.1 nM to 500 nM); the $IC_{50}$ values of some compounds are even less than 100 nM (such as 0.1 nM to 100 nM), or less than 50 nM (such as 0.1 nM to 50 nM). The experimental results of some of the compounds are shown in Table 2.

TABLE 2

| No. | HEK293 p-BTK (WT) $IC_{50}$ (nM) | HEK293 p-BTK (C481S) $IC_{50}$ (nM) |
|---|---|---|
| Z2 | 122.85 | 72.78 |
| Z3 | 358.56 | 339.96 |
| Z2-1 | 29.23 | 49.98 |
| Z2-2 | 41.50 | 56.56 |
| Z4 | 374.86 | 340.14 |
| Z5 | 35.79 | 36.65 |
| Z9 | 23.52 | 57.98 |
| Z4-1 | 70.82 | 97.59 |
| Z9-2 | 62.60 | 134.15 |
| Z13-1 | 36.20 | 42.21 |
| Z14 | 31.50 | 27.58 |
| Z16-1 | 17.33 | 36.60 |
| Z16-2 | 10.38 | 10.41 |
| Z64 | 65.78 | 90.03 |
| Z64-1 | 58.55 | 197.89 |
| Z24-a | 46.94 | 49.95 |
| Z24-b | 39.51 | 39.03 |
| Z24-c | 19.62 | 16.20 |
| Z24-d | 16.94 | 15.32 |
| Z169 | 10.16 | 20.06 |
| Z204 | 143.2 | 221.5 |
| Z66-1 | 29.65 | 38.13 |
| Z67-1 | 37.25 | 42.61 |
| Z71-1 | 32.29 | 40.29 |
| Z26-1 | 31.53 | 38.35 |
| Z41-2a | 48.12 | 50.10 |
| Z25-2 | 15.23 | 32.70 |
| Z132 | 16.53 | 36.05 |
| Z136 | 80.53 | 114.08 |
| Z137 | 50.14 | 49.39 |
| Z141 | 20.50 | 22.37 |
| Z78-2 | 68.30 | 118.63 |
| Z149 | 19.34 | 33.05 |
| Z155 | 28.00 | 48.25 |
| Z160 | 16.68 | 27.50 |
| Z168 | 3.98 | 7.26 |
| Z120 | 2.5 | 1.0 |
| Z195 | 2.8 | 1.4 |
| Z197 | 5.2 | 1.6 |
| Z41-la | 53.01 | 134.69 |
| Z41-1b | 25.14 | 79.03 |
| Z161 | 17.00 | 39.20 |

Test Embodiment 3: TMD-8 and OCI-LY10 Proliferation Inhibition Experiment

TMD-8 cells are human diffuse large B lymphoma (Mingzhou Bio, MZ-0832), cultured in 10% FBS+1% PS 1640 medium; OCI-LY10 is human diffuse large B lymphoma (BeNa Culture Collection, BNCC337742), cultured in 10% FBS+1% PS IMDM. Day 1: Cells at logarithmic growth phase were taken, counted and inoculated 600 TMD-8 or 2000 OCI-LY10 cells in a 384-well cell culture plate and cultured overnight. Day 2: A 3-fold gradient concentration stock solution of 400× compound was prepared with DMSO, and diluted 40-fold to a 10× compound stock solution with culture medium. The 10× compound stock solution was added to each cell culture well with a final concentration of 1× compound stock solution and a DMSO content of 0.25%. DMSO was used as experimental control, and culture medium was used as blank control. The incubation was continued for three days after compound addition. On the fifth day, 25 μL of ADP-Glo was added to each well, mixed well and incubated for 10 minutes, then the chemiluminescence value (RLU value) was read. The cell proliferation inhibition rate (%)=($RLU_{control}$−$RLU_{compound}$)/($RLU_{control}$−$RLU_{blank}$)×100% was calculated. The compound gradient dilution concentration and the corresponding cell proliferation inhibition rate were fit by using XLFit four-parameter method, and $IC_{50}$ value was calculated. As can be seen from the experimental results, the compounds of the present disclosure have a relatively high inhibitory activity to TMD-8 or OCI-LY10, and the $IC_{50}$ values are less than 500 nM (such as 0.1 nM to 500 nM); the $IC_{50}$ values of some compounds are even less than 100 nM (such as 0.1 nM to 100 nM), or less than 50 nM (such as 0.1 nM to 50 nM). The experimental results of some of the compounds are shown in Table 3.

TABLE 3

| No. | TMD-8 $IC_{50}$ (nM) | OCI-ly10 $IC_{50}$ (nM) |
|---|---|---|
| Z1 | 156.07 | — |
| Z1-1 | 183.46 | — |
| Z1-2 | 231.88 | — |
| Z2 | 188.13 | 238.24 |
| Z3 | 246.55 | 903.29 |
| Z2-1 | 122.82 | 200.10 |
| Z2-2 | 265.51 | 306.92 |
| Z6 | 151.42 | — |
| Z7 | 258.36 | — |
| Z8 | 468.59 | — |
| Z9 | 232.47 | — |
| Z4-1 | 305.15 | — |
| Z4-2 | 1201.57 | — |
| Z10 | 310.28 | — |
| Z11 | 372.50 | — |
| Z9-1 | 388.67 | — |
| Z9-2 | 73.77 | — |
| Z12 | 480.08 | — |
| Z13-1 | 37.90 | — |
| Z13-2 | 183.18 | — |
| Z14 | 56.98 | — |
| Z15 | 626.20 | — |
| Z16-1 | 42.83 | — |
| Z16-2 | 22.99 | — |
| Z73 | 208.68 | — |
| Z66 | 146.45 | — |
| Z67 | 261.95 | — |
| Z71 | 171.03 | — |
| Z24-1 | 55.39 | — |
| Z24-2 | 63.15 | — |
| Z52-1 | 201.21 | — |
| Z24-a | 112.75 | — |
| Z24-b | 80.76 | — |
| Z24-c | 50.60 | — |
| Z24-d | 52.00 | — |
| Z66-1 | 94.82 | — |
| Z66-2 | 298.78 | — |
| Z67-1 | 160.98 | — |
| Z71-1 | 179.63 | — |
| Z25 | 129.84 | — |
| Z26 | 142.35 | — |
| Z124-1 | 199.37 | — |
| Z178 | 256.69 | — |
| Z169 | 46.94 | — |
| Z147 | 279.14 | — |
| Z65 | 508.68 | — |

TABLE 3-continued

| No. | TMD-8 $IC_{50}$ (nM) | OCI-ly10 $IC_{50}$ (nM) |
|---|---|---|
| Z72 | 404.33 | — |
| Z126 | 183.07 | — |
| Z26-1 | 47.67 | — |
| Z26-2 | 159.43 | — |
| Z26-3 | 216.20 | — |
| Z41-2a | 50.85 | — |
| Z41-2b | 101.10 | — |
| Z25-1 | 100.93 | — |
| Z25-2 | 80.36 | — |
| Z25-3 | 107.67 | — |
| Z131 | 307.08 | — |
| Z132 | 133.07 | — |
| Z134 | 256.5 | — |
| Z136 | 177.6 | — |
| Z137 | 139.4 | — |
| Z25-3a | 101.62 | — |
| Z25-3b | 139.78 | — |
| Z139 | 105.60 | — |
| Z140 | 158.37 | — |
| Z141 | 58.35 | — |
| Z143 | 290.80 | — |
| Z144 | 226.79 | — |
| Z145 | 165.81 | — |
| Z146 | 194.69 | — |
| Z78-1 | 289.13 | — |
| Z78-2 | 254.06 | — |
| Z149 | 129.99 | — |
| Z153-1 | 342.02 | — |
| Z155 | 87.04 | — |
| Z156 | 117.34 | — |
| Z157 | 145.37 | — |
| Z160 | 107.79 | — |
| Z161 | 72.77 | — |
| Z162 | 168.96 | — |
| Z163 | 75.67 | — |
| Z164 | 144.90 | — |
| Z166 | 244.95 | — |
| Z167 | 371.61 | — |
| Z168 | 22.41 | — |
| Z173 | 365.54 | — |
| Z177 | 34.60 | — |
| Z187 | 41.31 | — |
| Z64-1 | 194.45 | — |
| Z165 | 366.30 | — |
| Z41-1a | 64.22 | — |
| Z41-1b | 49.68 | — |
| Z51 | 259.06 | — |
| Z51-1 | 280.42 | — |
| Z51-2 | 153.96 | — |

Although the specific embodiments of the present disclosure have been described in detail, according to all the disclosed teachings, those skilled in the art can make various modifications and substitutions to the details of the technical solutions of the present disclosure, and these changes are all within the protection scope of the present disclosure. The full scope of the present disclosure is given by the appended claims and any equivalents thereof.

What is claimed is:

1. A compound of formula (C), a pharmaceutically acceptable salt thereof, a stereoisomer thereof, or a solvate thereof:

(C)

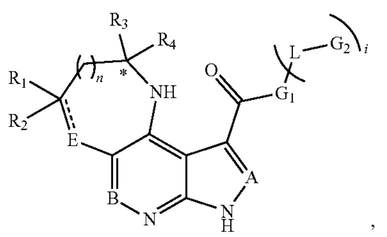

, in the formula, $R_1$ and $R_2$ are each independently selected from: H, $C_{1-6}$ alkoxy and $C_{1-6}$ thioalkyl; or $R_1$ and $R_2$ combining with the carbon atoms to which they are attached form: C═O or C═S; the $C_{1-6}$ alkoxy and the $C_{1-6}$ thioalkyl are each independently unsubstituted or substituted by 1, 2, 3 or 4 substituents independently selected from group S1;

$R_3$ and $R_4$ are each independently selected from: $C_{1-6}$ alkyl and $C_{3-6}$ monocyclic cycloalkyl; or $R_3$ and $R_4$ combining with the carbon atoms to which they are attached form: $C_{3-6}$ monocyclic cycloalkyl or 3- to 6-membered monocyclic heterocyclyl, the 3- to 6-membered monocyclic heterocyclyl has 1 or 2 heteroatoms selected from N and O as ring atoms; wherein $C_{1-6}$ alkyl, $C_{3-6}$ monocyclic cycloalkyl and 3- to 6-membered monocyclic heterocyclyl are each independently unsubstituted or substituted by 1, 2, 3 or 4 substituents independently selected from group S1;

n is 0;

E is $NR_5$, O or N;

$R_5$ is H, $C_{1-6}$ alkyl, deuterated $C_{1-6}$ alkyl, —$C_{1-4}$ alkylene-hydroxy, —$C_{1-4}$ alkylene-$C_{1-6}$ alkoxy or —$C_{1-4}$ alkylene-$NR^aR^b$;

when E is $NR_5$ or O, "---" connected with E represents a single bond;

when E is N, "---" connected with E represents a double bond and $R_2$ is absent;

A is $CR_6$ or N; wherein, $R_6$ is H;

B is $CR_7$; wherein, $R_7$ is H;

$G_1$ is $C_{6-14}$ aryl or 5- to 6-membered monocyclic heteroaryl; the 5- to 6-membered monocyclic heteroaryl has 1 or 2 heteroatoms selected from N, O and S as ring atoms, and the $C_{6-14}$ aryl and the 5- to 6-membered monocyclic heteroaryl are unsubstituted or substituted by 1, 2, 3 or 4 substituents independently selected from group S2;

$G_2$ is $C_{6-14}$ aryl or 5- to 6-membered monocyclic heteroaryl; the 5- to 6-membered monocyclic heteroaryl has 1 or 2 heteroatoms selected from N, O and S as ring atoms, and the $C_{6-14}$ aryl and the 5- to 6-membered monocyclic heteroaryl are unsubstituted or substituted by 1, 2, 3 or 4 substituents independently selected from group S2;

L is $CR^8R^9$ or O; wherein, $R^8$ and $R^9$ are each independently H;

i is 0 or 1;

substituents in the group S1 are selected from: deuterium, halogen, cyano, hydroxyl, $C_{1-6}$ alkyl, $C_{1-6}$ alkoxy, halo $C_{1-6}$ alkoxy, deuterated $C_{1-6}$ alkoxy, —$C_{1-4}$ alkylene-hydroxy, —C(O)$C_{1-6}$ alkyl, —C(O)$C_{3-6}$ monocyclic cycloalkyl, 3- to 6-membered monocyclic heterocyclyl, —O—$C_{3-6}$ monocyclic cycloalkyl, —$NR^aR^b$ and —$OR^c$, wherein the 3- to 6-membered monocyclic heterocyclyl has 1 or 2 heteroatoms selected from N and O as ring atoms;

substituents in the group S2 are selected from: halogen, cyano, $C_{1-6}$ alkyl, halo $C_{1-6}$ alkyl, deuterated $C_{1-6}$ alkyl, $C_{1-6}$ alkoxy, halo $C_{1-6}$ alkoxy, deuterated $C_{1-6}$ alkoxy, $C_{3-6}$ monocyclic cycloalkyl, halo $C_{3-6}$ monocyclic cycloalkyl, —O—$C_{3-6}$ monocyclic cycloalkyl, —$NR^aR^b$ and —$OR^c$;

$R^a$ and $R^b$ are each independently $C_{1-6}$ alkyl;

$R^c$ is —$C_{1-4}$ alkylene-$C_{1-6}$ alkoxy or $C_{3-6}$ monocyclic cycloalkyl substituted by 1 or 2 halogens;

a carbon atom marked at "*" is a chiral carbon atom or an achiral carbon atom.

2. The compound, the pharmaceutically acceptable salt thereof, the stereoisomer thereof, or the solvate thereof as claimed in claim 1, wherein, in $R_1$ and $R_2$, the $C_{1-6}$ alkoxy is each independently $C_{1-3}$ alkoxy;

or, in $R_1$ and $R_2$, the $C_{1-6}$ thioalkyl is each independently $C_{1-3}$ thioalkyl;

or, in $R_1$ and $R_2$, the $C_{1-6}$ alkoxy and the $C_{1-6}$ thioalkyl are each independently unsubstituted;

or, in $R_3$ and $R_4$, the $C_{1-6}$ alkyl is each independently $C_{1-3}$ alkyl;

or, in $R_3$ and $R_4$, the $C_{1-6}$ alkyl, the $C_{3-6}$ monocyclic cycloalkyl and the 3- to 6-membered heterocyclyl are each independently unsubstituted or substituted by 1 or 2 substituents selected from group S1;

or, in $R_5$, the $C_{1-6}$ alkyl is methyl, ethyl, n-propyl, isopropyl, n-butyl or isobutyl;

or, in $R_5$, the deuterated $C_{1-6}$ alkyl is deuterated $C_{1-3}$ alkyl;

or, in $R_5$, the —$C_{1-4}$ alkylene-hydroxy is —$C_{1-2}$ alkylene-hydroxy;

or, in $R_5$, the —$C_{1-4}$ alkylene-$C_{1-6}$ alkoxy is —$C_{1-2}$ alkylene-$C_{1-3}$ alkoxy;

or, in $R_5$, the —$C_{1-4}$ alkylene-$NR^aR^b$ is —$C_{1-2}$ alkylene-$NR^aR^b$;

or, A is CH;

or, B is CH;

or, in $G_1$, the $C_{6-14}$ aryl is phenyl;

or, in $G_1$, the 5- to 6-membered monocyclic heteroaryl is pyridinyl, pyrimidinyl, furyl, pyrrolyl, thiazolyl, pyrazolyl or thienyl;

or, in $G_1$, the $C_{6-14}$ aryl and the 5- to 6-membered monocyclic heteroaryl are unsubstituted or substituted by 1, 2 or 3 substituents independently selected from group S2;

or, in $G_2$, the $C_{6-14}$ aryl is phenyl;

or, in $G_2$, the 5- to 6-membered monocyclic heteroaryl is pyridinyl, pyrimidinyl, furyl, pyrrolyl, thiazolyl or pyrazolyl;

or, in $G_2$, the $C_{6-14}$ aryl and the 5- to 6-membered monocyclic heteroaryl are unsubstituted or substituted by 1, 2 or 3 substituents independently selected from group S2;

or, in $G_2$, substituents in the group S2 are selected from: halogen, cyano, —$C_{1-6}$ alkyl, halo C1-6 alkyl, $C_{1-6}$ alkoxy, deuterated $C_{1-6}$ alkoxy and $C_{3-6}$ monocyclic cycloalkyl;

or, in L, the $CR^8R^9$ is $CH_2$;

or, in the substituents in group S1, the halogen is each independently fluorine or chlorine;

or, in the substituents in group S1, the $C_{1-6}$ alkyl is each independently $C_{1-3}$ alkyl;

or, in the substituents in group S1, the $C_{1-6}$ alkoxy is each independently $C_{1-3}$ alkoxy;

or, in the substituents in group S1, the halo $C_{1-6}$ alkoxy is each independently halo $C_{1-3}$ alkoxy;

or, in the substituents in group S1, the deuterated $C_{1-6}$ alkoxy is each independently deuterated $C_{1-3}$ alkoxy;

or, in the substituents in group S1, the $C_{1-4}$ alkylene-hydroxy is each independently $C_{1-2}$ alkylene-hydroxy;

or, in the substituents in group S1, the —$C(O)C_{1-6}$ alkyl is each independently —$C(O)C_{1-3}$ alkyl;

or, in the substituents in group S1, the —$NR^aR^b$ is each independently —$N(CH_3)_2$;

or, in the substituents in group S1, the —$OR^c$ is each independently —$OCH_2CH_2OCH_3$ or —$CH_2CH_2OCH_2CH_3$;

or, in the substituents in group S2, the halogen is each independently fluorine, chlorine, bromine or iodine;

or, in the substituents in group S2, the $C_{1-6}$ alkyl is each independently $C_{1-3}$ alkyl;

or, in the substituents in group S2, the halo $C_{1-6}$ alkyl is each independently halo $C_{1-3}$ alkyl;

or, in the substituents in group S2, the deuterated $C_{1-6}$ alkyl is each independently deuterated $C_{1-3}$ alkyl;

or, in the substituents in group S2, the $C_{1-6}$ alkoxy is each independently $C_{1-3}$ alkoxy;

or, in the substituents in group S2, the halo $C_{1-6}$ alkoxy is each independently halo $C_{1-3}$ alkoxy;

or, in the substituents in group S2, the deuterated $C_{1-6}$ alkoxy is each independently deuterated $C_{1-3}$ alkoxy;

or, in the substituents in group S2, the —$NR^aR^b$ is each independently —$N(CH_3)_2$;

or, in the substituents in group S2, the —$OR^c$ is each independently —$OCH_2CH_2OCH_3$ or —$OCH_2CH_2OCH_2CH_3$;

or, $R^a$ and $R^b$ are each independently $C_{1-3}$ alkyl;

or, in $R^c$, the —$C_{1-4}$ alkylene-$C_{1-6}$ alkoxy is each independently-$C_{1-2}$ alkylene-$C_{1-3}$ alkoxy;

or, in $R^c$, halogen in the $C_{3-6}$ monocyclic cycloalkyl substituted by 1 or 2 halogens is fluorine, chlorine or bromine;

or, in $R^c$, $C_{3-6}$ monocyclic cycloalkyl in the $C_{3-6}$ monocyclic cycloalkyl substituted by 1 or 2 halogens is cyclopropyl.

3. The compound, the pharmaceutically acceptable salt thereof, the stereoisomer thereof, or the solvate thereof as claimed in claim 2, wherein, $R_1$ and $R_2$ are each independently selected from: H, methoxy, methylthio and ethylthio; or $R_1$ and $R_2$ combining with the carbon atoms to which they are attached form: C═O or C═S;

or, $R_3$ and $R_4$ are each independently selected from: —$CH_3$, —$CH_2CH_3$, cyclopropyl, trifluoromethyl ($CF_3$), deuterated methyl ($CD_3$), —$CH_2OH$, —$CH_2OCH_3$, —$CH_2OCF_3$, —$CH_2OCHF_2$, —$CH_2OCD_3$, —$CH_2OCH_2CH_3$, —$CH_2OCH_2CH_2OCH_3$, —$CH_2CH_2OCH_2CH_3$, —$CH_2O$-cyclopropyl, —$CH_2N(CH_3)_2$, —$CH(OH)CH_3$ and —$CH_2CH_3OCH_3$;

or, $R_5$ is H, methyl, ethyl, deuterated methyl, —$CH_2CH_2OH$, —$CH_2CH_2OCH_3$ or —$CH_2CH_2N(CH_3)_2$;

or, $G_1$ is phenyl, 2-chlorophenyl, 2-fluorophenyl, 2-trifluoromethylphenyl, 2-chloro-6-fluorophenyl, 2-chloro-3,4-difluorophenyl, 2-chloro-3-fluoro-4-methoxyphenyl, 2-chloro-4-cyclopentyloxyphenyl, 2-chloro-4-dimethylaminophenyl, 2-chloro-4-cyclopropyloxyphenyl, 2-chloro-4-methoxyphenyl, 2-chloro-4-isopropylphenyl, 2-chloro-4-cyclopropylphenyl, 2-chloro-4-methylphenyl, 2-chlorofuryl, furyl, thienyl, 2-bromothienyl, 2-chlorothienyl, pyridinyl, 3-chloropyridinyl, 2-methylphenyl, 2-chloro-4-cyanophenyl, 2-chloro-4-fluorophenyl, 2-iodophenyl, 2-chloro-5-fluorophenyl, 2-chloro-3-fluorophenyl, 2-chloro-trifluoromethoxyphenyl, 2-chloro-4-bromophenyl or 2,4-dichlorophenyl;

or, $G_2$ is phenyl, 2-fluorophenyl, 3-fluorophenyl, 4-trifluoromethylpyridinyl, 3-methylpyridinyl, 3-trifluoromethylpyridinyl, 4-methylpyridinyl, 4-cyclopropylpyridinyl, 4,6-dimethylpyridinyl, 4-chloro-6-methylpyridinyl, 2-methyl-6-chloropyridinyl, 3-cyanophenyl, 3-fluoro-4-methylpyridinyl, pyridinyl, 3-fluoropyridinyl, 2-methoxyphenyl, 2-chlorophenyl, 3-methoxyphenyl, 2-fluoro-6-methoxyphenyl, pyrazolyl, 3-methylpyrazolyl, 2-methoxy-3-fluorophenyl, 2-fluoro-3-deuterated methoxyphenyl, 2,4-dimethylpyridinyl, 2-chloropyridyl, 2-methoxy-3-fluorophenyl or 2-deuterated methoxy-3-fluorophenyl;

or, L is $CH_2$ or O;

or, substituents in the group S1 are selected from: deuterium, fluorine, cyano, hydroxyl, methyl, methoxy, ethoxy, difluoromethoxy, trifluoromethoxy, deuterated methoxy, —$CH_2OH$, —$C(O)CH_3$, —C(O)-cyclopropyl, morpholinyl, —O-cyclopropyl, —$N(CH_3)_2$, —$OCH_2CH_2OCH_3$ and —$CH_2CH_2OCH_2CH_3$;

or, substituents in the group S2 are selected from: fluorine, chlorine, bromine, iodine, cyano, methyl, deuterated methyl, isopropyl, trifluoromethyl, methoxy, trifluoromethoxy, deuterated methoxy, cyclopropyl, —O-cyclopropyl, —O-cyclopentyl, —$N(CH_3)_2$ and —$OCH_2CH_2OCH_3$.

4. The compound, the pharmaceutically acceptable salt thereof, the stereoisomer thereof, or the solvate thereof as claimed in claim 1, wherein, i, $G_1$, L, $G_2$ have any of the following definitions:

(1) i is 0, $G_1$ is phenyl, pyridinyl, furyl or thienyl; the phenyl, the pyridinyl, the furyl and the thienyl are unsubstituted or substituted by 1, 2, 3 or 4 substituents independently selected from group S2;

(2) i is 1, L is $CR^8R^9$ or O, $G_1$ is phenyl or pyridyl, $G_2$ is phenyl, pyridyl or pyrazolyl; the phenyl, the pyridinyl and the pyrazolyl are unsubstituted or substituted by 1, 2, 3 or 4 substituents independently selected from group S2;

(3) i is 1, L is $CR^8R^9$, $G_1$ is phenyl, $G_2$ is pyrazolyl; the phenyl and the pyrazolyl are unsubstituted or substituted by 1, 2, 3 or 4 substituents independently selected from group S2;

(4) i is 1, L is O, $G_1$ is phenyl or pyridyl, $G_2$ is phenyl or pyridyl; the phenyl and the pyridinyl are unsubstituted or substituted by 1, 2, 3 or 4 substituents independently selected from group S2.

5. The compound, the pharmaceutically acceptable salt thereof, the stereoisomer thereof, or the solvate thereof as claimed in claim 1, wherein, the structural moiety

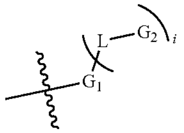

is selected from:

-continued
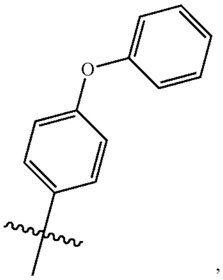
,
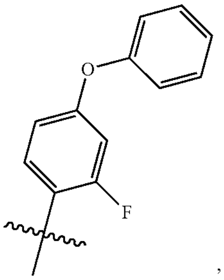
,
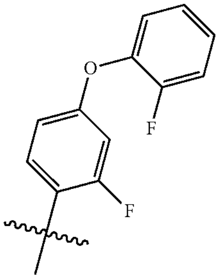
,
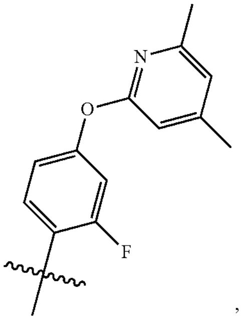
,
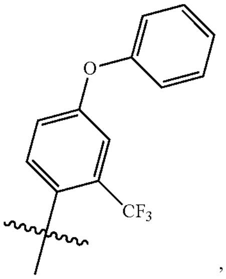
,
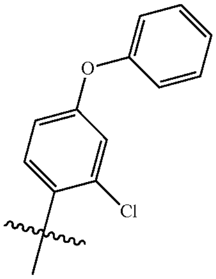
,
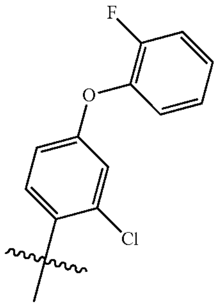
,
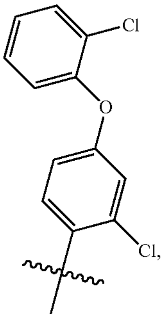
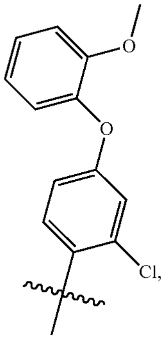
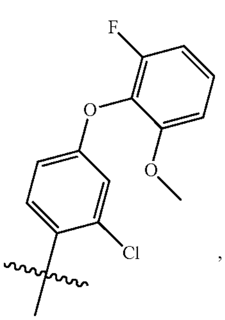
,
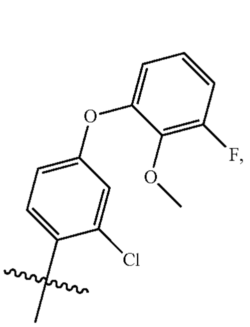
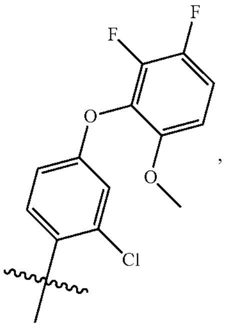
,
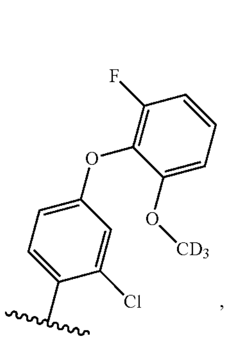
,
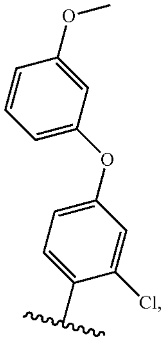
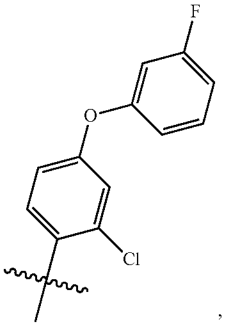
,
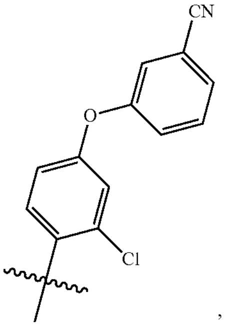
,
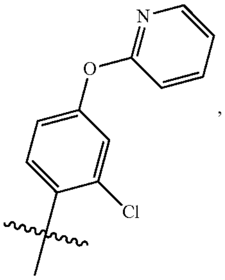
,
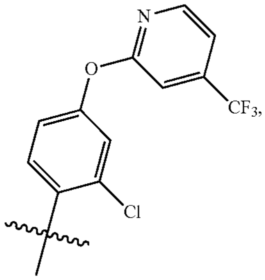
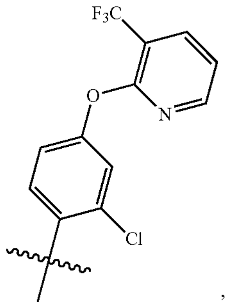
,
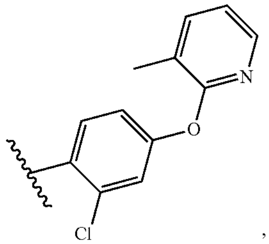
, -continued
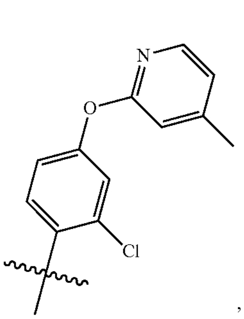
,
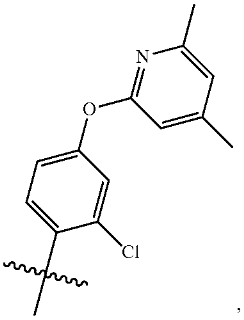
,
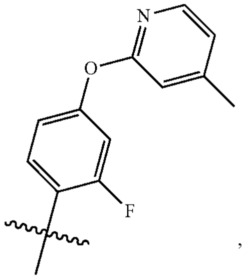
,
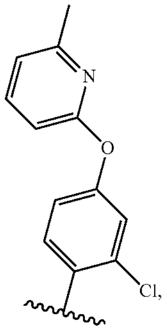
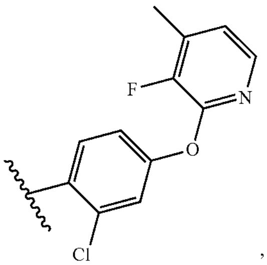
,
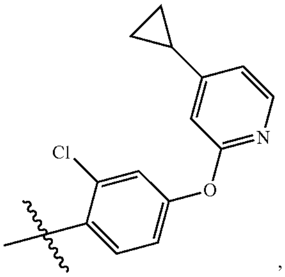
,
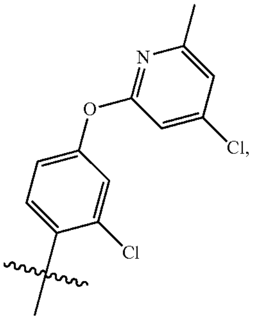
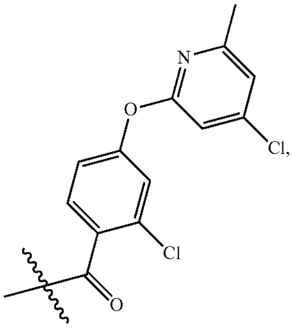
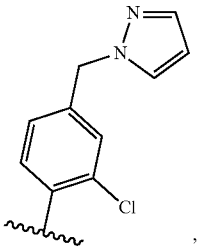
,
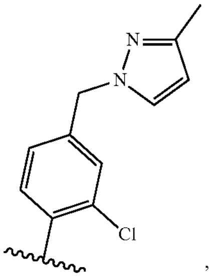
,
-continued
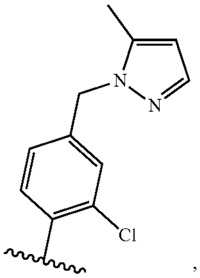
,
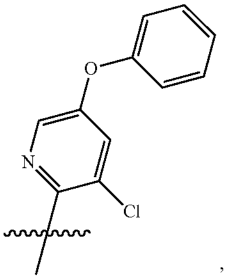
,
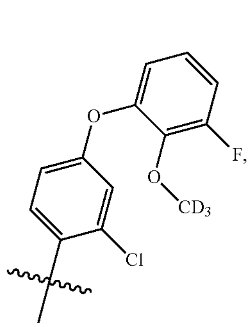
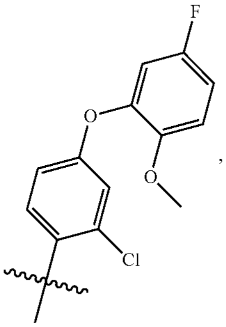
,
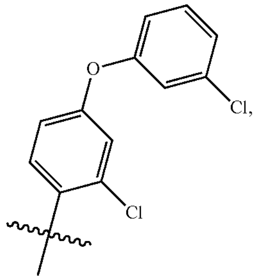
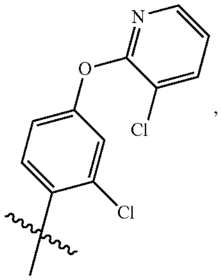
,
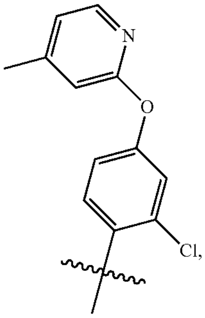
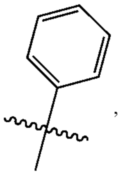
,
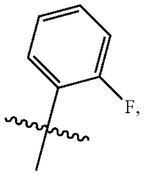
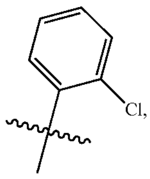
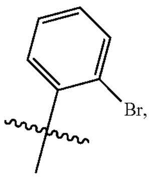
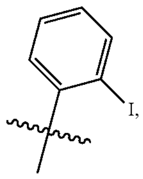
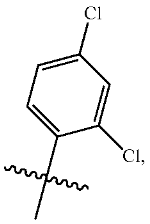
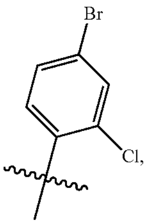
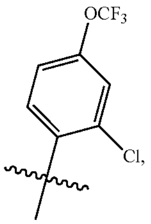

-continued
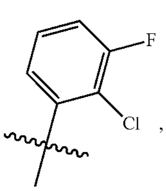 , 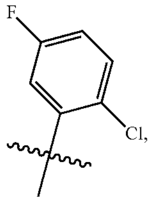 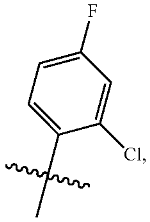
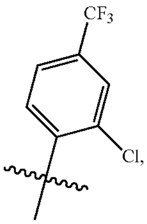 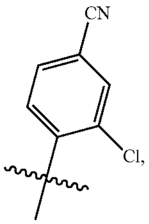 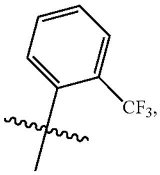
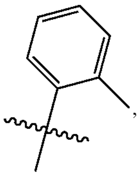 , 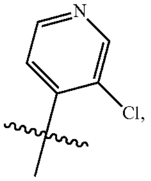 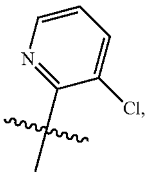
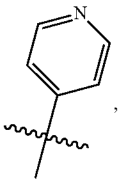 , 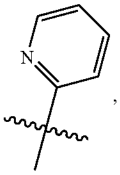 , 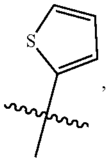 , 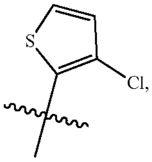
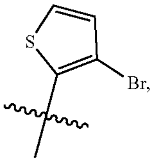 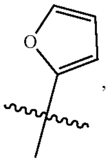 , 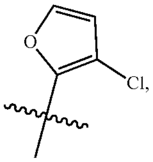
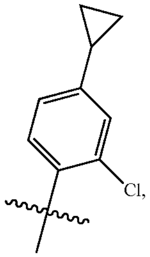 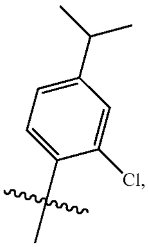 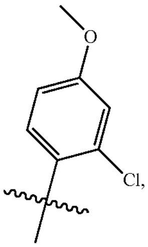
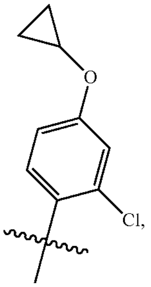 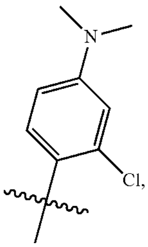 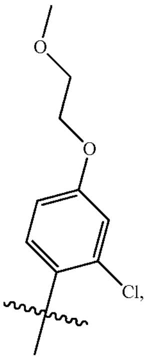
-continued
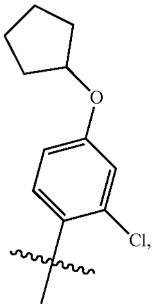 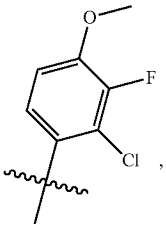 , 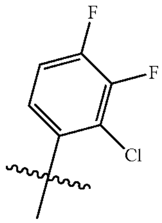 and
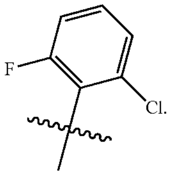
6. The compound, the pharmaceutically acceptable salt thereof, the stereoisomer thereof, or the solvate thereof as claimed in claim 1, wherein, the compound has any one of the following structures:
II′
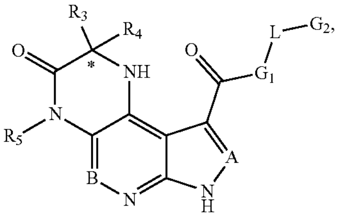
B1′
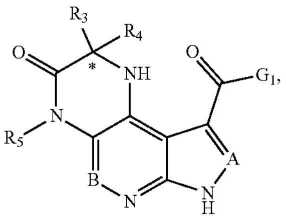
B2′
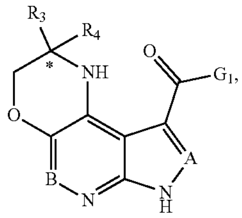
C1
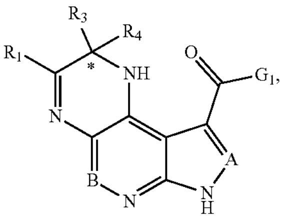

-continued

C2

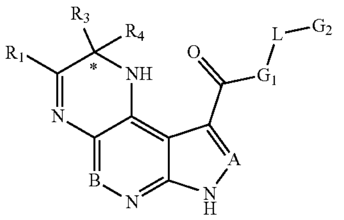

or

C3

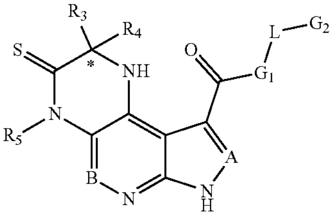

7. The compound, the pharmaceutically acceptable salt thereof, the stereoisomer thereof, or the solvate thereof as claimed in claim 1, wherein, the compound has any one of the following structures:

IIb′

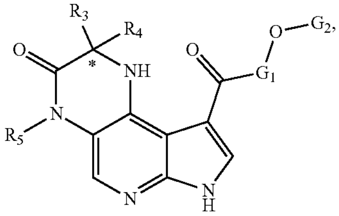

,

B1a′

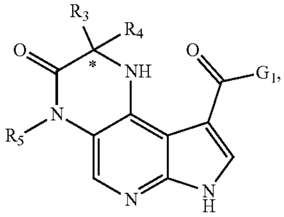

,

B2a′

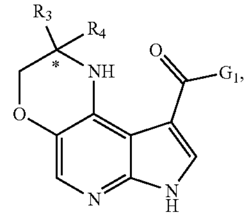

,

C1a

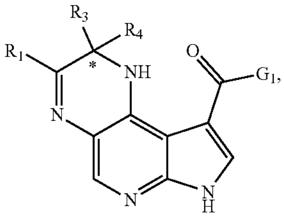

,

-continued

C2a

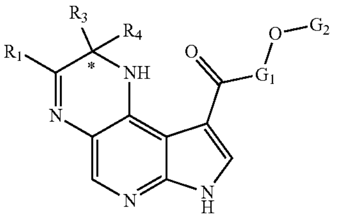

or

C3a

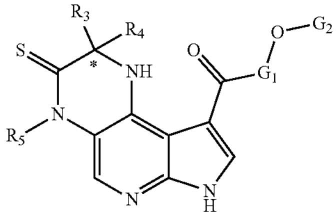

8. The compound, the pharmaceutically acceptable salt thereof, the stereoisomer thereof, or the solvate thereof as claimed in claim 6, wherein, $R_1$ is $C_{1-6}$ alkoxy or $C_{1-6}$ thioalkyl.

9. The compound, the pharmaceutically acceptable salt thereof, the stereoisomer thereof, or the solvate thereof as claimed in claim 1, wherein, the compound has any one of the following structures:

Z1

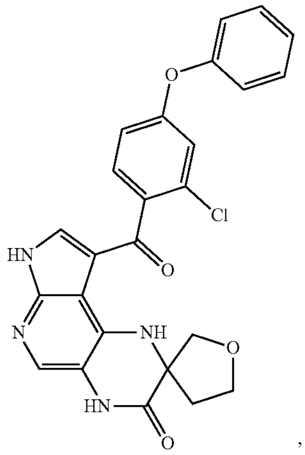

,

Z1-1

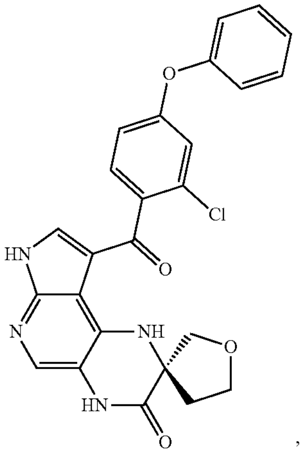

,

-continued
Z1-2
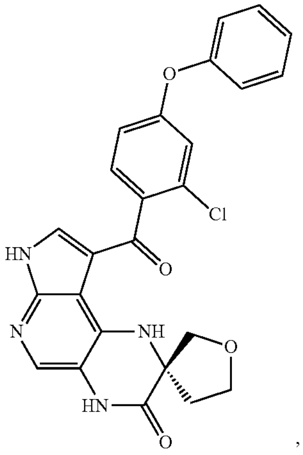
,
Z2
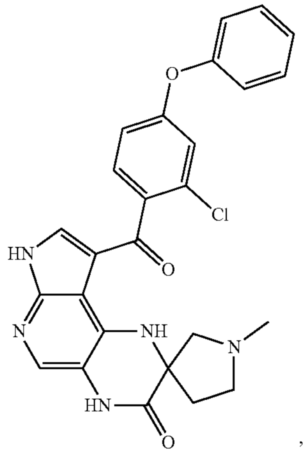
,
Z2-1
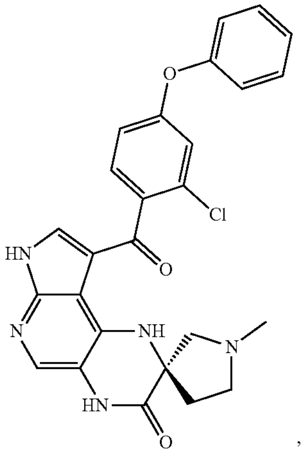
,
-continued
Z2-2
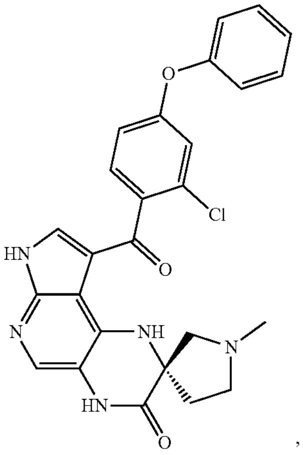
,
Z3
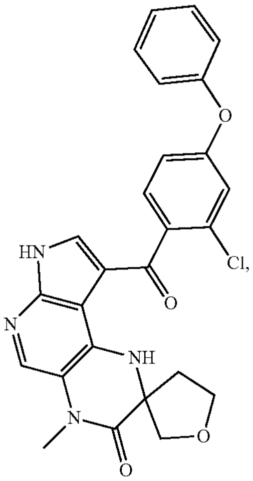
Z4
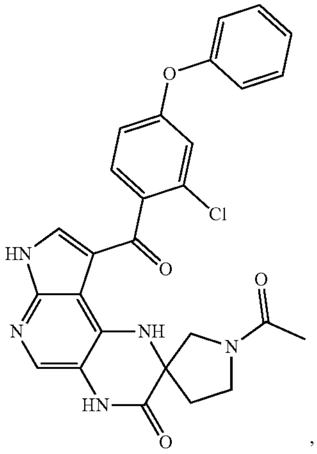
, Z4-1
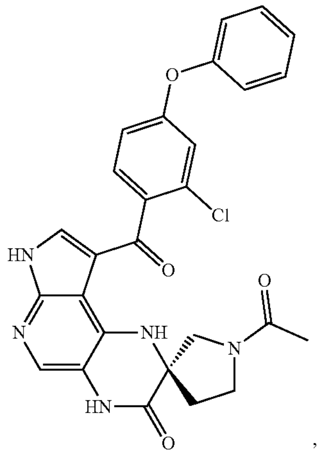
,
Z4-2
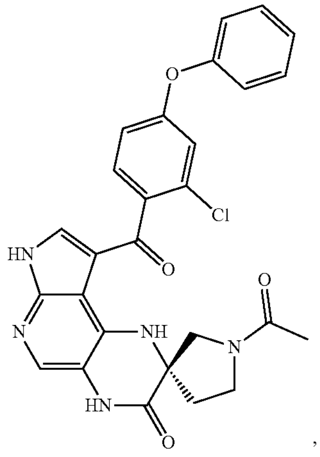
,
Z5
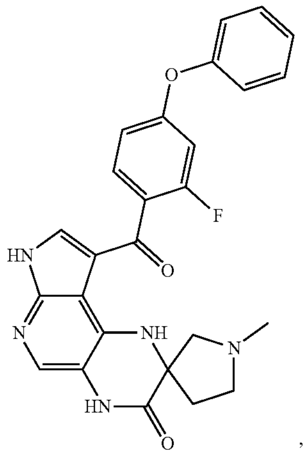
,
Z6
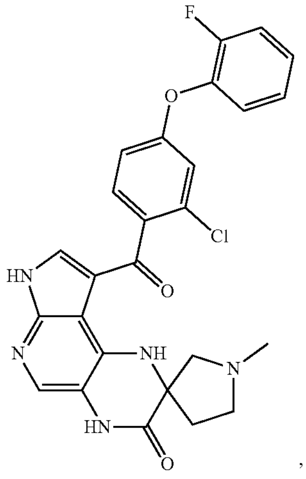
,
Z7
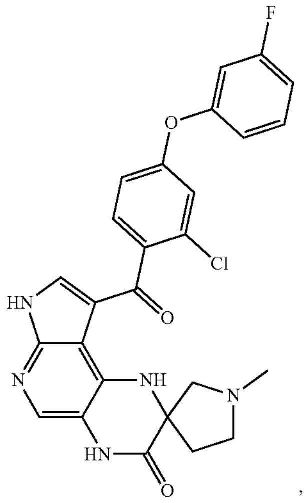
,
Z8
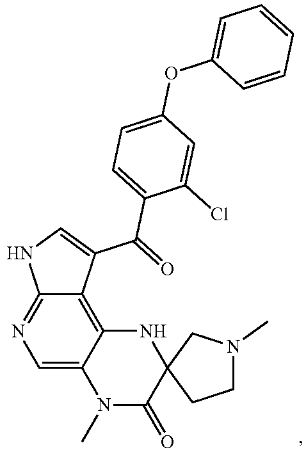
, -continued
Z9
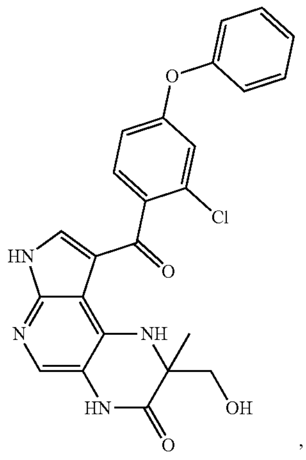
,
Z9-1
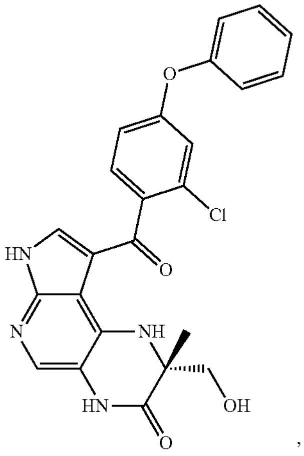
,
Z9-2
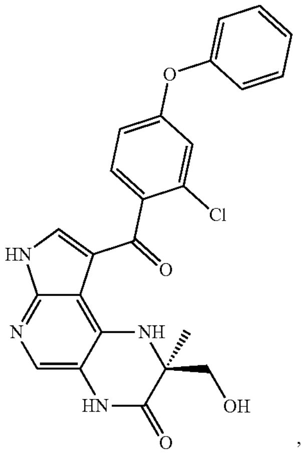
,
-continued
Z10
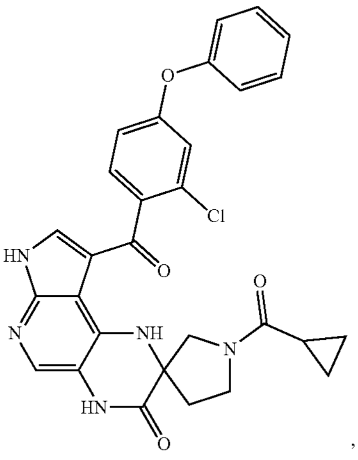
,
Z11
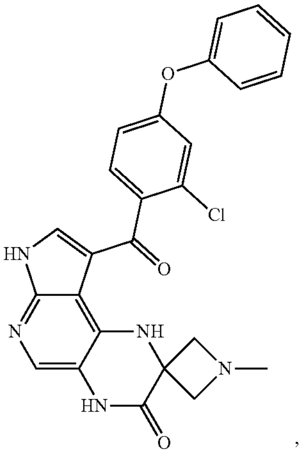
,
Z12
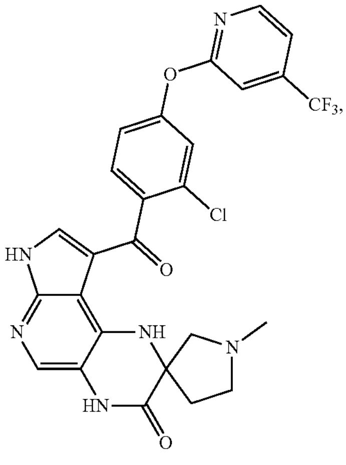
CF3, -continued
Z13
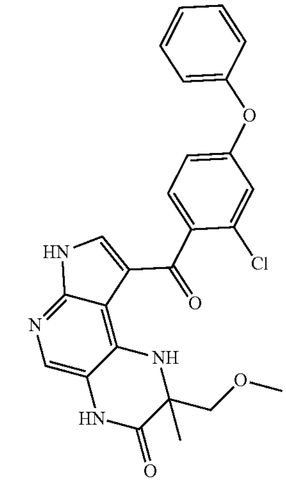
,
Z13-1
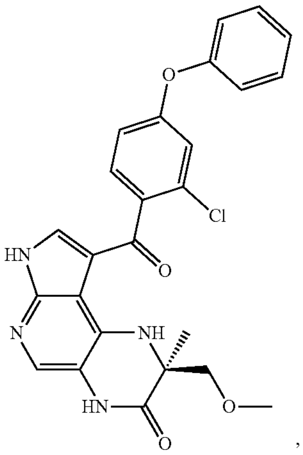
,
Z13-2
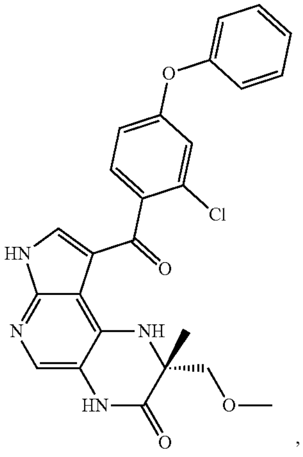
,
-continued
Z14
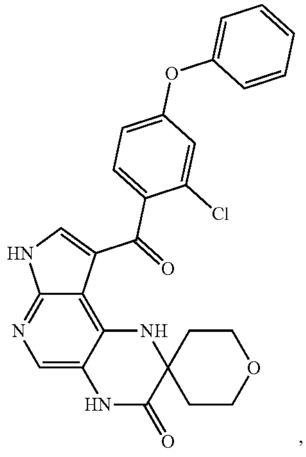
,
Z15
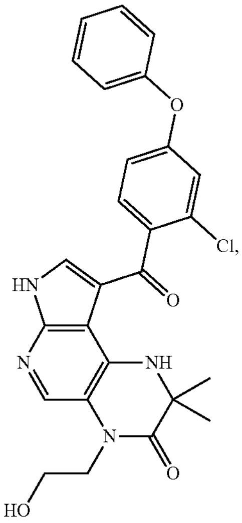
Cl,
Z16
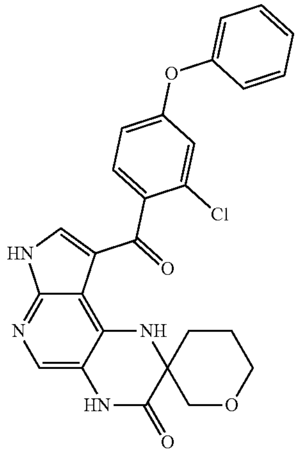
, Z16-1
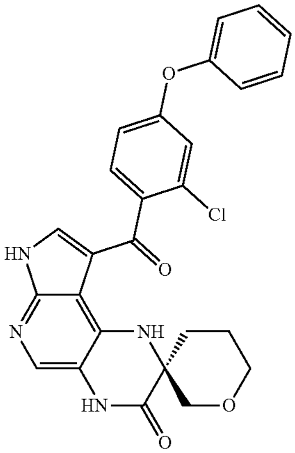
,
Z16-2
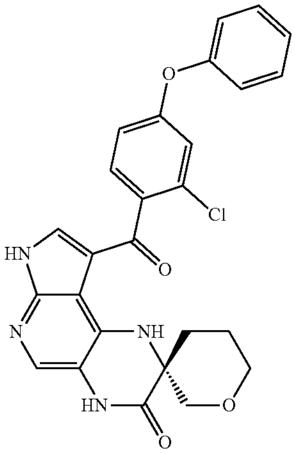
,
Z17
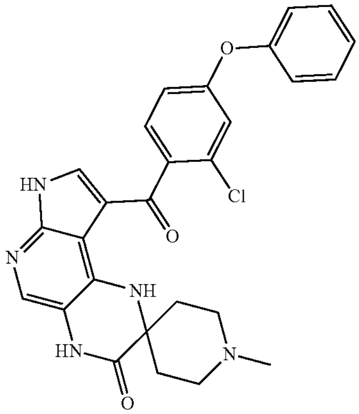
,
Z18
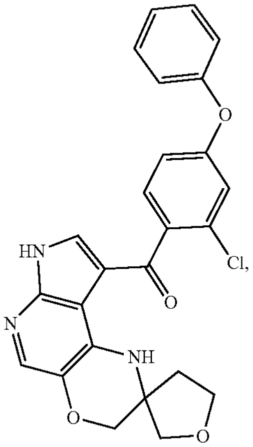
Z19
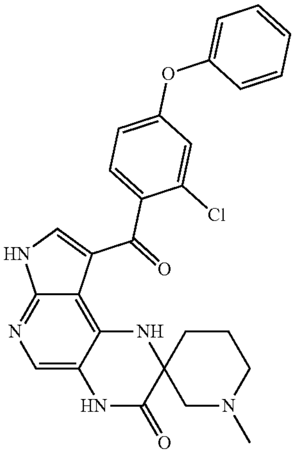
,
Z20
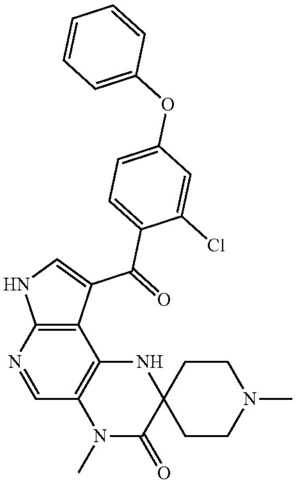
, -continued
Z21
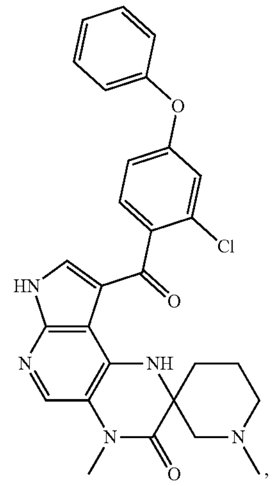
Z22
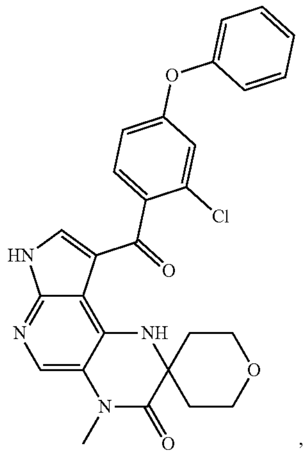
,
Z23
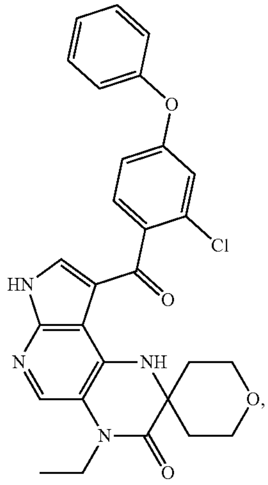
-continued
Z24-1
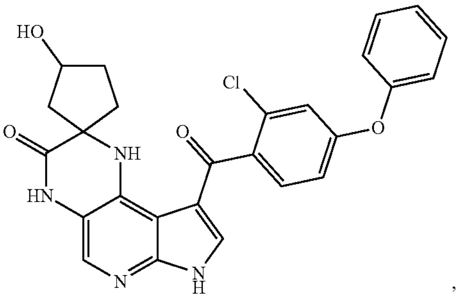
,
Z24-a
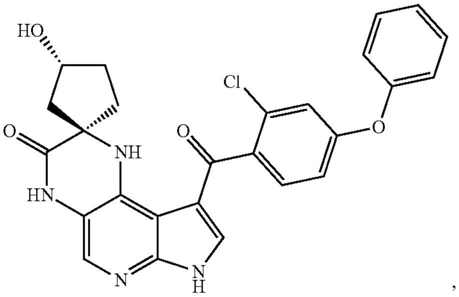
,
Z24-b
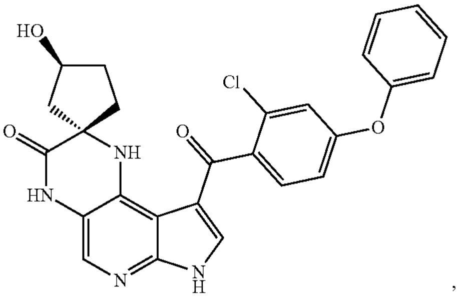
,
Z24-2
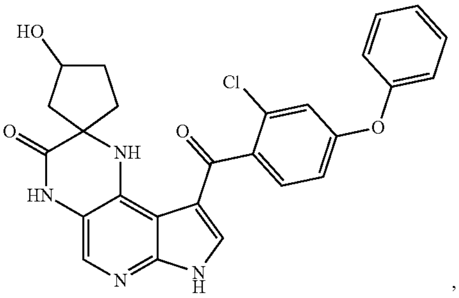
,
Z24-d
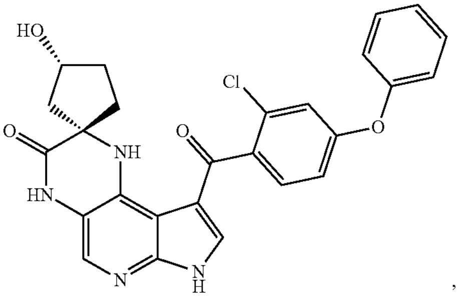
, Z24-c
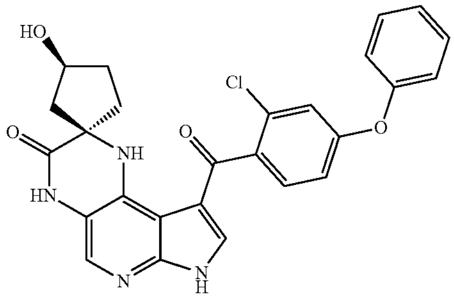
,
Z25
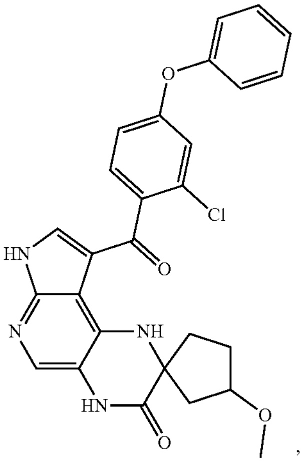
,
Z25-1
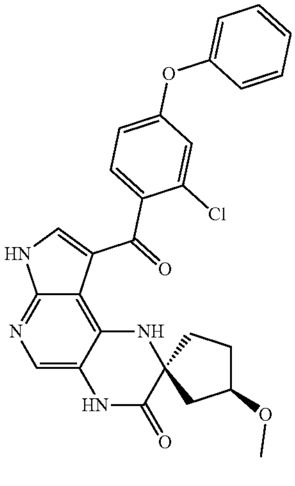
,
Z25-2
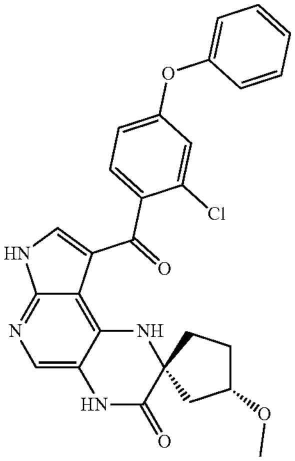
,
Z25-3a
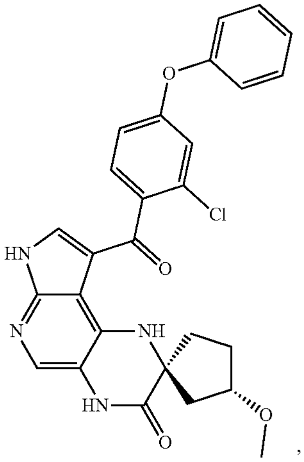
,
Z25-3b
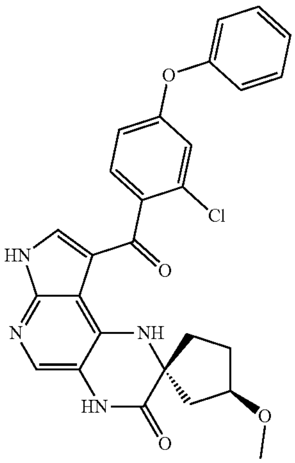
, -continued
Z26
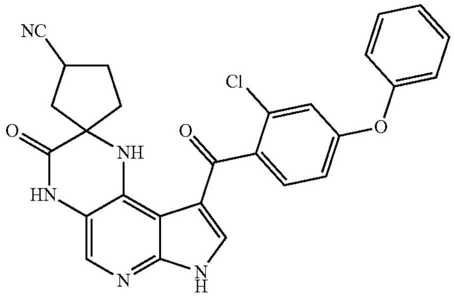
,
Z26-1
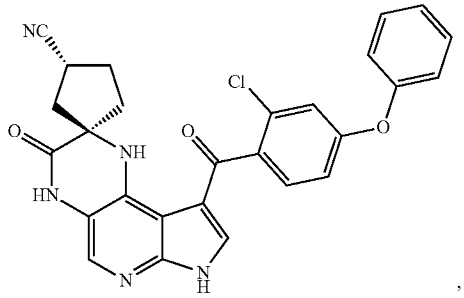
,
Z26-2
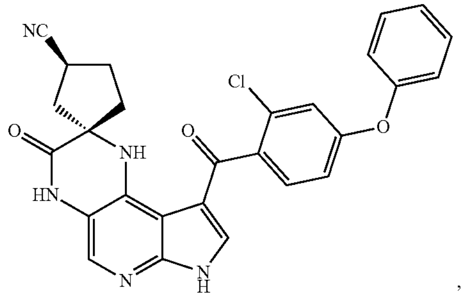
,
Z26-3
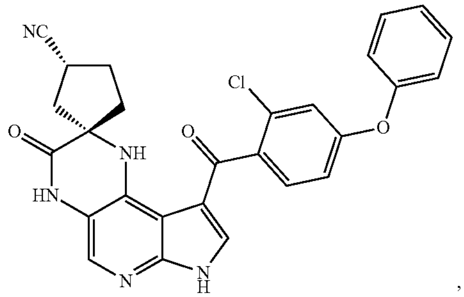
,
Z26-4
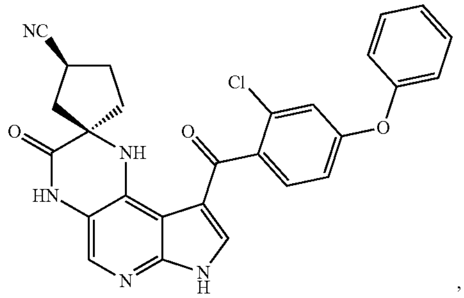
,
-continued
Z27
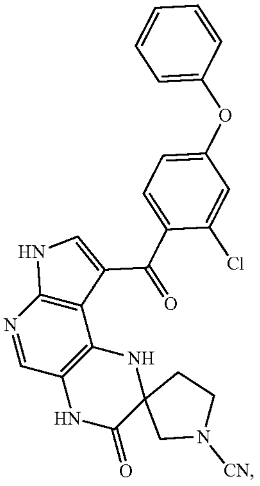
Z28
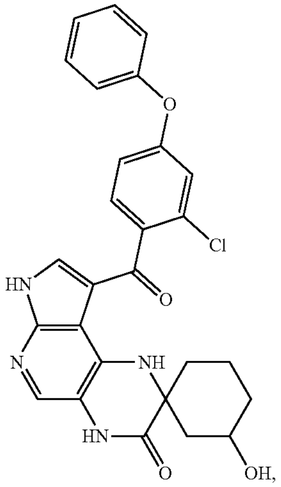
Z29
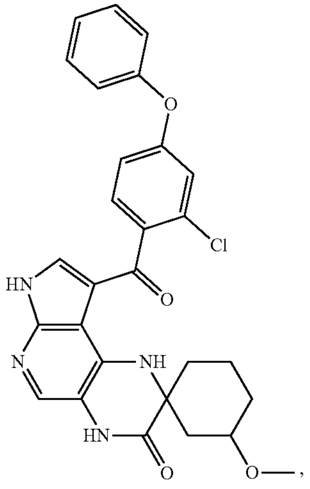

-continued
Z30
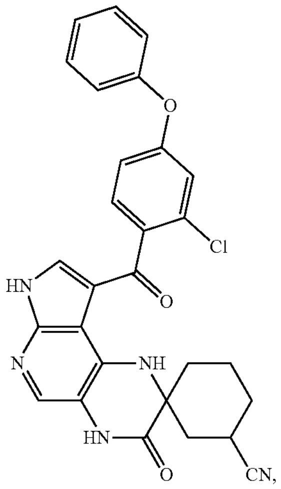
Z31
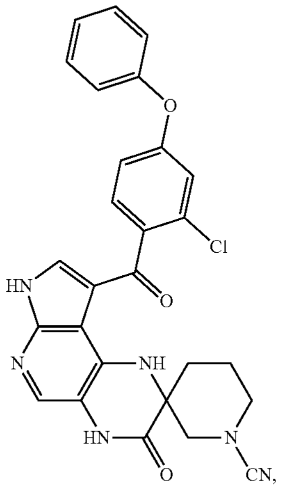
Z32
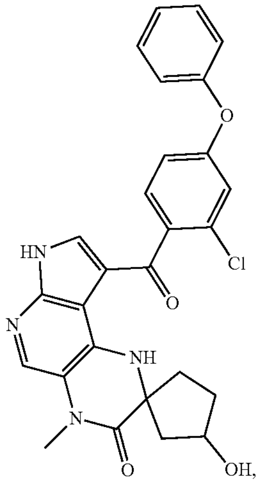
-continued
Z33
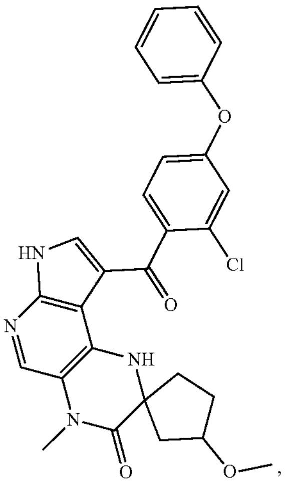
Z34
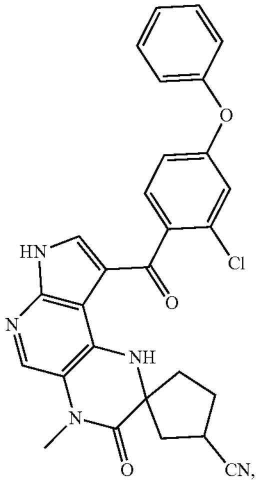
Z35
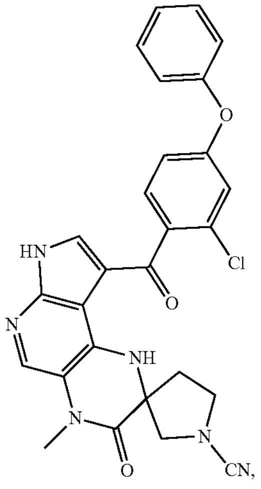

Z36
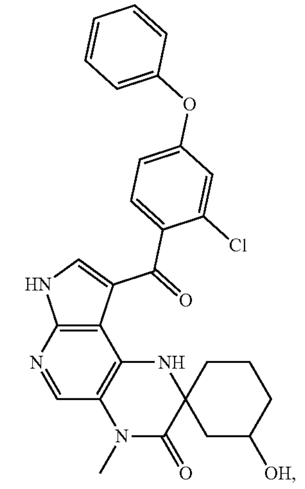
Z37
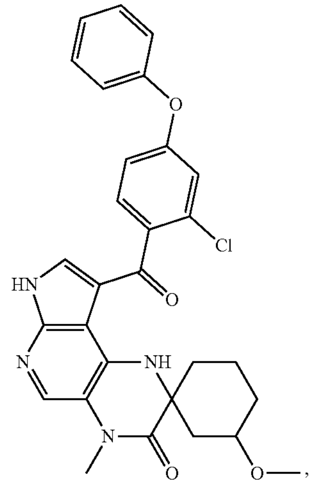
Z38
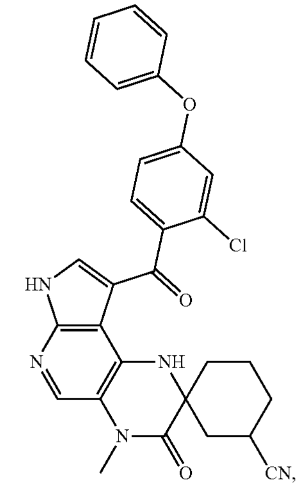
Z39
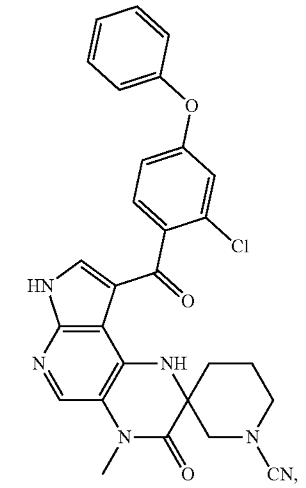
Z40
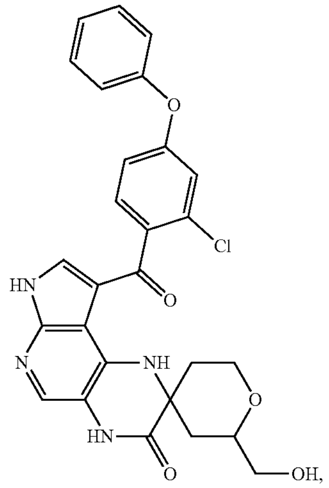
Z41-2
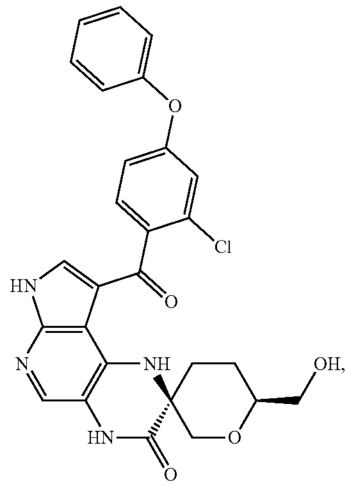

-continued
Z41-2a
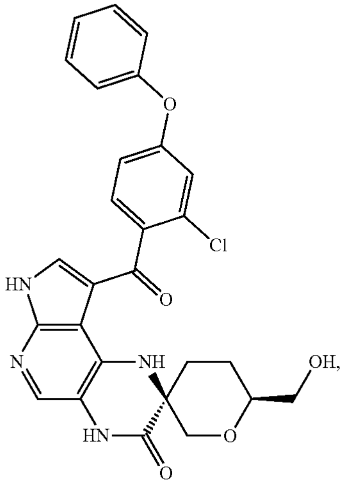
Z41-2b
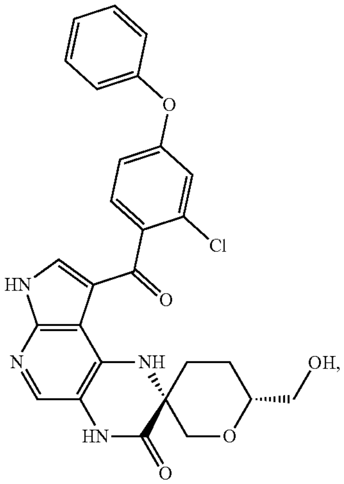
Z42
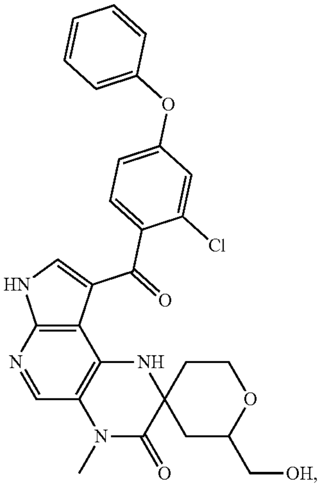
-continued
Z43
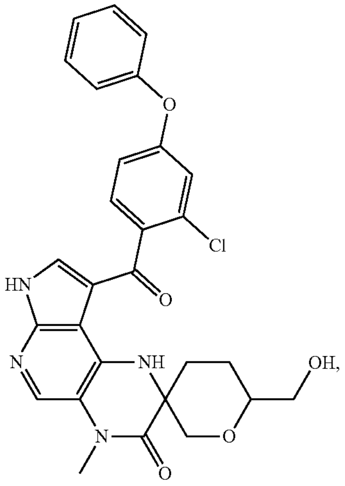
Z44
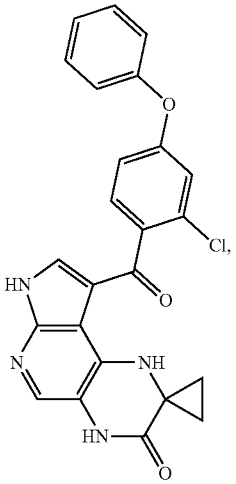
Z45
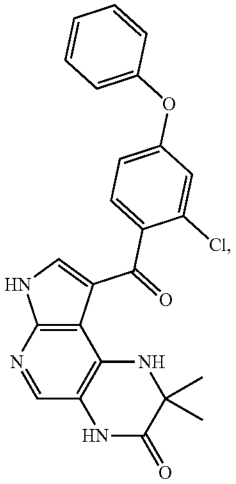

-continued
Z46
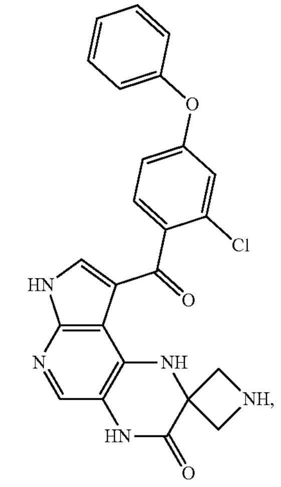
Z47
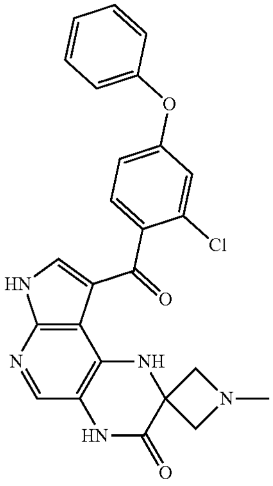
,
Z48
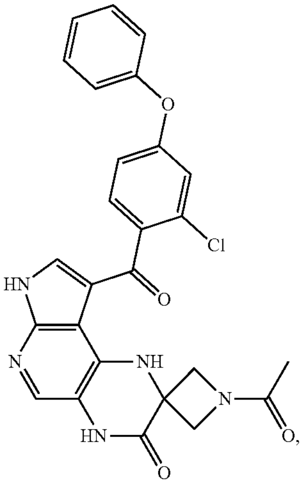
-continued
Z49
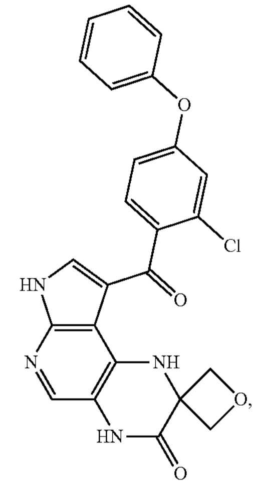
Z50
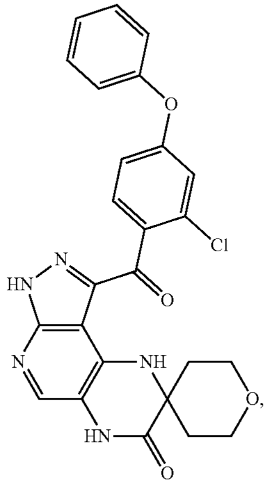
Z51
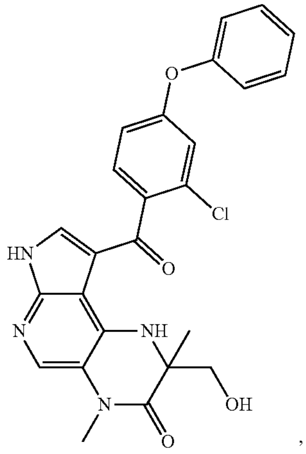
, -continued
Z52
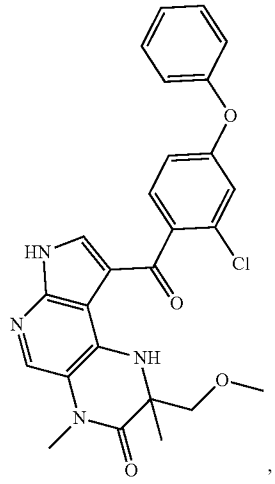
,
Z52-1
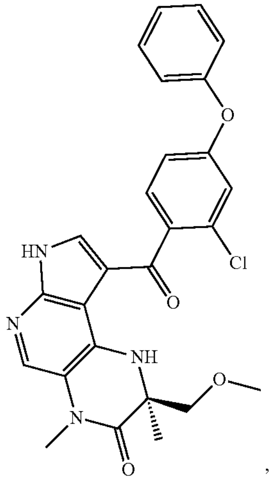
,
Z52-2
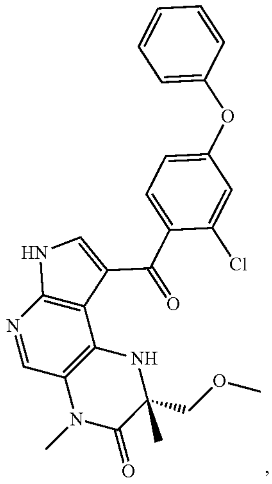
,
-continued
Z53-1
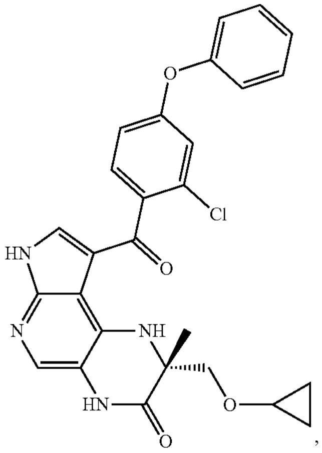
,
Z54-1
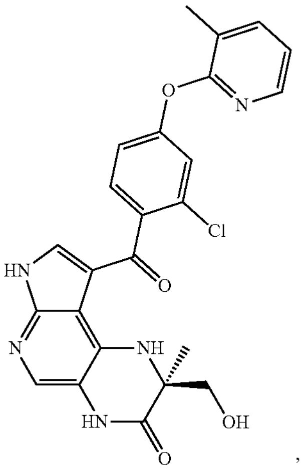
,
Z55
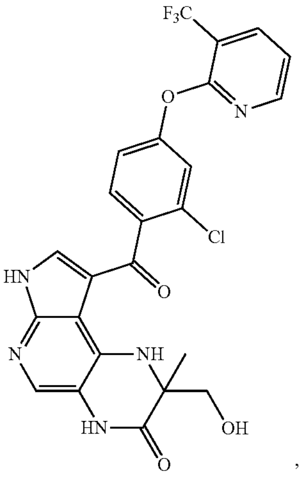
, Z56
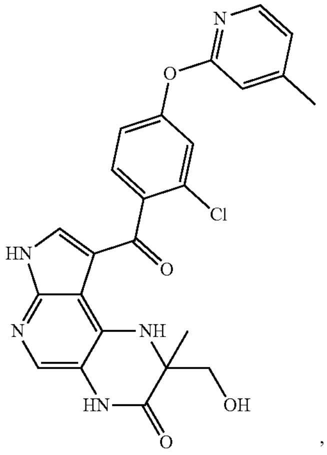
,
Z57
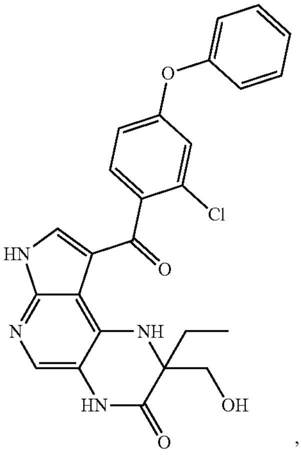
,
Z58
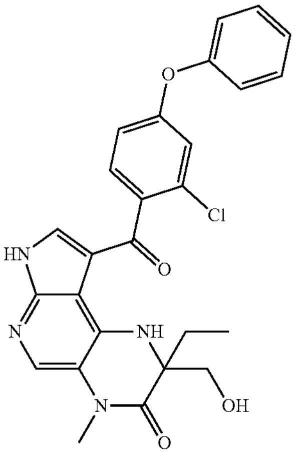
,
Z59
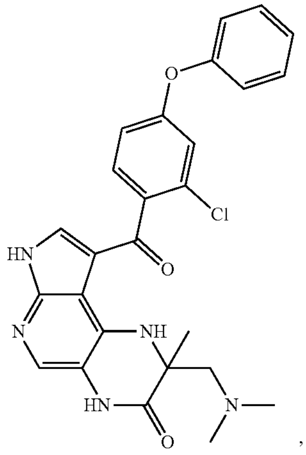
,
Z60
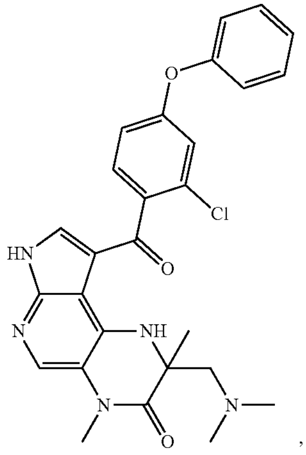
,
Z61
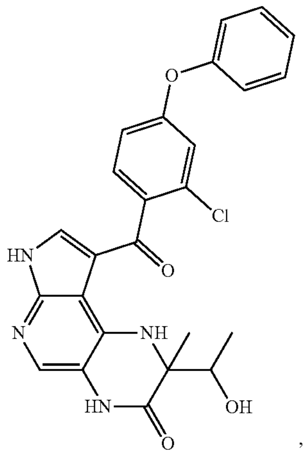
, -continued
Z62
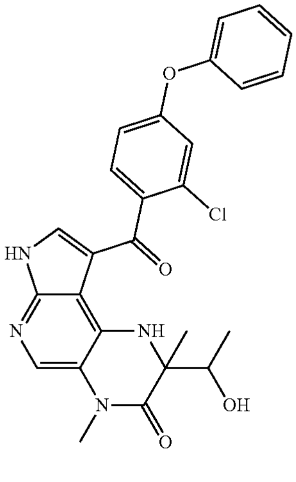
,
Z63
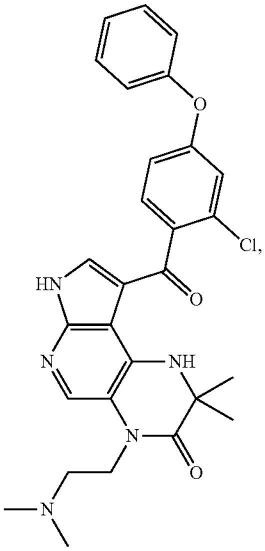
Z64
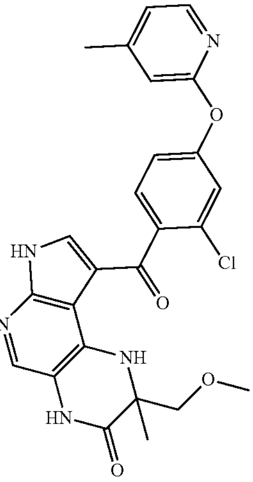
,
-continued
Z64-1
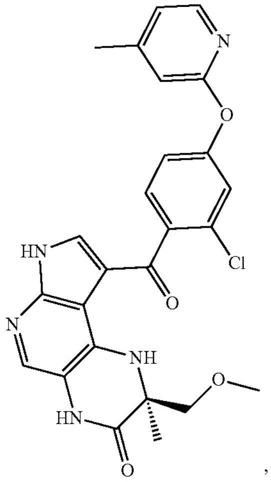
,
Z64-2
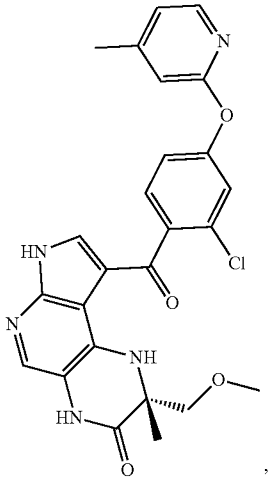
,
Z65
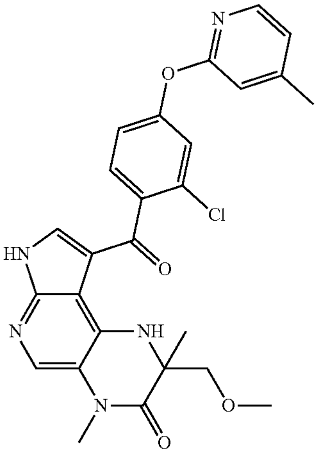
, -continued
Z66
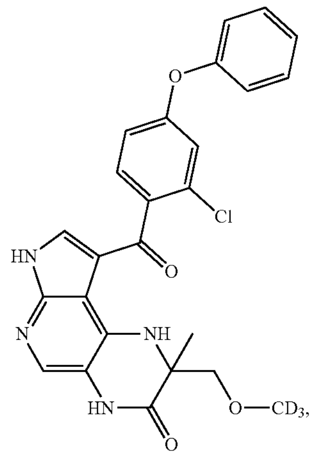
Z67
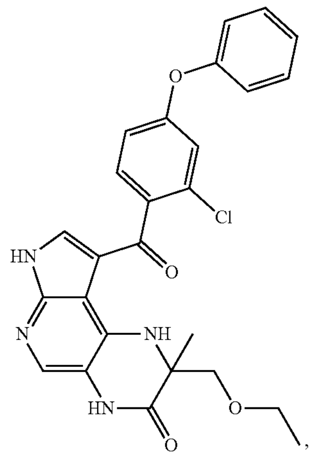
Z66-1
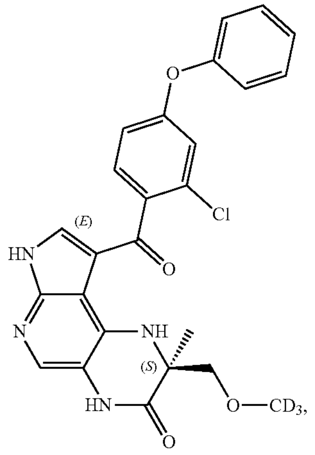
Z67-1
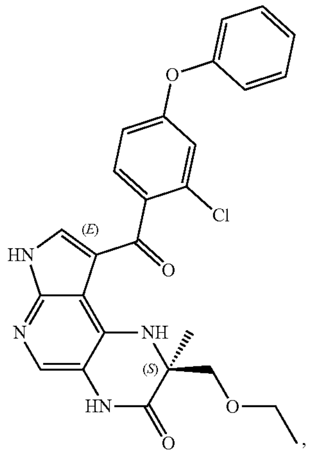
Z66-2
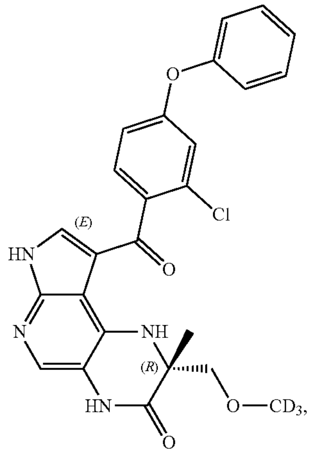
Z67-2
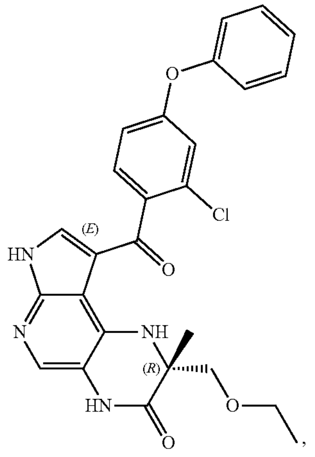

-continued
Z68
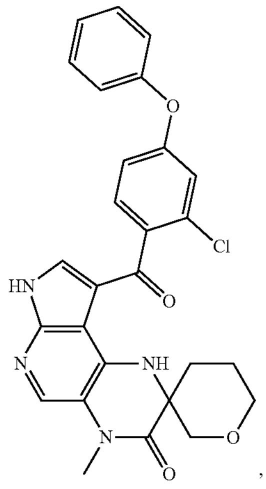
,
Z69
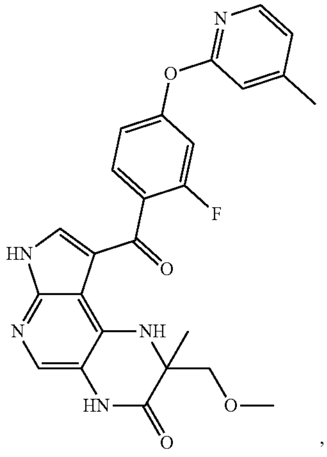
,
Z69-1
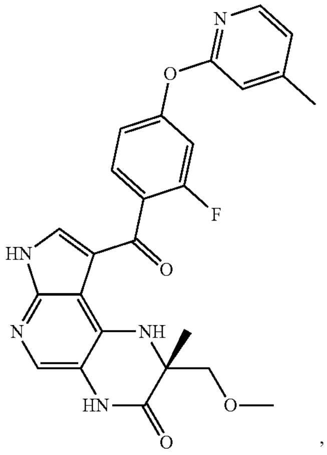
,
-continued
Z69-2
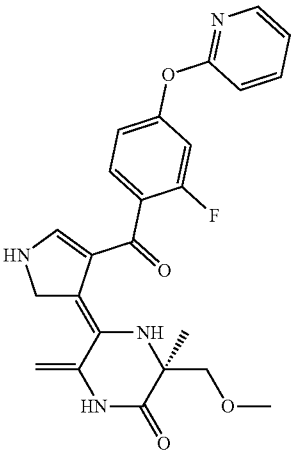
,
Z70
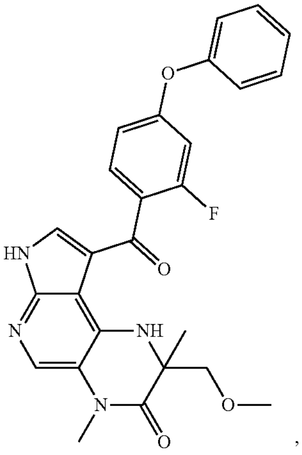
,
Z71
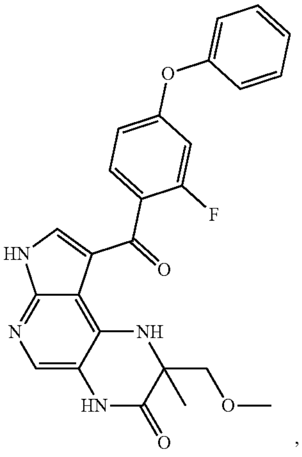
, -continued
Z71-1
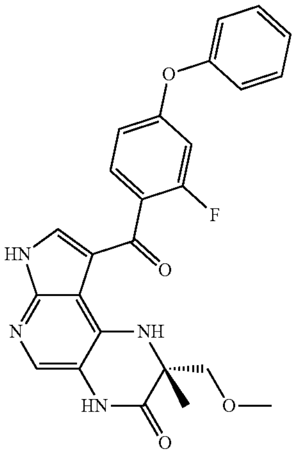
,
Z71-2
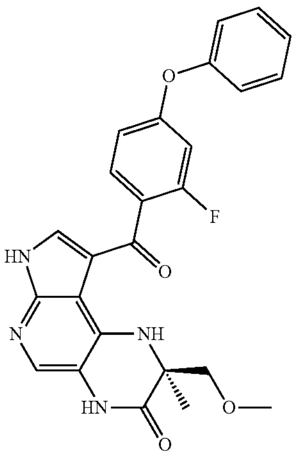
,
Z72
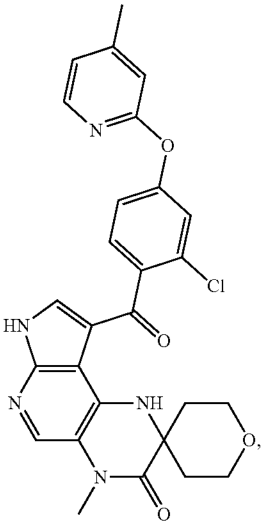
,
-continued
Z73
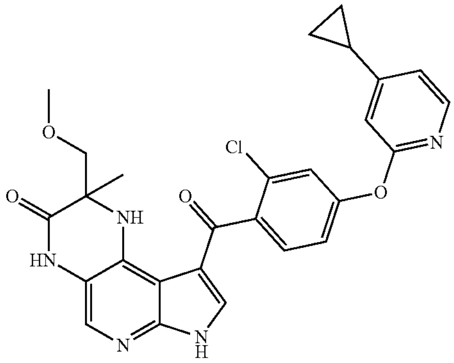
,
Z73-1
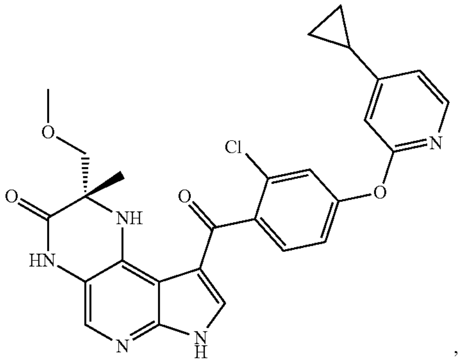
,
Z73-2
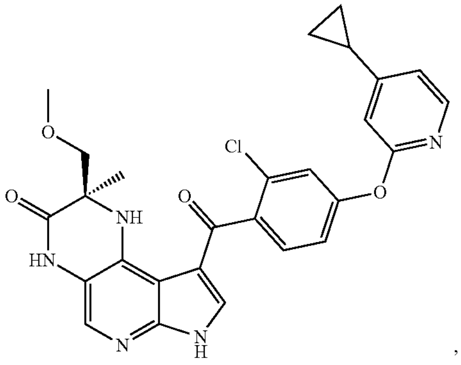
,
Z74
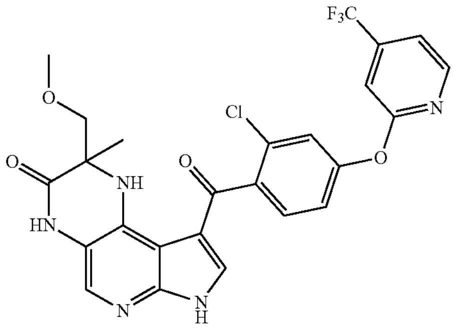
, -continued
Z75
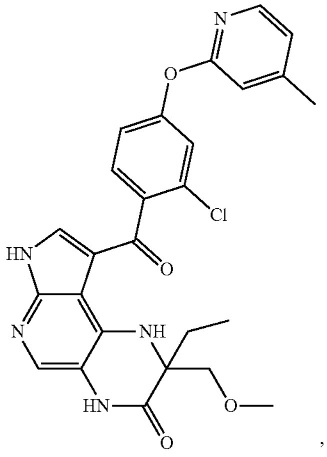
,
Z76
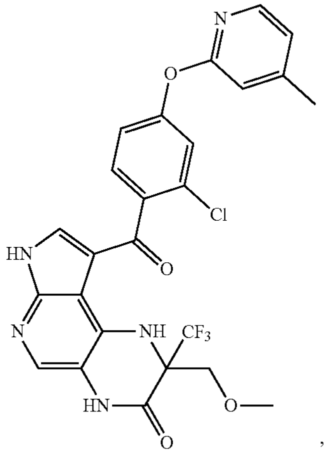
,
Z77
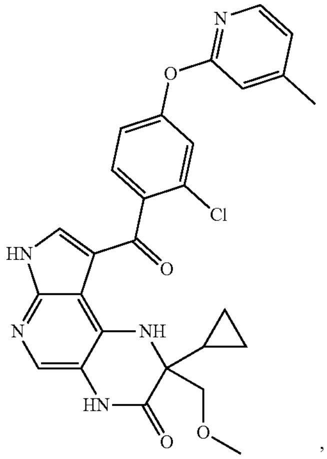
,
-continued
Z78
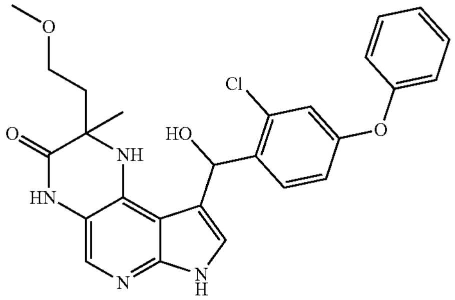
,
Z78-1
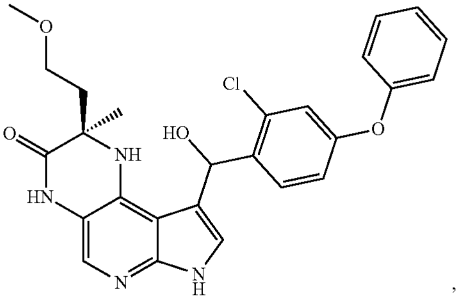
,
Z78-2
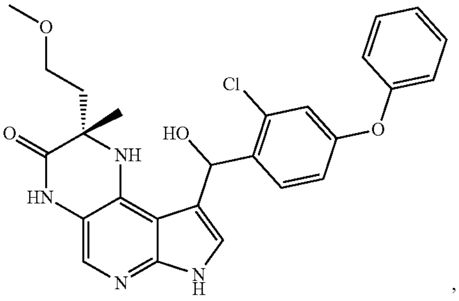
,
Z79
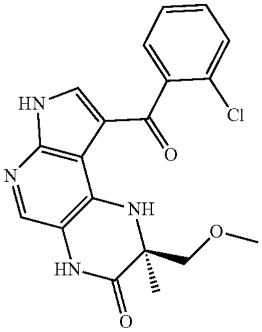
, -continued
Z80
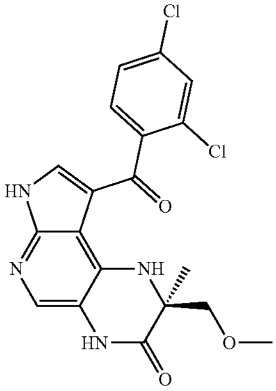
,
Z81
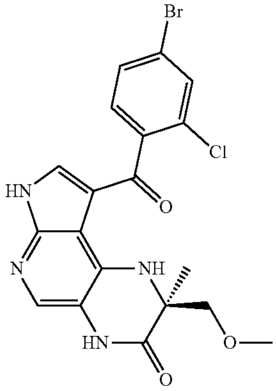
,
Z82
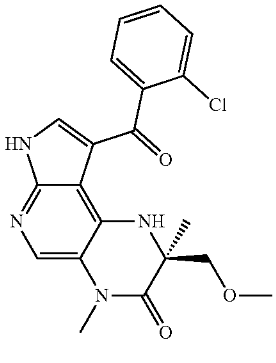
,
Z83
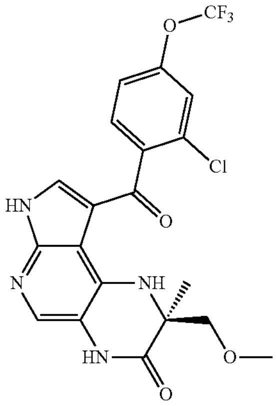
,
-continued
Z84
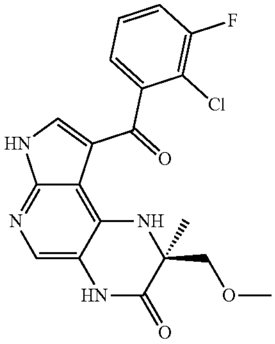
,
Z85
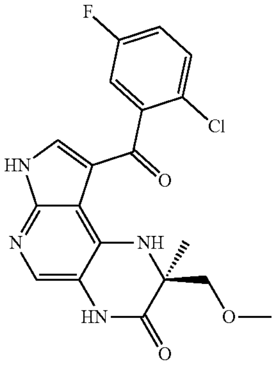
,
Z86
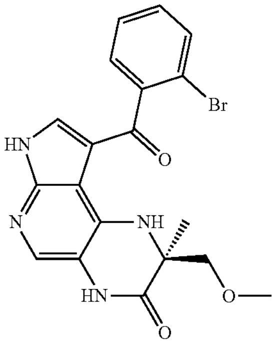
,
Z87
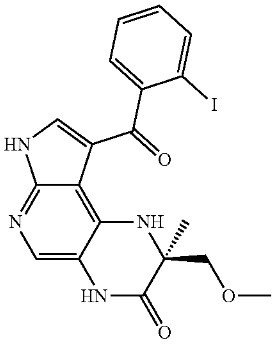
, -continued
Z88
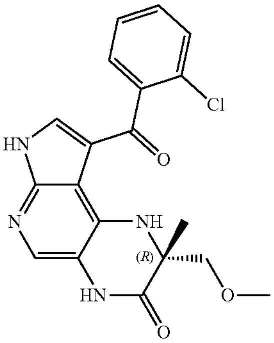
,
Z89
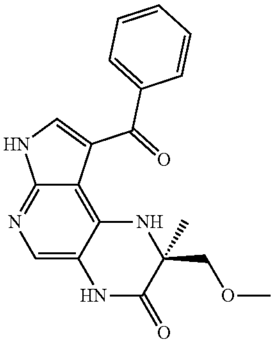
,
Z90
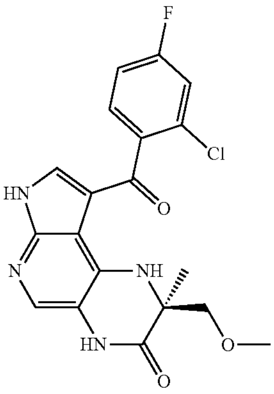
,
Z91
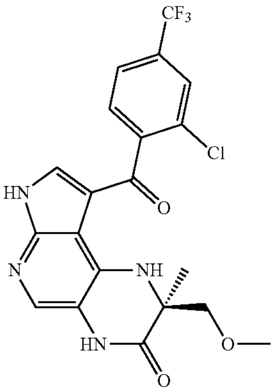
,
-continued
Z92
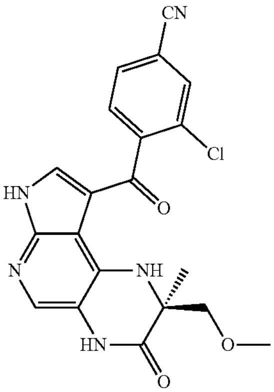
,
Z93
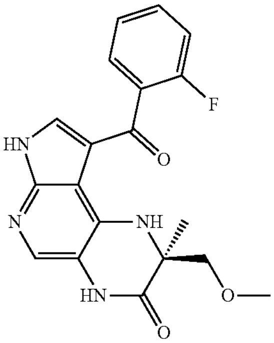
,
Z94
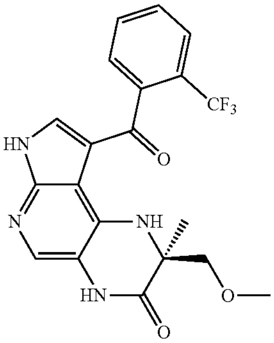
,
Z95
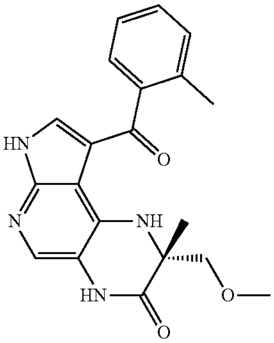
, -continued
Z96
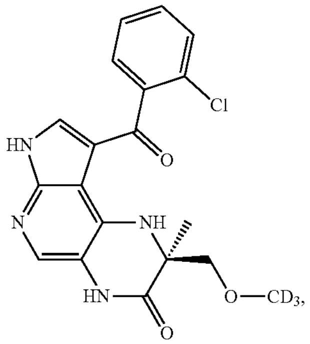
Z97
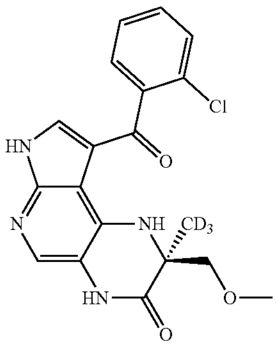
,
Z98
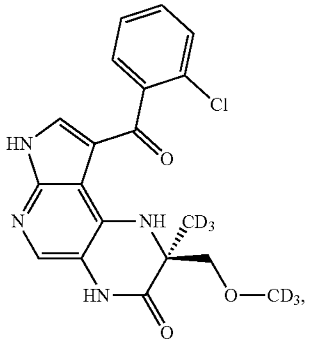
Z99
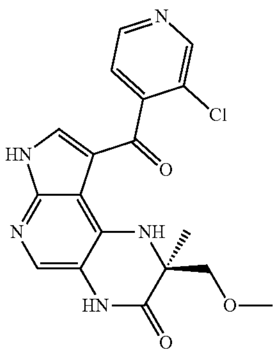
,
-continued
Z100
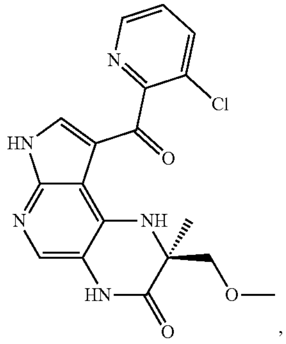
,
Z101
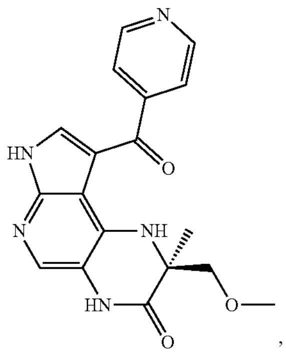
,
Z102
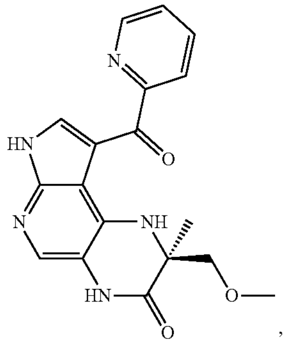
,
Z103
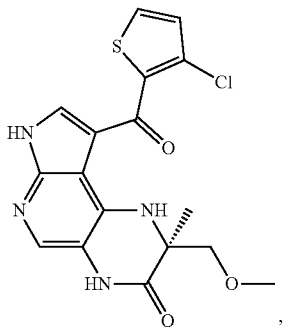
, -continued
Z104
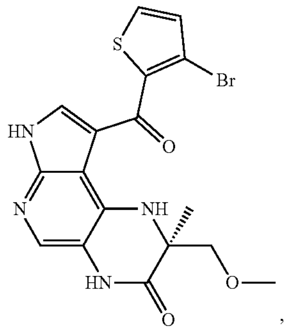
,
Z105
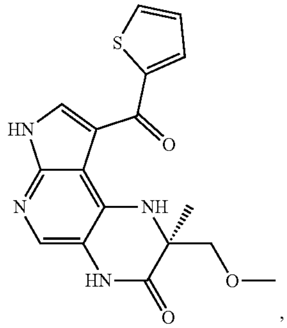
,
Z106
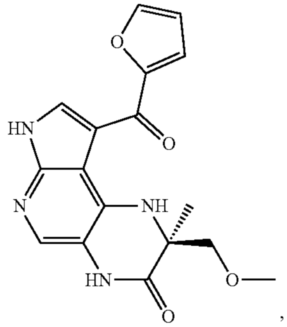
,
Z107
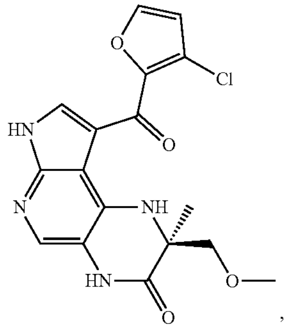
,
-continued
Z108
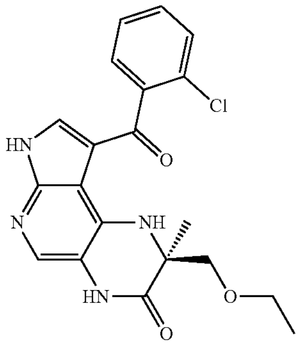
,
Z109
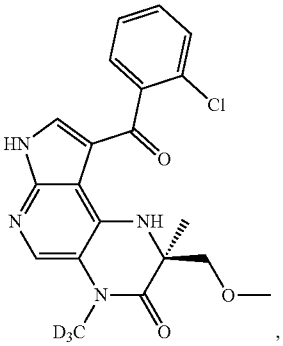
,
Z110
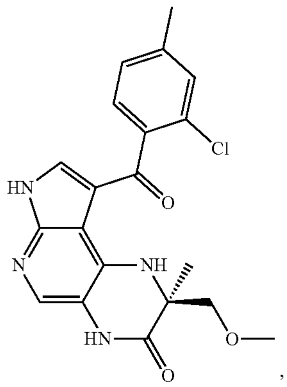
,
Z111
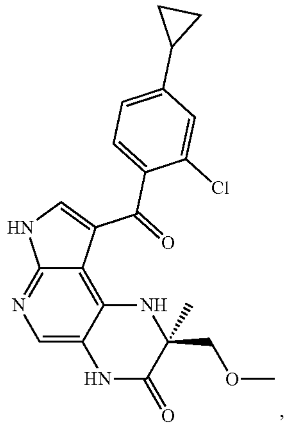
, -continued
Z112
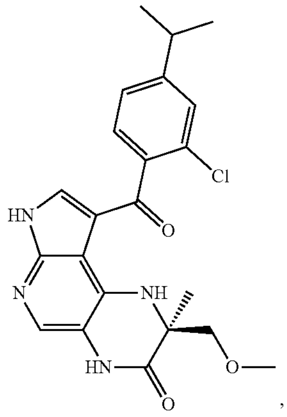
,
Z113
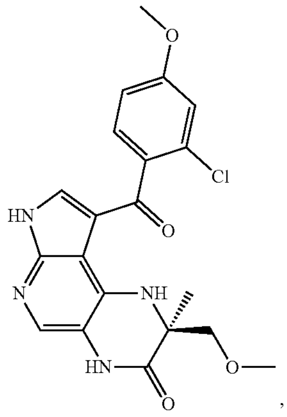
,
Z114
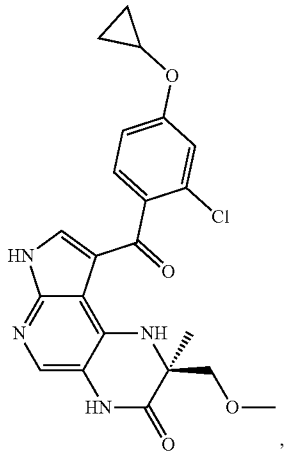
,
-continued
Z115
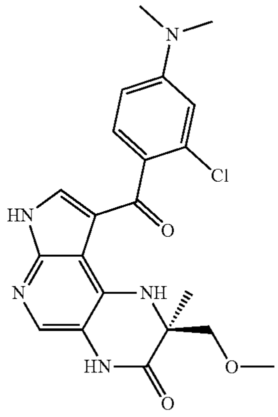
,
Z116
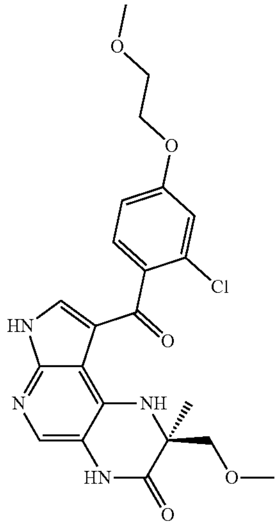
,
Z117
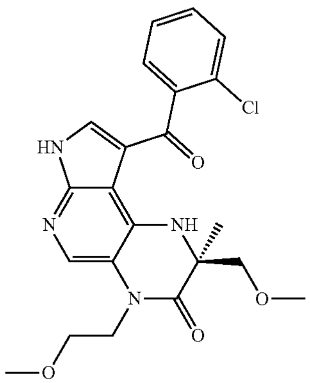
, -continued
Z118
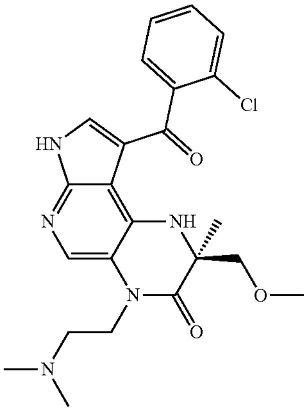
,
Z119
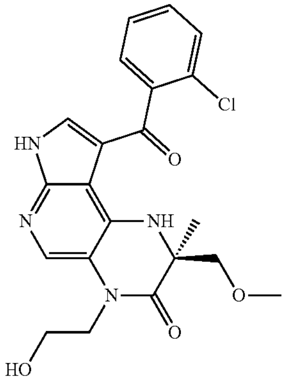
,
Z120
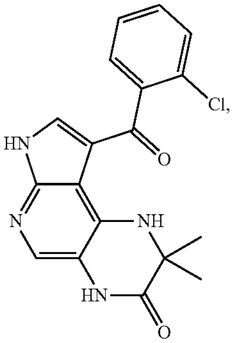
Z121
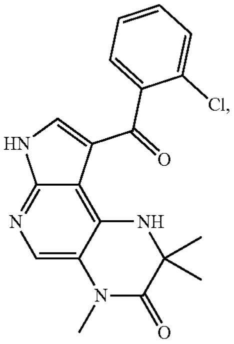
-continued
Z122
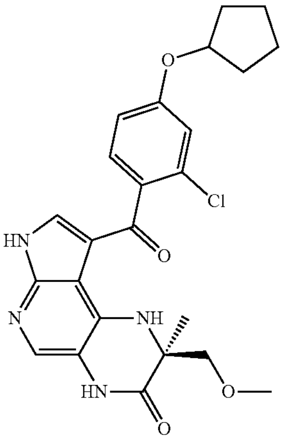
,
Z124-1
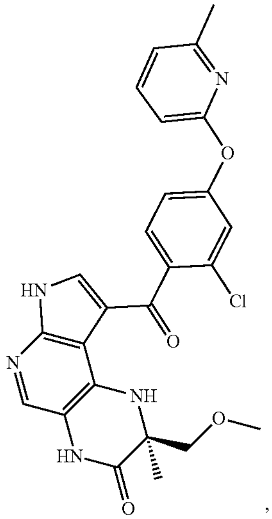
,
Z125-1
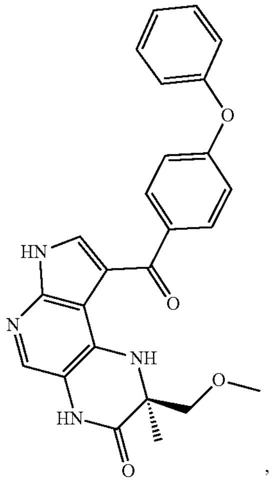
, -continued
Z126
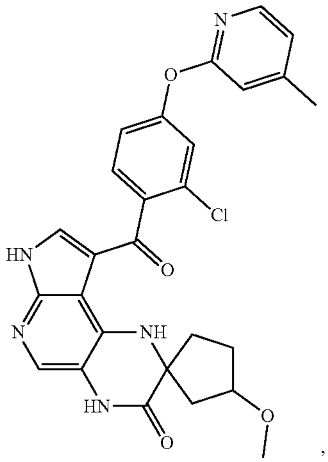
,
Z127-1
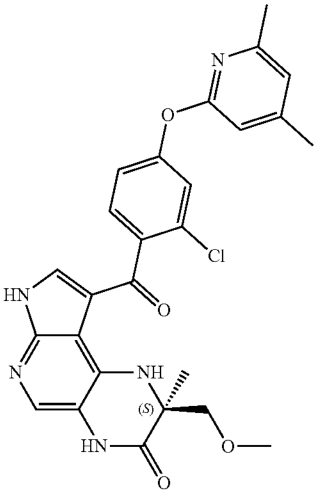
,
Z131
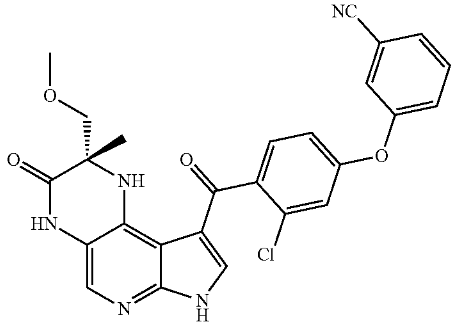
,
Z132
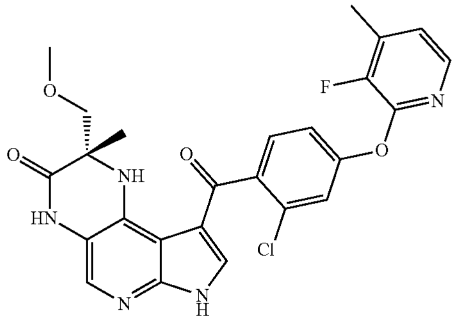
,
-continued
Z133
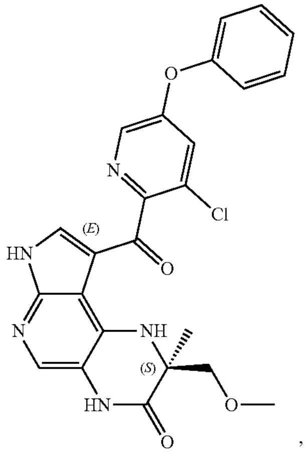
,
Z134
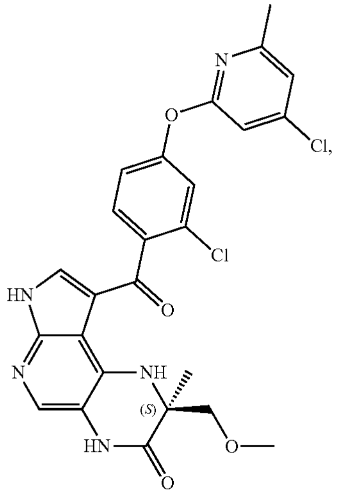
Z135
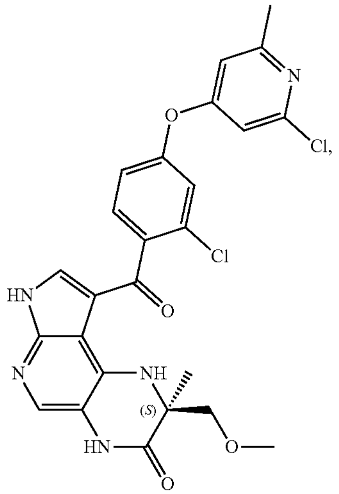

-continued
Z136
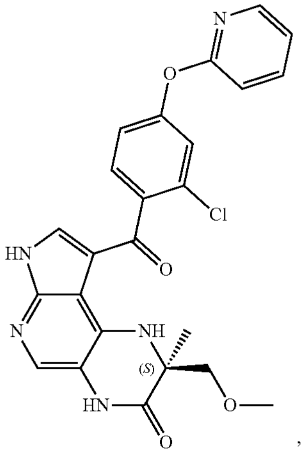
,
Z137
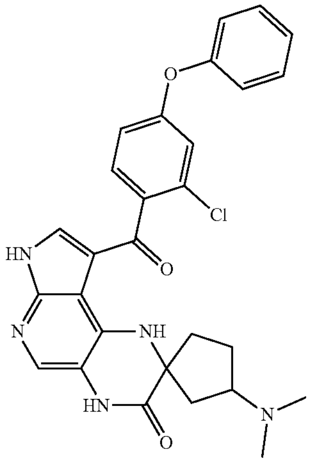
,
Z139
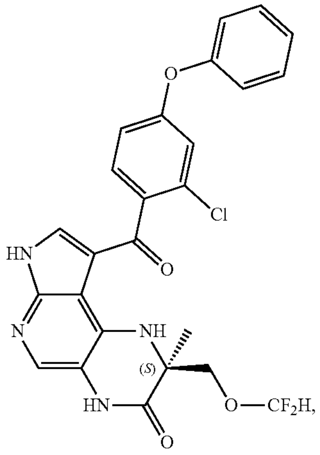
-continued
Z140
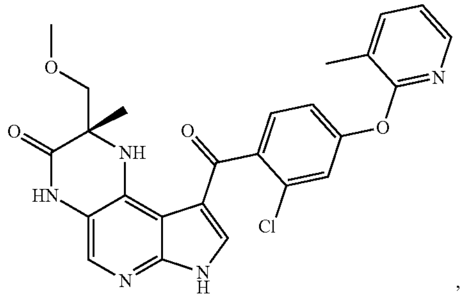
,
Z141
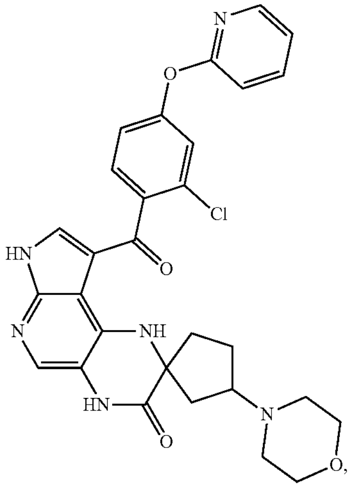
Z142
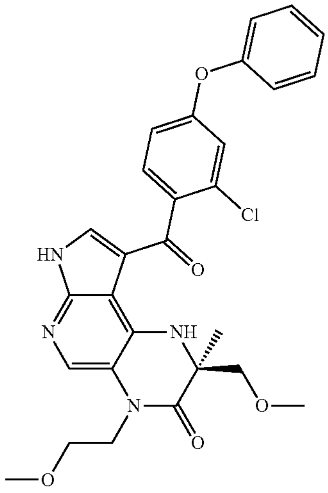
, -continued
Z143
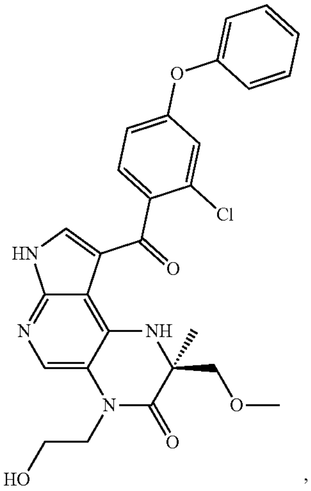
,
Z144
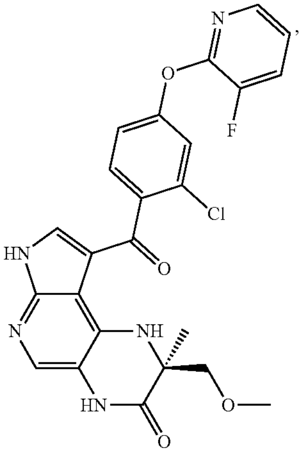
Z145
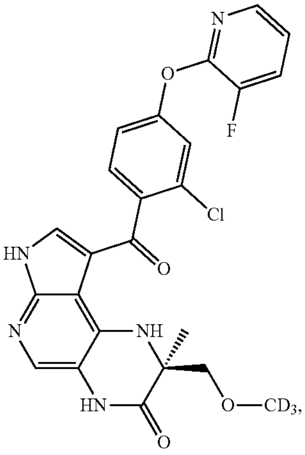
-continued
Z146
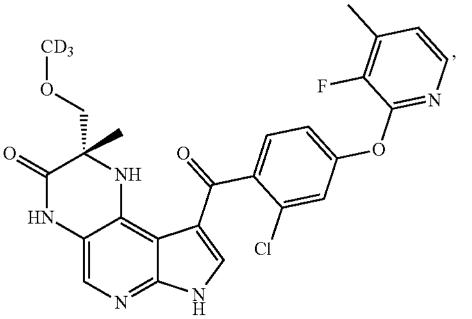
Z149
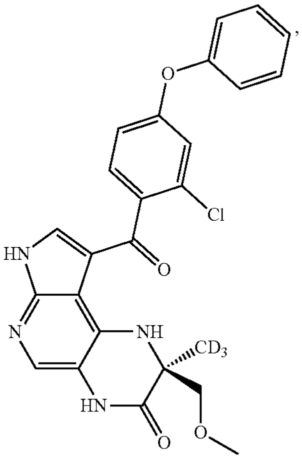
Z150
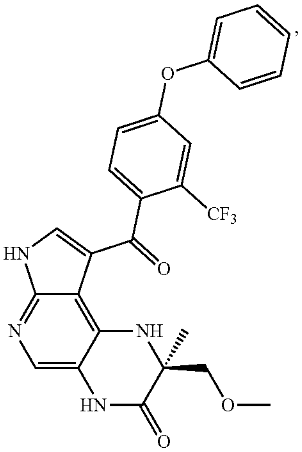

-continued
Z153
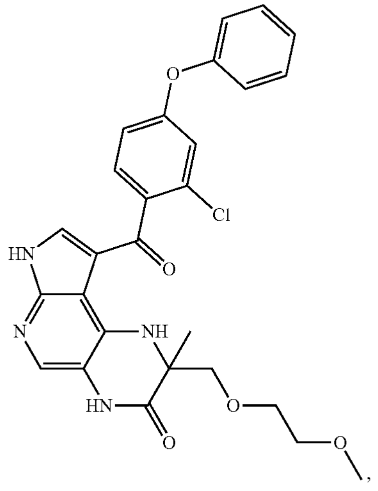
Z153-1
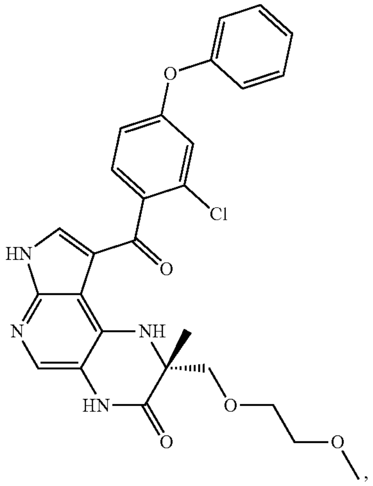
Z153-2
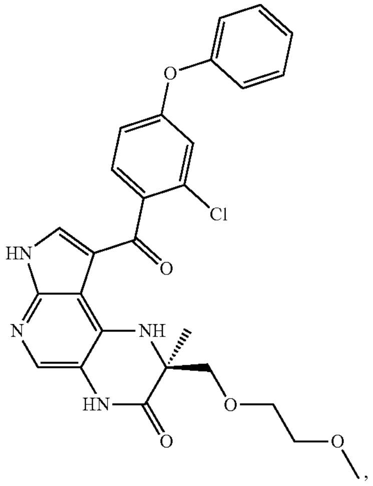
-continued
Z155
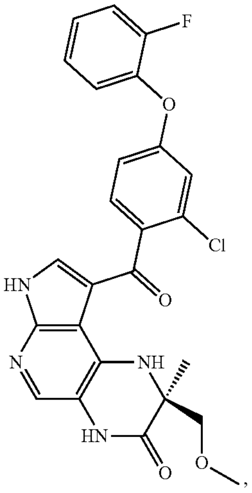
Z156
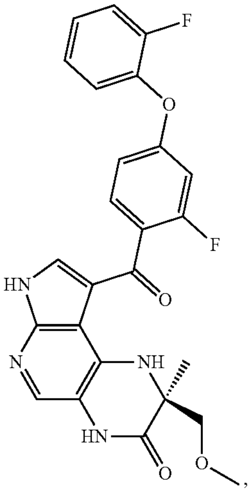
Z157
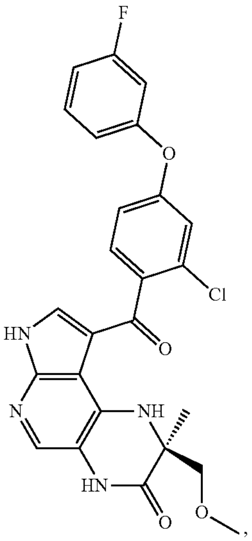

-continued
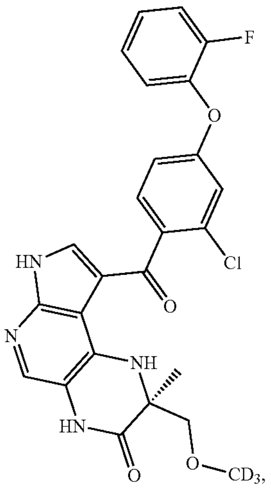
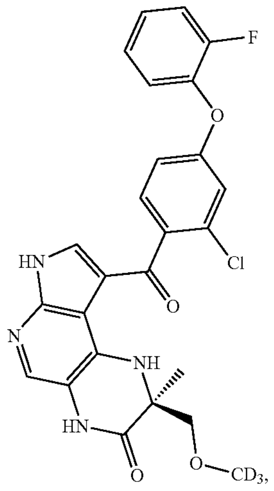
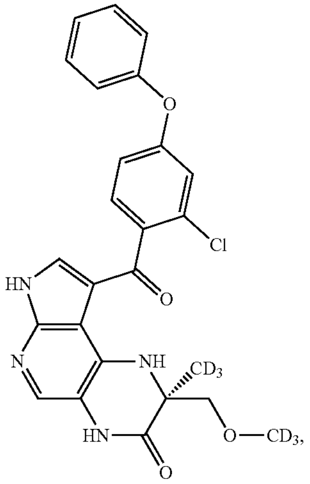
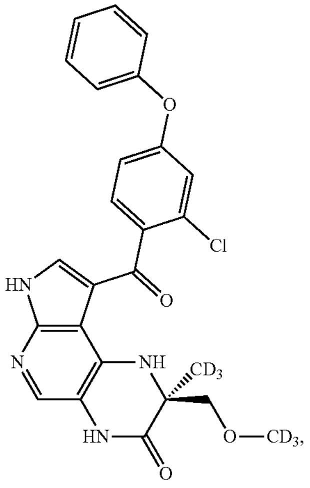 [SMILES: [2H]C([2H])([2H])OC[C@]1(C([2H])([2H])[2H])Nc2c(cnc3[nH]cc(C(=O)c4ccc(Oc5ccccc5)cc4Cl)c23)NC1=O]
-continued
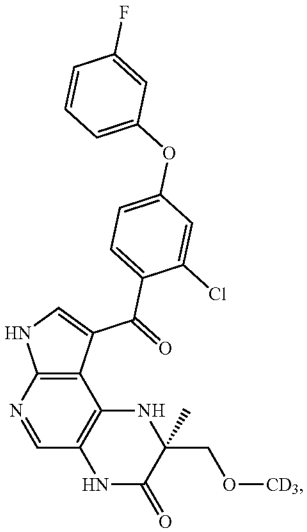
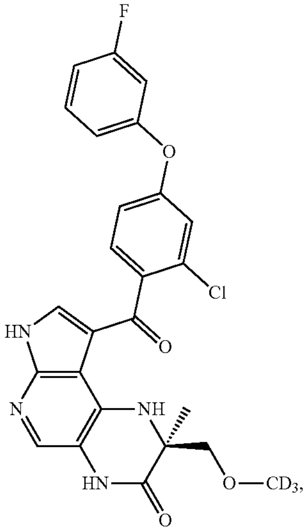
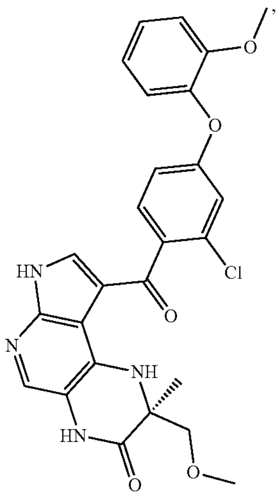
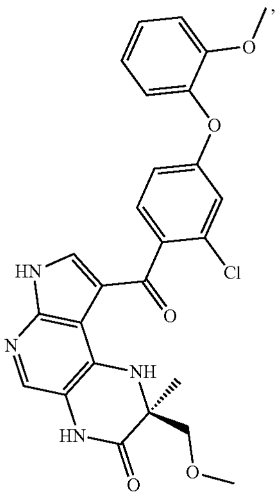

-continued
Z164
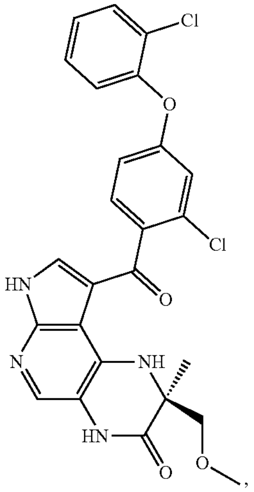
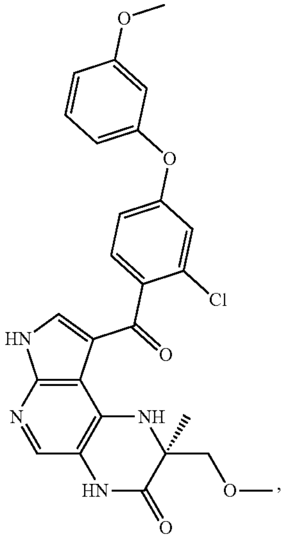
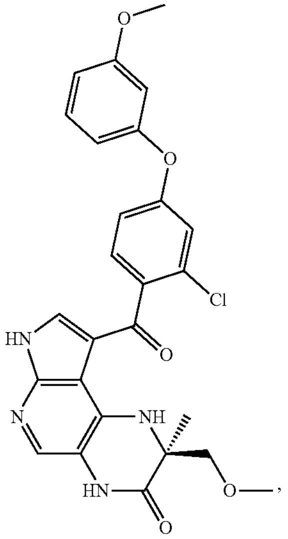
Z167
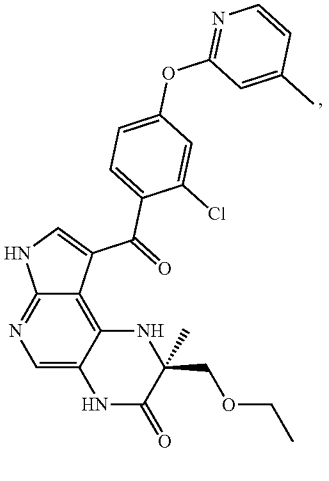
-continued
Z168
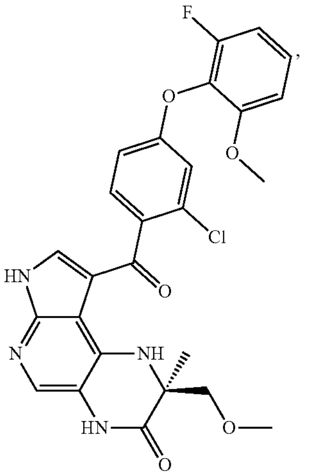
Z170
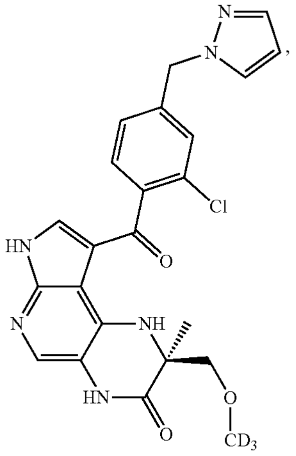
Z174
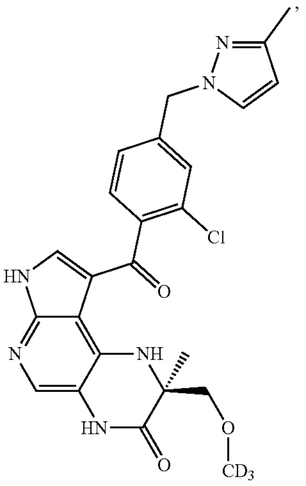

-continued
Z175
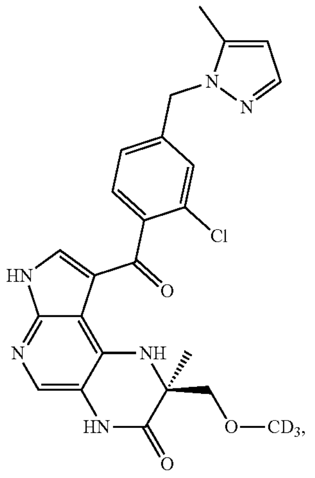
Z173
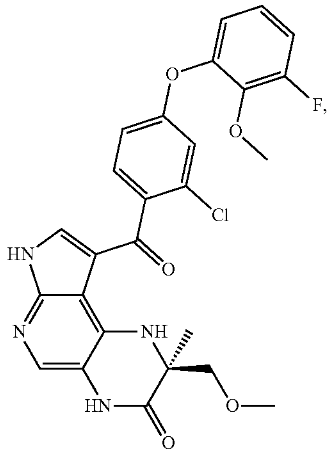
Z177
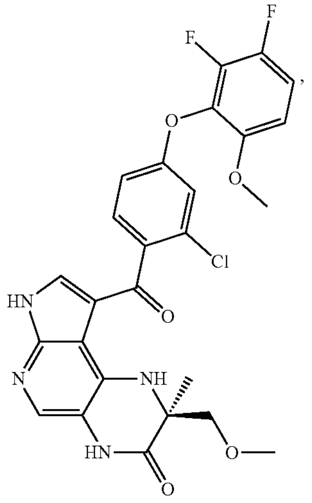
-continued
Z187
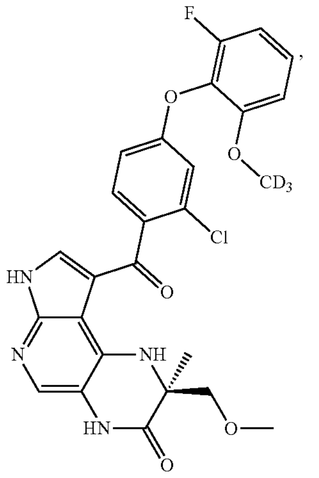
Z189-1
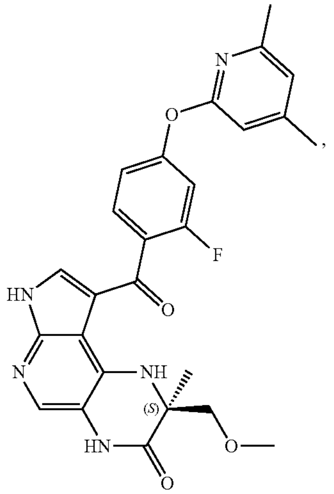
Z190
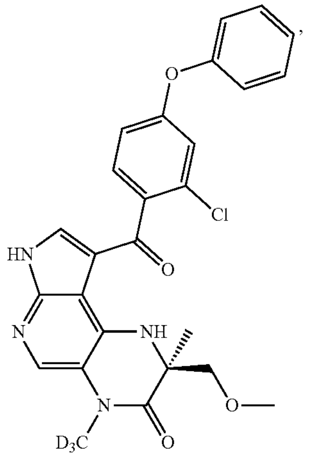

-continued
Z191
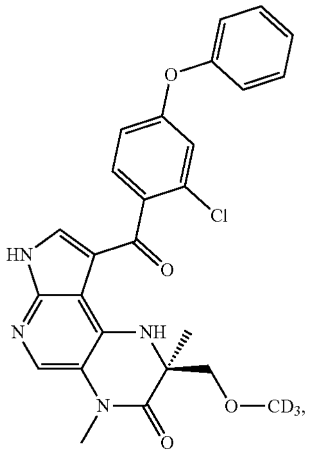
Z192
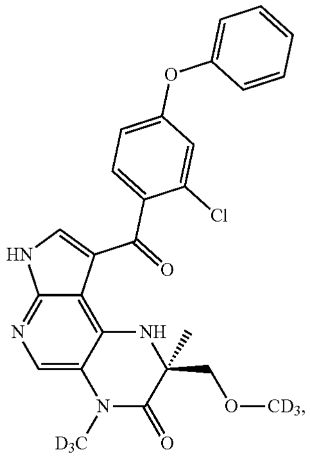
Z193
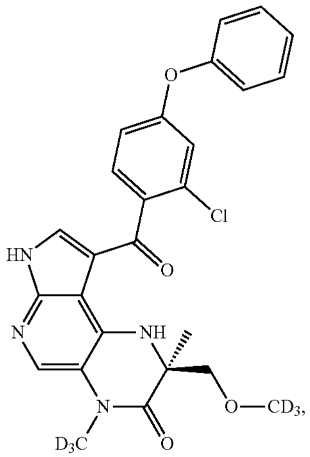
-continued
Z194
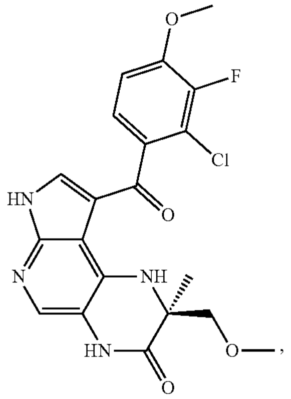
Z195
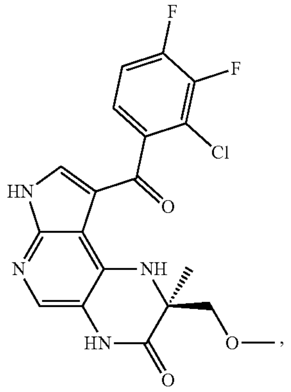
Z196
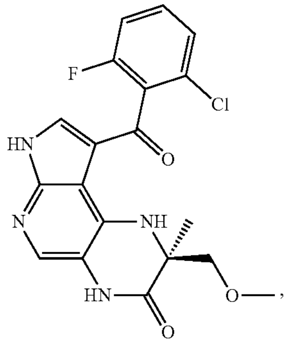
Z197
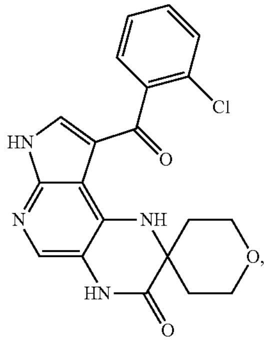

Z198
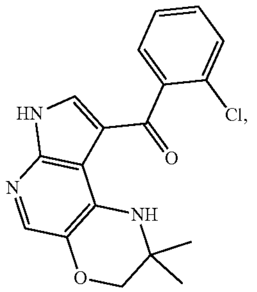
Z199
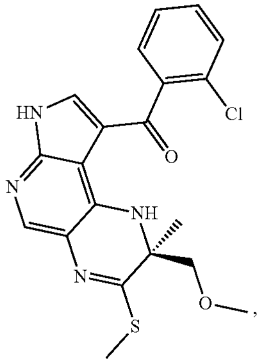
Z200
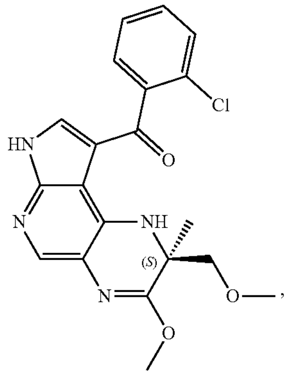
Z201
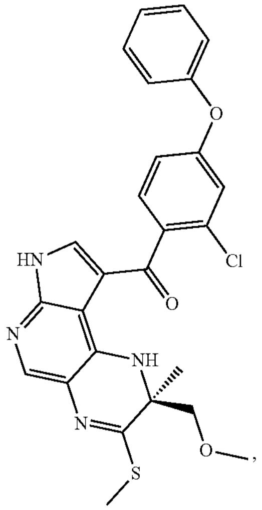
Z202
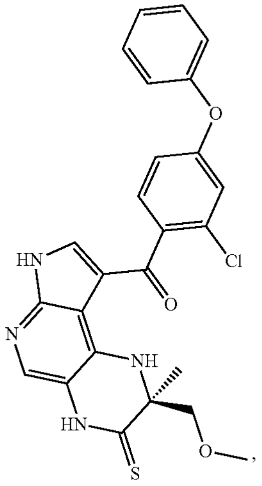
Z203
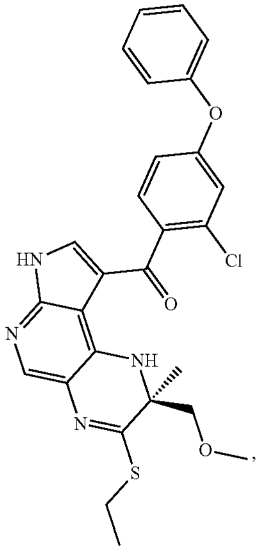
Z204
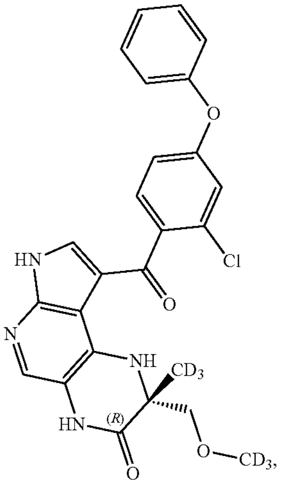

-continued
Z178
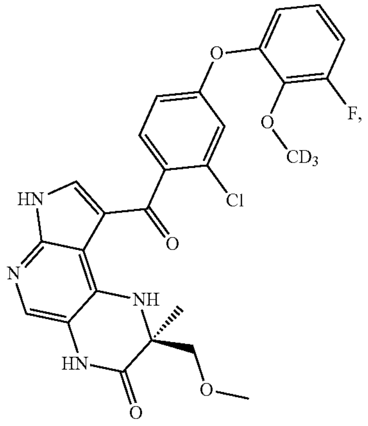
Z169
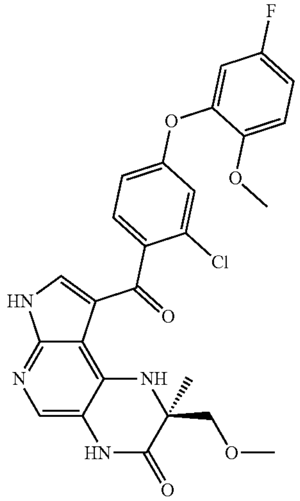
Z165
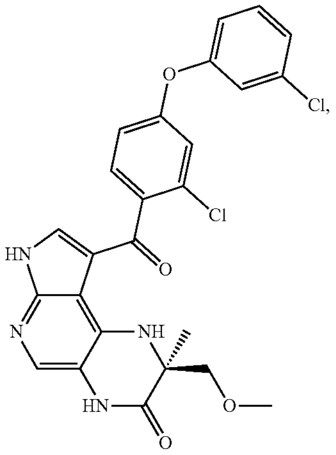
-continued
Z147
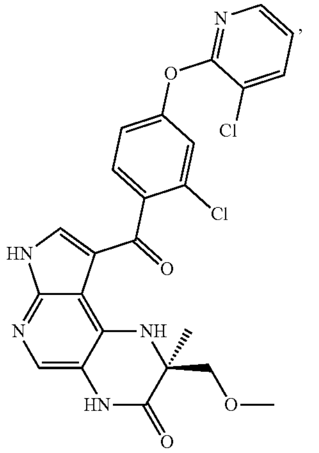
Z41-1a
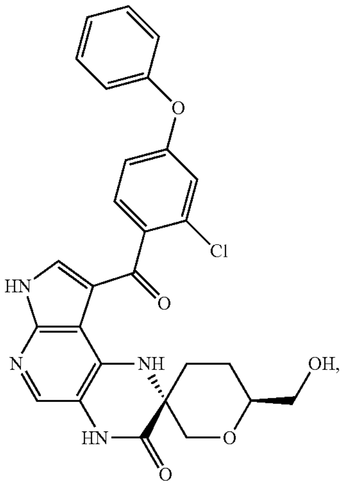
Z41-1b
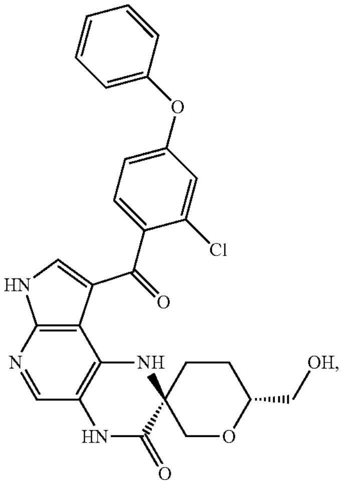

-continued

Z51-1

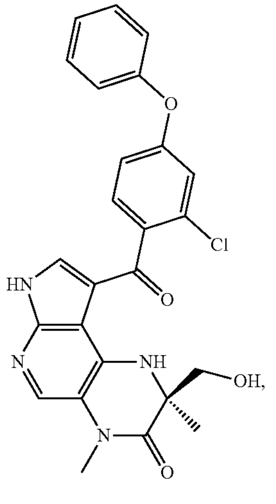

or

Z51-2

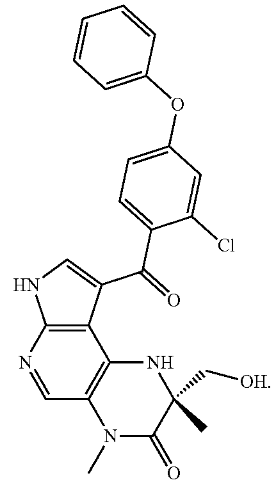

10. The compound, the pharmaceutically acceptable salt thereof, the stereoisomer thereof, or the solvate thereof as claimed in claim 2, wherein, in $R_1$ and $R_2$, the $C_{1-3}$ alkoxy is each independently methoxy;

or, in $R_1$ and $R_2$, the $C_{1-3}$ thioalkyl is each independently methylthio or ethylthio;

or, in $R_3$ and $R_4$, the $C_{1-3}$ alkyl is each independently methyl or ethyl;

or, in $R_3$ and $R_4$, the $C_{3-6}$ monocyclic cycloalkyl is each independently cyclopropyl;

or, in $R_5$, the $C_{1-6}$ alkyl is methyl or ethyl;

or, in $R_5$, the deuterated $C_{1-3}$ alkyl is deuterated methyl;

or, in $R_5$, the $—C_{1-2}$ alkylene-hydroxy is $—CH_2CH_2OH$;

or, in $R_5$, the $—C_{1-2}$ alkylene-$C_{1-3}$ alkoxy is $—CH_2CH_2OCH_3$;

or, in $R_5$, the $—C_{1-2}$ alkylene-$NR^aR^b$ is $—CH_2CH_2N(CH_3)_2$;

or, in $G_1$, the 5- to 6-membered monocyclic heteroaryl is pyridinyl, furyl or thienyl;

or, in $G_1$, substituents in the group S2 are selected from: fluorine, chlorine, bromine, iodine, cyano, methyl, isopropyl, trifluoromethyl, methoxy, trifluoromethoxy, cyclopropyl, —O-cyclopropyl, —O-cyclopentyl, $—N(CH_3)_2$ and $—OCH_2CH_2OCH_3$;

or, in $G_2$, the 5- to 6-membered monocyclic heteroaryl is pyridinyl or pyrazolyl;

or, in $G_2$, substituents in the group S2 are selected from: fluorine, chlorine, cyano, methyl, trifluoromethyl, methoxy, deuterated methoxy and cyclopropyl;

or, in the substituents in group S1, the $C_{1-3}$ alkyl is each independently methyl;

or, in the substituents in group S1, the $C_{1-3}$ alkoxy is each independently methoxy or ethoxy;

or, in the substituents in group S1, the halo $C_{1-3}$ alkoxy is each independently difluoromethoxy or trifluoromethoxy;

or, in the substituents in group S1, the deuterated $C_{1-3}$ alkoxy is each independently deuterated methoxy;

or, in the substituents in group S1, the $C_{1-2}$ alkylene-hydroxy is each independently $—CH_2OH$;

or, in the substituents in group S1, the $—C(O)C_{1-3}$ alkyl is each independently $—C(O)CH_3$;

or, in the substituents in group S2, the $C_{1-3}$ alkyl is each independently methyl or isopropyl;

or, in the substituents in group S2, the halo $C_{1-3}$ alkyl is each independently trifluoromethyl;

or, in the substituents in group S2, the deuterated $C_{1-3}$ alkyl is each independently deuterated methyl;

or, in the substituents in group S2, the $C_{1-3}$ alkoxy is each independently methoxy;

or, in the substituents in group S2, the halo $C_{1-3}$ alkoxy is each independently difluoromethoxy or trifluoromethoxy;

or, in the substituents in group S2, the deuterated $C_{1-3}$ alkoxy is each independently deuterated methoxy;

or, $R^a$ and $R^b$ are each independently methyl;

or, in $R^c$, the $—C_{1-2}$ alkylene-$C_{1-3}$ alkoxy is each independently $—CH_2CH_2OCH_3$ or $—CH_2CH_2OCH_2CH_3$.

11. The compound, the pharmaceutically acceptable salt thereof, the stereoisomer thereof, or the solvate thereof as claimed in claim 3, wherein, $R_3$ is selected from: $—CH_3$, $—CH_2CH_3$, trifluoromethyl, deuterated methyl and cyclopropyl, $R_4$ is selected from: $—CH_3$, $—CH_2OH$, $—CH_2OCH_3$, $—CH_2OCF_3$, $—CH_2OCHF_2$, $—CH_2OCF_3$, $—CH_2OCHF_2$, $—CH_2OCD_3$, $—CH_2OCH_2CH_3$, $—CH_2OCH_2CH_2OCH_3$, $—CH_2CH_2OCH_2CH_3$, $—CH_2O$-cyclopropyl, $—CH_2N(CH_3)_2$, $—CH(OH)CH_3$ and $—CH_2CH_3OCH_3$; or $R_3$ and $R_4$ combining with the carbon atoms to which they are attached form:

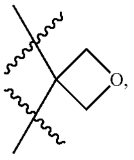

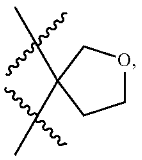

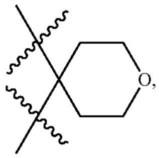

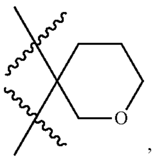

,

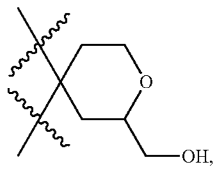

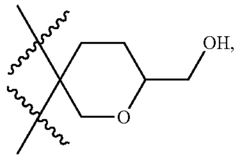

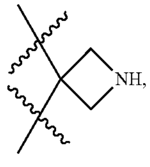

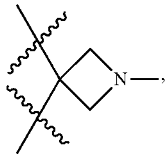

-continued

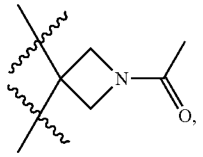
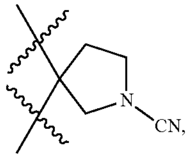
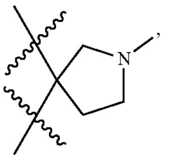
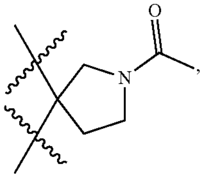
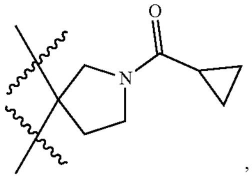
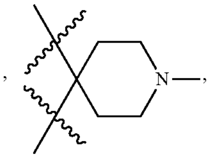
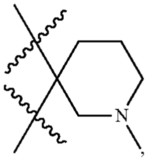
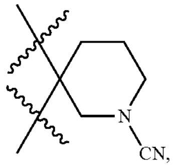
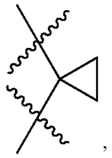
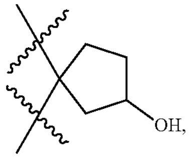
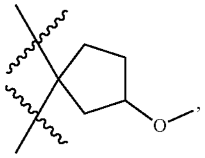
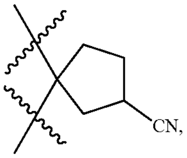
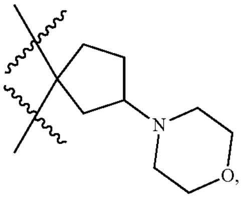
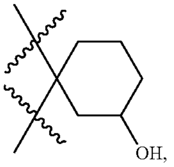
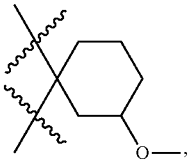

-continued

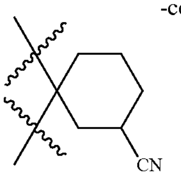
or
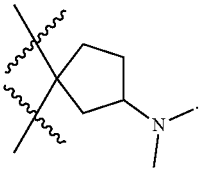

12. The compound, the pharmaceutically acceptable salt thereof, the stereoisomer thereof, or the solvate thereof as claimed in claim 7, wherein, $R_1$ is $C_{1-6}$ alkoxy or $C_{1-6}$ thioalkyl.

13. A pharmaceutical composition, comprising the compound, the pharmaceutically acceptable salt thereof, the stereoisomer thereof, or the solvate thereof as claimed in claim 1; and a pharmaceutically acceptable carrier.

14. A method for treating small lymphocytic lymphoma, acute lymphoblastic leukemia, chronic lymphocytic leukemia, acute myelogenous leukemia, chronic myelogenous leukemia, acute promyelocytic leukemia, chronic myeloid leukemia, diffuse large B-cell lymphoma, intravascular large B-cell lymphoma, primary exudative lymphoma, Waldenstrom's macroglobulinemia, follicular lymphoma, multiple myeloma, mantle cell lymphoma, marginal zone lymphoma or non-Hodgkin lymphoma, comprising: administering an effective amount of the compound, the pharmaceutically acceptable salt thereof, the stereoisomer thereof, or the solvate thereof as claimed in claim 1 to the subject in need thereof.

15. A method for inhibiting BTK and/or abnormal B-cell activation in a subject in need thereof, comprising: administering an effective amount of the compound, the pharmaceutically acceptable salt thereof, the stereoisomer thereof, or the solvate thereof as claimed in claim 1 to the subject in need thereof.

16. A method for inhibiting BTK and/or abnormal B-cell activation in a subject in need thereof, comprising: administering an effective amount of the compound, the pharmaceutically acceptable salt thereof, the stereoisomer thereof, or the solvate thereof as claimed in claim 9 to the subject in need thereof.

17. A method for treating small lymphocytic lymphoma, acute lymphoblastic leukemia, chronic lymphocytic leukemia, acute myelogenous leukemia, chronic myelogenous leukemia, acute promyelocytic leukemia, chronic myeloid leukemia, diffuse large B-cell lymphoma, intravascular large B-cell lymphoma, primary exudative lymphoma, Waldenstrom's macroglobulinemia, follicular lymphoma, multiple myeloma, mantle cell lymphoma, marginal zone lymphoma or non-Hodgkin lymphoma, comprising: administering an effective amount of the compound, the pharmaceutically acceptable salt thereof, the stereoisomer thereof, or the solvate thereof as claimed in claim 9 to the subject in need thereof.

* * * * *